(12) United States Patent
Mikkelsen et al.

(10) Patent No.: US 9,957,540 B2
(45) Date of Patent: May 1, 2018

(54) METHODS FOR IMPROVED PRODUCTION OF REBAUDIOSIDE D AND REBAUDIOSIDE M

(71) Applicant: Evolva SA, Reinach (CH)

(72) Inventors: Michael Dalgaard Mikkelsen, Værløse (DK); Jorgen Hansen, Frederiksberg (DK); Ernesto Simon, Copenhagen (DK); Federico Brianza, Riehen (CH); Angelika Semmler, Copenhagen (DK); Kim Olsson, Søborg (DK); Simon Carlsen, Copenhagen (DK); Louis Düring, Copenhagen (DK); Alexei Ouspenski, Mulhouse (FR); Paula Hicks, Bend, OR (US)

(73) Assignee: EVOLVA SA, Reinach (CH)

( * ) Notice: Subject to any disclaimer, the term of this patent is extended or adjusted under 35 U.S.C. 154(b) by 0 days. days.

(21) Appl. No.: 14/761,629

(22) PCT Filed: Feb. 6, 2014

(86) PCT No.: PCT/EP2014/052363
§ 371 (c)(1),
(2) Date: Jul. 17, 2015

(87) PCT Pub. No.: WO2014/122227
PCT Pub. Date: Aug. 14, 2014

(65) Prior Publication Data
US 2016/0186225 A1 Jun. 30, 2016

Related U.S. Application Data

(60) Provisional application No. 61/761,490, filed on Feb. 6, 2013, provisional application No. 61/886,442, filed on Oct. 3, 2013.

(51) Int. Cl.
| | |
|---|---|
| *C12P 19/56* | (2006.01) |
| *A23L 2/60* | (2006.01) |
| *C12N 9/02* | (2006.01) |
| *C12N 9/10* | (2006.01) |
| *C12N 9/90* | (2006.01) |
| *C12N 15/81* | (2006.01) |
| *A23L 27/30* | (2016.01) |

(52) U.S. Cl.
CPC ............ *C12P 19/56* (2013.01); *A23L 2/60* (2013.01); *A23L 27/36* (2016.08); *C12N 9/0071* (2013.01); *C12N 9/1051* (2013.01); *C12N 9/1081* (2013.01); *C12N 9/1085* (2013.01); *C12N 9/90* (2013.01); *C12N 15/81* (2013.01); *C12Y 204/01* (2013.01); *A23V 2002/00* (2013.01); *C12Y 204/99* (2013.01)

(58) Field of Classification Search
CPC ............... A23V 2250/262; A23V 2250/255
See application file for complete search history.

(56) References Cited

U.S. PATENT DOCUMENTS

| | | | |
|---|---|---|---|
| 4,590,160 A | 5/1986 | Nishihashi et al. | |
| 5,204,253 A | 4/1993 | Sanford et al. | |
| 5,306,862 A | 4/1994 | Chappell et al. | |
| 5,460,949 A | 10/1995 | Saunders et al. | |
| 5,538,880 A | 7/1996 | Lundquist et al. | |
| 6,013,863 A | 1/2000 | Lundquist et al. | |
| 6,215,051 B1 | 4/2001 | Yu et al. | |
| 6,255,557 B1 | 7/2001 | Brandle | |
| 6,284,493 B1 | 9/2001 | Roth | |
| 6,284,506 B1 | 9/2001 | Hoshino et al. | |
| 6,329,571 B1 | 12/2001 | Hiei | |
| 6,586,202 B2 | 7/2003 | Hoshino et al. | |
| 6,660,507 B2 | 12/2003 | Cheng et al. | |
| 6,806,076 B1 | 10/2004 | Miyake et al. | |
| 6,969,595 B2 | 11/2005 | Brzostowicz et al. | |
| 7,034,140 B2 | 4/2006 | Bramucci et al. | |
| 7,056,717 B2 | 6/2006 | Cheng et al. | |
| 7,098,000 B2 | 8/2006 | Cheng et al. | |
| 7,129,392 B2 | 10/2006 | Hahn et al. | |
| 7,132,268 B2 | 11/2006 | Miyake et al. | |
| 7,172,886 B2 | 2/2007 | Keasling et al. | |
| 7,183,089 B2 | 2/2007 | Keasling et al. | |
| 7,186,891 B1 | 3/2007 | Chappell et al. | |
| 7,208,298 B2 | 4/2007 | Miyake et al. | |
| 7,335,815 B2 | 2/2008 | Boronate et al. | |
| 7,364,885 B2 | 4/2008 | Miyake et al. | |
| 7,422,884 B2 | 9/2008 | Bai et al. | |
| 7,569,389 B2 | 9/2009 | Feldmann et al. | |
| 7,838,287 B2 | 11/2010 | Goldsmith et al. | |

(Continued)

FOREIGN PATENT DOCUMENTS

| | | |
|---|---|---|
| CN | 101720910 | 6/2010 |
| CN | 103397064 | 11/2013 |

(Continued)

OTHER PUBLICATIONS

Yu et al., "Bioconversion of ethyl 4-chloro-3-oxobutanoate by permeabilized fresh brewer's yeast cells in the presence of allyl bromide," J Ind Microbial Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14): e115 (Aug. 2004).
Zhu et al., "A multi-omic map of the lipid-producing yeast *Rhodosporidium toruloides*," Nature Commun. 3:1112 (Oct. 2012).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).

(Continued)

*Primary Examiner* — Karen Cochrane Carlson
(74) *Attorney, Agent, or Firm* — McDonnell Boehnen Hulbert & Berghoff LLP

(57) ABSTRACT

Methods for recombinant production of steviol glycoside and compositions containing steviol glycosides are provided herein.

30 Claims, 23 Drawing Sheets

(56) References Cited

U.S. PATENT DOCUMENTS

| | | | |
|---|---|---|---|
| 7,923,541 B2 | 4/2011 | Yang et al. | |
| 7,927,851 B2 | 4/2011 | Brandle et al. | |
| 9,562,251 B2* | 2/2017 | Kishore | C12N 15/8243 |
| 2002/0142408 A1 | 10/2002 | DiCosimo et al. | |
| 2003/0033626 A1 | 2/2003 | Hahn et al. | |
| 2003/0148416 A1 | 8/2003 | Berry et al. | |
| 2003/0148479 A1 | 8/2003 | Keasling et al. | |
| 2003/0190734 A1 | 10/2003 | Hoshino et al. | |
| 2003/0219798 A1 | 11/2003 | Gokarn et al. | |
| 2004/0010815 A1 | 1/2004 | Lange et al. | |
| 2004/0072311 A1 | 4/2004 | DiCosimo et al. | |
| 2004/0078846 A1 | 4/2004 | DeSouza et al. | |
| 2004/0176570 A1 | 9/2004 | Bacher et al. | |
| 2004/0194162 A1 | 9/2004 | Hahn et al. | |
| 2005/0003474 A1 | 1/2005 | DeSouza et al. | |
| 2005/0032169 A1 | 2/2005 | Miyake et al. | |
| 2006/0014264 A1 | 1/2006 | Sauer et al. | |
| 2006/0079476 A1 | 4/2006 | Keasling et al. | |
| 2006/0083838 A1 | 4/2006 | Jackson et al. | |
| 2007/0004000 A1 | 1/2007 | Miyake et al. | |
| 2007/0077616 A1 | 4/2007 | Keasling et al. | |
| 2007/0099261 A1 | 5/2007 | Keasling et al. | |
| 2007/0128311 A1 | 6/2007 | Prakash et al. | |
| 2007/0166782 A1 | 7/2007 | Keasling et al. | |
| 2007/0202579 A1 | 8/2007 | Berry et al. | |
| 2007/0238157 A1 | 10/2007 | Millis et al. | |
| 2007/0238159 A1 | 10/2007 | Millis et al. | |
| 2007/0238160 A1 | 10/2007 | Millis et al. | |
| 2007/0254354 A1 | 11/2007 | Millis et al. | |
| 2007/0269857 A1 | 11/2007 | Miyake et al. | |
| 2007/0286850 A1 | 12/2007 | Bai et al. | |
| 2008/0064063 A1 | 3/2008 | Brandle et al. | |
| 2008/0081358 A1 | 4/2008 | Viitanen et al. | |
| 2008/0131926 A1 | 6/2008 | Miyake et al. | |
| 2008/0261280 A1 | 10/2008 | Hahn et al. | |
| 2008/0271205 A1 | 10/2008 | Yamaguchi et al. | |
| 2008/0286870 A1 | 11/2008 | Vittanen et al. | |
| 2008/0292775 A1 | 11/2008 | Prakash et al. | |
| 2008/0318227 A1 | 12/2008 | Bacher et al. | |
| 2009/0004724 A1 | 1/2009 | Keasling et al. | |
| 2009/0047718 A1 | 2/2009 | Blaschek et al. | |
| 2009/0074935 A1 | 3/2009 | Lee | |
| 2009/0286262 A1 | 11/2009 | Slack | |
| 2010/0112156 A1 | 5/2010 | Abelyan et al. | |
| 2010/0221801 A1 | 9/2010 | Van Dyk | |
| 2010/0297722 A1 | 11/2010 | Anterola et al. | |
| 2011/0087011 A1 | 4/2011 | Chiang et al. | |
| 2011/0092684 A1 | 4/2011 | Varuzhan et al. | |
| 2011/0160311 A1 | 6/2011 | Prakash et al. | |
| 2012/0021111 A1 | 1/2012 | Pfister et al. | |
| 2012/0083593 A1 | 4/2012 | Liu et al. | |
| 2012/0164678 A1 | 6/2012 | Stephanopoulos et al. | |
| 2012/0178169 A1 | 7/2012 | Voytas et al. | |
| 2013/0137138 A1 | 5/2013 | Hansen | |
| 2015/0159188 A1 | 6/2015 | Ono et al. | |
| 2015/0342234 A1* | 12/2015 | Hicks | A23L 1/2363 536/18.1 |

FOREIGN PATENT DOCUMENTS

| | | |
|---|---|---|
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2902410 | 8/2015 |
| JP | 3-277275 | 12/1991 |
| JP | 05-115298 | 5/1993 |
| KR | 20150000258 | 1/2015 |
| WO | 1999/018224 | 4/1999 |
| WO | 2000/036081 | 6/2000 |
| WO | 2000/037663 | 6/2000 |
| WO | 2000/063400 | 10/2000 |
| WO | 2001/012828 | 2/2001 |
| WO | 2001/083769 | 11/2001 |
| WO | 2001/094561 | 12/2001 |
| WO | 2002/020728 | 3/2002 |
| WO | 2002/020815 | 3/2002 |
| WO | WO 2002/024865 | 3/2002 |
| WO | 2002/055709 | 7/2002 |
| WO | 2003/008540 | 1/2003 |
| WO | 2004/029255 | 4/2004 |
| WO | 2005/079183 | 9/2005 |
| WO | WO 2006/016395 | 2/2006 |
| WO | 2006/093289 | 9/2006 |
| WO | 2006/096392 | 9/2006 |
| WO | 2007/136847 | 11/2007 |
| WO | 2008/008256 | 1/2008 |
| WO | 2008/034648 | 3/2008 |
| WO | 2008/039499 | 4/2008 |
| WO | 2008/051349 | 5/2008 |
| WO | WO 2008/091547 | 7/2008 |
| WO | 2009/005704 | 1/2009 |
| WO | 2009/071277 | 6/2009 |
| WO | 2009/086049 | 7/2009 |
| WO | WO 2009/105612 | 8/2009 |
| WO | 2009/108680 | 9/2009 |
| WO | 2009/140394 | 11/2009 |
| WO | 2010/021001 | 2/2010 |
| WO | 2010/038911 | 4/2010 |
| WO | 2010/146463 | 12/2010 |
| WO | WO 2010/142305 | 12/2010 |
| WO | 2011/028671 | 3/2011 |
| WO | 2011/037959 | 3/2011 |
| WO | 2011/046423 | 4/2011 |
| WO | 2011/056834 | 5/2011 |
| WO | 2011/153378 | 8/2011 |
| WO | WO2011/140329 | 11/2011 |
| WO | 2011/151326 | 12/2011 |
| WO | 2011/153144 | 12/2011 |
| WO | 2011153378 A1 † | 12/2011 |
| WO | 2012/075030 | 6/2012 |
| WO | 2013/019050 | 2/2013 |
| WO | 2013/022989 | 2/2013 |
| WO | 2013/096420 | 6/2013 |
| WO | 2013/102793 | 7/2013 |
| WO | 2013/110673 | 8/2013 |
| WO | 2013/176738 | 11/2013 |
| WO | 2014/086890 | 6/2014 |
| WO | 2014/122328 | 8/2014 |
| WO | WO2014/191580 | 12/2014 |
| WO | WO 2014/191581 | 12/2014 |
| WO | WO 2015/011209 | 1/2015 |
| WO | WO 2015/014959 | 2/2015 |
| WO | WO 2015/014969 | 2/2015 |
| WO | WO 2015/016393 | 2/2015 |
| WO | WO 2016/023844 | 2/2016 |
| WO | WO 2016/038095 | 3/2016 |

OTHER PUBLICATIONS

GenBank Accession No. AAC39505, dated Jul. 26, 1998 (1 page).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAF61439.1, dated Sep. 25, 2000 (2 pages).
GenBank Accession No. AAH69913, dated Jul. 15, 2006 (2 pages).
GenBank Accession No. AAM53963.1, dated Jun. 17, 2002 (2 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06918.1, dated Dec. 28, 2004 (2 pages).
GenBank Accession No. AAR06920.1, dated Dec. 28, 2004 (2 pages).
GenBank Accession No. AAT93110.1, dated Apr. 24, 2007 (2 pages).

(56) References Cited

OTHER PUBLICATIONS

GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AEE36246, dated Oct. 6, 2014 (3 pages).
GenBank Accession No. AF034774, dated Apr. 17, 1998 (2 pages).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. BG521726.1, dated May. 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. CAG41604, dated Feb. 6, 2015 (2 pages).
EMBOSS Needle results for Pairwise Sequence Alignment of UGT91D1 and UGT91D2; dated Apr. 4, 2016, 2 pages.
Kumar et al., "A comprehensive analysis of fifteen genes of steviol glycosides biosynthesis pathwayin Stevia rebaudiana (Bertoni)" Gene 492:276-84 (Epub Oct. 20, 2011).
Shibata et al., "Glucosylation of Steviol and Steviol-Glucosides in Extracts from Stevia rebaudiana Bertoni" Plant Physiol. 95(1):152-56 (1991).
Xu et al., "Generation of hepatitis B virus PreS2-S antigen in Hansenula polymorpha," Virol Sin. 29(6):403-9 (Dec. 2014).
Final Office Action issued in U.S. Appl. No. 14/237,540; dated Jul. 8, 2016, pp. 1-19.
Extended European Search Report issued in EP 15193074.0; dated Feb. 12, 2016, pp. 1-9.
Third Party Submission in U.S. Appl. No. 14/648,747; dated Mar. 28, 2016, pp. 1-231.
Invitation to Pay Additional Fees and, Where Applicable, Protest Fee by the International Searching Authority for International Application No. PCT/EP2015/070620, dated Nov. 27, 2015 (pp. 1-14).
International Search Report by the International Searching Authority for International Application No. PCT/EP2015/070620; dated Mar. 29, 2016, pp. 1-10.
Written Opinion of the International Searching Authority for International Application No. PCT/EP2015/070620; dated Mar. 29, 2016, pp. 1-24.
International Search Report and Written Opinion of the International Searching Authority for International Application No. PCT/EP2015/052007; dated Jul. 4, 2016, pp. 1-24.

Flores et al., "Permeabilization of yeast cells (*Kluyveromyces lactis*) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).
Giaever & Nislow, "The yeast deletion collection: a decade of functional genomics," Genetics 197(2):451-65 (Jun. 2014).
Gietz & Schiestl, "High-efficiency yeast transformation using the LiAc/SS carrier DNA/PEG method," Nat Protoc. 2 (1):31-4 (2007).
Girvan et al., "Flavocytochrome P450 BM3 mutant W1046A is a NADH-dependent fatty acid hydroxylase: Implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Gossen & Bujard, "Studying gene function in eukaryotes by conditional gene inactivation," Ann Rev Genet. 36:153-73 (2002).
Gritz & Davies, "Plasmid-encoded hygromycin B resistance: the sequence of hygromycin B phosphotransferase gene and its expression in *Escherichia coli* and *Saccharomyces cerevisie*," Gene 25(2-3):179-88 (Nov. 1983).
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast *Schizosaccharomyces pombe*," Biotechnol. & Biotechnol. Eq. 20(3):76-82 (2006).
Hallstrom & Moye-Rowley, "Divergent transcriptional control of multidrug resistance genes in *Saccharomyces cerevisiae*," J. Biol. Chem. 273(4):2098-104 (Jan. 1998).
Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9)3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Iandolino et al., "High-Quality RNA, cDNA, and Derived EST Libraries From Grapevine (*Vitis vinifera* L.)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosynthesis: baxane 13 alpha-hydroxylase is a cytochrome P450-dependent monooxygenase," Proc Natl Acad Sci U S A 98(24):13595-600 (2001).
Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Katzmann et al., "Expression of an ATP-binding cassette transporter-encoding gene (YOR1) is required for oligomycin resistance in *Saccharomyces cerevisiae*," Mol. Cell Biol. 15(12):6875-83 (Dec. 1995).
Khoury et al., "Computational design of Candida boidinii xylose reductase for altered cofactor specificity," Protein Sci. 18(10)1125-38 (Oct. 2009).

(56) References Cited

OTHER PUBLICATIONS

Kim et al., "Hydroxylation of ent-Kaurenoic Acid to Steviol in Stevia rebaudiana Bertoni-Purification and Partial Characterization of the Enzyme," Arch Biochem Biophys. 332(2)123-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kusama et al., "Transglucosylation into stevioside by the enzyme system from *Streptomyces* sp.," Agric. Biol. Chem. 50(10)1445-51 (Oct. 1986).
Li et al., "Phylogenetic analysis of the UDP-glycosyltransferase multigene family of *Arabidopsis thaliana*," J Biol Chem. 276(6):4338-43 (2001).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast *Rhodosporidium toruloides* Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Expenmentalis Sinica 36(2):123-9 (2003).
Madan et al., "Stevia rebaudiana (Bert.) Bertoni—A Review," Indian Journal of Natural Products and Resources 1 (3):267-86 (2010).
Madhav et al., "Functional and structural variation of uridine diphosphate glycosyltransferase (UGT) gene of Stevia rebaudiana—UGTSr involved in the synthesis of rebaudioside A," Plant Physiol. Biochem. 63:245-53 (Feb. 2013).
MaLingBo, "1. Molecular Cloning and Functional Analysis of UDPG Glucosyltransferase Gene 2. Molecular Cloning, Sequence Analysis and Evolution of Actin and EF1a Genes in Stevia Rebaudiana," Chinese Doctor and Master Dissertations Full-Text Database, Agricultural Technology Part, vol. 2 (2004).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Masada et al., "An efficient chemoenzymatic production of small molecule glucosides with in situ UDP-glucose recycling," FEBS Lett. 581(13):2562-6 (2007).
Megeji et al., "Introducing Stevia rebaudiana, a natural zero-calorie sweetener," Current Science 88(5):801-4 (2005).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (2005).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nagy et al., "Role of the yeast ABC transporter Yor1p in cadmium detoxification," Biochimie 88(11):1665-71 (Jun. 2006).
Nakagiri et al., "cDNA cloning, functional expression and characterization of ent-copalyl diphosphate synthase from *Scoparia dulcis* L.," Plant Sci. 169:760-7 (2005).
Further Examination Report issued by the Intellectual Property Office of New Zealand for New Zealand Application No. 604915, dated Jun. 18, 2014.
Response to Further Examination Report issued by the Intellectual Property Office of New Zealand for New Zealand Application No. 604915, dated Sep. 15, 2014.
Notice of Acceptance issued by the Intellectual Property Office of New Zealand for New Zealand Application No. 604915, dated Oct. 7, 2014 (1 page).
First Examination Report issued by the Intellectual Property Office of New Zealand for New Zealand Application No. 700097, dated Oct. 6, 2014 (pp. 1-2).
Notice of Acceptance issued by the Intellectual Property Office of New Zealand for New Zealand Application No. 700097, dated Oct. 7, 2015 (1 page).
First Examination Report issued by the Intellectual Property Office of New Zealand for New Zealand Application No. 708078, dated May 28, 2015 (pp. 1-3).
Search Report issued by the Intellectual Property Office of Singapore for Singaporean Application No. 201208854-8, dated Nov. 3, 2014.
Wrtitten Opinion issued by the Intellectual Property Office of Singapore for Singaporean Application No. 201208854-8, dated Nov. 3, 2014.
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
International Preliminary Report on Patentability issued by the International Bureau for International Application No. PCT/US2012/050021, dated Feb. 11, 2014.
English Translation of First Office Action and Search Report issued by the State Intellectual Property Office of People's Republic of China for Chinese Application No. 201280038853.3, dated Feb. 16, 2015.
English Translation of Second Office Action and Search Report issued by the State Intellectual Property Office of People's Republic of China for Chinese Application No. 201280038853.3, dated Jan. 11, 2016.
Communication pursuant to Rules 161(1) and 162 (EPC) issued by the European Patent Office for European Application No. 12750513.9, dated Mar. 14, 2014.
Response to Communication pursuant to Rules 161(1) and 162 (EPC) issued by the European Patent Office for European Application No. 12750513.9, dated Aug. 4, 2014.
Examination Report issued by the European Patent Office for European Application No. 12750513.9, dated Nov. 26, 2014.
Response to Examination Report issued by the European Patent Office for European Application No. 12750513.9, dated Mar. 25, 2015.
Non-Final Office Action for U.S. Appl. No. 14/237,540, dated Dec. 30, 2015 (pp. 1-19).
International Search Report from the International Searching Authority for International Application No. PCT/EP2014/052363, dated Sep. 22, 2014 (12 pages).
Written Opinion of the International Searching Authority for International Application No. PCT/EP2014/052363, dated Sep. 22, 2014 (10 pages).

(56) References Cited

OTHER PUBLICATIONS

International Preliminary Report on Patentability issued by the International Bureau for International Application No. PCT/EP2014/052363, dated Aug. 11, 2015. (11 pages).
Communication pursuant to Rules 161(1) and 162 EPC for European Application No. 14702889.8, dated Oct. 14, 2015 (2 pages).
International Search Report by the International Searching Authority for International Application No. PCT/EP2014/052675, dated Apr. 23, 2014 (5 pages).
Written Opinion of the International Searching Authority for International Application No. PCT/EP2014/052675, dated Apr. 23, 2014 (7 pages).
International Preliminary Report on Patentability issued by the International Bureau for International Application No. PCT/EP2014/052675, dated Aug. 11, 2015. (8 pages).
Communication pursuant to Rules 161(1) and 162 EPC for European Application No. 14704558.7, dated Sep. 18, 2015 (2 pages).
International Search Report of the International Searching Authority for International Application No. PCT/EP2013/075587, dated Feb. 20, 2014 (pp. 1-5).
Written Opinion of the International Searching Authority for International Application No. PCT/EP2013/075587, dated Feb. 20, 2014 (pp. 1-9).
International Preliminary Report on Patentability from the International Bureau for International Application No. PCT/EP2013/075587, dated Jun. 9, 2015 (pp. 1-10).
Communication pursuant to Rules 161(1) and 162 EPC for European Application No. 13801569.8, dated Jul. 14, 2015 (2 pages).
Response to Communication pursuant to Rules 161(1) and 162 EPC for European Application No. 13801569.8, dated Jan. 13, 2016 (9 pages).
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).
Mattanovich et al., "Recombinant protein production in yeasts," Methods Mol Biol. 824:329-58 (2012).
Nour-Eldin et al., "USER cloning and USER fusion: the ideal cloning techniques for small and big laboratories," Methods Mol Biol. 643:185-200 (2010).
Abraham & Bhat, "Permeabilization of baker's yeast with N-lauroyl sarcosine," J Ind Microbial Biotechnol. 35 (8):799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31 (10):3307-30 (1992).
Ajikumar et al., "Terpenoids: opportunities for biosynthesis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42 (4):2827-37 (2010).
Bankar et al., "Environmental and industrial applications of Yarrowia lipolytica," Appl Microbiol Biotechnol. 84 (5):847-65 (Oct. 2009).
Bateman et al., "Pfam 3.1: 1313 multiple alignments and profile HMMs match the majority of proteins," Nucl Acids Res. 27(1):260-2 (1999).
Bay & Turner, "Diversity and evolution of the small multidrug resistance protein family," BMC Evol. Biol. 9:140 (Jun. 2009).
Baykov et al., "A malachite green procedure for orthophosphate determination and its use in alkaline phosphatase-based enzyme immunoassay," Anal Biochem. 171(2):266-70 (Jun. 1988).

Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis," Plant Mol Biol. 50(4-5):613-22 (2002).
Brachmann et al., "Designer deletion strains derived from *Saccharomyces cerevisiae* S288C: a useful set of strains and plasmids for PCR-mediated gene disruption and other applications," Yeast 14:115-32 (1998).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Carretero-Paulet et al., "Expression and Molecular Analysis of the *Arabidopsis* DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Ceunen & Geuns, "Steviol glycosides: chemical diversity, metabolism, and function," J. Nat. Prod. 76(6):1201-28 (Jun. 2013).
Chemler et al., "Biosynthesis of isoprenoids, polyunsaturated fatty acids and flavonoids in *Saccharomyces cerevisiae*," Microb Cell Fact. 5:20 (2006).
Chen et al., "Transferring a biosynthetic cycle into a productive *Escherichia coli* strain: large-scale synthesis of galactosides," J Am Chem Soc. 123(36):8866-7 (2001).
Chen et al., "MolProbity: all-atom structure validation for macromolecular crystallography," Acta Crystallogr D Biol Crystallogr 66(Pt 1):12-21 (Jan. 2010).
Chenna et al., "Multiple sequence alignment with the Clustal series of programs," Nucleic Acids Res. 31 (13):3497-500 (2003).
Chica et al., "Semi-rational approaches to engineering enzyme activity: combining the benefits of directed evolution and rational design," Curr Opin Biotechnol.16(4):378-84 (2005).
Chow & Palecek, "Enzyme encapsulation in permeabilized *Saccharomyces cerevisiae* cells," Biotechnol Prog. 20 (2):449-56 (2004).
Correa et al., "Genetic mapping of 1,3-beta-glucanase-encoding genes in *Saccharomyces cerevisiae*," Current Genet. 22(4):283-8 (1992).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Del Sorbo et al., "Fungal transporters involved in efflux of natural toxic compounds and fungicides," Fungal. Genet. Biol. 30(1)1-15 (Jun. 2000).
Diener et al., "*Arabidopsis* ALF5, a multidrug efflux transporter gene family member, confers resistance to toxins," Plant Cell 13(7):1625-38 (Jul. 2001).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28 (5):637-46 (2003).
Dubois & Stephenson, "Diterpenoid sweeteners. Synthesis and sensory evaluation of stevioside analogues with improved organoleptic properties," J. Med. Chem. 28(1):93-8 (Jan. 1985).
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).
Estrada De Martin et al., "Ice2p is important for the distribution and structure of the cortical ER network in *Saccharomyces cerevisiae*," J Cell Sci. 118(Pt 1):65-77 (Oct. 2006).

(56) References Cited

OTHER PUBLICATIONS

Fernandez et al., "Activation of chitin synthetase in permeabilized cells of a *Saccharomyces cerevisiae* mutant lacking proteinase B," J Bacteriol. 152(3):1255-64 (1982).
Nelson et al., "P450 superfamily: update on new sequences, gene mapping, accession numbers and nomenclature," Pharmacogenetics 6:1-42 (1996).
Niewman et al., "High-level production of amorpha-4,11-diene in a two-phase partitioning bioreactor of metabolically engineered *Escherichia coli*," Biotechnol Bioeng 95(4):684-91 (2006).
Niicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Niikaido & Takatsuk, "Mechanisms of RND multidrug efflux pumps," Biochim. Biophys. Acta. 1794(5):769-81 (May 2009).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Osmani et al., "Substrate specificity of plant UDP-dependent glycosyltransferases predicted from crystal structures and homology modeling," Phytochemistry 70(3):325-47 (2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Phys. 148 (3):1295-1308 (2008).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31 (6):532-7 (Dec. 2014).
Pompon et al., "Yeast Expression of Animal and Plant P450s in Optimized Redox Environments," Methods Enzymol 272:51-64 (1996).
Prelich, "Gene overexpression: uses, mechanisms, and interpretation," Genetics 190(3):841-54 (Mar. 2012).
Presecki & Vasic-Racki, "Production of L-malic acid by permeabilized cells of commercial *Saccharomyces* sp. strains," Biotechnol Lett. 27(23-24):1835-9 (2005).
Richman et al., "Functional genomics uncovers three glucosyltransferases involved in the synthesis of the major sweet glucosides of Stevia rebaudiana," Plant J. 41(1):56-67 (2005).
Riesmeier et al., "Isolation and characterization of a sucrose carrier cDNA from spinach by functional expression in yeast," EMBO J 11(13):4705-13 (1992).
Ro et al., "Production of the antimalarial drug precursor artemisinic acid in engineered yeast," Nature 440(7086):940-3 (2006).
Rodriguez-Concepcion & Boronat, "Elucidation of the methylerythritol phosphate pathway for isoprenoid biosynthesis in bacteria and plastids. A metabolic milestone achieved through genomics," Plant Physiol. 130 (3):1079-89 (2002).
Saenge et al., "Potential use of oleaginous red yeast *Rhodotorula glutinis* for the bioconversion of crude glycerol from biodiesel plant to lipids and carotenoids," Process Biochemistry 46(1):210-8 (Jan. 2011).

Shier JR et al., "The major facilitator superfamily," J. Mol. Microbiol. Biotechnol. 1(2):257-79 (Nov. 1999).
Saier et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coli*," J Biol Chem. 279(8):6613-9 (2004).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J Biol Chem. 280(2):899-906 (2005).
Schwab et al., Poster, "Watchmaker?—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol. 143 (3):212-23 (2007).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
Shao et al., "Enhanced production of alpha-galactosyl epitopes by metabolically engineered Pichia pastoris," Appl Environ Microbiol. 69(9):5238-42 (2003).
Shao et al., "Crystal structures of a multifunctional triterpene/flavonoid glycosyltransferase from Medicago truncatula," Plant Cell 17(11):3141-54 (2005).
Singh et al., "Compendium of Transgenic Crop Plants: Transgenic Sugar, Tuber and Fiber," Ed. Kole & Hall, Blackwell Publishing Ltd. pp. 97-115 (2008).
Son et al., "Production of flavonoid o-glucoside using sucrose synthase and flavonoid o-glucosyltransferase fusion protein," J Microbiol Biotechnol. 19(7):709-12 (2009).
Sonnhammer et al., "Pfam: multiple sequence alignments and HMM-profiles of protein domains," Nucleic Acids Res. 26(1):320-2 (1998).
Sonnhammer et al., "Pfam: a comprehensive database of protein domain families based on seed alignments," Proteins 28(3):405-420 (1997).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of Rebpure™ (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast *Kluyveromyces lactis*," FEMS Yeast Res. 6 (3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73 (13):4342-50 (2007).
Wallin, "Steviol Glycosides," Chem. Tech Assessment—63rd JECFA (2004).
Wallin, "Steviol Glycosides," Chem. Tech Assessment—69th JECFA (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583 (20):3303-9 (2009).
Yadav et al., "A review on the improvement of stevia [*Stevia rebaudiana* (Bertoni)]," Can J Plant Sci. 91:1-27 (2011).
Yao et al., "A genetic linkage map for Stevia rebaudiana," Genome 42:657-61 (1999).
Yazaki, "ABC transporters involved in the transport of plant secondary metabolites," FEBS Lett. 580(4):1183-91 Feb. 2006).

(56) References Cited

OTHER PUBLICATIONS

GenBank Accession No. Q269454.4, dated May 28, 2008 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).
GenBank Accession No. EU722415.1, dated Jun. 10, 2008 (2 pages).
GenBank Accession No. EU751291.1, dated Jun. 24, 2008 (2 pages).
GenBank Accession No. NM_116512, dated Jan. 22, 2014 (3 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. NP_194183, dated Jan. 22, 2014 (4 pages).
GenBank Accession No. NP_195399, dated Jan. 22, 2014 (3 pages).
GenBank Accession No. NP_197872.1, dated Jan. 22, 2014 (2 pages).
GenBank Accession No. Q9UVY5.1, dated Apr. 1, 2015 (3 pages).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
EBI Accession No. AAY05902, "Jerusalem artichoke in-chain hydroxylase CYP81B1" (1 page).
EBI Accession No. ABM86477, "Rice abiotic stress responsive polypeptide SEQ ID No. 4723" (1 page).
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
International Search Report issued by the International Searching Authority for International Application No. PCT/US2011/038967, dated Sep. 1, 2011 (10 pages).
Written Opinion of the International Searching Authority for International Application No. PCT/US2011/038967, dated Sep. 1, 2011 (12 pages).
International Preliminary Report on Patentability issued by the International Bureau for International Application No. PCT/US2011/038967, dated Dec. 4, 2012 (13 pages).
Third-Party Submission under 37 CFR 1.290 for U.S. Appl. No. 13/701,406, dated Mar. 22, 2013 (238 pages).
Patent Examination Report No. 1 issued by IP Australia for Australian Application No. 2011261394, dated Jan. 15, 2015.
Response to Patent Examination Report No. 1 issued by IP Australia for Australian Application No. 2011261394, dated Feb. 5, 2015.
Patent Examination Report No. 2 issued by IP Australia for Australian Application No. 2011261394, dated Feb. 23, 2015.
Notice of Acceptance issued by IP Australia for Australian Application No. 2011261394, dated Aug. 13, 2015 (pp. 1-3).
Office Action for Canadian Patent Application No. 2,802,627, dated Dec. 15, 2015 (pp. 1-5).
English Translation of First Office Action issued by the State Intellectual Property Office of People's Republic of China or CN Application No. 201180038475.4, dated Nov. 21, 2013.
English Translation on Response to First Office Action issued by the State Intellectual Property Office of People's Republic of China for CN Application No. 201180038475.4, dated Apr. 8, 2014.
English Translation of Second Office Action issued by the State Intellectual Property Office of People's Republic of China for Chinese Application No. 201180038475.4, dated Aug. 13, 2014.
English Translation of Response to Second Office Action issued by the State Intellectual Property Office of People's Republic of China for CN Application No. 201180038475.4, dated Oct. 28, 2014.
English Translation of Third Office Action issued by the State Intellectual Property Office of People's Republic of China for Chinese Application No. 201180038475.4, dated Mar. 3, 2015.
Notification of Grant of Patent Application issued by the State Intellectual Property Office of People's Republic of China for Chinese Application No. 201180038475.4, dated Dec. 1, 2015 (pp. 1-5). English translation included.
Extended European Search Report and Opinion issued by the European Patent Office for European Application No. 11790428.4, dated Dec. 20, 2013.
Response to Extended Search Report and Opinion issued by the European Patent Office for European Application No. 11790428.4, dated Jul. 16, 2014.
Communication pursuant to Rule 114(2) EPC for European Application No. 11790428.4, dated Nov. 28, 2014.
Examination Report issued by the European Patent Office for European Application No. 11790428.4, dated Dec. 1, 2014.
Response to Examination Report issued by the European Patent Office for European Application No. 11790428.4, dated Jun. 1, 2015 (16 pages).
English Translation of Notification of Reasons for Refusal of Japanese Application No. 2013-513355, dated Aug. 4, 2015 (pp. 1-10).
Examination Report issued by the Intellectual Property Corporation of Malaysia for Malaysian Application No. PI 2012005201, dated Jul. 31, 2014.
Response to Examination Report issued by the Intellectual Property Corporation of Malaysian for MY Application No. PI 2012005201, dated Sep. 18, 2014.
First Examination Report issued by the Intellectual Property Office of New Zealand for New Zealand Application No. 604915, dated Sep. 2, 2013.
Response to First Examination Report issued by the Intellectual Property Office of New Zealand for New Zealand Application No. 604915, dated Jan. 17, 2014.
Further Examination Report issued by the Intellectual Property Office of New Zealand for New Zealand Application No. 604915, dated Feb. 3, 2014.
Response to Further Examination Report issued by the Intellectual Property Office of New Zealand for New Zealand Application No. 604915, dated May 27, 2014.
Boer, "Strain and Process development for fermentative productive of Rebaudiosides", International Specialized Symposium of Yeasts, Abstract, (Jun. 2017).
"Kumar et al., ""A comprehensive analysis of fifteen genes of steviol glycosides biosynthesis pathwayin Stevia rebaudiana (Bertoni)"" Gene 492:276-84 (Epub Oct. 20, 2011)."
Liu et al., "Functional and biochemical characterization of *Escherichia coli* sugar efflux transporters" Journal of Biological Chemistry, 274(33):22977-84 (Aug. 1999).
Mahe et al., "The ATP Binding Cassette Transporters Pdr5 and Snq2 of *Saccharomyces cerevisiae* Can Mediate Transport of Steriods via in Vivo", JBC, 271(41):25167-25172. (Oct. 1996).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Starratt et al., "Rebaudioside F, a diterpene glycoside from Stevia redaudiana", Phytochemistry, 59(4):367-370 Abstract (Feb. 2002).
Sun & Vanderpool, "Regulation and Function of *Escherichia coli* Sugar Efflux Transporter A (SetA) during Glucose-Phosphate Stress" Journal of Bacteriology, 193(1):143-55 (Jan. 2011).
Yadav et al ., "Steviol Glycosides from Stevia: Biosynthesis Pathway Review and their Application in Foods and Medicine.", CritRev. 52(11):988-998 (2012).
Sequence alignment between the sequence of Uniprot database entry Q75183 version 31, updated Jul. 22, 2008 and SEQ ID No. 152 (from European Patent No. 2742142) as cited in Notice of Opposition against EP Application No. 12750513.9; dated Mar. 6, 2017; pp. 1-2.

(56) References Cited

OTHER PUBLICATIONS

Unitprot Accession No. Q75I83, dated Jul. 22, 2008 (pp. 1-2).
Unitprot Accession No. Q75I83, dated Jul. 5, 2004 (pp. 1-4).
Statement of Facts and Arguments in Support of Opposition for EP Application No. 12750513.9; dated Feb. 28, 2017; pp. 1-24.
Notice of Opposition against EP Application No. 12750513.9; dated Mar. 6, 2017, pp. 1-8.
Non-Final Office Action for U.S. Appl. No. 14/648,747, dated Mar. 23, 2017, pp. 1-20.
Third Party Observation in EP Application No. 13801569.8; dated Apr. 26, 2017, pp. 1-5.
International Preliminary Report on Patentability from the International Bureau for International Application PCTEP2015/068314; dated Feb. 14, 2017.
International Search Report and Written Opinion of the International Searching Authority for International Application No. PCT/EP2016/068259; dated Jan. 24, 2017, pp. 1-18.
Interntional Search Report and Written Opinion of International Search Authority for International Application No. PCTEP2016/080516; dated Mar. 15, 2017, pp. 1-21.
Intemational Search Report and Written Opinion of International Search Authority for International Application No. PCTEP2017/059028; dated Jun. 27, 2017, pp. 1-15.

\* cited by examiner
† cited by third party

FIGURE 2

| Rebaudioside M | Notation |
|---|---|
| 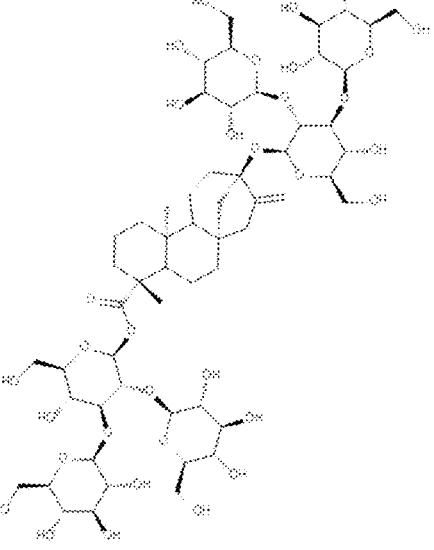 | Glc-(1->2)Glc<br><br>\|<br><br>(1->3)Glc<br><br><br><br>Glc-(1->2)Glc<br><br>(1->3)Glc |
| ChemAxon IUPAC name from structure [JCIUPACName() function]:<br><br>(2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl(1R,5R,9S,13R)-13-{[(2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl]oxy}-5,9-dimethyl-14-methylidenetetracyclo[11.2.1.0$^{1,10}$.0$^{4,9}$]hexadecane-5-carboxylate | |
| CambridgeSoft name from structure [CFW_CHEMICAL_NAME() function]:<br><br>(4R,6aR,9S,11bS)-(3R,4S,5R,6R)-5-hydroxy-6-(hydroxymethyl)-3-(((2S,3R,4S,5S,6R)-3,4,5-trihydroxy-6-(hydroxymethyl)tetrahydro-2H-pyran-2-yl)oxy)-4-(((3R,4S,5S,6R)-3,4,5-trihydroxy-6-(hydroxymethyl)tetrahydro-2H-pyran-2-yl)oxy)tetrahydro-2H-pyran-2-yl 9-(((3R,4S,5R,6R)-5-hydroxy-6-(hydroxymethyl)-3,4-bis(((3R,4S,5S,6R)-3,4,5-trihydroxy-6-(hydroxymethyl)tetrahydro-2H-pyran-2-yl)oxy)tetrahydro-2H-pyran-2-yl)oxy)-4,11b-dimethyl-8-methylenetetradecahydro-6a,9-methanocyclohepta[a]naphthalene-4-carboxylate | |

FIGURE 3

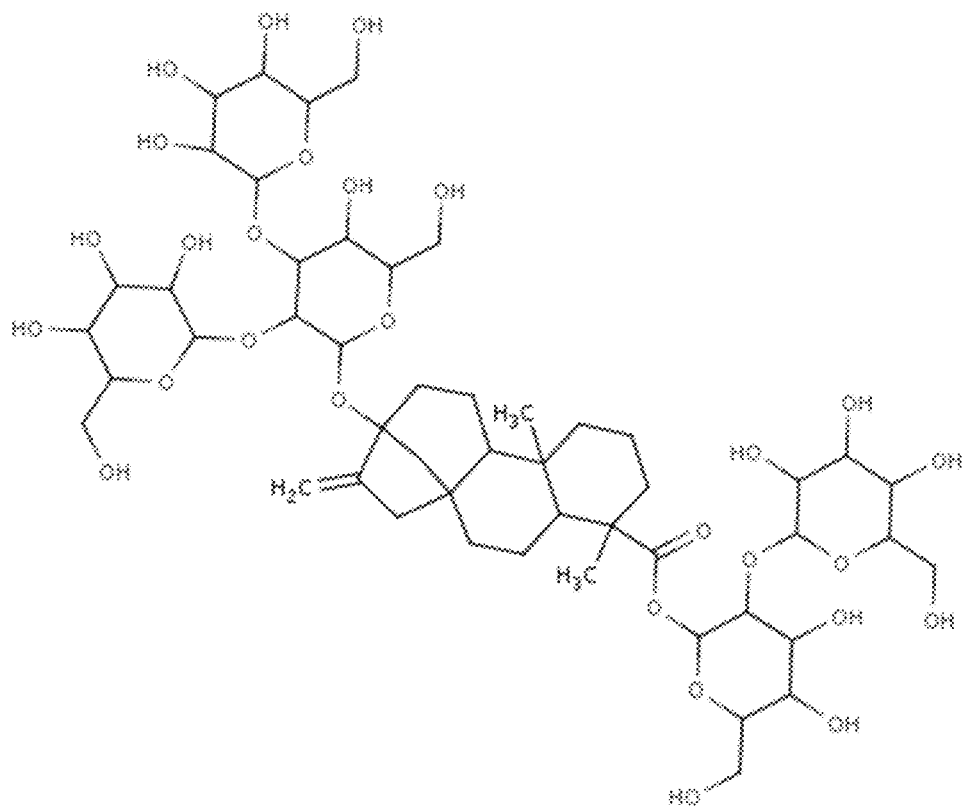

Rebaudioside D:
IUPAC Name: 4,5-dihydroxy-6-(hydroxymethyl)-3-{[3,4,5-trihydroxy-6-(hydroxymethyl)oxan-2-yl]oxy}oxan-2-yl 13-{[5-hydroxy-6-(hydroxymethyl)-3,4-bis({[3,4,5-trihydroxy-6-(hydroxymethyl)oxan-2-yl]oxy})oxan-2-yl]oxy}-5,9-dimethyl-14-methylidenetetracyclo[11.2.1.0$^{1,10}$.0$^{4,9}$]hexadecane-5-carboxylate Synonym: (4α)-13-[(O-β-D-Glucopyranosyl-(1→2)-O-[β-D-glucopyranosyl-(1→3)]-β-D-glucopyranosyl)oxy]kaur-16-en-18-oic acid 2-O-β-D-glucopyranosyl-β-D-glucopyranosyl ester Empirical Formula (Hill Notation) $C_{50}H_{80}O_{28}$
Average Molecular Weight 1129.15

FIGURE 8
FIGURE 8A
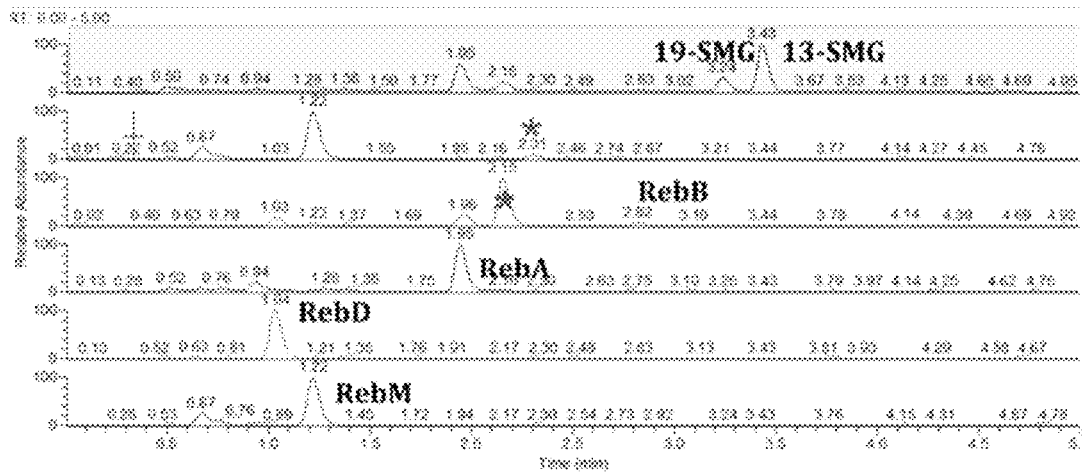
FIGURE 8B
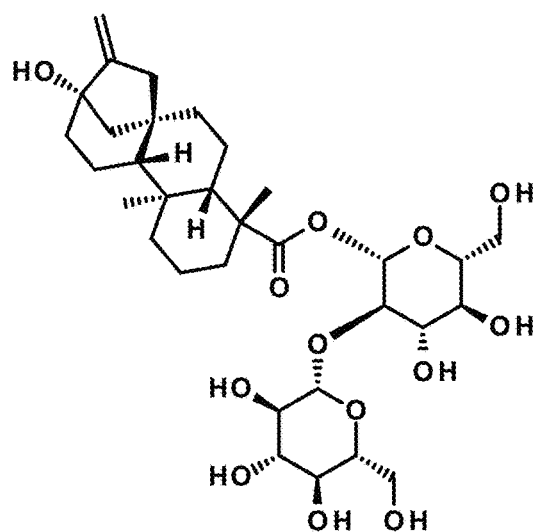

FIGURE 14

```
                1         11         21         31         41
76G1_1    --IILFPVPFQGHINPILQLANVLYSKGFSITIFHT FNKPKTSNYPHFT
76G1_2    RRIILFPVPFQGHINPILQLANVLYSKGFSITIFHTN FNKPKTSNYPH
76G1_3    RRIILFPVPFQGHINPILQLANVLYSKGFSITIFHTNF      SNYP
               51         61         71         81         91
76G1_1    FRFILDNDPQDERISNLPTHGP AGMRIPIINEHGAD LRRELELLMLAS
76G1_2       FILDNDPQDERISNLPTHGPLAGMRIPIINEHGADELRRELELLMLAS
76G1_3       FILDNDPQDERISNLPTHGPLAGMRIPIINE  A  L  ELELLM
              101        111        121        131        141
76G1_1    EEDEEVSCLITDALWYFAQSV  SLNLRRLVLMTSSLFNFHAHVSLPQFD
76G1_2    EEDE VSCLITD L          NLRRLVLMTSSLFNFHAHVSLPQFD
76G1_3    E  EEVSCLITDALWYFAQSVADS NLRRLVLMTSSLFNFHAHVSLPQFD
              151        161        171        181        191
76G1_1    ELGYLD  DKTRLEEQASGFPMLK K   AYS  QI  EILGKMIKQTK
76G1_2    ELGYLDPD   LEEQASGFPMLKVKD  SAYS WQILK  LGKMIKQT
76G1_3    ELGYLDPD  T LEEQASGFP  KVKDIKSA  NWQ  KEILGKMIKQTK
              201        211        221        231        241
76G1_1    ASSGVIWNSFKELEESELETVI   APSFLIP PKHLTASSSSLLDHDR
76G1_2    ASSGVIWNSFKELEESELETVIREIPAPSFLI    H TASSSSLLDHDR
76G1_3    ASSGVIWNSFKELEESELETVIREIPAPSFLI LP    TASSSSL   R
              251        261        271        281        291
76G1_1    T F WLDQQPPSSVLYVSFGSTSEVDEKDFLEIARGLVDSKQSFLWVVRP
76G1_2    TV  L QQPPSSVLYVSFG T  VDEKDFLEIARGLVDSKQSFLWVVR
76G1_3    T FQWLDQQPPSSVLYVSFGSTSEVDEKDFLEIARGLVDSKQSFLWVVRP
              301        311        321        331        341
76G1_1    G   S WVEPL DGFLGERG IVKWVPQQEVLAH   GAFWTHSGWNST
76G1_2    FVKGS  VEPLPD    GE  RIVKWVPQQEVLAHGAIGAFWTHSGWNST
76G1_3    GF     TWVEP PDG L ER RIVKWVPQQEVLAHGAIGAFWTHSGWNST
              351        361        371        381        391
76G1_1    LESVCEGVPMIFSDFGLDQPLNARYMSDVLKV-----------------
76G1_2    LESVCEGVPMIFSDFGLDQPLNARYMSDVLKVGVYLENGWERGEIANAIR
76G1_3    LESVCEGVPMIFSDFGLDQPLNARYMSDVLKVGVYLENGWERGEIANAIR
```

FIGURE 14 (cont'd)

```
            401       411       421       431       441
76G1_1      ------------------------KSSYESLESLVSY     -
76G1_2      RV DEEGEYIRQNARVLKQKADVSLMKG SSYESLESLVSYI  L
76G1_3      RV DEEGEYIRQNARVLKQKADVSLMKG SSYESLESLVSY   L
```

<1  2    >4 Å variance between models

SEQUENCE LISTING

```
<160> NUMBER OF SEQ ID NOS: 136

<210> SEQ ID NO 1
<211> LENGTH: 1616
<212> TYPE: DNA
<213> ORGANISM: Artificial Sequence
<220> FEATURE:
<223> OTHER INFORMATION: Synthetic oligonucleotide

<400> SEQUENCE: 1
cttgcgtgta aacgtcagtc aaacccaatg gaaaataaaa cggagaccac cgttcgccgg      60
cgccggagaa taatattatt cccggtacca tttcaaggcc acattaaccc aattcttcag     120
ctagccaatg tgttgtactc taaaggattc agtatcacca tctttcacac caacttcaac     180
aaacccaaaa catctaatta ccctcacttc actttcagat tcatcctcga caacgaccca     240
caagacgaac gcatttccaa tctaccgact catggtccgc tcgctggtat gcggattccg     300
attatcaacg aacacggagc tgacgaatta cgacgcgaac tggaactgtt gatgttagct     360
tctgaagaag atgaagaggt atcgtgttta atcacggatg ctctttggta cttcgcgcaa     420
tctgttgctg acagtcttaa cctccgacgg cttgttttga tgacaagcag cttgtttaat     480
tttcatgcac atgtttcact tcctcagttt gatgagcttg gttacctcga tcctgatgac     540
aaaacccgtt tggaagaaca agcgagtggg tttcctatgc taaagtgaa agacatcaag     600 tctgcgtatt cgaactggca aatactcaaa gagatattag ggaagatgat aaaacaaaca     660
aaagcatctt caggagtcat ctggaactca tttaaggaac tcgaagagtc tgagctcgaa     720
```

```
actgttatcc gtgagatccc ggctccaagt ttcttgatac cactccccaa gcatttgaca      780
gcctcttcca gcagcttact agaccacgat cgaaccgttt ttcaatggtt agaccaacaa      840
ccgccaagtt cggtactgta tgttagtttt ggtagtacta gtgaagtgga tgagaaagat      900
ttcttggaaa tagctcgtgg gttggttgat agcaagcagt cgtttttatg ggtggttcga      960
cctgggtttg tcaagggttc gacgtgggtc gaaccgttgc cagatgggtt cttgggtgaa     1020
agaggacgta ttgtgaaatg ggttccacag caagaagtgc tagctcatgg agcaataggc     1080
gcattctgga ctcatagcgg atggaactct acgttggaaa gcgtttgtga aggtgttcct     1140
atgatttttct cggattttgg gctcgatcaa ccgttgaatg ctagatacat gagtgatgtt     1200
ttgaaggtag gggtgtattt ggaaaatggg tgggaaagag gagagatagc aaatgcaata     1260
agaagagtta tggtggatga agaaggagaa tacattagac agaatgcaag agttttgaaa     1320
caaaaggcag atgtttcttt gatgaagggt ggttcgtctt acgaatcatt agagtctcta     1380
gtttcttaca tttcatcgtt gtaaataaca cgatgattaa tcaagcactt ggattgcatg     1440
ctagctgagt agctggtaat tgagttatt agaagcaaag actacttggt ttaaattaaa     1500
taaaggatgg ttgttggtta tgtgagctag tttatgttat gttttgtagg ctataaaagc     1560
cttcatatgt ttcttattgt ttctgtttct aaggtgaaaa aaatgctcgt ttttat        1616
```

<210> SEQ ID NO 2
<211> LENGTH: 458
<212> TYPE: PRT
<213> ORGANISM: Stevia rebaudiana

<400> SEQUENCE: 2

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
```

```
                    210                 215                 220
Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
            275                 280                 285

Glu Lys Asp Phe Leu Glu Ile Ala Arg Gly Leu Val Asp Ser Lys Gln
            290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
            370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
            450                 455

<210> SEQ ID NO 3
<211> LENGTH: 1446
<212> TYPE: DNA
<213> ORGANISM: Artificial Sequence
<220> FEATURE:
<223> OTHER INFORMATION: Synthetic oligonucleotide

<400> SEQUENCE: 3
atggatgcaa tggcaactac tgagaaaaag cctcatgtga tcttcattcc atttcctgca      60
caatctcaca taaaggcaat gctaaagtta gcacaactat tacaccataa gggattacag     120
ataactttcg tgaataccga cttcatccat aatcaattic tggaatctag tggccctcat     180
tgtttggacg gagccccagg gtttagattc gaaacaattc ctgacggtgt tcacattcc      240 ccagaggcct ccatcccaat aagagagagt ttactgaggt caatagaaac caacttttg      300 gatcgtttca ttgacttggt cacaaaactt ccagacccac caacttgcat aatctctgat     360
ggctttctgt cagtgtttac tatcgacgct gccaaaaagt tgggtatccc agttatgatg     420
tactggactc ttgctgcatg cggtttcatg ggtttctatc acatccattc tcttatcgaa     480
aagggttttg ctccactgaa agatgcatca tacttaacca acggctacct ggatactgtt     540
attgactggg taccaggtat ggaaggtata agacttaaag attttccttt ggattggtct     600
acagacctta tgataaagt attgatgttt actacagaag ctccacaaag atctcataag     660
```

```
gtttcacatc atatctttca cacctttgat gaattggaac catcaatcat caaaaccttg    720
tctctaagat acaatcatat ctacactatt ggtccattac aattacttct agatcaaatt    780
cctgaagaga aaaagcaaac tggtattaca tccttacacg gctactcttt agtgaaagag    840
gaaccagaat gttttcaatg ctacaaagt  aaagagccta attctgtggt ctacgtcaac    900
ttcggaagta caacagtcat gtccttggaa gatatgactg aatttggttg gggccttgct    960
aattcaaatc attactttct atggattatc aggtccaatt tggtaatagg ggaaaacgcc   1020
gtattacctc cagaattgga ggaacacatc aaaaagagag gtttcattgc ttcctggtgt   1080
tctcaggaaa aggtattgaa acatccttct gttggtggtt tccttactca ttgcggttgg   1140
ggctctacaa tcgaatcact aagtgcagga gttccaatga tttgttggcc atattcatgg   1200
gaccaactta caaattgtag gtatatctgt aaagagtggg aagttggatt agaaatggga   1260
acaaaggtta aacgtgatga agtgaaaaga ttggttcagg agttgatggg ggaaggtggc   1320
cacaagatga gaaacaaggc caaagattgg aaggaaaaag ccagaattgc tattgctcct   1380
aacgggtcat cctctctaaa cattgataag atggtcaaag agattacagt cttagccaga   1440
aactaa                                                              1446

<210> SEQ ID NO 4
<211> LENGTH: 707
<212> TYPE: PRT
<213> ORGANISM: Stevia rebaudiana

<400> SEQUENCE: 4

Met Gln Ser Asn Ser Val Lys Ile Ser Pro Leu Asp Leu Val Thr Ala
1               5                   10                  15

Leu Phe Ser Gly Lys Val Leu Asp Thr Ser Asn Ala Ser Glu Ser Gly
            20                  25                  30

Glu Ser Ala Met Leu Pro Thr Ile Ala Met Ile Met Glu Asn Arg Glu
        35                  40                  45

Leu Leu Met Ile Leu Thr Thr Ser Val Ala Val Leu Ile Gly Cys Val
    50                  55                  60

Val Val Leu Val Trp Arg Arg Ser Ser Thr Lys Lys Ser Ala Leu Glu
65                  70                  75                  80

Pro Pro Val Ile Val Pro Lys Arg Val Gln Glu Glu Glu Val Asp
                85                  90                  95

Asp Gly Lys Lys Lys Val Thr Val Phe Phe Gly Thr Gln Thr Gly Thr
            100                 105                 110

Ala Glu Gly Phe Ala Lys Ala Leu Val Glu Glu Ala Lys Ala Arg Tyr
        115                 120                 125

Glu Lys Ala Val Phe Lys Val Ile Asp Leu Asp Asp Tyr Ala Ala Asp
    130                 135                 140

Asp Asp Glu Tyr Glu Glu Lys Leu Lys Lys Glu Ser Leu Ala Phe Phe
145                 150                 155                 160

Phe Leu Ala Thr Tyr Gly Asp Gly Glu Pro Thr Asp Asn Ala Ala Arg
                165                 170                 175

Phe Tyr Lys Trp Phe Thr Glu Gly Asp Ala Lys Gly Glu Trp Leu Asn
            180                 185                 190

Lys Leu Gln Tyr Gly Val Phe Gly Leu Gly Asn Arg Gln Tyr Glu His
        195                 200                 205

Phe Asn Lys Ile Ala Lys Val Val Asp Asp Gly Leu Val Glu Gln Gly
    210                 215                 220

Ala Lys Arg Leu Val Pro Val Gly Leu Gly Asp Asp Asp Gln Cys Ile
```

-continued

```
            225                 230                 235                 240

Glu Asp Asp Phe Thr Ala Trp Lys Glu Leu Val Trp Pro Glu Leu Asp
                245                 250                 255

Gln Leu Leu Arg Asp Glu Asp Thr Thr Val Ala Thr Pro Tyr Thr
                260                 265                 270

Ala Ala Val Ala Glu Tyr Arg Val Phe His Glu Lys Pro Asp Ala
                275                 280                 285

Leu Ser Glu Asp Tyr Ser Tyr Thr Asn Gly His Ala Val His Asp Ala
        290                 295                 300

Gln His Pro Cys Arg Ser Asn Val Ala Val Lys Lys Glu Leu His Ser
305                 310                 315                 320

Pro Glu Ser Asp Arg Ser Cys Thr His Leu Glu Phe Asp Ile Ser Asn
                325                 330                 335

Thr Gly Leu Ser Tyr Glu Thr Gly Asp His Val Gly Val Tyr Cys Glu
                340                 345                 350

Asn Leu Ser Glu Val Val Asn Asp Ala Glu Arg Leu Val Gly Leu Pro
        355                 360                 365

Pro Asp Thr Tyr Ser Ser Ile His Thr Asp Ser Glu Asp Gly Ser Pro
        370                 375                 380

Leu Gly Gly Ala Ser Leu Pro Pro Phe Pro Pro Cys Thr Leu Arg
385                 390                 395                 400

Lys Ala Leu Thr Cys Tyr Ala Asp Val Leu Ser Ser Pro Lys Lys Ser
                405                 410                 415

Ala Leu Leu Ala Leu Ala Ala His Ala Thr Asp Pro Ser Glu Ala Asp
                420                 425                 430

Arg Leu Lys Phe Leu Ala Ser Pro Ala Gly Lys Asp Glu Tyr Ser Gln
                435                 440                 445

Trp Ile Val Ala Ser Gln Arg Ser Leu Leu Glu Val Met Glu Ala Phe
                450                 455                 460

Pro Ser Ala Lys Pro Ser Leu Gly Val Phe Phe Ala Ser Val Ala Pro
465                 470                 475                 480

Arg Leu Gln Pro Arg Tyr Tyr Ser Ile Ser Ser Ser Pro Lys Met Ala
                485                 490                 495

Pro Asp Arg Ile His Val Thr Cys Ala Leu Val Tyr Glu Lys Thr Pro
                500                 505                 510

Ala Gly Arg Ile His Lys Gly Val Cys Ser Thr Trp Met Lys Asn Ala
                515                 520                 525

Val Pro Met Thr Glu Ser Gln Asp Cys Ser Trp Ala Pro Ile Tyr Val
        530                 535                 540

Arg Thr Ser Asn Phe Arg Leu Pro Ser Asp Pro Lys Val Pro Val Ile
545                 550                 555                 560

Met Ile Gly Pro Gly Thr Gly Leu Ala Pro Phe Arg Gly Phe Leu Gln
                565                 570                 575

Glu Arg Leu Ala Leu Lys Glu Ala Gly Thr Asp Leu Gly Leu Ser Ile
                580                 585                 590

Leu Phe Phe Gly Cys Arg Asn Arg Lys Val Asp Phe Ile Tyr Glu Asn
                595                 600                 605

Glu Leu Asn Asn Phe Val Glu Thr Gly Ala Leu Ser Glu Leu Ile Val
                610                 615                 620

Ala Phe Ser Arg Glu Gly Pro Thr Lys Glu Tyr Val Gln His Lys Met
625                 630                 635                 640

Ser Glu Lys Ala Ser Asp Ile Trp Asn Leu Leu Ser Glu Gly Ala Tyr
                645                 650                 655
```

Leu Tyr Val Cys Gly Asp Ala Lys Gly Met Ala Lys Asp Val His Arg
            660                 665                 670

Thr Leu His Thr Ile Val Gln Glu Gln Gly Ser Leu Asp Ser Ser Lys
        675                 680                 685

Ala Glu Leu Tyr Val Lys Asn Leu Gln Met Ser Gly Arg Tyr Leu Arg
    690                 695                 700

Asp Val Trp
705

<210> SEQ ID NO 5
<211> LENGTH: 2124
<212> TYPE: DNA
<213> ORGANISM: Artificial Sequence
<220> FEATURE:
<223> OTHER INFORMATION: Synthetic oligonucleotide

<400> SEQUENCE: 5

| | | | | | |
|---|---|---|---|---|---|
| atgcaatcta | actccgtgaa | gatttcgccg | cttgatctgg | taactgcgct | gtttagcggc | 60 |
| aaggttttgg | acacatcgaa | cgcatcggaa | tcgggagaat | ctgctatgct | gccgactata | 120 |
| gcgatgatta | tggagaatcg | tgagctgttg | atgatactca | aacgtcggt | tgctgtattg | 180 |
| atcggatgcg | ttgtcgtttt | ggtgtggcgg | agatcgtcta | cgaagaagtc | ggcgttggag | 240 |
| ccaccggtga | ttgtggttcc | gaagagagtg | caagaggagg | aagttgatga | tggtaagaag | 300 |
| aaagttacgg | ttttcttcgg | cacccaaact | ggaacagctg | aaggcttcgc | taaggcactt | 360 |
| gttgaggaag | ctaaagctcg | atatgaaaag | gctgtcttta | agtaattga | tttggatgat | 420 |
| tatgctgctg | atgacgatga | gtatgaggag | aaactaaaga | aagaatcttt | ggccttttc | 480 |
| ttttggcta | cgtatggaga | tggtgagcca | acagataatg | ctgccagatt | ttataaatgg | 540 |
| tttactgagg | gagatgcgaa | aggagaatgg | cttaataagc | ttcaatatgg | agtatttggt | 600 |
| ttgggtaaca | gacaatatga | acattttaac | aagatcgcaa | aagtggttga | tgatggtctt | 660 |
| gtagaacagg | gtgcaaagcg | tcttgttcct | gttggacttg | agatgatga | tcaatgtatt | 720 |
| gaagatgact | tcaccgcatg | gaaagagtta | gtatggccgg | agttggatca | attacttcgt | 780 |
| gatgaggatg | acacaactgt | tgctactcca | tacacagctg | ctgttgcaga | atatcgcgtt | 840 |
| gtttttcatg | aaaaaccaga | cgcgcttttct | gaagattata | gttatacaaa | tggccatgct | 900 |
| gttcatgatg | ctcaacatcc | atgcagatcc | aacgtgctg | tcaaaaagga | acttcatagt | 960 |
| cctgaatctg | accggtcttg | cactcatctt | gaatttgaca | tctcgaacac | cggactatca | 1020 |
| tatgaaactg | gggaccatgt | tggagtttac | tgtgaaaact | tgagtgaagt | tgtgaatgat | 1080 |
| gctgaaagat | tagtaggatt | accaccagac | acttactcct | ccatccacac | tgatagtgaa | 1140 |
| gacgggtcgc | cacttggcgg | agcctcattg | ccgcctcctt | tcccgccatg | cactttaagg | 1200 |
| aaagcattga | cgtgttatgc | tgatgttttg | agttctccca | gaagtcggc | tttgcttgca | 1260 |
| ctagctgctc | atgccaccga | tcccagtgaa | gctgatagat | tgaaatttct | tgcatccccc | 1320 |
| gccggaaagg | atgaatattc | tcaatggata | gttgcaagcc | aaagaagtct | ccttgaagtc | 1380 |
| atggaagcat | tcccgtcagc | taagccttca | cttggtgttt | tctttgcatc | tgttgccccg | 1440 |
| cgcttacaac | caagatacta | ctctatttct | tcctcaccca | gatggcacc | ggataggatt | 1500 |
| catgttacat | gtgcattagt | ctatgagaaa | acacctgcag | ccgcatcca | caaggagtt | 1560 |
| tgttcaactt | ggatgaagaa | cgcagtgcct | atgaccgaga | gtcaagattg | cagttgggcc | 1620 |
| ccaatatacg | tccgaacatc | caatttcaga | ctaccatctg | accctaaggt | cccggttatc | 1680 |

| atgattggac ctggcactgg tttggctcct tttagaggtt tccttcaaga gcggttagct | 1740 |
| ttaaaggaag ccggaactga cctcggttta tccattttat tcttcggatg taggaatcgc | 1800 |
| aaagtggatt tcatatatga aaacgagctt aacaactttg tggagactgg tgctctttct | 1860 |
| gagcttattg ttgctttctc ccgtgaaggc ccgactaagg aatatgtgca acacaagatg | 1920 |
| agtgagaagg cttcggatat ctggaacttg ctttctgaag gagcatattt atacgtatgt | 1980 |
| ggtgatgcca aaggcatggc caaagatgta catcgaaccc tccacacaat tgtgcaagaa | 2040 |
| cagggatctc ttgactcgtc aaaggcagaa ctctacgtga agaatctaca aatgtcagga | 2100 |
| agatacctcc gtgacgtttg gtaa | 2124 |

<210> SEQ ID NO 6
<211> LENGTH: 2358
<212> TYPE: DNA
<213> ORGANISM: Artificial Sequence
<220> FEATURE:
<223> OTHER INFORMATION: Synthetic oligonucleotide

<400> SEQUENCE: 6

| atgtctatta atttgagatc ttccggttgt agctccccaa taagcgcaac tttggaaagg | 60 |
| ggtctagact ctgaagttca acaagagca acaatgtat cttttgagca gaccaaagag | 120 |
| aagatcagga aaatgcttga aaggtcgag ttgagcgtga gtgcctatga cactagttgg | 180 |
| gtagctatgt tcccatcacc atccagtcaa aacgcacctc ttttcccaca gtgcgtcaaa | 240 |
| tggctacttg ataatcaaca tgaggacggc tcttggggat tggataacca cgaccatcag | 300 |
| agcttaaaga aagatgtgtt gtcatccaca ttagcctcta tcctagctct taagaaatgg | 360 |
| ggaataggcg aaagacagat caataagggt ctacagttca ttgaattaaa ctctgcacta | 420 |
| gttaccgatg aaactataca aaaacctaca ggtttcgaca tcattttttcc aggaatgatt | 480 |
| aagtacgcca gggaccttaa tttgaccata cctcttggct cagaagtagt cgacgatatg | 540 |
| atcaggaaaa gagatctaga cttaaagtgt gatagcgaga aattcagcaa aggtagagag | 600 |
| gcttatcttg cctatgttct tgaaggaact aggaacttga aggactggga cttaattgtg | 660 |
| aaatatcaga gaaagaacgg tagtctattt gatagtccag ctacaaccgc cgcagctttc | 720 |
| actcaatttg gcaatgacgg ttgcttgagg tacttatgtt cacttttaca gaaattcgag | 780 |
| gccgcagtgc ctagtgtata tccatttgat caatacgcta gattaagcat aatcgtcact | 840 |
| ttagaatcat tgggaattga cagagatttc aagactgaga taaaaagcat attggatgag | 900 |
| acctataggc actggcttag aggtgacgaa gaaatttgcc tagatttggc cacatgtgca | 960 |
| cttgctttta ggttgctttt agcccacggc tatgacgtgt catacgatcc tctaaagcca | 1020 |
| tttgcagagg aatctggttt cagcgatacc cttgagggat atgttaaaaa cacctttttcc | 1080 |
| gtattagagc ttttcaaggc tgcccaaagt taccctcatg agagtgcttt gaaaaagcag | 1140 |
| tgttgctgga caaaacaata tctagaaatg gaactaagtt catgggttaa acaagcgtt | 1200 |
| agggacaagt acttgaaaaa ggaagtggag gatgcttttgg catttccatc atatgcctct | 1260 |
| ttagaaagaa gtgaccacag aaggaaaatt cttaatggct cagcagttga aaacacaaga | 1320 |
| gtaaccaaga cctcttacag gttgcataat atatgtacat cagatatctt aaaacttgct | 1380 |
| gtcgacgatt tcaacttttg ccaatctatt catagagagg aaatggaaag attggataga | 1440 |
| tggatagtgg agaatagact acaggaatta aagttcgcca gacaaaaatt ggcttactgt | 1500 |
| tactttagtg gcgctgccac actattctct ccagaattgt ctgacgcaag gatctcatgg | 1560 |
| gctaagggag gtgttctaac cacagtagtc gatgactttt ttgatgttgg cggtagtaaa | 1620 |

```
gaagagcttg agaacttaat tcacttggtg gaaaagtggg atcttaatgg agttcctgaa    1680
tactcttcag agcatgtaga aataattttc tctgtcctaa gagacactat cttagaaacc    1740
ggtgataaag cctttacata tcagggcaga aacgttactc accatattgt gaaaatatgg    1800
ttggacttac ttaagagcat gctaagggag gctgaatggt ccagtgacaa atcaacccca    1860
tctttggaag attacatgga gaatgcctat atcagcttcg cattaggtcc tattgtattg    1920
ccagctacat accttatagg acctccacta cctgaaaaga ctgtcgactc ccaccaatat    1980
aatcaattat acaaattggt tagtaccatg ggtagactat taaacgatat ccagggcttt    2040
aagagggaat cagccgaggg aaaacttaat gcagtgtctc tacatatgaa gcatgaaaga    2100
gacaacagaa gcaaagaggt tattatagaa tccatgaaag gattggctga aggaaaaga    2160 gaggaattac acaaacttgt actagaagag aaaggtagtg tcgttccaag agaatgcaag    2220
gaagcctcct taaaaatgtc aaaagtgttg aaccttttt ataggaagga tgatggcttc    2280
acatctaacg acttgatgag ccttgtgaaa tccgtcatct acgagcctgt ttcacttcaa    2340
aaggagagtc taacttga                                                  2358
```

<210> SEQ ID NO 7
<211> LENGTH: 785
<212> TYPE: PRT
<213> ORGANISM: Arabidopsis thaliana

<400> SEQUENCE: 7

```
Met Ser Ile Asn Leu Arg Ser Ser Gly Cys Ser Ser Pro Ile Ser Ala
1               5                   10                  15

Thr Leu Glu Arg Arg Leu Asp Ser Glu Val Gln Thr Arg Ala Asn Asn
            20                  25                  30

Val Ser Phe Glu Gln Thr Lys Glu Lys Ile Arg Lys Met Leu Glu Lys
        35                  40                  45

Val Glu Leu Ser Val Ser Ala Tyr Asp Thr Ser Trp Val Ala Met Val
    50                  55                  60

Pro Ser Pro Ser Gln Asn Ala Pro Leu Phe Pro Gln Cys Val Lys
65                  70                  75                  80

Trp Leu Leu Asp Asn Gln His Glu Asp Gly Ser Trp Gly Leu Asp Asn
                85                  90                  95

His Asp His Gln Ser Leu Lys Lys Asp Val Leu Ser Thr Leu Ala
            100                 105                 110

Ser Ile Leu Ala Leu Lys Lys Trp Gly Ile Gly Glu Arg Gln Ile Asn
        115                 120                 125

Lys Gly Leu Gln Phe Ile Glu Leu Asn Ser Ala Leu Val Thr Asp Glu
    130                 135                 140

Thr Ile Gln Lys Pro Thr Gly Phe Asp Ile Ile Phe Pro Gly Met Ile
145                 150                 155                 160

Lys Tyr Ala Arg Asp Leu Asn Leu Thr Ile Pro Leu Gly Ser Glu Val
                165                 170                 175

Val Asp Asp Met Ile Arg Lys Arg Asp Leu Asp Leu Lys Cys Asp Ser
            180                 185                 190

Glu Lys Phe Ser Lys Gly Arg Glu Ala Tyr Leu Ala Tyr Val Leu Glu
        195                 200                 205

Gly Thr Arg Asn Leu Lys Asp Trp Asp Leu Ile Val Lys Tyr Gln Arg
    210                 215                 220

Lys Asn Gly Ser Leu Phe Asp Ser Pro Ala Thr Ala Ala Ala Phe
225                 230                 235                 240
```

```
Thr Gln Phe Gly Asn Asp Gly Cys Leu Arg Tyr Leu Cys Ser Leu Leu
                245                 250                 255

Gln Lys Phe Glu Ala Ala Val Pro Ser Val Tyr Pro Phe Asp Gln Tyr
            260                 265                 270

Ala Arg Leu Ser Ile Ile Val Thr Leu Glu Ser Leu Gly Ile Asp Arg
            275                 280                 285

Asp Phe Lys Thr Glu Ile Lys Ser Ile Leu Asp Glu Thr Tyr Arg Tyr
            290                 295                 300

Trp Leu Arg Gly Asp Glu Glu Ile Cys Leu Asp Leu Ala Thr Cys Ala
305                 310                 315                 320

Leu Ala Phe Arg Leu Leu Ala His Gly Tyr Asp Val Ser Tyr Asp
            325                 330                 335

Pro Leu Lys Pro Phe Ala Glu Glu Ser Gly Phe Ser Asp Thr Leu Glu
            340                 345                 350

Gly Tyr Val Lys Asn Thr Phe Ser Val Leu Glu Leu Phe Lys Ala Ala
            355                 360                 365

Gln Ser Tyr Pro His Glu Ser Ala Leu Lys Gln Cys Cys Trp Thr
            370                 375                 380

Lys Gln Tyr Leu Glu Met Glu Leu Ser Ser Trp Val Leu Thr Ser Val
385                 390                 395                 400

Arg Asp Lys Tyr Leu Lys Lys Glu Val Glu Asp Ala Leu Ala Phe Pro
            405                 410                 415

Ser Tyr Ala Ser Leu Glu Arg Ser Asp His Arg Lys Ile Leu Asn
            420                 425                 430

Gly Ser Ala Val Glu Asn Thr Arg Val Thr Lys Thr Ser Tyr Arg Leu
            435                 440                 445

His Asn Ile Cys Thr Ser Asp Ile Leu Lys Leu Ala Val Asp Asp Phe
            450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
            485                 490                 495

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Gly Val Leu Thr Thr
            515                 520                 525

Val Val Asp Asp Phe Phe Asp Val Gly Gly Ser Lys Glu Glu Leu Glu
            530                 535                 540

Asn Leu Ile His Leu Val Glu Lys Trp Asp Leu Asn Gly Val Pro Glu
545                 550                 555                 560

Tyr Ser Ser Glu His Val Glu Ile Phe Ser Val Leu Arg Asp Thr
            565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
            595                 600                 605

Arg Glu Ala Glu Trp Ser Ser Asp Lys Ser Thr Pro Ser Leu Glu Asp
            610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
            645                 650                 655
```

```
Ser His Gln Tyr Asn Gln Leu Tyr Lys Leu Val Ser Thr Met Gly Arg
            660                 665                 670
Leu Leu Asn Asp Ile Gln Gly Phe Lys Arg Glu Ser Ala Glu Gly Lys
        675                 680                 685
Leu Asn Ala Val Ser Leu His Met Lys His Glu Arg Asp Asn Arg Ser
    690                 695                 700
Lys Glu Val Ile Ile Glu Ser Met Lys Gly Leu Ala Glu Arg Lys Arg
705                 710                 715                 720
Glu Glu Leu His Lys Leu Val Leu Glu Lys Gly Ser Val Val Pro
                725                 730                 735
Arg Glu Cys Lys Glu Ala Phe Leu Lys Met Ser Lys Val Leu Asn Leu
            740                 745                 750
Phe Tyr Arg Lys Asp Asp Gly Phe Thr Ser Asn Asp Leu Met Ser Leu
        755                 760                 765
Val Lys Ser Val Ile Tyr Glu Pro Val Ser Leu Gln Glu Glu Ser Leu
    770                 775                 780
Thr
785

<210> SEQ ID NO 8
<211> LENGTH: 1503
<212> TYPE: DNA
<213> ORGANISM: Artificial Sequence
<220> FEATURE:
<223> OTHER INFORMATION: Synthetic oligonucleotide

<400> SEQUENCE: 8
atggaagcct cttacctata catttctatt ttgcttttac tggcatcata cctgttcacc      60
actcaactta aaggaagag cgctaatcta ccaccaaccg tgtttccatc aataccaatc     120
attggacact tatacttact caaaaagcct ctttatagaa ctttagcaaa aattgccgct     180
aagtacggac caatactgca attcaactc ggctacagac gtgttctggt gatttcctca     240
ccatcagcag cagaagagtg ctttaccaat aacgatgtaa tcttcgcaaa tagacctaag     300
acattgtttg gcaaaatagt gggtggaaca tcccttggca gtttatccta cggcgatcaa     360
tggcgtaatc taaggagagt agcttctatc gaaatcctat cagttcatag gttgaacgaa     420
tttcatgata tcagagtgga tgagaacaga ttgttaatta gaaacttag aagttcatct     480 tctcctgtta ctcttataac agtcttttat gctctaacat gaacgtcat tatgagaatg     540 atctctggca aagatatttt cgacagtggg gatagagaat tggaggagga aggtaagaga     600
tttcgagaaa tcttagacga aacgttgctt ctagccggtg cttctaatgt tggcgactac     660
ttaccaatat tgaactggtt gggagttaag tctcttgaaa agaaattgat cgctttgcag     720
aaaaagagag atgactttt ccagggtttg attgaacagg ttagaaaatc tcgtggtgct     780
aaagtaggca aagtagaaa aacgatgatc gaactcttat tatctttgca agagtcagaa     840
cctgagtact atacagatgc tatgataaga tcttttgtcc taggtctgct ggctgcaggt     900
agtgatactt cagcgggcac tatggaatgg gccatgagct actggtcaa tcacccacat     960 gtattgaaga agctcaagc tgaaatcgat agagttatcg gtaataacag attgattgac    1020
gagtcagaca ttggaaatat cccttacatc gggtgtatta tcaatgaaac tctaagactc    1080
tatccagcag ggccattgtt gttcccacat gaaagttctg ccgactgcgt tatttccggt    1140
tacaatatac ctagaggtac aatgttaatc gtaaaccaat gggcgattca tcacgatcct    1200
aaagtctggg atgatcctga aacctttaaa cctgaaagat ttcaaggatt agaaggaact    1260
```

-continued

```
agagatggtt tcaaacttat gccattcggt tctgggagaa gaggatgtcc aggtgaaggt    1320
ttggcaataa ggctgttagg gatgacacta ggctcagtga tccaatgttt tgattgggag    1380
agagtaggag atgagatggt tgacatgaca gaaggtttgg gtgtcacact tcctaaggcc    1440
gttccattag ttgccaaatg taagccacgt tccgaaatga ctaatctcct atccgaactt    1500
taa                                                                  1503

<210> SEQ ID NO 9
<211> LENGTH: 712
<212> TYPE: PRT
<213> ORGANISM: Arabidopsis thaliana

<400> SEQUENCE: 9

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Asn Ala
                20                  25                  30

Ser Ala Tyr Glu Ser Val Ala Ala Glu Leu Ser Ser Met Leu Ile Glu
            35                  40                  45

Asn Arg Gln Phe Ala Met Ile Val Thr Thr Ser Ile Ala Val Leu Ile
50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Thr Leu Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
```

```
                    325                 330                 335
Phe Asp Ile Ala Gly Ser Gly Leu Thr Met Lys Leu Gly Asp His Val
                340                 345                 350
Gly Val Leu Cys Asp Asn Leu Ser Glu Thr Val Asp Glu Ala Leu Arg
                355                 360                 365
Leu Leu Asp Met Ser Pro Asp Thr Tyr Phe Ser Leu His Ala Glu Lys
            370                 375                 380
Glu Asp Gly Thr Pro Ile Ser Ser Ser Leu Pro Pro Phe Pro Pro
385                 390                 395                 400
Cys Asn Leu Arg Thr Ala Leu Thr Arg Tyr Ala Cys Leu Leu Ser Ser
                405                 410                 415
Pro Lys Lys Ser Ala Leu Val Ala Leu Ala Ala His Ala Ser Asp Pro
                420                 425                 430
Thr Glu Ala Glu Arg Leu Lys His Leu Ala Ser Pro Ala Gly Lys Asp
                435                 440                 445
Glu Tyr Ser Lys Trp Val Val Glu Ser Gln Arg Ser Leu Leu Glu Val
            450                 455                 460
Met Ala Glu Phe Pro Ser Ala Lys Pro Pro Leu Gly Val Phe Phe Ala
465                 470                 475                 480
Gly Val Ala Pro Arg Leu Gln Pro Arg Phe Tyr Ser Ile Ser Ser Ser
                485                 490                 495
Pro Lys Ile Ala Glu Thr Arg Ile His Val Thr Cys Ala Leu Val Tyr
                500                 505                 510
Glu Lys Met Pro Thr Gly Arg Ile His Lys Gly Val Cys Ser Thr Trp
            515                 520                 525
Met Lys Asn Ala Val Pro Tyr Glu Lys Ser Glu Lys Leu Phe Leu Gly
            530                 535                 540
Arg Pro Ile Phe Val Arg Gln Ser Asn Phe Lys Leu Pro Ser Asp Ser
545                 550                 555                 560
Lys Val Pro Ile Ile Met Ile Gly Pro Gly Thr Gly Leu Ala Pro Phe
                565                 570                 575
Arg Gly Phe Leu Gln Glu Arg Leu Ala Leu Val Glu Ser Gly Val Glu
                580                 585                 590
Leu Gly Pro Ser Val Leu Phe Phe Gly Cys Arg Asn Arg Arg Met Asp
                595                 600                 605
Phe Ile Tyr Glu Glu Glu Leu Gln Arg Phe Val Glu Ser Gly Ala Leu
            610                 615                 620
Ala Glu Leu Ser Val Ala Phe Ser Arg Glu Gly Pro Thr Lys Glu Tyr
625                 630                 635                 640
Val Gln His Lys Met Met Asp Lys Ala Ser Asp Ile Trp Asn Met Ile
                645                 650                 655
Ser Gln Gly Ala Tyr Leu Tyr Val Cys Gly Asp Ala Lys Gly Met Ala
                660                 665                 670
Arg Asp Val His Arg Ser Leu His Thr Ile Ala Gln Glu Gln Gly Ser
                675                 680                 685
Met Asp Ser Thr Lys Ala Glu Gly Phe Val Lys Asn Leu Gln Thr Ser
            690                 695                 700
Gly Arg Tyr Leu Arg Asp Val Trp
705                 710

<210> SEQ ID NO 10
<211> LENGTH: 2139
<212> TYPE: DNA
<213> ORGANISM: Artificial Sequence
```

<220> FEATURE:
<223> OTHER INFORMATION: Synthetic oligonucleotide

<400> SEQUENCE: 10

```
atgtcttcct cttcctcttc cagtacctct atgattgatt tgatggctgc tattattaaa      60
ggtgaaccag ttatcgtctc cgacccagca aatgcctctg cttatgaatc agttgctgca     120
gaattgtctt caatgttgat cgaaaacaga caattcgcca tgatcgtaac tacatcaatc     180
gctgttttga tcggttgtat tgtcatgttg gtatggagaa gatccggtag tggtaattct     240
aaaagagtcg aacctttgaa accattagta attaagccaa gagaagaaga aatagatgac     300
ggtagaaaga aagttacaat attttttcggt acccaaactg gtacagctga aggttttgca    360
aaagccttag gtgaagaagc taaggcaaga tacgaaaaga ctagattcaa gatagtcgat     420
ttggatgact atgccgctga tgacgatgaa tacgaagaaa agttgaagaa agaagatgtt     480
gcatttttct ttttggcaac ctatggtgac ggtgaaccaa ctgacaatgc agccagattc     540
tacaaatggt ttacagaggg taatgatcgt ggtgaatggt tgaaaaactt aaagtacggt     600
gttttcggtt tgggtaacag acaatacgaa catttcaaca aagttgcaaa ggttgtcgac     660
gatatttttgg tcgaacaagg tgctcaaaga ttagtccaag taggtttggg tgacgatgac    720
caatgtatag aagatgactt tactgcctgg agagaagctt tgtggcctga attagacaca     780
atcttgagag aagaaggtga caccgccgtt gctaccccat atactgctgc agtattagaa     840
tacagagttt ccatccatga tagtgaagac gcaaagttta tgatatcac tttggccaat      900
ggtaacggtt atacagtttt cgatgcacaa caccttaca aagctaacgt tgcagtcaag      960
agagaattac atacaccaga atccgacaga agttgtatac acttggaatt tgatatcgct    1020
ggttccggtt taaccatgaa gttgggtgac catgtaggtg ttttatgcga caatttgtct    1080
gaaactgttg atgaagcatt gagattgttg gatatgtccc ctgacactta ttttagtttg    1140
cacgctgaaa aagaagatgg tacaccaatt tccagttctt taccacctcc attccctcca    1200
tgtaacttaa gaacagcctt gaccagatac gcttgcttgt tatcatcccc taaaaagtcc    1260
gccttggttg ctttagccgc tcatgctagt gatcctactg aagcagaaag attgaaacac    1320
ttagcatctc cagccggtaa agatgaatat tcaaagtggg tagttgaatc tcaaagatca    1380
ttgttagaag ttatggcaga atttccatct gccaagcctc cattaggtgt cttctttgct    1440
ggtgtagcac ctagattgca accaagattc tactcaatca gttcttcacc taagatcgct    1500
gaaactagaa ttcatgttac atgtgcatta gtctacgaaa agatgccaac cggtagaatt    1560
cacaagggtg tatgctctac ttggatgaaa aatgctgttc cttacgaaaa atcagaaaag    1620
ttgttcttag gtagaccaat cttcgtaaga caatcaaact tcaagttgcc ttctgattca    1680
aaggttccaa taatcatgat aggtcctggt acaggtttag ccccattcag aggtttcttg    1740
caagaaagat tggctttagt tgaatctggt gtcgaattag gtccttcagt tttgttcttt    1800
ggttgtagaa acagaagaat ggatttcatc tatgaagaag aattgcaaag attcgtcgaa    1860
tctggtgcat tggccgaatt atctgtagct ttttcaagag aaggtccaac taaggaatac    1920
gttcaacata agatgatgga taaggcatcc gacatatgga acatgatcag tcaaggtgct    1980
tatttgtacg tttgcggtga cgcaaagggt atggccagag atgtccatag atctttgcac    2040
acaattgctc aagaacaagg ttccatggat agtaccaaag ctgaaggttt cgtaaagaac    2100
ttacaaactt ccggtagata cttgagagat gtctggtga                           2139
```

<210> SEQ ID NO 11

```
<211> LENGTH: 500
<212> TYPE: PRT
<213> ORGANISM: Stevia rebaudiana

<400> SEQUENCE: 11

Met Glu Ala Ser Tyr Leu Tyr Ile Ser Ile Leu Leu Leu Ala Ser
1               5                   10                  15

Tyr Leu Phe Thr Thr Gln Leu Arg Arg Lys Ser Ala Asn Leu Pro Pro
            20                  25                  30

Thr Val Phe Pro Ser Ile Pro Ile Gly His Leu Tyr Leu Leu Lys
        35                  40                  45

Lys Pro Leu Tyr Arg Thr Leu Ala Lys Ile Ala Ala Lys Tyr Gly Pro
50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95

Asn Arg Pro Lys Thr Leu Phe Gly Lys Ile Val Gly Gly Thr Ser Leu
            100                 105                 110

Gly Ser Leu Ser Tyr Gly Asp Gln Trp Arg Asn Leu Arg Arg Val Ala
        115                 120                 125

Ser Ile Glu Ile Leu Ser Val His Arg Leu Asn Glu Phe His Asp Ile
130                 135                 140

Arg Val Asp Glu Asn Arg Leu Leu Ile Arg Lys Leu Arg Ser Ser Ser
145                 150                 155                 160

Ser Pro Val Thr Leu Ile Thr Val Phe Tyr Ala Leu Thr Leu Asn Val
                165                 170                 175

Ile Met Arg Met Ile Ser Gly Lys Arg Tyr Phe Asp Ser Gly Asp Arg
            180                 185                 190

Glu Leu Glu Glu Glu Gly Lys Arg Phe Arg Glu Ile Leu Asp Glu Thr
        195                 200                 205

Leu Leu Leu Ala Gly Ala Ser Asn Val Gly Asp Tyr Leu Pro Ile Leu
210                 215                 220

Asn Trp Leu Gly Val Lys Ser Leu Glu Lys Lys Leu Ile Ala Leu Gln
225                 230                 235                 240

Lys Lys Arg Asp Asp Phe Phe Gln Gly Leu Ile Glu Gln Val Arg Lys
                245                 250                 255

Ser Arg Gly Ala Lys Val Gly Lys Gly Arg Lys Thr Met Ile Glu Leu
            260                 265                 270

Leu Leu Ser Leu Gln Glu Ser Glu Pro Glu Tyr Tyr Thr Asp Ala Met
        275                 280                 285

Ile Arg Ser Phe Val Leu Gly Leu Leu Ala Ala Gly Ser Asp Thr Ser
290                 295                 300

Ala Gly Thr Met Glu Trp Ala Met Ser Leu Leu Val Asn His Pro His
305                 310                 315                 320

Val Leu Lys Lys Ala Gln Ala Glu Ile Asp Arg Val Ile Gly Asn Asn
                325                 330                 335

Arg Leu Ile Asp Glu Ser Asp Ile Gly Asn Ile Pro Tyr Ile Gly Cys
            340                 345                 350

Ile Ile Asn Glu Thr Leu Arg Leu Tyr Pro Ala Gly Pro Leu Leu Phe
        355                 360                 365

Pro His Glu Ser Ser Ala Asp Cys Val Ile Ser Gly Tyr Asn Ile Pro
370                 375                 380

Arg Gly Thr Met Leu Ile Val Asn Gln Trp Ala Ile His His Asp Pro
```

```
                385                 390                 395                 400
Lys Val Trp Asp Asp Pro Glu Thr Phe Lys Pro Glu Arg Phe Gln Gly
                    405                 410                 415
Leu Glu Gly Thr Arg Asp Gly Phe Lys Leu Met Pro Phe Gly Ser Gly
                420                 425                 430
Arg Arg Gly Cys Pro Gly Glu Gly Leu Ala Ile Arg Leu Leu Gly Met
                435                 440                 445
Thr Leu Gly Ser Val Ile Gln Cys Phe Asp Trp Glu Arg Val Gly Asp
            450                 455                 460
Glu Met Val Asp Met Thr Glu Gly Leu Gly Val Thr Leu Pro Lys Ala
465                 470                 475                 480
Val Pro Leu Val Ala Lys Cys Lys Pro Arg Ser Glu Met Thr Asn Leu
                    485                 490                 495
Leu Ser Glu Leu
        500

<210> SEQ ID NO 12
<211> LENGTH: 2490
<212> TYPE: DNA
<213> ORGANISM: Artificial Sequence
<220> FEATURE:
<223> OTHER INFORMATION: Synthetic oligonucleotide

<400> SEQUENCE: 12
atggttttgt cttcttcttg tactacagta ccacacttat cttcattagc tgtcgtgcaa    60
cttggtcctt ggagcagtag gattaaaaag aaaaccgata ctgttgcagt accagccgct   120
gcaggaaggt ggagaagggc cttggctaga gcacagcaca catcagaatc cgcagctgtc   180
gcaaagggca gcagtttgac ccctatagtg agaactgacg ctgagtcaag agaacaaga   240
tggccaaccg atgacgatga cgccgaacct ttagtggatg agatcagggc aatgcttact   300
tccatgtctg atggtgacat tccgtgagc gcatacgata cagcctgggt cggattggtt   360
ccaagattag acggcggtga aggtcctcaa tttccagcag ctgtgagatg dataagaaat   420
aaccagttgc ctgacggaag ttggggcgat ccgcattat tctctgccta tgacaggctt   480
atcaataccc ttgcctgcgt tgtaactttg acaaggtggt ccctagaacc agagatgaga   540
ggtagaggac tatcttttt gggtaggaac atgtggaaat tagcaactga agatgaagag   600
tcaatgccta ttggcttcga attagcattt ccatctttga tagagcttgc taagagccta   660
ggtgtccatg acttccctta tgatcaccag gccctacaag gaatctactc ttcaagagag   720
atcaaaatga gaggattcc aaagaagtg atgcataccg ttccaacatc aatattgcac   780
agtttggagg gtatgcctgg cctagattgg gctaaactac ttaaactaca gagcagcgac   840
ggaagttttt tgttctcacc agctgccact gcatatgctt aatgaatac cggagatgac   900
aggtgtttta gctacatcga tagaacagta aagaaattca acggcggcgt ccctaatgtt   960
tatccagtgg atctatttga acatatttgg gccgttgata gacttgaaag attaggaatc  1020
tccaggtact tccaaaagga gatcgaacaa tgcatggatt atgtaaacag gcattggact  1080
gaggacggta tttgttgggc aaggaactct gatgtcaaag aggtggacga cacagctatg  1140
gcctttagac ttcttaggtt gcacggctac agcgtcagtc ctgatgtgtt taaaaacttc  1200
gaaaaggacg gtgaattttt cgcatttgtc ggacagtcta atcaagctgt taccggtatg  1260
tacaacttaa acagagcaag ccagatatcc ttcccaggcg aggatgtgct tcatagagct  1320
ggtgccttct catatgagtt cttgaggaga aagaagcag agggagcttt gagggacaag  1380
```

-continued

```
tggatcattt ctaaagatct acctggtgaa gttgtgtata ctttggattt tccatggtac   1440
ggcaacttac ctagagtcga ggccagagac tacctagagc aatacggagg tggtgatgac   1500
gtttggattg gcaagacatt gtataggatg ccacttgtaa acaatgatgt atatttggaa   1560
ttggcaagaa tggatttcaa ccactgccag gctttgcatc agttagagtg caaggacta   1620 aaaagatggt atactgaaaa taggttgatg gactttggtg tcgcccaaga agatgccctt   1680
agagcttatt ttcttgcagc cgcatctgtt tacgagcctt gtagagctgc cgagaggctt   1740
gcatgggcta gagccgcaat actagctaac gccgtgagca cccacttaag aaatagccca   1800
tcattcagag aaaggttaga gcattctctt aggtgtagac ctagtgaaga acagatggc   1860 tcctggttta actcctcaag tggctctgat gcagttttag taaaggctgt cttaagactt   1920
actgattcat tagccaggga agcacagcca atccatggag gtgacccaga agatattata   1980
cacaagttgt taagatctgc ttgggccgag tgggttaggg aaaaggcaga cgctgccgat   2040
agcgtgtgca atggtagttc tgcagtagaa caagagggat caagaatggt ccatgataaa   2100
cagacctgtc tattattggc tagaatgatc gaaatttctg ccggtagggc agctggtgaa   2160
gcagccagtg aggacggcga tagaagaata attcaattaa caggctccat ctgcgacagt   2220
cttaagcaaa aaatgctagt ttcacaggac cctgaaaaaa atgaagagat gatgtctcac   2280
gtggatgacg aattgaagtt gaggattaga gagttcgttc aatatttgct tagactaggt   2340
gaaaaaaaga ctggatctag cgaaaccagg caaacatttt taagtatagt gaaatcatgt   2400
tactatgctg ctcattgccc acctcatgtc gttgatagac acattagtag agtgattttc   2460
gagccagtaa gtgccgcaaa gtaaccgcgg                                    2490
```

<210> SEQ ID NO 13
<211> LENGTH: 827
<212> TYPE: PRT
<213> ORGANISM: Zea mays

<400> SEQUENCE: 13

```
Met Val Leu Ser Ser Ser Cys Thr Thr Val Pro His Leu Ser Ser Leu
1               5                   10                  15

Ala Val Val Gln Leu Gly Pro Trp Ser Ser Arg Ile Lys Lys Lys Thr
            20                  25                  30

Asp Thr Val Ala Val Pro Ala Ala Ala Gly Arg Trp Arg Arg Ala Leu
        35                  40                  45

Ala Arg Ala Gln His Thr Ser Glu Ser Ala Ala Val Ala Lys Gly Ser
    50                  55                  60

Ser Leu Thr Pro Ile Val Arg Thr Asp Ala Glu Ser Arg Arg Thr Arg
65                  70                  75                  80

Trp Pro Thr Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr
            100                 105                 110

Asp Thr Ala Trp Val Gly Leu Val Pro Arg Leu Asp Gly Gly Glu Gly
        115                 120                 125

Pro Gln Phe Pro Ala Ala Val Arg Trp Ile Arg Asn Asn Gln Leu Pro
    130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175
```

```
Pro Glu Met Arg Gly Arg Gly Leu Ser Phe Leu Gly Arg Asn Met Trp
            180                 185                 190
Lys Leu Ala Thr Glu Asp Glu Ser Met Pro Ile Gly Phe Glu Leu
        195                 200                 205
Ala Phe Pro Ser Leu Ile Glu Leu Ala Lys Ser Leu Gly Val His Asp
    210                 215                 220
Phe Pro Tyr Asp His Gln Ala Leu Gln Gly Ile Tyr Ser Ser Arg Glu
225                 230                 235                 240
Ile Lys Met Lys Arg Ile Pro Lys Glu Val Met His Thr Val Pro Thr
                245                 250                 255
Ser Ile Leu His Ser Leu Glu Gly Met Pro Gly Leu Asp Trp Ala Lys
            260                 265                 270
Leu Leu Lys Leu Gln Ser Ser Asp Gly Ser Phe Leu Phe Ser Pro Ala
        275                 280                 285
Ala Thr Ala Tyr Ala Leu Met Asn Thr Gly Asp Asp Arg Cys Phe Ser
    290                 295                 300
Tyr Ile Asp Arg Thr Val Lys Lys Phe Asn Gly Gly Val Pro Asn Val
305                 310                 315                 320
Tyr Pro Val Asp Leu Phe Glu His Ile Trp Ala Val Asp Arg Leu Glu
                325                 330                 335
Arg Leu Gly Ile Ser Arg Tyr Phe Gln Lys Glu Ile Glu Gln Cys Met
            340                 345                 350
Asp Tyr Val Asn Arg His Trp Thr Glu Asp Gly Ile Cys Trp Ala Arg
        355                 360                 365
Asn Ser Asp Val Lys Glu Val Asp Asp Thr Ala Met Ala Phe Arg Leu
    370                 375                 380
Leu Arg Leu His Gly Tyr Ser Val Ser Pro Asp Val Phe Lys Asn Phe
385                 390                 395                 400
Glu Lys Asp Gly Glu Phe Phe Ala Phe Val Gly Gln Ser Asn Gln Ala
                405                 410                 415
Val Thr Gly Met Tyr Asn Leu Asn Arg Ala Ser Gln Ile Ser Phe Pro
            420                 425                 430
Gly Glu Asp Val Leu His Arg Ala Gly Ala Phe Ser Tyr Glu Phe Leu
        435                 440                 445
Arg Arg Lys Glu Ala Glu Gly Ala Leu Arg Asp Lys Trp Ile Ile Ser
    450                 455                 460
Lys Asp Leu Pro Gly Glu Val Val Tyr Thr Leu Asp Phe Pro Trp Tyr
465                 470                 475                 480
Gly Asn Leu Pro Arg Val Glu Ala Arg Asp Tyr Leu Glu Gln Tyr Gly
                485                 490                 495
Gly Gly Asp Asp Val Trp Ile Gly Lys Thr Leu Tyr Arg Met Pro Leu
            500                 505                 510
Val Asn Asn Asp Val Tyr Leu Glu Leu Ala Arg Met Asp Phe Asn His
        515                 520                 525
Cys Gln Ala Leu His Gln Leu Glu Trp Gln Gly Leu Lys Arg Trp Tyr
    530                 535                 540
Thr Glu Asn Arg Leu Met Asp Phe Gly Val Ala Gln Glu Asp Ala Leu
545                 550                 555                 560
Arg Ala Tyr Phe Leu Ala Ala Ala Ser Val Tyr Glu Pro Cys Arg Ala
                565                 570                 575
Ala Glu Arg Leu Ala Trp Ala Arg Ala Ile Leu Ala Asn Ala Val
            580                 585                 590
Ser Thr His Leu Arg Asn Ser Pro Ser Phe Arg Glu Arg Leu Glu His
```

```
                595                 600                 605
Ser Leu Arg Cys Arg Pro Ser Glu Glu Thr Asp Gly Ser Trp Phe Asn
        610                 615                 620
Ser Ser Ser Gly Ser Asp Ala Val Leu Val Lys Ala Val Leu Arg Leu
625                 630                 635                 640
Thr Asp Ser Leu Ala Arg Glu Ala Gln Pro Ile His Gly Gly Asp Pro
                645                 650                 655
Glu Asp Ile Ile His Lys Leu Leu Arg Ser Ala Trp Ala Glu Trp Val
        660                 665                 670
Arg Glu Lys Ala Asp Ala Ala Asp Ser Val Cys Asn Gly Ser Ser Ala
        675                 680                 685
Val Glu Gln Glu Gly Ser Arg Met Val His Asp Lys Gln Thr Cys Leu
        690                 695                 700
Leu Leu Ala Arg Met Ile Glu Ile Ser Ala Gly Arg Ala Ala Gly Glu
705                 710                 715                 720
Ala Ala Ser Glu Asp Gly Asp Arg Arg Ile Ile Gln Leu Thr Gly Ser
                725                 730                 735
Ile Cys Asp Ser Leu Lys Gln Lys Met Leu Val Ser Gln Asp Pro Glu
                740                 745                 750
Lys Asn Glu Glu Met Met Ser His Val Asp Asp Glu Leu Lys Leu Arg
        755                 760                 765
Ile Arg Glu Phe Val Gln Tyr Leu Leu Arg Leu Gly Glu Lys Lys Thr
        770                 775                 780
Gly Ser Ser Glu Thr Arg Gln Thr Phe Leu Ser Ile Val Lys Ser Cys
785                 790                 795                 800
Tyr Tyr Ala Ala His Cys Pro Pro His Val Val Asp Arg His Ile Ser
                805                 810                 815
Arg Val Ile Phe Glu Pro Val Ser Ala Ala Lys
        820                 825

<210> SEQ ID NO 14
<211> LENGTH: 1377
<212> TYPE: DNA
<213> ORGANISM: Artificial Sequence
<220> FEATURE:
<223> OTHER INFORMATION: Synthetic oligonucleotide

<400> SEQUENCE: 14
atggaaaaca agaccgaaac aacagttaga cgtaggcgta gaatcattct gtttccagta      60 cctttttcaag ggcacatcaa tccaatacta caactagcca acgttttgta ctctaaaggt    120
ttttctatta caatctttca caccaatttc aacaaaccaa aaacatccaa ttacccacat     180
ttcacattca gattcatact tgataatgat ccacaagatg aacgtatttc aaacttacct     240
acccacggtc ctttagctgg aatgagaatt ccaatcatca tgaacatggt tgccgatgag     300
cttagaagag aattagagtt acttatgttg catccgaagg aggacgagga agtctcttgt     360
ctgattactg acgctctatg gtactttgcc aatctgtgg ctgatagttt gaatttgagg      420
agattggtac taatgacatc cagtctgttt aactttcacg ctcatgttag tttaccacaa     480
tttgacgaat tgggatactt ggaccctgat gacaagacta ggttagagga acaggcctct     540
ggttttccta tgttgaaagt caaagatatc aagtctgcct attctaattg gcaaatcttg     600
aaagagatct taggaaagat gatcaaacag acaaaggctt catctggagt gatttggaac     660
agtttcaaag agttagaaga gtctgaattg gagactgtaa tcagagaaat tccagcacct     720
tcattcctga taccattacc aaaacatttg actgcttcct cttcctcttt gttggatcat     780
```

```
gacagaacag ttttcaatg gttggaccaa caaccaccta gttctgtttt gtacgtgtca    840
tttggtagta cttctgaagt cgatgaaaag gacttccttg aaatcgcaag aggcttagtc    900
gatagtaagc agtcattcct ttgggtcgtg cgtccaggtt tcgtgaaagg ctcaacatgg    960
gtcgaaccac ttccagatgg ttttctaggc gaaagaggta gaatagtcaa atgggttcct   1020
caacaggaag ttttagctca tggcgctatt ggggcattct ggactcattc cggatggaat   1080
tcaactttag aatcagtatg cgaagggta cctatgatct tttcagattt tggtcttgat   1140
caaccactga acgcaagata catgtctgat gttttgaaag tgggtgtata tctagaaaat   1200
ggctgggaaa ggggtgaaat agctaatgca ataagacgtg ttatggttga tgaagagggg   1260
gagtatatca gacaaaacgc aagagtgctg aagcaaaagg ccgacgtttc tctaatgaag   1320
ggaggctctt catacgaatc cttagaatct cttgtttcct acatttcatc actgtaa     1377
```

<210> SEQ ID NO 15
<211> LENGTH: 473
<212> TYPE: PRT
<213> ORGANISM: Stevia rebaudiana

<400> SEQUENCE: 15

```
Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270
```

```
Gln Lys Gly Ser Val Val Tyr Val Ala Leu Gly Ser Glu Val Leu Val
            275                 280                 285

Ser Gln Thr Glu Val Val Glu Leu Ala Leu Gly Leu Glu Leu Ser Gly
        290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Asp Gly Cys Leu Thr Lys Glu Ser Val
                405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
            435                 440                 445

Glu Lys Glu Tyr Val Ser Gln Phe Val Asp Tyr Leu Glu Lys Asn Ala
        450                 455                 460

Arg Ala Val Ala Ile Asp His Glu Ser
465                 470

<210> SEQ ID NO 16
<211> LENGTH: 462
<212> TYPE: PRT
<213> ORGANISM: Oryza sativa

<400> SEQUENCE: 16

Met Asp Ser Gly Tyr Ser Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
            85                  90                  95

Asp Met Val Glu Leu His Arg Arg Ala Phe Asp Gly Leu Ala Ala Pro
                100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
```

```
                165                 170                 175
Gln Gly Arg Pro Ala Ala Pro Thr Phe Glu Val Ala Arg Met Lys
            180                 185                 190
Leu Ile Arg Thr Lys Gly Ser Ser Gly Met Ser Leu Ala Glu Arg Phe
            195                 200                 205
Ser Leu Thr Leu Ser Arg Ser Ser Leu Val Val Gly Arg Ser Cys Val
            210                 215                 220
Glu Phe Glu Pro Glu Thr Val Pro Leu Leu Ser Thr Leu Arg Gly Lys
225                 230                 235                 240
Pro Ile Thr Phe Leu Gly Leu Met Pro Pro Leu His Glu Gly Arg Arg
                245                 250                 255
Glu Asp Gly Glu Asp Ala Thr Val Arg Trp Leu Asp Ala Gln Pro Ala
            260                 265                 270
Lys Ser Val Val Tyr Val Ala Leu Gly Ser Glu Val Pro Leu Gly Val
            275                 280                 285
Glu Lys Val His Glu Leu Ala Leu Gly Leu Glu Leu Ala Gly Thr Arg
            290                 295                 300
Phe Leu Trp Ala Leu Arg Lys Pro Thr Gly Val Ser Asp Ala Asp Leu
305                 310                 315                 320
Leu Pro Ala Gly Phe Glu Arg Thr Arg Gly Arg Gly Val Val Ala
                325                 330                 335
Thr Arg Trp Val Pro Gln Met Ser Ile Leu Ala His Ala Ala Val Gly
            340                 345                 350
Ala Phe Leu Thr His Cys Gly Trp Asn Ser Thr Ile Glu Gly Leu Met
            355                 360                 365
Phe Gly His Pro Leu Ile Met Leu Pro Ile Phe Gly Asp Gln Gly Pro
370                 375                 380
Asn Ala Arg Leu Ile Glu Ala Lys Asn Ala Gly Leu Gln Val Ala Arg
385                 390                 395                 400
Asn Asp Gly Asp Gly Ser Phe Asp Arg Glu Gly Val Ala Ala Ala Ile
                405                 410                 415
Arg Ala Val Ala Val Glu Glu Glu Ser Ser Lys Val Phe Gln Ala Lys
            420                 425                 430
Ala Lys Lys Leu Gln Glu Ile Val Ala Asp Met Ala Cys His Glu Arg
            435                 440                 445
Tyr Ile Asp Gly Phe Ile Gln Gln Leu Arg Ser Tyr Lys Asp
            450                 455                 460

<210> SEQ ID NO 17
<211> LENGTH: 1389
<212> TYPE: DNA
<213> ORGANISM: Artificial Sequence
<220> FEATURE:
<223> OTHER INFORMATION: Synthetic oligonucleotide

<400> SEQUENCE: 17
atggactccg gctactcctc ctcctacgcc gccgccgccg ggatgcacgt cgtgatctgc      60
ccgtggctcg ccttcggcca cctgctcccg tgcctcgacc tcgcccagcg cctcgcgtcg     120
cggggccacc gcgtgtcgtt cgtctccacg ccgcggaaca tatcccgcct cccgccggtg     180
cgccccgcgc tcgcgccgct cgtcgccttc gtggcgctgc cgctcccgcg cgtcgagggg     240
ctccccgacg gcgccgagtc caccaacgac gtccccacg acaggccgga catggtcgag      300
ctccaccgga gggccttcga cgggctcgcc gcgcccttct cggagttctt ggcaccgcg      360 tgcgccgact gggtcatcgt cgacgtcttc caccactggg ccgcagccgc cgctctcgag     420
```

```
cacaaggtgc catgtgcaat gatgttgttg ggctctgcac atatgatcgc ttccatagca      480
gacagacggc tcgagcgcgc ggagacagag tcgcctgcgg ctgccgggca gggacgccca      540
gcggcggcgc caacgttcga ggtggcgagg atgaagttga tacgaaccaa aggctcatcg      600
ggaatgtccc tcgccgagcg cttctccttg acgctctcga ggagcagcct cgtcgtcggg      660
cggagctgcg tggagttcga gccggagacc gtcccgctcc tgtcgacgct ccgcggtaag      720
cctattacct tccttggcct tatgccgccg ttgcatgaag ccgccgcgca ggacggcgag      780
gatgccaccg tccgctggct cgacgcgcag ccggccaagt ccgtcgtgta cgtcgcgcta      840
ggcagcgagg tgccactggg agtggagaag gtccacgagc tcgcgctcgg gctggagctc      900
gccgggacgc gcttcctctg ggctcttagg aagcccactg gcgtctccga cgccgacctc      960
ctccccgccg gcttcgagga gcgcacgcgc ggccgcggcg tcgtggcgac gagatggggt     1020
cctcagatga gcatactggc gcacgccgcc gtgggcgcgt tcctgaccca ctgcggctgg     1080
aactcgacca tcgagggggct catgttcggc cacccgctta tcatgctgcc gatcttcggc     1140
gaccagggac cgaacgcgcg gctaatcgag gcgaagaacg ccggattgca ggtggcaaga     1200
aacgacggcg atggatcgtt cgaccgagaa ggcgtcgcgg cggcgattcg tgcagtcgcg     1260
gtggaggaag aaagcagcaa agtgtttcaa gccaaagcca agaagctgca ggagatcgtc     1320
gcggacatgg cctgccatga gaggtacatc gacggattca ttcagcaatt gagatcttac     1380
aaggattga                                                             1389
```

<210> SEQ ID NO 18
<211> LENGTH: 1389
<212> TYPE: DNA
<213> ORGANISM: Artificial Sequence
<220> FEATURE:
<223> OTHER INFORMATION: Synthetic oligonucleotide

<400> SEQUENCE: 18

```
atggatagtg gctactcctc atcttatgct gctgccgctg gtatgcacgt tgtgatctgc       60
ccttggttgg cctttggtca cctgttacca tgtctggatt tagcccaaag actggcctca      120
agaggccata gagtatcatt tgtgtctact cctagaaata tctctcgttt accaccagtc      180
agacctgctc tagctcctct agttgcattc gttgctcttc cacttccaag agtagaagga      240
ttgccagacg gcgctgaatc tactaatgac gtaccacatg atagacctga catggtcgaa      300
ttgcatagaa gagcctttga tggattggca gctccatttt ctgagttcct gggcacagca      360
tgtgcagact gggttatagt cgatgtattt catcactggg ctgctgcagc cgcattggaa      420
cataaggtgc cttgtgctat gatgttgtta gggtcagcac acatgatcgc atccatagct      480
gatagaagat tggaaagagc tgaaacagaa tccccagccg cagcaggaca aggtaggcca      540
gctgccgccc caaccttttga agtggctaga atgaaattga ttcgtactaa aggtagttca      600
gggatgagtc ttgctgaaag gttttctctg acattatcta gatcatcatt agttgtaggt      660
agatcctgcg tcgagttcga acctgaaaca gtacctttac tatctacttt gagaggcaaa      720
cctattactt tccttggtct aatgcctcca ttacatgaag gaaggagaga agatggtgaa      780
gatgctactg ttaggtggtt agatgcccaa cctgctaagt ctgttgttta cgttgcattg      840
ggttctgagg taccactagg ggtggaaaag gtgcatgaat tagcattagg acttgagctg      900 gccgaacaa gattcctttg ggctttgaga aaaccaaccg gtgtttctga cgccgacttg      960
ctaccagctg gggttcgaaga gagaacaaga ggccgtggtg tcgttgctac tagatgggtc     1020
```

-continued

```
ccacaaatga gtattctagc tcatgcagct gtagggggcct ttctaaccca ttgcggttgg    1080
aactcaacaa tagaaggact gatgtttggt catccactta ttatgttacc aatctttggc    1140
gatcagggac ctaacgcaag attgattgag gcaaagaacg caggtctgca ggttgcacgt    1200
aatgatggtg atggttcctt tgatagagaa ggcgttgcag ctgccatcag agcagtcgcc    1260
gttgaggaag agtcatctaa agttttccaa gctaaggcca aaaaattaca agagattgtg    1320
gctgacatgg cttgtcacga agatacatc gatggtttca tccaacaatt gagaagttat     1380
aaagactaa                                                             1389
```

<210> SEQ ID NO 19
<211> LENGTH: 460
<212> TYPE: PRT
<213> ORGANISM: Stevia rebaudiana

<400> SEQUENCE: 19

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300
```

-continued

```
Asn Phe Leu Trp Val Ile Lys His Lys Glu Gly Lys Leu Pro Glu
305                 310                 315                 320

Asn Leu Ser Glu Val Ile Lys Thr Gly Lys Gly Leu Ile Val Ala Trp
            325                 330                 335

Cys Lys Gln Leu Asp Val Leu Ala His Glu Ser Val Gly Cys Phe Val
                340                 345                 350

Thr His Cys Gly Phe Asn Ser Thr Leu Glu Ala Ile Ser Leu Gly Val
            355                 360                 365

Pro Val Val Ala Met Pro Gln Phe Ser Asp Gln Thr Thr Asn Ala Lys
        370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
                420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
        450                 455                 460

<210> SEQ ID NO 20
<211> LENGTH: 481
<212> TYPE: PRT
<213> ORGANISM: Stevia rebaudiana

<400> SEQUENCE: 20

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220
```

```
Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
            245                 250                 255

Leu Asp Gln Ile Pro Glu Glu Lys Lys Gln Thr Gly Ile Thr Ser Leu
        260                 265                 270

His Gly Tyr Ser Leu Val Lys Glu Glu Pro Glu Cys Phe Gln Trp Leu
    275                 280                 285

Gln Ser Lys Glu Pro Asn Ser Val Val Tyr Val Asn Phe Gly Ser Thr
290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
            325                 330                 335

Gly Glu Asn Ala Val Leu Pro Pro Glu Leu Glu Glu His Ile Lys Lys
        340                 345                 350

Arg Gly Phe Ile Ala Ser Trp Cys Ser Gln Glu Lys Val Leu Lys His
    355                 360                 365

Pro Ser Val Gly Gly Phe Leu Thr His Cys Gly Trp Gly Ser Thr Ile
370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
            405                 410                 415

Leu Glu Met Gly Thr Lys Val Lys Arg Asp Glu Val Lys Arg Leu Val
        420                 425                 430

Gln Glu Leu Met Gly Glu Gly His Lys Met Arg Asn Lys Ala Lys
    435                 440                 445

Asp Trp Lys Glu Lys Ala Arg Ile Ala Ile Ala Pro Asn Gly Ser Ser
450                 455                 460

Ser Leu Asn Ile Asp Lys Met Val Lys Glu Ile Thr Val Leu Ala Arg
465                 470                 475                 480

Asn

<210> SEQ ID NO 21
<211> LENGTH: 785
<212> TYPE: PRT
<213> ORGANISM: Arabidopsis thaliana

<400> SEQUENCE: 21

Met Ser Ile Asn Leu Arg Ser Ser Gly Cys Ser Ser Pro Ile Ser Ala
1               5                   10                  15

Thr Leu Glu Arg Gly Leu Asp Ser Glu Val Gln Thr Arg Ala Asn Asn
            20                  25                  30

Val Ser Phe Glu Gln Thr Lys Glu Lys Ile Arg Lys Met Leu Glu Lys
        35                  40                  45

Val Glu Leu Ser Val Ser Ala Tyr Asp Thr Ser Trp Val Ala Met Val
    50                  55                  60

Pro Ser Pro Ser Ser Gln Asn Ala Pro Leu Phe Pro Gln Cys Val Lys
65                  70                  75                  80

Trp Leu Leu Asp Asn Gln His Glu Asp Gly Ser Trp Gly Leu Asp Asn
            85                  90                  95

His Asp His Gln Ser Leu Lys Lys Asp Val Leu Ser Ser Thr Leu Ala
            100                 105                 110
```

```
Ser Ile Leu Ala Leu Lys Lys Trp Gly Ile Glu Arg Gln Ile Asn
    115                 120                 125
Lys Gly Leu Gln Phe Ile Glu Leu Asn Ser Ala Leu Val Thr Asp Glu
130                 135                 140
Thr Ile Gln Lys Pro Thr Gly Phe Asp Ile Ile Phe Pro Gly Met Ile
145                 150                 155                 160
Lys Tyr Ala Arg Asp Leu Asn Leu Thr Ile Pro Leu Gly Ser Glu Val
                165                 170                 175
Val Asp Asp Met Ile Arg Lys Arg Asp Leu Asp Leu Lys Cys Asp Ser
            180                 185                 190
Glu Lys Phe Ser Lys Gly Arg Glu Ala Tyr Leu Ala Tyr Val Leu Glu
        195                 200                 205
Gly Thr Arg Asn Leu Lys Asp Trp Asp Leu Ile Val Lys Tyr Gln Arg
    210                 215                 220
Lys Asn Gly Ser Leu Phe Asp Ser Pro Ala Thr Ala Ala Ala Phe
225                 230                 235                 240
Thr Gln Phe Gly Asn Asp Gly Cys Leu Arg Tyr Leu Cys Ser Leu Leu
                245                 250                 255
Gln Lys Phe Glu Ala Ala Val Pro Ser Val Tyr Pro Phe Asp Gln Tyr
            260                 265                 270
Ala Arg Leu Ser Ile Ile Val Thr Leu Glu Ser Leu Gly Ile Asp Arg
        275                 280                 285
Asp Phe Lys Thr Glu Ile Lys Ser Ile Leu Asp Glu Thr Tyr Arg Tyr
    290                 295                 300
Trp Leu Arg Gly Asp Glu Glu Ile Cys Leu Asp Leu Ala Thr Cys Ala
305                 310                 315                 320
Leu Ala Phe Arg Leu Leu Leu Ala His Gly Tyr Asp Val Ser Tyr Asp
                325                 330                 335
Pro Leu Lys Pro Phe Ala Glu Glu Ser Gly Phe Ser Asp Thr Leu Glu
            340                 345                 350
Gly Tyr Val Lys Asn Thr Phe Ser Val Leu Glu Leu Phe Lys Ala Ala
        355                 360                 365
Gln Ser Tyr Pro His Glu Ser Ala Leu Lys Lys Gln Cys Cys Trp Thr
    370                 375                 380
Lys Gln Tyr Leu Glu Met Glu Leu Ser Ser Trp Val Lys Thr Ser Val
385                 390                 395                 400
Arg Asp Lys Tyr Leu Lys Lys Glu Val Glu Asp Ala Leu Ala Phe Pro
                405                 410                 415
Ser Tyr Ala Ser Leu Glu Arg Ser Asp His Arg Arg Lys Ile Leu Asn
            420                 425                 430
Gly Ser Ala Val Glu Asn Thr Arg Val Thr Lys Thr Ser Tyr Arg Leu
        435                 440                 445
His Asn Ile Cys Thr Ser Asp Ile Leu Lys Leu Ala Val Asp Asp Phe
    450                 455                 460
Asn Phe Cys Gln Ser Ile His Arg Glu Glu Met Glu Arg Leu Asp Arg
465                 470                 475                 480
Trp Ile Val Glu Asn Arg Leu Gln Glu Leu Lys Phe Ala Arg Gln Lys
                485                 490                 495
Leu Ala Tyr Cys Tyr Phe Ser Gly Ala Ala Thr Leu Phe Ser Pro Glu
            500                 505                 510
Leu Ser Asp Ala Arg Ile Ser Trp Ala Lys Gly Gly Val Leu Thr Thr
        515                 520                 525
```

```
Val Val Asp Asp Phe Phe Asp Val Gly Gly Ser Lys Glu Glu Leu Glu
    530                 535                 540

Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
                565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
        595                 600                 605

Arg Glu Ala Glu Trp Ser Ser Asp Lys Ser Thr Pro Ser Leu Glu Asp
    610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
                645                 650                 655

Ser His Gln Tyr Asn Gln Leu Tyr Lys Leu Val Ser Thr Met Gly Arg
            660                 665                 670

Leu Leu Asn Asp Ile Gln Gly Phe Lys Arg Glu Ser Ala Glu Gly Lys
        675                 680                 685

Leu Asn Ala Val Ser Leu His Met Lys His Glu Arg Asp Asn Arg Ser
    690                 695                 700

Lys Glu Val Ile Ile Glu Ser Met Lys Gly Leu Ala Glu Arg Lys Arg
705                 710                 715                 720

Glu Glu Leu His Lys Leu Val Leu Glu Glu Lys Gly Ser Val Val Pro
                725                 730                 735

Arg Glu Cys Lys Glu Ala Phe Leu Lys Met Ser Lys Val Leu Asn Leu
            740                 745                 750

Phe Tyr Arg Lys Asp Asp Gly Phe Thr Ser Asn Asp Leu Met Ser Leu
        755                 760                 765

Val Lys Ser Val Ile Tyr Glu Pro Val Ser Leu Gln Lys Glu Ser Leu
    770                 775                 780

Thr
785

<210> SEQ ID NO 22
<211> LENGTH: 894
<212> TYPE: DNA
<213> ORGANISM: Artificial Sequence
<220> FEATURE:
<223> OTHER INFORMATION: Synthetic oligonucleotide

<400> SEQUENCE: 22
atggtcgcac aaactttcaa cctggatacc tacttatccc aaagacaaca acaagttgaa      60
gaggccctaa gtgctgctct tgtgccagct tatcctgaga gaatatacga agctatgaga     120
tactccctcc tggcaggtgg caaaagatta agacctatct tatgtttagc tgcttgcgaa     180
ttggcaggtg gttctgttga caagccatgc caactgcgt gtgcacttga atgatccat       240 acaatgtcac taattcatga tgacctgcca gccatggata cgatgatttt cagaagagga     300
aagccaacta atcacaaggt gttcggggaa gatatagcca tcttagcggg tgatgcgctt     360
ttagcttacg cttttgaaca tattgcttct caaacaagag gagtaccacc tcaattggtg     420
ctacaagtta ttgctagaat cggacacgcc gttgctgcaa caggcctcgt tggaggccaa     480
gtcgtagacc ttgaatctga aggtaaagct atttccttag aaacattgga gtatattcac     540
```

```
tcacataaga ctggagcctt gctggaagca tcagttgtct caggcggtat tctcgcaggg    600
gcagatgaag agcttttggc cagattgtct cattacgcta gagatatagg cttggctttt    660
caaatcgtcg atgatatcct ggatgttact gctacatctg aacagttggg gaaaaccgct    720
ggtaaagacc aggcagccgc aaaggcaact tatccaagtc tattgggttt agaagcctct    780
agacagaaag cggaagagtt gattcaatct gctaaggaag ccttaagacc ttacggttca    840
caagcagagc cactcctagc gctggcagac ttcatcacac gtcgtcagca ttaa          894

<210> SEQ ID NO 23
<211> LENGTH: 1542
<212> TYPE: DNA
<213> ORGANISM: Artificial Sequence
<220> FEATURE:
<223> OTHER INFORMATION: Synthetic oligonucleotide

<400> SEQUENCE: 23
atggatgctg tgacgggttt gttaactgtc ccagcaaccg ctataactat tggtggaact     60
gctgtagcat tggcggtagc gctaatcttt tggtacctga atcctacac atcagctaga    120 agatcccaat caaatcatct tccaagagtg cctgaagtcc caggtgttcc attgttagga    180
aatctgttac aattgaagga gaaaaagcca tacatgactt tacgagatg ggcagcgaca    240 tatggaccta tctatagtat caaaactggg gctacaagta tggttgtggt atcatctaat    300
gagatagcca aggaggcatt ggtgaccaga ttccaatcca tatctacaag gaacttatct    360
aaagccctga agtacttac agcagataag acaatggtcg caatgtcaga ttatgatgat    420
tatcataaaa cagttaagag acacatactg accgccgtct tgggtcctaa tgcacagaaa    480
aagcatagaa ttcacagaga tatcatgatg gataacatat ctactcaact tcatgaattc    540
gtgaaaaaca acccagaaca ggaagaggta gaccttagaa aaatctttca atctgagtta    600
ttcggcttag ctatgagaca agccttagga aaggatgttg aaagtttgta cgttgaagac    660
ctgaaaatca ctatgaatag agacgaaatc tttcaagtcc ttgttgttga tccaatgatg    720
ggagcaatcg atgttgattg gagagacttc tttccatacc taaagtgggt cccaaacaaa    780
aagttcgaaa atactattca acaaatgtac atcagaagag aagctgttat gaaatcttta    840
atcaaagagc acaaaagag aatagcgtca ggcgaaaagc taaatagtta tatcgattac    900
cttttatctg aagctcaaac tttaaccgat cagcaactat tgatgtcctt gtgggaacca    960
atcattgaat cttcagatac aacaatggtc acaacagaat gggcaatgta cgaattagct   1020
aaaaacccta aattgcaaga taggttgtac agagacatta agtccgtctg tggatctgaa   1080
aagataaccg aagagcatct atcacagctg ccttacatta cagctatttt ccacgaaaca   1140
ctgagaagac actcaccagt tcctatcatt cctctaagac atgtacatga agataccgtt   1200
ctaggcggct accatgttcc tgctggcaca gaacttgccg ttaacatcta cggttgcaac   1260
atggacaaaa acgtttggga aaatccagag gaatggaacc agaaagatt catgaaagag   1320 aatgagacaa ttgattttca aaagacgatg gccttcggtg gtgtaagag agtttgtgct   1380 ggttccttgc aagccctttt aactgcatct attgggattg ggagaatggt tcaagagttc   1440
gaatggaaac tgaaggatat gactcaagag gaagtgaaca cgataggcct aactacacaa   1500
atgttaagac cattgagagc tattatcaaa cctaggatct aa                     1542

<210> SEQ ID NO 24
<211> LENGTH: 297
<212> TYPE: PRT
<213> ORGANISM: Synechococcus sp.
```

<400> SEQUENCE: 24

Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
            20                  25                  30

Glu Arg Ile Tyr Glu Ala Met Arg Tyr Ser Leu Leu Ala Gly Gly Lys
        35                  40                  45

Arg Leu Arg Pro Ile Leu Cys Leu Ala Ala Cys Glu Leu Ala Gly Gly
    50                  55                  60

Ser Val Glu Gln Ala Met Pro Thr Ala Cys Ala Leu Glu Met Ile His
65                  70                  75                  80

Thr Met Ser Leu Ile His Asp Asp Leu Pro Ala Met Asp Asn Asp Asp
                85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
    130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
    210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
        275                 280                 285

Ala Asp Phe Ile Thr Arg Arg Gln His
    290                 295

<210> SEQ ID NO 25
<211> LENGTH: 513
<212> TYPE: PRT
<213> ORGANISM: Stevia rebaudiana

<400> SEQUENCE: 25

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

```
Leu Lys Glu Lys Lys Pro Tyr Met Thr Phe Thr Arg Trp Ala Ala Thr
 65                  70                  75                  80

Tyr Gly Pro Ile Tyr Ser Ile Lys Thr Gly Ala Thr Ser Met Val Val
             85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Tyr His Lys Thr
130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Val Asp Leu
            180                 185                 190

Arg Lys Ile Phe Gln Ser Glu Leu Phe Gly Leu Ala Met Arg Gln Ala
            195                 200                 205

Leu Gly Lys Asp Val Glu Ser Leu Tyr Val Glu Asp Leu Lys Ile Thr
210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
            275                 280                 285

Ala Ser Gly Glu Lys Leu Asn Ser Tyr Ile Asp Tyr Leu Leu Ser Glu
290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
            355                 360                 365

Gln Leu Pro Tyr Ile Thr Ala Ile Phe His Glu Thr Leu Arg Arg His
            370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
            435                 440                 445

Thr Met Ala Phe Gly Gly Gly Lys Arg Val Cys Ala Gly Ser Leu Gln
            450                 455                 460

Ala Leu Leu Thr Ala Ser Ile Gly Ile Gly Arg Met Val Gln Glu Phe
465                 470                 475                 480
```

```
Glu Trp Lys Leu Lys Asp Met Thr Gln Glu Val Asn Thr Ile Gly
                485                 490                 495
Leu Thr Thr Gln Met Leu Arg Pro Leu Arg Ala Ile Ile Lys Pro Arg
            500                 505                 510
Ile

<210> SEQ ID NO 26
<211> LENGTH: 480
<212> TYPE: PRT
<213> ORGANISM: Stevia rebaudiana

<400> SEQUENCE: 26

Met Asp Ala Met Ala Thr Thr Glu Lys Lys Pro His Val Ile Phe Ile
1               5                   10                  15
Pro Phe Pro Ala Gln Ser His Ile Lys Ala Met Leu Lys Leu Ala Gln
                20                  25                  30
Leu Leu His His Lys Gly Leu Gln Ile Thr Phe Val Asn Thr Asp Phe
            35                  40                  45
Ile His Asn Gln Phe Leu Glu Ser Ser Gly Pro His Cys Leu Asp Gly
        50                  55                  60
Ala Pro Gly Phe Arg Phe Glu Thr Ile Pro Asp Gly Val Ser His Ser
65                  70                  75                  80
Pro Glu Ala Ser Ile Pro Ile Arg Glu Ser Leu Leu Arg Ser Ile Glu
                85                  90                  95
Thr Asn Phe Leu Asp Arg Phe Ile Asp Leu Val Thr Lys Leu Pro Asp
            100                 105                 110
Pro Pro Thr Cys Ile Ile Ser Asp Gly Phe Leu Ser Val Phe Thr Ile
        115                 120                 125
Asp Ala Ala Lys Lys Leu Gly Ile Pro Val Met Met Tyr Trp Thr Leu
130                 135                 140
Ala Ala Cys Gly Phe Met Gly Phe Tyr His Ile His Ser Leu Ile Glu
145                 150                 155                 160
Lys Gly Phe Ala Pro Leu Lys Asp Ala Ser Tyr Leu Thr Asn Gly Tyr
                165                 170                 175
Leu Asp Thr Val Ile Asp Trp Val Pro Gly Met Glu Gly Ile Arg Leu
            180                 185                 190
Lys Asp Phe Pro Leu Asp Trp Ser Thr Asp Leu Asn Asp Lys Val Leu
        195                 200                 205
Met Phe Thr Thr Glu Ala Pro Gln Arg Ser His Lys Val Ser His His
210                 215                 220
Ile Phe His Thr Phe Asp Glu Leu Glu Pro Ser Ile Ile Lys Thr Leu
225                 230                 235                 240
Ser Leu Arg Tyr Asn His Ile Tyr Thr Ile Gly Pro Leu Gln Leu Leu
                245                 250                 255
Leu Asp Gln Ile Pro Glu Glu Lys Lys Gln Thr Gly Ile Thr Ser Leu
            260                 265                 270
His Gly Tyr Ser Leu Val Lys Glu Glu Pro Glu Cys Phe Gln Trp Leu
        275                 280                 285
Gln Ser Lys Glu Pro Asn Ser Val Val Tyr Val Asn Phe Gly Ser Thr
290                 295                 300
Thr Val Met Ser Leu Glu Asp Met Thr Glu Phe Gly Trp Gly Leu Ala
305                 310                 315                 320
Asn Ser Asn His Tyr Phe Leu Trp Ile Ile Arg Ser Asn Leu Val Ile
                325                 330                 335
```

```
Gly Glu Asn Ala Val Leu Pro Pro Glu Leu Glu His Ile Lys Lys
                340                 345                 350

Arg Gly Phe Ile Ala Ser Trp Cys Ser Gln Glu Lys Val Leu Lys His
            355                 360                 365

Pro Ser Val Gly Gly Phe Leu Thr His Cys Gly Trp Gly Ser Thr Ile
        370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly His Lys Met Arg Asn Lys Ala Lys
        435                 440                 445

Asp Trp Lys Glu Lys Ala Arg Ile Ala Ile Ala Pro Asn Gly Ser Ser
        450                 455                 460

Ser Leu Asn Ile Asp Lys Met Val Lys Glu Ile Thr Val Leu Ala Arg
465                 470                 475                 480

<210> SEQ ID NO 27
<211> LENGTH: 784
<212> TYPE: PRT
<213> ORGANISM: Stevia rebaudiana

<400> SEQUENCE: 27

Met Asn Leu Ser Leu Cys Ile Ala Ser Pro Leu Leu Thr Lys Ser Asn
1               5                   10                  15

Arg Pro Ala Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Gln Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Glu Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Met Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240
```

```
Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270

Val Tyr Pro His Asp Leu Phe Ile Arg Leu Ser Met Val Asp Thr Ile
        275                 280                 285

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile Asn
                325                 330                 335

Gly Tyr Glu Val Ser Pro Asp Pro Leu Ala Glu Ile Thr Asn Glu Leu
            340                 345                 350

Ala Leu Lys Asp Glu Tyr Ala Ala Leu Glu Thr Tyr His Ala Ser His
        355                 360                 365

Ile Leu Tyr Gln Glu Asp Leu Ser Ser Gly Lys Gln Ile Leu Lys Ser
    370                 375                 380

Ala Asp Phe Leu Lys Glu Ile Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Asp Tyr Leu Arg Leu Ala Val Asp Phe Tyr Thr Cys
450                 455                 460

Gln Ser Ile Tyr Arg Glu Glu Leu Lys Gly Leu Glu Arg Trp Val Val
465                 470                 475                 480

Glu Asn Lys Leu Asp Gln Leu Lys Phe Ala Arg Gln Lys Thr Ala Tyr
            485                 490                 495

Cys Tyr Phe Ser Val Ala Ala Thr Leu Ser Ser Pro Glu Leu Ser Asp
        500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
        530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
        580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
    610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655
```

```
Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
            675                 680                 685

Val Ala Leu His Leu Ser Asn Gly Glu Ser Gly Lys Val Glu Glu Glu
            690                 695                 700

Val Val Glu Glu Met Met Met Ile Lys Asn Lys Arg Lys Glu Leu
705                 710                 715                 720

Met Lys Leu Ile Phe Glu Glu Asn Gly Ser Ile Val Pro Arg Ala Cys
            725                 730                 735

Lys Asp Ala Phe Trp Asn Met Cys His Val Leu Asn Phe Phe Tyr Ala
            740                 745                 750

Asn Asp Asp Gly Phe Thr Gly Asn Thr Ile Leu Asp Thr Val Lys Asp
            755                 760                 765

Ile Ile Tyr Asn Pro Leu Val Leu Val Asn Glu Asn Glu Glu Gln Arg
            770                 775                 780

<210> SEQ ID NO 28
<211> LENGTH: 784
<212> TYPE: PRT
<213> ORGANISM: Stevia rebaudiana

<400> SEQUENCE: 28

Met Asn Leu Ser Leu Cys Ile Ala Ser Pro Leu Leu Thr Lys Ser Ser
1               5                   10                  15

Arg Pro Thr Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
            35                  40                  45

Ile Gln Lys Leu Phe Lys Asn Val Glu Ile Ser Val Ser Ser Tyr Asp
        50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
            115                 120                 125

Arg Trp Asn Val Gly Glu Asp Gln Ile Asn Lys Gly Leu Ser Phe Ile
        130                 135                 140

Glu Ser Asn Leu Ala Ser Ala Thr Asp Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Ile Asp Gly
            195                 200                 205

Tyr Leu Ala Tyr Ile Ser Glu Gly Leu Gly Asn Leu Tyr Asp Trp Asn
        210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255
```

```
Asn Tyr Leu Asn Ser Leu Leu Asp Lys Phe Gly Asn Ala Val Pro Thr
            260                 265                 270

Val Tyr Pro Leu Asp Leu Tyr Ile Arg Leu Ser Met Val Asp Thr Ile
        275                 280                 285

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile His
                325                 330                 335

Gly Tyr Lys Val Ser Pro Asp Gln Leu Ala Glu Ile Thr Asn Glu Leu
            340                 345                 350

Ala Phe Lys Asp Glu Tyr Ala Ala Leu Glu Thr Tyr His Ala Ser Gln
        355                 360                 365

Ile Leu Tyr Gln Glu Asp Leu Ser Ser Gly Lys Gln Ile Leu Lys Ser
    370                 375                 380

Ala Asp Phe Leu Lys Gly Ile Leu Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Tyr Tyr Leu Arg Leu Ala Val Glu Asp Phe Tyr Thr Cys
    450                 455                 460

Gln Ser Ile Tyr Arg Glu Glu Leu Lys Gly Leu Glu Arg Trp Val Val
465                 470                 475                 480

Gln Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
    530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
    610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670
```

```
Asp Ile His Ser Phe Lys Arg Glu Phe Lys Glu Gly Lys Leu Asn Ala
            675                 680                 685

Val Ala Leu His Leu Ser Asn Gly Glu Ser Gly Lys Val Glu Glu
        690                 695                 700

Val Val Glu Glu Met Met Met Met Ile Lys Asn Lys Arg Lys Glu Leu
705                 710                 715                 720

Met Lys Leu Ile Phe Glu Asn Gly Ser Ile Val Pro Arg Ala Cys
                725                 730                 735

Lys Asp Ala Phe Trp Asn Met Cys His Val Leu Asn Phe Phe Tyr Ala
                740                 745                 750

Asn Asp Asp Gly Phe Thr Gly Asn Thr Ile Leu Asp Thr Val Lys Asp
                755                 760                 765

Ile Ile Tyr Asn Pro Leu Val Leu Val Asn Glu Asn Glu Glu Gln Arg
770                 775                 780

<210> SEQ ID NO 29
<211> LENGTH: 590
<212> TYPE: PRT
<213> ORGANISM: Zea mays

<400> SEQUENCE: 29

Met Ala Met Pro Val Lys Leu Thr Pro Ala Ser Leu Ser Leu Lys Ala
1               5                   10                  15

Val Cys Cys Arg Phe Ser Ser Gly Gly His Ala Leu Arg Phe Gly Ser
                20                  25                  30

Ser Leu Pro Cys Trp Arg Arg Thr Pro Thr Gln Arg Ser Thr Ser Ser
            35                  40                  45

Ser Thr Thr Arg Pro Ala Ala Glu Val Ser Ser Gly Lys Ser Lys Gln
    50                  55                  60

His Asp Gln Glu Ala Ser Glu Ala Thr Ile Arg Gln Gln Leu Gln Leu
65                  70                  75                  80

Val Asp Val Leu Glu Asn Met Gly Ile Ser Arg His Phe Ala Ala Glu
                85                  90                  95

Ile Lys Cys Ile Leu Asp Arg Thr Tyr Arg Ser Trp Leu Gln Arg His
                100                 105                 110

Glu Glu Ile Met Leu Asp Thr Met Thr Cys Ala Met Ala Phe Arg Ile
            115                 120                 125

Leu Arg Leu Asn Gly Tyr Asn Val Ser Ser Asp Glu Leu Tyr His Val
        130                 135                 140

Val Glu Ala Ser Gly Leu His Asn Ser Leu Gly Gly Tyr Leu Asn Asp
145                 150                 155                 160

Thr Arg Thr Leu Leu Glu Leu His Lys Ala Ser Thr Val Ser Ile Ser
                165                 170                 175

Glu Asp Glu Ser Ile Leu Asp Ser Ile Gly Ser Arg Ser Arg Thr Leu
            180                 185                 190

Leu Arg Glu Gln Leu Glu Ser Gly Gly Ala Leu Arg Lys Pro Ser Leu
        195                 200                 205

Phe Lys Glu Val Glu His Ala Leu Asp Gly Pro Phe Tyr Thr Thr Leu
    210                 215                 220

Asp Arg Leu His His Arg Trp Asn Ile Glu Asn Phe Asn Ile Ile Glu
225                 230                 235                 240

Gln His Met Leu Glu Thr Pro Tyr Leu Ser Asn Gln His Thr Ser Arg
                245                 250                 255

Asp Ile Leu Ala Leu Ser Ile Arg Asp Phe Ser Ser Ser Gln Phe Thr
            260                 265                 270
```

Tyr Gln Gln Glu Leu Gln His Leu Glu Ser Trp Val Lys Glu Cys Arg
            275                 280                 285

Leu Asp Gln Leu Gln Phe Ala Arg Gln Lys Leu Ala Tyr Phe Tyr Leu
    290                 295                 300

Ser Ala Gly Thr Met Phe Ser Pro Glu Leu Ser Asp Ala Arg Thr
305                 310                 315                 320

Leu Trp Ala Lys Asn Gly Val Leu Thr Thr Ile Val Asp Asp Phe Phe
                325                 330                 335

Asp Val Ala Gly Ser Lys Glu Glu Leu Glu Asn Leu Val Met Leu Val
            340                 345                 350

Glu Met Trp Asp Glu His His Lys Val Glu Phe Tyr Ser Glu Gln Val
            355                 360                 365

Glu Ile Ile Phe Ser Ser Ile Tyr Asp Ser Val Asn Gln Leu Gly Glu
    370                 375                 380

Lys Ala Ser Leu Val Gln Asp Arg Ser Ile Thr Lys His Leu Val Glu
385                 390                 395                 400

Ile Trp Leu Asp Leu Leu Lys Ser Met Met Thr Glu Val Glu Trp Arg
                405                 410                 415

Leu Ser Lys Tyr Val Pro Thr Glu Lys Glu Tyr Met Ile Asn Ala Ser
            420                 425                 430

Leu Ile Phe Gly Leu Gly Pro Ile Val Leu Pro Ala Leu Tyr Phe Val
            435                 440                 445

Gly Pro Lys Ile Ser Glu Ser Ile Val Lys Asp Pro Glu Tyr Asp Glu
    450                 455                 460

Leu Phe Lys Leu Met Ser Thr Cys Gly Arg Leu Leu Asn Asp Val Gln
465                 470                 475                 480

Thr Phe Glu Arg Glu Tyr Asn Glu Gly Lys Leu Asn Ser Val Ser Leu
                485                 490                 495

Leu Val Leu His Gly Pro Met Ser Ile Ser Asp Ala Lys Arg Lys
            500                 505                 510

Leu Gln Lys Pro Ile Asp Thr Cys Arg Arg Asp Leu Leu Ser Leu Val
    515                 520                 525

Leu Arg Glu Glu Ser Val Val Pro Arg Pro Cys Lys Glu Leu Phe Trp
    530                 535                 540

Lys Met Cys Lys Val Cys Tyr Phe Phe Tyr Ser Thr Thr Asp Gly Phe
545                 550                 555                 560

Ser Ser Gln Val Glu Arg Ala Lys Glu Val Asp Ala Val Ile Asn Glu
            565                 570                 575

Pro Leu Lys Leu Gln Gly Ser His Thr Leu Val Ser Asp Val
            580                 585                 590

<210> SEQ ID NO 30
<211> LENGTH: 775
<212> TYPE: PRT
<213> ORGANISM: Populus trichocarpa

<400> SEQUENCE: 30

Met Ser Cys Ile Arg Pro Trp Phe Cys Pro Ser Ser Ile Ser Ala Thr
1               5                   10                  15

Leu Thr Asp Pro Ala Ser Lys Leu Val Thr Gly Glu Phe Lys Thr Thr
            20                  25                  30

Ser Leu Asn Phe His Gly Thr Lys Glu Arg Ile Lys Lys Met Phe Asp
        35                  40                  45

Lys Ile Glu Leu Ser Val Ser Ser Tyr Asp Thr Ala Trp Val Ala Met

```
        50                  55                  60
Val Pro Ser Pro Asp Cys Pro Glu Thr Pro Cys Phe Pro Glu Cys Thr
 65                  70                  75                  80

Lys Trp Ile Leu Glu Asn Gln Leu Gly Asp Gly Ser Trp Ser Leu Pro
                 85                  90                  95

His Gly Asn Pro Leu Leu Val Lys Asp Ala Leu Ser Ser Thr Leu Ala
                100                 105                 110

Cys Ile Leu Ala Leu Lys Arg Trp Gly Ile Gly Glu Glu Gln Ile Asn
                115                 120                 125

Lys Gly Leu Arg Phe Ile Glu Leu Asn Ser Ala Ser Val Thr Asp Asn
            130                 135                 140

Glu Gln His Lys Pro Ile Gly Phe Asp Ile Ile Phe Pro Gly Met Ile
145                 150                 155                 160

Glu Tyr Ala Lys Asp Leu Asp Leu Asn Leu Pro Leu Lys Pro Thr Asp
                165                 170                 175

Ile Asn Ser Met Leu His Arg Arg Ala Leu Glu Leu Thr Ser Gly Gly
                180                 185                 190

Gly Lys Asn Leu Glu Gly Arg Arg Ala Tyr Leu Ala Tyr Val Ser Glu
            195                 200                 205

Gly Ile Gly Lys Leu Gln Asp Trp Glu Met Ala Met Lys Tyr Gln Arg
210                 215                 220

Lys Asn Gly Ser Leu Phe Asn Ser Pro Ser Thr Thr Ala Ala Ala Phe
225                 230                 235                 240

Ile His Ile Gln Asp Ala Glu Cys Leu His Tyr Ile Arg Ser Leu Leu
                245                 250                 255

Gln Lys Phe Gly Asn Ala Val Pro Thr Ile Tyr Pro Leu Asp Ile Tyr
                260                 265                 270

Ala Arg Leu Ser Met Val Asp Ala Leu Glu Arg Leu Gly Ile Asp Arg
            275                 280                 285

His Phe Arg Lys Glu Arg Lys Phe Val Leu Asp Glu Thr Tyr Arg Phe
            290                 295                 300

Trp Leu Gln Gly Glu Glu Ile Phe Ser Asp Asn Ala Thr Cys Ala
305                 310                 315                 320

Leu Ala Phe Arg Ile Leu Arg Leu Asn Gly Tyr Asp Val Ser Leu Glu
                325                 330                 335

Asp His Phe Ser Asn Ser Leu Gly Gly Tyr Leu Lys Asp Ser Gly Ala
                340                 345                 350

Ala Leu Glu Leu Tyr Arg Ala Leu Gln Leu Ser Tyr Pro Asp Glu Ser
            355                 360                 365

Leu Leu Glu Lys Gln Asn Ser Arg Thr Ser Tyr Phe Leu Lys Gln Gly
            370                 375                 380

Leu Ser Asn Val Ser Leu Cys Gly Asp Arg Leu Arg Lys Asn Ile Ile
385                 390                 395                 400

Gly Glu Val His Asp Ala Leu Asn Phe Pro Asp His Ala Asn Leu Gln
                405                 410                 415

Arg Leu Ala Ile Arg Arg Ile Lys His Tyr Ala Thr Asp Asp Thr
                420                 425                 430

Arg Ile Leu Lys Thr Ser Tyr Arg Cys Ser Thr Ile Gly Asn Gln Asp
            435                 440                 445

Phe Leu Lys Leu Ala Val Glu Asp Phe Asn Ile Cys Gln Ser Ile Gln
            450                 455                 460

Arg Glu Glu Phe Lys His Ile Glu Arg Trp Val Val Glu Arg Arg Leu
465                 470                 475                 480
```

Asp Lys Leu Lys Phe Ala Arg Gln Lys Glu Ala Tyr Cys Tyr Phe Ser
             485                 490                 495
Ala Ala Ala Thr Leu Phe Ala Pro Glu Leu Ser Asp Ala Arg Met Ser
         500                 505                 510
Trp Ala Lys Asn Gly Val Leu Thr Thr Val Val Asp Phe Phe Asp
         515                 520                 525
Val Gly Gly Ser Glu Glu Leu Val Asn Leu Ile Glu Leu Ile Glu
    530                 535                 540
Arg Trp Asp Val Asn Gly Ser Ala Asp Phe Cys Ser Glu Glu Val Glu
545                 550                 555                 560
Ile Ile Tyr Ser Ala Ile His Ser Thr Ile Ser Glu Ile Gly Asp Lys
                565                 570                 575
Ser Phe Gly Trp Gln Gly Arg Asp Val Lys Ser His Val Ile Lys Ile
            580                 585                 590
Trp Leu Asp Leu Leu Lys Ser Met Leu Thr Glu Ala Gln Trp Ser Ser
        595                 600                 605
Asn Lys Ser Val Pro Thr Leu Asp Glu Tyr Met Thr Thr Ala His Val
610                 615                 620
Ser Phe Ala Leu Gly Pro Ile Val Leu Pro Ala Leu Tyr Phe Val Gly
625                 630                 635                 640
Pro Lys Leu Ser Glu Glu Val Ala Gly His Pro Glu Leu Leu Asn Leu
                645                 650                 655
Tyr Lys Val Met Ser Thr Cys Gly Arg Leu Leu Asn Asp Trp Arg Ser
            660                 665                 670
Phe Lys Arg Glu Ser Glu Glu Gly Lys Leu Asn Ala Ile Ser Leu Tyr
        675                 680                 685
Met Ile His Ser Gly Gly Ala Ser Thr Glu Glu Glu Thr Ile Glu His
    690                 695                 700
Phe Lys Gly Leu Ile Asp Ser Gln Arg Arg Gln Leu Leu Gln Leu Val
705                 710                 715                 720
Leu Gln Glu Lys Asp Ser Ile Ile Pro Arg Pro Cys Lys Asp Leu Phe
                725                 730                 735
Trp Asn Met Ile Lys Leu Leu His Thr Phe Tyr Met Lys Asp Asp Gly
            740                 745                 750
Phe Thr Ser Asn Glu Met Arg Asn Val Val Lys Ala Ile Ile Asn Glu
        755                 760                 765
Pro Ile Ser Leu Asp Glu Leu
    770                 775

<210> SEQ ID NO 31
<211> LENGTH: 2358
<212> TYPE: DNA
<213> ORGANISM: Artificial Sequence
<220> FEATURE:
<223> OTHER INFORMATION: Synthetic oligonucleotide

<400> SEQUENCE: 31
atgtctatca accttcgctc ctccggttgt tcgtctccga tctcagctac tttggaacga      60
ggattggact cagaagtaca gacaagagct aacaatgtga gctttgagca acaaaggag     120 aagattagga agatgttgga gaaagtggag ctttctgttt cggcctacga tactagttgg     180
gtagcaatgg ttccatcacc gagctcccaa aatgctccac ttttcccaca gtgtgtgaaa     240
tggttattgg ataatcaaca tgaagatgga tcttggggac ttgataacca tgaccatcaa     300
tctcttaaga aggatgtgtt atcatctaca ctggctagta tcctcgcgtt aaagaagtgg     360

```
ggaattggtg aaagacaaat aaacaagggt ctccagttta ttgagctgaa ttctgcatta    420
gtcactgatg aaaccataca gaaaccaaca gggtttgata ttatatttcc tgggatgatt    480
aaatatgcta gagatttgaa tctgacgatt ccattgggct cagaagtggt ggatgacatg    540
atacgaaaaa gagatctgga tcttaaatgt gatagtgaaa agttttcaaa gggaagagaa    600
gcatatctgg cctatgtttt agaggggaca agaaacctaa agattggga tttgatagtc     660 aaatatcaaa ggaaaaatgg gtcactgttt gattctccag ccacaacagc agctgctttt    720
actcagtttg gaatgatgg ttgtctccgt tatctctgtt ctctccttca gaaattcgag      780
gctgcagttc cttcagttta tccatttgat caatatgcac gccttagtat aattgtcact    840
cttgaaagct taggaattga tagagatttc aaaaccgaaa tcaaaagcat attggatgaa    900
acctatagat attggcttcg tggggatgaa gaaatatgtt tggacttggc cacttgtgct    960
ttggctttcc gattattgct tgctcatggc tatgatgtgt cttacgatcc gctaaaacca   1020
tttgcagaag aatctggttt ctctgatact ttggaaggat atgttaagaa tacgttttct   1080
gtgttagaat tatttaaggc tgctcaaagt tatccacatg aatcagcttt gaagaagcag   1140
tgttgttgga ctaaacaata tctggagatg gaattgtcca gctgggttaa gacctctgtt   1200
cgagataaat acctcaagaa agaggtcgag gatgctcttg cttttccctc ctatgcaagc   1260
ctagaaagat cagatcacag gagaaaaata ctcaatggtt ctgctgtgga aaacaccaga   1320
gttacaaaaa cctcatatcg tttgcacaat atttgcacct ctgatatcct gaagttagct   1380
gtggatgact tcaatttctg ccagtccata caccgtgaag aaatggaacg tcttgatagg   1440
tggattgtgg agaatagatt gcaggaactg aaatttgcca gacagaagct ggcttactgt   1500
tatttctctg gggctgcaac tttattttct ccagaactat ctgatgctcg tatatcgtgg   1560
gccaaaggtg gagtacttac aacggttgta gacgacttct tgatgttgg agggtccaaa    1620 gaagaactgg aaaacctcat acacttggtc gaaaagtggg atttgaacgg tgttcctgag   1680
tacagctcag aacatgttga gatcatattc tcagttctaa gggacaccat tctcgaaaca   1740
ggagacaaag cattcaccta tcaaggacgc aatgtgacac accacattgt gaaaatttgg   1800
ttggatctgc tcaagtctat gttgagagaa gccgagtggt ccagtgacaa gtcaacacca   1860
agcttggagg attacatgga aaatgcgtac atatcatttg cattaggacc aattgtcctc   1920
ccagctacct atctgatcgg acctccactt ccagagaaga cagtcgatag ccaccaatat   1980
aatcagctct acaagctcgt gagcactatg ggtcgtcttc taaatgacat acaaggtttt   2040
aagagagaaa gcgcggaagg gaagctgaat gcggtttcat tgcacatgaa acacgagaga   2100
gacaatcgca gcaaagaagt gatcatagaa tcgatgaaag gtttagcaga gagaagagg    2160 gaagaattgc ataagctagt tttggaggag aaaggaagtg tggttccaag ggaatgcaaa   2220
gaagcgttct tgaaaatgag caaagtgttg aacttatttt acaggaagga cgatggattc   2280
acatcaaatg atctgatgag tcttgttaaa tcagtgatct acgagcctgt tagcttacag   2340
aaagaatctt taacttga                                                 2358
```

<210> SEQ ID NO 32
<211> LENGTH: 785
<212> TYPE: PRT
<213> ORGANISM: Arabidopsis thaliana

<400> SEQUENCE: 32

```
Met Ser Ile Asn Leu Arg Ser Ser Gly Cys Ser Ser Pro Ile Ser Ala
1               5                   10                  15
```

```
Thr Leu Glu Arg Gly Leu Asp Ser Glu Val Gln Thr Arg Ala Asn Asn
            20                  25                  30

Val Ser Phe Glu Gln Thr Lys Glu Lys Ile Arg Lys Met Leu Glu Lys
        35                  40                  45

Val Glu Leu Ser Val Ser Ala Tyr Asp Thr Ser Trp Val Ala Met Val
50                  55                  60

Pro Ser Pro Ser Gln Asn Ala Pro Leu Phe Pro Gln Cys Val Lys
65                  70                  75                  80

Trp Leu Leu Asp Asn Gln His Glu Asp Gly Ser Trp Gly Leu Asp Asn
                85                  90                  95

His Asp His Gln Ser Leu Lys Lys Asp Val Leu Ser Ser Thr Leu Ala
            100                 105                 110

Ser Ile Leu Ala Leu Lys Lys Trp Gly Ile Gly Glu Arg Gln Ile Asn
        115                 120                 125

Lys Gly Leu Gln Phe Ile Glu Leu Asn Ser Ala Leu Val Thr Asp Glu
130                 135                 140

Thr Ile Gln Lys Pro Thr Gly Phe Asp Ile Ile Phe Pro Gly Met Ile
145                 150                 155                 160

Lys Tyr Ala Arg Asp Leu Asn Leu Thr Ile Pro Leu Gly Ser Glu Val
                165                 170                 175

Val Asp Asp Met Ile Arg Lys Arg Asp Leu Asp Leu Lys Cys Asp Ser
            180                 185                 190

Glu Lys Phe Ser Lys Gly Arg Glu Ala Tyr Leu Ala Tyr Val Leu Glu
        195                 200                 205

Gly Thr Arg Asn Leu Lys Asp Trp Asp Leu Ile Val Lys Tyr Gln Arg
210                 215                 220

Lys Asn Gly Ser Leu Phe Asp Ser Pro Ala Thr Thr Ala Ala Ala Phe
225                 230                 235                 240

Thr Gln Phe Gly Asn Asp Gly Cys Leu Arg Tyr Leu Cys Ser Leu Leu
                245                 250                 255

Gln Lys Phe Glu Ala Ala Val Pro Ser Val Tyr Pro Phe Asp Gln Tyr
            260                 265                 270

Ala Arg Leu Ser Ile Ile Val Thr Leu Glu Ser Leu Gly Ile Asp Arg
        275                 280                 285

Asp Phe Lys Thr Glu Ile Lys Ser Ile Leu Asp Glu Thr Tyr Arg Tyr
290                 295                 300

Trp Leu Arg Gly Asp Glu Glu Ile Cys Leu Asp Leu Ala Thr Cys Ala
305                 310                 315                 320

Leu Ala Phe Arg Leu Leu Ala His Gly Tyr Asp Val Ser Tyr Asp
                325                 330                 335

Pro Leu Lys Pro Phe Ala Glu Ser Gly Phe Ser Asp Thr Leu Glu
            340                 345                 350

Gly Tyr Val Lys Asn Thr Phe Ser Val Leu Glu Leu Phe Lys Ala Ala
        355                 360                 365

Gln Ser Tyr Pro His Glu Ser Ala Leu Lys Lys Gln Cys Cys Trp Thr
370                 375                 380

Lys Gln Tyr Leu Glu Met Glu Leu Ser Ser Trp Val Lys Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Arg Lys Ile Leu Asn
            420                 425                 430
```

```
Gly Ser Ala Val Glu Asn Thr Arg Val Thr Lys Thr Ser Tyr Arg Leu
            435                 440                 445

His Asn Ile Cys Thr Ser Asp Ile Leu Lys Leu Ala Val Asp Asp Phe
450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
                485                 490                 495

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Gly Val Leu Thr Thr
        515                 520                 525

Val Val Asp Asp Phe Phe Asp Val Gly Gly Ser Lys Glu Glu Leu Glu
    530                 535                 540

Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
                565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
        595                 600                 605

Arg Glu Ala Glu Trp Ser Ser Asp Lys Ser Thr Pro Ser Leu Glu Asp
    610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
                645                 650                 655

Ser His Gln Tyr Asn Gln Leu Tyr Lys Leu Val Ser Thr Met Gly Arg
            660                 665                 670

Leu Leu Asn Asp Ile Gln Gly Phe Lys Arg Glu Ser Ala Glu Gly Lys
        675                 680                 685

Leu Asn Ala Val Ser Leu His Met Lys His Glu Arg Asp Asn Arg Ser
    690                 695                 700

Lys Glu Val Ile Ile Glu Ser Met Lys Gly Leu Ala Glu Arg Lys Arg
705                 710                 715                 720

Glu Glu Leu His Lys Leu Val Leu Glu Glu Lys Gly Ser Val Val Pro
                725                 730                 735

Arg Glu Cys Lys Glu Ala Phe Leu Lys Met Ser Lys Val Leu Asn Leu
            740                 745                 750

Phe Tyr Arg Lys Asp Asp Gly Phe Thr Ser Asn Asp Leu Met Ser Leu
        755                 760                 765

Val Lys Ser Val Ile Tyr Glu Pro Val Ser Leu Gln Lys Glu Ser Leu
    770                 775                 780

Thr
785

<210> SEQ ID NO 33
<211> LENGTH: 513
<212> TYPE: PRT
<213> ORGANISM: Stevia rebaudiana

<400> SEQUENCE: 33

Met Asp Ala Val Thr Gly Leu Leu Thr Val Pro Ala Thr Ala Ile Thr
1               5                   10                  15
```

```
Ile Gly Gly Thr Ala Val Ala Leu Ala Val Ala Leu Ile Phe Trp Tyr
             20                  25                  30

Leu Lys Ser Tyr Thr Ser Ala Arg Arg Ser Gln Ser Asn His Leu Pro
         35                  40                  45

Arg Val Pro Glu Val Pro Gly Val Pro Leu Leu Gly Asn Leu Leu Gln
     50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                 85                  90                  95

Val Ser Ser Asn Glu Ile Ala Lys Glu Ala Leu Val Thr Arg Phe Gln
             100                 105                 110

Ser Ile Ser Thr Arg Asn Leu Ser Lys Ala Leu Lys Val Leu Thr Ala
         115                 120                 125

Asp Lys Thr Met Val Ala Met Ser Asp Tyr Asp Tyr His Lys Thr
     130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                 165                 170                 175

Leu His Glu Phe Val Lys Asn Asn Pro Glu Gln Glu Val Asp Leu
             180                 185                 190

Arg Lys Ile Phe Gln Ser Glu Leu Phe Gly Leu Ala Met Arg Gln Ala
         195                 200                 205

Leu Gly Lys Asp Val Glu Ser Leu Tyr Val Glu Asp Leu Lys Ile Thr
     210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                 245                 250                 255

Val Pro Asn Lys Lys Phe Glu Asn Thr Ile Gln Gln Met Tyr Ile Arg
             260                 265                 270

Arg Glu Ala Val Met Lys Ser Leu Ile Lys Glu His Lys Lys Arg Ile
         275                 280                 285

Ala Ser Gly Glu Lys Leu Asn Ser Tyr Ile Asp Tyr Leu Leu Ser Glu
     290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                 325                 330                 335

Tyr Glu Leu Ala Lys Asn Pro Lys Leu Gln Asp Arg Leu Tyr Arg Asp
             340                 345                 350

Ile Lys Ser Val Cys Gly Ser Glu Lys Ile Thr Glu Glu His Leu Ser
         355                 360                 365

Gln Leu Pro Tyr Ile Thr Ala Ile Phe His Glu Thr Leu Arg Arg His
     370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                 405                 410                 415

Tyr Gly Cys Asn Met Asp Lys Asn Val Trp Glu Asn Pro Glu Glu Trp
             420                 425                 430
```

```
Asn Pro Glu Arg Phe Met Lys Glu Asn Glu Thr Ile Asp Phe Gln Lys
            435                 440                 445

Thr Met Ala Phe Gly Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
                500                 505                 510

Ile

<210> SEQ ID NO 34
<211> LENGTH: 509
<212> TYPE: PRT
<213> ORGANISM: Arabidopsis thaliana

<400> SEQUENCE: 34

Met Ala Phe Phe Ser Met Ile Ser Ile Leu Leu Gly Phe Val Ile Ser
1               5                   10                  15

Ser Phe Ile Phe Ile Phe Phe Lys Lys Leu Leu Ser Phe Ser Arg
                20                  25                  30

Lys Asn Met Ser Glu Val Ser Thr Leu Pro Ser Val Pro Val Val Pro
                35                  40                  45

Gly Phe Pro Val Ile Gly Asn Leu Leu Gln Leu Lys Glu Lys Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
                100                 105                 110

Leu Ser Asn Ala Leu Thr Val Leu Thr Cys Asp Lys Ser Met Val Ala
            115                 120                 125

Thr Ser Asp Tyr Asp Asp Phe His Lys Leu Val Lys Arg Cys Leu Leu
            130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
            275                 280                 285
```

```
Cys Tyr Leu Asn Phe Leu Met Ser Glu Ala Lys Thr Leu Thr Lys Glu
            290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Gln Leu Ser Gln Val Pro Tyr Leu Asn Gly
            355                 360                 365

Val Phe His Glu Thr Leu Arg Lys Tyr Ser Pro Ala Pro Leu Val Pro
370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Pro Glu Arg Phe Leu Asp
            420                 425                 430

Asp Gly Lys Tyr Glu Thr Ser Asp Leu His Lys Thr Met Ala Phe Gly
            435                 440                 445

Ala Gly Lys Arg Val Cys Ala Gly Ala Leu Gln Ala Ser Leu Met Ala
450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
            500                 505

<210> SEQ ID NO 35
<211> LENGTH: 525
<212> TYPE: PRT
<213> ORGANISM: Fusarium fujikuroi

<400> SEQUENCE: 35

Met Ser Lys Ser Asn Ser Met Asn Ser Thr Ser His Glu Thr Leu Phe
1               5                   10                  15

Gln Gln Leu Val Leu Gly Leu Asp Arg Met Pro Leu Met Asp Val His
            20                  25                  30

Trp Leu Ile Tyr Val Ala Phe Gly Ala Trp Leu Cys Ser Tyr Val Ile
            35                  40                  45

His Val Leu Ser Ser Ser Thr Val Lys Val Pro Val Val Gly Tyr
        50                  55                  60

Arg Ser Val Phe Glu Pro Thr Trp Leu Leu Arg Leu Arg Phe Val Trp
65                  70                  75                  80

Glu Gly Gly Ser Ile Ile Gly Gln Gly Tyr Asn Lys Phe Lys Asp Ser
                85                  90                  95

Ile Phe Gln Val Arg Lys Leu Gly Thr Asp Ile Val Ile Pro Pro
            100                 105                 110

Asn Tyr Ile Asp Glu Val Arg Lys Leu Ser Gln Asp Lys Thr Arg Ser
            115                 120                 125

Val Glu Pro Phe Ile Asn Asp Phe Ala Gly Gln Tyr Thr Arg Gly Met
    130                 135                 140

Val Phe Leu Gln Ser Asp Leu Gln Asn Arg Val Ile Gln Gln Arg Leu
145                 150                 155                 160
```

Thr Pro Lys Leu Val Ser Leu Thr Lys Val Met Lys Glu Glu Leu Asp
            165                 170                 175

Tyr Ala Leu Thr Lys Glu Met Pro Asp Met Lys Asn Asp Glu Trp Val
            180                 185                 190

Glu Val Asp Ile Ser Ser Ile Met Val Arg Leu Ile Ser Arg Ile Ser
            195                 200                 205

Ala Arg Val Phe Leu Gly Pro Glu His Cys Arg Asn Gln Glu Trp Leu
            210                 215                 220

Thr Thr Thr Ala Glu Tyr Ser Glu Ser Leu Phe Ile Thr Gly Phe Ile
225                 230                 235                 240

Leu Arg Val Val Pro His Ile Leu Arg Pro Phe Ile Ala Pro Leu Leu
            245                 250                 255

Pro Ser Tyr Arg Thr Leu Leu Arg Asn Val Ser Ser Gly Arg Arg Val
            260                 265                 270

Ile Gly Asp Ile Ile Arg Ser Gln Gln Gly Asp Gly Asn Glu Asp Ile
            275                 280                 285

Leu Ser Trp Met Arg Asp Ala Ala Thr Gly Glu Glu Lys Gln Ile Asp
            290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Cys Pro
            325                 330                 335

Glu Tyr Ile Glu Pro Leu Arg Asp Glu Val Lys Ser Val Val Gly Ala
            340                 345                 350

Ser Gly Trp Asp Lys Thr Ala Leu Asn Arg Phe His Lys Leu Asp Ser
            355                 360                 365

Phe Leu Lys Glu Ser Gln Arg Phe Asn Pro Val Phe Leu Leu Thr Phe
            370                 375                 380

Asn Arg Ile Tyr His Gln Ser Met Thr Leu Ser Asp Gly Thr Asn Ile
385                 390                 395                 400

Pro Ser Gly Thr Arg Ile Ala Val Pro Ser His Ala Met Leu Gln Asp
            405                 410                 415

Ser Ala His Val Pro Gly Pro Thr Pro Pro Thr Glu Phe Asp Gly Phe
            420                 425                 430

Arg Tyr Ser Lys Ile Arg Ser Asp Ser Asn Tyr Ala Gln Lys Tyr Leu
            435                 440                 445

Phe Ser Met Thr Asp Ser Ser Asn Met Ala Phe Gly Tyr Gly Lys Tyr
            450                 455                 460

Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
            485                 490                 495

Arg Pro Arg Asn Ile Thr Ile Asp Ser Asp Met Ile Pro Asp Pro Arg
            500                 505                 510

Ala Arg Leu Cys Val Arg Lys Arg Ser Leu Arg Asp Glu
            515                 520                 525

<210> SEQ ID NO 36
<211> LENGTH: 499
<212> TYPE: PRT
<213> ORGANISM: Trametes versicolor

<400> SEQUENCE: 36

Met Glu Asp Pro Thr Val Leu Tyr Ala Cys Leu Ala Ile Ala Val Ala

```
              1               5                    10                   15
        Thr Phe Val Val Arg Trp Tyr Arg Asp Pro Leu Arg Ser Ile Pro Thr
                        20                  25                  30

Val Gly Gly Ser Asp Leu Pro Ile Leu Ser Tyr Ile Gly Ala Leu Arg
                        35                  40                  45

Trp Thr Arg Arg Gly Arg Glu Ile Leu Gln Glu Gly Tyr Asp Gly Tyr
                        50                  55                  60

Arg Gly Ser Thr Phe Lys Ile Ala Met Leu Asp Arg Trp Ile Val Ile
        65                  70                  75                  80

Ala Asn Gly Pro Lys Leu Ala Asp Glu Val Arg Arg Pro Asp Glu
                        85                  90                  95

Glu Leu Asn Phe Met Asp Gly Leu Gly Ala Phe Val Gln Thr Lys Tyr
                        100                 105                 110

Thr Leu Gly Glu Ala Ile His Asn Asp Pro Tyr His Val Asp Ile Ile
                        115                 120                 125

Arg Glu Lys Leu Thr Arg Gly Leu Pro Ala Val Leu Pro Asp Val Ile
                        130                 135                 140

Glu Glu Leu Thr Leu Ala Val Arg Gln Tyr Ile Pro Thr Glu Gly Asp
        145                 150                 155                 160

Glu Trp Val Ser Val Asn Cys Ser Lys Ala Ala Arg Asp Ile Val Ala
                        165                 170                 175

Arg Ala Ser Asn Arg Val Phe Val Gly Leu Pro Ala Cys Arg Asn Gln
                        180                 185                 190

Gly Tyr Leu Asp Leu Ala Ile Asp Phe Thr Leu Ser Val Val Lys Asp
                        195                 200                 205

Arg Ala Ile Ile Asn Met Phe Pro Glu Leu Leu Lys Pro Ile Val Gly
        210                 215                 220

Arg Val Val Gly Asn Ala Thr Arg Asn Val Arg Arg Ala Val Pro Phe
        225                 230                 235                 240

Val Ala Pro Leu Val Glu Glu Arg Arg Arg Leu Met Glu Glu Tyr Gly
                        245                 250                 255

Glu Asp Trp Ser Glu Lys Pro Asn Asp Met Leu Gln Trp Ile Met Asp
                        260                 265                 270

Glu Ala Ala Ser Arg Asp Ser Ser Val Lys Ala Ile Ala Glu Arg Leu
                        275                 280                 285

Leu Met Val Asn Phe Ala Ala Ile His Thr Ser Ser Asn Thr Ile Thr
                        290                 295                 300

His Ala Leu Tyr His Leu Ala Glu Met Pro Glu Thr Leu Gln Pro Leu
        305                 310                 315                 320

Arg Glu Glu Ile Glu Pro Leu Val Lys Glu Glu Gly Trp Thr Lys Ala
                        325                 330                 335

Ala Met Gly Lys Met Trp Trp Leu Asp Ser Phe Leu Arg Glu Ser Gln
                        340                 345                 350

Arg Tyr Asn Gly Ile Asn Ile Val Ser Leu Thr Arg Met Ala Asp Lys
                        355                 360                 365

Asp Ile Thr Leu Ser Asp Gly Thr Phe Leu Pro Lys Gly Thr Leu Val
        370                 375                 380

Ala Val Pro Ala Tyr Ser Thr His Arg Asp Ala Val Tyr Ala Asp
        385                 390                 395                 400

Ala Leu Val Phe Asp Pro Phe Arg Phe Ser Arg Met Arg Ala Arg Glu
                        405                 410                 415

Gly Glu Gly Thr Lys His Gln Phe Val Asn Thr Ser Val Glu Tyr Val
                        420                 425                 430
```

```
Pro Phe Gly His Gly Lys His Ala Cys Pro Gly Arg Phe Phe Ala Ala
        435                 440                 445

Asn Glu Leu Lys Ala Met Leu Ala Tyr Ile Val Leu Asn Tyr Asp Val
    450                 455                 460

Lys Leu Pro Gly Asp Gly Lys Arg Pro Leu Asn Met Tyr Trp Gly Pro
465                 470                 475                 480

Thr Val Leu Pro Ala Pro Ala Gly Gln Val Leu Phe Arg Lys Arg Gln
            485                 490                 495

Val Ser Leu

<210> SEQ ID NO 37
<211> LENGTH: 1678
<212> TYPE: DNA
<213> ORGANISM: Artificial Sequence
<220> FEATURE:
<223> OTHER INFORMATION: Synthetic oligonucleotide

<400> SEQUENCE: 37
```

| | |
|---|---|
| aaacaaagaa tgattcaagt tctaacaccg atccttctct tcctcatttt cttcgttttc | 60 |
| tggaaggttt acaagcacca gaaaaccaaa atcaatcttc caccgggaag cttcggatgg | 120 |
| ccatttctgg gcgaaactct ggcactccta cgtgcaggtt gggactcaga gccggagaga | 180 |
| tttgttcgtg aacggatcaa gaaacacgga agtcctctag tgtttaagac gtcgttgttt | 240 |
| ggcgaccgtt ttgcggtgtt gtgtggacct gccggaaaca agttcctgtt ctgcaacgag | 300 |
| aacaagctgg tggcgtcgtg gtggccggtt ccggtgagga agcttttcgg caagtctctg | 360 |
| ctcacgattc gtggtgatga agctaagtgg atgaggaaga tgttgttatc gtatctcggt | 420 |
| cctgatgctt tcgcaactca ttatgccgtc accatggacg tcgtcacccg tcggcatatc | 480 |
| gacgttcatt ggcgagggaa ggagaggtg aacgtattcc aaaccgttaa gttatatgcc | 540 |
| tttgagcttg catgtcgttt attcatgaac ctagacgacc caaaccacat tgcaaaactc | 600 |
| ggttccttgt tcaacatttt cttgaaaggc atcattgagc ttccaatcga cgtcccaggg | 660 |
| acacgatttt atagctccaa aaaagcagca gcagctatca ggattgaact aaaaaaattg | 720 |
| attaaagcaa gaaaactgga actgaaagaa gggaaggcat catcttcaca agacctctta | 780 |
| tcacatttgc ttacatctcc agatgaaaat ggtatgtttc taaccgaaga agagattgta | 840 |
| gacaacatct tgttactact ctttgcgggt catgataccc cggctctttc aatcactttg | 900 |
| ctcatgaaga ctcttggcga acattctgat gtttatgaca aggtgttaaa agagcaacta | 960 |
| gagatatcga agacgaaaga agcatgggag tccctgaaat gggaggacat acaaaagatg | 1020 |
| aaatactcct ggagtgttat atgtgaagtc atgagactaa atccacctgt tataggaacc | 1080 |
| tatagagagg cccttgtgga tattgattat gcgggttata ccatccccaa aggatggaag | 1140 |
| ctgcactgga gtgctgtatc gacacaaagg gacgaggcta actttgaaga cgtaacacgt | 1200 |
| tttgacccat cacggtttga aggcgcagga ccgactccat tcacctttgt tccgtttgga | 1260 |
| gggggccta gaatgtgttt agggaaagaa tttgctcgat tggaagtact tgcgtttctt | 1320 |
| cacaatattg tcaccaattt caaatgggac ctgttgatac ctgatgagaa aatagaatat | 1380 |
| gatcccatgg ctaccccagc aaagggggctt ccaattcgtc ttcatcccca tcaagtttga | 1440 |
| ttacttcaag catgaatcag tgatgtgaag gtaaaccata atggatctta ttggtagtta | 1500 |
| cagattatgt gttttatgg catgaagaag ttatgataaa taaaattgtg ttattctaca | 1560 |
| acttatgtaa tttgtgcctg taagtaactg aatctattaa tgttttatgt gacatgaaac | 1620 |

-continued ataaatgtat aattagtaaa ttttctgctc aaaaaaaaaa aaaaaaaaaa aaaaaaa    1678

<210> SEQ ID NO 38
<211> LENGTH: 476
<212> TYPE: PRT
<213> ORGANISM: Stevia rebaudiana

<400> SEQUENCE: 38

Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
            20                  25                  30

Gly Ser Phe Gly Trp Pro Phe Leu Gly Glu Thr Leu Ala Leu Leu Arg
        35                  40                  45

Ala Gly Trp Asp Ser Glu Pro Glu Arg Phe Val Arg Glu Arg Ile Lys
    50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
            100                 105                 110

Phe Gly Lys Ser Leu Leu Thr Ile Arg Gly Asp Glu Ala Lys Trp Met
        115                 120                 125

Arg Lys Met Leu Leu Ser Tyr Leu Gly Pro Asp Ala Phe Ala Thr His
    130                 135                 140

Tyr Ala Val Thr Met Asp Val Val Thr Arg Arg His Ile Asp Val His
145                 150                 155                 160

Trp Arg Gly Lys Glu Glu Val Asn Val Phe Gln Thr Val Lys Leu Tyr
                165                 170                 175

Ala Phe Glu Leu Ala Cys Arg Leu Phe Met Asn Leu Asp Asp Pro Asn
            180                 185                 190

His Ile Ala Lys Leu Gly Ser Leu Phe Asn Ile Phe Leu Lys Gly Ile
        195                 200                 205

Ile Glu Leu Pro Ile Asp Val Pro Gly Thr Arg Phe Tyr Ser Ser Lys
    210                 215                 220

Lys Ala Ala Ala Ile Arg Ile Glu Leu Lys Lys Leu Ile Lys Ala
225                 230                 235                 240

Arg Lys Leu Glu Leu Lys Glu Gly Lys Ala Ser Ser Gln Asp Leu
                245                 250                 255

Leu Ser His Leu Leu Thr Ser Pro Asp Glu Asn Gly Met Phe Leu Thr
            260                 265                 270

Glu Glu Glu Ile Val Asp Asn Ile Leu Leu Leu Phe Ala Gly His
        275                 280                 285

Asp Thr Ser Ala Leu Ser Ile Thr Leu Leu Met Lys Thr Leu Gly Glu
    290                 295                 300

His Ser Asp Val Tyr Asp Lys Val Leu Lys Glu Gln Leu Glu Ile Ser
305                 310                 315                 320

Lys Thr Lys Glu Ala Trp Glu Ser Leu Lys Trp Glu Asp Ile Gln Lys
                325                 330                 335

Met Lys Tyr Ser Trp Ser Val Ile Cys Glu Val Met Arg Leu Asn Pro
            340                 345                 350

Pro Val Ile Gly Thr Tyr Arg Glu Ala Leu Val Asp Ile Asp Tyr Ala
        355                 360                 365

```
Gly Tyr Thr Ile Pro Lys Gly Trp Lys Leu His Trp Ser Ala Val Ser
    370             375                 380

Thr Gln Arg Asp Glu Ala Asn Phe Glu Asp Val Thr Arg Phe Asp Pro
385                 390                 395                 400

Ser Arg Phe Glu Gly Ala Gly Pro Thr Pro Phe Thr Phe Val Pro Phe
                405                 410                 415

Gly Gly Gly Pro Arg Met Cys Leu Gly Lys Glu Phe Ala Arg Leu Glu
            420                 425                 430

Val Leu Ala Phe Leu His Asn Ile Val Thr Asn Phe Lys Trp Asp Leu
                435                 440                 445

Leu Ile Pro Asp Glu Lys Ile Glu Tyr Asp Pro Met Ala Thr Pro Ala
        450                 455                 460

Lys Gly Leu Pro Ile Arg Leu His Pro His Gln Val
465                 470                 475
```

<210> SEQ ID NO 39
<211> LENGTH: 476
<212> TYPE: PRT
<213> ORGANISM: Stevia rebaudiana

<400> SEQUENCE: 39

```
Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
                20                  25                  30

Gly Ser Phe Gly Trp Pro Phe Leu Gly Glu Thr Leu Ala Leu Leu Arg
            35                  40                  45

Ala Gly Trp Asp Ser Glu Pro Glu Arg Phe Val Arg Glu Arg Ile Lys
    50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
            100                 105                 110

Phe Gly Lys Ser Leu Leu Thr Ile Arg Gly Asp Glu Ala Lys Trp Met
        115                 120                 125

Arg Lys Met Leu Leu Ser Tyr Leu Gly Pro Asp Ala Phe Ala Thr His
    130                 135                 140

Tyr Ala Val Thr Met Asp Val Val Thr Arg Arg His Ile Asp Val His
145                 150                 155                 160

Trp Arg Gly Lys Glu Glu Val Asn Val Phe Gln Thr Val Lys Leu Tyr
                165                 170                 175

Ala Phe Glu Leu Ala Cys Arg Leu Phe Met Asn Leu Asp Asp Pro Asn
            180                 185                 190

His Ile Ala Lys Leu Gly Ser Leu Phe Asn Ile Phe Leu Lys Gly Ile
        195                 200                 205

Ile Glu Leu Pro Ile Asp Val Pro Gly Thr Arg Phe Tyr Ser Ser Lys
    210                 215                 220

Lys Ala Ala Ala Ala Ile Arg Ile Glu Leu Lys Lys Leu Ile Lys Ala
225                 230                 235                 240

Arg Lys Leu Glu Leu Lys Glu Gly Lys Ala Ser Ser Ser Gln Asp Leu
                245                 250                 255

Leu Ser His Leu Leu Thr Ser Pro Asp Glu Asn Gly Met Phe Leu Thr
            260                 265                 270
```

```
Glu Glu Glu Ile Val Asp Asn Ile Leu Leu Leu Phe Ala Gly His
            275                 280                 285

Asp Thr Ser Ala Leu Ser Ile Thr Leu Leu Met Lys Thr Leu Gly Glu
290                 295                 300

His Ser Asp Val Tyr Asp Lys Val Leu Lys Glu Gln Leu Glu Ile Ser
305                 310                 315                 320

Lys Thr Lys Glu Ala Trp Glu Ser Leu Lys Trp Glu Asp Ile Gln Lys
                325                 330                 335

Met Lys Tyr Ser Trp Ser Val Ile Cys Glu Val Met Arg Leu Asn Pro
            340                 345                 350

Pro Val Ile Gly Thr Tyr Arg Glu Ala Leu Val Asp Ile Asp Tyr Ala
        355                 360                 365

Gly Tyr Thr Ile Pro Lys Gly Trp Lys Leu His Trp Ser Ala Val Ser
    370                 375                 380

Thr Gln Arg Asp Glu Ala Asn Phe Glu Asp Val Thr Arg Phe Asp Pro
385                 390                 395                 400

Ser Arg Phe Glu Gly Ala Gly Pro Thr Pro Phe Thr Phe Val Pro Phe
                405                 410                 415

Gly Gly Gly Pro Arg Met Cys Leu Gly Lys Glu Phe Ala Arg Leu Glu
            420                 425                 430

Val Leu Ala Phe Leu His Asn Ile Val Thr Asn Phe Lys Trp Asp Leu
435                 440                 445

Leu Ile Pro Asp Glu Lys Ile Glu Tyr Asp Pro Met Ala Thr Pro Ala
        450                 455                 460

Lys Gly Leu Pro Ile Arg Leu His Pro His Gln Val
465                 470                 475

<210> SEQ ID NO 40
<211> LENGTH: 525
<212> TYPE: PRT
<213> ORGANISM: Arabidopsis thaliana

<400> SEQUENCE: 40

Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Pro Ser Ile Phe Asn Gly Asn Val Ser Glu Met Gln Arg
50                  55                  60

Ile Gln Ser Glu Ala Lys His Cys Ser Gly Asp Asn Ile Ile Ser His
65                  70                  75                  80

Asp Tyr Ser Ser Ser Leu Phe Pro His Phe Asp His Trp Arg Lys Gln
                85                  90                  95

Tyr Gly Arg Ile Tyr Thr Tyr Ser Thr Gly Leu Lys Gln His Leu Tyr
            100                 105                 110

Ile Asn His Pro Glu Met Val Lys Glu Leu Ser Gln Thr Asn Thr Leu
        115                 120                 125

Asn Leu Gly Arg Ile Thr His Ile Thr Lys Arg Leu Asn Pro Ile Leu
130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
```

```
              165                 170                 175
Gly Leu Met Val Glu Ser Ala Met Pro Met Leu Asn Lys Trp Glu Glu
            180                 185                 190

Met Val Lys Arg Gly Gly Glu Met Gly Cys Asp Ile Arg Val Asp Glu
            195                 200                 205

Asp Leu Lys Asp Val Ser Ala Asp Val Ile Ala Lys Ala Cys Phe Gly
            210                 215                 220

Ser Ser Phe Ser Lys Gly Lys Ala Ile Phe Ser Met Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
            275                 280                 285

Arg Glu Ile Glu Cys Lys Asp Thr His Lys Lys Asp Leu Met Gln Leu
            290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Val Lys Ile Arg Asp Glu Ile Leu
            355                 360                 365

Ser Ser Cys Lys Asn Gly Ile Pro Asp Ala Glu Ser Ile Pro Asn Leu
370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
            405                 410                 415

Leu Val Val Pro Lys Gly Val Cys Ile Trp Thr Leu Ile Pro Ala Leu
            420                 425                 430

His Arg Asp Pro Glu Ile Trp Gly Pro Asp Ala Asn Asp Phe Lys Pro
            435                 440                 445

Glu Arg Phe Ser Glu Gly Ile Ser Lys Ala Cys Lys Tyr Pro Gln Ser
            450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
            485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
            515                 520                 525

<210> SEQ ID NO 41
<211> LENGTH: 526
<212> TYPE: PRT
<213> ORGANISM: Vitis vinifera

<400> SEQUENCE: 41

Met Tyr Phe Leu Leu Gln Tyr Leu Asn Ile Thr Thr Val Gly Val Phe
1               5                   10                  15
```

-continued

```
Ala Thr Leu Phe Leu Ser Tyr Cys Leu Leu Trp Arg Ser Arg Ala
            20                  25                  30
Gly Asn Lys Lys Ile Ala Pro Glu Ala Ala Ala Trp Pro Ile Ile
         35                  40                  45
Gly His Leu His Leu Leu Ala Gly Gly Ser His Gln Leu Pro His Ile
     50                  55                  60
Thr Leu Gly Asn Met Ala Asp Lys Tyr Gly Pro Val Phe Thr Ile Arg
 65                  70                  75                  80
Ile Gly Leu His Arg Ala Val Val Ser Ser Trp Glu Met Ala Lys
                 85                  90                  95
Glu Cys Ser Thr Ala Asn Asp Gln Val Ser Ser Ser Arg Pro Glu Leu
                100                 105                 110
Leu Ala Ser Lys Leu Leu Gly Tyr Asn Tyr Ala Met Phe Gly Phe Ser
            115                 120                 125
Pro Tyr Gly Ser Tyr Trp Arg Glu Met Arg Lys Ile Ile Ser Leu Glu
    130                 135                 140
Leu Leu Ser Asn Ser Arg Leu Glu Leu Leu Lys Asp Val Arg Ala Ser
145                 150                 155                 160
Glu Val Val Thr Ser Ile Lys Glu Leu Tyr Lys Leu Trp Ala Glu Lys
                165                 170                 175
Lys Asn Glu Ser Gly Leu Val Ser Val Glu Met Lys Gln Trp Phe Gly
            180                 185                 190
Asp Leu Thr Leu Asn Val Ile Leu Arg Met Val Ala Gly Lys Arg Tyr
        195                 200                 205
Phe Ser Ala Ser Asp Ala Ser Glu Asn Lys Gln Ala Gln Arg Cys Arg
    210                 215                 220
Arg Val Phe Arg Glu Phe Phe His Leu Ser Gly Leu Phe Val Val Ala
225                 230                 235                 240
Asp Ala Ile Pro Phe Leu Gly Trp Leu Asp Trp Gly Arg His Glu Lys
                245                 250                 255
Thr Leu Lys Lys Thr Ala Ile Glu Met Asp Ser Ile Ala Gln Glu Trp
            260                 265                 270
Leu Glu Glu His Arg Arg Arg Lys Asp Ser Gly Asp Asp Asn Ser Thr
        275                 280                 285
Gln Asp Phe Met Asp Val Met Gln Ser Val Leu Asp Gly Lys Asn Leu
    290                 295                 300
Gly Gly Tyr Asp Ala Asp Thr Ile Asn Lys Ala Thr Cys Leu Thr Leu
305                 310                 315                 320
Ile Ser Gly Gly Ser Asp Thr Thr Val Val Ser Leu Thr Trp Ala Leu
                325                 330                 335
Ser Leu Val Leu Asn Asn Arg Asp Thr Leu Lys Lys Ala Gln Glu Glu
            340                 345                 350
Leu Asp Ile Gln Val Gly Lys Glu Arg Leu Val Asn Glu Gln Asp Ile
        355                 360                 365
Ser Lys Leu Val Tyr Leu Gln Ala Ile Val Lys Glu Thr Leu Arg Leu
    370                 375                 380
Tyr Pro Pro Gly Pro Leu Gly Gly Leu Arg Gln Phe Thr Glu Asp Cys
385                 390                 395                 400
Thr Leu Gly Gly Tyr His Val Ser Lys Gly Thr Arg Leu Ile Met Asn
                405                 410                 415
Leu Ser Lys Ile Gln Lys Asp Pro Arg Ile Trp Ser Asp Pro Thr Glu
            420                 425                 430
Phe Gln Pro Glu Arg Phe Leu Thr Thr His Lys Asp Val Asp Pro Arg
```

```
            435                 440                 445
Gly Lys His Phe Glu Phe Ile Pro Phe Gly Ala Gly Arg Arg Ala Cys
        450                 455                 460

Pro Gly Ile Thr Phe Gly Leu Gln Val Leu His Leu Thr Leu Ala Ser
465                 470                 475                 480

Phe Leu His Ala Phe Glu Phe Ser Thr Pro Ser Asn Glu Gln Val Asn
                485                 490                 495

Met Arg Glu Ser Leu Gly Leu Thr Asn Met Lys Ser Thr Pro Leu Glu
                500                 505                 510

Val Leu Ile Ser Pro Arg Leu Ser Ser Cys Ser Leu Tyr Asn
            515                 520                 525

<210> SEQ ID NO 42
<211> LENGTH: 479
<212> TYPE: PRT
<213> ORGANISM: Medicago truncatula

<400> SEQUENCE: 42

Met Glu Pro Asn Phe Tyr Leu Ser Leu Leu Leu Phe Val Thr Phe
1               5                   10                  15  Phe

Ile Ser Leu Ser Leu Phe Phe Ile Phe Tyr Lys Gln Lys Ser Pro Leu
            20                  25                  30

Asn Leu Pro Pro Gly Lys Met Gly Tyr Pro Ile Ile Gly Glu Ser Leu
        35                  40                  45

Glu Phe Leu Ser Thr Gly Trp Lys Gly His Pro Glu Lys Phe Ile Phe
    50                  55                  60

Asp Arg Met Arg Lys Tyr Ser Ser Glu Leu Phe Lys Thr Ser Ile Val
65                  70                  75                  80

Gly Glu Ser Thr Val Val Cys Cys Gly Ala Ala Ser Asn Lys Phe Leu
                85                  90                  95

Phe Ser Asn Glu Asn Lys Leu Val Thr Ala Trp Trp Pro Asp Ser Val
            100                 105                 110

Asn Lys Ile Phe Pro Thr Thr Ser Leu Asp Ser Asn Leu Lys Glu Glu
        115                 120                 125

Ser Ile Lys Met Arg Lys Leu Leu Pro Gln Phe Phe Lys Pro Glu Ala
    130                 135                 140

Leu Gln Arg Tyr Val Gly Val Met Asp Val Ile Ala Gln Arg His Phe
145                 150                 155                 160

Val Thr His Trp Asp Asn Lys Asn Glu Ile Thr Val Tyr Pro Leu Ala
                165                 170                 175

Lys Arg Tyr Thr Phe Leu Leu Ala Cys Arg Leu Phe Met Ser Val Glu
            180                 185                 190

Asp Glu Asn His Val Ala Lys Phe Ser Asp Pro Phe Gln Leu Ile Ala
        195                 200                 205

Ala Gly Ile Ile Ser Leu Pro Ile Asp Leu Pro Gly Thr Pro Phe Asn
    210                 215                 220

Lys Ala Ile Lys Ala Ser Asn Phe Ile Arg Lys Glu Leu Ile Lys Ile
225                 230                 235                 240

Ile Lys Gln Arg Arg Val Asp Leu Ala Glu Gly Thr Ala Ser Pro Thr
                245                 250                 255

Gln Asp Ile Leu Ser His Met Leu Leu Thr Ser Asp Glu Asn Gly Lys
            260                 265                 270

Ser Met Asn Glu Leu Asn Ile Ala Asp Lys Ile Leu Gly Leu Leu Ile
        275                 280                 285
```

```
Gly Gly His Asp Thr Ala Ser Val Ala Cys Thr Phe Leu Val Lys Tyr
    290                 295                 300

Leu Gly Glu Leu Pro His Ile Tyr Asp Lys Val Tyr Gln Glu Gln Met
305                 310                 315                 320

Glu Ile Ala Lys Ser Lys Pro Ala Gly Glu Leu Leu Asn Trp Asp Asp
                325                 330                 335

Leu Lys Lys Met Lys Tyr Ser Trp Asn Val Ala Cys Glu Val Met Arg
            340                 345                 350

Leu Ser Pro Pro Leu Gln Gly Gly Phe Arg Glu Ala Ile Thr Asp Phe
        355                 360                 365

Met Phe Asn Gly Phe Ser Ile Pro Lys Gly Trp Lys Leu Tyr Trp Ser
370                 375                 380

Ala Asn Ser Thr His Lys Asn Ala Glu Cys Phe Pro Met Pro Glu Lys
385                 390                 395                 400

Phe Asp Pro Thr Arg Phe Glu Gly Asn Gly Pro Ala Pro Tyr Thr Phe
                405                 410                 415

Val Pro Phe Gly Gly Gly Pro Arg Met Cys Pro Gly Lys Glu Tyr Ala
            420                 425                 430

Arg Leu Glu Ile Leu Val Phe Met His Asn Leu Val Lys Arg Phe Lys
        435                 440                 445

Trp Glu Lys Val Ile Pro Asp Glu Lys Ile Ile Val Asp Pro Phe Pro
450                 455                 460

Ile Pro Ala Lys Asp Leu Pro Ile Arg Leu Tyr Pro His Lys Ala
465                 470                 475

<210> SEQ ID NO 43
<211> LENGTH: 522
<212> TYPE: PRT
<213> ORGANISM: Stevia rebaudiana

<400> SEQUENCE: 43

Met Gly Leu Phe Pro Leu Glu Asp Ser Tyr Ala Leu Val Phe Glu Gly
1               5                   10                  15

Leu Ala Ile Thr Leu Ala Leu Tyr Tyr Leu Leu Ser Phe Ile Tyr Lys
            20                  25                  30

Thr Ser Lys Lys Thr Cys Thr Pro Lys Ala Ser Gly Glu His Pro
        35                  40                  45

Ile Thr Gly His Leu Asn Leu Leu Ser Gly Ser Ser Gly Leu Pro His
    50                  55                  60

Leu Ala Leu Ala Ser Leu Ala Asp Arg Cys Gly Pro Ile Phe Thr Ile
65                  70                  75                  80

Arg Leu Gly Ile Arg Arg Val Leu Val Val Ser Asn Trp Glu Ile Ala
                85                  90                  95

Lys Glu Ile Phe Thr Thr His Asp Leu Ile Val Ser Asn Arg Pro Lys
            100                 105                 110

Tyr Leu Ala Ala Lys Ile Leu Gly Phe Asn Tyr Val Ser Phe Ser Phe
        115                 120                 125

Ala Pro Tyr Gly Pro Tyr Trp Val Gly Ile Arg Lys Ile Ile Ala Thr
    130                 135                 140

Lys Leu Met Ser Ser Ser Arg Leu Gln Lys Leu Gln Phe Val Arg Val
145                 150                 155                 160

Phe Glu Leu Glu Asn Ser Met Lys Ser Ile Arg Glu Ser Trp Lys Glu
                165                 170                 175

Lys Lys Asp Glu Glu Gly Lys Val Leu Val Glu Met Lys Lys Trp Phe
            180                 185                 190
```

-continued

```
Trp Glu Leu Asn Met Asn Ile Val Leu Arg Thr Val Ala Gly Lys Gln
            195                 200                 205

Tyr Thr Gly Thr Val Asp Asp Ala Asp Ala Lys Arg Ile Ser Glu Leu
    210                 215                 220

Phe Arg Glu Trp Phe His Tyr Thr Gly Arg Phe Val Val Gly Asp Ala
225                 230                 235                 240

Phe Pro Phe Leu Gly Trp Leu Asp Leu Gly Gly Tyr Lys Lys Thr Met
            245                 250                 255

Glu Leu Val Ala Ser Arg Leu Asp Ser Met Val Ser Lys Trp Leu Asp
        260                 265                 270

Glu His Arg Lys Lys Gln Ala Asn Asp Asp Lys Lys Glu Asp Met Asp
    275                 280                 285

Phe Met Asp Ile Met Ile Ser Met Thr Glu Ala Asn Ser Pro Leu Glu
290                 295                 300

Gly Tyr Gly Thr Asp Thr Ile Ile Lys Thr Thr Cys Met Thr Leu Ile
305                 310                 315                 320

Val Ser Gly Val Asp Thr Thr Ser Ile Val Leu Thr Trp Ala Leu Ser
            325                 330                 335

Leu Leu Leu Asn Asn Arg Asp Thr Leu Lys Lys Ala Gln Glu Glu Leu
        340                 345                 350

Asp Met Cys Val Gly Lys Gly Arg Gln Val Asn Glu Ser Asp Leu Val
    355                 360                 365

Asn Leu Ile Tyr Leu Glu Ala Val Leu Lys Glu Ala Leu Arg Leu Tyr
370                 375                 380

Pro Ala Ala Phe Leu Gly Gly Pro Arg Ala Phe Leu Glu Asp Cys Thr
385                 390                 395                 400

Val Ala Gly Tyr Arg Ile Pro Lys Gly Thr Cys Leu Leu Ile Asn Met
            405                 410                 415

Trp Lys Leu His Arg Asp Pro Asn Ile Trp Ser Asp Pro Cys Glu Phe
        420                 425                 430

Lys Pro Glu Arg Phe Leu Thr Pro Asn Gln Lys Asp Val Asp Val Ile
    435                 440                 445

Gly Met Asp Phe Glu Leu Ile Pro Phe Gly Ala Gly Arg Arg Tyr Cys
450                 455                 460

Pro Gly Thr Arg Leu Ala Leu Gln Met Leu His Ile Val Leu Ala Thr
465                 470                 475                 480

Leu Leu Gln Asn Phe Glu Met Ser Thr Pro Asn Asp Ala Pro Val Asp
            485                 490                 495

Met Thr Ala Ser Val Gly Met Thr Asn Ala Lys Ala Ser Pro Leu Glu
        500                 505                 510

Val Leu Leu Ser Pro Arg Val Lys Trp Ser
    515                 520

<210> SEQ ID NO 44
<211> LENGTH: 710
<212> TYPE: PRT
<213> ORGANISM: Stevia rebaudiana

<400> SEQUENCE: 44

Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
```

```
                35                  40                  45
Leu Leu Thr Leu Phe Thr Thr Ser Phe Ala Val Leu Ile Gly Cys Leu
 50                  55                  60

Val Phe Leu Met Trp Arg Arg Ser Ser Lys Lys Leu Val Gln Asp
 65                  70                  75                  80

Pro Val Pro Gln Val Ile Val Lys Lys Glu Lys Glu Ser Glu
                 85                  90                  95

Val Asp Asp Gly Lys Lys Val Ser Ile Phe Tyr Gly Thr Gln Thr
                100                 105                 110

Gly Thr Ala Glu Gly Phe Ala Lys Ala Leu Val Glu Glu Ala Lys Val
                115                 120                 125

Arg Tyr Glu Lys Thr Ser Phe Lys Val Ile Asp Leu Asp Asp Tyr Ala
                130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
                180                 185                 190

Leu Lys Lys Leu Gln Tyr Gly Val Phe Gly Leu Gly Asn Arg Gln Tyr
                195                 200                 205

Glu His Phe Asn Lys Ile Ala Ile Val Val Asp Asp Lys Leu Thr Glu
                210                 215                 220

Met Gly Ala Lys Arg Leu Val Pro Val Gly Leu Gly Asp Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Asp Thr Ser Val Thr Thr Pro
                260                 265                 270

Tyr Thr Ala Ala Val Leu Glu Tyr Arg Val Val Tyr His Asp Lys Pro
                275                 280                 285

Ala Asp Ser Tyr Ala Glu Asp Gln Thr His Thr Asn Gly His Val Val
                290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
                340                 345                 350

Tyr Ser Glu Asn Leu Ser Glu Val Val Asp Glu Ala Leu Lys Leu Leu
                355                 360                 365

Gly Leu Ser Pro Asp Thr Tyr Phe Ser Val His Ala Asp Lys Glu Asp
                370                 375                 380

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
                420                 425                 430

Glu Ala Asp Arg Leu Lys Phe Leu Ala Ser Pro Ala Gly Lys Asp Glu
                435                 440                 445

Tyr Ala Gln Trp Ile Val Ala Asn Gln Arg Ser Leu Leu Glu Val Met
                450                 455                 460
```

```
Gln Ser Phe Pro Ser Ala Lys Pro Leu Gly Val Phe Ala Ala
465                 470                 475                 480

Val Ala Pro Arg Leu Gln Pro Arg Tyr Tyr Ser Ile Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
            515                 520                 525

Lys Asn Ala Val Pro Leu Thr Glu Ser Pro Asp Cys Ser Gln Ala Ser
530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
                580                 585                 590

Ser Ser Ile Phe Phe Gly Cys Arg Asn Arg Lys Val Asp Phe Ile
                595                 600                 605

Tyr Glu Asp Glu Leu Asn Asn Phe Val Glu Thr Gly Ala Leu Ser Glu
                610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
                660                 665                 670

Val His Arg Thr Leu His Thr Ile Val Gln Glu Gln Gly Ser Leu Asp
                675                 680                 685

Ser Ser Lys Ala Glu Leu Tyr Val Lys Asn Leu Gln Met Ser Gly Arg
                690                 695                 700

Tyr Leu Arg Asp Val Trp
705                 710

<210> SEQ ID NO 45
<211> LENGTH: 692
<212> TYPE: PRT
<213> ORGANISM: Arabidopsis thaliana

<400> SEQUENCE: 45

Met Thr Ser Ala Leu Tyr Ala Ser Asp Leu Phe Lys Gln Leu Lys Ser
1               5                   10                  15

Ile Met Gly Thr Asp Ser Leu Ser Asp Val Val Leu Val Ile Ala
                20                  25                  30

Thr Thr Ser Leu Ala Leu Val Ala Gly Phe Val Val Leu Leu Trp Lys
            35                  40                  45

Lys Thr Thr Ala Asp Arg Ser Gly Glu Leu Lys Pro Leu Met Ile Pro
            50                  55                  60

Lys Ser Leu Met Ala Lys Asp Glu Asp Asp Leu Asp Leu Gly Ser
65              70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
                100                 105                 110

Lys Ala Ala Val Lys Val Ile Asp Leu Asp Asp Tyr Ala Ala Asp Asp
```

-continued

```
            115                 120                 125
Asp Gln Tyr Glu Glu Lys Leu Lys Lys Glu Thr Leu Ala Phe Phe Cys
            130                 135                 140
Val Ala Thr Tyr Gly Asp Gly Glu Pro Thr Asp Asn Ala Ala Arg Phe
145                 150                 155                 160
Tyr Lys Trp Phe Thr Glu Glu Asn Glu Arg Asp Ile Lys Leu Gln Gln
                    165                 170                 175
Leu Ala Tyr Gly Val Phe Ala Leu Gly Asn Arg Gln Tyr Glu His Phe
                180                 185                 190
Asn Lys Ile Gly Ile Val Leu Asp Glu Glu Leu Cys Lys Lys Gly Ala
            195                 200                 205
Lys Arg Leu Ile Glu Val Gly Leu Gly Asp Asp Gln Ser Ile Glu
210                 215                 220
Asp Asp Phe Asn Ala Trp Lys Glu Ser Leu Trp Ser Glu Leu Asp Lys
225                 230                 235                 240
Leu Leu Lys Asp Glu Asp Lys Ser Val Ala Thr Pro Tyr Thr Ala
                245                 250                 255
Val Ile Pro Glu Tyr Arg Val Val Thr His Asp Pro Arg Phe Thr Thr
                260                 265                 270
Gln Lys Ser Met Glu Ser Asn Val Ala Asn Gly Asn Thr Thr Ile Asp
                275                 280                 285
Ile His His Pro Cys Arg Val Asp Val Ala Val Gln Lys Glu Leu His
            290                 295                 300
Thr His Glu Ser Asp Arg Ser Cys Ile His Leu Glu Phe Asp Ile Ser
305                 310                 315                 320
Arg Thr Gly Ile Thr Tyr Glu Thr Gly Asp His Val Gly Val Tyr Ala
                    325                 330                 335
Glu Asn His Val Glu Ile Val Glu Glu Ala Gly Lys Leu Leu Gly His
                340                 345                 350
Ser Leu Asp Leu Val Phe Ser Ile His Ala Asp Lys Glu Asp Gly Ser
            355                 360                 365
Pro Leu Glu Ser Ala Val Pro Pro Pro Phe Pro Gly Pro Cys Thr Leu
            370                 375                 380
Gly Thr Gly Leu Ala Arg Tyr Ala Asp Leu Leu Asn Pro Pro Arg Lys
385                 390                 395                 400
Ser Ala Leu Val Ala Leu Ala Ala Tyr Ala Thr Glu Pro Ser Glu Ala
                    405                 410                 415
Glu Lys Leu Lys His Leu Thr Ser Pro Asp Gly Lys Asp Glu Tyr Ser
                420                 425                 430
Gln Trp Ile Val Ala Ser Gln Arg Ser Leu Leu Glu Val Met Ala Ala
            435                 440                 445
Phe Pro Ser Ala Lys Pro Pro Leu Gly Val Phe Phe Ala Ala Ile Ala
            450                 455                 460
Pro Arg Leu Gln Pro Arg Tyr Tyr Ser Ile Ser Ser Ser Pro Arg Leu
465                 470                 475                 480
Ala Pro Ser Arg Val His Val Thr Ser Ala Leu Val Tyr Gly Pro Thr
                    485                 490                 495
Pro Thr Gly Arg Ile His Lys Gly Val Cys Ser Thr Trp Met Lys Asn
                500                 505                 510
Ala Val Pro Ala Glu Lys Ser His Glu Cys Ser Gly Ala Pro Ile Phe
            515                 520                 525
Ile Arg Ala Ser Asn Phe Lys Leu Pro Ser Asn Pro Ser Thr Pro Ile
            530                 535                 540
```

```
Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Leu Gly Ser Ser
            565                 570                 575

Leu Leu Phe Phe Gly Cys Arg Asn Arg Gln Met Asp Phe Ile Tyr Glu
                580                 585                 590

Asp Glu Leu Asn Asn Phe Val Asp Gln Gly Val Ile Ser Glu Leu Ile
                595                 600                 605

Met Ala Phe Ser Arg Glu Gly Ala Gln Lys Glu Tyr Val Gln His Lys
            610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Gln Glu Gly Val Ser Ser Ser
            660                 665                 670

Glu Ala Glu Ala Ile Val Lys Lys Leu Gln Thr Glu Gly Arg Tyr Leu
                675                 680                 685

Arg Asp Val Trp
            690

<210> SEQ ID NO 46
<211> LENGTH: 713
<212> TYPE: PRT
<213> ORGANISM: Fusarium fujikuroi

<400> SEQUENCE: 46

Met Ala Glu Leu Asp Thr Leu Asp Ile Val Val Leu Gly Val Ile Phe
1               5                   10                  15

Leu Gly Thr Val Ala Tyr Phe Thr Lys Gly Lys Leu Trp Gly Val Thr
                20                  25                  30

Lys Asp Pro Tyr Ala Asn Gly Phe Ala Ala Gly Ala Ser Lys Pro
            35                  40                  45

Gly Arg Thr Arg Asn Ile Val Glu Ala Met Glu Glu Ser Gly Lys Asn
50                  55                  60

Cys Val Val Phe Tyr Gly Ser Gln Thr Gly Thr Ala Glu Asp Tyr Ala
65                  70                  75                  80

Ser Arg Leu Ala Lys Glu Gly Lys Ser Arg Phe Gly Leu Asn Thr Met
                85                  90                  95

Ile Ala Asp Leu Glu Asp Tyr Asp Phe Asp Asn Leu Asp Thr Val Pro
                100                 105                 110

Ser Asp Asn Ile Val Met Phe Val Leu Ala Thr Tyr Gly Glu Gly Glu
            115                 120                 125

Pro Thr Asp Asn Ala Val Asp Phe Tyr Glu Phe Ile Thr Gly Glu Asp
            130                 135                 140

Ala Ser Phe Asn Glu Gly Asn Asp Pro Leu Gly Asn Leu Asn Tyr
145                 150                 155                 160

Val Ala Phe Gly Leu Gly Asn Asn Thr Tyr Glu His Tyr Asn Ser Met
                165                 170                 175

Val Arg Asn Val Asn Lys Ala Leu Glu Lys Leu Gly Ala His Arg Ile
            180                 185                 190

Gly Glu Ala Gly Glu Gly Asp Asp Gly Ala Gly Thr Met Glu Glu Asp
            195                 200                 205

Phe Leu Ala Trp Lys Asp Pro Met Trp Glu Ala Leu Ala Lys Lys Met
```

```
            210                 215                 220
Gly Leu Glu Glu Arg Glu Ala Val Tyr Glu Pro Ile Phe Ala Ile Asn
225                 230                 235                 240

Glu Arg Asp Asp Leu Thr Pro Glu Ala Asn Glu Val Tyr Leu Gly Glu
                245                 250                 255

Pro Asn Lys Leu His Leu Glu Gly Thr Ala Lys Gly Pro Phe Asn Ser
                260                 265                 270

His Asn Pro Tyr Ile Ala Pro Ile Ala Glu Ser Tyr Glu Leu Phe Ser
                275                 280                 285

Ala Lys Asp Arg Asn Cys Leu His Met Glu Ile Asp Ile Ser Gly Ser
                290                 295                 300

Asn Leu Lys Tyr Glu Thr Gly Asp His Ile Ala Ile Trp Pro Thr Asn
305                 310                 315                 320

Pro Gly Glu Glu Val Asn Lys Phe Leu Asp Ile Leu Asp Leu Ser Gly
                325                 330                 335

Lys Gln His Ser Val Val Thr Val Lys Ala Leu Glu Pro Thr Ala Lys
                340                 345                 350

Val Pro Phe Pro Asn Pro Thr Thr Tyr Asp Ala Ile Leu Arg Tyr His
                355                 360                 365

Leu Glu Ile Cys Ala Pro Val Ser Arg Gln Phe Val Ser Thr Leu Ala
370                 375                 380

Ala Phe Ala Pro Asn Asp Asp Ile Lys Ala Glu Met Asn Arg Leu Gly
385                 390                 395                 400

Ser Asp Lys Asp Tyr Phe His Glu Lys Thr Gly Pro His Tyr Tyr Asn
                405                 410                 415

Ile Ala Arg Phe Leu Ala Ser Val Ser Lys Gly Glu Lys Trp Thr Lys
                420                 425                 430

Ile Pro Phe Ser Ala Phe Ile Glu Gly Leu Thr Lys Leu Gln Pro Arg
                435                 440                 445

Tyr Tyr Ser Ile Ser Ser Ser Ser Leu Val Gln Pro Lys Lys Ile Ser
                450                 455                 460

Ile Thr Ala Val Val Glu Ser Gln Gln Ile Pro Gly Arg Asp Asp Pro
465                 470                 475                 480

Phe Arg Gly Val Ala Thr Asn Tyr Leu Phe Ala Leu Lys Gln Lys Gln
                485                 490                 495

Asn Gly Asp Pro Asn Pro Ala Pro Phe Gly Gln Ser Tyr Glu Leu Thr
                500                 505                 510

Gly Pro Arg Asn Lys Tyr Asp Gly Ile His Val Pro Val His Val Arg
                515                 520                 525

His Ser Asn Phe Lys Leu Pro Ser Asp Pro Gly Lys Pro Ile Ile Met
530                 535                 540

Ile Gly Pro Gly Thr Gly Val Ala Pro Phe Arg Gly Phe Val Gln Glu
545                 550                 555                 560

Arg Ala Lys Gln Ala Arg Asp Gly Val Glu Val Gly Lys Thr Leu Leu
                565                 570                 575

Phe Phe Gly Cys Arg Lys Ser Thr Glu Asp Phe Met Tyr Gln Lys Glu
                580                 585                 590

Trp Gln Glu Tyr Lys Glu Ala Leu Gly Asp Lys Phe Glu Met Ile Thr
                595                 600                 605

Ala Phe Ser Arg Glu Gly Ser Lys Lys Val Tyr Val Gln His Arg Leu
                610                 615                 620

Lys Glu Arg Ser Lys Glu Val Ser Asp Leu Leu Ser Gln Lys Ala Tyr
625                 630                 635                 640
```

Phe Tyr Val Cys Gly Asp Ala Ala His Met Ala Arg Glu Val Asn Thr
            645                 650                 655

Val Leu Ala Gln Ile Ile Ala Glu Gly Arg Gly Val Ser Glu Ala Lys
            660                 665                 670

Gly Glu Glu Ile Val Lys Asn Met Arg Ser Ala Asn Gln Tyr Gln Val
            675                 680                 685

Cys Ser Asp Phe Val Thr Leu His Cys Lys Glu Thr Thr Tyr Ala Asn
            690                 695                 700

Ser Glu Leu Gln Glu Asp Val Trp Ser
705                 710

<210> SEQ ID NO 47
<211> LENGTH: 480
<212> TYPE: PRT
<213> ORGANISM: Stevia rebaudiana

<400> SEQUENCE: 47

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr

```
                    290                 295                 300
Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu His Ile Lys Lys
                340                 345                 350

Arg Gly Phe Ile Ala Ser Trp Cys Ser Gln Glu Lys Val Leu Lys His
                355                 360                 365

Pro Ser Val Gly Gly Phe Leu Thr His Cys Gly Trp Gly Ser Thr Ile
            370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
            435                 440                 445

Asp Trp Lys Glu Lys Ala Arg Ile Ala Ile Ala Pro Asn Gly Ser Ser
            450                 455                 460

Ser Leu Asn Ile Asp Lys Met Val Lys Glu Ile Thr Val Leu Ala Arg
465                 470                 475                 480

<210> SEQ ID NO 48
<211> LENGTH: 787
<212> TYPE: PRT
<213> ORGANISM: Stevia rebaudiana

<400> SEQUENCE: 48

Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
                20                  25                  30

Ser Thr Gly Ile Val Ala Leu Arg Asp Ile Asn Phe Arg Cys Lys Ala
            35                  40                  45

Val Ser Lys Glu Tyr Ser Asp Leu Leu Gln Lys Asp Glu Ala Ser Phe
        50                  55                  60

Thr Lys Trp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
                85                  90                  95

Ala Met Phe Gly Ser Met Asn Asp Gly Glu Ile Asn Val Ser Ala Tyr
            100                 105                 110

Asp Thr Ala Trp Val Ala Leu Val Gln Asp Val Asp Gly Ser Gly Ser
        115                 120                 125

Pro Gln Phe Pro Ser Ser Leu Glu Trp Ile Ala Asn Asn Gln Leu Ser
    130                 135                 140

Asp Gly Ser Trp Gly Asp His Leu Leu Phe Ser Ala His Asp Arg Ile
145                 150                 155                 160

Ile Asn Thr Leu Ala Cys Val Ile Ala Leu Thr Ser Trp Asn Val His
                165                 170                 175

Pro Ser Lys Cys Glu Lys Gly Leu Asn Phe Leu Arg Glu Asn Ile Cys
            180                 185                 190
```

-continued

Lys Leu Glu Asp Glu Asn Ala Glu His Met Pro Ile Gly Phe Glu Val
            195                 200                 205

Thr Phe Pro Ser Leu Ile Asp Ile Ala Lys Lys Leu Asn Ile Glu Val
    210                 215                 220

Pro Glu Asp Thr Pro Ala Leu Lys Glu Ile Tyr Ala Arg Arg Asp Ile
225                 230                 235                 240

Lys Leu Thr Lys Ile Pro Met Glu Val Leu His Lys Val Pro Thr Thr
                245                 250                 255

Leu Leu His Ser Leu Glu Gly Met Pro Asp Leu Glu Trp Glu Lys Leu
            260                 265                 270

Leu Lys Leu Gln Cys Lys Asp Gly Ser Phe Leu Phe Ser Pro Ser Ser
            275                 280                 285

Thr Ala Phe Ala Leu Met Gln Thr Lys Asp Glu Lys Cys Leu Gln Tyr
    290                 295                 300

Leu Thr Asn Ile Val Thr Lys Phe Asn Gly Gly Val Pro Asn Val Tyr
305                 310                 315                 320

Pro Val Asp Leu Phe Glu His Ile Trp Val Val Asp Arg Leu Gln Arg
                325                 330                 335

Leu Gly Ile Ala Arg Tyr Phe Lys Ser Glu Ile Lys Asp Cys Val Glu
            340                 345                 350

Tyr Ile Asn Lys Tyr Trp Thr Lys Asn Gly Ile Cys Trp Ala Arg Asn
            355                 360                 365

Thr His Val Gln Asp Ile Asp Asp Thr Ala Met Gly Phe Arg Val Leu
    370                 375                 380

Arg Ala His Gly Tyr Asp Val Thr Pro Asp Val Phe Arg Gln Phe Glu
385                 390                 395                 400

Lys Asp Gly Lys Phe Val Cys Phe Ala Gly Gln Ser Thr Gln Ala Val
                405                 410                 415

Thr Gly Met Phe Asn Val Tyr Arg Ala Ser Gln Met Leu Phe Pro Gly
            420                 425                 430

Glu Arg Ile Leu Glu Asp Ala Lys Lys Phe Ser Tyr Asn Tyr Leu Lys
            435                 440                 445

Glu Lys Gln Ser Thr Asn Glu Leu Leu Asp Lys Trp Ile Ile Ala Lys
    450                 455                 460

Asp Leu Pro Gly Glu Val Gly Tyr Ala Leu Asp Ile Pro Trp Tyr Ala
465                 470                 475                 480

Ser Leu Pro Arg Leu Glu Thr Arg Tyr Tyr Leu Glu Gln Tyr Gly Gly
                485                 490                 495

Glu Asp Asp Val Trp Ile Gly Lys Thr Leu Tyr Arg Met Gly Tyr Val
            500                 505                 510

Ser Asn Asn Thr Tyr Leu Glu Met Ala Lys Leu Asp Tyr Asn Asn Tyr
            515                 520                 525

Val Ala Val Leu Gln Leu Glu Trp Tyr Thr Ile Gln Gln Trp Tyr Val
    530                 535                 540

Asp Ile Gly Ile Glu Lys Phe Glu Ser Asp Asn Ile Lys Ser Val Leu
545                 550                 555                 560

Val Ser Tyr Tyr Leu Ala Ala Ala Ser Ile Phe Glu Pro Glu Arg Ser
                565                 570                 575

Lys Glu Arg Ile Ala Trp Ala Lys Thr Thr Ile Leu Val Asp Lys Ile
            580                 585                 590

Thr Ser Ile Phe Asp Ser Ser Gln Ser Ser Lys Glu Asp Ile Thr Ala
            595                 600                 605

Phe Ile Asp Lys Phe Arg Asn Lys Ser Ser Ser Lys Lys His Ser Ile

```
            610                 615                 620
Asn Gly Glu Pro Trp His Glu Val Met Val Ala Leu Lys Lys Thr Leu
625                 630                 635                 640

His Gly Phe Ala Leu Asp Ala Leu Met Thr His Ser Gln Asp Ile His
                645                 650                 655

Pro Gln Leu His Gln Ala Trp Glu Met Trp Leu Thr Lys Leu Gln Asp
                660                 665                 670

Gly Val Asp Val Thr Ala Glu Leu Met Val Gln Met Ile Asn Met Thr
                675                 680                 685

Ala Gly Arg Trp Val Ser Lys Glu Leu Leu Thr His Pro Gln Tyr Gln
690                 695                 700

Arg Leu Ser Thr Val Thr Asn Ser Val Cys His Asp Ile Thr Lys Leu
705                 710                 715                 720

His Asn Phe Lys Glu Asn Ser Thr Thr Val Asp Ser Lys Val Gln Glu
                725                 730                 735

Leu Val Gln Leu Val Phe Ser Asp Thr Pro Asp Asp Leu Asp Gln Asp
                740                 745                 750

Met Lys Gln Thr Phe Leu Thr Val Met Lys Thr Phe Tyr Tyr Lys Ala
                755                 760                 765

Trp Cys Asp Pro Asn Thr Ile Asn Asp His Ile Ser Lys Val Phe Glu
770                 775                 780

Ile Val Ile
785

<210> SEQ ID NO 49
<211> LENGTH: 527
<212> TYPE: PRT
<213> ORGANISM: Streptomyces clavuligerus

<400> SEQUENCE: 49

Met Pro Asp Ala His Asp Ala Pro Pro Gln Ile Arg Gln Arg Thr
1               5                   10                  15

Leu Val Asp Glu Ala Thr Gln Leu Leu Thr Glu Ser Ala Glu Asp Ala
                20                  25                  30

Trp Gly Glu Val Ser Val Ser Glu Tyr Glu Thr Ala Arg Leu Val Ala
                35                  40                  45

His Ala Thr Trp Leu Gly Gly His Ala Thr Arg Val Ala Phe Leu Leu
            50                  55                  60

Glu Arg Gln His Glu Asp Gly Ser Trp Gly Pro Gly Gly Tyr Arg
65                  70                  75                  80

Leu Val Pro Thr Leu Ser Ala Val His Ala Leu Leu Thr Cys Leu Ala
                85                  90                  95

Ser Pro Ala Gln Asp His Gly Val Pro His Asp Arg Leu Leu Arg Ala
                100                 105                 110

Val Asp Ala Gly Leu Thr Ala Leu Arg Arg Leu Gly Thr Ser Asp Ser
            115                 120                 125

Pro Pro Asp Thr Ile Ala Val Glu Leu Val Ile Pro Ser Leu Leu Glu
130                 135                 140

Gly Ile Gln His Leu Leu Asp Pro Ala His Pro His Ser Arg Pro Ala
145                 150                 155                 160

Phe Ser Gln His Arg Gly Ser Leu Val Cys Pro Gly Gly Leu Asp Gly
                165                 170                 175

Arg Thr Leu Gly Ala Leu Arg Ser His Ala Ala Gly Thr Pro Val
                180                 185                 190
```

Pro Gly Lys Val Trp His Ala Ser Glu Thr Leu Gly Leu Ser Thr Glu
            195                 200                 205

Ala Ala Ser His Leu Gln Pro Ala Gln Gly Ile Ile Gly Gly Ser Ala
        210                 215                 220

Ala Ala Thr Ala Thr Trp Leu Thr Arg Val Ala Pro Ser Gln Gln Ser
225                 230                 235                 240

Asp Ser Ala Arg Arg Tyr Leu Glu Glu Leu Gln His Arg Tyr Ser Gly
                245                 250                 255

Pro Val Pro Ser Ile Thr Pro Ile Thr Tyr Phe Glu Arg Ala Trp Leu
            260                 265                 270

Leu Asn Asn Phe Ala Ala Gly Val Pro Cys Glu Ala Pro Ala Ala
        275                 280                 285

Leu Leu Asp Ser Leu Glu Ala Ala Leu Thr Pro Gln Gly Ala Pro Ala
    290                 295                 300

Gly Ala Gly Leu Pro Pro Asp Ala Asp Asp Thr Ala Ala Val Leu Leu
305                 310                 315                 320

Ala Leu Ala Thr His Gly Arg Gly Arg Pro Glu Val Leu Met Asp
                325                 330                 335

Tyr Arg Thr Asp Gly Tyr Phe Gln Cys Phe Ile Gly Glu Arg Thr Pro
            340                 345                 350

Ser Ile Ser Thr Asn Ala His Val Leu Glu Thr Leu Gly His His Val
        355                 360                 365

Ala Gln His Pro Gln Asp Arg Ala Arg Tyr Gly Ser Ala Met Asp Thr
    370                 375                 380

Ala Ser Ala Trp Leu Leu Ala Ala Gln Lys Gln Asp Gly Ser Trp Leu
385                 390                 395                 400

Asp Lys Trp His Ala Ser Pro Tyr Tyr Ala Thr Val Cys Cys Thr Gln
                405                 410                 415

Ala Leu Ala Ala His Ala Ser Pro Ala Thr Ala Pro Ala Arg Gln Arg
            420                 425                 430

Ala Val Arg Trp Val Leu Ala Thr Gln Arg Ser Asp Gly Gly Trp Gly
        435                 440                 445

Leu Trp His Ser Thr Val Glu Glu Thr Ala Tyr Ala Leu Gln Ile Leu
    450                 455                 460

Ala Pro Pro Ser Gly Gly Gly Asn Ile Pro Val Gln Gln Ala Leu Thr
465                 470                 475                 480

Arg Gly Arg Ala Arg Leu Cys Gly Ala Leu Pro Leu Thr Pro Leu Trp
                485                 490                 495

His Asp Lys Asp Leu Tyr Thr Pro Val Arg Val Arg Ala Ala Arg
            500                 505                 510

Ala Ala Ala Leu Tyr Thr Thr Arg Asp Leu Leu Leu Pro Pro Leu
        515                 520                 525

<210> SEQ ID NO 50
<211> LENGTH: 516
<212> TYPE: PRT
<213> ORGANISM: Bradyrhizobium diazoefficiens

<400> SEQUENCE: 50

Met Asn Ala Leu Ser Glu His Ile Leu Ser Glu Leu Arg Arg Leu Leu
1               5                   10                  15

Ser Glu Met Ser Asp Gly Gly Ser Val Gly Pro Ser Val Tyr Asp Thr
            20                  25                  30

Ala Gln Ala Leu Arg Phe His Gly Asn Val Thr Gly Arg Gln Asp Ala
        35                  40                  45

```
Tyr Ala Trp Leu Ile Ala Gln Gln Ala Asp Gly Gly Trp Gly Ser
    50                  55                  60

Ala Asp Phe Pro Leu Phe Arg His Ala Pro Thr Trp Ala Ala Leu Leu
65                  70                  75                  80

Ala Leu Gln Arg Ala Asp Pro Leu Pro Gly Ala Ala Asp Ala Val Gln
                85                  90                  95

Thr Ala Thr Arg Phe Leu Gln Arg Gln Pro Asp Pro Tyr Ala His Ala
            100                 105                 110

Val Pro Glu Asp Ala Pro Ile Gly Ala Glu Leu Ile Leu Pro Gln Phe
        115                 120                 125

Cys Gly Glu Ala Ala Trp Leu Leu Gly Gly Val Ala Phe Pro Arg His
    130                 135                 140

Pro Ala Leu Leu Pro Leu Arg Gln Ala Cys Leu Val Lys Leu Gly Ala
145                 150                 155                 160

Val Ala Met Leu Pro Ser Gly His Pro Leu Leu His Ser Trp Glu Ala
                165                 170                 175

Trp Gly Thr Ser Pro Thr Thr Ala Cys Pro Asp Asp Gly Ser Ile
            180                 185                 190

Gly Ile Ser Pro Ala Ala Thr Ala Ala Trp Arg Ala Gln Ala Val Thr
        195                 200                 205

Arg Gly Ser Thr Pro Gln Val Gly Arg Ala Asp Ala Tyr Leu Gln Met
    210                 215                 220

Ala Ser Arg Ala Thr Arg Ser Gly Ile Glu Gly Val Phe Pro Asn Val
225                 230                 235                 240

Trp Pro Ile Asn Val Phe Glu Pro Cys Trp Ser Leu Tyr Thr Leu His
                245                 250                 255

Leu Ala Gly Leu Phe Ala His Pro Ala Leu Ala Glu Ala Val Arg Val
                260                 265                 270

Ile Val Ala Gln Leu Glu Ala Arg Leu Gly Val His Gly Leu Gly Pro
        275                 280                 285

Ala Leu His Phe Ala Ala Asp Ala Asp Thr Ala Val Ala Leu Cys
        290                 295                 300

Val Leu His Leu Ala Gly Arg Asp Pro Ala Val Asp Ala Leu Arg His
305                 310                 315                 320

Phe Glu Ile Gly Glu Leu Phe Val Thr Phe Pro Gly Glu Arg Asn Ala
                325                 330                 335

Ser Val Ser Thr Asn Ile His Ala Leu His Ala Leu Arg Leu Leu Gly
            340                 345                 350

Lys Pro Ala Ala Gly Ala Ser Ala Tyr Val Glu Ala Asn Arg Asn Pro
        355                 360                 365

His Gly Leu Trp Asp Asn Glu Lys Trp His Val Ser Trp Leu Tyr Pro
    370                 375                 380

Thr Ala His Ala Val Ala Ala Leu Ala Gln Gly Lys Pro Gln Trp Arg
385                 390                 395                 400

Asp Glu Arg Ala Leu Ala Ala Leu Leu Gln Ala Gln Arg Asp Asp Gly
                405                 410                 415

Gly Trp Gly Ala Gly Arg Gly Ser Thr Phe Glu Glu Thr Ala Tyr Ala
            420                 425                 430

Leu Phe Ala Leu His Val Met Asp Gly Ser Glu Glu Ala Thr Gly Arg
        435                 440                 445

Arg Arg Ile Ala Gln Val Val Arg Ala Leu Glu Trp Met Leu Ala
    450                 455                 460
```

Arg His Ala Ala His Gly Leu Pro Gln Thr Pro Leu Trp Ile Gly Lys
465                 470                 475                 480

Glu Leu Tyr Cys Pro Thr Arg Val Val Arg Val Ala Glu Leu Ala Gly
                485                 490                 495

Leu Trp Leu Ala Leu Arg Trp Gly Arg Arg Val Leu Ala Glu Gly Ala
            500                 505                 510

Gly Ala Ala Pro
        515

<210> SEQ ID NO 51
<211> LENGTH: 2490
<212> TYPE: DNA
<213> ORGANISM: Artificial Sequence
<220> FEATURE:
<223> OTHER INFORMATION: Synthetic oligonucleotide

<400> SEQUENCE: 51

| | | | | | |
|---|---|---|---|---|---|
| atggttttgt | cttcttcttg | tactacagta | ccacacttat | cttcattagc | tgtcgtgcaa | 60 |
| cttggtcctt | ggagcagtag | gattaaaaag | aaaaccgata | ctgttgcagt | accagccgct | 120 |
| gcaggaaggt | ggagaagggc | cttggctaga | gcacagcaca | catcagaatc | cgcagctgtc | 180 |
| gcaaagggca | gcagtttgac | ccctatagtg | agaactgacg | ctgagtcaag | gagaacaaga | 240 |
| tggccaaccg | atgacgatga | cgccgaacct | ttagtggatg | agatcagggc | aatgcttact | 300 |
| tccatgtctg | atggtgacat | ttccgtgagc | gcatacgata | cagcctgggt | cggattggtt | 360 |
| ccaagattag | acggcggtga | aggtcctcaa | tttccagcag | ctgtgagatg | gataagaaat | 420 |
| aaccagttgc | ctgacggaag | ttggggcgat | gccgcattat | tctctgccta | tgacaggctt | 480 |
| atcaataccc | ttgcctgcgt | tgtaactttg | acaaggtggt | ccctagaacc | agagatgaga | 540 |
| ggtagaggac | tatctttttt | gggtaggaac | atgtggaaat | tagcaactga | agatgaagag | 600 |
| tcaatgccta | ttggcttcga | attagcattt | ccatctttga | tagagcttgc | taagagccta | 660 |
| ggtgtccatg | acttccctta | tgatcaccag | gccctacaag | gaatctactc | ttcaagagag | 720 |
| atcaaaatga | agaggattcc | aaaagaagtg | atgcataccg | ttccaacatc | aatattgcac | 780 |
| agtttggagg | gtatgcctgg | cctagattgg | gctaaactac | ttaaactaca | gagcagcgac | 840 |
| ggaagttttt | tgttctcacc | agctgccact | gcatatgctt | taatgaatac | cggagatgac | 900 |
| aggtgtttta | gctacatcga | tagaacagta | agaaaattca | acggcggcgt | ccctaatgtt | 960 |
| tatccagtgg | atctatttga | acatatttgg | gccgttgata | gacttgaaag | attaggaatc | 1020 |
| tccaggtact | tccaaaagga | gatcgaacaa | tgcatggatt | atgtaaacag | gcattggact | 1080 |
| gaggacggta | tttgttgggc | aaggaactct | gatgtcaaag | aggtggacga | cacagctatg | 1140 |
| gcctttagac | ttcttaggtt | gcacggctac | agcgtcagtc | ctgatgtgtt | taaaaacttc | 1200 |
| gaaaaggacg | gtgaattttt | cgcatttgtc | ggacagtcta | atcaagctgt | taccggtatg | 1260 |
| tacaacttaa | acagagcaag | ccagatatcc | ttcccaggcg | aggatgtgct | tcatagagct | 1320 |
| ggtgccttct | catatgagtt | cttgaggaga | aagaagcag | agggagcttt | gagggacaag | 1380 |
| tggatcattt | ctaaagatct | acctggtgaa | gttgtgtata | cttttggattt | tccatggtac | 1440 |
| ggcaacttac | ctagagtcga | ggccagagac | tacctagagc | aatacggagg | tggtgatgac | 1500 |
| gtttggattg | gcaagacatt | gtataggatg | ccacttgtaa | acaatgatgt | atatttggaa | 1560 |
| ttggcaagaa | tggatttcaa | ccactgccag | gctttgcatc | agttagagtg | gcaaggacta | 1620 |
| aaagatggt | atactgaaaa | taggttgatg | actttggttc | gcccaaga | agatgccctt | 1680 |
| agagcttatt | ttcttgcagc | cgcatctgtt | tacgagcctt | gtagagctgc | cgagaggctt | 1740 |

-continued

```
gcatgggcta gagccgcaat actagctaac gccgtgagca cccacttaag aaatagccca    1800
tcattcagag aaaggttaga gcattctctt aggtgtagac ctagtgaaga dacagatggc    1860
tcctggttta actcctcaag tggctctgat gcagttttag taaaggctgt cttaagactt    1920
actgattcat tagccaggga agcacagcca atccatggag gtgacccaga agatattata    1980
cacaagttgt taagatctgc ttgggccgag tgggttaggg aaaaggcaga cgctgccgat    2040
agcgtgtgca atggtagttc tgcagtagaa caagagggat caagaatggt ccatgataaa    2100
cagacctgtc tattattggc tagaatgatc gaaatttctg ccggtagggc agctggtgaa    2160
gcagccagtg aggacggcga tagaagaata attcaattaa caggctccat ctgcgacagt    2220
cttaagcaaa aaatgctagt ttcacaggac cctgaaaaaa atgaagagat gatgtctcac    2280
gtggatgacg aattgaagtt gaggattaga gagttcgttc aatatttgct tagactaggt    2340 gaaaaaaga  ctggatctag cgaaaccagg caaacatttt taagtatagt gaaatcatgt     2400
tactatgctg ctcattgccc acctcatgtc gttgatagac acattagtag agtgattttc    2460
gagccagtaa gtgccgcaaa gtaaccgcgg                                       2490
```

<210> SEQ ID NO 52
<211> LENGTH: 827
<212> TYPE: PRT
<213> ORGANISM: Zea mays

<400> SEQUENCE: 52

```
Met Val Leu Ser Ser Cys Thr Thr Val Pro His Leu Ser Ser Leu
1               5                  10                  15

Ala Val Val Gln Leu Gly Pro Trp Ser Ser Arg Ile Lys Lys Lys Thr
                20                  25                  30

Asp Thr Val Ala Val Pro Ala Ala Ala Gly Arg Trp Arg Arg Ala Leu
            35                  40                  45

Ala Arg Ala Gln His Thr Ser Glu Ser Ala Ala Val Ala Lys Gly Ser
        50                  55                  60

Ser Leu Thr Pro Ile Val Arg Thr Asp Ala Glu Ser Arg Arg Thr Arg
65              70                  75                  80

Trp Pro Thr Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr
            100                 105                 110

Asp Thr Ala Trp Val Gly Leu Val Pro Arg Leu Asp Gly Gly Glu Gly
        115                 120                 125

Pro Gln Phe Pro Ala Ala Val Arg Trp Ile Arg Asn Asn Gln Leu Pro
    130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175

Pro Glu Met Arg Gly Arg Gly Leu Ser Phe Leu Gly Arg Asn Met Trp
            180                 185                 190

Lys Leu Ala Thr Glu Asp Glu Glu Ser Met Pro Ile Gly Phe Glu Leu
        195                 200                 205

Ala Phe Pro Ser Leu Ile Glu Leu Ala Lys Ser Leu Gly Val His Asp
    210                 215                 220

Phe Pro Tyr Asp His Gln Ala Leu Gln Gly Ile Tyr Ser Ser Arg Glu
225                 230                 235                 240
```

-continued

Ile Lys Met Lys Arg Ile Pro Lys Glu Val Met His Thr Val Pro Thr
            245                 250                 255

Ser Ile Leu His Ser Leu Glu Gly Met Pro Gly Leu Asp Trp Ala Lys
            260                 265                 270

Leu Leu Lys Leu Gln Ser Ser Asp Gly Ser Phe Leu Phe Ser Pro Ala
            275                 280                 285

Ala Thr Ala Tyr Ala Leu Met Asn Thr Gly Asp Asp Arg Cys Phe Ser
290                 295                 300

Tyr Ile Asp Arg Thr Val Lys Lys Phe Asn Gly Val Pro Asn Val
305                 310                 315                 320

Tyr Pro Val Asp Leu Phe Glu His Ile Trp Ala Val Asp Arg Leu Glu
            325                 330                 335

Arg Leu Gly Ile Ser Arg Tyr Phe Gln Lys Glu Ile Glu Gln Cys Met
            340                 345                 350

Asp Tyr Val Asn Arg His Trp Thr Glu Asp Gly Ile Cys Trp Ala Arg
            355                 360                 365

Asn Ser Asp Val Lys Glu Val Asp Asp Thr Ala Met Ala Phe Arg Leu
            370                 375                 380

Leu Arg Leu His Gly Tyr Ser Val Ser Pro Asp Val Phe Lys Asn Phe
385                 390                 395                 400

Glu Lys Asp Gly Glu Phe Phe Ala Phe Val Gly Gln Ser Asn Gln Ala
            405                 410                 415

Val Thr Gly Met Tyr Asn Leu Asn Arg Ala Ser Gln Ile Ser Phe Pro
            420                 425                 430

Gly Glu Asp Val Leu His Arg Ala Gly Ala Phe Ser Tyr Glu Phe Leu
            435                 440                 445

Arg Arg Lys Glu Ala Glu Gly Ala Leu Arg Asp Lys Trp Ile Ile Ser
            450                 455                 460

Lys Asp Leu Pro Gly Glu Val Val Tyr Thr Leu Asp Phe Pro Trp Tyr
465                 470                 475                 480

Gly Asn Leu Pro Arg Val Glu Ala Arg Asp Tyr Leu Glu Gln Tyr Gly
            485                 490                 495

Gly Gly Asp Val Trp Ile Gly Lys Thr Leu Tyr Arg Met Pro Leu
            500                 505                 510

Val Asn Asn Asp Val Tyr Leu Glu Leu Ala Arg Met Asp Phe Asn His
            515                 520                 525

Cys Gln Ala Leu His Gln Leu Glu Trp Gln Gly Leu Lys Arg Trp Tyr
            530                 535                 540

Thr Glu Asn Arg Leu Met Asp Phe Gly Val Ala Gln Glu Asp Ala Leu
545                 550                 555                 560

Arg Ala Tyr Phe Leu Ala Ala Ser Val Tyr Glu Pro Cys Arg Ala
            565                 570                 575

Ala Glu Arg Leu Ala Trp Ala Arg Ala Ala Ile Leu Ala Asn Ala Val
            580                 585                 590

Ser Thr His Leu Arg Asn Ser Pro Ser Phe Arg Glu Arg Leu Glu His
            595                 600                 605

Ser Leu Arg Cys Arg Pro Ser Glu Glu Thr Asp Gly Ser Trp Phe Asn
            610                 615                 620

Ser Ser Ser Gly Ser Asp Ala Val Leu Val Lys Ala Val Leu Arg Leu
625                 630                 635                 640

Thr Asp Ser Leu Ala Arg Glu Ala Gln Pro Ile His Gly Gly Asp Pro
            645                 650                 655

```
Glu Asp Ile Ile His Lys Leu Leu Arg Ser Ala Trp Ala Glu Trp Val
            660                 665                 670

Arg Glu Lys Ala Asp Ala Ala Asp Ser Val Cys Asn Gly Ser Ser Ala
        675                 680                 685

Val Glu Gln Glu Gly Ser Arg Met Val His Asp Lys Gln Thr Cys Leu
    690                 695                 700

Leu Leu Ala Arg Met Ile Glu Ile Ser Ala Gly Arg Ala Ala Gly Glu
705                 710                 715                 720

Ala Ala Ser Glu Asp Gly Asp Arg Arg Ile Ile Gln Leu Thr Gly Ser
                725                 730                 735

Ile Cys Asp Ser Leu Lys Gln Lys Met Leu Val Ser Gln Asp Pro Glu
            740                 745                 750

Lys Asn Glu Glu Met Met Ser His Val Asp Asp Glu Leu Lys Leu Arg
        755                 760                 765

Ile Arg Glu Phe Val Gln Tyr Leu Leu Arg Leu Gly Glu Lys Lys Thr
    770                 775                 780

Gly Ser Ser Glu Thr Arg Gln Thr Phe Leu Ser Ile Val Lys Ser Cys
785                 790                 795                 800

Tyr Tyr Ala Ala His Cys Pro Pro His Val Val Asp Arg His Ile Ser
                805                 810                 815

Arg Val Ile Phe Glu Pro Val Ser Ala Ala Lys
            820                 825

<210> SEQ ID NO 53
<211> LENGTH: 2570
<212> TYPE: DNA
<213> ORGANISM: Artificial Sequence
<220> FEATURE:
<223> OTHER INFORMATION: Synthetic oligonucleotide

<400> SEQUENCE: 53
cttcttcact aaatacttag acagagaaaa cagagctttt taaagccatg tctcttcagt      60
atcatgttct aaactccatt ccaagtacaa cctttctcag ttctactaaa acaacaatat     120
cttcttcttt ccttaccatc tcaggatctc ctctcaatgt cgctagagac aaatccagaa     180
gcggttccat acattgttca aagcttcgaa ctcaagaata cattaattct caagaggttc     240
aacatgattt gcctctaata catgagtggc aacagcttca aggagaagat gctcctcaga     300
ttagtgttgg aagtaatagt aatgcattca agaagcagt gaagagtgtg aaaacgatct     360
tgagaaacct aacggacggg gaaattacga tatcggctta cgatacagct gggttgcat     420 tgatcgatgc cggagataaa actccggcgt ttccctccgc cgtgaaatgg atcgccgaga     480
accaactttc cgatggttct tggggagatg cgtatctctt ctcttatcat gatcgtctca     540
tcaataccct tgcatgcgtc gttgctctaa gatcatggaa tctctttcct catcaatgca     600 acaaggaat cacgtttttc cgggaaaata ttgggaagct agaagacgaa aatgatgagc     660
atatgccaat cggattcgaa gtagcattcc catcgttgct tgagatagct cgaggaataa     720
acattgatgt accgtacgat tctccggtct taaaagatat atacgccaag aaagagctaa     780
agcttacaag gataccaaaa gagataatgc acaagatacc aacaacattg ttgcatagtt     840
tggaggggat gcgtgattta gattgggaaa agctcttgaa acttcaatct caagacggat     900
ctttcctctt ctctccttcc tctaccgctt ttgcattcat gcagacccga gacagtaact     960
gcctcgagta tttgcgaaat gccgtcaaac gtttcaatgg aggagttccc aatgtctttc    1020
ccgtggatct tttcgagcac atatggatag tggatcggtt acaacgttta gggatatcga    1080
```

| | |
|---|---|
| gatactttga agaagagatt aaagagtgtc ttgactatgt ccacagatat tggaccgaca | 1140 |
| atggcatatg ttgggctaga tgttcccatg tccaagacat cgatgataca gccatggcat | 1200 |
| ttaggctctt aagacaacat ggataccaag tgtccgcaga tgtattcaag aactttgaga | 1260 |
| aagagggaga gttttctgc tttgtggggc aatcaaacca agcagtaacc ggtatgttca | 1320 |
| acctataccg ggcatcacaa ttggcgtttc aagggaaga gatattgaaa aacgccaaag | 1380 |
| agttttctta taattatctg ctagaaaaac gggagagaga ggagttgatt gataagtgga | 1440 |
| ttataatgaa agacttacct ggcgagattg ggtttgcgtt agagattcca tggtacgcaa | 1500 |
| gcttgcctcg agtagagacg agattctata ttgatcaata tggtggagaa aacgacgttt | 1560 |
| ggattggcaa gactctttat aggatgccat acgtgaacaa taatggatat ctggaattag | 1620 |
| caaaacaaga ttacaacaat tgccaagctc agcatcagct cgaatgggac atattccaaa | 1680 |
| agtggtatga agaaaatagg ttaagtgagt ggggtgtgcg cagaagtgag cttctcgagt | 1740 |
| gttactactt agcggctgca actatatttg aatcagaaag gtcacatgag agaatggttt | 1800 |
| gggctaagtc aagtgtattg gttaaagcca tttcttcttc ttttggggaa tcctctgact | 1860 |
| ccagaagaag cttctccgat cagtttcatg aatacattgc caatgctcga cgaagtgatc | 1920 |
| atcactttaa tgacaggaac atgagagattgg accgaccagg atcggttcag gccagtcggc | 1980 |
| ttgccggagt gttaatcggg actttgaatc aaatgtcttt tgacctttc atgtctcatg | 2040 |
| gccgtgacgt taacaatctc ctctatctat cgtggggaga ttggatggaa aaatggaaac | 2100 |
| tatatggaga tgaaggagaa ggagagctca tggtgaagat gataattcta atgaagaaca | 2160 |
| atgacctaac taacttcttc acccacactc acttcgttcg tctcgcggaa atcatcaatc | 2220 |
| gaatctgtct tcctcgccaa tacttaaagg caaggagaaa cgatgagaag gagaagacaa | 2280 |
| taaagagtat ggaaaggag atggggaaaa tggttgagtt agcattgtcg gagagtgaca | 2340 |
| catttcgtga cgtcagcatc acgtttcttg atgtagcaaa agcattttac tactttgctt | 2400 |
| tatgtggcga tcatctccaa actcacatct ccaaagtctt gtttcaaaaa gtctagtaac | 2460 |
| ctcatcatca tcatcgatcc attaacaatc agtggatcga tgtatccata gatgcgtgaa | 2520 |
| taatatttca tgtagagaag gagaacaaat tagatcatgt agggttatca | 2570 |

<210> SEQ ID NO 54
<211> LENGTH: 802
<212> TYPE: PRT
<213> ORGANISM: Arabidopsis thaliana

<400> SEQUENCE: 54

```
Met Ser Leu Gln Tyr His Val Leu Asn Ser Ile Pro Ser Thr Thr Phe
1               5                   10                  15

Leu Ser Ser Thr Lys Thr Thr Ile Ser Ser Ser Phe Leu Thr Ile Ser
            20                  25                  30

Gly Ser Pro Leu Asn Val Ala Arg Asp Lys Ser Arg Ser Gly Ser Ile
        35                  40                  45

His Cys Ser Lys Leu Arg Thr Gln Glu Tyr Ile Asn Ser Gln Glu Val
    50                  55                  60

Gln His Asp Leu Pro Leu Ile His Glu Trp Gln Gln Leu Gln Gly Glu
65                  70                  75                  80

Asp Ala Pro Gln Ile Ser Val Gly Ser Asn Ser Asn Ala Phe Lys Glu
                85                  90                  95

Ala Val Lys Ser Val Lys Thr Ile Leu Arg Asn Leu Thr Asp Gly Glu
            100                 105                 110
```

Ile Thr Ile Ser Ala Tyr Asp Thr Ala Trp Val Ala Leu Ile Asp Ala
115                 120                 125

Gly Asp Lys Thr Pro Ala Phe Pro Ser Ala Val Lys Trp Ile Ala Glu
130                 135                 140

Asn Gln Leu Ser Asp Gly Ser Trp Gly Asp Ala Tyr Leu Phe Ser Tyr
145                 150                 155                 160

His Asp Arg Leu Ile Asn Thr Leu Ala Cys Val Val Ala Leu Arg Ser
                165                 170                 175

Trp Asn Leu Phe Pro His Gln Cys Asn Lys Gly Ile Thr Phe Phe Arg
                180                 185                 190

Glu Asn Ile Gly Lys Leu Glu Asp Glu Asn Asp Glu His Met Pro Ile
                195                 200                 205

Gly Phe Glu Val Ala Phe Pro Ser Leu Leu Glu Ile Ala Arg Gly Ile
                210                 215                 220

Asn Ile Asp Val Pro Tyr Asp Ser Pro Val Leu Lys Asp Ile Tyr Ala
225                 230                 235                 240

Lys Lys Glu Leu Lys Leu Thr Arg Ile Pro Lys Glu Ile Met His Lys
                245                 250                 255

Ile Pro Thr Thr Leu Leu His Ser Leu Glu Gly Met Arg Asp Leu Asp
                260                 265                 270

Trp Glu Lys Leu Leu Lys Leu Gln Ser Gln Asp Gly Ser Phe Leu Phe
                275                 280                 285

Ser Pro Ser Ser Thr Ala Phe Ala Phe Met Gln Thr Arg Asp Ser Asn
                290                 295                 300

Cys Leu Glu Tyr Leu Arg Asn Ala Val Lys Arg Phe Asn Gly Gly Val
305                 310                 315                 320

Pro Asn Val Phe Pro Val Asp Leu Phe Glu His Ile Trp Ile Val Asp
                325                 330                 335

Arg Leu Gln Arg Leu Gly Ile Ser Arg Tyr Phe Glu Glu Glu Ile Lys
                340                 345                 350

Glu Cys Leu Asp Tyr Val His Arg Tyr Trp Thr Asp Asn Gly Ile Cys
                355                 360                 365

Trp Ala Arg Cys Ser His Val Gln Asp Ile Asp Asp Thr Ala Met Ala
370                 375                 380

Phe Arg Leu Leu Arg Gln His Gly Tyr Gln Val Ser Ala Asp Val Phe
385                 390                 395                 400

Lys Asn Phe Glu Lys Glu Gly Glu Phe Phe Cys Phe Val Gly Gln Ser
                405                 410                 415

Asn Gln Ala Val Thr Gly Met Phe Asn Leu Tyr Arg Ala Ser Gln Leu
                420                 425                 430

Ala Phe Pro Arg Glu Glu Ile Leu Lys Asn Ala Lys Glu Phe Ser Tyr
                435                 440                 445

Asn Tyr Leu Leu Glu Lys Arg Glu Arg Glu Glu Leu Ile Asp Lys Trp
450                 455                 460

Ile Ile Met Lys Asp Leu Pro Gly Glu Ile Gly Phe Ala Leu Glu Ile
465                 470                 475                 480

Pro Trp Tyr Ala Ser Leu Pro Arg Val Glu Thr Arg Phe Tyr Ile Asp
                485                 490                 495

Gln Tyr Gly Gly Glu Asn Asp Val Trp Ile Gly Lys Thr Leu Tyr Arg
                500                 505                 510

Met Pro Tyr Val Asn Asn Gly Tyr Leu Glu Leu Ala Lys Gln Asp
                515                 520                 525

Tyr Asn Asn Cys Gln Ala Gln His Gln Leu Glu Trp Asp Ile Phe Gln

```
                530            535            540
Lys Trp Tyr Glu Glu Asn Arg Leu Ser Glu Trp Gly Val Arg Arg Ser
545                550            555                560

Glu Leu Leu Glu Cys Tyr Tyr Leu Ala Ala Thr Ile Phe Glu Ser
            565            570            575

Glu Arg Ser His Glu Arg Met Val Trp Ala Lys Ser Ser Val Leu Val
            580            585            590

Lys Ala Ile Ser Ser Ser Phe Gly Glu Ser Ser Asp Ser Arg Arg Ser
            595            600            605

Phe Ser Asp Gln Phe His Glu Tyr Ile Ala Asn Ala Arg Arg Ser Asp
            610            615            620

His His Phe Asn Asp Arg Asn Met Arg Leu Asp Arg Pro Gly Ser Val
625            630            635            640

Gln Ala Ser Arg Leu Ala Gly Val Leu Ile Gly Thr Leu Asn Gln Met
            645            650            655

Ser Phe Asp Leu Phe Met Ser His Gly Arg Asp Val Asn Asn Leu Leu
            660            665            670

Tyr Leu Ser Trp Gly Asp Trp Met Glu Lys Trp Lys Leu Tyr Gly Asp
            675            680            685

Glu Gly Glu Gly Glu Leu Met Val Lys Met Ile Ile Leu Met Lys Asn
690            695            700

Asn Asp Leu Thr Asn Phe Phe Thr His Thr His Phe Val Arg Leu Ala
705            710            715            720

Glu Ile Ile Asn Arg Ile Cys Leu Pro Arg Gln Tyr Leu Lys Ala Arg
            725            730            735

Arg Asn Asp Glu Lys Glu Lys Thr Ile Lys Ser Met Glu Lys Glu Met
            740            745            750

Gly Lys Met Val Glu Leu Ala Leu Ser Glu Ser Asp Thr Phe Arg Asp
            755            760            765

Val Ser Ile Thr Phe Leu Asp Val Ala Lys Ala Phe Tyr Tyr Phe Ala
            770            775            780

Leu Cys Gly Asp His Leu Gln Thr His Ile Ser Lys Val Leu Phe Gln
785            790            795            800

Lys Val

<210> SEQ ID NO 55
<211> LENGTH: 983
<212> TYPE: PRT
<213> ORGANISM: Diaporthe amygdali

<400> SEQUENCE: 55

Met Glu Phe Asp Glu Pro Leu Val Asp Glu Ala Arg Ser Leu Val Gln
1               5               10              15

Arg Thr Leu Gln Asp Tyr Asp Asp Arg Tyr Gly Phe Gly Thr Met Ser
            20              25              30

Cys Ala Ala Tyr Asp Thr Ala Trp Val Ser Leu Val Thr Lys Thr Val
            35              40              45

Asp Gly Arg Lys Gln Trp Leu Phe Pro Glu Cys Phe Glu Phe Leu Leu
        50              55              60

Glu Thr Gln Ser Asp Ala Gly Gly Trp Glu Ile Gly Asn Ser Ala Pro
65              70              75              80

Ile Asp Gly Ile Leu Asn Thr Ala Ala Ser Leu Leu Ala Leu Lys Arg
            85              90              95

His Val Gln Thr Glu Gln Ile Ile Gln Pro Gln His Asp His Lys Asp
```

```
            100                 105                 110
Leu Ala Gly Arg Ala Glu Arg Ala Ala Ser Leu Arg Ala Gln Leu
        115                 120                 125

Ala Ala Leu Asp Val Ser Thr Thr Glu His Val Gly Phe Glu Ile Ile
130                 135                 140

Val Pro Ala Met Leu Asp Pro Leu Glu Ala Glu Asp Pro Ser Leu Val
145                 150                 155                 160

Phe Asp Phe Pro Ala Arg Lys Pro Leu Met Lys Ile His Asp Ala Lys
                165                 170                 175

Met Ser Arg Phe Arg Pro Glu Tyr Leu Tyr Gly Lys Gln Pro Met Thr
                180                 185                 190

Ala Leu His Ser Leu Glu Ala Phe Ile Gly Lys Ile Asp Phe Asp Lys
            195                 200                 205

Val Arg His His Arg Thr His Gly Ser Met Met Gly Ser Pro Ser Ser
        210                 215                 220

Thr Ala Ala Tyr Leu Met His Ala Ser Gln Trp Asp Gly Asp Ser Glu
225                 230                 235                 240

Ala Tyr Leu Arg His Val Ile Lys His Ala Ala Gly Gln Gly Thr Gly
                245                 250                 255

Ala Val Pro Ser Ala Phe Pro Ser Thr His Phe Glu Ser Ser Trp Ile
                260                 265                 270

Leu Thr Thr Leu Phe Arg Ala Gly Phe Ser Ala Ser His Leu Ala Cys
            275                 280                 285

Asp Glu Leu Asn Lys Leu Val Glu Ile Leu Glu Gly Ser Phe Glu Lys
        290                 295                 300

Glu Gly Gly Ala Ile Gly Tyr Ala Pro Gly Phe Gln Ala Asp Val Asp
305                 310                 315                 320

Asp Thr Ala Lys Thr Ile Ser Thr Leu Ala Val Leu Gly Arg Asp Ala
                325                 330                 335

Thr Pro Arg Gln Met Ile Lys Val Phe Glu Ala Asn Thr His Phe Arg
                340                 345                 350

Thr Tyr Pro Gly Glu Arg Asp Pro Ser Leu Thr Ala Asn Cys Asn Ala
            355                 360                 365

Leu Ser Ala Leu Leu His Gln Pro Asp Ala Ala Met Tyr Gly Ser Gln
        370                 375                 380

Ile Gln Lys Ile Thr Lys Phe Val Cys Asp Tyr Trp Trp Lys Ser Asp
385                 390                 395                 400

Gly Lys Ile Lys Asp Lys Trp Asn Thr Cys Tyr Leu Tyr Pro Ser Val
                405                 410                 415

Leu Leu Val Glu Val Leu Val Asp Leu Val Ser Leu Leu Glu Gln Gly
                420                 425                 430

Lys Leu Pro Asp Val Leu Asp Gln Glu Leu Gln Tyr Arg Val Ala Ile
            435                 440                 445

Thr Leu Phe Gln Ala Cys Leu Arg Pro Leu Leu Asp Gln Asp Ala Glu
        450                 455                 460

Gly Ser Trp Asn Lys Ser Ile Glu Ala Thr Ala Tyr Gly Ile Leu Ile
465                 470                 475                 480

Leu Thr Glu Ala Arg Arg Val Cys Phe Phe Asp Arg Leu Ser Glu Pro
                485                 490                 495

Leu Asn Glu Ala Ile Arg Arg Gly Ile Ala Phe Ala Asp Ser Met Ser
                500                 505                 510

Gly Thr Glu Ala Gln Leu Asn Tyr Ile Trp Ile Glu Lys Val Ser Tyr
            515                 520                 525
```

```
Ala Pro Ala Leu Leu Thr Lys Ser Tyr Leu Leu Ala Ala Arg Trp Ala
    530                 535                 540

Ala Lys Ser Pro Leu Gly Ala Ser Val Gly Ser Ser Leu Trp Thr Pro
545                 550                 555                 560

Pro Arg Glu Gly Leu Asp Lys His Val Arg Leu Phe His Gln Ala Glu
                565                 570                 575

Leu Phe Arg Ser Leu Pro Glu Trp Glu Leu Arg Ala Ser Met Ile Glu
                580                 585                 590

Ala Ala Leu Phe Thr Pro Leu Leu Arg Ala His Arg Leu Asp Val Phe
            595                 600                 605

Pro Arg Gln Asp Val Gly Glu Asp Lys Tyr Leu Asp Val Val Pro Phe
    610                 615                 620

Phe Trp Thr Ala Ala Asn Asn Arg Asp Arg Thr Tyr Ala Ser Thr Leu
625                 630                 635                 640

Phe Leu Tyr Asp Met Cys Phe Ile Ala Met Leu Asn Phe Gln Leu Asp
                645                 650                 655

Glu Phe Met Glu Ala Thr Ala Gly Ile Leu Phe Arg Asp His Met Asp
                660                 665                 670

Asp Leu Arg Gln Leu Ile His Asp Leu Leu Ala Glu Lys Thr Ser Pro
                675                 680                 685

Lys Ser Ser Gly Arg Ser Ser Gln Gly Thr Lys Asp Ala Asp Ser Gly
690                 695                 700

Ile Glu Glu Asp Val Ser Met Ser Asp Ser Ala Ser Asp Ser Gln Asp
705                 710                 715                 720

Arg Ser Pro Glu Tyr Asp Leu Val Phe Ser Ala Leu Ser Thr Phe Thr
                725                 730                 735

Lys His Val Leu Gln His Pro Ser Ile Gln Ser Ala Ser Val Trp Asp
                740                 745                 750

Arg Lys Leu Leu Ala Arg Glu Met Lys Ala Tyr Leu Leu Ala His Ile
                755                 760                 765

Gln Gln Ala Glu Asp Ser Thr Pro Leu Ser Glu Leu Lys Asp Val Pro
770                 775                 780

Gln Lys Thr Asp Val Thr Arg Val Ser Thr Ser Thr Thr Thr Phe Phe
785                 790                 795                 800

Asn Trp Val Arg Thr Thr Ser Ala Asp His Ile Ser Cys Pro Tyr Ser
                805                 810                 815

Phe His Phe Val Ala Cys His Leu Gly Ala Ala Leu Ser Pro Lys Gly
                820                 825                 830

Ser Asn Gly Asp Cys Tyr Pro Ser Ala Gly Lys Phe Leu Ala Ala
                835                 840                 845

Ala Val Cys Arg His Leu Ala Thr Met Cys Arg Met Tyr Asn Asp Leu
    850                 855                 860

Gly Ser Ala Glu Arg Asp Ser Asp Glu Gly Asn Leu Asn Ser Leu Asp
865                 870                 875                 880

Phe Pro Glu Phe Ala Asp Ser Ala Gly Asn Gly Ile Glu Ile Gln
                885                 890                 895

Lys Ala Ala Leu Leu Arg Leu Ala Glu Phe Glu Arg Asp Ser Tyr Leu
                900                 905                 910

Glu Ala Phe Arg Arg Leu Gln Asp Glu Ser Asn Arg Val His Gly Pro
            915                 920                 925

Ala Gly Gly Asp Glu Ala Arg Leu Ser Arg Arg Met Ala Ile Leu
    930                 935                 940
```

Glu Phe Phe Ala Gln Gln Val Asp Leu Tyr Gly Gln Val Tyr Val Ile
945                 950                 955                 960

Arg Asp Ile Ser Ala Arg Ile Pro Lys Asn Glu Val Glu Lys Lys Arg
            965                 970                 975

Lys Leu Asp Asp Ala Phe Asn
            980

<210> SEQ ID NO 56
<211> LENGTH: 881
<212> TYPE: PRT
<213> ORGANISM: Physcomitrella patens

<400> SEQUENCE: 56

Met Ala Ser Ser Thr Leu Ile Gln Asn Arg Ser Cys Gly Val Thr Ser
1               5                   10                  15

Ser Met Ser Ser Phe Gln Ile Phe Arg Gly Gln Pro Leu Arg Phe Pro
            20                  25                  30

Gly Thr Arg Thr Pro Ala Ala Val Gln Cys Leu Lys Lys Arg Arg Cys
        35                  40                  45

Leu Arg Pro Thr Glu Ser Val Leu Glu Ser Pro Gly Ser Gly Ser
50                  55                  60

Tyr Arg Ile Val Thr Gly Pro Ser Gly Ile Asn Pro Ser Ser Asn Gly
65                  70                  75                  80

His Leu Gln Glu Gly Ser Leu Thr His Arg Leu Pro Ile Pro Met Glu
                85                  90                  95

Lys Ser Ile Asp Asn Phe Gln Ser Thr Leu Tyr Val Ser Asp Ile Trp
            100                 105                 110

Ser Glu Thr Leu Gln Arg Thr Glu Cys Leu Leu Gln Val Thr Glu Asn
        115                 120                 125

Val Gln Met Asn Glu Trp Ile Glu Glu Ile Arg Met Tyr Phe Arg Asn
    130                 135                 140

Met Thr Leu Gly Glu Ile Ser Met Ser Pro Tyr Asp Thr Ala Trp Val
145                 150                 155                 160

Ala Arg Val Pro Ala Leu Asp Gly Ser His Gly Pro Gln Phe His Arg
                165                 170                 175

Ser Leu Gln Trp Ile Ile Asp Asn Gln Leu Pro Asp Gly Asp Trp Gly
            180                 185                 190

Glu Pro Ser Leu Phe Leu Gly Tyr Asp Arg Val Cys Asn Thr Leu Ala
        195                 200                 205

Cys Val Ile Ala Leu Lys Thr Trp Gly Val Gly Ala Gln Asn Val Glu
    210                 215                 220

Arg Gly Ile Gln Phe Leu Gln Ser Asn Ile Tyr Lys Met Glu Glu Asp
225                 230                 235                 240

Asp Ala Asn His Met Pro Ile Gly Phe Glu Ile Val Phe Pro Ala Met
                245                 250                 255

Met Glu Asp Ala Lys Ala Leu Gly Leu Asp Leu Pro Tyr Asp Ala Thr
            260                 265                 270

Ile Leu Gln Gln Ile Ser Ala Glu Arg Glu Lys Lys Met Lys Lys Ile
        275                 280                 285

Pro Met Ala Met Val Tyr Lys Tyr Pro Thr Thr Leu Leu His Ser Leu
    290                 295                 300

Glu Gly Leu His Arg Glu Val Asp Trp Asn Lys Leu Leu Gln Leu Gln
305                 310                 315                 320

Ser Glu Asn Gly Ser Phe Leu Tyr Ser Pro Ala Ser Thr Ala Cys Ala
                325                 330                 335

```
Leu Met Tyr Thr Lys Asp Val Lys Cys Phe Asp Tyr Leu Asn Gln Leu
            340                 345                 350

Leu Ile Lys Phe Asp His Ala Cys Pro Asn Val Tyr Pro Val Asp Leu
            355                 360                 365

Phe Glu Arg Leu Trp Met Val Asp Arg Leu Gln Arg Leu Gly Ile Ser
370                 375                 380

Arg Tyr Phe Glu Arg Glu Ile Arg Asp Cys Leu Gln Tyr Val Tyr Arg
385                 390                 395                 400

Tyr Trp Lys Asp Cys Gly Ile Gly Trp Ala Ser Asn Ser Ser Val Gln
                405                 410                 415

Asp Val Asp Asp Thr Ala Met Ala Phe Arg Leu Leu Arg Thr His Gly
            420                 425                 430

Phe Asp Val Lys Glu Asp Cys Phe Arg Gln Phe Phe Lys Asp Gly Glu
            435                 440                 445

Phe Phe Cys Phe Ala Gly Gln Ser Ser Gln Ala Val Thr Gly Met Phe
        450                 455                 460

Asn Leu Ser Arg Ala Ser Gln Thr Leu Phe Pro Gly Glu Ser Leu Leu
465                 470                 475                 480

Lys Lys Ala Arg Thr Phe Ser Arg Asn Phe Leu Arg Thr Lys His Glu
                485                 490                 495

Asn Asn Glu Cys Phe Asp Lys Trp Ile Ile Thr Lys Asp Leu Ala Gly
            500                 505                 510

Glu Val Glu Tyr Asn Leu Thr Phe Pro Trp Tyr Ala Ser Leu Pro Arg
            515                 520                 525

Leu Glu His Arg Thr Tyr Leu Asp Gln Tyr Gly Ile Asp Ile Trp
            530                 535                 540

Ile Gly Lys Ser Leu Tyr Lys Met Pro Ala Val Thr Asn Glu Val Phe
545                 550                 555                 560

Leu Lys Leu Ala Lys Ala Asp Phe Asn Met Cys Gln Ala Leu His Lys
                565                 570                 575

Lys Glu Leu Glu Gln Val Ile Lys Trp Asn Ala Ser Cys Gln Phe Arg
            580                 585                 590

Asp Leu Glu Phe Ala Arg Gln Lys Ser Val Glu Cys Tyr Phe Ala Gly
            595                 600                 605

Ala Ala Thr Met Phe Glu Pro Glu Met Val Gln Ala Arg Leu Val Trp
        610                 615                 620

Ala Arg Cys Cys Val Leu Thr Thr Val Leu Asp Asp Tyr Phe Asp His
625                 630                 635                 640

Gly Thr Pro Val Glu Glu Leu Arg Val Phe Val Gln Ala Val Arg Thr
                645                 650                 655

Trp Asn Pro Glu Leu Ile Asn Gly Leu Pro Glu Gln Ala Lys Ile Leu
            660                 665                 670

Phe Met Gly Leu Tyr Lys Thr Val Asn Thr Ile Ala Glu Glu Ala Phe
        675                 680                 685

Met Ala Gln Lys Arg Asp Val His His Leu Lys His Tyr Trp Asp
            690                 695                 700

Lys Leu Ile Thr Ser Ala Leu Lys Glu Ala Glu Trp Ala Glu Ser Gly
705                 710                 715                 720

Tyr Val Pro Thr Phe Asp Glu Tyr Met Glu Val Ala Glu Ile Ser Val
                725                 730                 735

Ala Leu Glu Pro Ile Val Cys Ser Thr Leu Phe Phe Ala Gly His Arg
            740                 745                 750
```

Leu Asp Glu Asp Val Leu Asp Ser Tyr Asp Tyr His Leu Val Met His
755                 760                 765

Leu Val Asn Arg Val Gly Arg Ile Leu Asn Asp Ile Gln Gly Met Lys
770                 775                 780

Arg Glu Ala Ser Gln Gly Lys Ile Ser Ser Val Gln Ile Tyr Met Glu
785                 790                 795                 800

Glu His Pro Ser Val Pro Ser Glu Ala Met Ala Ile Ala His Leu Gln
                805                 810                 815

Glu Leu Val Asp Asn Ser Met Gln Gln Leu Thr Tyr Glu Val Leu Arg
                820                 825                 830

Phe Thr Ala Val Pro Lys Ser Cys Lys Arg Ile His Leu Asn Met Ala
                835                 840                 845

Lys Ile Met His Ala Phe Tyr Lys Asp Thr Asp Gly Phe Ser Ser Leu
850                 855                 860

Thr Ala Met Thr Gly Phe Val Lys Lys Val Leu Phe Glu Pro Val Pro
865                 870                 875                 880

Glu

<210> SEQ ID NO 57
<211> LENGTH: 952
<212> TYPE: PRT
<213> ORGANISM: Gibberella fujikuroi

<400> SEQUENCE: 57

Met Pro Gly Lys Ile Glu Asn Gly Thr Pro Lys Asp Leu Lys Thr Gly
1               5                   10                  15

Asn Asp Phe Val Ser Ala Ala Lys Ser Leu Leu Asp Arg Ala Phe Lys
                20                  25                  30

Ser His His Ser Tyr Tyr Gly Leu Cys Ser Thr Ser Cys Gln Val Tyr
            35                  40                  45

Asp Thr Ala Trp Val Ala Met Ile Pro Lys Thr Arg Asp Asn Val Lys
50                  55                  60

Gln Trp Leu Phe Pro Glu Cys Phe His Tyr Leu Leu Lys Thr Gln Ala
65                  70                  75                  80

Ala Asp Gly Ser Trp Gly Ser Leu Pro Thr Thr Gln Thr Ala Gly Ile
                85                  90                  95

Leu Asp Thr Ala Ser Ala Val Leu Ala Leu Leu Cys His Ala Gln Glu
                100                 105                 110

Pro Leu Gln Ile Leu Asp Val Ser Pro Asp Glu Met Gly Leu Arg Ile
            115                 120                 125

Glu His Gly Val Thr Ser Leu Lys Arg Gln Leu Ala Val Trp Asn Asp
            130                 135                 140

Val Glu Asp Thr Asn His Ile Gly Val Glu Phe Ile Ile Pro Ala Leu
145                 150                 155                 160

Leu Ser Met Leu Glu Lys Glu Leu Asp Val Pro Ser Phe Glu Phe Pro
                165                 170                 175

Cys Arg Ser Ile Leu Glu Arg Met His Gly Glu Lys Leu Gly His Phe
                180                 185                 190

Asp Leu Glu Gln Val Tyr Gly Lys Pro Ser Ser Leu Leu His Ser Leu
            195                 200                 205

Glu Ala Phe Leu Gly Lys Leu Asp Phe Asp Arg Leu Ser His His Leu
            210                 215                 220

Tyr His Gly Ser Met Met Ala Ser Pro Ser Ser Thr Ala Ala Tyr Leu
225                 230                 235                 240

-continued

Ile Gly Ala Thr Lys Trp Asp Asp Glu Ala Glu Asp Tyr Leu Arg His
             245                 250                 255

Val Met Arg Asn Gly Ala Gly His Gly Asn Gly Gly Ile Ser Gly Thr
         260                 265                 270

Phe Pro Thr Thr His Phe Glu Cys Ser Trp Ile Ile Ala Thr Leu Leu
     275                 280                 285

Lys Val Gly Phe Thr Leu Lys Gln Ile Asp Gly Asp Gly Leu Arg Gly
 290                 295                 300

Leu Ser Thr Ile Leu Leu Glu Ala Leu Arg Asp Glu Asn Gly Val Ile
305                 310                 315                 320

Gly Phe Ala Pro Arg Thr Ala Asp Val Asp Asp Thr Ala Lys Ala Leu
             325                 330                 335

Leu Ala Leu Ser Leu Val Asn Gln Pro Val Ser Pro Asp Ile Met Ile
         340                 345                 350

Lys Val Phe Glu Gly Lys Asp His Phe Thr Thr Phe Gly Ser Glu Arg
     355                 360                 365

Asp Pro Ser Leu Thr Ser Asn Leu His Val Leu Ser Leu Leu Lys
 370                 375                 380

Gln Ser Asn Leu Ser Gln Tyr His Pro Gln Ile Leu Lys Thr Thr Leu
385                 390                 395                 400

Phe Thr Cys Arg Trp Trp Gly Ser Asp His Cys Val Lys Asp Lys
             405                 410                 415

Trp Asn Leu Ser His Leu Tyr Pro Thr Met Leu Leu Val Glu Ala Phe
         420                 425                 430

Thr Glu Val Leu His Leu Ile Asp Gly Gly Glu Leu Ser Ser Leu Phe
     435                 440                 445

Asp Glu Ser Phe Lys Cys Lys Ile Gly Leu Ser Ile Phe Gln Ala Val
 450                 455                 460

Leu Arg Ile Ile Leu Thr Gln Asp Asn Asp Gly Ser Trp Arg Gly Tyr
465                 470                 475                 480

Arg Glu Gln Thr Cys Tyr Ala Ile Leu Ala Leu Val Gln Ala Arg His
             485                 490                 495

Val Cys Phe Phe Thr His Met Val Asp Arg Leu Gln Ser Cys Val Asp
         500                 505                 510

Arg Gly Phe Ser Trp Leu Lys Ser Cys Ser Phe His Ser Gln Asp Leu
     515                 520                 525

Thr Trp Thr Ser Lys Thr Ala Tyr Glu Val Gly Phe Val Ala Glu Ala
 530                 535                 540

Tyr Lys Leu Ala Ala Leu Gln Ser Ala Ser Leu Glu Val Pro Ala Ala
545                 550                 555                 560

Thr Ile Gly His Ser Val Thr Ser Ala Val Pro Ser Ser Asp Leu Glu
             565                 570                 575

Lys Tyr Met Arg Leu Val Arg Lys Thr Ala Leu Phe Ser Pro Leu Asp
         580                 585                 590

Glu Trp Gly Leu Met Ala Ser Ile Ile Glu Ser Ser Phe Phe Val Pro
     595                 600                 605

Leu Leu Gln Ala Gln Arg Val Glu Ile Tyr Pro Arg Asp Asn Ile Lys
 610                 615                 620

Val Asp Glu Asp Lys Tyr Leu Ser Ile Ile Pro Phe Thr Trp Val Gly
625                 630                 635                 640

Cys Asn Asn Arg Ser Arg Thr Phe Ala Ser Asn Arg Trp Leu Tyr Asp
             645                 650                 655

Met Met Tyr Leu Ser Leu Leu Gly Tyr Gln Thr Asp Glu Tyr Met Glu

```
            660                 665                 670
Ala Val Ala Gly Pro Val Phe Gly Asp Val Ser Leu Leu His Gln Thr
            675                 680                 685

Ile Asp Lys Val Ile Asp Asn Thr Met Gly Asn Leu Ala Arg Ala Asn
        690                 695                 700

Gly Thr Val His Ser Gly Asn Gly His Gln His Glu Ser Pro Asn Ile
705                 710                 715                 720

Gly Gln Val Glu Asp Thr Leu Thr Arg Phe Thr Asn Ser Val Leu Asn
                725                 730                 735

His Lys Asp Val Leu Asn Ser Ser Ser Asp Gln Asp Thr Leu Arg
            740                 745                 750

Arg Glu Phe Arg Thr Phe Met His Ala His Ile Thr Gln Ile Glu Asp
            755                 760                 765

Asn Ser Arg Phe Ser Lys Gln Ala Ser Ser Asp Ala Phe Ser Ser Pro
        770                 775                 780

Glu Gln Ser Tyr Phe Gln Trp Val Asn Ser Thr Gly Gly Ser His Val
785                 790                 795                 800

Ala Cys Ala Tyr Ser Phe Ala Phe Ser Asn Cys Leu Met Ser Ala Asn
                805                 810                 815

Leu Leu Gln Gly Lys Asp Ala Phe Pro Ser Gly Thr Gln Lys Tyr Leu
            820                 825                 830

Ile Ser Ser Val Met Arg His Ala Thr Asn Met Cys Arg Met Tyr Asn
        835                 840                 845

Asp Phe Gly Ser Ile Ala Arg Asp Asn Ala Glu Arg Asn Val Asn Ser
    850                 855                 860

Ile His Phe Pro Glu Phe Thr Leu Cys Asn Gly Thr Ser Gln Asn Leu
865                 870                 875                 880

Asp Glu Arg Lys Glu Arg Leu Leu Lys Ile Ala Thr Tyr Glu Gln Gly
                885                 890                 895

Tyr Leu Asp Arg Ala Leu Glu Ala Leu Glu Arg Gln Ser Arg Asp Asp
            900                 905                 910

Ala Gly Asp Arg Ala Gly Ser Lys Asp Met Arg Lys Leu Lys Ile Val
        915                 920                 925

Lys Leu Phe Cys Asp Val Thr Asp Leu Tyr Asp Gln Leu Tyr Val Ile
    930                 935                 940

Lys Asp Leu Ser Ser Ser Met Lys
945                 950

<210> SEQ ID NO 58
<211> LENGTH: 361
<212> TYPE: PRT
<213> ORGANISM: Stevia rebaudiana

<400> SEQUENCE: 58

Met Ala Leu Val Asn Pro Thr Ala Leu Phe Tyr Gly Thr Ser Ile Arg
1               5                   10                  15

Thr Arg Pro Thr Asn Leu Leu Asn Pro Thr Gln Lys Leu Arg Pro Val
                20                  25                  30

Ser Ser Ser Ser Leu Pro Ser Phe Ser Ser Val Ser Ala Ile Leu Thr
            35                  40                  45

Glu Lys His Gln Ser Asn Pro Ser Glu Asn Asn Asn Leu Gln Thr His
        50                  55                  60

Leu Glu Thr Pro Phe Asn Phe Asp Ser Tyr Met Leu Glu Lys Val Asn
65                  70                  75                  80
```

Met Val Asn Glu Ala Leu Asp Ala Ser Val Pro Leu Lys Asp Pro Ile
                85                  90                  95

Lys Ile His Glu Ser Met Arg Tyr Ser Leu Leu Ala Gly Gly Lys Arg
            100                 105                 110

Ile Arg Pro Met Met Cys Ile Ala Ala Cys Glu Ile Val Gly Gly Asn
        115                 120                 125

Ile Leu Asn Ala Met Pro Ala Ala Cys Ala Val Glu Met Ile His Thr
    130                 135                 140

Met Ser Leu Val His Asp Leu Pro Cys Met Asp Asn Asp Asp Phe
145                 150                 155                 160

Arg Arg Gly Lys Pro Ile Ser His Lys Val Tyr Gly Glu Met Ala
                165                 170                 175

Val Leu Thr Gly Asp Ala Leu Leu Ser Leu Ser Phe Glu His Ile Ala
            180                 185                 190

Thr Ala Thr Lys Gly Val Ser Lys Asp Arg Ile Val Arg Ala Ile Gly
        195                 200                 205

Glu Leu Ala Arg Ser Val Gly Ser Glu Gly Leu Val Ala Gly Gln Val
    210                 215                 220

Val Asp Ile Leu Ser Glu Gly Ala Asp Val Gly Leu Asp His Leu Glu
225                 230                 235                 240

Tyr Ile His Ile His Lys Thr Ala Met Leu Leu Glu Ser Ser Val Val
                245                 250                 255

Ile Gly Ala Ile Met Gly Gly Gly Ser Asp Gln Gln Ile Glu Lys Leu
            260                 265                 270

Arg Lys Phe Ala Arg Ser Ile Gly Leu Leu Phe Gln Val Val Asp Asp
        275                 280                 285

Ile Leu Asp Val Thr Lys Ser Thr Glu Glu Leu Gly Lys Thr Ala Gly
    290                 295                 300

Lys Asp Leu Leu Thr Asp Lys Thr Thr Tyr Pro Lys Leu Leu Gly Ile
305                 310                 315                 320

Glu Lys Ser Arg Glu Phe Ala Glu Lys Leu Asn Lys Glu Ala Gln Glu
                325                 330                 335

Gln Leu Ser Gly Phe Asp Arg Arg Lys Ala Ala Pro Leu Ile Ala Leu
            340                 345                 350

Ala Asn Tyr Asn Ala Tyr Arg Gln Asn
        355                 360

<210> SEQ ID NO 59
<211> LENGTH: 342
<212> TYPE: PRT
<213> ORGANISM: Fusarium fujikuroi

<400> SEQUENCE: 59

Met Ala Glu Gln Gln Ile Ser Asn Leu Leu Ser Met Phe Asp Ala Ser
1               5                   10                  15

His Ala Ser Gln Lys Leu Glu Ile Thr Val Gln Met Met Asp Thr Tyr
            20                  25                  30

His Tyr Arg Glu Thr Pro Pro Asp Ser Ser Ser Glu Gly Gly Ser
        35                  40                  45

Leu Ser Arg Tyr Asp Glu Arg Arg Val Ser Leu Pro Leu Ser His Asn
    50                  55                  60

Ala Ala Ser Pro Asp Ile Val Ser Gln Leu Cys Phe Ser Thr Ala Met
65                  70                  75                  80

Ser Ser Glu Leu Asn His Arg Trp Lys Ser Gln Arg Leu Lys Val Ala
                85                  90                  95

```
Asp Ser Pro Tyr Asn Tyr Ile Leu Thr Leu Pro Ser Lys Gly Ile Arg
                100                 105                 110

Gly Ala Phe Ile Asp Ser Leu Asn Val Trp Leu Glu Val Pro Glu Asp
            115                 120                 125

Glu Thr Ser Val Ile Lys Glu Val Ile Gly Met Leu His Asn Ser Ser
        130                 135                 140

Leu Ile Ile Asp Asp Phe Gln Asp Asn Ser Pro Leu Arg Arg Gly Lys
145                 150                 155                 160

Pro Ser Thr His Thr Val Phe Gly Pro Ala Gln Ala Ile Asn Thr Ala
                165                 170                 175

Thr Tyr Val Ile Val Lys Ala Ile Glu Lys Ile Gln Asp Ile Val Gly
            180                 185                 190

His Asp Ala Leu Ala Asp Val Thr Gly Thr Ile Thr Thr Ile Phe Gln
        195                 200                 205

Gly Gln Ala Met Asp Leu Trp Trp Thr Ala Asn Ala Ile Val Pro Ser
210                 215                 220

Ile Gln Glu Tyr Leu Leu Met Val Asn Asp Lys Thr Gly Ala Leu Phe
225                 230                 235                 240

Arg Leu Ser Leu Glu Leu Leu Ala Leu Asn Ser Glu Ala Ser Ile Ser
                245                 250                 255

Asp Ser Ala Leu Glu Ser Leu Ser Ser Ala Val Ser Leu Leu Gly Gln
            260                 265                 270

Tyr Phe Gln Ile Arg Asp Asp Tyr Met Asn Leu Ile Asp Asn Lys Tyr
        275                 280                 285

Thr Asp Gln Lys Gly Phe Cys Glu Asp Leu Asp Glu Gly Lys Tyr Ser
290                 295                 300

Leu Thr Leu Ile His Ala Leu Gln Thr Asp Ser Ser Asp Leu Leu Thr
305                 310                 315                 320

Asn Ile Leu Ser Met Arg Arg Val Gln Gly Lys Leu Thr Ala Gln Lys
                325                 330                 335

Arg Cys Trp Phe Trp Lys
            340

<210> SEQ ID NO 60
<211> LENGTH: 300
<212> TYPE: PRT
<213> ORGANISM: Mus musculus

<400> SEQUENCE: 60

Met Glu Lys Thr Lys Glu Lys Ala Glu Arg Ile Leu Leu Glu Pro Tyr
1               5                   10                  15

Arg Tyr Leu Leu Gln Leu Pro Gly Lys Gln Val Arg Ser Lys Leu Ser
            20                  25                  30

Gln Ala Phe Asn His Trp Leu Lys Val Pro Glu Asp Lys Leu Gln Ile
        35                  40                  45

Ile Ile Glu Val Thr Glu Met Leu His Asn Ala Ser Leu Leu Ile Asp
    50                  55                  60

Asp Ile Glu Asp Ser Ser Lys Leu Arg Arg Gly Phe Pro Val Ala His
65                  70                  75                  80

Ser Ile Tyr Gly Val Pro Ser Val Ile Asn Ser Ala Asn Tyr Val Tyr
                85                  90                  95

Phe Leu Gly Leu Glu Lys Val Leu Thr Leu Asp His Pro Asp Ala Val
            100                 105                 110

Lys Leu Phe Thr Arg Gln Leu Leu Glu Leu His Gln Gly Gln Gly Leu
```

```
            115                 120                 125
Asp Ile Tyr Trp Arg Asp Thr Tyr Thr Cys Pro Thr Glu Glu Glu Tyr
    130                 135                 140

Lys Ala Met Val Leu Gln Lys Thr Gly Gly Leu Phe Gly Leu Ala Val
145                 150                 155                 160

Gly Leu Met Gln Leu Phe Ser Asp Tyr Lys Glu Asp Leu Lys Pro Leu
                165                 170                 175

Leu Asp Thr Leu Gly Leu Phe Phe Gln Ile Arg Asp Asp Tyr Ala Asn
            180                 185                 190

Leu His Ser Lys Glu Tyr Ser Glu Asn Lys Ser Phe Cys Glu Asp Leu
        195                 200                 205

Thr Glu Gly Lys Phe Ser Phe Pro Thr Ile His Ala Ile Trp Ser Arg
    210                 215                 220

Pro Glu Ser Thr Gln Val Gln Asn Ile Leu Arg Gln Arg Thr Glu Asn
225                 230                 235                 240

Ile Asp Ile Lys Lys Tyr Cys Val Gln Tyr Leu Glu Asp Val Gly Ser
                245                 250                 255

Phe Ala Tyr Thr Arg His Thr Leu Arg Glu Leu Glu Ala Lys Ala Tyr
            260                 265                 270

Lys Gln Ile Glu Ala Cys Gly Gly Asn Pro Ser Leu Val Ala Leu Val
        275                 280                 285

Lys His Leu Ser Lys Met Phe Thr Glu Glu Asn Lys
    290                 295                 300

<210> SEQ ID NO 61
<211> LENGTH: 339
<212> TYPE: PRT
<213> ORGANISM: Thalassiosira pseudonana

<400> SEQUENCE: 61

Met Ala Arg Phe Tyr Phe Leu Asn Ala Leu Leu Met Val Ile Ser Leu
1               5                   10                  15

Gln Ser Thr Thr Ala Phe Thr Pro Ala Lys Leu Ala Tyr Pro Thr Thr
            20                  25                  30

Thr Thr Ala Leu Asn Val Ala Ser Ala Glu Thr Ser Phe Ser Leu Asp
        35                  40                  45

Glu Tyr Leu Ala Ser Lys Ile Gly Pro Ile Glu Ser Ala Leu Glu Ala
    50                  55                  60

Ser Val Lys Ser Arg Ile Pro Gln Thr Asp Lys Ile Cys Glu Ser Met
65                  70                  75                  80

Ala Tyr Ser Leu Met Ala Gly Gly Lys Arg Ile Arg Pro Val Leu Cys
                85                  90                  95

Ile Ala Ala Cys Glu Met Phe Gly Gly Ser Gln Asp Val Ala Met Pro
            100                 105                 110

Thr Ala Val Ala Leu Glu Met Ile His Thr Met Ser Leu Ile His Asp
        115                 120                 125

Asp Leu Pro Ser Met Asp Asn Asp Leu Arg Arg Gly Lys Pro Thr
    130                 135                 140

Asn His Val Val Phe Gly Glu Asp Val Ala Ile Leu Ala Gly Asp Ser
145                 150                 155                 160

Leu Leu Ser Thr Ser Phe Glu His Val Ala Arg Glu Thr Lys Gly Val
                165                 170                 175

Ser Ala Glu Lys Ile Val Asp Val Ile Ala Arg Leu Gly Lys Ser Val
            180                 185                 190
```

```
Gly Ala Glu Gly Leu Ala Gly Gln Val Met Asp Leu Glu Cys Glu
            195                 200                 205

Ala Lys Pro Gly Thr Thr Leu Asp Asp Leu Lys Trp Ile His Ile His
    210                 215                 220

Lys Thr Ala Thr Leu Leu Gln Val Ala Val Ser Gly Ala Val Leu
225                 230                 235                 240

Gly Gly Ala Thr Pro Glu Val Ala Ala Cys Glu Leu Phe Ala Met
                245                 250                 255

Asn Ile Gly Leu Ala Phe Gln Val Ala Asp Asp Ile Leu Asp Val Thr
            260                 265                 270

Ala Ser Ser Glu Asp Leu Gly Lys Thr Ala Gly Lys Asp Glu Ala Thr
    275                 280                 285

Asp Lys Thr Thr Tyr Pro Lys Leu Leu Gly Leu Glu Glu Ser Lys Ala
    290                 295                 300

Tyr Ala Arg Gln Leu Ile Asp Glu Ala Lys Glu Ser Leu Ala Pro Phe
305                 310                 315                 320

Gly Asp Arg Ala Ala Pro Leu Leu Ala Ile Ala Asp Phe Ile Ile Asp
                325                 330                 335

Arg Lys Asn

<210> SEQ ID NO 62
<211> LENGTH: 355
<212> TYPE: PRT
<213> ORGANISM: Streptomyces clavuligerus

<400> SEQUENCE: 62

Met His Leu Ala Pro Arg Arg Val Pro Arg Gly Arg Ser Pro Pro
1               5                   10                  15

Asp Arg Val Pro Glu Arg Gln Gly Ala Leu Gly Arg Arg Gly Ala
            20                  25                  30

Gly Ser Thr Gly Cys Ala Arg Ala Ala Gly Val His Arg Arg Arg
        35                  40                  45

Gly Gly Gly Glu Ala Asp Pro Ser Ala Ala Val His Arg Gly Trp Gln
    50                  55                  60

Ala Gly Gly Gly Thr Gly Leu Pro Asp Glu Val Val Ser Thr Ala Ala
65                  70                  75                  80

Ala Leu Glu Met Phe His Ala Phe Ala Leu Ile His Asp Asp Ile Met
                85                  90                  95

Asp Asp Ser Ala Thr Arg Arg Gly Ser Pro Thr Val His Arg Ala Leu
            100                 105                 110

Ala Asp Arg Leu Gly Ala Ala Leu Asp Pro Asp Gln Ala Gly Gln Leu
    115                 120                 125

Gly Val Ser Thr Ala Ile Leu Val Gly Asp Leu Ala Leu Thr Trp Ser
130                 135                 140

Asp Glu Leu Leu Tyr Ala Pro Leu Thr Pro His Arg Leu Ala Ala Val
145                 150                 155                 160

Leu Pro Leu Val Thr Ala Met Arg Ala Glu Thr Val His Gly Gln Tyr
                165                 170                 175

Leu Asp Ile Thr Ser Ala Arg Arg Pro Gly Thr Asp Thr Ser Leu Ala
            180                 185                 190

Leu Arg Ile Ala Arg Tyr Lys Thr Ala Ala Tyr Thr Met Glu Arg Pro
    195                 200                 205

Leu His Ile Gly Ala Ala Leu Ala Gly Ala Arg Pro Glu Leu Leu Ala
    210                 215                 220
```

```
Gly Leu Ser Ala Tyr Ala Leu Pro Ala Gly Glu Ala Phe Gln Leu Ala
225                 230                 235                 240

Asp Asp Leu Leu Gly Val Phe Gly Asp Pro Arg Arg Thr Gly Lys Pro
            245                 250                 255

Asp Leu Asp Asp Leu Arg Gly Gly Lys His Thr Val Leu Val Ala Leu
            260                 265                 270

Ala Arg Glu His Ala Thr Pro Glu Gln Arg His Thr Leu Asp Thr Leu
            275                 280                 285

Leu Gly Thr Pro Gly Leu Asp Arg Gln Gly Ala Ser Arg Leu Arg Cys
    290                 295                 300

Val Leu Val Ala Thr Gly Ala Arg Ala Glu Ala Glu Arg Leu Ile Thr
305                 310                 315                 320

Glu Arg Arg Asp Gln Ala Leu Thr Ala Leu Asn Ala Leu Thr Leu Pro
                325                 330                 335

Pro Pro Leu Ala Glu Ala Leu Ala Arg Leu Thr Leu Gly Ser Thr Ala
            340                 345                 350

His Pro Ala
        355

<210> SEQ ID NO 63
<211> LENGTH: 330
<212> TYPE: PRT
<213> ORGANISM: Sulfolobus acidocaldarius

<400> SEQUENCE: 63

Met Ser Tyr Phe Asp Asn Tyr Phe Asn Glu Ile Val Asn Ser Val Asn
1               5                   10                  15

Asp Ile Ile Lys Ser Tyr Ile Ser Gly Asp Val Pro Lys Leu Tyr Glu
            20                  25                  30

Ala Ser Tyr His Leu Phe Thr Ser Gly Gly Lys Arg Leu Arg Pro Leu
        35                  40                  45

Ile Leu Thr Ile Ser Ser Asp Leu Phe Gly Gly Gln Arg Glu Arg Ala
    50                  55                  60

Tyr Tyr Ala Gly Ala Ala Ile Glu Val Leu His Thr Phe Thr Leu Val
65                  70                  75                  80

His Asp Asp Ile Met Asp Gln Asp Asn Ile Arg Arg Gly Leu Pro Thr
                85                  90                  95

Val His Val Lys Tyr Gly Leu Pro Leu Ala Ile Leu Ala Gly Asp Leu
            100                 105                 110

Leu His Ala Lys Ala Phe Gln Leu Leu Thr Gln Ala Leu Arg Gly Leu
        115                 120                 125

Pro Ser Glu Thr Ile Ile Lys Ala Phe Asp Ile Phe Thr Arg Ser Ile
    130                 135                 140

Ile Ile Ile Ser Glu Gly Gln Ala Val Asp Met Glu Phe Glu Asp Arg
145                 150                 155                 160

Ile Asp Ile Lys Glu Gln Glu Tyr Leu Asp Met Ile Ser Arg Lys Thr
                165                 170                 175

Ala Ala Leu Phe Ser Ala Ser Ser Ile Gly Ala Leu Ile Ala Gly
            180                 185                 190

Ala Asn Asp Asn Asp Val Arg Leu Met Ser Asp Phe Gly Thr Asn Leu
        195                 200                 205

Gly Ile Ala Phe Gln Ile Val Asp Asp Ile Leu Gly Leu Thr Ala Asp
    210                 215                 220

Glu Lys Glu Leu Gly Lys Pro Val Phe Ser Asp Ile Arg Glu Gly Lys
225                 230                 235                 240
```

```
Lys Thr Ile Leu Val Ile Lys Thr Leu Glu Leu Cys Lys Glu Asp Glu
                245                 250                 255

Lys Lys Ile Val Leu Lys Ala Leu Gly Asn Lys Ser Ala Ser Lys Glu
            260                 265                 270

Glu Leu Met Ser Ser Ala Asp Ile Ile Lys Lys Tyr Ser Leu Asp Tyr
        275                 280                 285

Ala Tyr Asn Leu Ala Glu Lys Tyr Tyr Lys Asn Ala Ile Asp Ser Leu
    290                 295                 300

Asn Gln Val Ser Ser Lys Ser Asp Ile Pro Gly Lys Ala Leu Lys Tyr
305                 310                 315                 320

Leu Ala Glu Phe Thr Ile Arg Arg Lys
                325                 330

<210> SEQ ID NO 64
<211> LENGTH: 297
<212> TYPE: PRT
<213> ORGANISM: Synechococcus sp.

<400> SEQUENCE: 64

Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
            20                  25                  30

Glu Arg Ile Tyr Glu Ala Met Arg Tyr Ser Leu Leu Ala Gly Gly Lys
        35                  40                  45

Arg Leu Arg Pro Ile Leu Cys Leu Ala Ala Cys Glu Leu Ala Gly Gly
    50                  55                  60

Ser Val Glu Gln Ala Met Pro Thr Ala Cys Ala Leu Glu Met Ile His
65                  70                  75                  80

Thr Met Ser Leu Ile His Asp Asp Leu Pro Ala Met Asp Asn Asp Asp
                85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
    130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
    210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
```

```
            275                 280                 285
Ala Asp Phe Ile Thr Arg Arg Gln His
    290                 295

<210> SEQ ID NO 65
<211> LENGTH: 371
<212> TYPE: PRT
<213> ORGANISM: Arabidopsis thaliana

<400> SEQUENCE: 65

Met Ala Ser Val Thr Leu Gly Ser Trp Ile Val His His Asn
1               5                   10                  15

His His His Pro Ser Ser Ile Leu Thr Lys Ser Arg Ser Arg Ser Cys
            20                  25                  30

Pro Ile Thr Leu Thr Lys Pro Ile Ser Phe Arg Ser Lys Arg Thr Val
        35                  40                  45

Ser Ser Ser Ser Ser Ile Val Ser Ser Val Val Thr Lys Glu Asp
    50                  55                  60

Asn Leu Arg Gln Ser Glu Pro Ser Ser Phe Asp Phe Met Ser Tyr Ile
65                  70                  75                  80

Ile Thr Lys Ala Glu Leu Val Asn Lys Ala Leu Asp Ser Ala Val Pro
                85                  90                  95

Leu Arg Glu Pro Leu Lys Ile His Glu Ala Met Arg Tyr Ser Leu Leu
            100                 105                 110

Ala Gly Gly Lys Arg Val Arg Pro Val Leu Cys Ile Ala Ala Cys Glu
        115                 120                 125

Leu Val Gly Gly Glu Glu Ser Thr Ala Met Pro Ala Ala Cys Ala Val
    130                 135                 140

Glu Met Ile His Thr Met Ser Leu Ile His Asp Asp Leu Pro Cys Met
145                 150                 155                 160

Asp Asn Asp Asp Leu Arg Arg Gly Lys Pro Thr Asn His Lys Val Phe
                165                 170                 175

Gly Glu Asp Val Ala Val Leu Ala Gly Asp Ala Leu Leu Ser Phe Ala
            180                 185                 190

Phe Glu His Leu Ala Ser Ala Thr Ser Ser Asp Val Val Ser Pro Val
        195                 200                 205

Arg Val Val Arg Ala Val Gly Glu Leu Ala Lys Ala Ile Gly Thr Glu
    210                 215                 220

Gly Leu Val Ala Gly Gln Val Val Asp Ile Ser Ser Glu Gly Leu Asp
225                 230                 235                 240

Leu Asn Asp Val Gly Leu Glu His Leu Glu Phe Ile His Leu His Lys
                245                 250                 255

Thr Ala Ala Leu Leu Glu Ala Ser Ala Val Leu Gly Ala Ile Val Gly
            260                 265                 270

Gly Gly Ser Asp Asp Glu Ile Glu Arg Leu Arg Lys Phe Ala Arg Cys
        275                 280                 285

Ile Gly Leu Leu Phe Gln Val Val Asp Asp Ile Leu Asp Val Thr Lys
    290                 295                 300

Ser Ser Lys Glu Leu Gly Lys Thr Ala Gly Lys Asp Leu Ile Ala Asp
305                 310                 315                 320

Lys Leu Thr Tyr Pro Lys Ile Met Gly Leu Glu Lys Ser Arg Glu Phe
                325                 330                 335

Ala Glu Lys Leu Asn Arg Glu Ala Arg Asp Gln Leu Leu Gly Phe Asp
            340                 345                 350
```

Ser Asp Lys Val Ala Pro Leu Leu Ala Leu Ala Asn Tyr Ile Ala Tyr
        355                 360                 365

Arg Gln Asn
    370

<210> SEQ ID NO 66
<211> LENGTH: 473
<212> TYPE: PRT
<213> ORGANISM: Stevia rebaudiana

<400> SEQUENCE: 66

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

```
Glu Ser Val Cys Gly Phe Leu Thr His Cys Gly Ser Gly Ser Ile Val
            355                 360                 365

Glu Gly Leu Met Phe Gly His Pro Leu Ile Met Leu Pro Ile Phe Gly
            370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Lys Gly Glu Ile Tyr
            420                 425                 430

Lys Ala Asn Ala Arg Glu Leu Ser Lys Ile Tyr Asn Asp Thr Lys Val
            435                 440                 445

Glu Lys Glu Tyr Val Ser Gln Phe Val Asp Tyr Leu Glu Lys Asn Ala
            450                 455                 460

Arg Ala Val Ala Ile Asp His Glu Ser
465                 470
```

<210> SEQ ID NO 67
<211> LENGTH: 459
<212> TYPE: PRT
<213> ORGANISM: Ipomoea purpurea

<400> SEQUENCE: 67

```
Met Gly Ser Gln Ala Thr Thr Tyr His Met Ala Met Tyr Pro Trp Phe
1               5                   10                  15

Gly Val Gly His Leu Thr Gly Phe Phe Arg Leu Ala Asn Lys Leu Ala
            20                  25                  30

Gly Lys Gly His Arg Ile Ser Phe Leu Ile Pro Lys Asn Thr Gln Ser
            35                  40                  45

Lys Leu Glu Ser Phe Asn Leu His Pro His Leu Ile Ser Phe Val Pro
    50                  55                  60

Ile Val Val Pro Ser Ile Pro Gly Leu Pro Pro Gly Ala Glu Thr Thr
65                  70                  75                  80

Ser Asp Val Pro Phe Pro Ser Thr His Leu Leu Met Glu Ala Met Asp
                85                  90                  95

Lys Thr Gln Asn Asp Ile Glu Ile Ile Leu Lys Asp Leu Lys Val Asp
            100                 105                 110

Val Val Phe Tyr Asp Phe Thr His Trp Leu Pro Ser Leu Ala Arg Lys
            115                 120                 125

Ile Gly Ile Lys Ser Val Phe Tyr Ser Thr Ile Ser Pro Leu Met His
    130                 135                 140

Gly Tyr Ala Leu Ser Pro Glu Arg Arg Val Val Gly Lys Gln Leu Thr
145                 150                 155                 160

Glu Ala Asp Met Met Lys Ala Pro Ala Ser Phe Pro Asp Pro Ser Ile
                165                 170                 175

Lys Leu His Ala His Glu Ala Arg Gly Phe Thr Ala Arg Thr Val Met
            180                 185                 190

Lys Phe Gly Gly Asp Ile Thr Phe Phe Asp Arg Ile Phe Thr Ala Val
            195                 200                 205

Ser Glu Ser Asp Gly Leu Ala Tyr Ser Thr Cys Arg Glu Ile Glu Gly
            210                 215                 220

Gln Phe Cys Asp Tyr Ile Glu Thr Gln Phe Gln Lys Pro Val Leu Leu
225                 230                 235                 240

Ala Gly Pro Ala Leu Pro Val Pro Ser Lys Ser Thr Met Glu Gln Lys
```

245                 250                 255
Trp Ser Asp Trp Leu Gly Lys Phe Lys Glu Gly Ser Val Ile Tyr Cys
            260                 265                 270

Ala Phe Gly Ser Glu Cys Thr Leu Arg Lys Asp Lys Phe Gln Glu Leu
            275                 280                 285

Leu Trp Gly Leu Glu Leu Thr Gly Met Pro Phe Phe Ala Ala Leu Lys
    290                 295                 300

Pro Pro Phe Glu Thr Glu Ser Val Glu Ala Ile Pro Glu Leu
305                 310                 315                 320

Lys Glu Lys Ile Gln Gly Arg Gly Ile Val His Gly Glu Trp Val Gln
                325                 330                 335

Gln Gln Leu Phe Leu Gln His Pro Ser Val Gly Cys Phe Val Ser His
            340                 345                 350

Cys Gly Trp Ala Ser Leu Ser Glu Ala Leu Val Asn Asp Cys Gln Ile
            355                 360                 365

Val Leu Leu Pro Gln Val Gly Asp Gln Ile Ile Asn Ala Arg Ile Met
    370                 375                 380

Ser Val Ser Leu Lys Val Gly Val Glu Val Lys Gly Glu Glu Asp
385                 390                 395                 400

Gly Val Phe Ser Arg Glu Ser Val Cys Lys Ala Val Lys Ala Val Met
                405                 410                 415

Asp Glu Lys Ser Glu Ile Gly Arg Glu Val Arg Gly Asn His Asp Lys
            420                 425                 430

Leu Arg Gly Phe Leu Met Asn Ala Asp Leu Asp Ser Lys Tyr Met Asp
            435                 440                 445

Ser Phe Asn Gln Lys Leu Gln Asp Leu Leu Gly
    450                 455

<210> SEQ ID NO 68
<211> LENGTH: 1380
<212> TYPE: DNA
<213> ORGANISM: Artificial Sequence
<220> FEATURE:
<223> OTHER INFORMATION: Synthetic oligonucleotide

<400> SEQUENCE: 68
atgggttctc aagctacaac ttaccatatg gccatgtatc catggtttgg ggttggacat      60
ttgactggtt tcttccgttt ggcaaacaaa ttagctggca aggacatag aatctcattt     120
ctaattccta aaacactca atctaagtta gaatctttca accttcatcc acacttaatc     180
tcttttgtgc ctatcgttgt cccaagtata ccaggcctgc cacctggtgc agagactaca     240
tcagatgttc ctttcccaag tacacatttg ctaatggaag caatggacaa gactcaaaac     300
gatatagaga ttatcctgaa ggatcttaaa gtagatgttg ttttctatga ttttactcac     360
tggttgcctt ctctggccag aaagattggc attaagagtg tcttttactc caccatttct     420
cctttaatgc atggatatgc tttatcacca gaaagacgtg tagttggtaa gcaattgaca     480
gaggcagata tgatgaaggc cccagcttct ttcccagacc catccattaa gctacatgca     540
catgaagcta ggggttttac agccagaacc gttatgaaat cggtggtga catcaccttt     600
ttcgatagaa tattcacagc agtttccgaa agtgatggcc tggcctactc tacttgtaga     660
gagatcgagg acaattctg tgattacatt gaaacacaat tccagaagcc agtcttgtta     720
gccggtccag ctttgccagt cccatccaaa tccactatgg aacaaaagtg gtcagattgg     780
ttggggaaat tcaaggaagg ctccgtcatc tactgtgctt cgggtctga atgtacattg     840

```
agaaaggaca aatttcagga acttttatgg ggtttggaat tgacaggaat gcctttcttc    900
gctgctctga agccacctt  tgagactgag tctgttgagg ctgctatccc tgaggaacta    960
aaggaaaaga ttcagggaag aggtatagta catggagaat gggtacaaca acaattgttt   1020
cttcaacacc catctgtcgg gtgcttcgtt tctcactgcg gctgggcaag tttatctgaa   1080
gcccttgtta atgattgtca aatcgtgtta cttccacaag ttggcgatca gattatcaac   1140
gccagaataa tgtcagtatc acttaaagtg ggcgtgaag ttgaaagg  tgaggaggac   1200 ggtgtctttt caagagaatc tgtgtgcaag ctgttaaag cagtaatgga tgaaaaatct   1260
gaaatcggta gagaagtcag aggtaatcat gataaactga ggggtttctt gatgaatgca   1320
gacttagatt caaagtacat ggattcattc aatcaaaagc tacaagattt gctaggttaa   1380
```

<210> SEQ ID NO 69
<211> LENGTH: 438
<212> TYPE: PRT
<213> ORGANISM: Bellis perennis

<400> SEQUENCE: 69

```
Met Asp Ser Lys Ile Asp Ser Lys Thr Phe Arg Val Val Met Leu Pro
1               5                   10                  15

Trp Leu Ala Tyr Ser His Ile Ser Ser Phe Leu Val Phe Ala Lys Arg
            20                  25                  30

Leu Thr Asn His Asn Phe His Ile Tyr Ile Cys Ser Ser Gln Thr Asn
        35                  40                  45

Met Gln Tyr Leu Lys Asn Asn Leu Thr Ser Gln Tyr Ser Lys Ser Ile
    50                  55                  60

Gln Leu Ile Glu Leu Asn Leu Pro Ser Ser Glu Leu Pro Leu Gln
65                  70                  75                  80

Tyr His Thr Thr His Gly Leu Pro Pro His Leu Thr Lys Thr Leu Ser
                85                  90                  95

Asp Asp Tyr Gln Lys Ser Gly Pro Asp Phe Glu Thr Ile Leu Ile Lys
            100                 105                 110

Leu Asn Pro His Leu Val Ile Tyr Asp Phe Asn Gln Leu Trp Ala Pro
        115                 120                 125

Glu Val Ala Ser Thr Leu His Ile Pro Ser Ile Gln Leu Leu Ser Gly
    130                 135                 140

Cys Val Ala Leu Tyr Ala Leu Asp Ala His Leu Tyr Thr Lys Pro Leu
145                 150                 155                 160

Asp Glu Asn Leu Ala Lys Phe Pro Phe Pro Glu Ile Tyr Pro Lys Asn
                165                 170                 175

Arg Asp Ile Pro Lys Gly Gly Ser Lys Tyr Ile Glu Arg Phe Val Asp
            180                 185                 190

Cys Met Arg Arg Ser Cys Glu Ile Ile Leu Val Arg Ser Thr Met Glu
        195                 200                 205

Leu Glu Gly Lys Tyr Ile Asp Tyr Leu Ser Lys Thr Leu Gly Lys Lys
    210                 215                 220

Val Leu Pro Val Gly Pro Leu Val Gln Glu Ala Ser Leu Leu Gln Asp
225                 230                 235                 240

Asp His Ile Trp Ile Met Lys Trp Leu Asp Lys Lys Glu Glu Ser Ser
                245                 250                 255

Val Val Phe Val Cys Phe Gly Ser Glu Tyr Ile Leu Ser Asp Asn Glu
            260                 265                 270

Ile Glu Asp Ile Ala Tyr Gly Leu Glu Leu Ser Gln Val Ser Phe Val
        275                 280                 285
```

```
Trp Ala Ile Arg Ala Lys Thr Ser Ala Leu Asn Gly Phe Ile Asp Arg
        290                 295                 300

Val Gly Asp Lys Gly Leu Val Ile Asp Lys Trp Val Pro Gln Ala Asn
305                 310                 315                 320

Ile Leu Ser His Ser Ser Thr Gly Gly Phe Ile Ser His Cys Gly Trp
                325                 330                 335

Ser Ser Thr Met Glu Ser Ile Arg Tyr Gly Val Pro Ile Ile Ala Met
            340                 345                 350

Pro Met Gln Phe Asp Gln Pro Tyr Asn Ala Arg Leu Met Glu Thr Val
        355                 360                 365

Gly Ala Gly Ile Glu Val Gly Arg Asp Gly Glu Gly Arg Leu Lys Arg
        370                 375                 380

Glu Glu Ile Ala Ala Val Val Arg Lys Val Val Val Glu Asp Ser Gly
385                 390                 395                 400

Glu Ser Ile Arg Glu Lys Ala Lys Glu Leu Gly Glu Ile Met Lys Lys
            405                 410                 415

Asn Met Glu Ala Glu Val Asp Gly Ile Val Ile Glu Asn Leu Val Lys
            420                 425                 430

Leu Cys Glu Met Asn Asn
        435
```

<210> SEQ ID NO 70
<211> LENGTH: 1317
<212> TYPE: DNA
<213> ORGANISM: Artificial Sequence
<220> FEATURE:
<223> OTHER INFORMATION: Synthetic oligonucleotide

<400> SEQUENCE: 70

| | | | | | |
|---|---|---|---|---|---|
| atggattcta | aaatcgattc | aaagacattc | agagtcgtta | tgttgccttg | gcttgcatac | 60 |
| tcacacattt | catcattcct | agtgtttgcc | aagagactaa | caaatcataa | cttccacatc | 120 |
| tacatttgtt | cctctcaaac | aaatatgcaa | tacctgaaaa | acaacttgac | gtctcagtat | 180 |
| tcaaaatcta | taactgat | tgagttgaat | cttccatcta | gttccgaatt | gcctctgcag | 240 |
| tatcatacta | ctcacggact | accaccacac | cttacgaaaa | cattgtctga | tgattatcaa | 300 |
| aagtccggac | tgactttga | aaccattttg | atcaaattga | acccacatct | ggtaatctac | 360 |
| gactttaatc | aactttgggc | tccagaggtt | gctagtacac | ttcatattcc | atccatacag | 420 |
| ttactgtctg | gttgcgtcgc | cttatatgcc | ttagacgccc | atctgtacac | aaagccacta | 480 |
| gacgaaaact | tggctaagtt | tcctttccca | gaaatctatc | ctaaaaacag | agatattcct | 540 |
| aagggaggta | gtaaatacat | cgaaaggttc | gtagactgta | tgagaagatc | ttgtgaaatc | 600 |
| atattagtca | gaagtaccat | ggaacttgaa | ggaaaataca | ttgattactt | gtctaagaca | 660 |
| ttagggaaaa | aggtgttgcc | agtagggcct | ctggtgcaag | aggcttcttt | gttgcaagat | 720 |
| gatcatatat | ggattatgaa | gtggttagac | aaaaaggagg | agtcatccgt | cgtgtttgtt | 780 |
| tgttttggtt | ctgagtacat | cttatcagac | aacgaaatag | aagatattgc | ttatggccta | 840 |
| gagttgtccc | aagtaagttt | cgtttgggca | ataagagcta | agacttctgc | cttaaatggc | 900 |
| ttcattgata | gagtgggtga | taaaggctta | gtcatcgata | aatgggttcc | acaggctaac | 960 |
| atcttatctc | actcttctac | tggtggattc | attagtcatt | gcggttggtc | atcaacaatg | 1020 |
| gaatctatta | gatatggggt | tcctattatc | gccatgccaa | tgcaattcga | tcaaccttac | 1080 |
| aatgctaggt | tgatggaaac | tgttggtgca | ggtatcgaag | ttggcagaga | tggcgaaggt | 1140 |

```
agattgaaaa gagaagagat tgctgccgtg gttagaaagg tcgttgttga agattctggg    1200
gaatccataa gggagaaggc aaaggaattg ggagaaatca tgaaaaaaaa catggaggcc    1260
gaagtagatg gtatagtgat tgaaaatcta gttaagctat gtgagatgaa caattaa      1317
```

<210> SEQ ID NO 71
<211> LENGTH: 477
<212> TYPE: PRT
<213> ORGANISM: Arabidopsis thaliana

<400> SEQUENCE: 71

```
Met Met Thr Leu Asn Ser Leu Ser Pro Ala Glu Ser Lys Ala Ile Ser
1               5                   10                  15

Phe Leu Asp Thr Ser Arg Phe Asn Pro Ile Pro Lys Leu Ser Gly Gly
            20                  25                  30

Phe Ser Leu Arg Arg Arg Asn Gln Gly Arg Gly Phe Gly Lys Gly Val
        35                  40                  45

Lys Cys Ser Val Lys Val Gln Gln Gln Gln Pro Pro Ala Trp
    50                  55                  60

Pro Gly Arg Ala Val Pro Glu Ala Pro Arg Gln Ser Trp Asp Gly Pro
65                  70                  75                  80

Lys Pro Ile Ser Ile Val Gly Ser Thr Gly Ser Ile Gly Thr Gln Thr
                85                  90                  95

Leu Asp Ile Val Ala Glu Asn Pro Asp Lys Phe Arg Val Val Ala Leu
            100                 105                 110

Ala Ala Gly Ser Asn Val Thr Leu Leu Ala Asp Gln Val Arg Arg Phe
        115                 120                 125

Lys Pro Ala Leu Val Ala Val Arg Asn Glu Ser Leu Ile Asn Glu Leu
    130                 135                 140

Lys Glu Ala Leu Ala Asp Leu Asp Tyr Lys Leu Glu Ile Ile Pro Gly
145                 150                 155                 160

Glu Gln Gly Val Ile Glu Val Ala Arg His Pro Glu Ala Val Thr Val
                165                 170                 175

Val Thr Gly Ile Val Gly Cys Ala Gly Leu Lys Pro Thr Val Ala Ala
            180                 185                 190

Ile Glu Ala Gly Lys Asp Ile Ala Leu Ala Asn Lys Glu Thr Leu Ile
        195                 200                 205

Ala Gly Gly Pro Phe Val Leu Pro Leu Ala Asn Lys His Asn Val Lys
    210                 215                 220

Ile Leu Pro Ala Asp Ser Glu His Ser Ala Ile Phe Gln Cys Ile Gln
225                 230                 235                 240

Gly Leu Pro Glu Gly Ala Leu Arg Lys Ile Ile Leu Thr Ala Ser Gly
                245                 250                 255

Gly Ala Phe Arg Asp Trp Pro Val Glu Lys Leu Lys Glu Val Lys Val
            260                 265                 270

Ala Asp Ala Leu Lys His Pro Asn Trp Asn Met Gly Lys Lys Ile Thr
        275                 280                 285

Val Asp Ser Ala Thr Leu Phe Asn Lys Gly Leu Glu Val Ile Glu Ala
    290                 295                 300

His Tyr Leu Phe Gly Ala Glu Tyr Asp Asp Ile Glu Ile Val Ile His
305                 310                 315                 320

Pro Gln Ser Ile Ile His Ser Met Ile Glu Thr Gln Asp Ser Ser Val
                325                 330                 335

Leu Ala Gln Leu Gly Trp Pro Asp Met Arg Leu Pro Ile Leu Tyr Thr
            340                 345                 350
```

```
Met Ser Trp Pro Asp Arg Val Pro Cys Ser Glu Val Thr Trp Pro Arg
            355                 360                 365

Leu Asp Leu Cys Lys Leu Gly Ser Leu Thr Phe Lys Lys Pro Asp Asn
        370                 375                 380

Val Lys Tyr Pro Ser Met Asp Leu Ala Tyr Ala Ala Gly Arg Ala Gly
385                 390                 395                 400

Gly Thr Met Thr Gly Val Leu Ser Ala Ala Asn Glu Lys Ala Val Glu
                405                 410                 415

Met Phe Ile Asp Glu Lys Ile Ser Tyr Leu Asp Ile Phe Lys Val Val
            420                 425                 430

Glu Leu Thr Cys Asp Lys His Arg Asn Glu Leu Val Thr Ser Pro Ser
        435                 440                 445

Leu Glu Glu Ile Val His Tyr Asp Leu Trp Ala Arg Glu Tyr Ala Ala
    450                 455                 460

Asn Val Gln Leu Ser Ser Gly Ala Arg Pro Val His Ala
465                 470                 475

<210> SEQ ID NO 72
<211> LENGTH: 440
<212> TYPE: PRT
<213> ORGANISM: Leishmania infantum

<400> SEQUENCE: 72

Met His Ser Thr Arg His Ile Leu Arg Gln Arg Ala Val Leu Val Thr
1               5                   10                  15

Gly Ala Arg Thr Pro Phe Val Lys Ser Phe Gly Ala Leu Met Lys Ala
            20                  25                  30

Asp Thr Leu Glu Leu Ala Ser Ala Ser Val Ala Gly Leu Leu Asn Lys
        35                  40                  45

Thr Ser Leu Asp Pro Arg Asp Ile Asp His Ile Val Trp Gly Asn Val
    50                  55                  60

Val Leu Gln Gly Ser Ala His Asn Cys Ala Arg Glu Ile Val Ile Asp
65                  70                  75                  80

Leu Asn Met Pro Lys Lys Ile Ile Gly Asn Leu Thr Ser Met Ala Cys
                85                  90                  95

Ala Ser Gly Leu Ser Ser Leu Ser Gln Ala Cys Met Leu Ile Glu Gly
            100                 105                 110

Gly His Ala Asp Val Val Ile Ala Gly Gly Ser Asp Ser Val Ser Asn
        115                 120                 125

Thr Glu Val Pro Leu Pro Arg Ser Val Thr Tyr Gly Leu Met Met Ala
    130                 135                 140

Gln Arg Lys Gly Val Met Gly Phe Phe Lys Glu Ala Gly Tyr Asn Pro
145                 150                 155                 160

Phe Lys Trp Phe Pro Gly Gly Ile Ala Leu Thr Glu Arg Ser Thr Gly
                165                 170                 175

Lys Thr Met Gly Trp His Gly Asp Leu Ile Ala Glu Leu Asn Ser Ile
            180                 185                 190

Ser Arg Asp Asp Gln Glu Ala Leu Ala Val Ala Ser His Ala Asn Ala
        195                 200                 205

Ala Arg Ala Glu Lys Ala Gly Tyr Phe Lys Glu Ile Val Pro Val
    210                 215                 220

Thr Ile Asp Lys Lys Gly Lys Lys Thr Glu Val Thr Cys Asp Asp Val
225                 230                 235                 240

Met Gln Arg Asp Thr Glu Lys Met Lys Ala Lys Met Pro Ser Leu Lys
```

-continued

```
                245                 250                 255
Pro Val Phe Arg Lys Glu Gly Gly Thr Ile Thr Ala Ala Thr Ser Ser
                260                 265                 270

Thr Leu Thr Asp Gly Gly Ser Ala Met Leu Val Met Ser Glu Glu Lys
            275                 280                 285

Ala Lys Lys Leu Gly Tyr Pro Thr Asp Val Cys Val Lys Ser Trp Tyr
290                 295                 300

Phe Ser Gly Ile Asp Pro Tyr Pro Gln Leu Leu Leu Ala Pro Val Leu
305                 310                 315                 320

Gly Trp Gly Pro Ala Leu Lys Lys Ala Gly Leu Thr Pro Lys Asp Ile
                325                 330                 335

Asp Leu Tyr Glu Ile His Glu Ala Phe Ala Ala Gln Val Leu Ala Thr
            340                 345                 350

Ile Lys Cys Leu Lys Ser Gln Glu Phe Phe Asp Arg Tyr Ala Asn Gly
        355                 360                 365

Ala Lys Pro Val Leu Thr Glu Asp Ile Asp Leu Ser Lys Leu Asn Val
    370                 375                 380

Asn Gly Gly Ser Leu Ala Leu Gly His Pro Phe Ala Ala Thr Gly Gly
385                 390                 395                 400

Arg Ile Val Ile Ser Leu Ala Asn Glu Leu Arg Arg Ser Gly Lys Arg
                405                 410                 415

His Gly Leu Val Ser Ile Cys Ala Ala Gly Gly Leu Gly Gly Val Ala
            420                 425                 430

Ile Leu Glu His Thr Ala Ser Lys
        435                 440

<210> SEQ ID NO 73
<211> LENGTH: 527
<212> TYPE: PRT
<213> ORGANISM: Saccharomyces cerevisiae

<400> SEQUENCE: 73

Met Ala Ala Asp Gln Leu Val Lys Thr Glu Val Thr Lys Lys Ser Phe
1               5                   10                  15

Thr Ala Pro Val Gln Lys Ala Ser Thr Pro Val Leu Thr Asn Lys Thr
                20                  25                  30

Val Ile Ser Gly Ser Lys Val Lys Ser Leu Ser Ser Ala Gln Ser Ser
            35                  40                  45

Ser Ser Gly Pro Ser Ser Ser Glu Glu Asp Asp Ser Arg Asp Ile
        50                  55                  60

Glu Ser Leu Asp Lys Lys Ile Arg Pro Leu Glu Leu Glu Ala Leu
65                  70                  75                  80

Leu Ser Ser Gly Asn Thr Lys Gln Leu Lys Asn Lys Glu Val Ala Ala
                85                  90                  95

Leu Val Ile His Gly Lys Leu Pro Leu Tyr Ala Leu Glu Lys Lys Leu
            100                 105                 110

Gly Asp Thr Thr Arg Ala Val Ala Val Arg Arg Lys Ala Leu Ser Ile
        115                 120                 125

Leu Ala Glu Ala Pro Val Leu Ala Ser Asp Arg Leu Pro Tyr Lys Asn
    130                 135                 140

Tyr Asp Tyr Asp Arg Val Phe Gly Ala Cys Cys Glu Asn Val Ile Gly
145                 150                 155                 160

Tyr Met Pro Leu Pro Val Gly Val Ile Gly Pro Leu Val Ile Asp Gly
                165                 170                 175
```

Thr Ser Tyr His Ile Pro Met Ala Thr Thr Glu Gly Cys Leu Val Ala
            180                 185                 190

Ser Ala Met Arg Gly Cys Lys Ala Ile Asn Ala Gly Gly Gly Ala Thr
            195                 200                 205

Thr Val Leu Thr Lys Asp Gly Met Thr Arg Gly Pro Val Val Arg Phe
            210                 215                 220

Pro Thr Leu Lys Arg Ser Gly Ala Cys Lys Ile Trp Leu Asp Ser Glu
225                 230                 235                 240

Glu Gly Gln Asn Ala Ile Lys Lys Ala Phe Asn Ser Thr Ser Arg Phe
                245                 250                 255

Ala Arg Leu Gln His Ile Gln Thr Cys Leu Ala Gly Asp Leu Leu Phe
            260                 265                 270

Met Arg Phe Arg Thr Thr Thr Gly Asp Ala Met Gly Met Asn Met Ile
            275                 280                 285

Ser Lys Gly Val Glu Tyr Ser Leu Lys Gln Met Val Glu Glu Tyr Gly
            290                 295                 300

Trp Glu Asp Met Glu Val Val Ser Val Ser Gly Asn Tyr Cys Thr Asp
305                 310                 315                 320

Lys Lys Pro Ala Ala Ile Asn Trp Ile Glu Gly Arg Gly Lys Ser Val
                325                 330                 335

Val Ala Glu Ala Thr Ile Pro Gly Asp Val Val Arg Lys Val Leu Lys
            340                 345                 350

Ser Asp Val Ser Ala Leu Val Glu Leu Asn Ile Ala Lys Asn Leu Val
            355                 360                 365

Gly Ser Ala Met Ala Gly Ser Val Gly Gly Phe Asn Ala His Ala Ala
            370                 375                 380

Asn Leu Val Thr Ala Val Phe Leu Ala Leu Gly Gln Asp Pro Ala Gln
385                 390                 395                 400

Asn Val Glu Ser Ser Asn Cys Ile Thr Leu Met Lys Glu Val Asp Gly
                405                 410                 415

Asp Leu Arg Ile Ser Val Ser Met Pro Ser Ile Glu Val Gly Thr Ile
            420                 425                 430

Gly Gly Gly Thr Val Leu Glu Pro Gln Gly Ala Met Leu Asp Leu Leu
            435                 440                 445

Gly Val Arg Gly Pro His Ala Thr Ala Pro Gly Thr Asn Ala Arg Gln
            450                 455                 460

Leu Ala Arg Ile Val Ala Cys Ala Val Leu Ala Gly Glu Leu Ser Leu
465                 470                 475                 480

Cys Ala Ala Leu Ala Ala Gly His Leu Val Gln Ser His Met Thr His
                485                 490                 495

Asn Arg Lys Pro Ala Glu Pro Thr Lys Pro Asn Asn Leu Asp Ala Thr
            500                 505                 510

Asp Ile Asn Arg Leu Lys Asp Gly Ser Val Thr Cys Ile Lys Ser
            515                 520                 525

<210> SEQ ID NO 74
<211> LENGTH: 1226
<212> TYPE: PRT
<213> ORGANISM: Ganoderma lucidum

<400> SEQUENCE: 74

Met Arg Ala Val Leu Arg Leu Leu Ser Thr His Thr Val Phe Ser Pro
1               5                   10                  15

Ile Glu Thr Ile Val Ser Val Phe Val Leu Ala Thr Leu Ala Tyr Phe
            20                  25                  30

```
His Ile Leu Ser Gly Ile Lys His Ser Ser Phe Phe Ala Ser Ser His
         35                  40                  45

Pro Pro Ala Ile Arg Pro Ala Phe Ala His Leu Thr Asn Gly Glu Trp
 50                  55                  60

Val Ala Val Ser Gln His Asp Trp Thr Glu Ala Trp Lys His Pro Gly
 65                  70                  75                  80

Gly Ser Leu Asp Ala Leu Glu Leu Gln Gln Val Val Phe Thr Leu Asp
                 85                  90                  95

Asp Lys Thr Gln Pro Ser Ala Val Leu Asp Ala Ser Ala Ile Ser Gln
            100                 105                 110

His Leu Val Ser Asn Val Pro Ala Leu Ser Gly Lys Ala Tyr Ser Ser
            115                 120                 125

Leu Cys His His Pro Asn Val Ser Gly Thr Ser Cys Phe Thr Ser Val
130                 135                 140

Ser Gly Pro Gly Ala Ser Pro Ile Leu Thr Leu Ser Phe Lys Pro Gly
145                 150                 155                 160

Thr Arg Asp Asp Trp Leu Gly Ser Leu Arg Lys Glu Lys Thr Ile Thr
                165                 170                 175

Leu Asp Gly Val Lys Tyr Asp Val Gly Ala Gly Lys Arg Gln Glu Ser
            180                 185                 190

Ile Gly Asp Met Glu Ser Ser Lys Trp Val Ala Tyr Ala Leu Ser Ala
            195                 200                 205

Leu Val Leu Arg Phe Trp Glu Leu Thr Lys Ala Asp Ser Leu Asp Ile
210                 215                 220

Leu Val Val Leu Thr Gly Tyr Ile Leu Met His Val Thr Phe Met Arg
225                 230                 235                 240

Leu Phe Leu Ala Ser Arg Ala Leu Gly Ser Asn Phe Trp Leu Ser Ala
                245                 250                 255

Gly Ile Phe Ser Ser Ala Thr Ile Ser Phe Leu Phe Thr Leu Pro Met
            260                 265                 270

Cys Arg Ser Met Asp Ile Pro Leu Asp Pro Ile Ala Leu Thr Glu Ala
            275                 280                 285

Leu Pro Phe Leu Val Cys Thr Val Gly Phe Asp Lys Pro Leu Arg Leu
290                 295                 300

Ala Arg Ala Val Met Ala His Pro Asn Ile Leu Lys Pro Gln Asp Asp
305                 310                 315                 320

Gly Arg Met Lys Ala Ala Gly Asp Val Ile Leu Glu Ala Leu Asp Arg
                325                 330                 335

Val Gly Asn Met Ile Leu Arg Asp Tyr Ala Leu Glu Ile Ala Val Leu
            340                 345                 350

Phe Val Gly Val Asn Ser Arg Val Gly Gly Leu Lys Glu Phe Cys Ala
            355                 360                 365

Val Ala Ala Ala Leu Leu Ala Met Asp Arg Leu Met Thr Phe Thr Leu
370                 375                 380

Tyr Thr Ala Val Leu Thr Ile Met Val Glu Val Arg Arg Ile Lys Lys
385                 390                 395                 400

Val Arg Asp Met Thr Lys Ala Arg Ser Arg Ser Ser Ile Thr Ala
                405                 410                 415

Val Thr Ala Asn Gly Thr Ala Ile Arg Gly Val Leu Ser Arg Lys Ser
            420                 425                 430

Ser Lys Gln Ser Val Thr Glu Pro Glu Thr Thr Lys Asn Leu Arg Gln
            435                 440                 445
```

```
Arg Ala Thr Asp Ser Ala Ile Gly Val Lys Gly Ser Leu Leu Lys Asp
    450                 455                 460
Gly Gly Arg Leu Gln Glu Ala Glu Glu Asn Pro Met Ala Arg Leu Lys
465                 470                 475                 480
Leu Leu Leu Ile Ala Ser Phe Leu Thr Leu His Ile Leu Asn Phe Cys
                485                 490                 495
Thr Thr Leu Thr Ser Ala Thr Ala Asn Ala Arg His Gln Arg His Pro
                500                 505                 510
Phe Arg Thr Val Gln Glu Val Val Pro Ile Pro Arg Val Asp Ile Thr
                515                 520                 525
Thr Pro Ala Ile Ala Asn Ile Leu Ser His Leu Ala Val Ala Gln Glu
530                 535                 540
Pro Met Phe Thr Val Val Gly Ser Glu Pro Ile Glu Leu Leu Val Lys
545                 550                 555                 560
Val Ala Ala Pro Val Tyr Val His Ala Leu Pro Leu Ala Pro Ala Leu
                565                 570                 575
Arg Ala Ser Asn Thr Asn Thr Gly Glu Ala Ile Glu Asn Phe Met Ser
                580                 585                 590
Ser Trp Ser Ser Leu Val Gly Asp Pro Val Val Ser Lys Trp Ile Val
                595                 600                 605
Ala Leu Leu Ala Val Ser Val Ala Leu Asn Gly Tyr Leu Leu Lys Gly
610                 615                 620
Ile Ala Ala Gly Ser Gly Leu Ala Ala Met Arg Ala Val Arg Ser Gln
625                 630                 635                 640
Gly Val Arg Phe Arg Ser Arg Ala Arg Ser Ile Val Lys Ile Ser Asp
                645                 650                 655
Glu Pro Glu Pro Glu Pro Glu His Ser Ile Asp Pro Ala Pro Val Val
                660                 665                 670
Phe Phe Ala Ser Ala Ala Pro Ala Val Glu Ala Pro Ala Pro Ala Pro
                675                 680                 685
Ala Pro Glu Pro Glu Pro Val Asn Arg Pro Pro Leu Thr Ile
                690                 695                 700
Phe Ser Arg Pro Leu Asn Leu Glu Thr Val Asp Lys Lys Leu Gln Asp
705                 710                 715                 720
Ala Leu Pro Ile Arg Ser Pro Pro Val Glu Pro Ile Thr Pro Glu
                725                 730                 735
Ser Arg Glu Val Glu Pro Thr Gln Val Glu Val Arg Ser Leu Ala Glu
                740                 745                 750
Cys Val Asp Val Phe Glu Asn Gly Pro Arg Pro Val Ser Val Ala Leu
                755                 760                 765
Lys Thr Leu Asn Asp Glu Glu Val Ile Leu Leu Cys Gln Thr Gly Lys
770                 775                 780
Ile Ala Pro Tyr Ala Leu Val Lys Met Leu Ala Asp Phe Asp Arg Ala
785                 790                 795                 800
Val Arg Val Arg Arg Ala Leu Ile Ser Arg Ala Ser Arg Thr Lys Thr
                805                 810                 815
Leu Glu Asn Ser Leu Val Pro Met Lys Asp Tyr Asp Tyr Ala Arg Val
                820                 825                 830
Met Gly Ala Cys Cys Glu Asn Val Ile Gly Tyr Met Pro Leu Pro Leu
                835                 840                 845
Gly Ile Ala Gly Pro Leu Lys Ile Asp Gly Leu Met Tyr Pro Ile Pro
850                 855                 860
Met Ala Thr Ala Glu Gly Thr Leu Val Ala Ser Thr Ser Arg Gly Cys
```

```
                865                 870                 875                 880
Lys Ala Leu Asn Ala Gly Gly Val Thr Thr Val Leu Thr Ala Asp
                885                 890                 895
Gly Met Thr Arg Gly Pro Ala Ile Asp Phe Pro Ser Ile Val Arg Ala
                900                 905                 910
Ala Glu Ala Lys Ala Phe Ile Glu Ser Glu Asp Gly Tyr Ala Thr Ile
                915                 920                 925
Arg Glu Ala Phe Glu Ser Thr Ser Arg Phe Ala Lys Leu Gln Lys Ile
                930                 935                 940
Lys Cys Ala Leu Ala Gly Arg Thr Leu Phe Val Arg Phe Ala Thr Arg
945                 950                 955                 960
Thr Gly Asp Ala Met Gly Met Asn Met Ile Ser Lys Ala Thr Glu Lys
                965                 970                 975
Ala Leu Asp Val Leu Ser His Glu Phe Pro Glu Met Val Leu Ala
                980                 985                 990
Leu Ser Gly Asn Tyr Cys Thr Asp Lys Lys Pro Ala Ala Ile Ser Trp
                995                 1000                1005
Ile Glu Gly Arg Gly Lys Ser Ile Val Ala Glu Ala Val Ile Pro
    1010                1015                1020
Gly Lys Val Val Lys Ser Val Leu Lys Thr Thr Val Glu Ser Leu
    1025                1030                1035
Cys Asn Val Asn Thr Lys Lys Asn Leu Ile Gly Ser Ala Met Ala
    1040                1045                1050
Gly Ser Val Gly Gly Phe Asn Ala His Ala Ala Asn Ile Leu Thr
    1055                1060                1065
Ala Val Phe Leu Ala Thr Gly Gln Asp Pro Ala Gln Asn Val Glu
    1070                1075                1080
Ser Ser Asn Cys Met Thr Leu Met Glu Pro Thr Asn Gly Gly Glu
    1085                1090                1095
Asp Leu Leu Met Thr Ile Ser Met Pro Cys Ile Glu Val Gly Thr
    1100                1105                1110
Val Gly Gly Gly Thr Ile Leu Glu Pro Gln Gly Ala Val Leu Asp
    1115                1120                1125
Leu Leu Gly Val Arg Gly Ala His Pro Thr Asn Pro Gly Gln Asn
    1130                1135                1140
Ala Gln Gln Leu Ala Arg Ile Ile Ala Ser Ala Val Met Ala Gly
    1145                1150                1155
Glu Leu Ser Leu Ile Ser Ala Leu Ala Ala Gly His Leu Val Arg
    1160                1165                1170
Ala His Leu Ala His Asn Arg Ser Gln Leu Asn Thr Pro Met Pro
    1175                1180                1185
Ser Arg Pro His Thr Pro Gly Pro Glu Asp Val Ser His Val Gln
    1190                1195                1200
Gln Leu Pro Thr Pro Ser Ala Ser Asp Asp Lys Gly Val Thr Ala
    1205                1210                1215
Gln Gly Tyr Val Val Glu Ala Lys
    1220                1225

<210> SEQ ID NO 75
<211> LENGTH: 888
<212> TYPE: PRT
<213> ORGANISM: Bos taurus

<400> SEQUENCE: 75
```

-continued

```
Met Leu Ser Arg Leu Phe Arg Met His Gly Leu Phe Val Ala Ser His
  1               5                  10                  15

Pro Trp Glu Val Ile Val Gly Thr Val Thr Leu Thr Ile Cys Met Met
              20                  25                  30

Ser Met Asn Met Phe Thr Gly Asn Asn Lys Ile Cys Gly Trp Asn Tyr
          35                  40                  45

Glu Cys Pro Lys Leu Glu Glu Asp Val Leu Ser Ser Asp Ile Ile Ile
      50                  55                  60

Leu Thr Ile Thr Arg Cys Ile Ala Ile Leu Tyr Ile Tyr Phe Gln Phe
 65                  70                  75                  80

Gln Asn Leu Arg Gln Leu Gly Ser Lys Tyr Ile Leu Gly Ile Ala Gly
              85                  90                  95

Leu Phe Thr Ile Phe Ser Ser Phe Val Phe Ser Thr Val Val Ile His
              100                 105                 110

Phe Leu Asp Lys Glu Leu Thr Gly Leu Asn Glu Ala Leu Pro Phe Phe
          115                 120                 125

Leu Leu Leu Val Asp Leu Ser Arg Ala Ser Ala Leu Ala Lys Phe Ala
          130                 135                 140

Leu Ser Ser Asn Ser Gln Asp Glu Val Arg Glu Asn Ile Ala Arg Gly
145                 150                 155                 160

Met Ala Ile Leu Gly Pro Thr Phe Thr Leu Asp Ala Leu Val Glu Cys
              165                 170                 175

Leu Val Ile Gly Val Gly Thr Met Ser Gly Val Arg Gln Leu Glu Ile
              180                 185                 190

Met Cys Cys Phe Gly Cys Met Ser Val Leu Ala Asn Tyr Phe Val Phe
              195                 200                 205

Met Thr Phe Phe Pro Ala Cys Val Ser Leu Val Leu Glu Leu Ser Arg
      210                 215                 220

Glu Ser Arg Glu Gly Arg Pro Ile Trp Gln Leu Ser His Phe Ala Arg
225                 230                 235                 240

Val Leu Glu Glu Glu Asn Lys Pro Asn Pro Val Thr Gln Arg Val
              245                 250                 255

Lys Met Ile Met Ser Leu Gly Leu Val Leu Val His Ala His Ser Arg
              260                 265                 270

Trp Ile Ala Asp Pro Ser Pro Gln Asn Ser Thr Ala Asp Asn Ser Lys
      275                 280                 285

Val Ser Leu Gly Leu Asp Glu Asn Val Ser Lys Arg Ile Glu Pro Ser
              290                 295                 300

Val Ser Leu Trp Gln Phe Tyr Leu Ser Lys Met Ile Ser Met Asp Ile
305                 310                 315                 320

Glu Gln Val Ile Thr Leu Ser Leu Ala Leu Leu Ala Val Lys Tyr
              325                 330                 335

Ile Phe Phe Glu Gln Ala Glu Thr Glu Ser Thr Leu Ser Leu Lys Asn
              340                 345                 350

Pro Ile Thr Ser Pro Val Val Thr Gln Lys Lys Ile Thr Asp Asp Cys
          355                 360                 365

Cys Arg Arg Asp Pro Val Leu Val Arg Asn Asp Gln Lys Phe His Ala
      370                 375                 380

Met Glu Glu Glu Thr Arg Lys Asn Arg Glu Lys Val Glu Val Ile
385                 390                 395                 400

Lys Pro Leu Leu Ala Glu Asn Asp Thr Ser His Arg Ala Thr Phe Val
              405                 410                 415

Val Gly Asn Ser Ser Leu Leu Gly Thr Ser Leu Glu Leu Glu Thr Gln
```

```
                420             425             430
Glu Pro Glu Met Glu Leu Pro Val Glu Pro Arg Pro Asn Glu Glu Cys
            435             440             445

Leu Gln Ile Leu Glu Asn Ala Glu Lys Gly Ala Lys Phe Leu Ser Asp
        450             455             460

Ala Glu Ile Ile Gln Leu Val Asn Ala Lys His Ile Pro Ala Tyr Lys
465             470             475             480

Leu Glu Thr Leu Met Glu Thr His Glu Arg Gly Val Ser Ile Arg Arg
                485             490             495

Gln Leu Leu Ser Lys Lys Leu Pro Glu Pro Ser Ser Leu Gln Tyr Leu
            500             505             510

Pro Tyr Arg Asp Tyr Asn Tyr Ser Leu Val Met Gly Ala Cys Cys Glu
        515             520             525

Asn Val Ile Gly Tyr Met Pro Ile Pro Val Gly Val Ala Gly Pro Leu
    530             535             540

Cys Leu Asp Gly Lys Glu Phe Gln Val Pro Met Ala Thr Thr Glu Gly
545             550             555             560

Cys Leu Val Ala Ser Thr Asn Arg Gly Cys Arg Ala Ile Gly Leu Gly
                565             570             575

Gly Gly Ala Ser Ser Arg Val Leu Ala Asp Gly Met Thr Arg Gly Pro
            580             585             590

Val Val Arg Phe Pro Arg Ala Cys Asp Ser Ala Glu Val Lys Ala Trp
        595             600             605

Leu Glu Thr Pro Glu Gly Phe Thr Val Ile Lys Glu Ala Phe Asp Ser
    610             615             620

Thr Ser Arg Val Ala Arg Leu Gln Lys Leu His Met Ser Val Ala Gly
625             630             635             640

Arg Asn Leu Tyr Ile Arg Phe Gln Ser Arg Ser Gly Asp Ala Met Gly
                645             650             655

Met Asn Met Ile Ser Lys Gly Thr Glu Lys Ala Leu Ser Lys Leu Gln
            660             665             670

Glu Tyr Phe Pro Glu Met Gln Ile Leu Ala Val Ser Gly Asn Tyr Cys
        675             680             685

Thr Asp Lys Lys Pro Ala Ala Ile Asn Trp Ile Glu Gly Arg Gly Lys
    690             695             700

Ser Val Val Cys Glu Ala Val Ile Pro Ala Lys Val Val Arg Glu Val
705             710             715             720

Leu Lys Thr Thr Thr Glu Ala Met Ile Glu Val Asn Ile Asn Lys Asn
                725             730             735

Leu Val Gly Ser Ala Met Ala Gly Ser Ile Gly Gly Tyr Asn Ala His
            740             745             750

Ala Ala Asn Ile Val Thr Ala Ile Tyr Ile Ala Cys Gly Gln Asp Ala
        755             760             765

Ala Gln Asn Val Gly Ser Ser Asn Cys Ile Thr Leu Met Glu Ala Ser
    770             775             780

Gly Pro Thr Asn Glu Asp Leu Tyr Ile Ser Cys Thr Met Pro Ser Ile
785             790             795             800

Glu Ile Gly Thr Val Gly Gly Gly Thr Asn Leu Leu Pro Gln Gln Ala
                805             810             815

Cys Leu Gln Met Leu Gly Val Gln Gly Ala Cys Arg Asp Asn Pro Gly
            820             825             830

Glu Asn Ala Arg Gln Leu Ala Arg Ile Val Cys Gly Thr Val Met Ala
        835             840             845
```

```
Gly Glu Leu Ser Leu Met Ala Ala Leu Ala Ala Gly His Leu Val Arg
        850                 855                 860

Ser His Met Ile His Asn Arg Ser Lys Ile Asn Leu Gln Asp Leu Gln
865                 870                 875                 880

Gly Thr Cys Thr Lys Lys Ala Ala
                885

<210> SEQ ID NO 76
<211> LENGTH: 567
<212> TYPE: PRT
<213> ORGANISM: Artemisia annua

<400> SEQUENCE: 76

Met Asp Leu Arg Arg Lys Leu Pro Pro Lys Pro Pro Ser Ser Thr Thr
1               5                   10                  15

Thr Lys Gln Pro Ser His Arg Ser His Ser Pro Thr Pro Ile Pro Lys
                20                  25                  30

Ala Ser Asp Ala Leu Pro Leu Pro Leu Tyr Leu Thr Asn Thr Phe Phe
            35                  40                  45

Phe Thr Leu Phe Phe Ser Val Ala Tyr Tyr Leu Leu His Arg Trp Arg
        50                  55                  60

Asp Lys Ile Arg Ser Gly Thr Pro Leu His Val Val Thr Leu Thr Glu
65                  70                  75                  80

Leu Ser Ala Ile Val Leu Leu Ile Ala Ser Phe Ile Tyr Leu Leu Gly
                85                  90                  95

Phe Phe Gly Ile Asp Phe Val Gln Ser Phe Thr Ser Arg Glu Asn Glu
            100                 105                 110

Gln Leu Asn Asn Asp His Asn Val Val Ser Thr Asn Asn Val Leu
        115                 120                 125

Ser Asp Arg Arg Leu Val Tyr Asp Tyr Gly Phe Asp Val Thr Gly Asp
    130                 135                 140

Asn Asp Asn Asp Asn Asp Asp Val Ile Val Lys Ser Val Val Ser
145                 150                 155                 160

Gly Glu Val Asn Ser Tyr Ser Leu Glu Ala Ser Leu Gly Asp Cys Tyr
                165                 170                 175

Arg Ala Ala Lys Ile Arg Lys Arg Ala Val Glu Arg Ile Val Gly Arg
            180                 185                 190

Glu Val Leu Gly Leu Gly Phe Glu Gly Phe Asp Tyr Glu Ser Ile Leu
        195                 200                 205

Gly Gln Cys Cys Glu Met Pro Ile Gly Tyr Val Gln Val Pro Val Gly
    210                 215                 220

Val Ala Gly Pro Leu Leu Leu Asn Gly Gly Glu Phe Met Val Pro Met
225                 230                 235                 240

Ala Thr Thr Glu Gly Cys Leu Val Ala Ser Thr Asn Arg Gly Cys Lys
                245                 250                 255

Ala Ile Cys Leu Ser Gly Gly Ala Thr Ala Ile Leu Leu Lys Asp Gly
            260                 265                 270

Met Thr Arg Ala Pro Val Val Arg Phe Ala Thr Ala Glu Arg Ala Ser
        275                 280                 285

Gln Leu Lys Phe Tyr Leu Glu Asp Gly Val Asn Phe Asp Thr Leu Ser
    290                 295                 300

Val Val Phe Asn Lys Ser Ser Arg Phe Ala Arg Leu Gln Asn Ile Gln
305                 310                 315                 320

Cys Ser Ile Ala Gly Lys Asn Leu Tyr Ile Arg Phe Thr Cys Ser Thr
```

```
                    325                 330                 335
Gly Asp Ala Met Gly Met Asn Met Val Ser Lys Gly Val Gln Asn Val
            340                 345                 350
Leu Asp Phe Leu Gln Asn Asp Phe Pro Asp Met Asp Val Ile Gly Ile
            355                 360                 365
Ser Trp Lys Phe Cys Ser Asp Lys Pro Thr Ala Val Asn Trp Ile
        370                 375                 380
Glu Gly Arg Gly Lys Ser Val Val Phe Gln Ala Val Ile Thr Lys Lys
385                 390                 395                 400
Val Val Arg Lys Ser Ala Leu Asn Pro Gln Thr Cys Thr Cys Arg Thr
                405                 410                 415
Leu Thr Cys Leu Arg Pro Leu Val Leu Leu Leu Val Leu Leu
                420                 425                 430
Val Asp Leu Met His Met Leu His Ile Val Ser Ala Val Phe Ile Ala
            435                 440                 445
Thr Gly Gln Asp Pro Ala Gln Asn Ile Glu Ser Ser His Cys Ile Thr
        450                 455                 460
Met Met Glu Ala Val Asn Asn Gly Lys Asp Leu His Val Asn Val Thr
465                 470                 475                 480
Met Pro Ser Ile Glu Val Gly Thr Val Gly Gly Thr Gln Leu Ala
                485                 490                 495
Ser Gln Ser Ala Cys Leu Asn Leu Leu Gly Val Lys Gly Ala Cys Ile
            500                 505                 510
Glu Ser Pro Gly Ser Asn Ala Gln Leu Leu Ala Arg Ile Val Ala Gly
        515                 520                 525
Ser Val Leu Ala Gly Glu Leu Ser Leu Met Ser Ala Ile Ser Ala Gly
        530                 535                 540
Gln Leu Val Lys Ser His Met Lys Tyr Asn Arg Ser Ser Arg Asp Met
545                 550                 555                 560
Ser Ala Ile Ala Ser Lys Val
                565

<210> SEQ ID NO 77
<211> LENGTH: 435
<212> TYPE: PRT
<213> ORGANISM: Trypanosoma cruzi

<400> SEQUENCE: 77

Met Phe Arg Arg Ala Ile Leu Leu Gly Cys Ser Ala Ala Lys Thr Pro
1               5                   10                  15
Trp Ser Glu Cys Ser Asn Ala Gln Leu Val Asp Ala Val Lys Ser Arg
            20                  25                  30
Lys Ile Ser Phe Tyr Gly Leu Glu Gln Ala Leu Glu Pro Asp Tyr Arg
        35                  40                  45
Arg Ala Ile Glu Val Arg Arg Glu Val Val Ser Glu Ile Ala Ser Gln
    50                  55                  60
Gln Pro Glu Ala Lys Lys Lys Gln Ser Ala Leu His Thr Ile Pro Phe
65                  70                  75                  80
Glu Asn Tyr Asp Trp Asn Lys Val Val Gly Gln Asn Cys Glu Asn Ile
                85                  90                  95
Ile Gly Tyr Val Pro Ile Pro Leu Gly Val Ala Gly Pro Ile Leu Ile
            100                 105                 110
Asp Gly Lys Glu Tyr Pro Ile Pro Met Ala Thr Thr Glu Gly Ala Leu
        115                 120                 125
```

```
Val Ala Ser Thr His Arg Gly Ala Arg Ala Ile Thr Arg Ser Gly Gly
    130                 135                 140

Cys Lys Thr Leu Leu Leu Gly Glu Gly Met Thr Arg Ala Pro Val Val
145                 150                 155                 160

Glu Leu Pro Ser Leu Glu Glu Ala Gly Arg Leu His Lys Tyr Cys Asn
                165                 170                 175

Glu Asn Phe Leu Ser Leu Lys Glu Ala Phe Glu Ser Thr Thr Gln Tyr
                180                 185                 190

Gly Lys Leu Asn Ser Leu Lys Cys Val Leu Ala Gly Lys Ala Tyr
                195                 200                 205

Leu Arg Phe Arg Ala Thr Thr Gly Asp Ala Met Gly Met Asn Met Ile
    210                 215                 220

Thr Lys Gly Val Asp Lys Ala Leu Ser Val Leu Gln Gln His Phe Pro
225                 230                 235                 240

Ser Met Glu Ile Leu Ala Leu Ser Gly Asn Tyr Cys Thr Asp Lys Lys
                245                 250                 255

Pro Ser Ala Val Asn Trp Ile Asp Gly Arg Gly Lys Ser Val Val Ala
                260                 265                 270

Glu Ala Thr Leu Leu Ala Asp Val Val Glu Asp Thr Leu Lys Cys Thr
                275                 280                 285

Val Asp Ser Leu Val Ser Leu Asn Ile Asp Lys Asn Leu Val Gly Ser
    290                 295                 300

Ala Met Ala Gly Ser Val Gly Gly Phe Asn Ala Gln Ala Ala Asn Ala
305                 310                 315                 320

Val Ala Ala Ile Phe Ile Ala Thr Gly Gln Asp Pro Ala Gln Val Val
                325                 330                 335

Glu Ser Ser Met Cys Ile Thr Thr Met Ser Lys Val Gly Asn Asp Leu
                340                 345                 350

Leu Ile Ser Val Thr Met Pro Ser Ile Glu Val Gly Val Val Gly Gly
                355                 360                 365

Gly Thr Gly Leu Ala Ala Gln Arg Gly Cys Leu Glu Leu Ile Gly Cys
    370                 375                 380

Gly Gly Pro Ser Lys Glu Ser Pro Gly Thr Asn Ala Gln Leu Leu Ser
385                 390                 395                 400

Arg Val Val Ala Ala Gly Val Leu Ser Ala Glu Leu Ser Leu Met Ser
                405                 410                 415

Gly Leu Ala Ala Gly His Leu Leu Ser Ala His Met Arg Leu Asn Arg
                420                 425                 430

Lys Lys Lys
    435

<210> SEQ ID NO 78
<211> LENGTH: 426
<212> TYPE: PRT
<213> ORGANISM: Staphylococcus aureus

<400> SEQUENCE: 78

Met Gln Ser Leu Asp Lys Asn Phe Arg His Leu Ser Arg Gln Gln Lys
1               5                   10                  15

Leu Gln Gln Leu Val Asp Lys Trp Leu Ser Glu Glu Gln Phe Asn
                20                  25                  30

Ile Leu Leu Asn His Pro Leu Ile Asp Glu Glu Val Ala Asn Ser Leu
            35                  40                  45

Ile Glu Asn Val Ile Ala Gln Gly Ala Leu Pro Val Gly Leu Leu Pro
        50                  55                  60
```

```
Asn Ile Ile Val Asp Asp Lys Ala Tyr Val Val Pro Met Met Val Glu
 65                  70                  75                  80

Glu Pro Ser Val Val Ala Ala Ala Ser Tyr Gly Ala Lys Leu Val Asn
                 85                  90                  95

Gln Thr Gly Gly Phe Lys Thr Val Ser Ser Glu Arg Ile Met Ile Gly
            100                 105                 110

Gln Ile Val Phe Asp Gly Val Asp Asp Thr Glu Lys Leu Ser Ala Asp
            115                 120                 125

Ile Lys Ala Leu Glu Lys Gln Ile His Gln Ile Ala Asp Glu Ala Tyr
    130                 135                 140

Pro Ser Ile Lys Ala Arg Gly Gly Tyr Gln Arg Ile Ala Ile Asp
145                 150                 155                 160

Thr Phe Pro Glu Gln Gln Leu Leu Ser Leu Lys Val Phe Val Asp Thr
                165                 170                 175

Lys Asp Ala Met Gly Ala Asn Met Leu Asn Thr Ile Leu Glu Ala Ile
            180                 185                 190

Thr Ala Phe Leu Lys Asn Glu Phe Pro Gln Ser Asp Ile Leu Met Ser
    195                 200                 205

Ile Leu Ser Asn His Ala Thr Ala Ser Val Val Lys Val Gln Gly Glu
    210                 215                 220

Ile Asp Val Lys Asp Leu Ala Arg Gly Glu Arg Thr Gly Glu Val
225                 230                 235                 240

Ala Lys Arg Met Glu Arg Ala Ser Val Leu Ala Gln Val Asp Ile His
                245                 250                 255

Arg Ala Ala Thr His Asn Lys Gly Val Met Asn Gly Ile His Ala Val
            260                 265                 270

Val Leu Ala Thr Gly Asn Asp Thr Arg Gly Ala Glu Ala Ser Ala His
    275                 280                 285

Ala Tyr Ala Ser Lys Asp Gly Gln Tyr Arg Gly Ile Ala Thr Trp Arg
    290                 295                 300

Tyr Asp Gln Glu Arg Gln Arg Leu Ile Gly Thr Ile Glu Val Pro Met
305                 310                 315                 320

Thr Leu Ala Ile Val Gly Gly Gly Thr Lys Val Leu Pro Ile Ala Lys
                325                 330                 335

Ala Ser Leu Glu Leu Leu Asn Val Glu Ser Ala Gln Glu Leu Gly His
            340                 345                 350

Val Val Ala Ala Val Gly Leu Ala Gln Asn Phe Ala Ala Cys Arg Ala
    355                 360                 365

Leu Val Ser Glu Gly Ile Gln Gln Gly His Met Ser Leu Gln Tyr Lys
    370                 375                 380

Ser Leu Ala Ile Val Val Gly Ala Lys Gly Asp Glu Ile Ala Gln Val
385                 390                 395                 400

Ala Glu Ala Leu Lys Gln Glu Pro Arg Ala Asn Thr Gln Val Ala Glu
                405                 410                 415

Arg Ile Leu Gln Asp Leu Arg Ser Gln Gln
            420                 425

<210> SEQ ID NO 79
<211> LENGTH: 481
<212> TYPE: PRT
<213> ORGANISM: Arabidopsis thaliana

<400> SEQUENCE: 79

Met His Ile Thr Lys Pro His Ala Ala Met Phe Ser Ser Pro Gly Met
```

-continued

```
1               5                   10                  15
Gly His Val Ile Pro Val Ile Glu Leu Gly Lys Arg Leu Ser Ala Asn
                20                  25                  30

Asn Gly Phe His Val Thr Val Phe Val Leu Glu Thr Asp Ala Ala Ser
                35                  40                  45

Ala Gln Ser Lys Phe Leu Asn Ser Thr Gly Val Asp Ile Val Lys Leu
                50                  55                  60

Pro Ser Pro Asp Ile Tyr Gly Leu Val Asp Pro Asp Asp His Val Val
65                  70                  75                  80

Thr Lys Ile Gly Val Ile Met Arg Ala Ala Val Pro Ala Leu Arg Ser
                    85                  90                  95

Lys Ile Ala Ala Met His Gln Lys Pro Thr Ala Leu Ile Val Asp Leu
                100                 105                 110

Phe Gly Thr Asp Ala Leu Cys Leu Ala Lys Glu Phe Asn Met Leu Ser
                115                 120                 125

Tyr Val Phe Ile Pro Thr Asn Ala Arg Phe Leu Gly Val Ser Ile Tyr
                130                 135                 140

Tyr Pro Asn Leu Asp Lys Asp Ile Lys Glu Glu His Thr Val Gln Arg
145                 150                 155                 160

Asn Pro Leu Ala Ile Pro Gly Cys Glu Pro Val Arg Phe Glu Asp Thr
                    165                 170                 175

Leu Asp Ala Tyr Leu Val Pro Asp Glu Pro Val Tyr Arg Asp Phe Val
                180                 185                 190

Arg His Gly Leu Ala Tyr Pro Lys Ala Asp Gly Ile Leu Val Asn Thr
                    195                 200                 205

Trp Glu Glu Met Glu Pro Lys Ser Leu Lys Ser Leu Leu Asn Pro Lys
                210                 215                 220

Leu Leu Gly Arg Val Ala Arg Val Pro Val Tyr Pro Ile Gly Pro Leu
225                 230                 235                 240

Cys Arg Pro Ile Gln Ser Ser Glu Thr Asp His Pro Val Leu Asp Trp
                    245                 250                 255

Leu Asn Glu Gln Pro Asn Glu Ser Val Leu Tyr Ile Ser Phe Gly Ser
                260                 265                 270

Gly Gly Cys Leu Ser Ala Lys Gln Leu Thr Glu Leu Ala Trp Gly Leu
                    275                 280                 285

Glu Gln Ser Gln Gln Arg Phe Val Trp Val Val Arg Pro Pro Val Asp
                290                 295                 300

Gly Ser Cys Cys Ser Glu Tyr Val Ser Ala Asn Gly Gly Thr Glu
305                 310                 315                 320

Asp Asn Thr Pro Glu Tyr Leu Pro Glu Gly Phe Val Ser Arg Thr Ser
                    325                 330                 335

Asp Arg Gly Phe Val Val Pro Ser Trp Ala Pro Gln Ala Glu Ile Leu
                340                 345                 350

Ser His Arg Ala Val Gly Gly Phe Leu Thr His Cys Gly Trp Ser Ser
                    355                 360                 365

Thr Leu Glu Ser Val Val Gly Gly Val Pro Met Ile Ala Trp Pro Leu
                370                 375                 380

Phe Ala Glu Gln Asn Met Asn Ala Ala Leu Leu Ser Asp Glu Leu Gly
385                 390                 395                 400

Ile Ala Val Arg Leu Asp Asp Pro Lys Glu Asp Ile Ser Arg Trp Lys
                    405                 410                 415

Ile Glu Ala Leu Val Arg Lys Val Met Thr Glu Lys Glu Gly Glu Ala
                420                 425                 430
```

```
Met Arg Arg Lys Val Lys Lys Leu Arg Asp Ser Ala Glu Met Ser Leu
            435                 440                 445

Ser Ile Asp Gly Gly Gly Leu Ala His Glu Ser Leu Cys Arg Val Thr
            450                 455                 460

Lys Glu Cys Gln Arg Phe Leu Glu Arg Val Val Asp Leu Ser Arg Gly
465                 470                 475                 480

Ala

<210> SEQ ID NO 80
<211> LENGTH: 513
<212> TYPE: PRT
<213> ORGANISM: Arabidopsis thaliana

<400> SEQUENCE: 80

Met Gly Ala Tyr Glu Thr Glu Lys Pro Thr Lys Asp Ala Ala Ala Leu
1               5                   10                  15

Glu Thr Gln Ser Pro Glu Asp Phe Asp Gln Pro Ser Pro Leu Arg Lys
            20                  25                  30

Ile Ile Ser Val Ala Ser Ile Ala Ala Gly Val Gln Phe Gly Trp Ala
            35                  40                  45

Leu Gln Leu Ser Leu Leu Thr Pro Tyr Val Gln Leu Leu Gly Ile Pro
    50                  55                  60

His Lys Trp Ser Ser Leu Ile Trp Leu Cys Gly Pro Val Ser Gly Met
65              70                  75                  80

Ile Val Gln Pro Ile Val Gly Phe His Ser Asp Arg Cys Arg Ser Lys
                85                  90                  95

Phe Gly Arg Arg Arg Pro Phe Ile Ala Thr Gly Ala Ala Leu Val Ala
            100                 105                 110

Val Ala Val Phe Leu Ile Gly Tyr Ala Ala Asp Phe Gly Tyr Lys Met
            115                 120                 125

Gly Asp Lys Leu Glu Glu Lys Val Lys Val Arg Ala Ile Gly Ile Phe
130                 135                 140

Ala Leu Gly Phe Trp Ile Leu Asp Val Ala Asn Asn Thr Leu Gln Gly
145                 150                 155                 160

Pro Cys Arg Ala Phe Leu Ala Asp Leu Ala Ala Gly Asp Ala Lys Arg
                165                 170                 175

Thr Arg Val Ala Asn Ala Phe Phe Ser Phe Phe Met Ala Val Gly Asn
            180                 185                 190

Val Leu Gly Tyr Ala Ala Gly Ser Tyr Thr Asn Leu His Lys Met Phe
            195                 200                 205

Pro Phe Thr Met Thr Lys Ala Cys Asp Ile Tyr Cys Ala Asn Leu Lys
            210                 215                 220

Thr Cys Phe Phe Leu Ser Ile Thr Leu Leu Ile Val Thr Val Thr
225                 230                 235                 240

Ser Leu Trp Tyr Val Asn Asp Lys Gln Trp Ser Pro Pro Arg Asn
                245                 250                 255

Ala Asp Asp Asp Glu Lys Thr Ser Ser Val Pro Leu Phe Gly Glu Ile
            260                 265                 270

Phe Gly Ala Phe Lys Val Met Lys Arg Pro Met Trp Met Leu Leu Ile
            275                 280                 285

Val Thr Ala Leu Asn Trp Ile Ala Trp Phe Pro Phe Leu Leu Phe Asp
            290                 295                 300

Thr Asp Trp Met Gly Arg Glu Val Phe Gly Gly Asp Ser Asp Gly Asn
305                 310                 315                 320
```

-continued

```
Glu Arg Ser Lys Lys Leu Tyr Ser Leu Gly Val Gln Ser Gly Ala Met
            325                 330                 335

Gly Leu Met Phe Asn Ser Ile Val Leu Gly Phe Met Ser Leu Gly Val
        340                 345                 350

Glu Trp Ile Gly Arg Lys Leu Gly Gly Ala Lys Arg Leu Trp Gly Ile
    355                 360                 365

Val Asn Phe Ile Leu Ala Ala Gly Leu Ala Met Thr Val Leu Val Thr
370                 375                 380

Lys Phe Ala Glu Asp His Arg Lys Thr Ala Gly Asp Leu Ala Gly Pro
385                 390                 395                 400

Ser Ala Ser Val Lys Ala Gly Ala Leu Ser Leu Phe Ala Val Leu Gly
                405                 410                 415

Ile Pro Leu Ala Ile Thr Phe Ser Thr Pro Phe Ala Leu Ala Ser Ile
            420                 425                 430

Phe Ser Ser Cys Ser Gly Ala Gly Gln Gly Leu Ser Leu Gly Val Leu
        435                 440                 445

Asn Leu Ala Ile Val Ile Pro Gln Met Ile Val Ser Leu Gly Gly Gly
    450                 455                 460

Pro Phe Asp Ala Leu Phe Gly Gly Asn Leu Pro Ala Phe Ile Val
465                 470                 475                 480

Ala Ala Ile Ala Ala Ile Ser Gly Val Leu Ala Leu Thr Val Leu
                485                 490                 495

Pro Ser Pro Pro Pro Asp Ala Pro Lys Ala Thr Thr Met Gly Gly Phe
            500                 505                 510

His

<210> SEQ ID NO 81
<211> LENGTH: 806
<212> TYPE: PRT
<213> ORGANISM: Coffea arabica

<400> SEQUENCE: 81

Met Ala Glu Arg Val Leu Thr Arg Val His Ser Leu Arg Glu Arg Leu
1               5                   10                  15

Asp Ala Thr Leu Ala Ala His Arg Asn Asp Val Leu Leu Phe Met Ser
            20                  25                  30

Arg Leu Glu Thr His Gly Lys Gly Ile Leu Lys Pro His Gln Leu Leu
        35                  40                  45

Ala Glu Phe Glu Glu Ile Asn Lys Asp Gly Lys Gln Lys Ile His Asp
    50                  55                  60

His Ala Phe Glu Glu Val Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Val Arg Val Asn Val His Ala Leu Val Val Glu Glu Leu Thr Val
            100                 105                 110

Pro Glu Tyr Leu His Phe Lys Glu Glu Leu Val Asp Gly Ser Lys Asn
        115                 120                 125

Gly Asn Phe Val Leu Glu Leu Asp Phe Glu Pro Phe Thr Ala Ser Phe
    130                 135                 140

Pro Lys Pro Thr Leu Thr Lys Tyr Ile Gly Asp Gly Val Glu Phe Leu
145                 150                 155                 160

Asn Arg His Leu Ser Ala Lys Met Phe His Asp Lys Glu Ser Met Ala
                165                 170                 175
```

```
Pro Leu Leu Asp Phe Leu Arg Val His Gln Tyr Lys Gly Lys Thr Met
            180                 185                 190

Met Leu Asn Asp Arg Ile Lys Asp Leu Asn Thr Leu Gln Ala Val Leu
        195                 200                 205

Arg Lys Ala Glu Glu Tyr Leu Thr Thr Leu Ser Ala Asp Thr Pro Tyr
    210                 215                 220

Ser Glu Phe Glu His Lys Phe Gln Glu Ile Gly Leu Glu Arg Gly Trp
225                 230                 235                 240

Gly Asp Thr Ala Glu Arg Val Leu Glu Met Ile Cys Met Leu Leu Asp
                245                 250                 255

Leu Leu Gly Ala Pro Asp Ser Cys Thr Leu Glu Lys Phe Leu Gly Arg
            260                 265                 270

Ile Pro Met Val Phe Asn Val Val Ile Leu Ser Pro His Gly Tyr Phe
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Val Lys Pro Arg Ile Leu Ile Ile Thr
                325                 330                 335

Arg Leu Leu Pro Asp Ala Pro Gly Thr Thr Cys Gly Gln Arg Leu Glu
            340                 345                 350

Lys Val Tyr Gly Ser Glu Tyr Ser His Ile Leu Arg Val Pro Phe Arg
        355                 360                 365

Thr Glu Lys Gly Val Val Arg Lys Trp Ile Ser Arg Phe Glu Val Trp
    370                 375                 380

Pro Tyr Met Glu Thr Phe Thr Glu Asp Val Ala Lys Glu Val Thr Ala
385                 390                 395                 400

Glu Leu Gln Ala Lys Pro Asp Leu Val Ile Gly Asn Tyr Ser Glu Gly
                405                 410                 415

Asn Leu Val Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Leu Ser Lys Phe Asp Glu Lys Tyr His Phe Ser Cys Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val His Gly Ile
            500                 505                 510

Asp Val Phe Asp Pro Lys Phe Asn Ile Val Ser Pro Gly Ala Asp Thr
        515                 520                 525

Asn Leu Tyr Phe Pro His Thr Glu Lys Glu Lys Arg Leu Thr Ser Phe
    530                 535                 540

His Pro Glu Ile Glu Glu Leu Leu Phe Ser Asp Val Glu Asn Glu Glu
545                 550                 555                 560

His Leu Cys Val Leu Lys Asp Lys Lys Pro Ile Leu Phe Thr Met
                565                 570                 575

Ala Arg Leu Asp Arg Val Lys Asn Leu Thr Gly Leu Val Glu Leu Tyr
            580                 585                 590
```

```
Ala Lys Asn Pro Lys Leu Arg Glu Leu Val Asn Leu Val Val Gly
        595                 600                 605

Gly Asp Arg Arg Lys Glu Ser Lys Asp Leu Glu Gln Ala Glu Met
610                 615                 620

Lys Lys Met Tyr Ser Leu Ile Glu Thr Tyr Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Arg Gly Ala Phe Val Gln Pro Ala Phe Tyr
                660                 665                 670

Glu Ala Phe Gly Leu Thr Val Val Glu Ala Met Thr Cys Gly Leu Pro
        675                 680                 685

Thr Phe Ala Thr Asn His Gly Gly Pro Ala Glu Ile Ile His Gly
690                 695                 700

Lys Ser Gly Phe His Ile Asp Pro Tyr His Gly Glu Gln Val Ser Glu
705                 710                 715                 720

Leu Leu Ala Asn Phe Phe Glu Arg Cys Lys Glu Pro Ser Tyr Trp
                725                 730                 735

Asp Thr Ile Ser Ala Gly Gly Leu Lys Arg Ile Gln Glu Lys Tyr Thr
                740                 745                 750

Trp Gln Ile Tyr Ser Asp Arg Leu Leu Thr Leu Ala Gly Val Tyr Gly
        755                 760                 765

Phe Trp Lys Cys Val Ser Lys Leu Asp Arg Gln Glu Ile Arg Arg Tyr
770                 775                 780

Leu Glu Met Phe Tyr Ala Leu Lys Tyr Arg Lys Leu Ala Glu Ala Val
785                 790                 795                 800

Pro Leu Ala Val Asp Gln
                805

<210> SEQ ID NO 82
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 82
tgaattcgtt aacgaattc                                              19

<210> SEQ ID NO 83
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 83
tgaattcgtt aacgaactc                                              19

<210> SEQ ID NO 84
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 84
tgaattcgtt aacgaagtc                                              19
```

-continued

```
<210> SEQ ID NO 85
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 85
tgaattcgtt aacgaaatt                                                  19

<210> SEQ ID NO 86
<211> LENGTH: 473
<212> TYPE: PRT
<213> ORGANISM: Stevia rebaudiana

<400> SEQUENCE: 86
```

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Val Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

```
Asp Ser Val Glu Leu Pro Asp Gly Phe Val Glu Arg Thr Arg Asp Arg
            325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
            355                 360                 365

Glu Gly Leu Met Phe Gly His Pro Leu Ile Met Leu Pro Ile Phe Gly
            370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
            435                 440                 445

Glu Lys Glu Tyr Val Ser Gln Phe Val Asp Tyr Leu Lys Asn Thr
            450                 455                 460

Arg Ala Val Ala Ile Asp His Glu Ser
465                 470
```

<210> SEQ ID NO 87
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 87
cggtaggtat tgattgtaat t                                      21

<210> SEQ ID NO 88
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 88
cttttcggtt agagcggatg t                                      21

<210> SEQ ID NO 89
<211> LENGTH: 1422
<212> TYPE: DNA
<213> ORGANISM: Artificial Sequence
<220> FEATURE:
<223> OTHER INFORMATION: Synthetic oligonucleotide

<400> SEQUENCE: 89
atggctacat ctgattctat tgttgatgac aggaagcagt tgcatgtggc tactttccct    60
tggcttgctt tcggtcatat actgccttac ctacaactat caaaactgat agctgaaaaa   120
ggacataaag tgtcattcct ttcaacaact agaaacattc aaagattatc ttcccacata   180
tcaccattga ttaacgtcgt tcaattgaca cttccaagag tacaggaatt accagaagat   240
gctgaagcta acagatgt gcatcctgaa gatatccctt acttgaaaaa ggcatccgat   300
ggattacagc tgaggtcac tagattcctt gagcaacaca gtccagattg gatcatatac   360
gactacactc actattggtt gccttcaatt gcagcatcac taggcatttc tagggcacat   420
ttcagtgtaa ccacaccttg ggccattgct tacatgggtc catccgctga tgctatgatt   480

```
aacggcagtg atggtagaac taccgttgaa gatttgacaa ccccaccaaa gtggttccca      540
tttccaacta aagtctgttg gagaaaacac gacttagcaa gactggttcc atacaaggca      600
ccaggaatct cagacggcta tagaatgggt ttagtcctta aagggtctga ctgcctattg      660
tctaagtgtt accatgagtt tgggacacaa tggctaccac ttttggaaac attacaccaa      720
gttcctgtcg taccagttgg tctattacct ccagaaatcc ctggtgatga aaggacgag       780 acttgggttt caatcaaaaa gtggttagac gggaagcaaa aaggctcagt ggtatatgtg      840
gcactgggtt ccgaagtttt agtatctcaa acagaagttg tggaacttgc cttaggtttg      900
gaactatctg gattgccatt tgtctgggcc tacagaaaac caaaaggccc tgcaaagtcc      960
gattcagttg aattgccaga cggctttgtc gagagaacta gagatagagg gttggtatgg     1020
acttcatggg ctccacaatt gagaatcctg agtcacgaat ctgtgtgcgg tttcctaaca     1080
cattgtggtt ctggttctat agttgaagga ctgatgtttg gtcatccact tatcatgttg     1140
ccaatctttg gtgaccagcc tttgaatgca cgtctgttag aagataaaca agttggaatt     1200
gaaatcccac gtaatgagga agatggatgt ttaaccaagg agtctgtggc cagatcatta     1260
cgttccgttg tcgttgaaaa ggaaggcgaa atctacaagg ccaatgcccg tgaactttca     1320
aagatctaca atgacacaaa agtagagaag gaatatgttt ctcaatttgt agattaccta     1380
gagaaaaacg ctagagccgt agctattgat catgaatcct aa                        1422

<210> SEQ ID NO 90
<211> LENGTH: 1422
<212> TYPE: DNA
<213> ORGANISM: Artificial Sequence
<220> FEATURE:
<223> OTHER INFORMATION: Synthetic oligonucleotide

<400> SEQUENCE: 90
atggctactt ctgattccat cgttgacgat agaaagcaat tgcatgttgc tacttttcca       60
tggttggctt tcggtcatat tttgccatac ttgcaattgt ccaagttgat tgctgaaaag      120
ggtcacaagg tttcattctt gtctaccacc agaaacatcc aaagattgtc ctctcatatc      180 tcccccattga tcaacgttgt tcaattgact ttgccaagag tccaagaatt gccagaagat     240
gctgaagcta ctactgatgt tcatccagaa gatatccctt acttgaaaaa ggcttccgat      300
ggtttacaac cagaagttac tagattcttg gaacaacatt ccccagattg gatcatctac      360
gattatactc attactggtt gccatccatt gctgcttcat gggtatttc tagagcccat       420 ttctctgtta ctactccatg ggctattgct tatatgggtc catctgctga tgctatgatt      480
aacggttctg atggtagaac taccgttgaa gatttgacta ctccaccaaa gtggttccca      540
tttccaacaa aagtctgttg gagaaaacac gatttggcta gattggttcc atacaaagct      600
ccaggtattt ctgatggtta cagaatgggt atggttttga aaggttccga ttgcttgttg      660
tctaagtgct atcatgaatt cggtactcaa tggttgcctt gttggaaac attgcatcaa       720 gttccagttg ttccagtagg tttgttgcca ccagaaattc caggtgacga aaaagacgaa      780
acttgggttt ccatcaaaaa gtggttggat ggtaagcaaa agggttctgt tgtttatgtt      840
gctttgggtt ccgaagcttt ggtttctcaa accgaagttg ttgaattggc tttgggtttg      900
gaattgtctg gtttgccatt tgtttgggct tacagaaaac ctaaaggtcc agctaagtct      960
gattctgttg aattgccaga tggtttcgtt gaaagaacta gagatagagg tttggtttgg     1020
acttcttggg ctccacaatt gagaattttg tctcatgaat ccgtctgtgg tttcttgact     1080
```

-continued

```
cattgtggtt ctggttctat cgttgaaggt ttgatgtttg gtcacccatt gattatgttg      1140
ccaatctttg gtgaccaacc attgaacgct agattattgg aagataagca agtcggtatc      1200
gaaatcccaa gaaatgaaga agatggttgc ttgaccaaag aatctgttgc tagatctttg      1260
agatccgttg tcgttgaaaa agaaggtgaa atctacaagg ctaacgctag agaattgtcc      1320
aagatctaca acgataccaa ggtcgaaaaa gaatacgttt cccaattcgt tgactacttg      1380
gaaaagaatg ctagagctgt tgccattgat catgaatctt ga                         1422
```

<210> SEQ ID NO 91
<211> LENGTH: 1503
<212> TYPE: DNA
<213> ORGANISM: Stevia rebaudiana

<400> SEQUENCE: 91

```
atggaggctt catatctata catttccatt cttctgcttc tagcttcgta cctcttcacc       60
acccaacttc gtcgtaaatc cgccaatcta ccgccgacgg tgttcccatc catccccata      120
atcggtcatc tctacctcct caaaaaacca ctctatagaa cactagccaa aattgccgcc      180
aaatacggcc ctatcctcca actccaacta gggtaccgcc gtgtcctcgt aatctcctcc      240
ccttccgccg ccgaagaatg cttcaccaac aacgacgtta tcttcgccaa ccgtccgaag      300
acgctattcg aaaaattgt aggggtacc agcctcgggt cgctgtcgta cggcgaccag      360
tggcgcaacc tccgccgcgt tgcatccatc gagattctat cagtccaccg gctcaacgag      420
tttcacgaca tacgtgttga cgaaaaccgg cttctgatcc gtaaactaag atccagttct      480
tctccggtga ctctgataac ggtgtttttac gcactaacgt taaatgtgat tatgagaatg      540
atctccggaa agaggtattt cgactcgggt gatcgggaat ggaggagga agggaagcga      600 ttccgggaga tactcgatga cacttttg ctcgcgggtg cttctaatgt tgggattac       660 ttgccgattc tgaattggtt gggggtgaag agcttggaga agaagctaat cgcattgcag      720 aaaagagag atgatttctt tcagggactg atcgagcaag ttcggaaatc tagaggggct      780 aagtgggaa aaggaaggaa gacgatgatc gagttgtgt tatccctaca gaatctgaa       840 cctgagtatt acactgacgc catgatccga tcatttgtgc tgggtttatt agcagcaggg      900
agtgatacat cggctggaac tatggaatgg gcgatgtctc tttttggtaaa ccacccgcac      960 gtattaaaaa aggcacaggc tgaaattgat cgagtcatcg gcaacaaccg tctaattgat     1020
gagtccgaca tagggaatat accttacatt ggttgcatca taaacgagac gctcagattg     1080
taccctgcgg gcccgttgct atttcccat gagtcatcag cggactgtgt tatcagcggg     1140
tacaacatcc ctcgtgggac gatgcttatt gtcaaccaat gggcgataca tcatgacca      1200 aaggtgtggg acgaccctga gacattcaaa ccggaaagat tccaagggct gaagggaca      1260 cgagacgggt ttaagctgat gccttttggg tccggaagga ggggttgtcc aggggaggga     1320
ttggcgattc gtttgcttgg gatgactctc ggtcggtta ccaatgctt tgattggaa       1380 cgagtcggtg acgagatggt tgatatgacc gaaggtcttg gggtcacgtt gcctaaagct     1440
gtaccattag tcgccaagtg caagccgcgt tccgaaatga cgaatctact ctctgagcta     1500
tga                                                                   1503
```

<210> SEQ ID NO 92
<211> LENGTH: 436
<212> TYPE: PRT
<213> ORGANISM: Archaeoglobus fulgidus

<400> SEQUENCE: 92

```
Met Gln Val Leu Arg Leu Asp Arg Arg His Tyr Lys Ser Gly Lys Ile
1               5                   10                  15

Arg Arg Ala Met Ser Ser Arg Ile Pro Gly Phe Tyr Lys Leu Ser Val
            20                  25                  30

Glu Glu Arg Leu Lys Lys Val Ala Glu Phe Ala Gly Leu Ser Asp Glu
            35                  40                  45

Glu Val Lys Ala Val Leu Ser Gln Gly Leu Pro Leu Asp Val Ala Asp
50                  55                  60

Arg Met Ile Glu Asn Val Ile Gly Thr Phe Glu Leu Pro Leu Gly Ile
65                  70                  75                  80

Ala Thr Asn Phe Leu Ile Asp Gly Lys Asp Tyr Leu Ile Pro Met Ala
                85                  90                  95

Ile Glu Glu Pro Ser Val Val Ala Ala Ala Ser Asn Ala Ala Arg Met
                100                 105                 110

Ala Arg Glu Ser Gly Gly Phe Thr Thr Asp Tyr Thr Gly Ser Leu Met
            115                 120                 125

Ile Gly Gln Ile Gln Val Thr Lys Leu Leu Asn Pro Asn Ala Ala Lys
            130                 135                 140

Phe Glu Val Leu Arg Gln Lys Asp Glu Ile Ile Glu Arg Ala Asn Glu
145                 150                 155                 160

Cys Asp Pro Met Leu Val Asn Leu Gly Gly Cys Lys Asp Ile Glu
                165                 170                 175

Ala Arg Val Ile Asp Thr Ile Met Gly Lys Met Leu Ile Val His Leu
                180                 185                 190

Ile Val Asp Val Lys Asp Ala Met Gly Ala Asn Ala Val Asn Thr Met
            195                 200                 205

Cys Glu Lys Val Ala Pro Phe Ile Glu Arg Ile Thr Gly Gly Lys Val
210                 215                 220

Tyr Leu Arg Ile Ile Ser Asn Leu Ala Ala Tyr Arg Leu Ala Arg Ala
225                 230                 235                 240

Lys Ala Val Phe Asp Lys Asp Val Ile Gly Gly Glu Glu Val Val Glu
                245                 250                 255

Gly Ile Met Leu Ala Tyr Ala Phe Ala Ala Asp Pro Phe Arg Cys
            260                 265                 270

Ala Thr His Asn Lys Gly Ile Met Asn Gly Ile Ser Ala Leu Met Ile
            275                 280                 285

Ala Thr Gly Asn Asp Phe Arg Ala Ile Glu Ala Gly Ala His Ser Tyr
            290                 295                 300

Ala Ala Ile Gly Gly Tyr Lys Pro Leu Thr Thr Tyr Glu Val Asp Arg
305                 310                 315                 320

Lys Gly Asn Leu Val Gly Thr Ile Glu Ile Pro Met Ala Val Gly Val
                325                 330                 335

Ile Gly Gly Ala Thr Lys Val Asn Pro Leu Ala Lys Ile Ser Leu Lys
            340                 345                 350

Ile Leu Gly Val Asn Thr Ala Glu Glu Leu Ala Arg Val Ala Ala Ala
            355                 360                 365

Leu Gly Leu Ala Gln Asn Phe Ala Ala Leu Arg Ala Leu Ala Thr Glu
370                 375                 380

Gly Ile Gln Arg Gly His Met Glu Leu His Ala Arg Asn Leu Ala Ile
385                 390                 395                 400

Met Ala Gly Ala Thr Gly Asp Glu Val Asp Arg Val Val Glu Ile Met
                405                 410                 415
```

Val Arg Asp Gly Lys Ile Arg Leu Asp Tyr Ala Lys Glu Val Leu Glu
            420                 425                 430

Arg Leu Arg Ser
            435

<210> SEQ ID NO 93
<211> LENGTH: 428
<212> TYPE: PRT
<213> ORGANISM: Pseudomonas mevalonii

<400> SEQUENCE: 93

Met Ser Leu Asp Ser Arg Leu Pro Ala Phe Arg Asn Leu Ser Pro Ala
1               5                   10                  15

Ala Arg Leu Asp His Ile Gly Gln Leu Gly Leu Ser His Asp Asp
            20                  25                  30

Val Ser Leu Leu Ala Asn Ala Gly Ala Leu Pro Met Asp Ile Ala Asn
            35                  40                  45

Gly Met Ile Glu Asn Val Ile Gly Thr Phe Glu Leu Pro Tyr Ala Val
50                  55                  60

Ala Ser Asn Phe Gln Ile Asn Gly Arg Asp Val Leu Val Pro Leu Val
65                  70                  75                  80

Val Glu Glu Pro Ser Ile Val Ala Ala Ser Tyr Met Ala Lys Leu
                85                  90                  95

Ala Arg Ala Asn Gly Gly Phe Thr Thr Ser Ser Ser Ala Pro Leu Met
            100                 105                 110

His Ala Gln Val Gln Ile Val Gly Ile Gln Asp Pro Leu Asn Ala Arg
            115                 120                 125

Leu Ser Leu Leu Arg Arg Lys Asp Glu Ile Ile Glu Leu Ala Asn Arg
130                 135                 140

Lys Asp Gln Leu Leu Asn Ser Leu Gly Gly Gly Cys Arg Asp Ile Glu
145                 150                 155                 160

Val His Thr Phe Ala Asp Thr Pro Arg Gly Pro Met Leu Val Ala His
                165                 170                 175

Leu Ile Val Asp Val Arg Asp Ala Met Gly Ala Asn Thr Val Asn Thr
            180                 185                 190

Met Ala Glu Ala Val Ala Pro Leu Met Glu Ala Ile Thr Gly Gly Gln
            195                 200                 205

Val Arg Leu Arg Ile Leu Ser Asn Leu Ala Asp Leu Arg Leu Ala Arg
210                 215                 220

Ala Gln Val Arg Ile Thr Pro Gln Gln Leu Glu Thr Ala Glu Phe Ser
225                 230                 235                 240

Gly Glu Ala Val Ile Glu Gly Ile Leu Asp Ala Tyr Ala Phe Ala Ala
                245                 250                 255

Val Asp Pro Tyr Arg Ala Ala Thr His Asn Lys Gly Ile Met Asn Gly
            260                 265                 270

Ile Asp Pro Leu Ile Val Ala Thr Gly Asn Asp Trp Arg Ala Val Glu
            275                 280                 285

Ala Gly Ala His Ala Tyr Ala Cys Arg Ser Gly His Tyr Gly Ser Leu
290                 295                 300

Thr Thr Trp Glu Lys Asp Asn Asn Gly His Leu Val Gly Thr Leu Glu
305                 310                 315                 320

Met Pro Met Pro Val Gly Leu Val Gly Gly Ala Thr Lys Thr His Pro
                325                 330                 335

Leu Ala Gln Leu Ser Leu Arg Ile Leu Gly Val Lys Thr Ala Gln Ala
            340                 345                 350

```
Leu Ala Glu Ile Ala Val Ala Val Gly Leu Ala Gln Asn Leu Gly Ala
        355                 360                 365

Met Arg Ala Leu Ala Thr Glu Gly Ile Gln Arg Gly His Met Ala Leu
370                 375                 380

His Ala Arg Asn Ile Ala Val Val Ala Gly Ala Arg Gly Asp Glu Val
385                 390                 395                 400

Asp Trp Val Ala Arg Gln Leu Val Glu Tyr His Asp Val Arg Ala Asp
                405                 410                 415

Arg Ala Val Ala Leu Leu Lys Gln Lys Arg Gly Gln
            420                 425

<210> SEQ ID NO 94
<211> LENGTH: 1323
<212> TYPE: DNA
<213> ORGANISM: Artificial sequence
<220> FEATURE:
<223> OTHER INFORMATION: Synthetic oligonucleotide

<400> SEQUENCE: 94
atgcattcta ccagacatat cttaagacaa agggccgtcc tagttacagg cgctagaaca      60
ccattcgtga atcatttggg gctcttatg aaagcagata ccttggaatt ggcatcagca     120
tcagtcgctg ggttgctgaa caagacctca ctggacccta gagatatcga tcatatcgtt     180
tggggtaatg ttgtacttca aggatcagct cataactgcg ccagagaaat agttatcgac     240
cttaacatgc taaaaagat catcggtaat ttgacatcta tggcctgtgc ttcaggctta     300
tcttctttgt cacaagcctg tatgctaata gagggtggtc atgccgatgt cgtcattgct     360
ggcggttctg attcagtctc caacactgaa gtgcctttgc aagatccgt cacttacggt     420
ctaatgatgg cccaaaggaa gggtgttatg ggcttcttta aggaagcagg atacaaccca     480
ttcaaatggt ttccaggcgg tattgcttta accgaacgta gtacaggaaa actatgggt     540
tggcatggag acttaattgc tgagttaaac tctatatcta gagatgacca ggaagccctg     600
gctgtggctt ctcatgcaaa tgctgctaga gcagaaaaag ctgggtactt taggaggaa     660
attgtacctg tgacaatcga caaaaagggc aaaagactg aagtaacatg tgatgatgtt     720
atgcaaagag atacagaaaa gatgaaggcc aagatgccat cattgaagcc tgttttcaga     780
aaagagggag gtacaataac agcagccact tccagtactc tgactgatgg tggctctgca     840
atgttggtta tgtcagagga aaaggccaaa aagttgggtt atccaactga tgtctgcgtg     900
aagtcttggt atttcagtgg tatcgatcct tacccacaac ttttgttagc accagttcta     960
ggttggggtc cagctttgaa aaaggccgga ttaaccccta agatatcga tttgtacgaa    1020
attcacgaag catttgctgc acaagttcta gccacaatta gtgtttgaa gtctcaggaa    1080
ttcttcgata ggtacgctaa cggtgcaaag ccagtattaa ctgaggatat tgatctttct    1140
aaactaaatg ttaatggcgg ttccttagca cttggccacc cattcgccgc tacaggaggt    1200
agaatcgtaa tctctctagc aaatgagttg agaagatccg gaaagagaca cgggctggtc    1260
agtatttgtg cagctggagg gttaggcgga gtagctatac ttgagcatac agcaagtaag    1320
taa                                                                1323

<210> SEQ ID NO 95
<211> LENGTH: 1584
<212> TYPE: DNA
<213> ORGANISM: Artificial Sequence
<220> FEATURE:
<223> OTHER INFORMATION: Synthetic oligonucleotide
```

<400> SEQUENCE: 95

```
atggcagctg accaattggt gaaaactgaa gtcaccaaga agtcttttac tgctcctgta      60
caaaaggctt ctacaccagt tttaaccaat aaaacagtca tttctggatc gaaagtcaaa     120
agtttatcat ctgcgcaatc gagctcatca ggaccttcat catctagtga ggaagatgat     180
tcccgcgata ttgaaagctt ggataagaaa atacgtcctt tagaagaatt agaagcatta     240
ttaagtagtg gaaatacaaa acaattgaag aacaaagagg tcgctgcctt ggttattcac     300
ggtaagttac ctttgtacgc tttggagaaa aaattaggtg atactacgag agcggttgcg     360
gtacgtagga aggctctttc aattttggca gaagctcctg tattagcatc tgatcgttta     420
ccatataaaa attatgacta cgaccgcgta tttggcgctt gttgtgaaaa tgttataggt     480
tacatgcctt tgcccgttgg tgttataggc cccttggtta tcgatggtac atcttatcat     540
ataccaatgg caactacaga gggttgtttg gtagcttctg ccatgcgtgg ctgtaaggca     600
atcaatgctg gcggtggtgc aacaactgtt ttaactaagg atggtatgac aagaggccca     660
gtagtccgtt tcccaacttt gaaaagatct ggtgcctgta agatatggtt agactcagaa     720
gagggacaaa acgcaattaa aaaagctttt aactctacat caagatttgc acgtctgcaa     780
catattcaaa cttgtctagc aggagattta ctcttcatga gatttagaac aactactggt     840
gacgcaatgg gtatgaatat gatttctaaa ggtgtcgaat actcattaaa gcaaatggta     900
gaagagtatg gctgggaaga tatggaggtt gtctccgttt ctggtaacta ctgtaccgac     960
aaaaaaccag ctgccatcaa ctggatcgaa ggtcgtggta agagtgtcgt cgcagaagct    1020
actattcctg gtgatgttgt cagaaaagtg ttaaaaagtg atgtttccgc attggttgag    1080
ttgaacattg ctaagaattt ggttggatct gcaatggctg gtctgttgg tggatttaac    1140
gcacatgcag ctaatttagt gacagctgtt ttcttggcat taggacaaga tcctgcacaa    1200
aatgttgaaa gttccaactg tataacattg atgaaagaag tggacggtga tttgagaatt    1260
tccgtatcca tgccatccat cgaagtaggt accatcggtg gtggtactgt tctagaacca    1320
caaggtgcca tgttggactt attaggtgta agaggcccgc atgctaccgc tcctggtacc    1380
aacgcacgtc aattagcaag aatagttgcc tgtgccgtct ggcaggtga  attatcctta    1440
tgtgctgccc tagcagccgg ccatttggtt caaagtcata tgacccacaa caggaaacct    1500
gctgaaccaa caaaacctaa caatttggac gccactgata taaatcgttt gaaagatggg    1560
tccgtcacct gcattaaatc ctaa                                           1584
```

<210> SEQ ID NO 96
<211> LENGTH: 3681
<212> TYPE: DNA
<213> ORGANISM: Artificial Sequence
<220> FEATURE:
<223> OTHER INFORMATION: Synthetic oligonucleotide

<400> SEQUENCE: 96

```
atgagagctg tccttagatt gttatcaaca catactgttt tctctcctat tgaaacaatt      60
gtatctgttt tcgtgttagc tacattagct tacttccaca tcttgtccgg aatcaagcac     120
tcaagtttct ttgcatcttc tcatcctcct gctatcagac ctgcttttgc acatctgacc     180
aacgggaat gggttgccgt ctcccaacat gattggactg aagcatggaa gcatcctggc     240
ggttcacttg atgcattaga acttcaacaa gtagttttca ctttagatga caagactcaa     300
ccatctgctg tgctagatgc atccgcaatt agtcagcact agtttccaa tgttcctgca     360
```

```
ttatctggaa aagcctactc ttcattgtgc caccatccaa atgtatcagg cacctcctgt    420
tttacatcag tttctggtcc aggagcttca ccaatcttga cactgagttt taagcctgga    480
actagagacg attggttagg atcattaagg aaggagaaaa ctatcacact agatggggtt    540
aagtacgacg ttggagccgg aaaaagacaa gagtcaatcg gcgatatgga atcatctaag    600
tgggttgctt atgcattatc agctttggta cttagatttt gggaattaac aaaggcagat    660
tccttagata tactagtggt tctaactggg tacatcctaa tgcacgtaac attcatgaga    720
ttgttcttgg catccagagc acttggcagt aacttttggt tatcagctgg catattctcc    780
tccgcaacaa tttctttcct attcacttta ccaatgtgta gatctatgga tattccactt    840
gatccaattg ccttgacaga agccctgcca ttcttggtgt gtaccgtagg ttttgacaaa    900
ccacttagat tggcaagagc tgtgatggct catcctaata tccttaaacc tcaagatgat    960
ggtaggatga aagctgccgg agatgtcatt cttgaggcac tggacagagt tggtaacatg   1020
atattgagag attacgcttt agagatcgca gttctattcg ttggcgttaa ctccagagtt   1080
ggcggtctta aggaattttg tgctgtagct gcagcattac ttgctatgga cagattaatg   1140
acattcacac tttatacagc agtgttaacc atcatggttg aggtaaggcg tatcaaaaag   1200
gtcagagata tgactaaggc tagatctaga agttcttcta ttaccgccgt tacagccaac   1260
ggcaccgcca taagaggcgt tttgagtaga aaatcttcaa aacaatctgt gacagaacca   1320
gagacaacta aaaacctaag acaaagagcc actgattcag ccatcggtgt taagggttca   1380
ttgctgaaag atggaggcag attgcaggaa gccgaggaga atccaatggc aagattaaag   1440
ctattgttaa tcgcttcctt cttaacacta cacatcttga acttttgtac tactttgact   1500
tcagccacag ctaacgcaag acatcaaaga catcctttta gaaccgttca agaggtagta   1560
ccaattccta gagttgacat tactaccccca gccatagcca atatcttgtc tcatctagct   1620
gtggctcagg aacctatgtt cactgttgtt ggcagtgaac ctatcgaact tcttgttaaa   1680
gtcgctgctc cagtctacgt ccatgctcta ccattggccc ctgctttaag agcttcaaac   1740
actaatactg gagaagctat tgaaaacttt atgagttcat ggtctagtct ggtaggtgac   1800
ccagttgtta gtaagtggat cgtagcattg ctagctgtct ctgttgcatt gaatggatac   1860
ttgttaaagg gtatagccgc aggttccggg ttggctgcca tgagagctgt tagatctcaa   1920
ggtgttcgtt tcagatctag agctagaagt atcgtaaaga tatctgatga acctgagcca   1980
gagccagaac actctatcga cccagcacca gtagtgttct tcgcttccgc agcaccagct   2040
gtagaggccc ctgctccagc tcctgcacct gaaccagaac caccagtcaa cagaccacca   2100
ccattgacta ttttctcaag accactgaac ttagaaacag tggacaaaaa gttacaagat   2160
gctctgccaa taagatcccc accacctgtt gaaccaatca ctccagaatc tagagaagtg   2220
gaaccaaccc aagtagaagt aagatctcta gctgaatgtg tggatgtgtt cgagaatggg   2280
ccaagaccag tctcagtggc tttaaagact ctgaatgatg aggaagttat cctgctttgc   2340
caaacaggta agatagctcc atatgcattg gttaagatgt tggctgattt cgatagggcc   2400
gtacgtgtca gaagagcact tattagtaga gcttcacgta caaaaacttt agaaaactca   2460
ctggttccta tgaaagatta tgattacgcc agagtcatgg gtgcctgttg tgaaaacgtt   2520
atcggataca tgccattacc actagggatt gcaggtccat tgaagattga tggcttgatg   2580
tatcctatac caatggcaac cgcagaaggt accttggttg catctacttc tagggctgt    2640
aaggccttaa atgctggtgg aggggtcaca actgtcttga cagcagatgg catgacaaga   2700
gggccagcta tagactttcc ttccatcgtc agagctgcag aggctaaggc cttcattgaa   2760
```

```
tcagaagatg gatacgctac aatcagggag gctttcgagt ctacttctag atttgccaag    2820
ttgcaaaaga tcaagtgtgc actagctggt cgtactcttt ttgtcagatt tgctactaga    2880
acaggagatg ccatgggtat gaacatgatt tctaaggcta ccgaaaaggc acttgatgtc    2940
ctgagtcacg agttccctga aatggtcgtc cttgctttgt ctggtaacta ctgcacagac    3000
aaaaagcctg cagctatttc atggatcgaa ggtaggggaa atctattgt agcagaagca     3060 gttattcctg gtaaggtcgt taagtcagtc ctgaaaacaa cagtcgagtc tctttgcaat    3120
gtcaacacta agaaaaacct gattggttca gccatggcag ttctgttgg tggtttcaac    3180 gctcatgccg ccaacatcct aacagctgtg ttcctagcca caggtcagga tcctgctcaa    3240
aatgtcgaat cttctaattg catgacttta atggaaccaa caaacggcgg tgaggatttg    3300
ctaatgacaa tttcaatgcc atgtatagag gtaggaaccg ttggtggagg acaattctg    3360 gaaccacaag gtgcagtttt ggatttgttg ggcgttagag gggctcaccc tactaatcct    3420
ggtcaaaacg ctcaacagtt agccagaatt atcgcatcag ctgtaatggc aggcgaattg    3480
tctttgataa gtgccttagc cgcaggtcat ttggttagag ctcatcttgc ccacaatcgt    3540
tctcaattga atacaccaat gccatccaga ccacatactc ctggccctga ggatgtctca    3600
catgtgcagc agctacctac accatctgca tctgatgata aaggtgttac agctcaaggt    3660
tacgttgtcg aagcaaaata a                                              3681

<210> SEQ ID NO 97
<211> LENGTH: 2667
<212> TYPE: DNA
<213> ORGANISM: Artificial Sequence
<220> FEATURE:
<223> OTHER INFORMATION: Synthetic oligonucleotide

<400> SEQUENCE: 97
atgttatcaa gattgttcag aatgcatggt ctatttgttg cttctcaccc ttgggaagta      60
atagttggta ctgtaacatt aacgatctgt atgatgtcta tgaacatgtt taccggaaac     120
aacaagattt gtggttggaa ttatgagtgt cctaagctgg aagaggatgt gttgagttca     180
gacatcatca tacttactat aacaagatgc attgcaatat tgtatatcta cttccaattt     240
caaaacctta gacaattggg tagtaaatac atcctaggca tcgccggatt gttcactatt     300
ttctctagtt ttgttttctc aaccgtcgtt attcactttt tggacaaaga gttaactggt     360
ttgaacgaag ctctaccatt cttcttgctg ctggtagatt tgtccagagc ttccgcttta     420
gctaaattcg ctctgtcctc taattctcaa gatgaagtta gagagaatat agcaagggga     480
atggccatac ttggacctac tttcacactt gatgcccttg tcgaatgttt ggttattggg     540
gttggcacaa tgtccggcgt tagacagtta gaaatcatgt tgtgttttgg ctgtatgagt     600
gtcttggcta actactttgt ctttatgaca ttctttccag cttgcgtttc tttggtattg     660
gagctgtcaa gagaatcaag agaaggcaga ccaatatggc aactatcaca tttcgccaga     720
gtgttagaag aggaggaaaa caaacctaat cctgtcacac agagagtgaa aatgatcatg     780
tctttgggtt tagtcctagt gcatgctcat tctagatgga tcgcagatcc atcccctcag     840
aattctacag ctgataactc taaagttagt ttaggtttag atgaaaatgt aagtaagagg     900 attgaaccttt ccgtgtcttt gtggcaattc tacttatcaa aaatgatttc catggatatt     960
gaacaagtga taacgttgtc tttggcttta ttgttagccg ttaagtacat tttcttgag    1020 caagccgaaa cggaatctac attatcactg aaaaacccaa ttacatcccc agtcgttacc    1080
```

```
cagaaaaaga taactgatga ttgctgtaga agagatccag tgttggtcag gaatgatcaa    1140
aagttccacg ccatggagga ggaaactagg aaaaacagag aaaggaaagt tgaagttatc    1200
aagcctctat tagcagaaaa tgacacttca catagggcca cttttcgttgt cggcaattca   1260 tctcttttag gtacgtcatt ggagctggaa acacaggaac cagaaatgga actaccagtt    1320
gaaccaagac caaatgagga atgtttgcaa atactagaga acgctgaaaa gggagccaag    1380
ttcctatctg atgccgagat tatccagctg gtcaatgcca agcacattcc tgcctacaag    1440
ttggaaaccc ttatggagac acatgagaga ggtgtgtcta ttaggagaca attactatct    1500
aaaaagttac ctgaaccaag ttccctacaa tacctgcctt atagagatta caattactcc    1560
ttggtaatgg gagcttgttg tgaaaatgtc attgggtaca tgccaattcc agtgggtgtc    1620
gccggtccac tatgtttgga cggtaaggaa tttcaagtac ctatggcaac gactgaaggc    1680
tgcttagttg catctacaaa cagaggttgt agagccattg gattaggtgg cggtgcttct    1740
tcaagagtct tggctgacgg tatgactaga ggtcctgttg tgagatttcc tagggcctgt    1800
gactctgcag aagttaaggc ttggttggaa actccagaag gtttcaccgt aatcaaagag    1860
gcctttgatt ccacatcaag ggtggccaga ttacaaaaac tacacatgtc tgtcgctggg    1920
agaaatctgt atatcagatt tcaatccaga tccggcgacg caatgggtat gaatatgatt    1980
tcaaaaggga cagaaaaggc tttgtcaaag ctgcaggagt atttcccaga gatgcaaatc    2040
ttggccgtat ctggcaacta ttgcacagac aaaaagcctg ccgccatcaa ctggattgaa    2100
ggaagaggca aatctgtggt ttgtgaagct gtaattccag ccaaagttgt tagagaagtg    2160
ttaaagacca caacagaagc tatgattgaa gtaaacataa acaaaaactt agtagggtct    2220
gccatggctg gttcaattgg aggatacaac gctcatgctg ccaatattgt aaccgctatc    2280
tacatcgcat gtgacaaga tgctgcccaa aatgtcggtt cctcaaattg catcacattg    2340
atggaagcat ctggccctac aaacgaggat ttgtatatca gttgcacaat gccatctata    2400 gaaatagggga ctgtgggagg aggaactaac ttacttccac agcaagcctg cttacaaatg    2460
ctgggtgtac aaggagcctg tagagataat ccaggggaga acgctagaca acttgccaga    2520
attgtttgtg ggacagttat ggctggtgaa cttagtctaa tggcagcttt ggctgctggg    2580
cacctggtga gatctcatat gattcataat agaagtaaga ttaaccttca agatttgcaa    2640
ggtacgtgta cgaaaaaggc tgcctaa                                        2667
```

<210> SEQ ID NO 98
<211> LENGTH: 1704
<212> TYPE: DNA
<213> ORGANISM: Artificial Sequence
<220> FEATURE:
<223> OTHER INFORMATION: Synthetic oligonucleotide

<400> SEQUENCE: 98

```
atggatttga aaggaaatt accacctaag cctccatctt caacaacaac aaaacagcca      60
agtcataggt cccattctcc tacgccaatt ccaaaggctt cagatgcatt gcctcttcca    120
ttgtacctga ccaatacgtt tttcttcact cttttctttt ccgtagcata ttacctgttg    180
cataggtgga gagacaagat tagatccgga acacctttac acgttgtgac actgactgaa    240
ctatccgcaa ttgtactgct gattgcttcc ttcatctatc ttttaggctt tttcggtatt    300
gattttgtgc aatctttcac atcaagagaa aatgagcaac taaacaacga tgatcacaac    360
gtcgtgtcaa caaacaatgt tttatctgat agaaggttag tttacgacta tggattcgat    420
gtgacaggag acaacgataa cgataatgat gacgatgtta ttgtgaaaag tgtcgtttct    480
```

```
ggggaagtta attcttatag tttggaggct tccctaggag attgttacag agccgcaaag      540
attagaaaga gagccgtcga gagaattgtc gggagagaag tattaggctt gggtttcgag      600
ggatttgatt atgaatctat cctggggcaa tgttgtgaaa tgcctatcgg gtacgtccaa      660
gtgccagtag gtgtcgctgg acctttattg ttaaatggtg gggaattcat ggttccaatg      720
gctacaactg aaggctgtct tgtagcttcc actaatagag gttgtaaagc catatgctta      780
tcaggtggtg ccactgccat attgctaaaa gatggtatga caagagcccc agtagtgaga      840
ttcgccacag ctgagagagc ttcacaacta agttttact tggaagatgg tgtcaatttc       900
gatacattgt ctgttgtctt taacaaaagt tcaagatttg ccagattgca aaacatccaa      960
tgctcaattg ccggtaaaaa cttgtacatt aggtttactt gctccacagg cgacgccatg     1020
ggtatgaaca tggtttcaaa aggagtacaa aatgtattag actttttaca aaatgatttt     1080
cctgatatgg acgtaattgg gatctcttgg aagttctgct ctgacaaaaa gccaacagct     1140
gtcaactgga ttgagggcag aggaaagtct gtcgttttcc aggccgtaat taccaaaaag     1200
gtggttagaa agtctgcact gaaccctcaa acttgcacat gtagaacttt gacctgttta     1260
agaccattat tggttctgct acttctggtt ttgctagtgg acttaatgca tatgcttcat     1320
atcgtgtctg ccgtgttcat cgctaccggt caagatccag ctcagaatat cgaatctagt     1380
cactgtatca ctatgatgga ggctgtcaac aatggtaagg atttgcacgt taatgttacg     1440
atgccatcta tagaagttgg cacggtggga ggtggcactc agctagcctc tcaatcagcc     1500
tgtttgaact tgcttggtgt aaagggtgcc tgtatagaat ccccaggatc aaacgcccag     1560
ttgttagcta gaatcgttgc tggttctgtt ctggcaggcg aattaagttt gatgtcagct     1620
ataagtgctg gcaactagt taaatctcat atgaaataca ataggtctag tagagatatg      1680
tcagcaatag cttctaaggt ctaa                                             1704

<210> SEQ ID NO 99
<211> LENGTH: 1308
<212> TYPE: DNA
<213> ORGANISM: Artificial Sequence
<220> FEATURE:
<223> OTHER INFORMATION: Synthetic oligonucleotide

<400> SEQUENCE: 99
atgtttagaa gagctatact gttaggatgc tctgctgcca agacaccatg gtctgagtgt       60
tctaacgctc aattagttga tgcagttaag tctagaaaga tctcattcta cggtcttgaa      120
caagccttgg aaccagatta tagaagggct atcgaagtaa ggagagaggt tgtctctgaa      180
atcgcctcac aacagccaga agcaaaaaag aagcaatccg cattgcacac aataccattt      240
gagaattatg attggaataa ggtcgttggc caaaactgtg aaaacattat tggatacgtc      300
ccaataccac tgggcgttgc tggccctatt ttgattgatg gtaaagagta cccaatacca      360
atggctacaa cagaaggcgc tttggtcgct agtactcata gaggtgctag agctattaca      420
agatccggag gttgtaagac attgttatta ggtgaaggta tgacaagagc accagtggtt      480
gaattgcctt cattagagga agctgggcgt tgcacaagt actgtaatga gaacttctta      540
tctttaaagg aagcatttga atcaactacc caatatggaa aacttaattc tttaaagtgc      600
gtactagctg gtagaaaagc ataccttaga ttcagagcca ctacaggcga tgctatgggc      660
atgaacatga taacaagggg tgtagacaaa gcactgtctg ttctacagca acatttccct      720
tcaatggaaa tcctagccct aagtggtaat tactgtaccg acaaaaagcc atctgctgta      780
```

-continued

| | |
|---|---|
| aattggattg atggcagagg taaatcagtg gttgcagaag ccactttatt ggctgatgtt | 840 |
| gtcgaagata ctctgaaatg tacagtcgat tctttggtat ccttgaatat cgacaaaaac | 900 |
| cttgttgggt cagctatggc tggttctgtt ggaggtttta acgcccaggc tgcaaacgct | 960 |
| gtggcagcca ttttcattgc aaccggtcaa gatcctgctc aagtggtaga aagttcaatg | 1020 |
| tgtatcacta caatgtccaa ggtaggtaac gatctattga tctctgtgac catgccttct | 1080 |
| atcgaggtcg gggtcgtggg aggagggact ggtcttgctg cccaaagagg atgcttagag | 1140 |
| ttaatagggt gcggaggccc atctaaggag tctcctggta ctaatgccca acttctaagt | 1200 |
| agagttgttg cagctggcgt tttatcagcc gaactttcct tgatgtccgg actggcagca | 1260 |
| ggtcatctat tgtcagcaca tatgagattg aacagaaaga gaaataa | 1308 |

<210> SEQ ID NO 100
<211> LENGTH: 1281
<212> TYPE: DNA
<213> ORGANISM: Artificial Sequence
<220> FEATURE:
<223> OTHER INFORMATION: Synthetic oligonucleotide

<400> SEQUENCE: 100

| | |
|---|---|
| atgcaatccc tggacaaaaa ctttagacac ttatcaagac aacagaagtt acaacagcta | 60 |
| gttgataaac aatggctatc agaggaacaa ttcaatattc tacttaacca cccacttatt | 120 |
| gatgaagagg tagcaaactc attgatagaa atgtcatcg cacagggcgc actgcctgtt | 180 |
| ggtttactac caaatatcat cgttgatgac aaagcatacg tcgtgcctat gatggtggaa | 240 |
| gagccatctg ttgttgccgc tgcttcatac ggcgctaaat tggtgaacca acaggtggt | 300 |
| ttcaaaaccg tgtcctcaga acgtatcatg ataggtcaaa tagtatttga tggagtcgat | 360 |
| gataccgaga aactgtctgc agatatcaag gctcttgaaa acaaatcca tcagattgca | 420 |
| gatgaggctt acccttctat taaggccaga ggtggaggct atcaaaggat cgccatcgat | 480 |
| acattcccag aacaacagtt gctttcattg aaggttttcg ttgatactaa ggatgctatg | 540 |
| ggcgctaata tgttaaacac aatcctagaa gcaatcacag cctttttgaa aaacgaattc | 600 |
| ccacaatctg atatcttgat gtctatcctt tccaaccacg caacagccag tgttgtcaag | 660 |
| gtccagggtg aaatagacgt taaggatttg gcaagaggag aacgtactgg agaagaggtc | 720 |
| gctaagagaa tggaaagagc atctgtgtta gctcaagtgg acattcatag agcagcaaca | 780 |
| cacaataagg gtgttatgaa tggcattcat gctgtagtct ggctacagg taatgatact | 840 |
| agaggtgcag aagcctctgc tcacgcttac gcttccaaag acggtcaata tagagggata | 900 |
| gctacatgga gatacgatca agagagacaa aggttaatag gaactataga agttccaatg | 960 |
| actctggcca ttgttggtgg cggtaccaag gtactgccta ttgctaaggc ctctttagaa | 1020 |
| ctgttaaacg tagaaagtgc ccaagagttg ggacatgttg tcgctgccgt tggactagct | 1080 |
| caaaacttcg ctgcatgtag agctttggtt tccgaaggta ttcaacaagg catatgtct | 1140 |
| ttgcaataca agtctttagc catcgtagtc ggggctaagg gcgatgaaat tgctcaggta | 1200 |
| gccgaagcac taaagcaaga gccaagagca acactcaag ttgcagagag aattttgcaa | 1260 |
| gatttgagaa gtcaacaata a | 1281 |

<210> SEQ ID NO 101
<211> LENGTH: 1311
<212> TYPE: DNA
<213> ORGANISM: Artificial Sequence
<220> FEATURE:
<223> OTHER INFORMATION: Synthetic oligonucleotide

<400> SEQUENCE: 101

```
atgcaggtct taagattgga taggagacat tacaaaagtg gcaagattag aagagcaatg        60
agttctagaa ttcctggttt ctacaaattg tcagtcgagg aaagactgaa aaaggttgct       120
gaatttgcag ggttatctga tgaggaagtg aaagctgttt tgtcacaagg tttacctttg       180
gacgtagctg atagaatgat cgaaaatgtg atcggtacat ttgaattacc acttggtata       240
gcaaccaatt tccttattga tggcaaggat tatctaatcc ctatggctat agaggaacca       300
tcagtagttg cagctgcttc taacgcagct agaatggcca gagagtctgg cgggtttaca       360
actgattaca cagggtccct gatgattggt caaattcaag tcacaaaact gttgaatcca       420
aatgcagcta agttcgaagt tctacgtcaa aaagacgaaa tcatagaaag agcaaatgag       480
tgtgatccaa tgttggtgaa tttgggcggt ggatgtaaag atatagaagc aagggtgatc       540
gatacaatca tgggtaagat gctaattgtt catctgatcg ttgatgttaa agacgctatg       600
ggtgcaaatg ctgtcaacac tatgtgtgaa aaagttgctc cttttcatcga acgtattact       660
gggggaaagg tctatcttag aatcatttcc aacttggctg catatagact tgctagagca       720
aaggccgttt ttgacaaaga cgttattggc ggagaggagg ttgtagaagg gatcatgctt       780
gcatacgcct tcgctgccgc tgacccattt cgttgcgcca cccacaataa gggtatcatg       840
aatggcatat cagccttaat gatcgctaca ggaaacgact ttagagccat tgaagcagga       900
gctcattcct atgctgcaat aggtggatac aaaccactaa ctacctacga agttgataga       960
aaaggtaatc tagtaggcac aattgaaata cctatggcag taggcgtgat tggtggtgca      1020
accaaagtca acccactagc caagatctct cttaagatac taggagtgaa cactgctgaa      1080
gagttagcca gagtcgcagc cgctctaggt ttggctcaaa actttgctgc cttaagagcc      1140
ttggccacag aaggtatcca aagaggtcac atggaattac atgccaggaa cttagcaatc      1200
atggctggag ctactggaga tgaggttgac agagttgtag agattatggt gagagatggc      1260
aaaatcagat tggactacgc taaggaagta ttggagagac tgcgttccta a              1311
```

<210> SEQ ID NO 102
<211> LENGTH: 1287
<212> TYPE: DNA
<213> ORGANISM: Artificial Sequence
<220> FEATURE:
<223> OTHER INFORMATION: Synthetic oligonucleotide

<400> SEQUENCE: 102

```
atgtccttag attcaagact gccagctttc agaaatctgt ctccagctgc aagactagat        60
cacattggcc aacttttggg actaagtcat gacgacgttt ccctttttagc aaacgccggt       120
gcttaccaa tggatatcgc taatggtatg attgaaaatg taatcgggac ctttgaactg       180
ccatatgcag tggccagtaa ctttcagatc aatggccgtg acgtcttagt accattagtt       240
gtggaggaac ctagtatcgt tgctgcagcc tcttacatgg caaagttagc tagagccaat       300
ggtgggttca ctacatcttc atctgctcca ctaatgcatg cacaagtaca aattgtcggc       360
attcaggatc cactaaacgc aagattgtct ttactgcgta gaaaggatga gatcatagaa       420
ttagccaata ggaaggacca acttctgaat tcattgggcg gtggttgcag agacatagag       480
gtgcatacat ttgccgatac tccaagagga ccaatgcttg tagcacacct tattgtcgat       540
gtgcgtgatg ccatgggagc taatactgtt aacactatgg ctgaagcagt agcacctctg       600
atggaagcca taacaggtgg ccaggtaaga ttgagaatcc tttccaattt ggctgatctt       660
```

| | |
|---|---|
| agattggcca gagcccaagt gagaatcact cctcagcaat tggaaactgc cgaattctca | 720 |
| ggtgaggcag taattgaggg tatcttggac gcatatgctt ttgccgctgt ggacccttac | 780 |
| agagccgcta cccacaacaa aggcataatg aacggtatcg atcctttgat cgtcgctaca | 840 |
| ggaaatgatt ggagagctgt tgaggcagga gctcatgcat acgcttgtag atccggacat | 900 |
| tacggttcat taacaacatg ggaaaaagat aacaatggac acttggtcgg acattggaa | 960 |
| atgcctatgc cagttggttt agttgggggt gctacaaaaa cccatcctct tgctcaattg | 1020 |
| tctttgagga tacttggtgt caaaactgct caagcactag ccgaaattgc cgttgctgtt | 1080 |
| ggtttggcac aaaacttggg tgcaatgcgt gctttagcta cagaaggcat ccaaagagga | 1140 |
| catatggctc tacacgctag aaacattgca gttgttgcag gagccagagg tgatgaggtt | 1200 |
| gattgggtgg ctagacaact tgtcgaatat catgatgtca gagcagacag ggctgtggca | 1260 |
| ttactgaaac agaagagagg tcaataa | 1287 |

<210> SEQ ID NO 103
<211> LENGTH: 2355
<212> TYPE: DNA
<213> ORGANISM: Artificial Sequence
<220> FEATURE:
<223> OTHER INFORMATION: Synthetic oligonucleotide

<400> SEQUENCE: 103

| | |
|---|---|
| atgaatttga gtttgtgtat agcatctcca ctattgacca aatctaatag accagctgct | 60 |
| ttatcagcaa ttcatacagc tagtacatcc catggtggcc aaaccaaccc tacgaatctg | 120 |
| ataatcgata cgaccaagga gagaatacaa aaacaattca aaatgttga atttcagtt | 180 |
| tcttcttatg atactgcgtg ggttgccatg gttccatcac ctaattctcc aaagtctcca | 240 |
| tgtttcccag aatgtttgaa ttggctgatt aacaaccagt tgaatgatgg atcttggggt | 300 |
| ttagtcaatc acacgcacaa tcacaaccat ccacttttga agattctttt atcctcaact | 360 |
| ttggcttgca tcgtggccct aaagagatgg aacgtaggtg aggatcagat taacaagggg | 420 |
| cttagtttca ttgaatctaa cttggcttcc gcgactgaaa atctcaacc atctccaata | 480 |
| ggattcgata tcatctttcc aggtctgtta gagtacgcca aaaatctaga tatcaactta | 540 |
| ctgtctaagc aaactgattt ctcactaatg ttacacaaga gagaattaga acaaaagaga | 600 |
| tgtcattcaa acgaaatgga tggttaccta gcttatatct ctgaaggtct tggtaatctt | 660 |
| tacgattgga atatggtgaa aaagtaccag atgaaaaatg gctcagtttt caattcccct | 720 |
| tctgcaactg cggcagcatt cattaaccat caaaatccag gatgcctgaa ctatttgaat | 780 |
| tcactactag acaaattcgg caacgcagtt ccaactgtat accctcacga tttgtttatc | 840 |
| agattgagta tggtggatac aattgaagga cttggtatat cccaccactt tagagtcgag | 900 |
| atcaaaaatg ttttggatga gacataccgt tgttgggtgg agagagatga acaaatcttt | 960 |
| atggatgttg tgacgtgcgc gttggccttt agattgttgc gtattaacgg ttacgaagtt | 1020 |
| agtccagatc cacttgccga aattacaaac gaattagctt taaaggatga atcgccgct | 1080 |
| cttgaaacat atcatgcgtc acatatcctt taccaagagg acttatcatc tggaaaacaa | 1140 |
| attcttaaat ctgctgattt cctgaaggaa atcatatcca ctgatagtaa tagactgtcc | 1200 |
| aaactgatcc ataaagaggt tgaaaatgca cttaagttcc ctattaacac cggcttagaa | 1260 |
| cgtattaaca aagacgtaa catccagctt tacaacgtag acaatactag aatcttgaaa | 1320 |
| accacttacc attcttccaa catatcaaac actgattacc taagattagc tgttgaagat | 1380 |
| ttctacacat gtcagtctat ctatagagaa gagctgaaag gattagagag atgggtcgtt | 1440 |

-continued

```
gagaataagc tagatcaatt gaaatttgcc agacaaaaga cagcttattg ttacttctca    1500
gttgccgcca ctttatcaag tccagaattg tcagatgcac gtatttcttg ggctaaaaac    1560
ggaattttga caactgttgt tgatgatttc tttgatattg gcgggacaat cgacgaattg    1620
acaaacctga ttcaatgcgt tgaaaagtgg aatgtcgatg tcgataaaga ctgttgctca    1680
gaacatgtta gaatactgtt cttggctctg aaagatgcta tctgttggat cggggatgag    1740
gctttcaaat ggcaagctag agatgtgacg tctcacgtca ttcaaacctg ctagaactg     1800 atgaactcta tgttgagaga agcaatttgg actagagatg catacgttcc tacattaaac    1860
gagtatatgg aaaacgctta tgtctccttt gctttgggtc ctatcgttaa gcctgccata    1920
tactttgtag gaccaaagct atccgaggaa atcgtcgaat catcagaata ccataacttg    1980
ttcaagttaa tgtccacaca aggcagatta cttaatgata ttcattcttt caaaagagag    2040
tttaaggaag gaaagttaaa tgctgttgct ctgcatcttt ctaatggcga agtggtaaa     2100 gtcgaagagg aagtagttga ggaaatgatg atgatgatca aaaacaagag aaaggagttg    2160
atgaaactaa tcttcgaaga gaacggttca attgttccta gagcatgtaa ggatgcattt    2220
tggaacatgt gtcatgtgct aaactttttc tacgcaaacg acgatggttt tactgggaac    2280
acaatactag atacagtaaa agcatcata  tacaacccct tggtcttagt aaacgaaaac    2340
gaggagcaaa gataa                                                    2355
```

<210> SEQ ID NO 104
<211> LENGTH: 2355
<212> TYPE: DNA
<213> ORGANISM: Artificial Sequence
<220> FEATURE:
<223> OTHER INFORMATION: Synthetic oligonucleotide

<400> SEQUENCE: 104

```
atgaatctgt ccctttgtat agctagtcca ctgttgacaa atcttctag  accaactgct      60 cttctgcaa  ttcatactgc cagtactagt catggaggtc aaacaaaccc aacaaatttg     120
ataatcgata ctactaagga gagaatccaa aagctattca aaaatgttga atctcagta      180 tcatcttatg acaccgcatg ggttgcaatg gtgccatcac ctaattcccc aaaaagtcca     240
tgttttccag agtgcttgaa ttggttaatc aataatcagt taaacgatgg ttcttggggt     300
ttagtcaacc acactcataa ccacaatcat ccattattga aggactcttt atcatcaaca     360
ttagcctgta ttgttgcatt gaaaagatgg aatgtaggtg aagatcaaat caacaagggt     420
ttatcattca tagaatccaa tctagcttct gctaccgaca atcacaacc  atctccaatc     480 gggttcgaca taatcttccc tggtttgctg gagtatgcca aaaaccttga tatcaactta     540
ctgtctaaac aaacagattt ctctttgatg ctacacaaaa gagagttaga gcagaaaaga    600
tgccattcta acgaaattga cgggtactta gcatatatct cagaaggttt gggtaatttg    660
tatgactgga acatggtcaa aaagtatcag atgaaaaatg gatccgtatt caattctcct    720
tctgcaactg ccgcagcatt cattaatcat caaaaccctg ggtgtcttaa ctacttgaac    780
tcactattag ataagtttgg aaatgcagtt ccaacagtct atcctttgga cttgtacatc    840
agattatcta tggttgacac tatagagaga ttaggtattc tcatcatttt cagagttgag    900
atcaaaaatg ttttggacga gacatacaga tgttgggtcg aaagagatga gcaaatcttt    960
atggatgtcg tgacctgcgc tctggcttttt agattgctaa ggatacacgg atacaaagta   1020
tctcctgatc aactggctga gattacaaac gaactggctt tcaaagacga atacgccgca   1080
```

| | |
|---|---|
| ttagaaacat accatgcatc ccaaatactt taccaggaag acctaagttc aggaaaacaa | 1140 |
| atcttgaagt ctgcagattt cctgaaaggc attctgtcta cagatagtaa taggttgtct | 1200 |
| aaattgatac acaaggaagt agaaaacgca ctaaagtttc ctattaacac tggtttagag | 1260 |
| agaatcaata ctaggagaaa cattcagctg tacaacgtag ataatacaag gattcttaag | 1320 |
| accacctacc atagttcaaa catttccaac acctattact taagattagc tgtcgaagac | 1380 |
| ttttacactt gtcaatcaat ctacagagag gagttaaagg gcctagaaag atgggtagtt | 1440 |
| caaaacaagt tggatcaact gaagtttgct agacagaaga cagcatactg ttatttctct | 1500 |
| gttgctgcta cccttcatc cccagaattg tctgatgcca gaataagttg ggccaaaaat | 1560 |
| ggtattctta caactgtagt cgatgatttc tttgatattg gaggtactat tgatgaactg | 1620 |
| acaaatctta ttcaatgtgt tgaaaagtgg aacgtggatg tagataagga ttgctgcagt | 1680 |
| gaacatgtga gaatactttt cctggctcta aaagatgcaa tatgttggat tggcgacgag | 1740 |
| gccttcaagt ggcaagctag agatgttaca tctcatgtca tccaaacttg gcttgaactg | 1800 |
| atgaactcaa tgctaagaga agcaatctgg acaagagatg catacgttcc aacattgaac | 1860 |
| gaatacatgg aaaacgctta cgtctcattt gccttgggtc ctattgttaa gccagccata | 1920 |
| tactttgttg ggccaaagtt atccgaagag attgttgagt cttccgaata tcataaccta | 1980 |
| ttcaagttaa tgtcaacaca aggcagactt ctgaacgata tccactcctt caaaagagaa | 2040 |
| ttcaaggaag gtaagctaaa cgctgttgct ttgcacttgt ctaatggtga atctggcaaa | 2100 |
| gtggaagagg aagtcgttga ggaaatgatg atgatgatca aaaacaagag aaaggaattg | 2160 |
| atgaaattga ttttcgagga aaatggttca atcgtaccta gagcttgtaa agatgctttt | 2220 |
| tggaatatgt gccatgttct taacttcttt tacgctaatg atgatggctt cactggaaat | 2280 |
| acaatattgg atacagttaa agatatcatc tacaacccac ttgttttggt caatgagaac | 2340 |
| gaggaacaaa gataa | 2355 |

<210> SEQ ID NO 105
<211> LENGTH: 1773
<212> TYPE: DNA
<213> ORGANISM: Artificial Sequence
<220> FEATURE:
<223> OTHER INFORMATION: Synthetic oligonucleotide

<400> SEQUENCE: 105

| | |
|---|---|
| atggctatgc cagtgaagct aacacctgcg tcattatcct taaaagctgt gtgctgcaga | 60 |
| ttctcatccg gtggccatgc tttgagattc gggagtagtc tgccatgttg gagaaggacc | 120 |
| cctacccaaa gatctacttc ttcctctact actagaccag ctgccgaagt gtcatcaggt | 180 |
| aagagtaaac aacatgatca ggaagctagt gaagcgacta tcagacaaca attcaacttt | 240 |
| gtggatgtcc tggagaatat gggaatatcc agacattttg ctgcagagat aaagtgcata | 300 |
| ctagacagaa cttacagatc ttggttacaa agacacgagg aaatcatgct ggacactatg | 360 |
| acatgtgcta tggcttttag aatcctaaga ttgaacggat acaacgtttc atcagatgaa | 420 |
| ctataccacg ttgtagaggc atctggtctg cataattctt gggtgggta tcttaacgat | 480 |
| accagaacac tacttgaatt acacaaggct tcaacagtta gtatctctga ggatgaatct | 540 |
| atcttagatt caattggctc tagatccaga acattgctta gagaacaatt ggagtctggt | 600 |
| ggcgcactga gaaagccttc tttattcaaa gaggttgaac atgcactgga tggacctttt | 660 |
| tacaccacac ttgatagact tcatcatagg tggaatattg aaaacttcaa cattattgag | 720 |
| caacacatgt ggagactcc atacttatct aaccagcata catcaaggga tatcctagca | 780 |

```
ttgtcaatta gagattttc ctcctcacaa ttcacttatc aacaagagct acagcatctg    840
gagagttggg ttaaggaatg tagattagat caactacagt tcgcaagaca gaaattagcg    900
tacttttacc tatcagccgc aggcaccatg ttttctcctg agctttctga tgcgagaaca    960
ttatgggcca aaaacggggt gttgacaact attgttgatg atttctttga tgttgccggt   1020
tctaaagagg aattggaaaa cttagtcatg ctggtcgaaa tgtgggatga acatcacaaa   1080
gttgaattct attctgagca ggtcgaaatc atcttctctt ccatctacga ttctgtcaac   1140
caattgggtg agaaggcctc tttggttcaa gacagatcaa ttacaaaaca ccttgttgaa   1200
atatggttag acttgttaaa gtccatgatg acggaagttg aatggagact gtcaaaatac   1260
gtgcctacag aaaaggaata catgattaat gcctctctta tcttcggcct aggtccaatc   1320
gttttaccag ctttgtattt cgttggtcca aagatttcag aaagtatagt aaaggaccca   1380
gaatatgatg aattgttcaa actaatgtca acatgtggta gattgttgaa tgacgtgcaa   1440
acgttcgaaa gagaatacaa tgagggtaaa ctgaattctg tcagtctatt ggttcttcac   1500
ggaggcccaa tgtctatttc agacgcaaag aggaaattac aaaagcctat tgatacgtgt   1560
agaagagatc ttcttttcttt ggtccttaga gaagagtctg tagtaccaag accatgtaag   1620
gaactattct ggaaaatgtg taaagtgtgc tatttctttt actcaacaac tgatgggttt   1680
tctagtcaag tcgaaagagc aaaagaggta gacgctgtca taaatgagcc actgaagttg   1740
caaggttctc atacactggt atctgatgtt taa                                 1773

<210> SEQ ID NO 106
<211> LENGTH: 2232
<212> TYPE: DNA
<213> ORGANISM: Artificial Sequence
<220> FEATURE:
<223> OTHER INFORMATION: Synthetic oligonucleotide

<400> SEQUENCE: 106
atgcagaact tccatggtac aaaggaaagg atcaaaaaga tgtttgacaa gattgaattg     60 tccgttttctt cttatgatac agcctgggtt gcaatggtcc catcccctga ttgcccagaa    120
acaccttgtt ttccagaatg tactaaatgg atcctagaaa atcagttggg tgatggtagt    180
tggtcacttc ctcatggcaa tccacttcta gttaaagatg cattatcttc cactcttgct    240
tgtattctgg ctcttaaaag atggggaatc ggtgaggaac agattaacaa aggactgaga    300
ttcatagaac tcaactctgc tagtgtaacc gataacgaac aacacaaacc aattggatttt    360 gacattatct ttccaggtat gattgaatac gctatagact tagacctgaa tctaccacta    420
aaaccaactg acattaactc catgttgcat cgtagagccc ttgaattgac atcaggtgga    480
ggcaaaaatc tagaaggtag aagagcttac ttggcctacg tctctgaagg aatcggtaag    540
ctgcaagatt gggaaatggc tatgaaatac caacgtaaaa acggatctct gttcaatagt    600
ccatcaacaa ctgcagctgc attcatccat atacaagatg ctgaatgcct ccactatatt    660
cgttctcttc tccagaaatt tggaaacgca gtccctacaa tataccctct cgatatctat    720
gccagacttt caatggtaga tgccctggaa cgtcttggta ttgatagaca tttcagaaag    780
gagagaaagt tcgttctgga tgaaacatac agatttggt tgcaaggaga agaggagatt    840
ttctccgata acgcaacctg tgctttggcc ttcagaatat tgagacttaa tggttacgat    900
gtctctcttg aagatcactt ctctaactct ctgggcggtt acttaaagga ctcaggagca    960
gctttagaac tgtacagagc cctccaattg tcttacccag acgagtccct cctggaaaag   1020
```

| | |
|---|---|
| caaaattcta gaacttctta cttcttaaaa caaggtttat ccaatgtctc cctctgtggt | 1080 |
| gacagattgc gtaaaaacat aattggagag gtgcatgatg ctttaaactt ttccgaccac | 1140 |
| gctaacttac aaagattagc tattcgtaga aggattaagc attacgctac tgacgataca | 1200 |
| aggattctaa aaacttccta cagatgctca acaatcggta accaagattt tctaaaactt | 1260 |
| gcagtggaag atttcaatat ctgtcaatca atacaaagag aggaattcaa gcatattgaa | 1320 |
| agatgggtcg ttgaaagacg tctagacaag ttaaagttcg ctagacaaaa agaggcctat | 1380 |
| tgctatttct cagccgcagc aacattgttt gcccctgaat tgtctgatgc tagaatgtct | 1440 |
| tgggccaaaa atggtgtatt gacaactgtg gttgatgatt cttcgatgt cggaggctct | 1500 |
| gaagaggaat tagttaactt gatagaattg atcgagcgtt gggatgtgaa tggcagtgca | 1560 |
| gattttgta gtgaggaagt tgagattatc tattctgcta tccactcaac tatctctgaa | 1620 |
| ataggtgata agtcatttgg ctggcaaggt agagatgtaa agtctcaagt tatcaagatc | 1680 |
| tggctggact tattgaaatc aatgttaact gaagctcaat ggtcttcaaa caagtctgtt | 1740 |
| cctaccctag atgagtatat gacaaccgcc catgtttcat tcgcacttgg tccaattgta | 1800 |
| cttccagcct tatacttcgt tggcccaaag ttgtcagaag aggttgcagg tcatcctgaa | 1860 |
| ctactaaacc tctacaaagt cacatctact tgtggcagac tactgaatga ttggagaagt | 1920 |
| tttaagagag aatccgagga aggtaagctc aacgctatta gtttatacat gatccactcc | 1980 |
| ggtggtgctt ctacagaaga ggaaacaatc gaacatttca aaggtttgat tgattctcag | 2040 |
| agaaggcaac tgttacaatt ggtgttgcaa gagaaggata gtatcatacc tagaccatgt | 2100 |
| aaagatctat tttggaatat gattaagtta ttacacactt tctacatgaa agatgatggc | 2160 |
| ttcacctcaa atgagatgag gaatgtagtt aaggcaatca ttaacgaacc aatctcactg | 2220 |
| gatgaattat ga | 2232 |

<210> SEQ ID NO 107
<211> LENGTH: 1542
<212> TYPE: DNA
<213> ORGANISM: Artificial Sequence
<220> FEATURE:
<223> OTHER INFORMATION: Synthetic oligonucleotide

<400> SEQUENCE: 107

| | |
|---|---|
| atggatgctg tgacgggttt gttaactgtc ccagcaaccg ctataactat tggtggaact | 60 |
| gctgtagcat tggcggtagc gctaatcttt tggtacctga atcctacac atcagctaga | 120 |
| agatcccaat caaatcatct tccaagagtg cctgaagtcc caggtgttcc attgttagga | 180 |
| aatctgttac aattgaagga gaaaaagcca tacatgactt ttacgagatg ggcagcgaca | 240 |
| tatggaccta tctatagtat caaaactggg gctacaagta tggttgtggt atcatctaat | 300 |
| gagatagcca aggaggcatt ggtgaccaga ttccaatcca tatctacaag gaacttatct | 360 |
| aaagccctga agtacttac agcagataag acaatggtcg caatgtcaga ttatgatgat | 420 |
| tatcataaaa cagttaagag acacatactg accgccgtct gggtcctaa tgcacagaaa | 480 |
| aagcatagaa ttcacagaga tatcatgatg gataacatat ctactcaact tcatgaattc | 540 |
| gtgaaaaaca acccagaaca ggaagaggta gaccttagaa aaatctttca atctgagtta | 600 |
| ttcggcttag ctatgagaca agccttagga aaggatgttg aaagtttgta cgttgaagac | 660 |
| ctgaaaatca ctatgaatag agacgaaatc tttcaagtcc ttgttgttga tccaatgatg | 720 |
| ggagcaatcg atgttgattg gagagacttc tttccatacc taaagtgggt cccaaacaaa | 780 |
| aagttcgaaa atactattca acaaatgtac atcagaagag aagctgttat gaaatcttta | 840 |

| | |
|---|---|
| atcaaagagc acaaaaagag aatagcgtca ggcgaaaagc taaatagtta tatcgattac | 900 |
| cttttatctg aagctcaaac tttaaccgat cagcaactat tgatgtcctt gtgggaacca | 960 |
| atcattgaat cttcagatac aacaatggtc acaacagaat gggcaatgta cgaattagct | 1020 |
| aaaaaccta aattgcaaga taggttgtac agagacatta agtccgtctg tggatctgaa | 1080 |
| aagataaccg aagagcatct atcacagctg ccttacatta cagctatttt ccacgaaaca | 1140 |
| ctgagaagac actcaccagt tcctatcatt cctctaagac atgtacatga agataccgtt | 1200 |
| ctaggcggct accatgttcc tgctggcaca gaacttgccg ttaacatcta cggttgcaac | 1260 |
| atggacaaaa acgtttggga aaatccagag gaatggaacc cagaaagatt catgaaagag | 1320 |
| aatgagacaa ttgattttca aaagacgatg gccttcggtg gtggtaagag agtttgtgct | 1380 |
| ggttccttgc aagccctttt aactgcatct attgggattg ggagaatggt tcaagagttc | 1440 |
| gaatggaaac tgaaggatat gactcaagag gaagtgaaca cgataggcct aactacacaa | 1500 |
| atgttaagac cattgagagc tattatcaaa cctaggatct aa | 1542 |

<210> SEQ ID NO 108
<211> LENGTH: 1530
<212> TYPE: DNA
<213> ORGANISM: Artificial Sequence
<220> FEATURE:
<223> OTHER INFORMATION: Synthetic oligonucleotide

<400> SEQUENCE: 108

| | |
|---|---|
| atggcatttt tctctatgat ttcaattttg ttgggatttg ttatttcttc tttcatcttc | 60 |
| atctttttct tcaaaaagtt acttagtttt agtaggaaaa acatgtcaga agtttctact | 120 |
| ttgccaagtg ttccagtagt gcctggtttt ccagttattg ggaatttgtt gcaactaaag | 180 |
| gagaaaaagc ctcataaaac tttcactaga tggtcagaga tatatggacc tatctactct | 240 |
| ataaagatgg ttcttcatc tcttattgta ttgaacagta cagaaactgc taaggaagca | 300 |
| atggtcacta gattttcatc aatatctacc agaaaattgt caaacgccct aacagttcta | 360 |
| acctgcgata gtctatggt cgccacttct gattatgatg acttccacaa attagttaag | 420 |
| agatgtttgc taaatggact tcttggtgct aatgctcaaa agagaaaaag acactacaga | 480 |
| gatgctttga ttgaaaatgt gagttccaag ctacatgcac acgctagaga tcatccacaa | 540 |
| gagccagtta actttagagc aattttcgaa cacgaattgt ttggtgtagc attaaagcaa | 600 |
| gccttcggta agacgtaga atccatatac gtcaaggagt taggcgtaac attatcaaaa | 660 |
| gatgaaatct ttaaggtgct tgtacatgat atgatggagg gtgcaattga tgtagattgg | 720 |
| agagatttct tcccatattt gaaatggatc cctaataagt cttttgaagc taggatacaa | 780 |
| caaaagcaca agagaagact agctgttatg aacgcactta tacaggacag attgaagcaa | 840 |
| aatgggtctg aatcagatga tgattgttac cttaacttct taatgtctga ggctaaaaca | 900 |
| ttgactaagg aacagatcgc aatccttgtc tgggaaacaa tcattgaaac agcagatact | 960 |
| accttagtca caactgaatg gccatatac gagctagcca acatccatc tgtgcaagat | 1020 |
| aggttgtgta aggagatcca gaacgtgtgt ggtggagaga aattcaagga agagcagttg | 1080 |
| tcacaagttc cttaccttaa cggcgttttc catgaaacct tgagaaaata ctcacctgca | 1140 |
| ccattagttc ctattagata cgcccacgaa gatacacaaa tcggtggcta ccatgttcca | 1200 |
| gctgggtccg aaattgctat aaacatctac gggtgcaaca tggacaaaaa gagatgggaa | 1260 |
| agaccagaag attggtggcc agaaagattc ttagatgatg gcaaatatga acatctgat | 1320 |

| | |
|---|---|
| ttgcataaaa caatggcttt cggagctggc aaaagagtgt gtgccggtgc tctacaagcc | 1380 |
| tccctaatgg ctggtatcgc tattggtaga ttggtccaag agttcgaatg gaaacttaga | 1440 |
| gatggtgaag aggaaaatgt cgatacttat gggttaacat ctcaaaagtt atacccacta | 1500 |
| atggcaatca tcaatcctag aagatcctaa | 1530 |

<210> SEQ ID NO 109
<211> LENGTH: 1578
<212> TYPE: DNA
<213> ORGANISM: Artificial Sequence
<220> FEATURE:
<223> OTHER INFORMATION: Synthetic oligonucleotide

<400> SEQUENCE: 109

| | |
|---|---|
| atgagtaagt ctaatagtat gaattctaca tcacacgaaa ccctttttca acaattggtc | 60 |
| ttgggtttgg accgtatgcc attgatggat gttcactggt tgatctacgt tgctttcggc | 120 |
| gcatggttat gttcttatgt gatacatgtt ttatcatctt cctctacagt aaaagtgcca | 180 |
| gttgttggat acaggtctgt attcgaacct acatggttgc ttagacttag attcgtctgg | 240 |
| gaaggtggct ctatcatagg tcaagggtac aataagttta aagactctat tttccaagtt | 300 |
| aggaaattgg gaactgatat tgtcattata ccacctaact atattgatga agtgagaaaa | 360 |
| ttgtcacagg acaagactag atcagttgaa cctttcatta atgattttgc aggtcaatac | 420 |
| acaagaggca tggttttctt gcaatctgac ttacaaaacc gtgttataca acaagacta | 480 |
| actccaaaat tggtttcctt gaccaaggtc atgaaggaag agttggatta tgctttaaca | 540 |
| aaagagatgc ctgatatgaa aaatgacgaa tgggtagaag tagatatcag tagtataatg | 600 |
| gtgagattga tttccaggat ctccgccaga gtctttctag ggcctgaaca ctgtcgtaac | 660 |
| caggaatggt tgactactac agcagaatat tcagaatcac ttttcattac agggtttatc | 720 |
| ttaagagttg tacctcatat cttaagacca ttcatcgccc tctattacc ttcatacagg | 780 |
| actctactta gaaacgtttc aagtggtaga agagtcatcg gtgacatcat aagatctcag | 840 |
| caaggggatg gtaacgaaga tatactttcc tggatgagag atgctgccac aggagaggaa | 900 |
| aagcaaatcg ataacattgc tcagagaatg ttaattcttt ctttagcatc aatccacact | 960 |
| actgcgatga ccatgacaca tgccatgtac gatctatgtg cttgccctga gtacattgaa | 1020 |
| ccattaagag atgaagttaa atctgttgtt ggggcttctg gctgggacaa gacagcgtta | 1080 |
| aacagatttc ataagttgga ctccttccta aaagagtcac aaagattcaa cccagtattc | 1140 |
| ttattgacat tcaatagaat ctaccatcaa tctatgacct tatcagatgg cactaacatt | 1200 |
| ccatctggaa cacgtattgc tgttccatca cacgcaatgt tgcaagattc tgcacatgtc | 1260 |
| ccaggtccaa ccccacctac tgaatttgat ggattcagat atagtaagat acgttctgat | 1320 |
| agtaactacg cacaaaagta cctattctcc atgaccgatt cttcaaacat ggctttcgga | 1380 |
| tacggcaagt atgcttgtcc aggtagattt tacgcgtcta atgagatgaa actaacatta | 1440 |
| gccattttgt tgctacaatt tgagttcaaa ctaccagatg gtaaaggtcg tcctagaaat | 1500 |
| atcactatcg attctgatat gattccagac ccaagagcta gactttgcgt cagaaaaaga | 1560 |
| tcacttagag atgaatga | 1578 |

<210> SEQ ID NO 110
<211> LENGTH: 1500
<212> TYPE: DNA
<213> ORGANISM: Artificial Sequence
<220> FEATURE:
<223> OTHER INFORMATION: Synthetic oligonucleotide

<400> SEQUENCE: 110

```
atggaagatc ctactgtctt atatgcttgt cttgccattg cagttgcaac tttcgttgtt      60
agatggtaca gagatccatt gagatccatc ccaacagttg gtggttccga tttgcctatt     120
ctatcttaca tcggcgcact aagatggaca agacgtggca gagagatact tcaagaggga     180
tatgatggct acagaggatc tacattcaaa tcgcgatgt tagaccgttg gatcgtgatc      240
gcaaatggtc ctaaactagc tgatgaagtc agacgtagac cagatgaaga gttaaacttt     300
atggacggat taggagcatt cgtccaaact aagtacacct taggtgaagc tattcataac     360
gatccatacc atgtcgatat cataagagaa aaactaacaa gaggccttcc agccgtgctt     420
cctgatgtca ttgaagagtt gacacttgcg gttagacagt acattccaac agaaggtgat     480
gaatgggtgt ccgtaaactg ttcaaaggcc gcaagagata ttgttgctag agcttctaat     540
agagtctttg taggtttgcc tgcttgcaga aaccaaggtt acttagattt ggcaatagac     600
tttacattgt ctgttgtcaa ggatagagcc atcatcaata tgtttccaga attgttgaag     660
ccaatagttg gcagagttgt aggtaacgcc accagaaatg ttcgtagagc tgttcctttt     720
gttgctccat ggtggagga agacgtaga cttatggaag agtacggtga agactggtct        780
gaaaaaccta atgatatgtt acagtggata atggatgaag ctgcatccag agatagttca     840
gtgaaggcaa tcgcagagag attgttaatg gtgaacttcg cggctattca tacctcatca     900
aacactatca ctcatgcttt gtaccacctt gccgaaatgc ctgaaacttt gcaaccactt     960
agagaagaga tcgaaccatt agtcaaagag gagggctgga ccaaggctgc tatgggaaaa    1020
atgtggtggt tagattcatt tctaagagaa tctcaaagat acaatggcat taacatcgta    1080
tctttaacta gaatggctga caaagatatt acattgagtg atggcacatt tttgccaaaa    1140
ggtactctag tggccgttcc agcgtattct actcatagag atgatgctgt ctacgctgat    1200
gccttagtat tcgatccttt cagattctca cgtatgagag cgagagaagg tgaaggtaca    1260
aagcaccagt tcgttaatac ttcagtcgag tacgttccat ttggtcacgg aaagcatgct    1320
tgtccaggaa gattcttcgc cgcaaacgaa ttgaaagcaa tgttggctta cattgttcta    1380
aactatgatg taaagttgcc tggtgacggt aaacgtccat tgaacatgta ttggggtcca    1440
acagttttgc ctgcaccagc aggccaagta ttgttcagaa agagacaagt tagtctataa    1500
```

<210> SEQ ID NO 111
<211> LENGTH: 1578
<212> TYPE: DNA
<213> ORGANISM: Artificial Sequence
<220> FEATURE:
<223> OTHER INFORMATION: Synthetic oligonucleotide

<400> SEQUENCE: 111

```
atgggtttgt tcccattaga ggattcctac gcgctggtct ttgaaggact agcaataaca      60
ctggctttgt actatctact gtctttcatc tacaaaacat ctaaaaagac atgtacacct     120
cctaaagcat ctggtgaaat cattccaatt acaggaatca tattgaatct gctatctggc     180
tcaagtggtc tacctattat cttagcactt gcctctttag cagacagatg tggtcctatt     240
ttcaccatta ggctgggtat taggagagtg ctagtagtat caaattggga atcgctaag      300
gagattttca ctacccacga tttgatagtt tctaatagac caaaatactt agccgctaag    360
attcttggtt tcaattatgt ttcattctct ttcgctccat acggcccata ttgggtcgga    420
atcagaaaga ttattgctac aaaactaatg tcttcttcca gacttcagaa gttgcaattt    480
```

```
gtaagagttt ttgaactaga aaactctatg aaatctatca gagaatcatg gaaggagaaa      540
aaggatgaag agggaaaggt attagttgag atgaaaaagt ggttctggga actgaatatg      600
aacatagtgt taaggacagt tgctggtaaa caatacactg gtacagttga tgatgccgat      660
gcaaagcgta tctccgagtt attcagagaa tggtttcact acactggcag atttgtcgtt      720
ggagacgctt ttcctttcct aggttggttg gacctgggcg gatacaaaaa gacaatggaa      780
ttagttgcta gtagattgga ctcaatggtc agtaaatggt tagatgagca tcgtaaaaag      840
caagctaacg atgacaaaaa ggaggatatg gatttcatgg atatcatgat ctccatgaca      900
gaagcaaatt caccacttga aggatacggc actgatacta ttatcaagac acatgtatg      960 actttgattg tttcaggagt tgatacaacc tcaatcgtac ttacttgggc cttatcactt     1020
ttgttaaaca acagagatac tttgaaaaag gcacaagagg aattagatat gtgcgtaggt     1080
aaaggaagac aagtcaacga gtctgatctt gttaacttga tatacttgga agcagtgctt     1140
aaagaggctt taagacttta cccagcagcg ttcttaggcg gaccaagagc attcttggaa     1200
gattgtactg ttgctggtta tagaattcca aagggcacct gcttgttgat taacatgtgg     1260
aaactgcata gagatccaaa catttggagt gatccttgcg aattcaagcc agaaagattt     1320
ttgacaccta atcaaaagga tgttgatgtg atcggtatgg atttcgaatt gataccattt     1380
ggtgccggca agatatattg tccaggtact agattggctt tacagatgtt gcatatcgta     1440
ttagcgacat tgctgcaaaa cttcgaaatg tcaacaccaa acgatgcgcc agtcgatatg     1500
actgcttctg ttggcatgac aaatgccaaa gcatcacctt tagaagtctt gctatcacct     1560
cgtgttaaat ggtcctaa                                                   1578

<210> SEQ ID NO 112
<211> LENGTH: 1431
<212> TYPE: DNA
<213> ORGANISM: Artificial Sequence
<220> FEATURE:
<223> OTHER INFORMATION: Synthetic oligonucleotide

<400> SEQUENCE: 112
atgatacaag ttttaactcc aattctactc ttcctcatct tcttcgtttt ctggaaagtc       60
tacaaacatc aaaagactaa aatcaatcta ccaccaggtt ccttcggctg gccattttg      120 ggtgaaacct tagccttact tagagcaggc tgggattctg agccagaaag attcgtaaga      180
gagcgtatca aaaagcatgg atctccactt gttttcaaga catcactatt tggagacaga      240
ttcgctgttc tttgcggtcc agctggtaat aagttttgt tctgcaacga aaacaaatta      300
gtggcatctt ggtggccagt ccctgtaagg aagttgttcg gtaaaagttt actcacaata      360
agaggagatg aagcaaaatg gatgagaaaa atgctattgt cttacttggg tccagatgca      420
tttgccacac attatgccgt tactatggat gttgtaacac gtagacatat tgatgtccat      480
tggaggggca aggaggaagt taatgtattt caaacagtta agttgtacgc attcgaatta      540
gcttgtagat tattcatgaa cctagatgac ccaaaccaca tcgcgaaact cggtagtctt      600
ttcaacattt tcctcaaagg gatcatcgag cttcctatag acgttcctgg aactagattt      660
tactccagta aaaaggccgc agctgccatt agaattgaat tgaaaaagct cattaaagct      720
agaaaactcg aattgaagga gggtaaggcg tcttcttcac aggacttgct ttctcatcta     780
ttaacatcac ctgatgagaa tgggatgttc ttgacagaag aggaaatagt cgataacatt     840
ctacttttgt tattcgctgg tcacgatacc tctgcactat caataacact tttgatgaaa     900
accttaggtg aacacagtga tgtgtacgac aaggttttga aggaacaatt agaaatttcc     960
```

```
aaaacaaagg aggcttggga atcactaaag tgggaagata tccagaagat gaagtactca   1020
tggtcagtaa tctgtgaagt catgagattg aatcctcctg tcatagggac atacagagag   1080
gcgttggttg atatcgacta tgctggttac actatcccaa aaggatggaa gttgcattgg   1140
tcagctgttt ctactcaaag agacgaagcc aatttcgaag atgtaactag attcgatcca   1200
tccagatttg aaggggcagg ccctactcca ttcacatttg tgcctttcgg tggaggtcct   1260
agaatgtgtt taggcaaaga gtttgccagg ttagaagtgt tagcatttct ccacaacatt   1320
gttaccaact ttaagtggga tcttctaatc cctgatgaga agatcgaata tgatccaatg   1380
gctactccag ctaagggctt gccaattaga cttcatccac accaagtcta a            1431

<210> SEQ ID NO 113
<211> LENGTH: 1578
<212> TYPE: DNA
<213> ORGANISM: Artificial Sequence
<220> FEATURE:
<223> OTHER INFORMATION: Synthetic oligonucleotide

<400> SEQUENCE: 113
atggagtctt tagtggttca tacagtaaat gctatctggt gtattgtaat cgtcgggatt     60
ttctcagttg gttatcacgt ttacggtaga gctgtggtcg aacaatggag aatgagaaga    120
tcactgaagc tacaaggtgt taaaggccca ccaccatcca tcttcaatgg taacgtctca    180
gaaatgcaac gtatccaatc cgaagctaaa cactgctctg gcgataacat tatctcacat    240
gattattctt cttcattatt cccacacttc gatcactgga gaaaacagta cggcagaatc    300
tacacatact ctactggatt aaagcaacac ttgtacatca atcatccaga aatggtgaag    360
gagctatctc agactaacac attgaacttg ggtagaatca cccatataac caaaagattg    420
aatcctatct taggtaacgg aatcataacc tctaatggtc tcattgggc  ccatcagcgt    480 agaattatcg cctacgagtt tactcatgat aagatcaagg gtatggttgg tttgatggtt    540
gagtctgcta tgcctatgtt gaataagtgg gaggagatgt aaagagagg cggagaaatg    600 ggatgcgaca taagagttga tgaggacttg aaagatgttt cagcagatgt gattgcaaaa    660
gcctgtttcg gatcctcatt ttctaaaggt aaggctattt tctctatgat aagagatttg    720
cttacagcta tcacaaagag aagtgttcta ttcagattca acggattcac tgatatggtc    780
tttgggagta aaaagcatgg tgacgttgat atagacgctt tagaaatgga attggaatca    840
tccatttggg aaactgtcaa ggaacgtgaa atagaatgta aagatactca caaaaaggat    900
ctgatgcaat tgattttgga aggggcaatg cgttcatgtg acggtaacct ttgggataaa    960
tcagcatata gaagatttgt tgtagataat tgtaaatcta tctacttcgc agggcatgat   1020
agtacagctg tctcagtgtc atggtgtttg atgttactgg ccctaaaccc atcatggcaa   1080
gttaagatcc gtgatgaaat tctgtcttct tgcaaaaatg gtattccaga tgccgaaagt   1140
atcccaaacc ttaaaacagt gactatggtt attcaagaga caatgagatt ataccctcca   1200
gcaccaatcg tcgggagaga agcctctaaa gatatcagat tgggcgatct agttgttcct   1260
aaaggcgtct gtatatggac actaatacca gctttacaca gagatcctga gatttgggga   1320
ccagatgcaa acgatttcaa accagaaaga ttttctgaag gaatttcaaa ggcttgtaag   1380
tatcctcaaa gttacattcc atttggtctg gtcctagaa catgcgttgg taaaaacttt   1440
ggcatgatgg aagtaaaggt tcttgttttcc ctgattgtct ccaagttctc tttcactcta   1500
tctcctacct accaacatag tcctagtcac aaacttttag tagaaccaca acatggggtg   1560
```
gtaattagag tggtttaa                                                  1578

<210> SEQ ID NO 114
<211> LENGTH: 1590
<212> TYPE: DNA
<213> ORGANISM: Artificial Sequence
<220> FEATURE:
<223> OTHER INFORMATION: Synthetic oligonucleotide

<400> SEQUENCE: 114
atgtacttcc tactacaata cctcaacatc acaaccgttg gtgtctttgc cacattgttt      60
ctctcttatt gtttacttct ctggagaagt agagcgggta acaaaaagat tgccccagaa     120
gctgccgctg catggcctat tatcggccac ctccacttac ttgcaggtgg atcccatcaa     180
ctaccacata ttacattggg taacatggca gataagtacg gtcctgtatt cacaatcaga     240
ataggcttgc atagagctgt agttgtctca tcttgggaaa tggcaaagga atgttcaaca     300
gctaatgatc aagtgtcttc ttcaagacct gaactattag cttctaagtt gttgggttat     360
aactacgcca tgtttggttt ttcaccatac ggttcatact ggagagaaat gagaaagatc     420
atctctctcg aattactatc taattccaga ttgaactat tgaaagatgt tagagcctca      480
gaagttgtca catctattaa ggaactatac aaattgtggg cggaaaagaa gaatgagtca     540
ggattggttt ctgtcgagat gaaacaatgg ttcggagatt tgactttaaa cgtgatcttg     600
agaatggtgg ctggtaaaag atacttctcc gcgagtgacg cttcagaaaa caaacaggcc     660
cagcgttgta gaagagtctt cagagaattc ttccatctct ccggcttgtt tgtggttgct     720
gatgctatac ctttcttgg atggctcgat tggggaagac acgagaagac cttgaaaaag      780
accgccatag aaatggattc catcgcccag gagtggcttg aggaacatag acgtagaaaa     840
gattctggag atgataattc tacccaagat ttcatggacg ttatgcaatc tgtgctagat     900
ggcaaaaatc taggcggata cgatgctgat acgattaaca aggctacatg cttaactctt     960
atatcaggtg gcagtgatac tactgtagtt tctttgacat gggctcttag tcttgtgtta    1020
aacaatagag atactttgaa aaaggcacag gaagagttag acatccaagt cggtaaggaa    1080
agattggtta acgagcaaga catcagtaag ttagtttact tgcaagcaat agtaaaagag    1140
acactcagac tttatccacc aggtcctttg ggtggtttga acaattcac tgaagattgt      1200
acactaggtg gctatcacgt tcaaaaagga actagattaa tcatgaactt atccaagatt    1260
caaaaagatc cacgtatttg gtctgatcct actgaattcc aaccagagag attccttacg    1320
actcataaag atgtcgatcc acgtggtaaa cactttgaat tcattccatt cggtgcagga    1380
agacgtgcat gtcctggtat cacattcgga ttacaagtac tacatctaac attggcatct    1440
ttcttgcatg cgtttgaatt ttcaacacca tcaaatgagc aggttaacat gagagaatca    1500
ttaggtctta cgaatatgaa atctaccca ttagaagttt tgatttctcc aagactatcc      1560
cttaattgct caaccttat gaaaatttga                                       1590

<210> SEQ ID NO 115
<211> LENGTH: 1440
<212> TYPE: DNA
<213> ORGANISM: Artificial Sequence
<220> FEATURE:
<223> OTHER INFORMATION: Synthetic oligonucleotide

<400> SEQUENCE: 115
atggaaccta acttttactt gtcattacta ttgttgttcg tgaccttcat ttctttaagt      60
ctgttttca tcttttacaa acaaaagtcc ccattgaatt tgccaccagg gaaaatgggt     120

```
taccctatca taggtgaaag tttagaattc ctatccacag gctggaaggg acatcctgaa      180
aagttcatat ttgatagaat gcgtaagtac agtagtgagt tattcaagac ttctattgta      240
ggcgaatcca cagttgtttg ctgtggggca gctagtaaca aattcctatt ctctaacgaa      300
aacaaactgg taactgcctg gtggccagat tctgttaaca aaatcttccc aacaacttca      360
ctggattcta atttgaagga ggaatctata aagatgagaa agttgctgcc acagttcttc      420
aaaccagaag cacttcaaag atacgtcggc gttatgatg taatcgcaca agacattt         480 gtcactcact gggacaacaa aaatgagatc acagtttatc cacttgctaa agatacact       540 ttcttgcttg cgtgtagact gttcatgtct gttgaggatg aaaatcatgt ggcgaaattc      600
tcagacccat tccaactaat cgctgcaggc atcatttcac ttcctatcga tcttcctggt      660
actccattca acaaggccat aaaggcttca aatttcatta gaaaagagct gataaagatt      720
atcaaacaaa gacgtgttga tctggcagag ggtacagcat ctccaaccca ggatatcttg      780
tcacatatgc tattaacatc tgatgaaaac ggtaaatcta tgaacgagtt gaacattgcc      840
gacaagattc ttggactatt gataggaggc cacgatacag cttcagtagc ttgcacattt      900
ctagtgaagt acttaggaga attaccacat atctacgata aagtctacca agagcaaatg      960
gaaattgcca agtccaaacc tgctggggaa ttgttgaatt gggatgactt gaaaaagatg     1020
aagtattcat ggaatgtggc atgtgaggta atgagattgt caccacccttt acaaggtggt    1080 tttagagagg ctataactga cttatgtttt aacggtttct ctattccaaa agggtggaag     1140
ttatactggt ccgccaactc tacacacaaa aatgcagaat gtttcccaat gcctgagaaa     1200
ttcgatccta ccagatttga aggtaatggt ccagcgcctt atacatttgt accattcggt     1260
ggaggcccta gaatgtgtcc tggaaaggaa tacgctagat tagaaatctt ggttttcatg     1320
cataatctgg tcaaacgttt taagtgggaa aaggttattc cagacgaaaa gattattgtc     1380
gatccattcc caatcccagc taaagatctt ccaatccgtt tgtatcctca caaagcttaa     1440
```

<210> SEQ ID NO 116
<211> LENGTH: 2133
<212> TYPE: DNA
<213> ORGANISM: Artificial Sequence
<220> FEATURE:
<223> OTHER INFORMATION: Synthetic oligonucleotide

<400> SEQUENCE: 116

```
atgcaatcag attcagtcaa agtctctcca tttgatttgg tttccgctgc tatgaatggc       60
aaggcaatgg aaaagttgaa cgctagtgaa tctgaagatc caacaacatt gcctgcacta      120
aagatgctag ttgaaaatag agaattgttg acactgttca caacttcctt cgcagttctt      180
attgggtgtc ttgtatttct aatgtggaga cgttcatcct ctaaaaagct ggtacaagat      240
ccagttccac aagttatcgt tgtaaagaag aaagagaagg agtcagaggt tgatgacggg      300
aaaaagaaag tttctatttt ctacggcaca caaacaggaa ctgccgaagg ttttgctaaa      360
gcattagtcg aggaagcaaa agtgagatat gaaaagacct ctttcaaggt tatcgatcta      420
gatgactacg ctgcagatga tgatgaatat gaggaaaaac tgaaaaagga atccttagcc      480
ttcttcttct tggccacata cggtgatggt gaacctactg ataatgctgc taacttctac      540
aagtggttca cagaaggcga cgataaaggt gaatggctga aaagttaca atacggagta      600 tttggtttag gtaacagaca atatgaacat ttcaacaaga tcgctattgt agttgatgat      660
aaacttactg aaatgggagc caaaagatta gtaccagtag gattagggga tgatgatcag     720
```

| | |
|---|---:|
| tgtatagaag atgacttcac cgcctggaag gaattggtat ggccagaatt ggatcaactt | 780 |
| ttaagggacg aagatgatac ttctgtgact accccataca ctgcagccgt attggagtac | 840 |
| agagtggttt accatgataa accagcagac tcatatgctg aagatcaaac ccatacaaac | 900 |
| ggtcatgttg ttcatgatgc acagcatcct tcaagatcta atgtggcttt caaaaaggaa | 960 |
| ctacacacct ctcaatcaga taggtcttgt actcacttag aattcgatat ttctcacaca | 1020 |
| ggactgtctt acgaaactgg cgatcacgtt ggcgtttatt ccgagaactt gtccgaagtt | 1080 |
| gtcgatgaag cactaaaact gttagggtta tcaccagaca catacttctc agtccatgct | 1140 |
| gataaggagg atgggacacc tatcggtggt gcttcactac caccacctttt cctccttgc | 1200 |
| acattgagag acgctctaac cagatacgca gatgtcttat cctcacctaa aaaggtagct | 1260 |
| ttgctggcat tggctgctca tgctagtgat cctagtgaag ccgataggtt aaagttcctg | 1320 |
| gcttcaccag ccggaaaaga tgaatatgca caatggatcg tcgccaacca acgttctttg | 1380 |
| ctagaagtga tgcaaagttt tccatctgcc aagcctccat taggtgtgtt cttcgcagca | 1440 |
| gtagctccac gtttacaacc aagatactac tctatcagtt catctcctaa gatgtctcct | 1500 |
| aacagaatac atgttacatg tgctttggtg tacgagacta ctccagcagg cagaattcac | 1560 |
| agaggattgt gttcaacctg gatgaaaaat gctgtcccctt taacagagtc acctgattgc | 1620 |
| tctcaagcat ccattttcgt tagaacatca aatttcagac ttccagtgga tccaaaagtt | 1680 |
| ccagtcatta tgataggacc aggcactggt cttgccccat tcaggggctt tcttcaagag | 1740 |
| agattggcct tgaaggaatc tggtacagaa ttgggttctt ctatcttttt ctttggttgc | 1800 |
| cgtaatagaa aagttgactt tatctacgag gacgagctta acaattttgt tgagacagga | 1860 |
| gcattgtcag aattgatcgt cgcattttca agagaaggga ctgccaaaga gtacgttcag | 1920 |
| cacaagatga gtcaaaaagc ctccgatata tggaaacttc taagtgaagg tgcctatctt | 1980 |
| tatgtctgtg gcgatgcaaa gggcatggcc aaggatgtcc atagaactct gcatacaatt | 2040 |
| gttcaggaac aagggagtct ggattcttcc aaggctgaat tgtacgtcaa aaacttacag | 2100 |
| atgtctggaa gatacttaag agatgtttgg taa | 2133 |

<210> SEQ ID NO 117
<211> LENGTH: 2079
<212> TYPE: DNA
<213> ORGANISM: Artificial Sequence
<220> FEATURE:
<223> OTHER INFORMATION: Synthetic oligonucleotide

<400> SEQUENCE: 117

| | |
|---|---:|
| atgacttctg cactttatgc ctccgatctt ttcaaacaat tgaaaagtat catgggaacg | 60 |
| gattctttgt ccgatgatgt tgtattagtt attgctacaa cttctctggc actggttgct | 120 |
| ggtttcgttg tcttattgtg gaaaaagacc acggcagatc gttccggcga gctaaagcca | 180 |
| ctaatgatcc ctaagtctct gatggcgaaa gatgaggatg atgacttaga tctaggttct | 240 |
| ggaaaaacga gagtctctat cttcttcggc acacaaaccg gaacagccga aggattcgct | 300 |
| aaagcacttt cagaagagat caaagcaaga tacgaaaagg cggctgtaaa agtaatcgat | 360 |
| ttggatgatt acgctgccga tgatgaccaa tatgaggaaa agttgaaaaa ggaaacattg | 420 |
| gctttctttt gtgtagccac gtatggtgat ggtgaaccaa ccgataacgc cgcaagattc | 480 |
| tacaagtggt ttactgaaga gaacgaaaga gatatcaagt tgcagcaact tgcttacggc | 540 |
| gttttttgcct taggtaacag acaatacgag cactttaaca gataggtat tgtcttagat | 600 |
| gaagagttat gcaaaaaggg tgcgaagaga ttgattgaag tcggtttagg agatgatgat | 660 |

| | |
|---|---|
| caatctatcg aggatgactt taatgcatgg aaggaatctt tgtggtctga attagataag | 720 |
| ttacttaagg acgaagatga taaatccgtt gccactccat acacagccgt cattccagaa | 780 |
| tatagagtag ttactcatga tccaagattc acaacacaga aatcaatgga aagtaatgtg | 840 |
| gctaatggta atactaccat cgatattcat catccatgta gagtagacgt tgcagttcaa | 900 |
| aaggaattgc acactcatga atcagacaga tcttgcatac atcttgaatt tgatatatca | 960 |
| cgtactggta tcacttacga aacaggtgat cacgtgggtg tctacgctga aaaccatgtt | 1020 |
| gaaattgtag aggaagctgg aaagttgttg ggccatagtt tagatcttgt tttctcaatt | 1080 |
| catgccgata agaggatggg ctcaccacta gaaagtgcag tgcctccacc atttccagga | 1140 |
| ccatgcaccc taggtaccgg tttagctcgt tacgcggatc tgttaaatcc tccacgtaaa | 1200 |
| tcagctctag tggccttggc tgcgtacgcc acagaacctt ctgaggcaga aaaactgaaa | 1260 |
| catctaactt caccagatgg taaggatgaa tactcacaat ggatagtagc tagtcaacgt | 1320 |
| tctttactag aagttatggc tgcttttccca tccgctaaac ctccctttggg tgttttcttc | 1380 |
| gccgcaatag cgcctagact gcaaccaaga tactattcaa tttcatcctc acctagactg | 1440 |
| gcaccatcaa gagttcatgt cacatccgct ttagtgtacg gtccaactcc tactggtaga | 1500 |
| atccataagg gcgtttgttc aacatggatg aaaaacgcgg ttccagcaga gaagtctcac | 1560 |
| gaatgttctg gtgctccaat ctttatcaga gcctccaact tcaaactgcc ttccaatcct | 1620 |
| tctactccta ttgtcatggt cggtcctggt acaggtcttg ctccattcag aggtttctta | 1680 |
| caagagagaa tggccttaaa ggaggatggt gaagagttgg gatcttcttt gttgttttc | 1740 |
| ggctgtagaa acagacaaat ggatttcatc tacgaagatg aactgaataa ctttgtagat | 1800 |
| caaggagtta tttcagagtt gataatggct ttttctagag aaggtgctca gaaggagtac | 1860 |
| gtccaacaca aaatgatgga aaaggccgca caagtttggg acttaatcaa agaggaaggc | 1920 |
| tatctatatg tctgtggtga tgcaaagggt atggcaagag atgttcacag aacacttcat | 1980 |
| actatagtcc aggaacagga aggcgttagt tcttctgaag cggaagcaat tgtgaaaaag | 2040 |
| ttacaaacag agggaagata cttgagagat gtgtggtaa | 2079 |

<210> SEQ ID NO 118
<211> LENGTH: 2142
<212> TYPE: DNA
<213> ORGANISM: Artificial Sequence
<220> FEATURE:
<223> OTHER INFORMATION: Synthetic oligonucleotide

<400> SEQUENCE: 118

| | |
|---|---|
| atggcagaat tagatacact tgatatagta gtattaggtg ttatcttttt gggtactgtg | 60 |
| gcatacttta ctaagggtaa attgtggggt gttaccaagg atccatacgc taacggattc | 120 |
| gctgcaggtg gtgcttccaa gcctggcaga actagaaaca tcgtcgaagc tatggaggaa | 180 |
| tcaggtaaaa actgtgttgt tttctacggc agtcaaacag gtacagcgga ggattacgca | 240 |
| tcaagacttg caaaggaagg aaagtccaga ttcggtttga acactatgat cgccgatcta | 300 |
| gaagattatg acttcgataa cttagacact gttccatctg ataacatcgt tatgtttgta | 360 |
| ttggctactt acggtgaagg cgaaccaaca gataacgccg tggatttcta tgagttcatt | 420 |
| actggcgaag atgcctcttt caatgagggc aacgatcctc cactaggtaa cttgaattac | 480 |
| gttgcgttcg gtctgggcaa caataccttac gaacactaca actcaatggt caggaacgtt | 540 |
| aacaaggctc tagaaaagtt aggagctcat agaattggag aagcaggtga gggtgacgac | 600 |

```
ggagctggaa ctatggaaga ggacttttta gcttggaaag atccaatgtg ggaagccttg      660
gctaaaaaga tgggcttgga ggaaagagaa gctgtatatg aacctatttt cgctatcaat      720
gagagagatg atttgacccc tgaagcgaat gaggtatact tgggagaacc taataagcta      780
cacttggaag gtacagcgaa aggtccattc aactcccaca acccatatat cgcaccaatt      840
gcagaatcat acgaactttt ctcagctaag gatagaaatt gtctgcatat ggaaattgat      900
atttctggta gtaatctaaa gtatgaaaca ggcgaccata tcgcgatctg gcctaccaac      960
ccaggtgaag aggtcaacaa atttcttgac attctagatc tgtctggtaa gcaacattcc     1020
gtcgtaacag tgaaagcctt agaacctaca gccaaagttc cttttccaaa tccaactacc     1080
tacgatgcta tattgagata ccatctggaa atatgcgctc cagtttctag acagtttgtc     1140
tcaactttag cagcattcgc ccctaatgat gatatcaaag ctgagatgaa ccgtttggga     1200
tcagacaaag attacttcca cgaaaagaca ggaccacatt actacaatat cgctagattt     1260
ttggcctcag tctctaaagg tgaaaaatgg acaaagatac cattttctgc tttcatagaa     1320
ggccttacaa aactacaacc aagatactat tctatctctt cctctagttt agttcagcct     1380
aaaaagatta gtattactgc tgttgtcgaa tctcagcaaa ttccaggtag agatgaccca     1440
ttcagaggtg tagcgactaa ctacttgttc gctttgaagc agaaacaaaa cggtgatcca     1500
aatccagctc cttttggcca atcatacgag ttgacaggac caaggaataa gtatgatggt     1560
atacatgttc cagtccatgt aagacattct aactttaagc taccatctga tccaggcaaa     1620
cctattatca tgatcggtcc aggtaccggt gttgcccctt ttagaggctt cgtccaagag     1680
agggcaaaac aagccagaga tggtgtagaa gttggtaaaa cactgctgtt ctttggatgt     1740
agaaagagta cagaagattt catgtatcaa aaagagtggc aagagtacaa ggaagctctt     1800
ggcgacaaat tcgaaatgat tacagctttt tcaagagaag gatctaaaaa ggtttatgtt     1860
caacacagac tgaaggaaag atcaaaggaa gtttctgatc ttctatccca aaaagcatac     1920
ttctacgttt gcggagacgc cgcacatatg gcacgtgaag tgaacactgt gttagcacag     1980
atcatagcag aaggccgtgg tgtatcagaa gccaagggtg aggaaattgt caaaaacatg     2040
agatcagcaa atcaatacca agtgtgttct gatttcgtaa ctttacactg taaagagaca     2100
acatacgcga attcagaatt gcaagaggat gtctggagtt aa                        2142
```

<210> SEQ ID NO 119
<211> LENGTH: 2364
<212> TYPE: DNA
<213> ORGANISM: Artificial Sequence
<220> FEATURE:
<223> OTHER INFORMATION: Synthetic oligonucleotide

<400> SEQUENCE: 119

```
atgaaaaccg ggtttatctc accagcaaca gtatttcatc acagaatctc accagcgacc       60
actttcagac atcacttatc acctgctact acaaactcta caggcattgt cgccttaaga      120
gacatcaact tcagatgtaa agcagtttct aaagagtact ctgatctgtt gcagaaagat      180
gaggcttctt tcacaaaatg ggacgatgac aaggtgaaag atcatcttga taccaacaaa      240
aacttatacc caaatgatga gattaaggaa tttgttgaat cagtaaaggc tatgttcggt      300
agtatgaatg acggggagat aaacgtctct gcatacgata ctgcatgggt tgctttggtt      360
caagatgtcg atggatcagg tagtcctcag ttcccttctt ctttagaatg gattgccaac      420
aatcaattgt cagatggatc atggggagat catttgctgt tctcagctca cgatagaatc      480
atcaacacat tagcatgcgt tattgcactt acaagttgga atgttcatcc ttctaagtgt      540
```

```
gaaaaaggtt tgaattttct gagagaaaac atttgcaaat tagaagatga aaacgcagaa      600
catatgccaa ttggttttga agtaacattc ccatcactaa ttgatatcgc gaaaaagttg      660
aacattgaag tacctgagga tactccagca cttaaagaga tctacgcacg tagagatatc      720
aagttaacta agatcccaat ggaagttctt cacaaggtac ctactacttt gttacattct      780
ttggaaggaa tgcctgattt ggagtgggaa aaactgttaa agctacaatg taaagatggt      840
agtttcttgt tttccccatc tagtaccgca ttcgccctaa tgcaaacaaa agatgagaaa      900
tgcttacagt atctaacaaa tatcgtcact aagttcaacg gtggcgtgcc taatgtgtac      960
ccagtcgatt tgtttgaaca tatttgggtt gttgatagac tgcagagatt ggggattgcc     1020
agatacttca aatcagagat aaaagattgt gtagagtata tcaataagta ctggaccaaa     1080
aatggaattt gttgggctag aaatactcac gttcaagata tcgatgatac agccatggga     1140
ttcagagtgt tgagagcgca cggttatgac gtcactccag atgtttttag acaatttgaa     1200
aaagatggta aattcgtttg ctttgcaggg caatcaacac aagccgtgac aggaatgttt     1260
aacgtttaca gagcctctca aatgttgttc ccaggggaga aattttggaa agatgccaaa     1320
aagttctctt acaattactt aaaggaaaag caaagtacca acgaattgct ggataaatgg     1380
ataatcgcta agatctacc tggtgaagtt ggttatgctc tggatatccc atggtatgct     1440
tccttaccaa gattggaaac tcgttattac cttgaacaat acggcggtga agatgatgtc     1500
tggataggca agacattata cagaatgggt tacgtgtcca ataacacata tctagaaatg     1560
gcaaagctgg attacaataa ctatgttgca gtccttcaat tagaatggta cacaatacaa     1620
caatggtacg tcgatattgg tatagagaag ttcgaatctg acaacatcaa gtcagtcctg     1680
gtttcttact acttggctgc ggcttcaata ttcgaacctg agagatctaa ggagagaatc     1740
gcttgggcaa agacaacaat cttagtcgat aagatcacat caattttcga ttcctctcag     1800
tcaagtaagg aagatattac tgcctttatt gacaagtttc gtaacaagtc ctcctctaaa     1860
aagcactcta tcaacggtga accatggcat gaagttatgg tagctttgaa aaagaccttta     1920 cacggctttg ctctggatgc tcttatgact cattctcaag atatacatcc acagttacat     1980
caagcctggg aaatgtggtt gactaaaacta caagacggcg tagatgttac tgctgagcta     2040
atggtccaaa tgatcaacat gactgctggc agatgggtat caaaggaatt acttactcat     2100
ccacaatatc aaagattgtc tactgtgaca aattctgtgt gtcacgatat taccaaactt     2160
cacaatttca aggagaattc caccacagtg gattcaaagg ttcaggaact agtccagttg     2220
gtttttagtg acacaccaga tgatttggat caagatatga aacaaacatt cctgacagtg     2280
atgaagacat tctactacaa ggcgtggtgt gatccaaaca ctataaacga tcatatatct     2340
aaagttttcg aaatcgtaat ttga                                             2364
```

<210> SEQ ID NO 120
<211> LENGTH: 1584
<212> TYPE: DNA
<213> ORGANISM: Artificial Sequence
<220> FEATURE:
<223> OTHER INFORMATION: Synthetic oligonucleotide

<400> SEQUENCE: 120

```
atgcctgatg cacacgatgc tccacctcca caaataagac agagaacact agtagatgag       60
gctacccaac tgctaactga gtccgcagaa gatgcatggg gtgaagtcag tgtgtcagaa      120
tacgaaacag caaggctagt tgcccatgct acatggttag gtggacacgc cacaagagtg      180
```

```
gccttccttc tggagagaca acacgaagac gggtcatggg gtccaccagg tggatatagg      240
ttagtcccta cattatctgc tgttcacgca ttattgacat gtcttgcctc tcctgctcag      300
gatcatggcg ttccacatga tagactttta agagctgttg acgcaggctt gactgccttg      360
agaagattgg ggacatctga ctccccacct gatactatag cagttgagct ggttatccca      420
tctttgctag agggcattca acacttactg gaccctgctc atcctcatag tagaccagcc      480
ttctctcaac atagaggctc tcttgtttgt cctggtggac tagatgggag aactctagga      540
gctttgagat cacacgccgc agcaggtaca ccagtaccag gaaaagtctg gcacgcttcc      600
gagactttgg gcttgagtac cgaagctgct tctcacttgc aaccagccca aggtataatc      660
ggtggctctg ctgctgccac agcaacatgg ctaaccaggg ttgcaccatc tcaacagtca      720
gattctgcca gaagatacct tgaggaatta caacacagat actctggccc agttccttcc      780
attaccccta tcacatactt cgaaagagca tggttattga caattttgc agcagccggt       840 gttccttgtg aggctccagc tgctttgttg gattccttag aagcagcact tacaccacaa      900
ggtgctcctg ctggagcagg attgcctcca gatgctgatg atacagccgc tgtgttgctt      960
gcattggcaa cacatgggag aggtagaaga ccagaagtac tgatggatta caggactgac     1020
gggtatttcc aatgctttat tggggaaagg actccatcaa tttcaacaaa cgctcacgta     1080
ttggaaacat tagggcatca tgtggcccaa catccacaag atagagccag atacggatca     1140
gccatggata ccgcatcagc ttggctgctg gcagctcaaa agcaagatgg ctcttggtta     1200
gataaatggc atgcctcacc atactacgct actgtttgtt gcacacaagc cctagccgct     1260
catgcaagtc ctgcaactgc accagctaga cagagagctg tcagatgggt tttagccaca     1320
caaagatccg atggcggttg gggtctatgg cattcaactg ttgaagagac tgcttatgcc     1380
ttacagatct tggccccacc ttctggtggt ggcaatatcc cagtccaaca agcacttact     1440
agaggcagag caagattgtg tggagccttg ccactgactc ctttatggca tgataaggat     1500
ttgtatactc cagtaagagt agtcagagct gccagagctg ctgctctgta cactaccaga     1560
gatctattgt taccaccatt gtaa                                             1584
```

<210> SEQ ID NO 121
<211> LENGTH: 1551
<212> TYPE: DNA
<213> ORGANISM: Artificial Sequence
<220> FEATURE:
<223> OTHER INFORMATION: Synthetic oligonucleotide

<400> SEQUENCE: 121

```
atgaacgccc tatccgaaca catttttgtct gaattgagaa gattattgtc tgaaatgagt       60
gatggcggat ctgttggtcc atctgtgtat gatacggccc aggccctaag attccacggt      120
aacgtaacag gtagacaaga tgcatatgct tggttgatcg cccagcaaca agcagatgga      180
ggttggggct ctgccgactt tccactcttt agacatgctc caacatgggc tgcacttctc      240
gcattacaaa gagctgatcc acttcctggc gcagcagacg cagttcagac cgcaacaaga      300
ttcttgcaaa gacaaccaga tccatacgct catgccgttc ctgaggatgc ccctattggt      360
gctgaactga tcttgcctca gttttgtgga gaggctgctt ggttgttggg aggtgtggcc      420
ttccctagac acccagccct attaccatta agacaggctt gtttagtcaa actgggtgca      480
gtcgccatgt tgccttcagg acacccattg ctccactcct gggaggcatg gggtacttct      540
ccaacaacag cctgtccaga cgatgatggt tctataggta tctcaccagc agctacagcc      600
gcctggagag cccaggctgt gaccagaggc tcaactcctc aagtgggcag agctgacgca      660
```

```
tacttacaaa tggcttcaag agcaacgaga tcaggcatag aaggagtctt ccctaatgtt    720
tggcctataa acgtattcga accatgctgg tcactgtaca ctctccatct tgccggtctg    780
ttcgcccatc cagcactggc tgaggctgta agagttatcg ttgctcaact tgaagcaaga    840
ttgggagtgc atggcctcgg accagcttta cattttgctg ccgacgctga tgatactgca    900
gttgccttat gcgttctgca tttggctggc agagatcctg cagttgacgc attgagacat    960
tttgaaattg gtgagctctt tgttacattc ccaggagaga gaaatgctag tgtctctacg   1020
aacattcacg ctcttcatgc tttgagattg ttaggtaaac cagctgccgg agcaagtgca   1080
tacgtcgaag caaatagaaa tccacatggt tgtgggaca acgaaaaatg gcacgtttca    1140
tggctttatc caactgcaca cgccgttgca gctctagctc aaggcaagcc tcaatggaga   1200
gatgaaagag cactagccgc tctactacaa gctcaaagag atgatggtgg ttggggagct   1260
ggtagaggat ccactttcga ggaaaccgcc tacgctcttt tcgctttaca cgttatggac   1320
ggatctgagg aagccacagg cagaagaaga atcgctcaag tcgtcgcaag agccttagaa   1380
tggatgctag ctagacatgc cgcacatgga ttaccacaaa caccactctg gattggtaag   1440
gaattgtact gtcctactag agtcgtaaga gtagctgagc tagctggcct gtggttagca   1500
ttaagatggg gtagaagagt attagctgaa ggtgctggtg ctgcacctta a            1551

<210> SEQ ID NO 122
<211> LENGTH: 2952
<212> TYPE: DNA
<213> ORGANISM: Artificial Sequence
<220> FEATURE:
<223> OTHER INFORMATION: Synthetic oligonucleotide

<400> SEQUENCE: 122
atggaatttg atgaaccatt ggttgacgaa gcaagatctt tagtgcagcg tactttacaa      60
gattatgatg acagatacgg cttcggtact atgtcatgtg ctgcttatga tacagcctgg     120
gtgtctttag ttacaaaaac agtcgatggg agaaaacaat ggcttttccc agagtgtttt     180
gaatttctac tagaaacaca atctgatgcc ggaggatggg aaatcgggaa ttcagcacca     240
atcgacggta tattgaatac agctgcatcc ttacttgctc taaaacgtca cgttcaaact     300
gagcaaatca tccaacctca acatgaccat aaggatctag caggtagagc tgaacgtgcc     360
gctgcatctt tgagagcaca attggctgca ttggatgtgt ctacaactga acacgtcggt     420
tttgagataa ttgttcctgc aatgctagac ccattagaag ccgaagatcc atctctagtt     480
ttcgattttc cagctaggaa acctttgatg aagattcatg atgctaagat gagtagattc     540
aggccagaat acttgtatgg caaacaacca atgaccgcct acattcatt agaggctttc     600 ataggcaaaa tcgacttcga taaggtaaga caccaccgta cccatgggtc tatgatgggt     660
tctccttcat ctaccgcagc ctacttaatg cacgcttcac aatgggatgg tgactcagag     720
gcttacctta gacacgtgat taaacacgca gcagggcagg gaactggtgc tgtaccatct     780
gctttcccat caacacattt tgagtcatct tggattctta ccacattgtt tagagctgga     840
ttttcagctt ctcatcttgc ctgtgatgag ttgaacaagt tggtcgagat acttgagggc     900
tcattcgaga aggaaggtgg ggcaatcggt tacgctccag ggtttcaagc agatgttgat     960
gatactgcta aaacaataag tacattagca gtccttggaa gagatgctac accaagacaa    1020
atgatcaagg tatttgaagc taatacacat tttagaacat ccctggtga agagatcct     1080 tctttgacag ctaattgtaa tgctctatca gccttactac accaaccaga tgcagcaatg    1140
```

| | |
|---|---|
| tatggatctc aaattcaaaa gattaccaaa tttgtctgtg actattggtg gaagtctgat | 1200 |
| ggtaagatta aagataagtg gaacacttgc tacttgtacc catctgtctt attagttgag | 1260 |
| gttttggttg atcttgttag tttattggag cagggtaaat tgcctgatgt tttggatcaa | 1320 |
| gagcttcaat acagagtcgc catcacattg ttccaagcat gtttaaggcc attactagac | 1380 |
| caagatgccg aaggatcatg aacaagtct atcgaagcca cagcctacgg catccttatc | 1440 |
| ctaactgaag ctaggagagt ttgtttcttc gacagattgt ctgagccatt gaatgaggca | 1500 |
| atccgtagag gtatcgcttt cgccgactct atgtctggaa ctgaagctca gttgaactac | 1560 |
| atttggatcg aaaaggttag ttacgcacct gcattattga ctaaatccta tttgttagca | 1620 |
| gcaagatggg ctgctaagtc tcctttaggc gcttccgtag gctcttcttt gtggactcca | 1680 |
| ccaagagaag gattggataa gcatgtcaga ttattccatc aagctgagtt attcagatcc | 1740 |
| cttccagaat gggaattaag agcctccatg attgaagcag ctttgttcac accacttcta | 1800 |
| agagcacata gactagacgt tttccctaga caagatgtag gtgaagacaa atatcttgat | 1860 |
| gtagttccat tcttttggac tgccgctaac aacagagata gaacttacgc ttccactcta | 1920 |
| ttcctttacg atatgtgttt tatcgcaatg ttaaacttcc agttagacga attcatggag | 1980 |
| gccacagccg gtatcttatt cagagatcat atggatgatt tgaggcaatt gattcatgat | 2040 |
| cttttggcag agaaaacttc cccaaagagt tctggtagaa gtagtcaggg cacaaaagat | 2100 |
| gctgactcag gtatagagga agacgtgtca atgtccgatt cagcttcaga ttcccaggat | 2160 |
| agaagtccag aatacgactt ggttttcagt gcattgagta cctttacaaa acatgtcttg | 2220 |
| caacacccat ctatacaaag tgcctctgta tgggatagaa aactacttgc tagagagatg | 2280 |
| aaggcttact tacttgctca tatccaacaa gcagaagatt caactccatt gtctgaattg | 2340 |
| aaagatgtgc ctcaaaagac tgatgtaaca agagtttcta catctactac taccttcttt | 2400 |
| aactgggtta gaacaacttc cgcagaccat atatcctgcc catactcctt ccactttgta | 2460 |
| gcatgccatc taggcgcagc attgtcacct aaagggtcta acggtgattg ctatccttca | 2520 |
| gctggtgaga agttcttggc agctgcagtc tgcagacatt tggccaccat gtgtagaatg | 2580 |
| tacaacgatc ttggatcagc tgaacgtgat tctgatgaag gtaatttgaa ctccttggac | 2640 |
| ttccctgaat tcgccgattc cgcaggaaac ggagggatag aaattcagaa ggccgctcta | 2700 |
| ttaaggttag ctgagtttga gagagattca tacttagagg ccttccgtcg tttacaagat | 2760 |
| gaatccaata gagttcacgg tccagccggt ggtgatgaag ccagattgtc cagaaggaga | 2820 |
| atggcaatcc ttgaattctt cgcccagcag gtagatttgt acggtcaagt atacgtcatt | 2880 |
| agggatattt ccgctcgtat tcctaaaaac gaggttgaga aaagagaaa attggatgat | 2940 |
| gctttcaatt ga | 2952 |

<210> SEQ ID NO 123
<211> LENGTH: 2646
<212> TYPE: DNA
<213> ORGANISM: Artificial Sequence
<220> FEATURE:
<223> OTHER INFORMATION: Synthetic oligonucleotide

<400> SEQUENCE: 123

| | |
|---|---|
| atggcttcta gtacacttat ccaaaacaga tcatgtggcg tcacatcatc tatgtcaagt | 60 |
| tttcaaatct tcagaggtca accactaaga tttcctggca ctagaacccc agctgcagtt | 120 |
| caatgcttga aaagaggag atgccttagg ccaaccgaat ccgtactaga atcatctcct | 180 |
| ggctctggtt catatagaat agtaactggc ccttctggaa ttaaccctag ttctaacggg | 240 |

```
cacttgcaag agggttcctt gactcacagg ttaccaatac caatggaaaa atctatcgat    300
aacttccaat ctactctata tgtgtcagat atttggtctg aaacactaca gagaactgaa    360
tgtttgctac aagtaactga aaacgtccag atgaatgagt ggattgagga aattagaatg    420
tactttagaa atatgacttt aggtgaaatt tccatgtccc cttacgacac tgcttgggtg    480
gctagagttc cagcgttgga cggttctcat gggcctcaat ccacagatc tttgcaatgg     540 attatcgaca accaattacc agatggggac tggggcgaac cttctctttt cttgggttac    600
gatagagttt gtaatacttt agcctgtgtg attgcgttga aaacatgggg tgttggggca    660
caaaacgttg aaagaggaat tcagttccta caatctaaca tatacaagat ggaggaagat    720
gacgctaatc atatgccaat aggattcgaa atcgtattcc ctgctatgat ggaagatgcc    780
aaagcattag gtttggattt gccatacgat gctactattt tgcaacagat ttcagccgaa    840
agagagaaaa agatgaaaaa gatcccaatg gcaatggtgt acaaataccc aaccactta    900 cttcactcct tagaaggctt gcatagaaa gttgattgga ataagttgtt acaattacaa     960
tctgaaaatg gtagttttct ttattcacct gcttcaaccg catgcgcctt aatgtacact    1020
aaggacgtta aatgttttga ttacttaaac cagttgttga tcaagttcga ccacgcatgc    1080
ccaaatgtat atccagtcga tctattcgaa agattatgga tggttgacag attgcagaga    1140
ttagggatct ccagatactt tgaaagagag attagagatt gtttacaata cgtctacaga    1200
tattggaaag attgtggaat cggatgggct tctaactctt ccgtacaaga tgttgatgat    1260
acagccatgg cgtttagact tttaaggact catggtttcg acgtaaagga agattgcttt    1320
agacagtttt tcaaggacgg agaattcttc tgcttcgcag gccaatcatc tcaagcagtt    1380
acaggcatgt ttaatctttc aagagccagt caaacattgt ttccaggaga atctttattg    1440
aaaaaggcta gaaccttctc tagaaacttc ttgagaacaa agcatgagaa caacgaatgt    1500
ttcgataaat ggatcattac taaagatttg gctggtgaag tcgagtataa cttgaccttc    1560
ccatggtatg cctcttgcc tagattagaa cataggacat acttagatca atatggaatc    1620
gatgatatct ggataggcaa atctttatac aaaatgcctg ctgttaccaa cgaagttttc    1680
ctaaagttgg caaaggcaga ctttaacatg tgtcaagctc tacacaaaaa ggaattggaa    1740
caagtgataa agtggaacgc gtcctgtcaa ttcagagatc ttgaattcgc cagacaaaaa    1800
tcagtagaat gctattttgc tggtgcagcc acaatgttcg aaccagaaat ggttcaagct    1860
agattagtct gggcaagatg ttgtgtattg acaactgtct tagacgatta ctttgaccac    1920
gggacacctg ttgaggaact tagagtgttt gttcaagctg tcagaacatg gaatccagag    1980
ttgatcaacg gtttgccaga gcaagctaaa atcttgttta tgggcttata caaaacagtt    2040
aacacaattg cagaggaagc attcatggca cagaaaagag acgtccatca tcatttgaaa    2100
cactattggg acaagttgat aacaagtgcc ctaaggagg ccgaatgggc agagtcaggt     2160
tacgtcccaa catttgatga atacatggaa gtagctgaaa tttctgttgc tctagaacca    2220
attgtctgta gtaccttgtt ctttgcgggt catagactag atgaggatgt tctagatagt    2280
tacgattacc atctagttat gcatttggta aacagagtcg gtagaatctt gaatgatata    2340
caaggcatga agagggaggc ttcacaaggt aagatctcat cagttcaaat ctacatggag    2400
gaacatccat ctgttccatc tgaggccatg gcgatcgctc atcttcaaga gttagttgat    2460
aattcaatgc agcaattgac atacgaagtt cttaggttca ctgcggttcc aaaaagttgt    2520
aagagaatcc acttgaatat ggctaaaatc atgcatgcct tctacaagga tactgatgga    2580
```

| | |
|---|---|
| ttctcatccc ttactgcaat gacaggattc gtcaaaaagg ttcttttcga acctgtgcct | 2640 |
| gagtaa | 2646 |

<210> SEQ ID NO 124
<211> LENGTH: 2859
<212> TYPE: DNA
<213> ORGANISM: Artificial Sequence
<220> FEATURE:
<223> OTHER INFORMATION: Synthetic oligonucleotide

<400> SEQUENCE: 124

| | |
|---|---|
| atgcctggta aaattgaaaa tggtacccca aaggacctca agactggaaa tgattttgtt | 60 |
| tctgctgcta agagtttact agatcgagct ttcaaaagtc atcattccta ctacggatta | 120 |
| tgctcaactt catgtcaagt ttatgataca gcttgggttg caatgattcc aaaaacaaga | 180 |
| gataatgtaa acagtggtt gtttccagaa tgtttccatt acctcttaaa acacaagcc | 240 |
| gcagatggct catggggttc attgcctaca acacagacag cgggtatcct agatacagcc | 300 |
| tcagctgtgc tggcattatt gtgccacgca caagagcctt acaaatatt ggatgtatct | 360 |
| ccagatgaaa tgggggttgag aatagaacac ggtgtcacat ccttgaaacg tcaattagca | 420 |
| gtttggaatg atgtggagga caccaaccat attggcgtcg agtttatcat accagcctta | 480 |
| ctttccatgc tagaaaagga attagatgtt ccatcttttg aatttccatg taggtccatc | 540 |
| ttagagagaa tgcacgggga gaaattaggt catttcgacc tggaacaagt ttacggcaag | 600 |
| ccaagctcat tgttgcactc attggaagca tttctcggta agctagattt tgatcgacta | 660 |
| tcacatcacc tataccacgg cagtatgatg gcatctccat cttcaacggc tgcttatctt | 720 |
| attggggcta caaaatggga tgacgaagcc gaagattacc taagacatgt aatgcgtaat | 780 |
| ggtgcaggac atgggaatgg aggtatttct ggtacatttc caactactca tttcgaatgt | 840 |
| agctggatta tagcaacgtt gttaaaggtt ggctttactt tgaagcaaat tgacggcgat | 900 |
| ggcttaagag gttatcaac catcttactt gaggcgcttc gtgatgagaa tggtgtcata | 960 |
| ggctttgccc ctagaacagc agatgtagat gacacagcca aagctctatt ggccttgtca | 1020 |
| ttggtaaacc agccagtgtc acctgatatc atgattaagg tctttgaggg caaagaccat | 1080 |
| tttaccactt ttggttcaga aagagatcca tcattgactt ccaacctgca cgtccttta | 1140 |
| tctttactta acaatctaa cttgtctcaa taccatcctc aaatcctcaa acaacatta | 1200 |
| ttcacttgta gatggtggtg gggttccgat cattgtgtca agacaaatg gaatttgagt | 1260 |
| cacctatatc caactatgtt gttggttgaa gccttcactg aagtgctcca tctcattgac | 1320 |
| ggtggtgaat tgtctagtct gttttgatgaa tcctttaagt gtaagattgg tcttagcatc | 1380 |
| tttcaagcgg tacttagaat aatcctcacc caagacaacg acggctcttg gagaggatac | 1440 |
| agagaacaga cgtgttacgc aatattggct ttagttcaag cgagacatgt atgcttttc | 1500 |
| actcacatgg ttgacagact gcaatcatgt gttgatcgag gttcctcatg gttgaaatct | 1560 |
| tgctcttttc attctcaaga cctgacttgg acctctaaaa cagcttatga agtgggtttc | 1620 |
| gtagctgaag catataaact agctgcttta caatctgctt ccctggaggt tcctgctgcc | 1680 |
| accattggac attctgtcac gtctgccgtt ccatcaagtg atcttgaaaa atacatgaga | 1740 |
| ttggtgagaa aaactgcgtt attctctcca ctggatgagt ggggtctaat ggcttctatc | 1800 |
| atcgaatctt cattttttcgt accattactg caggcacaaa gagttgaaat ataccctaga | 1860 |
| gataatatca aggtggacga agataagtac tgtctattta tcccattcac atgggtcgga | 1920 |
| tgcaataata ggtctagaac tttcgcaagt aacagatggc tatacgatat gatgtacctt | 1980 |

```
tcattactcg gctatcaaac cgacgagtac atggaagctg tagctgggcc agtgtttggg    2040
gatgtttcct tgttacatca aacaattgat aaggtgattg ataatacaat gggtaacctt    2100
gcgagagcca atggaacagt acacagtggt aatggacatc agcacgaatc tcctaatata    2160
ggtcaagtcg aggacacctt gactcgtttc acaaattcag tcttgaatca caaagacgtc    2220
cttaactcta gctcatctga tcaagatact ttgagaagag agtttagaac attcatgcac    2280
gctcatataa cacaaatcga agataactca cgattcagta agcaagcctc atccgatgcg    2340 tttcctctc ctgaacaatc ttactttcaa tgggtgaact caactggtgg ctcacatgtc      2400
gcttgcgcct attcatttgc cttctctaat tgcctcatgt ctgcaaattt gttgcagggt    2460
aaagacgcat ttccaagcgg aacgcaaaag tacttaatct cctctgttat gagacatgcc    2520
acaaacatgt gtagaatgta taacgacttt ggctctattg ccagagacaa cgctgagaga    2580
aatgttaata gtattcattt tcctgagttt actctctgta acggaacttc tcaaaaccta    2640
gatgaaagga aggaaagact tctgaaaatc gcaacttacg aacaagggta tttggataga    2700
gcactagagg ccttggaaag acagagtaga gatgatgccg gagacagagc tggatctaaa    2760
gatatgagaa agttgaaaat cgttaagtta ttctgtgatg ttacggactt atacgatcag    2820
ctctacgtta tcaaagattt gtcatcctct atgaagtaa                            2859
```

<210> SEQ ID NO 125
<211> LENGTH: 1086
<212> TYPE: DNA
<213> ORGANISM: Artificial Sequence
<220> FEATURE:
<223> OTHER INFORMATION: Synthetic oligonucleotide

<400> SEQUENCE: 125

```
atggctttgg taaacccaac cgctctttc tatggtacct ctatcagaac aagacctaca       60
aacttactaa atccaactca aaagctaaga ccagtttcat catcttcctt accttctttc     120
tcatcagtta gtgcgattct tactgaaaaa catcaatcta atccttctga gaacaacaat     180
ttgcaaactc atctagaaac tccttcaac tttgatagtt atatgttgga aaagtcaac       240 atggttaacg aggcgcttga tgcatctgtc ccactaaaag acccaatcaa atccatgaa      300 tccatgagat actctttatt ggcaggcggt aagagaatca gaccaatgat gtgtattgca    360
gcctgcgaaa tagtcggagg taatatcctt aacgccatgc cagccgcatg tgccgtggaa    420
atgattcata ctatgtcttt ggtgcatgac gatcttccat gtatggataa tgatgacttc     480
agaagaggta aacctatttc acacaaggtc tacggggagg aaatggcagt attgaccggc    540
gatgctttac taagtttatc tttcgaacat atagctactg ctacaaaggg tgtatcaaag    600
gatagaatcg tcagagctat aggggagttg gcccgttcag ttggctccga aggtttagtg    660
gctggacaag ttgtagatat cttgtcagag ggtgctgatg ttggattaga tcacctagaa    720
tacattcaca tccacaaaac agcaatgttg cttgagtcct cagtagttat tggcgctatc    780
atgggaggag gatctgatca gcagatcgaa aagttgagaa aattcgctag atctattggt     840
ctactattcc aagttgtgga tgacatttg gatgttacaa aatctaccga agagttgggg    900
aaaacagctg gtaaggattt gttgacagat aagacaactt acccaaagtt gttaggtata    960
gaaaagtcca gagaatttgc cgaaaaactt aacaaggaag cacaagagca attaagtggc   1020
tttgatagac gtaaggcagc tcctttgatc gcgttagcca actacaatgc gtaccgtcaa   1080
aattga                                                              1086
```

<210> SEQ ID NO 126
<211> LENGTH: 1029
<212> TYPE: DNA
<213> ORGANISM: Artificial Sequence
<220> FEATURE:
<223> OTHER INFORMATION: Synthetic oligonucleotide

<400> SEQUENCE: 126

```
atggctgagc aacaaatatc taacttgctg tctatgtttg atgcttcaca tgctagtcag      60
aaattagaaa ttactgtcca aatgatggac ataccatt acagagaaac gcctccagat      120
tcctcatctt ctgaaggcgg ttcattgtct agatacgacg agagaagagt ctctttgcct      180
ctcagtcata atgctgcctc tccagatatt gtatcacaac tatgttttc cactgcaatg      240
tcttcagagt tgaatcacag atggaaatct caaagattaa aggtggccga ttctccttac      300
aactatatcc taacattacc atcaaaagga attagaggtg cctttatcga ttccctgaac      360
gtatggttgg aggttccaga ggatgaaaca tcagtcatca aggaagttat tggtatgctc      420
cacaactctt cattaatcat tgatgacttc aagataatt ctccacttag aagaggaaag      480
ccatctaccc atacagtctt cggccctgcc caggctatca atactgctac ttacgttata      540
gttaaagcaa tcgaaaagat acaagacata gtgggacacg atgcattggc agatgttacg      600
ggtactatta caactatttt ccaaggtcag gccatggact tgtggtggac agcaaatgca      660
atcgttccat caatacagga atacttactt atggtaaacg ataaaaccgg tgctctcttt      720
agactgagtt tggagttgtt agctctgaat tccgaagcca gtatttctga ctctgcttta      780
gaaagtttat ctagtgctgt ttccttgcta ggtcaatact tccaaatcag agacgactat      840
atgaacttga tcgataacaa gtatacagat cagaaaggct tctgcgaaga tcttgatgaa      900
ggcaagtact cactaacact tattcatgcc ctccaaactg attcatccga tctactgacc      960
aacatccttt caatgagaag agtgcaagga aagttaacgg cacaaaagag atgttggttc     1020
tggaaatga                                                              1029
```

<210> SEQ ID NO 127
<211> LENGTH: 903
<212> TYPE: DNA
<213> ORGANISM: Artificial Sequence
<220> FEATURE:
<223> OTHER INFORMATION: Synthetic oligonucleotide

<400> SEQUENCE: 127

```
atggaaaaga ctaaggagaa agcagaacgt atcttgctgg agccatacag atacttatta      60
caactaccag gaaagcaagt ccgttctaaa ctatcacaag cgttcaatca ctggttaaaa     120
gttcctgaag ataagttaca aatcattatt gaagtcacag aaatgctaca caatgcttct     180
ttactgatcg atgatataga ggattcttcc aaactgagaa gaggttttcc tgtcgctcat     240
tccatatacg gggtaccaag tgtaatcaac tcagctaatt acgtctactt cttgggattg     300
gaaaaagtat tgacattaga tcatccagac gctgtaaagc tattcaccag acaacttctt     360
gaattgcatc aaggtcaagg tttggatatc tattggagag acacttatac ttgcccaaca     420
gaagaggagt acaaagcaat ggttctacaa aagactggcg gtttgttcgg acttgccgtt     480
ggtctgatgc aacttttctc tgattacaag gaggacttaa agcctctgtt ggataccttg     540
ggcttgtttt tccagattag agatgactac gctaacttac attcaaagga atattcagaa     600
acaaatcat tctgtgaaga tttgactgaa gggaagttta gttttccaac aatccacgcc     660
atttggtcaa gaccagaatc tactcaagtg caaaacattc tgcgtcagag aacagagaat     720
```

| | |
|---|---|
| attgacatca aaaagtattg tgttcagtac ttggaagatg ttggttcttt tgcttacaca | 780 |
| agacatacac ttagagaatt agaggcaaaa gcatacaagc aaatagaagc ctgtggaggc | 840 |
| aatccttctc tagtggcatt ggttaaacat ttgtccaaaa tgttcaccga ggaaaacaag | 900 |
| taa | 903 |

<210> SEQ ID NO 128
<211> LENGTH: 1020
<212> TYPE: DNA
<213> ORGANISM: Artificial Sequence
<220> FEATURE:
<223> OTHER INFORMATION: Synthetic oligonucleotide

<400> SEQUENCE: 128

| | |
|---|---|
| atggcaagat tctattttct taacgcacta ttgatggtta tctcattaca atcaactaca | 60 |
| gccttcactc cagctaaact tgcttatcca acaacaacaa cagctctaaa tgtcgcctcc | 120 |
| gccgaaactt ctttcagtct agatgaatac ttggcctcta agataggacc tatagagtct | 180 |
| gccttggaag catcagtcaa atccagaatt ccacagaccg ataagatctg cgaatctatg | 240 |
| gcctactctt tgatggcagg aggcaagaga attagaccag tgttgtgtat cgctgcatgt | 300 |
| gagatgttcg gtggatccca agatgtcgct atgcctactg ctgtggcatt agaaatgata | 360 |
| cacacaatgt ctttgattca tgatgatttg ccatccatgg ataacgatga cttgagaaga | 420 |
| ggtaaaccaa caaaccatgt cgtttcggc gaagatgtag ctattcttgc aggtgactct | 480 |
| ttattgtcaa cttccttcga gcacgtcgct agagaaacaa aaggagtgtc agcagaaaag | 540 |
| atcgtggatg ttatcgctag attaggcaaa tctgttggtg ccgagggcct tgctggcggt | 600 |
| caagttatgg acttagaatg tgaagctaaa ccaggtacca cattagacga cttgaaatgg | 660 |
| attcatatcc ataaaaccgc tacattgtta caagttgctg tagcttctgg tgcagttcta | 720 |
| ggtggtgcaa ctcctgaaga ggttgctgca tgcgagttgt ttgctatgaa tataggtctt | 780 |
| gcctttcaag ttgccgacga tatccttgat gtaaccgctt catcagaaga tttgggtaaa | 840 |
| actgcaggca agatgaagc tactgataag acaacttacc caaagttatt aggattagaa | 900 |
| gagagtaagg catacgcaag acaactaatc gatgaagcca aggaaagttt ggctcctttt | 960 |
| ggagatagag ctgccccttt attggccatt gcagatttca ttattgatag aaagaattga | 1020 |

<210> SEQ ID NO 129
<211> LENGTH: 1068
<212> TYPE: DNA
<213> ORGANISM: Artificial Sequence
<220> FEATURE:
<223> OTHER INFORMATION: Synthetic oligonucleotide

<400> SEQUENCE: 129

| | |
|---|---|
| atgcacttag caccacgtag agtccctaga ggtagaagat caccacctga cagagttcct | 60 |
| gaaagacaag gtgccttggg tagaagacgt ggagctggct ctactggctg tgcccgtgct | 120 |
| gctgctggtg ttcaccgtag aagaggagga ggcgaggctg atccatcagc tgctgtgcat | 180 |
| agaggctggc aagccggtgg tggcaccggt ttgcctgatg aggtggtgtc taccgcagcc | 240 |
| gccttagaaa tgtttcatgc ttttgcttta atccatgatg atatcatgga tgatagtgca | 300 |
| actagaagag gctccccaac tgttcacaga gccctagctg atcgtttagg cgctgctctg | 360 |
| gacccagatc aggccggtca actaggagtt tctactgcta tcttggttgg agatctggct | 420 |
| ttgacatggt ccgatgaatt gttatacgct ccattgactc cacatagact ggcagcagta | 480 |

```
ctaccattgg taacagctat gagagctgaa accgttcatg gccaatatct tgatataact     540
agtgctagaa gacctgggac cgatacttct cttgcattga aatagccag atataagaca      600 gcagcttaca caatggaacg tccactgcac attggtgcag ccctggctgg ggcaagacca     660
gaactattag cagggctttc agcatacgcc ttgccagctg gagaagcctt ccaattggca     720
gatgacctgc taggcgtctt cggtgatcca agacgtacag ggaaacctga cctagatgat     780
cttagaggtg gaaagcatac tgtcttagtc gccttggcaa gagaacatgc cactccagaa     840
cagagacaca cattggatac attattgggt acaccaggtc ttgatagaca aggcgcttca     900
agactaagat gcgtattggt agcaactggt gcaagagccg aagccgaaag acttattaca     960
gagagaagag atcaagcatt aactgcattg aacgcattaa cactgccacc tcctttagct    1020
gaggcattag caagattgac attagggtct acagctcatc ctgcctaa                 1068
```

<210> SEQ ID NO 130
<211> LENGTH: 993
<212> TYPE: DNA
<213> ORGANISM: Artificial Sequence
<220> FEATURE:
<223> OTHER INFORMATION: Synthetic oligonucleotide

<400> SEQUENCE: 130

```
atgtcatatt tcgataacta cttcaatgag atagttaatt ccgtgaacga catcattaag      60
tcttacatct ctggcgacgt accaaaacta tacgaagcct cctaccattt gtttacatca     120
ggaggaaaga gactaagacc attgatcctt acaatttctt ctgatctttt cggtggacag     180
agagaaagag catactatgc tggcgcagca atcgaagttt gcacacatt cactttggtt      240 cacgatgata tcatggatca agataacatt cgtagaggtc ttcctactgt acatgtcaag     300
tatggcctac ctttggccat tttagctggt gacttattgc atgcaaaagc ctttcaattg     360
ttgactcagg cattgagagg tctaccatct gaaactatca tcaaggcgtt tgatatcttt     420
acaagatcta tcattatcat atcagaaggt caagctgtcg atatgaatt cgaagataga     480 attgatatca aggaacaaga gtatttggat atgatatctc gtaaaaccgc tgccttattc     540
tcagcttctt cttccattgg ggcgttgata gctggagcta atgataacga tgtgagatta     600
atgtccgatt tcggtacaaa tcttgggatc gcatttcaaa ttgtagatga tatacttggt     660
ttaacagctg atgaaaaaga gctaggaaaa cctgtttttca gtgatatcag agaaggtaaa     720
aagaccatat tagtcattaa gacttttagaa ttgtgtaagg aagacgagaa aaagattgtg    780
ttaaaagcgc taggcaacaa gtcagcatca aaggaagagt tgatgagttc tgctgacata     840
atcaaaaagt actcattgga ttacgcctac aacttagctg agaaatacta caaaaacgcc     900
atcgattctc taaatcaagt ttcaagtaaa agtgatattc cagggaaggc attgaaatat     960
cttgctgaat tcaccatcag aagacgtaag taa                                  993
```

<210> SEQ ID NO 131
<211> LENGTH: 894
<212> TYPE: DNA
<213> ORGANISM: Artificial Sequence
<220> FEATURE:
<223> OTHER INFORMATION: Synthetic oligonucleotide

<400> SEQUENCE: 131

```
atggtcgcac aaactttcaa cctggatacc tacttatccc aaagacaaca acaagttgaa      60
gaggccctaa gtgctgctct tgtgccagct tatcctgaga gaatatacga agctatgaga     120 tactcccctcc tggcaggtgg caaaagatta agacctatct tatgtttagc tgcttgcgaa    180
```

```
ttggcaggtg gttctgttga acaagccatg ccaactgcgt gtgcacttga aatgatccat    240
acaatgtcac taattcatga tgacctgcca gccatggata cgatgatttt cagaagagga    300
aagccaacta atcacaaggt gttcggggaa gatatagcca tcttagcggg tgatgcgctt    360
ttagcttacg cttttgaaca tattgcttct caaacaagag gagtaccacc tcaattggtg    420
ctacaagtta ttgctagaat cggacacgcc gttgctgcaa caggcctcgt tggaggccaa    480
gtcgtagacc ttgaatctga aggtaaagct atttccttag aaacattgga gtatattcac    540
tcacataaga ctggagcctt gctggaagca tcagttgtct caggcggtat tctcgcaggg    600
gcagatgaag agcttttggc cagattgtct cattacgcta gagatatagg cttggctttt    660
caaatcgtcg atgatatcct ggatgttact gctacatctg aacagttggg gaaaaccgct    720
ggtaaagacc aggcagccgc aaaggcaact tatccaagtc tattgggttt agaagcctct    780
agacagaaag cggaagagtt gattcaatct gctaaggaag ccttaagacc ttacggttca    840
caagcagagc cactcctagc gctggcagac ttcatcacac gtcgtcagca ttaa          894
```

<210> SEQ ID NO 132
<211> LENGTH: 1116
<212> TYPE: DNA
<213> ORGANISM: Artificial Sequence
<220> FEATURE:
<223> OTHER INFORMATION: Synthetic oligonucleotide

<400> SEQUENCE: 132

```
atggcctctg ttactttggg ttcctggatc gtcgtccacc accataacca tcaccatcca     60
tcatctatcc taactaaatc tcgttcaaga tcctgtccta ttacactaac caaaccaatc    120
tcttttcgtt caaagagaac agtttcctct agtagttcta tcgtgtcctc tagtgtcgtc    180
actaaggaag acaatctgag acagtctgaa ccttcttcct ttgatttcat gtcatatatc    240
attactaagg cagaactagt gaataaggct cttgattcag cagttccatt aagagagcca    300
ttgaaaatcc atgaagcaat gagatactct cttctagctg gcgggaagag agtcagacct    360
gtactctgca tagcagcgtg cgaattagtt ggtggcgagg aatcaaccgc tatgcctgcc    420
gcttgtgctg tagaaatgat tcatacaatg tcactgatac acgatgatt t gccatgtatg    480 gataacgatg atctgagaag gggtaagcca actaaccata aggttttcgg cgaagatgtt    540
gccgtcttag ctggtgatgc tttgttatct ttcgcgttcg aacatttggc atccgcaaca    600
tcaagtgatg ttgtgtcacc agtaagagta gttagagcag ttggagaact ggctaaagct    660
attggaactg agggtttagt tgcaggtcaa gtcgtcgata tctcttccga aggtcttgat    720
ttgaatgatg taggtcttga acatctcgaa ttcatccatc ttcacaagac agctgcactt    780
ttagaagcca gtgcggttct cggcgcaatt gttggcggag ggagtgatga cgaaattgag    840
agattgagga agtttgctag atgtatagga ttactgttcc aagtagtaga cgatatacta    900
gatgtgacaa agtcttccaa agagttggga aaaacagctg gtaaagattt gattgccgac    960
aaattgacct accctaagat tatggggcta gaaaaatcaa gagaatttgc cgagaaactc   1020
aatagagagg cgcgtgatca actgttgggt ttcgattctg ataaagttgc accactctta   1080
gccttagcca actacatcgc ttacagacaa aactaa                              1116
```

<210> SEQ ID NO 133
<211> LENGTH: 2340
<212> TYPE: DNA
<213> ORGANISM: Artificial Sequence
<220> FEATURE:

<223> OTHER INFORMATION: Synthetic oligonucleotide

<400> SEQUENCE: 133

```
gcacagcaca catcagaatc cgcagctgtc gcaaagggca gcagtttgac ccctatagtg        60
agaactgacg ctgagtcaag gagaacaaga tggccaaccg atgacgatga cgccgaacct       120
ttagtggatg agatcagggc aatgcttact tccatgtctg atggtgacat ttccgtgagc       180
gcatacgata cagcctgggt cggattggtt ccaagattag acggcggtga aggtcctcaa       240
tttccagcag ctgtgagatg gataagaaat aaccagttgc ctgacggaag ttggggcgat       300
gccgcattat tctctgccta tgacaggctt atcaatacccc ttgcctgcgt tgtaactttg       360
acaaggtggt ccctagaacc agagatgaga ggtagaggac tatcttttt gggtaggaac       420
atgtggaaat tagcaactga agatgaagag tcaatgccta ttggcttcga attagcattt       480
ccatctttga tagagcttgc taagagccta ggtgtccatg acttcccttta tgatcaccag       540
gccctacaag gaatctactc ttcaagagag atcaaaatga agaggattcc aaaagaagtg       600
atgcataccg ttccaacatc aatattgcac agtttggagg gtatgcctgg cctagattgg       660
gctaaactac ttaaactaca gagcagcgac ggaagttttt tgttctcacc agctgccact       720
gcatatgctt aatgaatac cggagatgac aggtgtttta gctacatcga tagaacagta       780
aagaaattca acggcggcgt ccctaatgtt tatccagtgg atctatttga acatatttgg       840
gccgttgata gacttgaaag attaggaatc tccaggtact tccaaaagga gatcgaacaa       900
tgcatggatt atgtaaacag gcattggact gaggacggta tttgttgggc aaggaactct       960
gatgtcaaag aggtggacga cacagctatg gcctttagac ttcttaggtt gcacggctac      1020
agcgtcagtc ctgatgtgtt taaaaacttc gaaaaggacg gtgaattttt cgcatttgtc      1080
ggacagtcta atcaagctgt taccggtatg tacaacttaa acagagcaag ccagatatcc      1140
ttcccaggcg aggatgtgct tcatagagct ggtgccttct catatgagtt cttgaggaga      1200
aaagaagcag agggagcttt gagggacaag tggatcattt ctaaagatct acctggtgaa      1260
gttgtgtata ctttggattt tccatggtac ggcaacttac ctagagtcga ggccagagac      1320
tacctagagc aatacggagg tggtgatgac gtttggattg caagacatt gtataggatg      1380
ccacttgtaa acaatgatgt atatttggaa ttggcaagaa tggatttcaa ccactgccag      1440
gctttgcatc agttagagtg gcaaggacta aaaagatggt atactgaaaa taggttgatg      1500
gactttggtg tcgcccaaga agatgccctt agagcttatt ttcttgcagc cgcatctgtt      1560
tacgagcctt gtagagctgc cgagaggctt gcatgggcta gagccgcaat actagctaac      1620
gccgtgagca cccacttaag aaatagccca tcattcagag aaaggttaga gcattctctt      1680
aggtgtagac ctagtgaaga gacagatggc tcctggttta actcctcaag tggctctgat      1740
gcagttttag taaaggctgt cttaagactt actgattcat tagccaggga agcacagcca      1800
atccatggag gtgacccaga agatattata cacaagttgt taagatctgc ttgggccgag      1860
tgggttaggg aaaaggcaga cgctgccgat agcgtgtgca atggtagttc tgcagtagaa      1920
caagagggat caagaatggt ccatgataaa cagacctgtc tattattggc tagaatgatc      1980
gaaatttctg ccggtagggc agctggtgaa gcagccagtg aggacggcga tagaagaata      2040
attcaattaa caggctccat ctgcgacagt cttaagcaaa aaatgctagt ttcacaggac      2100
cctgaaaaaa atgaagagat gatgtctcac gtggatgacg aattgaagtt gaggattaga      2160
gagttcgttc aatatttgct tagactaggt gaaaaaaaga ctggatctag cgaaaccagg      2220
caaacatttt taagtatagt gaaatcatgt tactatgctg ctcattgccc acctcatgtc      2280
```
gttgatagac acattagtag agtgattttc gagccagtaa gtgccgcaaa gtaaccgcgg    2340

<210> SEQ ID NO 134
<211> LENGTH: 777
<212> TYPE: PRT
<213> ORGANISM: Zea mays

<400> SEQUENCE: 134

```
Ala Gln His Thr Ser Glu Ser Ala Ala Val Ala Lys Gly Ser Ser Leu
1               5                   10                  15

Thr Pro Ile Val Arg Thr Asp Ala Glu Ser Arg Arg Thr Arg Trp Pro
            20                  25                  30

Thr Asp Asp Asp Ala Glu Pro Leu Val Asp Glu Ile Arg Ala Met
        35                  40                  45

Leu Thr Ser Met Ser Asp Gly Asp Ile Ser Val Ser Ala Tyr Asp Thr
50                  55                  60

Ala Trp Val Gly Leu Val Pro Arg Leu Asp Gly Gly Glu Gly Pro Gln
65                  70                  75                  80

Phe Pro Ala Ala Val Arg Trp Ile Arg Asn Asn Gln Leu Pro Asp Gly
                85                  90                  95

Ser Trp Gly Asp Ala Ala Leu Phe Ser Ala Tyr Asp Arg Leu Ile Asn
            100                 105                 110

Thr Leu Ala Cys Val Val Thr Leu Thr Arg Trp Ser Leu Glu Pro Glu
        115                 120                 125

Met Arg Gly Arg Gly Leu Ser Phe Leu Gly Arg Asn Met Trp Lys Leu
    130                 135                 140

Ala Thr Glu Asp Glu Glu Ser Met Pro Ile Gly Phe Glu Leu Ala Phe
145                 150                 155                 160

Pro Ser Leu Ile Glu Leu Ala Lys Ser Leu Gly Val His Asp Phe Pro
                165                 170                 175

Tyr Asp His Gln Ala Leu Gln Gly Ile Tyr Ser Ser Arg Glu Ile Lys
            180                 185                 190

Met Lys Arg Ile Pro Lys Glu Val Met His Thr Val Pro Thr Ser Ile
        195                 200                 205

Leu His Ser Leu Glu Gly Met Pro Gly Leu Asp Trp Ala Lys Leu Leu
    210                 215                 220

Lys Leu Gln Ser Ser Asp Gly Ser Phe Leu Phe Ser Pro Ala Ala Thr
225                 230                 235                 240

Ala Tyr Ala Leu Met Asn Thr Gly Asp Asp Arg Cys Phe Ser Tyr Ile
                245                 250                 255

Asp Arg Thr Val Lys Lys Phe Asn Gly Gly Val Pro Asn Val Tyr Pro
            260                 265                 270

Val Asp Leu Phe Glu His Ile Trp Ala Val Asp Arg Leu Glu Arg Leu
        275                 280                 285

Gly Ile Ser Arg Tyr Phe Gln Lys Glu Ile Glu Gln Cys Met Asp Tyr
    290                 295                 300

Val Asn Arg His Trp Thr Glu Asp Gly Ile Cys Trp Ala Arg Asn Ser
305                 310                 315                 320

Asp Val Lys Glu Val Asp Asp Thr Ala Met Ala Phe Arg Leu Leu Arg
                325                 330                 335

Leu His Gly Tyr Ser Val Ser Pro Asp Val Phe Lys Asn Phe Glu Lys
            340                 345                 350

Asp Gly Glu Phe Phe Ala Phe Val Gly Gln Ser Asn Gln Ala Val Thr
        355                 360                 365
```

```
Gly Met Tyr Asn Leu Asn Arg Ala Ser Gln Ile Ser Phe Pro Gly Glu
    370                 375                 380

Asp Val Leu His Arg Ala Gly Ala Phe Ser Tyr Glu Phe Leu Arg Arg
385                 390                 395                 400

Lys Glu Ala Glu Gly Ala Leu Arg Asp Lys Trp Ile Ile Ser Lys Asp
                405                 410                 415

Leu Pro Gly Glu Val Val Tyr Thr Leu Asp Phe Pro Trp Tyr Gly Asn
            420                 425                 430

Leu Pro Arg Val Glu Ala Arg Asp Tyr Leu Glu Gln Tyr Gly Gly Gly
        435                 440                 445

Asp Asp Val Trp Ile Gly Lys Thr Leu Tyr Arg Met Pro Leu Val Asn
    450                 455                 460

Asn Asp Val Tyr Leu Glu Leu Ala Arg Met Asp Phe Asn His Cys Gln
465                 470                 475                 480

Ala Leu His Gln Leu Glu Trp Gln Gly Leu Lys Arg Trp Tyr Thr Glu
                485                 490                 495

Asn Arg Leu Met Asp Phe Gly Val Ala Gln Glu Asp Ala Leu Arg Ala
            500                 505                 510

Tyr Phe Leu Ala Ala Ser Val Tyr Glu Pro Cys Arg Ala Ala Glu
        515                 520                 525

Arg Leu Ala Trp Ala Arg Ala Ala Ile Leu Ala Asn Ala Val Ser Thr
    530                 535                 540

His Leu Arg Asn Ser Pro Ser Phe Arg Glu Arg Leu Glu His Ser Leu
545                 550                 555                 560

Arg Cys Arg Pro Ser Glu Glu Thr Asp Gly Ser Trp Phe Asn Ser Ser
                565                 570                 575

Ser Gly Ser Asp Ala Val Leu Val Lys Ala Val Leu Arg Leu Thr Asp
            580                 585                 590

Ser Leu Ala Arg Glu Ala Gln Pro Ile His Gly Gly Asp Pro Glu Asp
        595                 600                 605

Ile Ile His Lys Leu Leu Arg Ser Ala Trp Ala Glu Trp Val Arg Glu
    610                 615                 620

Lys Ala Asp Ala Ala Asp Ser Val Cys Asn Gly Ser Ser Ala Val Glu
625                 630                 635                 640

Gln Glu Gly Ser Arg Met Val His Asp Lys Gln Thr Cys Leu Leu Leu
                645                 650                 655

Ala Arg Met Ile Glu Ile Ser Ala Gly Arg Ala Ala Gly Glu Ala Ala
            660                 665                 670

Ser Glu Asp Gly Asp Arg Arg Ile Ile Gln Leu Thr Gly Ser Ile Cys
        675                 680                 685

Asp Ser Leu Lys Gln Lys Met Leu Val Ser Gln Asp Pro Glu Lys Asn
    690                 695                 700

Glu Glu Met Met Ser His Val Asp Asp Glu Leu Lys Leu Arg Ile Arg
705                 710                 715                 720

Glu Phe Val Gln Tyr Leu Leu Arg Leu Gly Glu Lys Lys Thr Gly Ser
                725                 730                 735

Ser Glu Thr Arg Gln Thr Phe Leu Ser Ile Val Lys Ser Cys Tyr Tyr
            740                 745                 750

Ala Ala His Cys Pro Pro His Val Val Asp Arg His Ile Ser Arg Val
        755                 760                 765

Ile Phe Glu Pro Val Ser Ala Ala Lys
    770                 775
```

<210> SEQ ID NO 135
<211> LENGTH: 1555
<212> TYPE: DNA
<213> ORGANISM: Artificial Sequence
<220> FEATURE:
<223> OTHER INFORMATION: Synthetic oligonucleotide

<400> SEQUENCE: 135

| | | | | | |
|---|---|---|---|---|---|
| atggcggaac | aacaaaagat | caagaaatca | ccacacgttc | tactcatccc | attcccttta | 60 |
| caaggccata | taaacccttt | catccagttt | ggcaaacgat | taatctccaa | aggtgtcaaa | 120 |
| acaacacttg | ttaccaccat | ccacaccta | aactcaaccc | taaaccacag | taacaccacc | 180 |
| accacctcca | tcgaaatcca | agcaatttcc | gatggttgtg | atgaaggcgg | ttttatgagt | 240 |
| gcaggagaat | catatttgga | aacattcaaa | caagttgggt | ctaaatcact | agctgactta | 300 |
| atcaagaagc | ttcaaagtga | aggaaccaca | attgatgcaa | tcatttatga | ttctatgact | 360 |
| gaatgggttt | tagatgttgc | aattgagttt | ggaatcgatg | gtggttcgtt | tttcactcaa | 420 |
| gcttgtgttg | taaacagctt | atattatcat | gttcataagg | gtttgatttc | tttgccattg | 480 |
| ggtgaaactg | tttcggttcc | tggatttcca | gtgcttcaac | ggtgggagac | accgttaatt | 540 |
| ttgcagaatc | atgagcaaat | acagagccct | tggtctcaga | tgttgtttgg | tcagtttgct | 600 |
| aatattgatc | aagcacgttg | ggtcttcaca | aatagttttt | acaagctcga | ggaagaggta | 660 |
| atagagtgga | cgagaaagat | atggaacttg | aaggtaatcg | gccaacact | tccatccatg | 720 |
| taccttgaca | aacgacttga | tgatgataaa | gataacggat | ttaatctcta | caaagcaaac | 780 |
| catcatgagt | gcatgaactg | gttagacgat | aagccaaagg | aatcagttgt | ttacgtagca | 840 |
| tttggtagcc | tggtgaaaca | tggacccgaa | caagtggaag | aaatcacacg | ggctttaata | 900 |
| gatagtgatg | tcaacttctt | gtgggttatc | aaacataaag | aagagggaaa | gctcccagaa | 960 |
| aatctttcgg | aagtaataaa | aaccggaaag | ggtttgattg | tagcatggtg | caaacaattg | 1020 |
| gatgtgttag | cacacgaatc | agtaggatgc | tttgttacac | attgtgggtt | caactcaact | 1080 |
| cttgaagcaa | taagtcttgg | agtccccgtt | gttgcaatgc | ctcaattttc | ggatcaaact | 1140 |
| acaaatgcca | agcttctaga | tgaaattttg | ggtgttggag | ttagagttaa | ggctgatgag | 1200 |
| aatgggatag | tgagaagagg | aaatcttgcg | tcatgtatta | agatgattat | ggaggaggaa | 1260 |
| agaggagtaa | taatccgaaa | gaatgcggta | aaatggaagg | attggctaa | agtagccgtt | 1320 |
| catgaaggtg | gtagctcaga | caatgatatt | gtcgaatttg | taagtgagct | aattaaggct | 1380 |
| taaatttttg | ttgctttgta | ttttatgtgt | tatggttttt | tgatttagat | gtattcaatt | 1440 |
| aatattgaat | cataactaaa | ttcaagatta | ttgtttgtaa | tattctttgt | cctaaaattt | 1500 |
| tgcgacttaa | aacctttagt | ttataaaaag | aaattagaaa | atactattgc | acgga | 1555 |

<210> SEQ ID NO 136
<211> LENGTH: 2409
<212> TYPE: DNA
<213> ORGANISM: Artificial Sequence
<220> FEATURE:
<223> OTHER INFORMATION: Synthetic oligonucleotide

<400> SEQUENCE: 136

| | | | | | |
|---|---|---|---|---|---|
| atgtctcttc | agtatcatgt | tctaaactcc | attccaagta | caacctttct | cagttctact | 60 |
| aaaacaacaa | tatcttcttc | tttccttacc | atctcaggat | ctcctctcaa | tgtcgctaga | 120 |
| gacaaatcca | gaagcggttc | catacattgt | tcaaagcttc | gaactcaaga | atacattaat | 180 |
| tctcaagagg | ttcaacatga | tttgcctcta | atacatgagt | ggcaacagct | tcaaggagaa | 240 |

```
gatgctcctc agattagtgt tggaagtaat agtaatgcat tcaaagaagc agtgaagagt      300
gtgaaaacga tcttgagaaa cctaacggac ggggaaatta cgatatcggc ttacgataca      360
gcttgggttg cattgatcga tgccggagat aaaactccgg cgtttccctc cgccgtgaaa      420
tggatcgccg agaaccaact ttccgatggt tcttggggag atgcgtatct cttctcttat      480
catgatcgtc tcatcaatac ccttgcatgc gtcgttgctc taagatcatg aatctctttt      540
cctcatcaat gcaacaaagg aatcacgttt tccgggaaaa atattgggaa gctagaagac      600
gaaaatgatg agcatatgcc aatcggattc gaagtagcat tcccatcgtt gcttgagata      660
gctcgaggaa taaacattga tgtaccgtac gattctccgg tcttaaaaga tatatacgcc      720
aagaaagagc taaagcttac aaggatacca aaagagataa tgcacaagat accaacaaca      780
ttgttgcata gtttggaggg gatgcgtgat ttagattggg aaaagctctt gaaacttcaa      840
tctcaagacg gatctttcct cttctctcct tcctctaccg cttttgcatt catgcagacc      900
cgagacagta actgcctcga gtatttgcga aatgccgtca acgtttcaa tggaggagtt      960 cccaatgtct ttcccgtgga tcttttcgag cacatatgga tagtggatcg gttacaacgt     1020
ttagggatat cgagatactt tgaagaagag attaaagagt gtcttgacta tgtccacaga     1080
tattggaccg acaatggcat atgttgggct agatgttccc atgtccaaga catcgatgat     1140
acagccatgg catttaggct cttaagacaa catggatacc aagtgtccgc agatgtattc     1200
aagaactttg agaagaggg agagtttttc tgctttgtgg ggcaatcaaa ccaagcagta     1260
accggtatgt tcaacctata ccggcatca caattggcgt ttccaaggga agagatattg     1320
aaaaacgcca aagagttttc ttataattat ctgctagaaa aacgggagag agaggagttg     1380
attgataagt ggattataat gaaagactta cctggcgaga ttgggtttgc gttagagatt     1440
ccatggtacg caagcttgcc tcgagtagag acgagattct atattgatca atatggtgga     1500
gaaaacgacg tttggattgg caagactctt tataggatgc catacgtgaa caataatgga     1560
tatctggaat tagcaaaaca agattacaac aattgccaag ctcagcatca gctcgaatgg     1620
gacatattcc aaaagtggta tgaagaaaat aggttaagtg agtggggtgt gcgcagaagt     1680
gagcttctcg agtgttacta cttagcggct gcaactatat ttgaatcaga aaggtcacat     1740
gagagaatgg tttgggctaa gtcaagtgta ttggttaaag ccatttcttc ttcttttggg     1800
gaatcctctg actccagaag aagcttctcc gatcagtttc atgaatacat tgccaatgct     1860
cgacgaagtg atcatcactt taatgacagg aacatgagat tggaccgacc aggatcggtt     1920
caggccagtc ggcttgccgg agtgttaatc gggactttga atcaaatgtc ttttgacctt     1980
ttcatgtctc atggccgtga cgttaacaat ctcctctatc tatcgtgggg agattggatg     2040
gaaaaatgga actatatgg agatgaagga gaaggagagc tcatggtgaa gatgataatt     2100
ctaatgaaga acaatgacct aactaacttc ttcacccaca ctcacttcgt tcgtctcgcg     2160
gaaatcatca atcgaatctg tcttcctcgc caatacttaa aggcaaggag aaacgatgag     2220
aaggagaaga caataaagag tatggagaag gagatgggga aaatggttga gttagcattg     2280
tcggagagtg acacatttcg tgacgtcagc atcacgtttc ttgatgtagc aaaagcatt     2340 tactactttg ctttatgtgg cgatcatctc caaactcaca tctccaaagt cttgtttcaa     2400
aaagtctag                                                             2409
```

METHODS FOR IMPROVED PRODUCTION OF REBAUDIOSIDE D AND REBAUDIOSIDE M

BACKGROUND OF THE INVENTION

Field of the Invention

The invention disclosed herein relates generally to the field of recombinant production of steviol glycosides. Particularly, the invention provides methods for recombinant production of steviol glycoside and compositions containing steviol glycosides.

Description of Related Art

Sweeteners are well known as ingredients used most commonly in the food, beverage, or confectionary industries. The sweetener can either be incorporated into a final food product during production or for stand-alone use, when appropriately diluted or as a tabletop sweetener. Sweeteners include natural sweeteners such as sucrose, high fructose corn syrup, molasses, maple syrup, and honey and artificial sweeteners such as aspartame, saccharine and sucralose. Stevia extract is a natural sweetener that can be isolated and extracted from a perennial shrub, Stevia rebaudiana. Stevia is commonly grown in South America and Asia for commercial production of stevia extract. Stevia extract, purified to various degrees, is used commercially as a high intensity sweetener in foods and in blends or alone as a tabletop sweetener.

Extracts of the Stevia plant contain Rebaudiosides and other steviol glycosides that contribute to the sweet flavor, although the amount of each glycoside often varies among different production batches. Existing commercial products are predominantly Rebaudioside A with lesser amounts of other glycosides such as Rebaudioside C, D, and F. Stevia extracts can also contain contaminants such as plant-derived compounds that contribute to off-flavors or have other undesirable effects. These contaminants can be more or less problematic depending on the food system or application of choice. Potential contaminants include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, beta-sitosterol, alpha- and beta-amyrin, lupeol, beta-amryin acetate, pentacyclic triterpenes, centauredin, quercitin, epi-alpha-cadinol, carophyllenes and derivatives, beta-pinene, beta-sitosterol, and gibberellin.

As recovery and purification of steviol glycosides from the Stevia plant have proven to be labor intensive and inefficient, there remains a need for a recombinant production system that can produce high yields of desired steviol glycosides such as Rebaudioside D and Rebaudioside M with less plant-based contaminants, including but not limited to stevioside. Steviol glycoside-producing Saccharomyces cerevisiae strains as well as bio-conversion and biosynthesis in vitro are described in PCT Application Nos. PCT/US2012/050021 and PCT/US2011/038967, which are incorporated herein by reference in their entirety.

In nature, the Stevia uridine diphosphate dependent glycosyltransferase 76G1 (UGT76G1) catalyzes several glycosylation reactions on the steviol backbone, which leads to the production of steviol glycosides. Recently, it has been shown that UGT76G1 can convert 1,2-stevioside to Rebaudioside A and 1,2-bioside to Rebaudioside B (see Richman et al., 2005, The Plant Journal 41:56-67). Thus, there is a need in the art to identify reactions directed towards producing glycosylated Rebaudiosides by UGT76G1 or other UGT enzymes. Particularly, there is a need to explore or identify other reactions catalysed by UGT76G1 as well a need to increase UGT76G1's catalytic capability in order to produce higher yields of steviol glycosides such as Rebaudioside D and Rebaudioside M.

SUMMARY OF THE INVENTION

It is against the above background that the present invention provides certain advantages and advancements over the prior art.

In particular, the invention is directed to biosynthesis of Rebaudioside D and Rebaudioside M and Rebaudioside D and Rebaudioside M preparations from genetically modified cells.

In particular embodiments, the invention is directed to Rebaudioside D and Rebaudioside M preparations from genetically modified cells having significantly improved biosynthesis rates and yields.

This disclosure relates to the production of steviol glycosides. In particular, this disclosure relates to the production of steviol glycosides including Rebaudioside M: (2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl(1R,5R,9S,13R)-13-{[(2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl]oxy}-5,9-dimethyl-14-methylidenetetracyclo[11.2.1.$0^{1,10}$.$0^{4,9}$]hexadecane-5-carboxylate and Rebaudioside D: 4,5-dihydroxy-6-(hydroxymethyl)-3-{[3,4,5-trihydroxy-6-(hydroxymethyl)oxan-2-yl]oxy}oxan-2-yl 13-{[5-hydroxy-6-(hydroxymethyl)-3,4-bis({[3,4,5-trihydroxy-6-(hydroxymethyl) oxan-2-yl]oxy})oxan-2-yl]oxy}-5,9-dimethyl-14-methylidene tetracyclo[11.2.1.$0^{1,10}$.$0^{4,9}$]hexadecane-5-carboxylate by means not limited to in recombinant hosts such as recombinant microorganisms, through bioconversion, and in vitro.

Thus, in one aspect, the disclosure provides a recombinant host, for example, a microorganism, comprising one or more biosynthetic genes, wherein the expression of one or more biosynthetic genes results in production of steviol glycosides including Rebaudioside M and Rebaudioside D.

In particular, expression of one or more uridine 5'-diphospho (UDP) glycosyl transferases described herein, such as EUGT11, UGT74G1, UGT76G1, UGT85C2, and UGT91D2, facilitate production and accumulation of Rebaudioside M or Rebaudioside D in recombinant hosts or certain in vitro systems.

Although this invention disclosed herein is not limited to specific advantages or functionality, the invention provides a composition comprising from about 1% to about 99% w/w of Rebaudioside M, wherein the composition has a reduced level of Stevia-derived contaminants relative to a stevia extract, wherein at least one of said contaminants is a plant-derived compound. In certain instances, said plant-derived contaminating compound can, inter alia, contribute to off-flavors.

In some aspects, the composition comprising from about 1% to about 99% w/w of Rebaudioside M has less than 0.1% of Stevia-derived contaminants relative to a stevia extract, wherein at least one of said contaminants is a plant-derived compound. In certain instances, said plant-derived contaminating compound can, inter alia, contribute to off-flavors.

The invention further provides a food product comprising the composition as described above.

In some aspects, the food product is a beverage or a beverage concentrate.

The invention further provides a recombinant host cell that expresses:

(a) a recombinant gene encoding a GGPPS;
(b) a recombinant gene encoding an ent-copalyl diphosphate synthase (CDPS) polypeptide;
(c) a recombinant gene encoding a kaurene oxidase (KO) polypeptide;
(d) a recombinant gene encoding a kaurene synthase (KS) polypeptide;
(e) a recombinant gene encoding a steviol synthase (KAH) polypeptide;
(f) a recombinant gene encoding a cytochrome P450 reductase (CPR) polypeptide;
(g) a recombinant gene encoding a UGT85C2 polypeptide;
(h) a recombinant gene encoding a UGT74G1 polypeptide;
(i) a recombinant gene encoding a UGT76G1 polypeptide;
(j) a recombinant gene encoding a UGT91d2 polypeptide; and
(k) a recombinant gene encoding a EUGT11 polypeptide;
wherein at least one of said genes is a recombinant gene and wherein the cell produces Rebaudioside D, Rebaudioside M, Rebaudioside Q, and/or Rebaudioside I.

The invention further provides a recombinant host cell comprising exogenous nucleic acids comprising:

(a) a recombinant gene encoding a GGPPS;
(b) a recombinant gene encoding an ent-copalyl diphosphate synthase (CDPS) polypeptide;
(c) a recombinant gene encoding a kaurene oxidase (KO) polypeptide;
(d) a recombinant gene encoding a kaurene synthase (KS) polypeptide;
(e) a recombinant gene encoding a steviol synthase (KAH) polypeptide;
(f) a recombinant gene encoding a cytochrome P450 reductase (CPR) polypeptide;
(g) a recombinant gene encoding a UGT85C2 polypeptide;
(h) a recombinant gene encoding a UGT74G1 polypeptide;
(i) a recombinant gene encoding a UGT76G1 polypeptide;
(j) a recombinant gene encoding a UGT91d2 polypeptide; and
(k) a recombinant gene encoding a EUGT11 polypeptide;
wherein the cell produces Rebaudioside D, Rebaudioside M, Rebaudioside Q, and/or Rebaudioside I.

The invention further provides a recombinant host cell that expresses a GGPPS, an ent-copalyl diphosphate synthase (CDPS) polypeptide, a kaurene oxidase (KO) polypeptide, a kaurene synthase (KS) polypeptide; a steviol synthase (KAH) polypeptide, a cytochrome P450 reductase (CPR) polypeptide, a UGT74G1 polypeptide, a UGT76G1 polypeptide, a UGT91d2 polypeptide, and a EUGT11 polypeptide, wherein at least one of said polypeptides is encoded by an exogenous or heterologous gene having been introduced into said cell;

wherein the cell produces a di-glycosylated steviol glycoside (13-hydroxy kaur-16-en-18-oic acid, [2-O-β-D-glucopyranosyl-β-D-glucopyranosyl] ester) or a tri-glycosylated steviol glycoside (13-hydroxy kaur-16-en-18-oic acid; [2-O-β-D-glucopyranosyl-3-O-β-D-glucopyranosyl-β-D-glucopyranosyl] ester).

In some embodiments, targeted production of individual Rebaudiosides can be accomplished by controlling the relative levels of UDP-glycosyl transferase activities (see FIG. 1).

In some aspects, targeted production of individual Rebaudiosides can be accomplished by differential copy numbers of the UGT-encoding genes (see FIG. 1) in the recombinant cell, differential promoter strengths, and/or by utilizing mutants with increased specificity/activity towards the product of interest. For example, low levels of Rebaudioside D, E, and M will be formed if EUGT11 is expressed at low levels in comparison to the other UGTs, which would favor Rebaudioside A formation. High levels of EUGT11 expression result in production of more 19-O 1,2 diglucoside that can serve as substrate for UGT76G1 to form Rebaudioside M. In certain advantageous embodiments, additional copies or mutant versions of UGT76G1 in recombinant cells of the invention can improve the rate of Rebaudioside M formation from Rebaudioside D.

In some embodiments, UGT76G1 catalyzes glycosylation of steviol and steviol glycosides at the 19-0 position. Thus, in some embodiments, one or more of RebM, RebQ, RebI, di-glycosylated steviol glycoside (13-hydroxy kaur-16-en-18-oic acid, [2-O-β-D-glucopyranosyl-β-D-glucopyranosyl] ester), or tri-glycosylated steviol glycoside ((13-hydroxy kaur-16-en-18-oic acid; [2-O-β-D-glucopyranosyl-3-O-β-D-glucopyranosyl-β-D-glucopyranosyl] ester) are produced in a recombinant host expressing a recombinant gene encoding a UGT76G1 polypeptide, through bioconversion, or through catalysis by UGT76G1 in vitro. In some embodiments, UGT76G1 catalyzes the glycosylation of steviol and steviol glycosides at the 13-0 position and preferentially glycosylates steviol glycoside substrates that are 1,2-diglycosylated at the 13-0 position or mono-glycosylated at the 13-0 position. In some embodiments, UGT76G1 does not show a preference for the glycosylation state of the 19-0 position.

In some aspects, the GGPPS comprises *Synechococcus* sp. GGPPS set forth in SEQ ID NO:24.

In some aspects, the CDP polypeptide comprises a *Z. mays* CDPS polypeptide set forth in SEQ ID NO:13, wherein the polypeptide is lacking a chloroplast transit peptide.

In some aspects, the KO polypeptide comprises a KO polypeptide having 70% or greater identity to the amino acid sequence of the *S. rebaudiana* KO polypeptide set forth in SEQ ID NO:25.

In some aspects, the KS polypeptide comprises a KS polypeptide having 40% or greater identity to the amino acid sequence of the *A. thaliana* KS polypeptide set forth in SEQ ID NO:21.

In some aspects, the KAH polypeptide comprises a KAH polypeptide having 60% or greater identity to the *S. rebaudiana* KAH amino acid sequence set forth in SEQ ID NO:11.

In some aspects, the CPR polypeptide comprises a CPR polypeptide having 65% or greater identity to a *S. rebaudiana* CPR amino acid sequence set forth in SEQ ID NO:4, an *A. thaliana* CPR polypeptide of the amino acid sequence set forth in SEQ ID NO:9 or a combination thereof.

In some aspects, the UGT85C2 polypeptide comprises a UGT85C2 polypeptide having 55% or greater identity to the amino acid sequence set forth in SEQ ID NO:26.

In some aspects, the UGT74G1 polypeptide comprises a UGT74G1 polypeptide having 55% or greater identity to the amino acid sequence set forth in SEQ ID NO:19.

In some aspects, the UGT76G1 polypeptide comprises a UGT76G1 polypeptide having 50% or greater identity to the amino acid sequence set forth in SEQ ID NO:2.

In some aspects, the UGT91d2 polypeptide comprises a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof.

In some aspects, the EUGT11 polypeptide comprises a EUGT11 polypeptide having 65% or greater identity to the Os03g0702000 amino acid sequence set forth in SEQ ID NO:16.

In some aspects, the UGT76G1 polypeptide comprises one or more of the UGT76G1 polypeptide variants comprising: T55K, T55E, S56A, Y128S, Y128E, H155L, H155R, Q198R, S285R, S285T, S253W, S253G, T284R, T284G, S285G, K337E, K337P and L379V of SEQ ID NO:2.

In some aspects, the UGT76G1 polypeptide comprises one or more of the UGT76G1 polypeptide variants comprising: Q23G, Q23H, I26F, I26W, T146A, T146G, T146P, H155R, L257P, L257W, L257T, L257G, L257A, L257R, L257E, S283G and S283N of SEQ ID NO:2.

In some aspects, the recombinant host cell is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a *Saccharomycete*.

In some aspects, the yeast cell is a cell from *Saccharomyces cerevisiae* species.

The invention further provides the cell as disclosed herein that produces Rebaudioside D.

The invention further provides the cell as disclosed herein that produces Rebaudioside M, Rebaudioside Q or Rebaudioside I.

The invention further provides the cell as disclosed herein that produces the di-glycosylated steviol glycoside (13-hydroxy kaur-16-en-18-oic acid, [2-O-β-D-glucopyranosyl-β-D-glucopyranosyl] ester) or the tri-glycosylated steviol glycoside (13-hydroxy kaur-16-en-18-oic acid; [2-O-β-D-glucopyranosyl-3-O-β-D-glucopyranosyl-β-D-glucopyranosyl] ester).

In some aspects, the Rebaudioside D is produced in the cell as disclosed herein at a concentration of between about 1,000 mg/L and about 2,900 mg/L.

In some aspects, the Rebaudioside D and Rebaudioside M are produced in the cell as disclosed herein at a ratio of between about 1:1 to about 1.7:1.

In some aspects, the Rebaudioside M is produced in the cell as disclosed herein at a concentration of between about 600 mg/L and about 2,800 mg/L.

In some aspects, the Rebaudioside M and Rebaudioside D are produced in the cell as disclosed herein at a ratio of between about 0.6:1 to about 1.1:1.

The invention further provides a method of producing Rebaudioside D, Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl] ester) or tri-glycosylated steviol glycoside (13-hydroxy kaur-16-en-18-oic acid; [2-O-β-D-glucopyranosyl-3-O-β-D-glucopyranosyl-β-D-glucopyranosyl] ester), comprising:

(a) culturing a recombinant cell in a culture medium, under conditions wherein genes encoding a GGPPS; an ent-copalyl diphosphate synthase (CDPS) polypeptide; a kaurene oxidase (KO) polypeptide; a kaurene synthase (KS) polypeptide; a steviol synthase (KAH) polypeptide; a cytochrome P450 reductase (CPR) polypeptide; a UGT85C2 polypeptide; a UGT74G1 polypeptide; a UGT76G1 polypeptide; a UGT91d2 polypeptide; and a EUGT11 polypeptide are expressed, comprising inducing expression of said genes or constitutively expressing said genes; and (b) synthesizing Rebaudioside D, Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl] ester) or tri-glycosylated steviol glycoside (13-hydroxy kaur-16-en-18-oic acid; [2-O-β-D-glucopyranosyl-3-O-β-D-glucopyranosyl-β-D-glucopyranosyl] ester) in the cell; and optionally (c) isolating Rebaudioside D, Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl] ester) or tri-glycosylated steviol glycoside (13-hydroxy kaur-16-en-18-oic acid; [2-O-β-D-glucopyranosyl-3-O-β-D-glucopyranosyl-β-D-glucopyranosyl] ester).

In some aspects, Rebaudioside D is produced by a cell as disclosed herein.

In some aspects, Rebaudioside M, Rebaudioside Q or Rebaudioside I is produced by a cell as disclosed herein.

In some aspects, di-glycosylated steviol glycoside (13-hydroxy kaur-16-en-18-oic acid, [2-O-β-D-glucopyranosyl-β-D-glucopyranosyl] ester) or the tri-glycosylated steviol glycoside (13-hydroxy kaur-16-en-18-oic acid; [2-O-β-D-glucopyranosyl-3-O-β-D-glucopyranosyl-β-D-glucopyranosyl] ester) is produced by a cell as disclosed herein.

In some aspects, Rebaudioside D is produced at a concentration of between about 1,000 mg/L and about 2,900 mg/L.

In some aspects, Rebaudioside D and Rebaudioside M are produced at a ratio of between about 1:1 to about 1.7:1.

In some aspects, Rebaudioside M is produced at a concentration of between about 600 mg/L and about 2,800 mg/L.

In some aspects, Rebaudioside M and Rebaudioside D are produced at a ratio of between about 0.6:1 to about 1.1:1.

In some aspects, a cell for practicing the methods disclosed herein is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Atxula adeninivorans, Xanthophyllomyces dendrorhous* or *Candida albicans* species.

In some aspects, the yeast cell is a *Saccharomycete*.

In some aspects, the yeast cell is a cell from *Saccharomyces cerevisiae* species.

The invention further provides methods for producing Rebaudioside D, Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl] ester) or tri-glycosylated steviol glycoside (13-hydroxy kaur-16-en-18-oic acid; [2-O-β-D-glucopyranosyl-3-O-β-D-glucopyranosyl-β-D-glucopyranosyl] ester) through in vitro bioconversion of plant-derived or synthetic steviol or steviol glycosides using one or more UGT polypeptides.

In some aspects, said methods for producing Rebaudioside D or Rebaudioside M comprise using at least one UGT polypeptide that is:

a UGT85C2 polypeptide comprising a UGT85C2 polypeptide having 55% or greater identity to the amino acid sequence set forth in SEQ ID NO:26;

a UGT74G1 polypeptide comprising a UGT74G1 polypeptide having 55% or greater identity to the amino acid sequence set forth in SEQ ID NO:19;

a UGT76G1 polypeptide comprising a UGT76G1 polypeptide having 50% or greater identity to the amino acid sequence set forth in SEQ ID NO:2;

a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof; or a EUGT11 polypeptide comprising a EUGT11 polypeptide having 65% or greater identity to the Os03g0702000 amino acid sequence set forth in SEQ ID NO:16.

In some aspects, the steviol glycoside used for production of Rebaudioside D comprises stevioside, RebA, RebB, RebE or mixtures thereof.

In some aspects, the steviol glycoside used for production of Rebaudioside M comprises stevioside, RebA, RebB, RebE, RebD or mixtures thereof.

In some aspects, methods for producing Rebaudioside Q comprise using at least one UGT polypeptide that is:

a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; or a UGT76G1 polypeptide comprising a UGT76G1 polypeptide having 50% or greater identity to the amino acid sequence set forth in SEQ ID NO:2.

In some aspects, the steviol glycoside used for producing Rebaudioside Q comprises rubusoside, RebG or mixtures thereof.

In some aspects, methods for producing Rebaudioside I comprise using at least one UGT polypeptide that is:

a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2; a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15; or a combination thereof.

In some aspects, the steviol glycoside used for producing Rebaudioside I comprises 1,2-stevioside, RebA, or mixtures thereof.

In some aspects, methods for producing di-glycosylated steviol glycoside (13-hydroxy kaur-16-en-18-oic acid, [2-O-β-D-glucopyranosyl-β-D-glucopyranosyl] ester) comprise using at least one or UGT polypeptide that is:

a UGT74G1 polypeptide comprising a UGT74G1 polypeptide having 55% or greater identity to the amino acid sequence set forth in SEQ ID NO:19; or a EUGT11 polypeptide comprising a EUGT11 polypeptide having 65% or greater identity to the Os03g0702000 amino acid sequence set forth in SEQ ID NO:16.

In some aspects, the steviol glycoside used for producing di-glycosylated steviol glycoside (13-hydroxy kaur-16-en-18-oic acid, [2-O-β-D-glucopyranosyl-β-D-glucopyranosyl] ester) comprises steviol-19-O-glucoside.

In some aspects, methods for producing tri-glycosylated steviol glycoside (13-hydroxy kaur-16-en-18-oic acid; [2-O-β-D-glucopyranosyl-3-O-β-D-glucopyranosyl-β-D-glucopyranosyl] ester) comprise using at least one UGT polypeptide that is:

a UGT76G1 polypeptide comprising a UGT76G1 polypeptide having 50% or greater identity to the amino acid sequence set forth in SEQ ID NO:2; a UGT74G1 polypeptide comprising a UGT74G1 polypeptide having 55% or greater identity to the amino acid sequence set forth in SEQ ID NO:19; or a EUGT11 polypeptide comprising a EUGT11 polypeptide having 65% or greater identity to the Os03g0702000 amino acid sequence set forth in SEQ ID NO:16.

In some aspects, the steviol glycoside used for producing tri-glycosylated steviol glycoside (13-hydroxy kaur-16-en-18-oic acid; [2-O-β-D-glucopyranosyl-3-O-β-D-glucopyranosyl-β-D-glucopyranosyl] ester) comprises di-glycosylated steviol glycoside (13-hydroxy kaur-16-en-18-oic acid, [2-O-β-D-glucopyranosyl-β-D-glucopyranosyl] ester), steviol-19-O-glucoside, or mixtures thereof.

In some aspects, bioconversion methods as disclosed herein comprise enzymatic bioconversion or whole cell bioconversion.

In some aspects, a cell for practicing the methods disclosed herein is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a *Saccharomycete*.

In some aspects, the yeast cell is a cell from *Saccharomyces cerevisiae* species.

The invention further provides a recombinant host cell comprising exogenous nucleic acids comprising:

(a) a recombinant gene encoding a GGPPS;

(b) a recombinant gene encoding an ent-copalyl diphosphate synthase (CDPS) polypeptide;

(c) a recombinant gene encoding a kaurene oxidase (KO) polypeptide;

(d) a recombinant gene encoding a kaurene synthase (KS) polypeptide;

(e) a recombinant gene encoding a steviol synthase (KAH) polypeptide;

(f) a recombinant gene encoding a cytochrome P450 reductase (CPR) polypeptide; and/or (g) a one or more recombinant genes encoding a one or more UGT polypeptide;

wherein the cell produces Rebaudioside D, Rebaudioside M, Rebaudioside Q, or Rebaudioside I, di-glycosylated steviol glycoside (13-hydroxy kaur-16-en-18-oic acid, [2-O-β-D-glucopyranosyl-β-D-glucopyranosyl] ester) or tri-glycosylated steviol glycoside (13-hydroxy kaur-16-en-18-oic acid; [2-O-β-D-glucopyranosyl-3-O-β-D-glucopyranosyl-β-D-glucopyranosyl] ester).

In some aspects of said recombinant host cells, the GGPPS comprises *Synechococcus* sp. GGPPS set forth in SEQ ID NO:24; the CDP polypeptide comprises a *Z. mays* CDPS polypeptide set forth in SEQ ID NO:13, wherein the polypeptide is lacking a chloroplast transit peptide; the KO polypeptide comprises a KO polypeptide having 70% or greater identity to the amino acid sequence of the *S. rebaudiana* KO polypeptide set forth in SEQ ID NO:25; the KS polypeptide comprises a KS polypeptide having 40% or greater identity to the amino acid sequence of the *A. thaliana* KS polypeptide set forth in SEQ ID NO:21; the KAH polypeptide comprises a KAH polypeptide having 60% or greater identity to the *S. rebaudiana* KAH amino acid sequence set forth in SEQ ID NO:11; the CPR polypeptide comprises a CPR polypeptide having 65% or greater identity to a *S. rebaudiana* CPR amino acid sequence set forth in SEQ ID NO:4, an *A. thaliana* CPR polypeptide of the amino acid sequence set forth in SEQ ID NO:9 or a combination thereof.

In some aspects, the cell produces Rebaudioside D or Rebaudioside M, wherein the UGT polypeptide is at least one UGT polypeptide that is:

a UGT85C2 polypeptide comprising a UGT85C2 polypeptide having 55% or greater identity to the amino acid sequence set forth in SEQ ID NO:26;

a UGT74G1 polypeptide comprising a UGT74G1 polypeptide having 55% or greater identity to the amino acid sequence set forth in SEQ ID NO:19;

a UGT76G1 polypeptide comprising a UGT76G1 polypeptide having 50% or greater identity to the amino acid sequence set forth in SEQ ID NO:2;

a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof; or a EUGT11 polypeptide comprising a EUGT11 polypeptide having 65% or greater identity to the Os03g0702000 amino acid sequence set forth in SEQ ID NO:16.

In some aspects, the cell produces Rebaudioside Q, wherein the UGT polypeptide is at least one UGT polypeptide that is:

a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; or a UGT76G1 polypeptide comprising a UGT76G1 polypeptide having 50% or greater identity to the amino acid sequence set forth in SEQ ID NO:2.

In some aspects, the cell produces Rebaudioside I, wherein the UGT polypeptide is at least one UGT polypeptide that is:

a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2; a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15; or a combination thereof.

In some aspects, the cell produces di-glycosylated steviol glycoside (13-hydroxy kaur-16-en-18-oic acid, [2-O-β-D-glucopyranosyl-β-D-glucopyranosyl] ester), wherein the UGT polypeptide is at least one UGT polypeptide that is:

a UGT74G1 polypeptide comprising a UGT74G1 polypeptide having 55% or greater identity to the amino acid sequence set forth in SEQ ID NO:19; or a EUGT11 polypeptide comprising a EUGT11 polypeptide having 65% or greater identity to the Os03g0702000 amino acid sequence set forth in SEQ ID NO:16.

In some aspects, the cell produces tri-glycosylated steviol glycoside (13-hydroxy kaur-16-en-18-oic acid; [2-O-β-D-glucopyranosyl-3-O-β-D-glucopyranosyl-β-D-glucopyranosyl] ester), wherein the UGT polypeptide is at least one UGT polypeptide that is:

a UGT76G1 polypeptide comprising a UGT76G1 polypeptide having 50% or greater identity to the amino acid sequence set forth in SEQ ID NO:2; a UGT74G1 polypeptide comprising a UGT74G1 polypeptide having 55% or greater identity to the amino acid sequence set forth in SEQ ID NO:19; or a EUGT11 polypeptide comprising a EUGT11 polypeptide having 65% or greater identity to the Os03g0702000 amino acid sequence set forth in SEQ ID NO:16

In some aspects, the UGT76G1 polypeptide comprises one or more of the UGT76G1 polypeptide variants comprising: Q23G, Q23H, I26F, I26W, T146A, T146G, T146P, H155R, L257P, L257W, L257T, L257G, L257A, L257R, L257E, S283G and S283N of SEQ ID NO:2.

In some aspects, the UGT76G1 polypeptide comprises one or more of the UGT76G1 polypeptide variants comprising: T55K, T55E, S56A, Y128S, Y128E, H155L, H155R, Q198R, S285R, 5285T, S253W, S253G, T284R, T284G, S285G, K337E, K337P and L379V of SEQ ID NO:2.

In some aspects, the recombinant host cell is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

In some aspects, the yeast cell is a *Saccharomycete*.

In some aspects, the yeast cell is a cell from *Saccharomyces cerevisiae* species.

The invention further provides methods for producing Rebaudioside D by fermentation using a recombinant cell as disclosed herein.

The invention further provides methods for producing Rebaudioside M by fermentation using a recombinant cell as disclosed herein.

The invention further provides methods for producing Rebaudioside Q by fermentation using a recombinant cell as disclosed herein.

The invention further provides methods for producing Rebaudioside I by fermentation using a recombinant cell as disclosed herein.

The invention further provides methods for producing di-glycosylated steviol glycoside (13-hydroxy kaur-16-en- 18-oic acid, [2-O-β-D-glucopyranosyl-β-D-glucopyranosyl] ester) by fermentation using a recombinant cell as disclosed herein.

The invention further provides methods for producing tri-glycosylated steviol glycoside (13-hydroxy kaur-16-en-18-oic acid; [2-O-13-D-glucopyranosyl-3-O-β-D-glucopyranosyl-β-D-glucopyranosyl] ester) by fermentation using a recombinant cell as disclosed herein.

In some aspects, a cell for practicing the methods disclosed herein is a yeast cell, a plant cell, a mammalian cell, an insect cell, a fungal cell or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorphs, Candida boidinii, Arxula adeninivorans, Xanthophyllomyces dendrorhous* or *Candida albicans* species.

In some aspects, the yeast cell is a *Saccharomycete*.

In some aspects, the yeast cell is a cell from *Saccharomyces cerevisiae* species.

The invention further provides in vitro methods for producing Rebaudioside D or Rebaudioside M, comprising:

(a) adding one or more of a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2; a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof; a EUGT11 polypeptide comprising a EUGT11 polypeptide having 65% or greater identity to the Os03g0702000 amino acid sequence set forth in SEQ ID NO:16, and plant-derived or synthetic steviol or steviol glycosides to the reaction mixture; and (b) synthesizing Rebaudioside D or Rebaudioside M in the reaction mixture; and optionally (c) isolating Rebaudioside D or Rebaudioside M in the reaction mixture.

The invention further provides in vitro methods for producing Rebaudioside Q, comprising:

(a) adding one or more of a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2, and plant-derived or synthetic steviol or steviol glycosides to the reaction mixture; and (b) synthesizing Rebaudioside Q in the reaction mixture; and optionally (c) isolating Rebaudioside Q in the reaction mixture.

The invention further provides in vitro methods for producing Rebaudioside I, comprising:

(a) adding one or more of a UGT85C2 polypeptide comprising a UGT85C2 polypeptide having 55% or greater identity to the amino acid sequence set forth in SEQ ID NO:26; a UGT74G1 polypeptide comprising a UGT74G1 polypeptide having 55% or greater identity to the amino acid sequence set forth in SEQ ID NO:19; a UGT76G1 polypeptide comprising a UGT76G1 polypeptide having 50% or greater identity to the amino acid sequence set forth in SEQ ID NO:2; a UGT91d2 polypeptide comprising a UGT91d2 polypeptide having 90% or greater identity to the amino acid sequence set forth in SEQ ID NO:26 or a functional homolog thereof, a UGT91d2e polypeptide having a substitution at residues 211 and 286 of SEQ ID NO:15 or a combination thereof, and plant-derived or synthetic steviol or steviol glycosides to the reaction mixture; and (b) synthesizing Rebaudioside I in the reaction mixture; and optionally (c) isolating Rebaudioside I in the reaction mixture.

The invention further provides in vitro methods for producing a di-glycosylated steviol glycoside (13-hydroxy kaur-16-en-18-oic acid, [2-O-β-D-glucopyranosyl-β-D-glucopyranosyl] ester), comprising:

(a) adding one or more of a a UGT74G1 polypeptide comprising a UGT74G1 polypeptide having 55% or greater identity to the amino acid sequence set forth in SEQ ID NO:19; a EUGT11 polypeptide comprising a EUGT11 polypeptide having 65% or greater identity to the Os03g0702000 amino acid sequence set forth in SEQ ID NO:16, and plant-derived or synthetic steviol or steviol glycosides to the reaction mixture; and (b) synthesizing the di-glycosylated steviol glycoside (13-hydroxy kaur-16-en-18-oic acid, [2-O-β-D-glucopyranosyl-β-D-glucopyranosyl] ester) in the reaction mixture; and optionally (c) isolating di-glycosylated steviol glycoside (13-hydroxy kaur-16-en-18-oic acid, [2-O-β-D-glucopyranosyl-β-D-glucopyranosyl] ester) in the reaction mixture.

The invention further provides in vitro methods for producing a tri-glycosylated steviol glycoside (13-hydroxy kaur-16-en-18-oic acid; [2-O-β-D-glucopyranosyl-3-O-β-D-glucopyranosyl-β-D-glucopyranosyl] ester), comprising:

(a) adding one or more of a a UGT76G1 polypeptide comprising a UGT76G1 polypeptide having 50% or greater identity to the amino acid sequence set forth in SEQ ID NO:2; a UGT74G1 polypeptide comprising a UGT74G1 polypeptide having 55% or greater identity to the amino acid sequence set forth in SEQ ID NO:19; a EUGT11 polypeptide comprising a EUGT11 polypeptide having 65% or greater identity to the Os03g0702000 amino acid sequence set forth in SEQ ID NO:16, and plant-derived or synthetic steviol or steviol glycosides to the reaction mixture; and (b) synthesizing tri-glycosylated steviol glycoside (13-hydroxy kaur-16-en-18-oic acid; [2-O-β-D-glucopyranosyl-3-O-β-D-glucopyranosyl-β-D-glucopyranosyl] ester) in the reaction mixture; and optionally (c) isolating tri-glycosylated steviol glycoside (13-hydroxy kaur-16-en-18-oic acid; [2-O-β-D-glucopyranosyl-3-O-β-D-glucopyranosyl-β-D-glucopyranosyl] ester) in the reaction mixture.

In some aspects, the UGT76G1 polypeptide for producing Rebaudioside D comprises one or more of the UGT76G1 polypeptide variants selected from the group consisting of: Q23G, Q23H, 126F, I26W, T146A, T146G, T146P, H155R, L257P, L257W, L257T, L257G, L257A, L257R, L257E, S283G and S283N of SEQ ID NO:2.

In some aspects, the UGT76G1 polypeptide for producing Rebaudioside M, Rebaudioside Q, Rebaudioside I, di-glycosylated steviol glycoside and tri-glycosylated steviol glycoside comprises one or more of the UGT76G1 polypeptide variants selected from the group consisting of: T55K, T55E, S56A, Y128S, Y128E, H155L, H155R, Q198R, S285R, S285I, S253W, S253G, T284R, T284G, S285G, K337E, K337P and L379V of SEQ ID NO:2.

In some aspects, the in vitro method disclosed is enzymatic in vitro method or whole cell in vitro method.

In some aspects, a cell for practicing the methods disclosed herein is a yeast cell, a plant cell, a mammalian cell, an insect cell, a fungal cell or a bacterial cell.

In some aspects, the yeast cell is a cell from *Saccharomyces cerevisiae*, *Schizosaccharomyces pombe*, *Yarrowia lipolytica*, *Candida glabrata*, *Ashbya gossypii*, *Cyberlindnera jadinii*, *Pichia pastoris*, *Kluyveromyces lactis*, *Hansenula polymorpha*, *Candida boidinii*, *Arxula adeninivorans*, *Xanthophyllomyces dendrorhous* or *Candida albicans* species.

In some aspects, the yeast cell is a *Saccharomycete*.

In some aspects, the yeast cell is a cell from *Saccharomyces cerevisiae* species.

The invention further provides Rebaudioside Q produced by the methods disclosed herein.

The invention further provides Rebaudioside I produced by the methods disclosed herein.

The invention further provides a di-glycosylated steviol glycoside (13-hydroxy kaur-16-en-18-oic acid, [2-O-β-D-glucopyranosyl-β-D-glucopyranosyl] ester) produced by the methods disclosed herein.

The invention further provides a tri-glycosylated steviol glycoside (13-hydroxy kaur-16-en-18-oic acid; [2-O-β-D-glucopyranosyl-3-O-β-D-glucopyranosyl-β-D-glucopyranosyl] ester) produced by the methods disclosed herein.

The invention further provides a UGT76G1 polypeptide for producing Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl] ester) or tri-glycosylated steviol glycoside (13-hydroxy kaur-16-en-18-oic acid; [2-O-β-D-glucopyranosyl-3-O-β-D-glucopyranosyl-β-D-glucopyranosyl] ester), wherein the UGT76G1 polypeptide comprises a UGT76G1 polypeptide of SEQ ID NO:2 or one or more of the UGT76G1 polypeptide variants comprising: T55K, T55E, S56A, Y128S, Y128E, H155L, H155R, Q198R, S285R, S285T, S253W, S253G, T284R, T284G, S285G, K337E, K337P and L379V of SEQ ID NO:2.

The invention further provides a UGT76G1 polypeptide for producing Rebaudioside D, wherein the UGT76G1 polypeptide comprises a UGT76G1 polypeptide of SEQ ID NO:2 or one or more of the UGT76G1 polypeptide variants comprising: Q23G, Q23H, I26F, I26W, T146A, T146G, T146P, H155R, L257P, L257W, L257T, L257G, L257A, L257R, L257E, S283G and S283N of SEQ ID NO:2.

The invention further provides recombinant host cell comprising a recombinant gene encoding a UGT76G1 polypeptide, wherein the UGT76G1 polypeptide comprises one or more of the UGT76G1 polypeptide variants comprising: T55K, T55E, S56A, Y128S, Y128E, H155L, H155R, Q198R, S285R, S285T, S253W, S253G, T284R, T284G, S285G, K337E, K337P and L379V of SEQ ID NO:2.

In some aspects, the recombinant host cell as disclosed herein produces Rebaudioside D.

The invention further provides a recombinant host cell comprising a recombinant gene encoding a UGT76G1 polypeptide, wherein the UGT76G1 polypeptide comprises one or more of the UGT76G1 polypeptide variants comprising: Q23G, Q23H, I26F, I26W, T146A, T146G, T146P, H155R, L257P, L257W, L257T, L257G, L257A, L257R, L257E, S283G and S283N of SEQ ID NO:2.

In some aspects, the recombinant host cell as disclosed herein produces Rebaudioside M, Rebaudioside Q, Rebaudioside I, di-glycosylated steviol glycoside (13-hydroxy kaur-16-en-18-oic acid, [2-O-β-D-glucopyranosyl-β-D-glucopyranosyl] ester) or tri-glycosylated steviol glycoside (13-hydroxy kaur-16-en-18-oic acid; [2-O-βD-glucopyranosyl-3-O-β-D-glucopyranosyl-β-D-glucopyranosyl] ester).

In some aspects, the recombinant host cell is a yeast cell, a plant cell, a mammalian cell, an insect cell, a fungal cell or a bacterial cell.

In some aspects, the yeast cell is a cell from *Saccharomyces cerevisiae*, *Schizosaccharomyces pombe*, *Yarrowia lipolytica*, *Candida glabrata*, *Ashbya gossypii*, *Cyberlindnera jadinii*, *Pichia pastoris*, *Kluyveromyces lactis*, *Hansenula polymorpha*, *Candida boidinii*, *Arxula adeninivorans*, *Xanthophyllomyces dendrorhous* or *Candida albicans* species.

In some aspects, the yeast cell is a *Saccharomycete*.

In some aspects, the yeast cell is a cell from *Saccharomyces cerevisiae* species.

The invention further provides a composition comprising from about 1% to about 99% w/w of Rebaudioside D, wherein the composition has a reduced level of *Stevia*-derived contaminants relative to a *stevia* extract. In certain instances, the at least one of said contaminants is a plant-derived compound that inter alia contributes to off-flavors in the steviol glycoside product.

In some aspects, the composition has less than 0.1% of *Stevia*-derived contaminants relative to a *stevia* extract. In certain instances, the at least one of said contaminants is a plant-derived compound that inter alia contributes to off-flavors in the steviol glycoside product.

The invention further provides a food product comprising the composition as disclosed herein.

In some aspects, the food product is a beverage or a beverage concentrate.

Any of the hosts described herein can be a microorganism (e.g., a *Saccharomycete* such as *Saccharomyces cerevisiae*, or *Escherichia coli*), or a plant or plant cell (e.g., a *Stevia* such as a *Stevia rebaudiana* or *Physcomitrella*).

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 2 shows the chemical structure of Rebaudioside M (RebM).

FIG. 3 shows the chemical structure of Rebaudioside D (RebD).

FIG. 8A is a chromatogram indicating compounds produced by fermentation of yeast strain EFSC 3044. FIG. 8B is the NMR structure of the indicated di-glycosylated steviol glycoside (13-hydroxy kaur-16-en-18-oic acid, [2-O-β-D-glucopyranosyl-☐β-D-glucopyranosyl] ester), an analog of steviol-1,2-bioside. The IUPAC name for di-glycosylated steviol glycoside is (2S,3R,4S,5S,6R)-4,5-dihydroxy-6-(hydroxymethyl)-3-{[(2S,3R,4S,5S,6R)-3,4,5-trihydroxy-6-(hydroxymethyl)oxan-2-yl]oxy}oxan-2-yl(1R,4S,5R,9S,10R,13S)-13-hydroxy-5,9-dimethyl-14-methylidenetetracyclo[11.2.1.0^{1,10}.0^{4,9}] hexadecane-5-carboxylate.

FIG. 14 shows the variance in the three homology models of UGT76G1.

Figure 1:
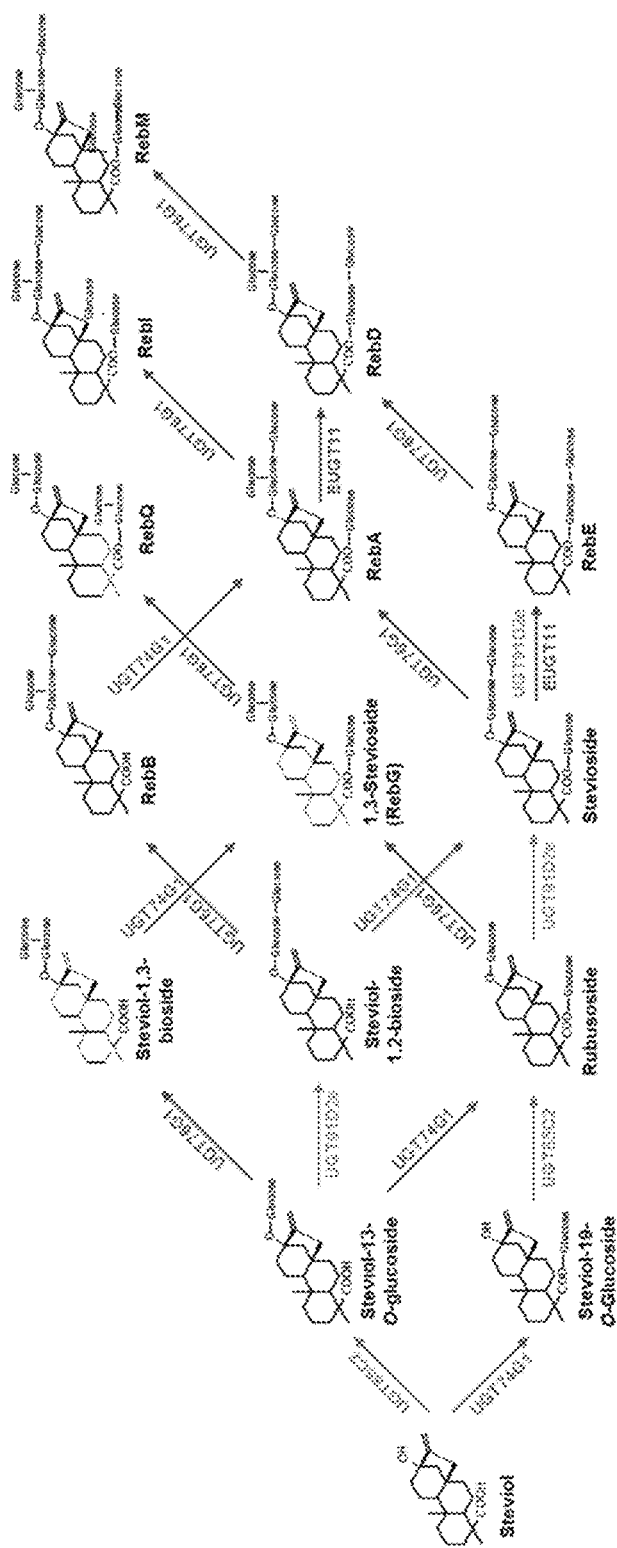
FIG. 1 shows the steviol glycoside glycosylation reactions and the enzymes by which they are catalyzed.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and *PCR Protocols: A Guide to Methods and Applications* (Innis et al., 1990, Academic Press, San Diego, Calif.).

Before describing the present invention in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the terms "polynucleotide", "nucleotide", "oligonucleotide", and "nucleic acid" can be used interchangeably to refer to nucleic acid comprising DNA, RNA, derivatives thereof, or combinations thereof.

As used herein, the term "and/or" is utilized to describe multiple components in combination or exclusive of one another. For example, "x, y, and/or z" can refer to "x" alone, "y" alone, "z" alone, "x, y, and z," "(x and y) or z," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of steviol glycosides, wherein one or more steviol glycosides selected from a group are produced. In some embodiments, "and/or" is used to refer to production of steviol glycosides, wherein one or more steviol glycosides are produced through one or more of the following steps: culturing a recombinant cell, synthesizing one or more steviol glycosides in a cell, and isolating one or more steviol glycosides.

Highly-glycosylated steviol glycosides can be present in trace amounts in the *Stevia* plant, but at levels so low that extraction from the plant is impractical for use of such glycosides in food and beverage systems. See, Hellfritsch et al., J. Agric. Food Chem. 60: 6782-6793 (2012); DuBois G E, Stephenson R A., J Med Chem. January; 28:93-98 (1985); and US Patent Publication 2011-0160311.

Typically, stevioside and Rebaudioside A are the primary compounds in commercially-produced *stevia* extracts. Stevioside is reported to have a more bitter and less sweet taste than Rebaudioside A. The composition of *stevia* extract can vary from lot to lot depending on the soil and climate in which the plants are grown. Depending upon the sourced plant, the climate conditions, and the extraction process, the amount of Rebaudioside A in commercial preparations is reported to vary from 20 to 97% of the total steviol glycoside content.

Other steviol glycosides are present in varying amounts in *stevia* extracts. For example, Rebaudioside B is typically present at less than 1-2%, whereas Rebaudioside C can be present at levels as high as 7-15%. Rebaudioside D is typically present in levels of 2% or less, and Rebaudioside F is typically present in compositions at 3.5% or less of the total steviol glycosides. The amount of the minor steviol glycosides, including but not limited to Rebaudioside M, can affect the flavor profile of a *Stevia* extract.

In addition, Rebaudioside D and other higher glycosylated steviol glycosides are thought to be higher quality sweeteners than Rebaudioside A. As such, the recombinant hosts and methods described herein are particularly useful for producing steviol glycoside compositions having an increased amount of Rebaudioside D for use, for example, as a non-caloric sweetener with functional and sensory properties superior to those of many high-potency sweeteners.

Rebaudioside M, a hexa-glycosylated steviol glycoside has been reported to be present in the *Stevia* plant and has an IUPAC name of (2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl(1R,5R,9S,13R)-13-{[(2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl]oxy}-5,9-dimethyl-14-methylidenetetracyclo[11.2.1.0$^{1,10}$.0$^{4,9}$] hexadecane-5-carboxylate. See, Ohta et al., MassBank record: FU000341, FU000342, FU000343 (2010) and Ohta et al (J. Applied Glycosides, 57(3):199-209, 2010). Rebaudioside M has been given a CAS number of 1220616-44-3. See FIG. 2 for the structure of Rebaudioside M.

Rebaudioside D, a penta-glycosylated steviol glycoside, has also been reported to be present in the *Stevia* plant and has an IUPAC name of 4,5-dihydroxy-6-(hydroxymethyl)-3-{[3,4,5-trihydroxy-6-(hydroxymethyl)oxan-2-yl]oxy}oxan-2-yl 13-{[5-hydroxy-6-(hydroxymethyl)-3,4-bis({[3,4,5-trihydroxy-6-(hydroxymethyl)oxan-2-yl]oxy})oxan-2-yl]oxy}-5,9-dimethyl-14-methylidenetetracyclo [11.2.1.0$^{1,10}$.0$^{4,9}$]hexadecane-5-carboxylate. Rebaudioside D has been given a CAS number of 64849-39-4. See FIG. 3 for the structure of Rebaudioside D.

Provided herein are recombinant hosts such as microorganisms that express polypeptides useful for de novo biosynthesis of Rebaudioside M or Rebaurdioside D. Hosts described herein express one or more uridine 5'-diphospho (UDP) glycosyl transferases suitable for producing steviol glycosides. Expression of these biosynthetic polypeptides in various microbial systems allows steviol glycosides to be produced in a consistent, reproducible manner from energy and carbon sources such as sugars, glycerol, $CO_2$, $H_2$, and sunlight. The proportion of each steviol glycoside produced by a recombinant host can be tailored by incorporating preselected biosynthetic enzymes into the hosts and expressing them at appropriate levels, to produce a sweetener composition with a consistent taste profile. Furthermore, the concentrations of steviol glycosides produced by recombinant hosts are expected to be higher than the levels of steviol glycosides produced in the *Stevia* plant, which improves the efficiency of the downstream purification. Such sweetener compositions advantageously contain little or no plant based contaminants, relative to the amount of contaminants present in *Stevia* extracts.

The practice of the methods and recombinant host cells as disclosed are provided wherein at least one of the genes encoding a UGT85C2 polypeptide; a UGT74G1 polypeptide; a UGT76G1 polypeptide; or a UGT91d2 polypeptide is a recombinant gene, the particular recombinant gene(s) depending on the species or strain selected for use. Additional genes or biosynthetic modules can be included in order to increase steviol glycoside yield, improve efficiency with which energy and carbon sources are converted to steviol and its glycosides, and/or to enhance productivity from the cell culture. As used herein, "biosynthetic modules" refer to a collection of genes that are part of a common biosynthetic pathway and thus are often co-expressed in a recombinant organism. As used herein, such additional biosynthetic modules include genes involved in the synthesis of the terpenoid precursors, isopentenyl diphosphate and dimethylallyl diphosphate. Additional biosynthetic modules include terpene synthase and terpene cyclase genes, such as genes encoding geranylgeranyl diphosphate synthase and copalyl diphosphate synthase; these genes can be endogenous genes or recombinant genes.

I. Steviol and Steviol Glycoside Biosynthesis Polypeptides

A. Steviol Biosynthesis Polypeptides

Figure 4:
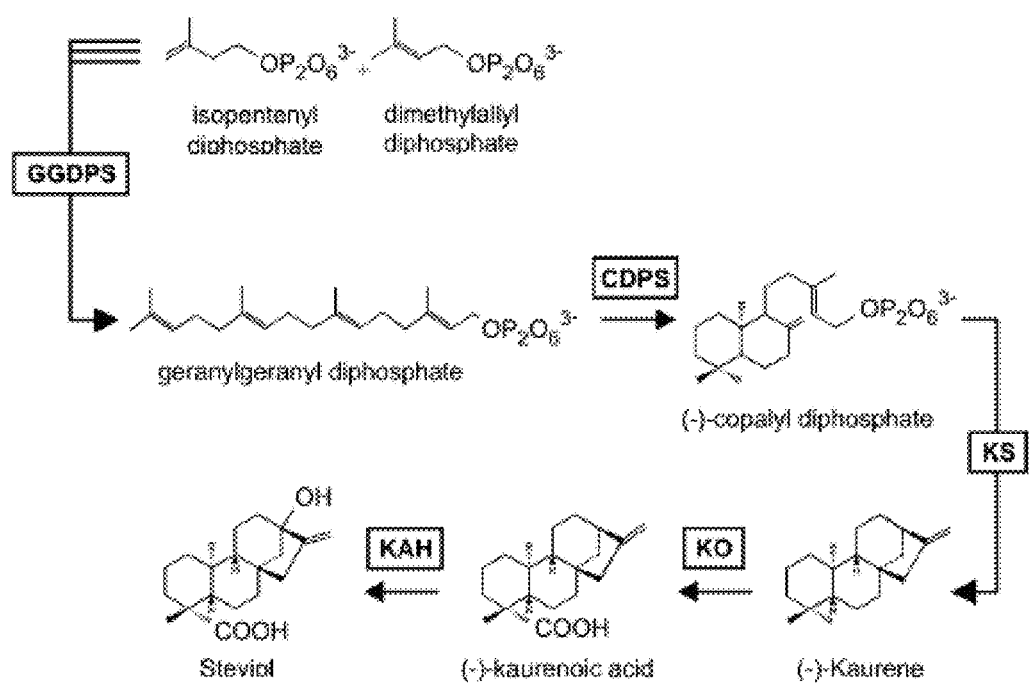
FIG. 4 shows biochemical pathway for the production of steviol.

The biochemical pathway to produce steviol involves formation of the precursor, geranylgeranyl diphosphate (catalyzed by GGDPS), cyclization to (−) copalyl diphosphate (catalyzed by CDPS), followed by formation of (−)-kaurene (catalyzed by KS), followed by oxidation (catalyzed by KO), and hydroxylation (catalyzed by KAH) to form steviol. See FIG. 4. Thus, conversion of geranylgeranyl diphosphate to steviol in a recombinant microorganism involves the expression of a gene encoding a kaurene synthase (KS), a gene encoding a kaurene oxidase (KO), and a gene encoding a steviol synthetase (KAH). Steviol synthetase also is known as kaurenoic acid 13-hydroxylase.

Suitable KS polypeptides are known. For example, suitable KS enzymes include those made by *Stevia rebaudiana, Zea mays, Populus trichocarpa,* and *Arabidopsis thaliana.* See, Table 2 and PCT Application Nos. PCT/US2012/050021 and PCT/US2011/038967, which are incorporated herein by reference in their entirety. The nucleotide sequence encoding the *A. thaliana* KS polypeptide is set forth in SEQ ID NO:6, and the amino acid sequence of the *A. thaliana* KS polypeptide is set forth in SEQ ID NO:21.

TABLE 2

Kaurene synthase (KS) clones.

| Enzyme Source Organism | gi Number | Accession Number | Construct Name | Length (nts) |
|---|---|---|---|---|
| Stevia rebaudiana | 4959241 | AAD34295 (amino acid SEQ ID NO: 27) | MM-12 | 2355 (nt SEQ ID NO: 103) |
| Stevia rebaudiana | 4959239 | AAD34294 (amino acid SEQ ID NO: 28) | MM-13 | 2355 (nt SEQ ID NO: 104) |
| Zea mays | 162458963 | NP_001105097 (amino acid SEQ ID NO: 29) | MM-14 | 1773 (nt SEQ ID NO: 105) |
| Populus trichocarpa | 224098838 | XP_002311286 (amino acid SEQ ID NO: 30) | MM-15 | 2232 (nt SEQ ID NO: 106) |
| Arabidopsis thaliana | 3056724 | AF034774 (amino acid SEQ ID NO: 32) | EV-70 | 2358 (nt SEQ ID NO: 31) |

Suitable KO polypeptides are known. For example, suitable KO enzymes include those made by *Stevia rebaudiana, Arabidopsis thaliana, Gibberella* fujikoroi and *Trametes versicolor*. See, e.g., Table 3 and PCT Application Nos. PCT/US2012/050021 and PCT/US2011/038967, which are incorporated herein by reference in their entirety.

TABLE 3

Kaurene oxidase (KO) clones.

| Enzyme Source Organism | gi Number | Accession Number | Construct Name | Length (nts) |
|---|---|---|---|---|
| Stevia rebaudiana | 76446107 | ABA42921 (amino acid SEQ ID NO: 33) | MM-18 | 1542 (nt SEQ ID NO: 107) |
| Arabidopsis thaliana | 3342249 | AAC39505 (amino acid SEQ ID NO: 34) | MM-19 | 1530 (nt SEQ ID NO: 108) |
| Gibberella fujikoroi | 4127832 | CAA76703 (amino acid SEQ ID NO: 35) | MM-20 | 1578 (nt SEQ ID NO: 109) |

TABLE 3-continued

Kaurene oxidase (KO) clones.

| Enzyme Source Organism | gi Number | Accession Number | Construct Name | Length (nts) |
|---|---|---|---|---|
| Trametes versicolor | 14278967 | BAB59027 (amino acid SEQ NO: 36) | MM-21 | 1500 (nt SEQ ID NO: 110) |

Suitable KAH polypeptides are known. For example, suitable KAH enzymes include those made by *Stevia rebaudiana, Arabidopsis thaliana, Vitis vinifera* and *Medicago trunculata*. See, e.g., Table 4, PCT Application Nos. PCT/US2012/050021 and PCT/US2011/038967, U.S. Patent Publication Nos. 2008/0271205 and 2008/0064063, and Genbank Accession No. gi 189098312 (SEQ ID NO: 37) and GenBank Accession ABD60225; GI:89242710 (SEQ ID NO: 38), which are incorporated herein by reference in their entirety. The steviol synthetase from *A. thaliana* is classified as a CYP714A2.

TABLE 4

Steviol synthetase (KAH) clones.

| Enzyme Source Organism | gi Number | Accession Number | Plasmid Name | Construct Name | Length (nts) |
|---|---|---|---|---|---|
| Stevia rebaudiana | * | (amino acid SEQ ID NO: 43) | pMUS35 | MM-22 | 1578 (nt SEQ ID NO: 111) |
| Stevia rebaudiana | 189418962 | ACD93722 (amino acid SEQ ID NO: 39) | pMUS36 | MM-23 | 1431 (nt SEQ ID NO: 112) |
| Arabidopsis thaliana | 15238644 | NP_197872 (amino acid SEQ ID NO: 40) | pMUS37 | MM-24 | 1578 (nt SEQ ID NO: 113) |
| Vitis vinifera | 225458454 | XP_002282091 (amino acid SEQ ID NO: 41) | pMUS38 | MM-25 | 1590 (nt SEQ ID NO: 114) |

TABLE 4-continued

Steviol synthetase (KAH) clones.

| Enzyme Source Organism | gi Number | Accession Number | Plasmid Name | Construct Name | Length (nts) |
|---|---|---|---|---|---|
| Medicago trunculata | 84514135 | ABC59076 (amino acid SEQ ID NO: 42) | pMUS39 | MM-26 | 1440 (nt SEQ ID NO: 115) |

* = Sequence is identified with sequence identifier number 2 as shown in U.S. Patent Publication No. 2008-0064063.

In addition, a KAH polypeptide from *Stevia rebaudiana* that was identified as described in PCT Application No. PCT/US2012/050021, which is incorporated herein by reference in its entirety, is particularly useful in a recombinant host. The nucleotide sequence encoding the *S. rebaudiana* KAH (SrKAHe1) is set forth in SEQ ID NO:91. A nucleotide sequence encoding the *S. rebaudiana* KAH that has been codon-optimized for expression in yeast is set forth in SEQ ID NO:8, and the amino acid sequence of the *S. rebaudiana* KAH polypeptide is set forth in SEQ ID NO:11. When expressed in *S. cerevisiae*, the *S. rebaudiana* KAH (SEQ ID NO:11) shows significantly higher steviol synthase activity as compared to the *A. thaliana* ent-kaurenoic acid hydroxylase described by Yamaguchi et al. (U.S. Patent Publication No. 2008/0271205 A1) and other *S. rebaudiana* KAH enzymes described in U.S. Patent Publication No. 2008/0064063 as well as the protein sequence deposited in GenBank as ACD93722. The *S. rebaudiana* KAH polypeptide (SEQ ID NO:11) has less than 20% identity to the KAH from U.S. Patent Publication No. 2008/0271205 and less than 35% identity to the KAH from U.S. Patent Publication No. 2008/0064063.

For example, the steviol synthase encoded by SrKAHe1 is activated by the *S. cerevisiae* CPR encoded by gene NCP1 (YHR042W). Greater activation levels of the steviol synthase encoded by SrKAHe1 is observed when the *A. thaliana* CPR encoded by the gene ATR2 (SEQ ID NO:10) and the *S. rebaudiana* CPR encoded by the gene CPR8 (SEQ ID NO:5) are co-expressed. The amino acid sequence of the *A. thaliana* ATR2 is set forth in SEQ ID NO:9, and the amino acid sequence for *S. rebaudiana* CPR8 polypeptides is set forth in SEQ ID NO:4.

In some embodiments, a recombinant microorganism contains a recombinant gene encoding a KO, KS, and a KAH polypeptide. Such microorganisms also typically contain a recombinant gene encoding a cytochrome P450 reductase (CPR) polypeptide, since certain combinations of KO and/or KAH polypeptides require expression of an exogenous CPR polypeptide. In particular, the activity of a KO and/or a KAH polypeptide of plant origin can be significantly increased by the inclusion of a recombinant gene encoding an exogenous CPR polypeptide. Suitable CPR polypeptides are known. For example, suitable CPR enzymes include those made by *S. rebaudiana* and *A. thaliana*. See, e.g., Table 5 and PCT Application Nos. PCT/US2012/050021 and PCT/US2011/038967, which are incorporated herein by reference in their entirety.

TABLE 5

Cytochrome P450 reductase (CPR) Clones.

| Enzyme Source Organism | gi Number | Accession Number | Plasmid Name | Construct Name | Length (nts) |
|---|---|---|---|---|---|
| Stevia rebaudiana | 93211213 | ABB88839 (amino acid SEQ ID NO: 44) | pMUS40 | MM-27 | 2133 (nt SEQ ID NO: 116) |
| Arabidopsis thaliana | 15233853 | NP_194183 (amino acid SEQ ID NO: 45) | pMUS41 | MM-28 | 2079 (nt SEQ ID NO: 117) |
| Giberella fujikuroi | 32562989 | CAE09055 (amino acid SEQ ID NO: 46) | pMUS42 | MM-29 | 2142 (nt SEQ ID NO: 118) |

The yeast gene DPP1 and/or the yeast gene LPP1 can reduce the yield of steviol by converting the GGPP and FPP precursors by these enzymes. These genes can be disrupted or deleted such that the degradation of farnesyl pyrophosphate (FPP) to farnesol is reduced and the degradation of geranylgeranylpyrophosphate (GGPP) to geranylgeraniol (GGOH) is reduced. Alternatively, the promoter or enhancer elements of an endogenous gene encoding a phosphatase can be altered such that the expression of their encoded proteins is altered. Homologous recombination can be used to disrupt an endogenous gene. For example, a "gene replacement" vector can be constructed in such a way to include a selectable marker gene. The selectable marker gene can be operably linked, at both 5' and 3' end, to portions of the gene of sufficient length to mediate homologous recombination using methods known to those skilled in the art.

A selectable marker can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, Southern blot analysis. Subsequent to its use in selection, a selectable marker can be removed from the genome of the host cell by, e.g., Cre-loxP systems (see, e.g., Gossen et al., 2002, *Ann. Rev. Genetics* 36:153-173 and U.S. Application Publication No. 20060014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

Expression in a recombinant microorganism of these genes can result in the conversion of geranylgeranyl diphosphate to steviol.

B. Steviol Glycoside Biosynthesis Polypeptides

Recombinant host cells are described herein that can convert steviol to a steviol glycoside. Such hosts (e.g., microorganisms) contains genes encoding one or more UDP Glycosyl Transferases, also known as UGTs. UGTs transfer a monosaccharide unit from an activated nucleotide sugar to an acceptor moiety, in this case, an —OH or —COOH moiety on steviol or steviol derivative or an —OH moiety on a glucose already attached to the steviol backbone. UGTs have been classified into families and subfamilies based on sequence homology. See Li et al., 2001, J. Biol. Chem. 276:4338-4343.

Rubusoside Biosynthesis Polypeptides

Biosynthesis of rubusoside involves glycosylation of the 13-OH and the 19-COOH of steviol. See FIG. 1. Conversion of steviol to rubusoside in a recombinant host such as a microorganism can be accomplished by expression of gene (s) encoding UGTs 85C2 and 74G1, which transfer a glucose unit to the 13-OH or the 19-COOH, respectively, of steviol.

A suitable UGT85C2 functions as a uridine 5'-diphosphoglucosyl:steviol 13-OH transferase, and a uridine 5'-diphosphoglucosyl:steviol-19-O-glucoside 13-OH transferase. Exemplary reactions for UGT85C2 include conversion of steviol and UDP-glucose to Steviol-13-O-glucoside or conversion of Steviol-19-O-glucoside and UDP-glucose to Rubusoside. See FIG. 1. Functional UGT85C2 polypeptides also can catalyze glucosyl transferase reactions that utilize steviol glycoside substrates other than steviol and steviol-19-O-glucoside.

A suitable UGT74G1 polypeptide functions as a uridine 5'-diphospho glucosyl: steviol 19-COOH transferase and a uridine 5'-diphospho glucosyl: steviol-13-O-glucoside 19-COOH transferase. Exemplary reactions of 74G1 include conversion of steviol to steviol-19-O-glucoside and conversion of steviol-13-O-glucoside to Rubusoside. See FIG. 19 for these and other non-limiting examples of UGT74G1 reactions. Functional UGT74G1 polypeptides also can catalyze glycosyl transferase reactions that utilize steviol glycoside substrates other than steviol and steviol-13-O-glucoside, or that transfer sugar moieties from donors other than uridine diphosphate glucose.

A recombinant microorganism expressing a functional UGT74G1 and a functional UGT85C2 can make rubusoside and both steviol monosides (i.e., steviol 13-O-monoglucoside and steviol 19-O-monoglucoside) when steviol is used as a feedstock in the medium. Typically, however, genes encoding UGT74G1 and UGT85C2 are recombinant genes that have been transformed into a host (e.g., microorganism) that does not naturally possess them.

As used herein, the term "recombinant host" is intended to refer to (including but not limited to) a host cell, the genome of which has been augmented by at least one incorporated DNA sequence; extrachromosomal examples, like plasmids in bacteria and episomes comprising the 2-micron circle in yeast. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. Generally, the introduced DNA is not originally resident in the host that is the recipient of the DNA, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, mammalian cells, insect cells, fungal cells, plant cells, and plants.

The term "recombinant gene" refers to a gene or DNA sequence that is introduced into a recipient host, regardless of whether the same or a similar gene or DNA sequence can already be present in such a host. "Introduced," or "augmented" in this context, is known in the art to mean introduced or augmented by the hand of man. Thus, a recombinant gene can be a DNA sequence from another species, or can be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified (including but not limited to regulated or inducible) expression of the gene product of that DNA.

Suitable UGT74G1 and UGT85C2 polypeptides include those made by *S. rebaudiana*. Genes encoding functional UGT74G1 and UGT85C2 polypeptides from *Stevia* are reported in Richman et al., 2005, Plant J. 41: 56-67. Amino acid sequences of *S. rebaudiana* UGT74G1 (SEQ ID NO: 19) and UGT85C2 (SEQ ID NO: 26) polypeptides are set forth in SEQ ID NOs: 1 and 3, respectively, of PCT Application No. PCT/US2012/050021, as are nucleotide sequences that encode UGT74G1 and UGT85C2 that have been optimized for expression in yeast and DNA 2.0 codon-optimized sequence for UGTs 85C2, 91D2e, 74G1 and 76G1. The Gene Art codon optimized nucleotide sequence encoding a *S. rebaudiana* UGT85C2 is set forth in SEQ ID NO:3. See also, the UGT85C2 and UGT74G1 variants described below in the "Functional Homolog" section. For example, a UGT85C2 polypeptide can contain substitutions at any one of the positions 65, 71, 270, 289, and 389 (e.g., A65S, E71Q, T270M, Q289H, and A389V) or a combination thereof.

In some embodiments, the recombinant host is a microorganism. Recombinant microorganism can be grown on media containing steviol in order to produce rubusoside. In other embodiments, however, the recombinant microorganism expresses genes involved in steviol biosynthesis, e.g., a CDPS gene, a KS gene, a KO gene, and a KAH gene. Suitable CDPS polypeptides are known. For example, suitable CDPS enzymes include those made by *S. rebaudiana, Streptomyces clavuligerus, Bradyrhizobium japonicum, Zea mays*, and *Arabidopsis* sp. See, e.g., Table 6 and PCT Application Nos. PCT/US2012/050021 and PCT/US2011/038967, which are incorporated herein by reference in their entirety.

In some embodiments, CDPS polypeptides that lack a chloroplast transit peptide at the amino terminus of the unmodified polypeptide can be used. For example, the first 150 nucleotides from the 5' end of the *Zea mays* CDPS coding sequence (SEQ ID NO:12) can be removed, the truncated nucleotide sequence is shown in SEQ ID NO:133. Doing so removes the amino terminal 50 residues of the amino acid sequence shown in SEQ ID NO:13, which encode a chloroplast transit peptide; the truncated amino acid sequence is shown in SEQ ID NO:134. The truncated CDPS gene can be fitted with a new ATG translation start site and operably linked to a promoter, typically a constitutive or highly expressing promoter. When a plurality of copies, including but not limited to, one copy, two copies or three copies of the truncated coding sequence are introduced into a microorganism, expression of the CDPS polypeptide from the promoter results in an increased carbon flux towards ent-kaurene biosynthesis.

yeast (see PCT Application No. PCT/US2012/050021, which is incorporated herein by reference in its entirety). A bifunctional enzyme from *Gibberella fujikuroi* also can be used.

TABLE 7

CDPS-KS Clones.

| Enzyme Source Organism | gi Number | Accession Number | Construct Name | Length (nts) |
|---|---|---|---|---|
| *Phomopsis amygdali* | 186704306 | BAG30962 (amino acid SEQ ID NO: 55) | MM-16 | 2952 (nt SEQ ID NO: 122) |
| *Physcomitrella patens* | 146325986 | BAF61135 (amino acid SEQ ID NO: 56) | MM-17 | 2646 (nt SEQ ID NO: 123) |
| *Gibberella fujikuroi* | 62900107 | Q9UVY5.1 (amino acid SEQ ID NO: 57) | | 2859 (nt SEQ ID NO: 124) |

Thus, a microorganism containing a CDPS gene, a KS gene, a KO gene and a KAH gene in addition to a UGT74G1 and a UGT85C2 gene is capable of producing both steviol monosides and rubusoside without the necessity for using steviol as a feedstock.

In some embodiments, the recombinant microorganism further expresses a recombinant gene encoding a geranylgeranyl diphosphate synthase (GGPPS). Suitable GGPPS polypeptides are known. For example, suitable GGPPS enzymes include those made by *S. rebaudiana, Gibberella fujikuroi, Mus musculus, Thalassiosira pseudonana, Streptomyces clavuligerus, Sulfulobus acidocaldarius, Synechoc-*

TABLE 6

CDPS Clones.

| Enzyme Source Organism | gi Number | Accession Number | Plasmid Name | Construct Name | Length (nts) |
|---|---|---|---|---|---|
| *Stevia rebaudiana* | 2642661 | AAB87091 (amino acid SEQ ID NO: 48) | pMUS22 | MM-9 | 2364 (nt SEQ ID NO: 119) |
| *Streptomyces clavuligerus* | 197705855 | EDY51667 (amino acid SEQ ID NO: 49) | pMUS23 | MM-10 | 1584 (nt SEQ ID NO: 120) |
| *Bradyrhizobium japonicum* | 529968 | AAC28895.1 (amino acid SEQ ID NO: 50) | pMUS24 | MM-11 | 1551 (nt SEQ ID NO: 121) |
| *Zea mays* | 50082774 | AY562490 (amino acid SEQ ID NO: 52) | | EV65 | 2484 (nt SEQ ID NO: 51) |
| *Arabidopsis thaliana* | 18412041 | NM_116512 (SEQ ID NO: 54) | | EV64 | 2409 (nt SEQ ID NO: 53) |

CDPS-KS bifunctional proteins also can be used. Nucleotide sequences encoding the CDPS-KS bifunctional enzymes shown in Table 7 were modified for expression in *occus* sp. and *A. thaliana*. See, Table 8 and PCT Application Nos. PCT/US2012/050021 and PCT/US2011/038967, which are incorporated herein by reference in their entirety.

TABLE 8

GGPPS Clones.

| Enzyme Source Organism | gi Number | Accession Number | Plasmid Name | Construct Name | Length (nts) |
|---|---|---|---|---|---|
| Stevia rebaudiana | 90289577 | ABD92926 (amino acid SEQ ID NO: 58) | pMUS14 | MM-1 | 1086 (nt SEQ ID NO: 125) |
| Gibberella fujikuroi | 3549881 | CAA75568 (amino acid SEQ ID NO: 59) | pMUS15 | MM-2 | 1029 (nt SEQ ID NO: 126) |
| Mus musculus | 47124116 | AAH69913 (amino acid SEQ ID NO: 60) | pMUS16 | MM-3 | 903 (nt SEQ ID NO: 127) |
| Thalassiosira pseudonana | 223997332 | XP_002288339 (amino acid SEQ ID NO: 61) | pMUS17 | MM-4 | 1020 (nt SEQ ID NO: 128) |
| Streptomyces clavuligerus | 254389342 | ZP_05004570 (amino acid SEQ ID NO: 62) | pMUS18 | MM-5 | 1068 (nt SEQ ID NO: 129) |
| Sulfulobus acidocaldarius | 506371 | BAA43200 (amino acid SEQ ID NO: 63) | pMUS19 | MM-6 | 993 (nt SEQ ID NO: 130) |
| Synechococcus sp. | 86553638 | ABC98596 (amino acid SEQ ID NO: 64) | pMUS20 | MM-7 | 894 (nt SEQ ID NO: 131) |
| Arabidopsis thaliana | 15234534 | NP_195399 (amino acid SEQ ID NO: 63) | pMUS21 | MM-8 | 1113 (nt SEQ ID NO: 132) |

In some aspects, the KAH gene encoding the KAH polypeptide set forth in SEQ ID NO:11, comprising a recombinant cell of the invention is overexpressed. In some aspects, the KAH gene can be present in (including but not limited to) one, two or three copies. In some aspects, the KS gene encoding the KS polypeptide, set forth in SEQ ID NO:21, comprising a recombinant cell of the invention is overexpressed. In some aspects, the KS gene can be present in (including but not limited to) one, two or three copies.

In some embodiments, the recombinant microorganism further can express recombinant genes involved in diterpene biosynthesis or production of terpenoid precursors, e.g., genes in the methylerythritol 4-phosphate (MEP) pathway or genes in the mevalonate (MEV) pathway discussed below, have reduced phosphatase activity, and/or express a sucrose synthase (SUS) as discussed herein.

Rebaudioside A, Rebaudioside D, and Rebaudioside E Biosynthesis Polypeptides

Biosynthesis of Rebaudioside A involves glucosylation of the aglycone steviol. Specifically, Rebaudioside A can be formed by glucosylation of the 13-OH of steviol which forms the 13-O-steviolmonoside, glucosylation of the C-2' of the 13-O-glucose of steviolmonoside which forms steviol-1,2-bioside, glucosylation of the C-19 carboxyl of steviol-1,2-bioside which forms stevioside, and glucosylation of the C-3' of the C-13-O-glucose of stevioside to produce Reb A. The order in which each glucosylation reaction occurs can vary. See FIG. 1.

Biosynthesis of Rebaudioside E and/or Rebaudioside D involves glucosylation of the aglycone steviol. Specifically, Rebaudioside E can be formed by glucosylation of the 13-OH of steviol which forms steviol-13-O-glucoside, glucosylation of the C-2' of the 13-O-glucose of steviol-13-O-glucoside which forms the steviol-1,2-bioside, glucosylation of the C-19 carboxyl of the 1,2-bioside to form 1,2-stevioside, and glucosylation of the C-2' of the 19-O-glucose of the 1,2-stevioside to form Rebaudioside E. Rebaudioside D can be formed by glucosylation of the C-3' of the C-13-O-glucose of Rebaudioside E. The order in which each glycosylation reaction occurs can vary. For example, the glucosylation of the C-2' of the 19-O-glucose can be the last step in the pathway, wherein Rebaudioside A is an intermediate in the pathway. See FIG. 1.

Rebaudioside M Polypeptides

As provided herein, conversion of steviol to Rebaudioside M in a recombinant host can be accomplished by expressing combinations of the following functional UGTs: 91D2, EUGT11, 74G1, 85C2, and 76G1. See FIG. 1. It is particularly useful to express EUGT11 at high levels using a high copy number plasmid, or using a strong promoter, or multiple integrated copies of the gene, or episome under selection for high copy number of the gene. Thus, a recombinant microorganism expressing combinations of these UGTs can make Rebaudioside A (85C2; 76G1; 74G1; 91D2e), Rebaudioside D (85C2; 76G1; 74G1; 91D2e; EUGT11), Rebaudioside E (85C2; 74G1; 91D2e; EUGT11), or Rebaudioside M (85C2; 76G1; 74G1; 91D2e; EUGT11). See FIG. 1. Typically, one or more of these genes are recombinant genes that have been transformed into a microorganism that does not naturally possess them. It has also been discovered that UGTs designated herein as SM12UGT can be substituted for UGT91D2.

Targeted production of individual Rebaudiosides can be accomplished by differential copy numbers of the UGT-encoding genes (see FIG. 1) in the recombinant cell, differential promoter strengths, and/or by utilizing mutants with increased specificity/activity towards the product of interest. For example, low levels of Rebaudioside D, E, and M will be formed if EUGT11 is expressed at low levels in comparison to the other UGTs, which would favor Rebaudioside A formation. High levels of EUGT11 expression result in production of more 19-O 1,2 diglucoside that can serve as substrate for UGT76G1 to form Rebaudioside M. In certain advantageous embodiments, additional copies or mutant versions of UGT76G1 in recombinant cells of the invention can improve the rate of Rebaudioside M formation from Rebaudioside D.

In some embodiments, UGT76G1 catalyzes glycosylation of steviol and steviol glycosides at the 19-O position. Thus, in some embodiments, one or more of RebM, RebQ, RebI, di-glycosylated steviol glycoside (13-hydroxy kaur-16-en-18-oic acid, [2-O-β-D-glucopyranosyl-β-D-glucopyranosyl] ester), or tri-glycosylated steviol glycoside ((13-hydroxy kaur-16-en-18-oic acid; [2-O-β-D-glucopyranosyl-3-O-β-D-glucopyranosyl-β-D-glucopyranosyl] ester) are produced in a recombinant host expressing a recombinant gene encoding a UGT76G1 polypeptide, through bioconversion, or through catalysis by UGT76G1 in vitro. In some embodiments, UGT76G1 catalyzes the glycosylation of steviol and steviol glycosides at the 13-O position and preferentially glycosylates steviol glycoside substrates that are 1,2-di-glycosylated at the 13-O position or mono-glycosylated at the 13-O position. In some embodiments, UGT76G1 does not show a preference for the glycosylation state of the 19-O position.

In some aspects, a recombinant host cell of the invention comprises the gene encoding the UGT76G1 polypeptide set forth in SEQ ID NO:2. In some aspects, the gene encoding the UGT76G1 polypeptide set forth in SEQ ID NO:2, comprising a recombinant cell of the invention is overexpressed. In some aspects, the gene can be present in (including but not limited to) two or three copies.

Figure 12:
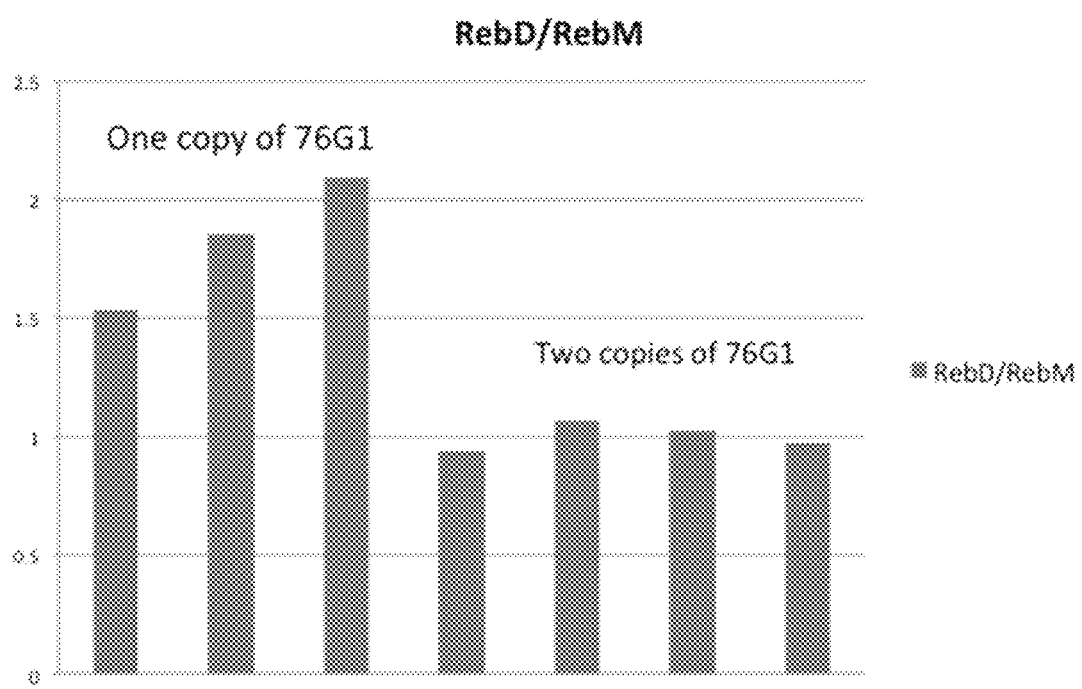
FIG. 12 compares RebD/RebM produced with one or two copies of UGT76G1.

In some embodiments, the gene encoding the UGT76G1 polypeptide set forth in SEQ ID NO:2 is present in one copy. As shown in FIG. 12 (Example 9), a lower copy number (one copy) of the gene encoding the UGT76G1 polypeptide results in lower UGT76G1 expression and increases the Rebaudioside D/Rebaudioside M ratio.

In some embodiments, less than five (e.g., one, two, three, or four) UGTs are expressed in a host. For example, a recombinant microorganism expressing a functional EUGT11 can make Rebaudioside D when Rebaudioside A is used as a feedstock. A recombinant microorganism expressing a functional UGT76G1 can make Rebaudioside M when Rebaudioside D or Rebaudioside E is used as a feedstock. Rebaudioside M can be formed from either Rebaudioside D or Rebaudioside E by glycosylation of the C-3' of the 19-O-glucose of Rebaudioside D or Rebaudioside E; in the case of Rebaudioside E a second glucosylation is required, of the 13-O-glucose to produce Rebaudioside M.

A recombinant microorganism expressing EUGT11, 74G1 or 76G1, and 91D2 can make Rebaudioside D or Rebaudioside M when rubusoside or 1,2-stevioside is used as a feedstock. As another alternative, a recombinant microorganism expressing EUGT11, 74G1, 76G1, and 91D2 can make Rebaudioside D or Rebaudioside M when the monoside, steviol-13-O-glucoside are added to the medium. Similarly, conversion of steviol-19-O-glucoside to Rebaudioside D in a recombinant microorganism can be accomplished by expressing in the cell genes encoding UGTs EUGT11, 85C2, 76G1, and 91D2e, when fed steviol-19-O-glucoside.

Suitable UGT74G1 and UGT85C2 polypeptides include those discussed above. A suitable UGT76G1 adds a glucose moiety to the C-3' of the C-13-O-glucose of the acceptor molecule, a steviol 1,2 glycoside. UGT76G1 functions, for example, as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. Functional UGT76G1 polypeptides can also catalyze glucosyl transferase reactions that utilize steviol glycoside substrates that contain sugars other than glucose, e.g., steviol rhamnosides and steviol xylosides. See, FIG. 1. Suitable UGT76G1 polypeptides include those made by S. rebaudiana and reported in Richman et al., 2005, Plant J. 41: 56-67. A nucleotide sequence encoding the S. rebaudiana UGT76G1 polypeptide optimized for expression in yeast is set forth in SEQ ID NO:14. See also the UGT76G1 variants set forth in the "Functional Homolog" section.

A suitable EUGT11 or UGT91D2 polypeptide functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside.

A suitable EUGT11 or UGT91D2 polypeptide also functions as a uridine 5'-diphospho glucosyl: rubusoside transferase transferring a glucose moiety to the C-2' of the 13-0-glucose of the acceptor molecule, rubusoside, to produce stevioside. EUGT11 polypeptides also can transfer a glucose moiety to the C-2' of the 19-O-glucose of the acceptor molecule, rubusoside, to produce a 19-O-1,2-diglycosylated rubusoside (see FIG. 1).

Functional EUGT11 or UGT91D2 polypeptides also can catalyze reactions that utilize steviol glycoside substrates other than steviol-13-O-glucoside and rubusoside. For example, a functional EUGT11 polypeptide can utilize stevioside as a substrate, transferring a glucose moiety to the C-2' of the 19-O-glucose residue to produce Rebaudioside E (see FIG. 1). Functional EUGT11 and UGT91D2 polypeptides can also utilize Rebaudioside A as a substrate, transferring a glucose moiety to the C-2' of the 19-O-glucose residue of Rebaudioside A to produce Rebaudioside D. EUGT11 can convert Rebaudioside A to Rebaudioside D at a rate that is least 20 times faster (e.g., as least 25 times or at least 30 times faster) than the corresponding rate of wildtype UGT91D2e (SEQ ID NO: 15) when the reactions are performed under similar conditions, i.e., similar time, temperature, purity, and substrate concentration. As such, EUGT11 produces greater amounts of RebD than UGT91D2e under similar conditions in cells or in vitro, under conditions where the temperature-sensitive EUGT11 is stable.

In addition, a functional EUGT11 exhibits significant C-2' 19-O-diglycosylation activity with rubusoside or stevioside as substrates, whereas UGT91D2e has no detectable diglycosylation activity with these substrates under some conditions. Thus, a functional EUGT11 can be distinguished from UGT91D2e by the differences in steviol glycoside substrate-specificity.

A functional EUGT11 or UGT91D2 polypeptide does not transfer a glucose moiety to steviol compounds having a 1,3-bound glucose at the C-13 position, i.e., transfer of a glucose moiety to steviol-1,3-bioside and 1,3-stevioside (RebG) does not occur.

Functional EUGT11 and UGT91D2 polypeptides can transfer sugar moieties from donors other than uridine diphosphate glucose. For example, a functional EUGT11 or UGT91D2 polypeptide can act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a functional EUGT11 or UGT91D2 polypeptide can act as a uridine 5'-diphospho L-rhamnosyl: steviol-13-O-glucoside transferase, transferring a rhamnose moiety to the C-2' of the 13-O-glucose of the acceptor molecule, steviol-13-O-glucoside.

Suitable EUGT11 polypeptides are described herein and can include the EUGT11 polypeptide from Oryza sativa (GenBank Accession No. AC133334; SEQ ID NO:16). For example, an EUGT11 polypeptide can have an amino acid sequence with at least 70% sequence identity (e.g., at least 75, 80, 85, 90, 95, 96, 97, 98, or 99% sequence identity) to the amino acid sequence set forth in SEQ ID NO:16. The nucleotide sequence encoding the amino acid sequence of EUGT11 also is set forth in SEQ ID NO:17, as is a codon optimized nucleotide sequence for expression in yeast (SEQ ID NO:18).

Suitable functional UGT91D2 polypeptides include, e.g., the polypeptides designated UGT91D2e and UGT91D2m and functional homologs as described herein. The amino acid sequence of an exemplary UGT91D2e polypeptide from S. rebaudiana is set forth in SEQ ID NO:15, as is the nucleotide sequence encoding the UGT91D2e polypeptide that has been codon optimized for expression in yeast (SEQ ID NO:89). The amino acid sequences of exemplary UGT91D2m (SEQ ID NO:86) polypeptides from S. rebaudiana are set forth as SEQ ID NO: 10 in PCT Application No. PCT/US2012/050021, which is incorporated herein by reference in its entirety. In addition, UGT91D2 variants containing a substitution at amino acid residues 206, 207, and 343 can be used. For example, the amino acid sequence having G206R, Y207C, and W343R mutations with respect to wild-type UGT91D2e can be used. In addition, a UGT91D2 variant containing substitutions at amino acid residues 211 and 286 can be used. For example, a UGT91D2 variant can include a substitution of a methionine for leucine at position 211 and a substitution of an alanine for valine at position 286 (referred to as UGT91D2e-b). These variants, L211M and V286A, are variants of SEQ ID NO: 5 from PCT/US2012/050021, which is disclosed herein as SEQ ID NO: 66. Additional variants can include variants (except T144S, M152L, L213F, S364P, and G384C variants) described in Table 12 and Example 11 of the PCT/US2012/050021, which is incorporated herein by reference in its entirety.

As indicated above, UGTs designated herein as SMI2UGT can be substituted for UGT91D2. Suitable functional SMI2UGT polypeptides include those made by *Ipomoea purpurea* (Japanese morning glory) and described in Morita et al., 2005, Plant J. 42, 353-363. The amino acid sequence encoding the *I. purpurea* IP3GGT (SEQ ID NO: 67) (which is set forth in PCT Application No. PCT/US2012/050021, which is incorporated herein by reference in its entirety) as a nucleotide sequence (SEQ ID NO: 68) that encodes the polypeptide and that has been codon optimized for expression in yeast. Another suitable SM12UGT polypeptide is a UGT94B1 polypeptide having an R25S mutation (Bp94B1 polypeptide). See Osmani et al., 2008, Plant Phys. 148: 1295-1308 and Sawada et al., 2005, J. Biol. Chem. 280:899-906. The amino acid sequence of the *Bellis perennis* (red daisy) UGT94B1 (SEQ ID NO: 69) and the nucleotide sequence that has been codon optimized for expression in yeast (SEQ ID NO: 70) are set forth in PCT Application No. PCT/US2012/050021, which is incorporated herein by reference in its entirety.

In some embodiments, the recombinant microorganism is grown on media containing steviol-13-O-glucoside or steviol-19-O-glucoside in order to produce Rebaudioside M. In such embodiments, the microorganism contains and expresses genes encoding a functional EUGT11, a functional UGT74G1, a functional UGT85C2, a functional UGT76G1, and a functional UGT91D2, and is capable of accumulating Rebaudioside A, Rebaudioside D, Rebaudioside M or a combination thereof, depending on the relative levels of UDP-glycosyl transferase activities, when steviol, one or both of the steviolmonosides, or rubusoside is used as feedstock.

In other embodiments, the recombinant microorganism is grown on media containing rubusoside in order to produce Rebaudioside A, D, or M. In such embodiments, the microorganism contains and expresses genes encoding a functional EUGT11, a functional UGT76G1, and a functional UGT91D2, and is capable of producing Rebaudioside A, D, M or a combination thereof, depending on the relative levels of UDP-glycosyl transferase activities, when rubusoside is used as feedstock.

In other embodiments the recombinant microorganism expresses genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a EUGT11, a UGT74G1, a UGT85C2, a UGT76G1, and a functional UGT91D2 (e.g., UGT91D2e), is capable of producing Rebaudioside A, D, E, and/or M without the necessity of including steviol in the culture media.

In some embodiments, the recombinant host further contains and expresses a recombinant GGPPS gene in order to provide increased levels of the diterpene precursor geranylgeranyl diphosphate, for increased flux through the steviol biosynthetic pathway.

In some embodiments, the recombinant host further contains a construct to silence expression of non-steviol pathways consuming geranylgeranyl diphosphate, ent-Kaurenoic acid or farnesyl pyrophosphate, thereby providing increased flux through the steviol and steviol glycosides biosynthetic pathways. As discussed below, flux to sterol production pathways such as ergosterol can be reduced by downregulation of the ERG9 gene. In cells that produce gibberellins, gibberellin synthesis can be downregulated to increase flux of ent-kaurenoic acid to steviol. In carotenoid-producing organisms, flux to steviol can be increased by downregulation of one or more carotenoid biosynthetic genes. In some embodiments, the recombinant microorganism further can express recombinant genes involved in diterpene biosynthesis or production of terpenoid precursors, e.g., genes in the MEP or MEV pathways discussed below, have reduced phosphatase activity, and/or express a SUS as discussed herein.

One with skill in the art will recognize that by modulating relative expression levels of different UGT genes, a recombinant host can be tailored to specifically produce steviol glycoside products in a desired proportion. Transcriptional regulation of steviol biosynthesis genes and steviol glycoside biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycoside. One with skill in the art will recognize that a higher proportion of Rebaudioside D or M, or more efficient conversion to Rebaudioside D or M can be obtained with a diglycosylation enzyme that has a higher activity for the 19-O-glucoside reaction as compared to the 13-O-glucoside reaction (substrates Rebaudioside A and stevioside).

In some embodiments, a recombinant host such as a microorganism produces Rebaudioside M-enriched steviol glycoside compositions that have greater than at least 3% Rebaudioside M by weight total steviol glycosides, e.g., at least 4% Rebaudioside M, at least 5% Rebaudioside M, at least 10-20% Rebaudioside M, at least 20-30% Rebaudioside M, at least 30-40% Rebaudioside M, at least 40-50%

Rebaudioside M, at least 50-60% Rebaudioside M, at least 60-70% Rebaudioside M, or at least 70-80% Rebaudioside M. Other steviol glycosides present can include those depicted in FIG. 1 such as steviol monosides, steviol glucobiosides, Rebaudioside A, Rebaudioside D, Rebaudioside E, and stevioside. In some embodiments, the Rebaudioside M-enriched composition produced by the host (e.g., microorganism) can be further purified and the Rebaudioside M so purified can then be mixed with other steviol glycosides, flavors, or sweeteners to obtain a desired flavor system or sweetening composition. For instance, a Rebaudioside M-enriched composition produced by a recombinant host can be combined with a Rebaudioside A, C, D, or E-enriched composition produced by a different recombinant host, with Rebaudioside A, C, D, or E purified from a Stevia extract, or with Rebaudioside A, C, D, or E produced in vitro.

In some embodiments, Rebaudioside M can be produced using in vitro methods while supplying the appropriate UDP-sugar and/or a cell-free system for regeneration of UDP-sugars. In some embodiments, sucrose and a sucrose synthase can be provided in the reaction vessel in order to regenerate UDP-glucose from the UDP generated during glycosylation reactions. The sucrose synthase can be from any suitable organism. For example, a sucrose synthase coding sequence from A. thaliana, S. rebaudiana, or Coffea arabica can be cloned into an expression plasmid under control of a suitable promoter, and expressed in a host such as a microorganism or a plant.

Conversions requiring multiple reactions can be carried out together, or stepwise. For example, Rebaudioside M can be produced from Rebaudioside D or Rebaudioside E that is commercially available as an enriched extract or produced via biosynthesis, with the addition of stoichiometric or excess amounts of UDP-glucose and UGT76G1. As an alternative, Rebaudioside D and Rebaudioside M can be produced from steviol glycoside extracts that are enriched for stevioside and Rebaudioside A, using EUGT11 and a suitable UGT76G1 enzyme. In some embodiments, phosphatases are used to remove secondary products and improve reaction yields. UGTs and other enzymes for in vitro reactions can be provided in soluble forms or in immobilized forms.

In some embodiments, Rebaudioside M can be produced using whole cells that are fed raw materials that contain precursor molecules such as steviol and/or steviol glycosides, including mixtures of steviol glycosides derived from plant extracts. The raw materials can be fed during cell growth or after cell growth. The whole cells can be in suspension or immobilized. The whole cells can be entrapped in beads, for example calcium or sodium alginate beads. The whole cells can be linked to a hollow fiber tube reactor system. The whole cells can be concentrated and entrapped within a membrane reactor system. The whole cells can be in fermentation broth or in a reaction buffer. Similar methodology can be applied to fermentation of recombinant cells.

In some embodiments, a permeabilizing agent is utilized for efficient transfer of substrate into the cells. In some embodiments, the cells are permeabilized with a solvent such as toluene, or with a detergent such as Triton-X or Tween. In some embodiments, the cells are permeabilized with a surfactant, for example a cationic surfactant such as cetyltrimethylammonium bromide (CTAB). In some embodiments, the cells are permeabilized with periodic mechanical shock such as electroporation or a slight osmotic shock. The cells can contain one recombinant UGT or multiple recombinant UGTs. For example, the cells can contain UGT76G1, 91D2e, 85C2, 74G1 and EUGT11 such that mixtures of steviol and/or steviol glycosides are efficiently converted to Rebaudioside M. In some embodiments, the whole cells are the host cells described below. In some embodiments, the whole cells are a Gram-negative bacterium such as E. coli. In some embodiments, the whole cell is a Gram-positive bacterium such as Bacillus. In some embodiments, the whole cell is a fungal species such as Aspergillus, or yeast such as Saccharomyces. In some embodiments, the term "whole cell biocatalysis" is used to refer to the process in which the whole cells are grown as described above (e.g., in a medium and optionally permeabilized) and a substrate such as Rebaudioside D, Rebaudioside E, or stevioside is provided and converted to the end product using the enzymes from the cells. The cells can or cannot be viable, and can or cannot be growing during the bioconversion reactions. In contrast, in fermentation, the cells are cultured in a growth medium and fed a carbon and energy source such as glucose and the end product is produced with viable cells.

C. Other Polypeptides

Genes for additional polypeptides whose expression facilitates more efficient or larger scale production of steviol or a steviol glycoside can also be introduced into a recombinant host. For example, a recombinant microorganism, plant, or plant cell can also contain one or more genes encoding a geranylgeranyl diphosphate synthase (GGPPS, also referred to as GGDPS). As another example, the recombinant host can contain one or more genes encoding a rhamnose synthetase, or one or more genes encoding a UDP-glucose dehydrogenase and/or a UDP-glucuronic acid decarboxylase. As another example, a recombinant host can also contain one or more genes encoding a cytochrome P450 reductase (CPR). Expression of a recombinant CPR facilitates the cycling of NADP+ to regenerate NADPH, which is utilized as a cofactor for terpenoid biosynthesis. Other methods can be used to regenerate NADHP levels as well. In circumstances where NADPH becomes limiting, for example, strains can be further modified to include exogenous transhydrogenase genes. See, e.g., Sauer et al., 2004, J. Biol. Chem. 279: 6613-6619. Other methods are known to those with skill in the art to reduce or otherwise modify the ratio of NADH/NADPH such that the desired cofactor level is increased.

As another example the recombinant host can contain one or more genes encoding a sucrose synthase, and additionally can contain sucrose uptake genes if desired. The sucrose synthase reaction can be used to increase the UDP-glucose pool in a fermentation host, or in a whole cell bioconversion process. This regenerates UDP-glucose from UDP produced during glycosylation and sucrose, allowing for efficient glycosylation. In some organisms, disruption of the endogenous invertase is advantageous to prevent degradation of sucrose. For example, the S. cerevisiae SUC2 invertase can be disrupted. The sucrose synthase (SUS) can be from any suitable organism. For example, a sucrose synthase coding sequence from, without limitation, A. thaliana, S. rebaudiana, or C. arabica can be cloned into an expression plasmid under control of a suitable promoter, and expressed in a host (e.g., a microorganism or a plant). The sucrose synthase can be expressed in such a strain in combination with a sucrose transporter (e.g., the A. thaliana SUC1 transporter or a functional homolog thereof) and one or more UGTs (e.g., UGT85C2, UGT74G1, UGT76G1, and UGT91D2e, EUGT11 or functional homologs thereof). Culturing the host in a medium that contains sucrose can promote production of UDP-glucose, as well as one or more glucosides (e.g., steviol glycosides).

Expression of the ERG9 gene, which encodes squalene synthase (SQS), also can be reduced in recombinant hosts such that there is a build-up of precursors to squalene synthase in the recombinant host. SQS is classified under EC 2.5.1.21 and is the first committed enzyme of the biosynthesis pathway that leads to the production of sterols. It catalyzes the synthesis of squalene from farnesyl pyrophosphate via the intermediate presqualene pyrophosphate, wherein two units of farnesyl pyrophosphate are converted into squalene. This enzyme is a branch point enzyme in the biosynthesis of terpenoids/isoprenoids and is thought to regulate the flux of isoprene intermediates through the sterol pathway. The enzyme is sometimes referred to as farnesyl-diphosphate farnesyltransferase (FDFT1). In addition, a recombinant host can have reduced phosphatase activity as discussed herein.

MEP Biosynthesis Polypeptides

As another example, the recombinant host can contain one or more genes encoding one or more enzymes in the MEP pathway or the mevalonate pathway. Such genes are useful because they can increase the flux of carbon into the diterpene biosynthesis pathway, producing geranylgeranyl diphosphate from isopentenyl diphosphate and dimethylallyl diphosphate generated by the pathway. The geranylgeranyl diphosphate so produced can be directed towards steviol and steviol glycoside biosynthesis due to expression of steviol biosynthesis polypeptides and steviol glycoside biosynthesis polypeptides. See, e.g., Brandle et al., 2007, Phytochemistry 68:1855-1863.

In some embodiments, a recombinant host contains one or more genes encoding enzymes involved in the methylerythritol 4-phosphate (MEP) pathway for isoprenoid biosynthesis. Enzymes in the MEP pathway include deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS) and 1-hydroxy-2-methyl-2(E)-butenyl 4-diphosphate reductase (HDR). One or more DXS genes, DXR genes, CMS genes, CMK genes, MCS genes, HDS genes and/or HDR genes can be incorporated into a recombinant microorganism. See, Rodriguez-Concepcion and Boronat, Plant Phys. 130: 1079-1089 (2002).

Suitable genes encoding DXS, DXR, CMS, CMK, MCS, HDS and/or HDR polypeptides include those made by *E. coli, A. thaliana* and *Synechococcus leopoliensis*. Nucleotide sequences encoding DXR polypeptides (e.g., SEQ ID NO: 71) are described, for example, in U.S. Pat. No. 7,335,815.

Mevalonate Biosynthesis Polypeptides

*S. cerevisiae* contains endogenous genes encoding the enzymes of a functional mevalonate pathway for isoprenoid synthesis. In some embodiments, a recombinant host also contains one or more heterologous genes encoding enzymes involved in the mevalonate pathway. Genes suitable for transformation into a host encode enzymes in the mevalonate pathway such as a truncated 3-hydroxy-3-methyl-glutaryl (HMG)-CoA reductase (tHMG), and/or a gene encoding a mevalonate kinase (MK), and/or a gene encoding a phosphomevalonate kinase (PMK), and/or a gene encoding a mevalonate pyrophosphate decarboxylase (MPPD). Thus, one or more HMG-CoA reductase genes, MK genes, PMK genes, and/or MPPD genes can be incorporated into a recombinant host such as a microorganism.

Suitable genes encoding mevalonate pathway polypeptides are known. For example, suitable polypeptides include those made by *E. coli, Paracoccus denitrificans, S. cerevisiae, A. thaliana, Kitasatospora griseola, Homo sapiens, Drosophila melanogaster, Gallus gallus, Streptomyces* sp. KO-3988, *Nicotiana attenuata, Kitasatospora griseola, Hevea brasiliensis, Enterococcus faecium* and *Haematococcus pluvialis*. See, e.g., Table 9, U.S. Pat. Nos. 7,183,089, 5,460,949, and 5,306,862, and PCT Application Nos. PCT/US2012/050021 and PCT/US2011/038967, which are incorporated herein by reference in their entirety.

TABLE 9

Sources of HMG CoA Reductases and other Mevalonate Genes

| Accession# | Organism | Enzyme | Size (nt) | Gene name |
|---|---|---|---|---|
| XM_001467423 (amino acid SEQ ID NO: 72) | *Leishmania infantum* | Acetyl-CoA C-acetyltransferase | 1323 (nt SEQ ID NO: 94) | MEV-4 |
| YML075C (amino acid SEQ ID NO: 73) | *Saccharomyces cerevisiae* | Truncated HMG (tHMG1) | 1584 (nt SEQ ID NO: 95) | tHMG1 |
| EU263989 (amino acid SEQ ID NO: 74) | *Ganoderma lucidum* | 3-HMG-CoA reductase | 3681 (nt SEQ ID NO: 96) | MEV-11 |
| BC153262 (amino acid SEQ ID NO: 75) | *Bos taurus* | 3-HMG-CoA reductase | 2667 (nt SEQ ID NO: 97) | MEV-12 |
| AAD47596 (amino acid SEQ ID NO: 76) | *Artemisia annua* | 3-HMG-CoA reductase | 1704 (nt SEQ ID NO: 98) | MEV-13 |
| AAB62280 (amiono acid SEQ ID NO: 77) | *Trypanosoma cruzi* | 3-HMG-CoA reductase | 1308 (nt SEQ ID NO: 99) | MEV-14 |
| CAG41604 (amino acid SEQ | *Staph aureus* | 3-HMG-CoA reductase | 1281 (nt SEQ | MEV-15 |

TABLE 9-continued

Sources of HMG CoA Reductases and other Mevalonate Genes

| Accession# | Organism | Enzyme | Size (nt) | Gene name |
|---|---|---|---|---|
| ID NO: 78) DNA2.0 sequence (amino acid SEQ ID NO: 92) | *Archaeoglobus fulgidus* | 3-HMG-CoA reductase | ID NO: 100) 1311 (nt SEQ ID NO: 101) | HMG reductase |
| DNA2.0 sequence (amino acid SEQ ID NO: 93) | *Pseudomonas mevalonii* | 3-HMG-CoA reductase | 1287 (nt SEQ ID NO: 102) | HMG reductase |

Sucrose Synthase Polypeptides

Sucrose synthase (SUS) can be used as a tool for generating UDP-sugar, in particular UDP-glucose. SUS (EC 2.4.1.13) catalyzes the formation of UDP-glucose and fructose from sucrose and UDP. UDP generated by the reaction of UGTs thus can be converted by SUS into UDP-glucose in the presence of sucrose. See, e.g., Chen et al., 2001, J. Am. Chem. Soc. 123:8866-8867; Shao et al., 2003, Appl. Env. Microbiol. 69:5238-5242; Masada et al., 2007, FEBS Lett. 581:2562-2566; and Son et al., 2009, J. Microbiol. Biotechnol. 19:709-712.

Sucrose synthases can be used to generate UDP-glucose and remove UDP, facilitating efficient glycosylation of compounds in various systems. For example, yeast deficient in the ability to utilize sucrose can be made to grow on sucrose by introducing a sucrose transporter and a SUS. For example, *S. cerevisiae* does not have an efficient sucrose uptake system, and relies on extracellular SUC2 to utilize sucrose. The combination of disrupting the endogenous *S. cerevisiae* SUC2 invertase and expressing recombinant SUS resulted in a yeast strain that was able to metabolize intracellular but not extracellular sucrose (Riesmeier et al., 1992, EMBO J. 11:4705-4713). The strain was used to isolate sucrose transporters by transformation with a cDNA expression library and selection of transformants that had gained the ability to take up sucrose.

The combined expression of recombinant sucrose synthase and a sucrose transporter in vivo can lead to increased UDP-glucose availability and removal of unwanted UDP. For example, functional expression of a recombinant sucrose synthase, a sucrose transporter, and a glycosyltransferase, in combination with knockout of the natural sucrose degradation system (SUC2 in the case of *S. cerevisiae*) can be used to generate a cell that is capable of producing increased amounts of glycosylated compounds such as steviol glycosides. This higher glycosylation capability is due to at least (a) a higher capacity for producing UDP-glucose in a more energy efficient manner, and (b) removal of UDP from growth medium, as UDP can inhibit glycosylation reactions.

The sucrose synthase can be from any suitable organism. For example, a sucrose synthase coding sequence from, without limitation, *A. thaliana* (e.g. SEQ ID NO: 79 or 80), or *C. arabica* (e.g., SEQ ID NO: 81) (see e.g., SEQ ID NOs: 178, 179, and 180 of PCT/US2012/050021, which is incorporated herein by reference in its entirety) includes the amino acid sequence of the sucrose transporter SUC1 from *A. thaliana* (SEQ ID NO: 80), and the amino acid sequence of the sucrose synthase from coffee (SEQ ID NO: 81).

The sucrose synthase can be from any suitable organism. For example, a sucrose synthase coding sequence from, without limitation, *A. thaliana*, *S. rebaudiana*, or *C. arabica* (see e.g., SEQ ID NOs: 79-81) can be cloned into an expression plasmid under control of a suitable promoter, and expressed in a host (e.g., a microorganism or a plant). A SUS coding sequence can be expressed in a SUC2 (sucrose hydrolyzing enzyme) deficient *S. cerevisiae* strain, so as to avoid degradation of extracellular sucrose by the yeast.

The sucrose synthase can be expressed in such a strain in combination with a sucrose transporter (e.g., the *A. thaliana* SUC1 transporter or a functional homolog thereof) and one or more UGTs (e.g., UGT85C2, UGT74G1, UGT76G1, EUGT11, and UGT91D2e, or functional homologs thereof). Culturing the host in a medium that contains sucrose can promote production of UDP-glucose, as well as one or more glucosides (e.g., steviol glucoside). It is to be noted that in some cases, a sucrose synthase and a sucrose transporter can be expressed along with a UGT in a host cell that also is recombinant for production of a particular compound (e.g., steviol).

Modulating Expression of ERG9 Gene

Expression of the endogenous ERG9 gene can be altered in a recombinant host described herein using a nucleic acid construct. The construct can include two regions that are homologous to parts of the genome sequence within the ERG9 promoter or 5' end of the ERG9 open reading frame (ORF), respectively. The construct can further include a promoter, such as either the wild type ScKex2 or wild type ScCyc1, and the promoter further can include a heterologous insert such as a hairpin at its 3'-end. The polypeptide encoded by the ORF advantageously has at least 70% identity to a squalene synthase (EC 2.5.1.21) or a biologically active fragment thereof, said fragment having at least 70% sequence identity to said squalene synthase in a range of overlap of at least 100 amino acids. See, for example, PCT/US2012/050021 (incorporated herein for all purposes in its entirety).

The heterologous insert can adapt the secondary structure element of a hairpin with a hairpin loop. The heterologous insert sequence has the general formula (I):

-X1-X2-X3-X4-X5, wherein

X2 comprises at least 4 consecutive nucleotides being complementary to, and forming a hairpin secondary structure element with at least 4 consecutive nucleotides of X4, and X3 is optional and if present comprises nucleotides involved in forming a hairpin loop between X2 and X4, and X1 and X5 individually and optionally comprise one or more nucleotides, and X2 and X4 can individually consist of any suitable number of nucleotides, so long as a consecutive sequence of at least 4 nucleotides of X2 is complementary to a consecutive sequence of at least 4 nucleotides of X4. In some embodiments, X2 and X4 consist of the same number of nucleotides.

The heterologous insert is long enough to allow a hairpin to be completed, but short enough to allow limited translation of an ORF that is present in-frame and immediately 3' to the heterologous insert. Typically, the heterologous insert is from 10-50 nucleotides in length, e.g., 10-30 nucleotides, 15-25 nucleotides, 17-22 nucleotides, 18-21 nucleotides, 18-20 nucleotides, or 19 nucleotides in length. As provided herein:

X2 can for example consist of in the range of 4 to 25 nucleotides, such as in the range of 4 to 20, 4 to 15, 6 to 12, 8 to 12, or 9 to 11 nucleotides.

X4 can for example consist of in the range of 4 to 25 nucleotides, such as in the range of 4 to 20, 4 to 15, 6 to 12, 8 to 12, or 9 to 11 nucleotides.

In some embodiments, X2 consists of a nucleotide sequence that is complementary to the nucleotide sequence of X4, all nucleotides of X2 are complementary to the nucleotide sequence of X4.

X3 can be absent, i.e., X3 can consist of zero nucleotides. It is also possible that X3 consists of in the range of 1 to 5 nucleotides, such as in the range of 1 to 3 nucleotides.

X1 can be absent, i.e., X1 can consist of zero nucleotides. It is also possible that X1 consists of in the range of 1 to 25 nucleotides, such as in the range of 1 to 20, 1 to 15, 1 to 10, 1 to 5, or 1 to 3 nucleotides.

X5 can be absent, i.e., X5 can consist of zero nucleotides. It is also possible that X5 can consist of in the range 1 to 5 nucleotides, such as in the range of 1 to 3 nucleotides.

The heterologous insert can be any suitable sequence fulfilling the requirements defined herein. For example, the heterologous insert can comprise tgaattcgttaacgaattc (SEQ ID NO: 82), tgaattcgttaacgaactc (SEQ ID NO: 83), tgaattcgttaacgaagtc (SEQ ID NO: 84), or tgaattcgttaacgaaatt (SEQ ID NO: 85).

Without being bound to a particular mechanism, ERG9 expression can be decreased by at least partly, sterically hindering binding of the ribosome to the RNA thus reducing the translation of squalene synthase. Thus, the translation rate of a functional squalene synthase (EC 2.5.1.21) can be reduced, for example. Using such a construct also can decrease turnover of farnesyl-pyrophosphate to squalene and/or enhance accumulation of a compound selected from the group consisting of farnesyl-pyrophosphate, isopentenyl-pyrophosphate, dimethylallyl-pyrophosphate, geranyl-pyrophosphate and geranylgeranyl-pyrophosphate.

In some instances it can be advantageous to include a squalene synthase inhibitor when culturing recombinant hosts described herein. Chemical inhibition of squalene synthase, e.g., by lapaquistat, is known in the art. Other squalene synthase inhibitors include Zaragozic acid and RPR 107393. Thus, in one embodiment the culturing step of the method(s) defined herein are performed in the presence of a squalene synthase inhibitor.

In some embodiments, the recombinant hosts described herein contain a mutation in the ERG9 open reading frame.

In some embodiments, the recombinant hosts described herein contain an ERG9[Delta]::HIS3 deletion/insertion allele.

D. Functional Homologs

Functional homologs of the polypeptides described above are also suitable for use in producing steviol or steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide can be natural occurring polypeptides, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional UGT polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol or steviol glycoside biosynthesis polypeptides. Sequence analysis can involve BLAST, Reciprocal BLAST, or PSI-BLAST analysis of nonredundant databases using a GGPPS, a CDPS, a KS, a KO or a KAH amino acid sequence as the reference sequence. Amino acid sequence is, in some instances, deduced from the nucleotide sequence. Those polypeptides in the database that have greater than 40% sequence identity are candidates for further evaluation for suitability as a steviol or steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol biosynthesis polypeptides, e.g., conserved functional domains.

Conserved regions can be identified by locating a region within the primary amino acid sequence of a steviol or a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol glycosides in a recombinant host include functional homologs of EUGT11 (SEQ ID NO: 16), UGT91D2e (SEQ ID NO: 15), UGT91D2m (SEQ ID NO: 86), UGT85C (SEQ ID NO: 26), and UGT76G (SEQ ID NO:2). Such homologs have greater than 90% (e.g., at least 95% or 99%) sequence identity to the amino acid sequence of EUGT11, UGT91D2e, UGT91D2m, UGT85C, or UGT76G disclosed herein or in PCT Application No. PCT/US2012/050021, which is incorporated herein by reference in its entirety. Variants of EUGT11, UGT91D2, UGT85C, and UGT76G polypeptides typically have 10 or fewer amino acid substitutions within the primary amino acid sequence, e.g., 7 or fewer amino acid substitutions, 5 or conservative amino acid substitutions, or between 1 and 5 substitutions. However, in some embodiments, variants of EUGT11, UGT91D2, UGT85C, and UGT76G polypeptides can have 10 or more amino acid substitutions (e.g., 10, 15, 20, 25, 30, 35, 10-20, 10-35, 20-30, or 25-35 amino acid substitutions). The substitutions can be conservative, or in some embodiments, non-conservative. Non-limiting examples of non-conservative changes in UGT91D2e polypeptides include glycine to arginine and tryptophan to arginine. Non-limiting examples of non-conservative substitutions in UGT76G polypeptides include valine to glutamic acid, glycine to glutamic acid, glutamine to alanine, and serine to proline. Non-limiting examples of changes to UGT85C polypeptides include histidine to aspartic acid, proline to serine, lysine to threonine, and threonine to arginine.

In some embodiments, a useful UGT91D2 homolog can have amino acid substitutions (e.g., conservative amino acid substitutions) in regions of the polypeptide that are outside of predicted loops, e.g., residues 20-26, 39-43, 88-95, 121-124, 142-158, 185-198, and 203-214 are predicted loops in the N-terminal domain and residues 381-386 are predicted loops in the C-terminal domain of 91D2e (see SEQ ID NO:15). For example, a useful UGT91D2 homolog can include at least one amino acid substitution at residues 1-19, 27-38, 44-87, 96-120, 125-141, 159-184, 199-202, 215-380, or 387-473. In some embodiments, a UGT91D2 homolog can have an amino acid substitution at one or more residues selected from the group consisting of residues 30, 93, 99, 122, 140, 142, 148, 153, 156, 195, 196, 199, 206, 207, 211, 221, 286, 343, 427, and 438. For example, a UGT91D2 functional homolog can have an amino acid substitution at one or more of residues 206, 207, and 343, such as an arginine at residue 206, a cysteine at residue 207, and an arginine at residue 343. Other functional homologs of UGT91D2 can have one or more of the following: a tyrosine or phenylalanine at residue 30, a proline or glutamine at residue 93, a serine or valine at residue 99, a tyrosine or a phenylalanine at residue 122, a histidine or tyrosine at residue 140, a serine or cysteine at residue 142, an alanine or threonine at residue 148, a methionine at residue 152, an alanine at residue 153, an alanine or serine at residue 156, a glycine at residue 162, a leucine or methionine at residue 195, a glutamic acid at residue 196, a lysine or glutamic acid at residue 199, a leucine or methionine at residue 211, a leucine at residue 213, a serine or phenylalanine at residue 221, a valine or isoleucine at residue 253, a valine or alanine at residue 286, a lysine or asparagine at residue 427, an alanine at residue 438, and either an alanine or threonine at residue 462. In another embodiment, a UGT91D2 functional homolog contains a methionine at residue 211 and an alanine at residue 286.

In some embodiments, a useful UGT85C homolog can have one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471. Non-limiting examples of useful UGT85C homologs include polypeptides having substitutions (with respect to SEQ ID NO: 26) at residue 65 (e.g., a serine at residue 65), at residue 65 in combination with residue 15 (a leucine at residue 15), 270 (e.g., a methionine, arginine, or alanine at residue 270), 418 (e.g., a valine at residue 418), 440 (e.g., an aspartic acid at residue at residue 440), or 441 (e.g., an asparagine at residue 441); residues 13 (e.g., a phenylalanine at residue 13), 15, 60 (e.g., an aspartic acid at residue 60), 270, 289 (e.g., a histidine at residue 289), and 418; substitutions at residues 13, 60, and 270; substitutions at residues 60 and 87 (e.g., a phenylalanine at residue 87); substitutions at residues 65, 71 (e.g., a glutamine at residue 71), 220 (e.g., a threonine at residue 220), 243 (e.g., a tryptophan at residue 243), and 270; substitutions at residues 65, 71, 220, 243, 270, and 441; substitutions at residues 65, 71, 220, 389 (e.g., a valine at residue 389), and 394 (e.g., a valine at residue 394); substitutions at residues 65, 71, 270, and 289; substitutions at residues 220, 243, 270, and 334 (e.g., a serine at residue 334); or substitutions at residues 270 and 289. The following amino acid mutations did not result in a loss of activity in 85C2 polypeptides: V13F, F15L, H60D, A65S, E71Q, I87F, K220T, R243W, T270M, T270R, Q289H, L334S, A389V, I394V, P397S, E418V, G440D, and H441N. Additional mutations that were seen in active clones include K9E, K10R, Q21H, M27V, L91P, Y298C, K350T, H368R, G420R, L431P, R444G, and M471T. In some embodiments, an UGT85C2 contains substitutions at positions 65 (e.g., a serine), 71 (a glutamine), 270 (a methionine), 289 (a histidine), and 389 (a valine).

In some embodiments, a useful UGT76G1 homolog (SEQ ID NO: 2) can have one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 (see TABLE 10). Non-limiting examples of useful UGT76G1 homologs include polypeptides having substitutions at residues 74, 87, 91, 116, 123, 125, 126, 130, 145, 192, 193, 194, 196, 198, 199, 200, 203, 204, 205, 206, 207, 208, and 291; residues 74, 87, 91, 116, 123, 125, 126, 130, 145, 192, 193, 194, 196, 198, 199, 200, 203, 204, 205, 206, 207, 208, 266, 273, 274, 284, 285, and 291; or residues 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346. See, Table 10.

TABLE 10

| Clone | Variants |
| --- | --- |
| 76G_G7 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion, L330V, G331A, L346I |
| 76G_H12 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion |

TABLE 10-continued

| Clone | Variants |
|---|---|
| 76G_C4 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I |

Methods to modify the substrate specificity of, for example, EUGT11 or UGT91D2e, are known to those skilled in the art, and include without limitation site-directed/rational mutagenesis approaches, random directed evolution approaches and combinations in which random mutagenesis/saturation techniques are performed near the active site of the enzyme. For example see Sarah A. Osmani, et at, Phytochemistry 70 (2009) 325-347.

A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A functional homolog polypeptide typically has a length that is from 95 percent to 105 percent of the length of the reference sequence, e.g., 90, 93, 95, 97, 99, 100, 105, 110, 115, or 120 percent of the length of the reference sequence, or any range between. A percent identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bc-m.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional UGTs can include additional amino acids that are not involved in glucosylation or other enzymatic activities carried out by the enzyme, and thus such a polypeptide can be longer than would otherwise be the case. For example, a EUGT11 polypeptide can include a purification tag (e.g., HIS tag or GST tag), a chloroplast transit peptide, a mitochondrial transit peptide, an amyloplast peptide, signal peptide, or a secretion tag added to the amino or carboxy terminus. In some embodiments, a EUGT11 polypeptide includes an amino acid sequence that functions as a reporter, e.g., a green fluorescent protein or yellow fluorescent protein.

II. Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also can include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region can be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it can be desirable to downregulate synthesis of sterols in a yeast strain in order to further increase steviol or steviol glycoside production, e.g., by downregulating squalene epoxidase. As another example, it can be desirable to inhibit degradative functions of certain endogenous gene products, e.g., glycohydrolases that remove glucose moieties from secondary metabolites or phosphatases as discussed herein. As another example, expression of membrane transporters involved in transport of steviol glycosides can be inhibited, such that secretion of glycosylated steviosides is inhibited. Such regulation can be beneficial in that secretion of steviol glycosides can be inhibited for a desired period of time during culture of the microorganism, thereby increasing the yield of glycoside product(s) at harvest. In such cases, a nucleic acid that inhibits expression of the polypeptide or gene product can be included in a recombinant construct that is transformed into the strain. Alternatively, mutagenesis can be used to generate mutants in genes for which it is desired to inhibit function.

III. Hosts

Microorganisms

Recombinant hosts can be used to express polypeptides for the production of steviol glycosides, including mammalian, insect, and plant cells. A number of prokaryotes and eukaryotes are also suitable for use in constructing the recombinant microorganisms described herein, e.g., gram-negative bacteria, yeast and fungi. A species and strain selected for use as a steviol or steviol glycoside production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species can be suitable. For example, suitable species can be in a genus selected from the group consisting of *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* and *Yarrowia*. Exemplary species from such genera include *Lentinus tigrinus, Laetiporus sulphureus, Phanerochaete chtysosporium, Pichia pastoris, Cyberlindnera jadinfi, Physcomitrella patens, Rhodoturula glutinis* 32, *Rhodoturula mucilaginosa, Phaffia rhodozyma* UBV-AX, *Xanthophyllomyces dendrorhous, Fusarium fujikuroi/Gibberella fujikuroi, Candida utilis, Candida glabrata, Candida albicans,* and *Yarrowia lipolytica*. In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii,* or *Saccharomyces cerevisiae*. In some embodiments, a microorganism can be a prokaryote such as *Escherichia coli, Rhodobacter sphaeroides,* or *Rhodobacter capsulatus*. It will be appreciated that certain microorganisms can be used to screen and test genes of interest in a high throughput manner, while other microorganisms with desired productivity or growth characteristics can be used for large-scale production of steviol glycosides.

*Saccharomyces cerevisiae*

*Saccharomyces cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms.

A steviol biosynthesis gene cluster can be expressed in yeast using any of a number of known promoters. Strains that overproduce terpenes are known and can be used to increase the amount of geranylgeranyl diphosphate available for steviol and steviol glycoside production.

*Aspergillus* spp.

*Aspergillus* species such as *A. oryzae, A. niger* and *A. sojae* are widely used microorganisms in food production, and can also be used as the recombinant microorganism platform. Nucleotide sequences are available for genomes of

*A. nidulans, A. fumigatus, A. oryzae, A. clavatus, A. flavus, A. niger,* and *A. terreus,* allowing rational design and modification of endogenous pathways to enhance flux and increase product yield. Metabolic models have been developed for *Aspergillus,* as well as transcriptomic studies and proteomics studies. *A. niger* is cultured for the industrial production of a number of food ingredients such as citric acid and gluconic acid, and thus species such as *A. niger* are generally suitable for the production of food ingredients such as steviol and steviol glycosides.

*Escherichia coli*

*Escherichia coli,* another widely used platform organism in synthetic biology, can also be used as the recombinant microorganism platform. Similar to *Saccharomyces,* there are libraries of mutants, plasmids, detailed computer models of metabolism and other information available for *E. coli,* allowing for rational design of various modules to enhance product yield. Methods similar to those described above for *Saccharomyces* can be used to make recombinant *E. coli* microorganisms.

*Agaricus, Gibberella,* and *Phanerochaete* spp.

*Agaricus, Gibberella,* and *Phanerochaete* spp. can be useful because they are known to produce large amounts of gibberellin in culture. Thus, the terpene precursors for producing large amounts of steviol and steviol glycosides are already produced by endogenous genes. Thus, modules containing recombinant genes for steviol or steviol glycoside biosynthesis polypeptides can be introduced into species from such genera without the necessity of introducing mevalonate or MEP pathway genes.

*Arxula adeninivorans (Blastobotrys adeninivorans)*

*Arxula adeninivorans* is a dimorphic yeast (it grows as a budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is a dimorphic yeast (see *Arxula adeninivorans*) that can grow on a wide range of substrates. It has a high potential for industrial applications but there are no recombinant products commercially available yet.

*Rhodobacter* spp.

*Rhodobacter* can be used as the recombinant microorganism platform. Similar to *E. coli,* there are libraries of mutants available as well as suitable plasmid vectors, allowing for rational design of various modules to enhance product yield. Isoprenoid pathways have been engineered in membraneous bacterial species of *Rhodobacter* for increased production of carotenoid and CoQ10. See, U.S. Patent Publication Nos. 20050003474 and 20040078846. Methods similar to those described above for *E. coli* can be used to make recombinant *Rhodobacter* microorganisms.

*Candida boidinii*

*Candida boidinii* is a methylotrophic yeast (it can grow on methanol). Like other methylotrophic species such as *Hansenula polymorpha* and *Pichia pastoris,* it provides an excellent platform for the production of heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH.

*Hansenula polymorpha (Pichia angusta)*

*Hansenula polymorpha* is another methylotrophic yeast (see *Candida boidinii*). It can furthermore grow on a wide range of other substrates; it is thermo-tolerant and can assimilate nitrate (see also *Kluyveromyces lactis*). It has been applied to the production of hepatitis B vaccines, insulin and interferon alpha-2a for the treatment of hepatitis C, furthermore to a range of technical enzymes.

*Kluyveromyces lactis*

*Kluyveromyces lactis* is yeast regularly applied to the production of kefir. It can grow on several sugars, most importantly on lactose which is present in milk and whey. It has successfully been applied among others to the production of chymosin (an enzyme that is usually present in the stomach of calves) for the production of cheese. Production takes place in fermenters on a 40,000 L scale.

*Pichia pastoris*

*Pichia pastoris* is a methylotrophic yeast (see *Candida boidinii* and *Hansenula polymorpha*). It provides an efficient platform for the production of foreign proteins. Platform elements are available as a kit and it is worldwide used in academia for the production of proteins. Strains have been engineered that can produce complex human N-glycan (yeast glycans are similar but not identical to those found in humans).

*Physcomitrella* spp.

*Physcomitrella* mosses, when grown in suspension culture, have characteristics similar to yeast or other fungal cultures. This genera is becoming an important type of cell for production of plant secondary metabolites, which can be difficult to produce in other types of cells.

IV. Methods of Producing Steviol Glycosides

Recombinant hosts described herein can be used in methods to produce steviol glycosides such as Rebaudioside M. For example, if the recombinant host is a microorganism, the method can include growing the recombinant microorganism in a culture medium under conditions in which steviol and/or steviol glycoside biosynthesis genes are expressed. The recombinant microorganism can be grown in a fed batch or continuous process. Typically, the recombinant microorganism is grown in a fermentor at a defined temperature(s) for a desired period of time. In certain embodiments, microorganisms include, but are not limited to *S. cerevisiae, A. niger, A. oryzae, E. coli, L. lactis* and *B. subtilis.* The constructed and genetically engineered microorganisms provided by the invention can be cultivated using conventional fermentation processes, including, inter alia, chemostat, batch, fed-batch cultivations, continuous perfusion fermentation, and continuous perfusion cell culture.

Depending on the particular microorganism used in the method, other recombinant genes such as isopentenyl biosynthesis genes and terpene synthase and cyclase genes can also be present and expressed. Levels of substrates and intermediates, e.g., isopentenyl diphosphate, dimethylallyl diphosphate, geranylgeranyl diphosphate, kaurene and kaurenoic acid, can be determined by extracting samples from culture media for analysis according to published methods.

After the recombinant microorganism has been grown in culture for the desired period of time, steviol and/or one or more steviol glycosides can then be recovered from the culture using various techniques known in the art. In some embodiments, a permeabilizing agent can be added to aid the feedstock entering into the host and product getting out. If the recombinant host is a plant or plant cells, steviol or steviol glycosides can be extracted from the plant tissue using various techniques known in the art. For example, a crude lysate of the cultured microorganism or plant tissue can be centrifuged to obtain a supernatant. The resulting supernatant can then be applied to a chromatography column, e.g., a C18 column such as Aqua® C18 column from Phenomenex or a Synergi™ Hydro RP 80 Å column, and washed with water to remove hydrophilic compounds, followed by elution of the compound(s) of interest with a solvent such as acetonitrile or methanol. The compound(s) can then be further purified by preparative HPLC. See also WO 2009/140394.

The amount of steviol glycoside (e.g., Rebaudioside M) produced can be from about 1 mg/L to about 2800 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing steviol while a second microorganism comprises steviol glycoside biosynthesis genes. Alternatively, the two or more microorganisms each can be grown in a separate culture medium and the product of the first culture medium, e.g., steviol, can be introduced into second culture medium to be converted into a subsequent intermediate, or into an end product such as Rebaudioside A. The product produced by the second, or final microorganism is then recovered. It will also be appreciated that in some embodiments, a recombinant microorganism is grown using nutrient sources other than a culture medium and utilizing a system other than a fermentor.

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., Rebaudioside M) and have a consistent taste profile. Thus, the recombinant microorganisms, plants, and plant cells described herein can facilitate the production of compositions that are tailored to meet the sweetening profile desired for a given food product and that have a proportion of each steviol glycoside that is consistent from batch to batch. Microorganisms described herein do not produce the undesired plant byproducts found in Stevia extracts. Thus, steviol glycoside compositions produced by the recombinant microorganisms described herein are distinguishable from compositions derived from Stevia plants.

V. Food Products

The steviol glycosides obtained by the methods disclosed herein can be used to make food and beverage products, dietary supplements and sweetener compositions. For example, substantially pure steviol glycoside such as Rebaudioside M can be included in food products such as ice cream, carbonated beverages, fruit juices, yogurts, baked goods, chewing gums, hard and soft candies, and sauces. Substantially pure steviol glycoside also can be included in non-food products such as pharmaceutical products, medicinal products, dietary supplements and nutritional supplements. Substantially pure steviol glycosides can also be included in animal feed products for both the agriculture industry and the companion animal industry. Alternatively, a mixture of steviol glycosides can be made by culturing recombinant microorganisms separately or growing different plants/plant cells, each producing a specific steviol or steviol glycoside, recovering the steviol or steviol glycoside in substantially pure form from each microorganism or plant/plant cells and then combining the compounds to obtain a mixture containing each compound in the desired proportion (e.g., Rebaudioside M with one or more other steviol glycosides). The recombinant microorganisms, plants, and plant cells described herein permit more precise and consistent mixtures to be obtained compared to current Stevia products. In another alternative, a substantially pure steviol glycoside can be incorporated into a food product along with other sweeteners, e.g. saccharin, dextrose, sucrose, fructose, erythritol, aspartame, sucralose, monatin, or acesulfame potassium. The weight ratio of steviol glycoside relative to other sweeteners can be varied as desired to achieve a satisfactory taste in the final food product. See, e.g., U.S. Patent Publication No. 2007/0128311. In some embodiments, the steviol glycoside can be provided with a flavor (e.g., citrus) as a flavor modulator.

Compositions produced by a recombinant microorganism, plant, or plant cell described herein can be incorporated into food products. For example, a steviol glycoside composition produced by a recombinant microorganism, plant, or plant cell can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism, plant, or plant cell can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism, plant, or plant cell can be incorporated into a baked good (e.g., a biscuit) such that the food product has a maximum of 300 mg steviol glycoside/kg food on a dry weight basis. A steviol glycoside composition produced by a recombinant microorganism, plant, or plant cell can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism, plant, or plant cell can be incorporated into bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art.

Steviol glycoside compositions enriched for Rebaudioside M can be package in a sachet, for example, at from 10,000 to 30,000 mg steviol glycoside/kg product on a dry weight basis, for tabletop use.

The invention will be further described in the following examples, which do not limit the scope of the invention described in the claims.

EXAMPLES

The Examples that follow are illustrative of specific embodiments of the invention and various uses thereof. They are set forth for explanatory purposes only and are not to be taken as limiting the invention.

Example 1: Strain Engineering and Fermentation of EFSC 3044

Yeast strain EFSC 3044 was derived from a wild type *Saccharomyces cerevisiae* strain containing three auxotrophic modifications, namely the deletions of URA3, LEU2 and HIS3. The strain can be manipulated using standard genetic methods and can be used as a regular diploid or haploid yeast strain. The strain was converted to steviol glycosides-producing yeast by genomic-integration of five DNA constructs. Each construct contained multiple genes and was introduced into the yeast genome by homologous recombination. Furthermore, the first, second, and fifth construct were assembled by homologous recombination in yeast.

The first construct contained eight genes and was inserted in the DPP1 locus and disrupted and partially deleted DPP1 (phosphatase). The DNA inserted contained: the *Ashbya gossypii* TEF1 promoter expressing the natMX gene (selectable marker) followed by the TEF1 terminator from *A. gossypii*; Gene Art codon optimized Ste via *rebaudiana* UGT85C2 (GenBank AAR06916.1; SEQ ID NO:3) expressed from the native yeast GPD1 promoter and followed by the native yeast CYC1 terminator; *S. rebaudiana* CPR-8 (SEQ ID NO:5) expressed using the native yeast TPI1 promoter followed by the native yeast TDH1 terminator; *Arabidopsis thaliana* kaurene synthase (SEQ ID NO:6, similar to GenBank AEE36246.1) expressed from the native yeast PDC1 promoter and followed by the native yeast FBA1 terminator; synthetic *Synechococcus* sp. GGPPS (SEQ ID NO: 22, GenBank ABC98596.1) expressed using the native yeast TEF2 promoter and followed by the native yeast PGI1 terminator; DNA2.0 codon-optimized *S. rebaudiana* KAHe1 (SEQ ID NO:8) expressed from the native yeast TEF1 promoter and followed by the native yeast ENO2 terminator; synthetic *S. rebaudiana* KO-1 (SEQ ID NO: 23, GenBank ABA42921.1) expressed using the native yeast FBA1 promoter and followed by the native yeast TDH2 terminator; and *Zea mays* truncated CDPS (SEQ ID NO:133) expressed using the native yeast PGK1 promoter and followed by the native yeast ADH2 terminator.

The second construct was inserted at the YPRCΔ15 locus and contained: the TEF1 promoter from *A. gossypii* in front of the kanMX gene (selectable marker) followed by the TEF1 terminator from *A. gossypii*; the Gene Art codon optimized *A. thaliana* ATR2 (SEQ ID NO: 10) expressed from the native yeast PGK1 promoter followed by the native yeast ADH2 terminator; *S. rebaudiana* UGT74G1 (SEQ ID NO:135, GenBank AAR06920.1) expressed from the native yeast TPI1 promoter followed by the native yeast TDH1 terminator; Gene Art codon-optimized *S. rebaudiana* UGT76G1 (SEQ ID NO:14, encodes GenBank AAR06912) expressed from the native yeast TEF1 promoter followed by the native yeast ENO2 terminator; and GeneArt codon-optimized sequence encoding a *S. rebaudiana* UGT91D2e-b with the amino acid modifications L211M and V286A (SEQ ID NO:15 for UGT91D2e amino acid sequence for the wild type sequence; codon optimized nucleotide sequence is set forth in SEQ ID NO:90) and expressed from the native yeast GPD1 promoter and followed by the native yeast CYC1 terminator. UGT91D2e-b is disclosed herein as SEQ ID NO: 66 with mutations at methionine residue at residue 211 and an alanine residue at residue 286.

The first and the second construct were combined in the same spore clone by mating and dissection. This yeast strain was subsequently transformed with construct three and four in two successive events.

Construct three was integrated between genes PRP5 and YBR238C and contained the *Kluyveromyces lactis* leu2 promoter expressing the *K. lactis* leu2 gene followed by the leu2 terminator from *K. lactis*, the native yeast GPD1 promoter expressing the DNA2.0-optimized *S. rebaudiana* KAHe1 (SEQ ID NO:8) followed by the native yeast CYC1 terminator, and the native yeast TPI1 promoter expressing the *Zea mays* truncated CDPS (SEQ ID NO: 133) followed by the native yeast TPI1 terminator.

Construct four was integrated in the genome between genes ECM3 and YOR093C with an expression cassette containing the TEF1 promoter from *A. gossypii* expressing the *K. pneumoniae* hphMX gene followed by the TEF1 terminator from *A. gossypii*, *Synechococcus* sp. GGPPS (SEQ ID NO: 22) expressed from the native yeast GPD1 promoter followed by the native yeast CYC1 terminator, and the native yeast TPI1 promoter expressing the *A. thaliana* KS (SEQ ID NO: 6) followed by the native yeast TPI1 terminator.

The four introduced selectable markers natMX, kanMX, *K. lactis* LEU2 and *K. pneumoniae* hphMX and the promoters preceding and terminators succeeding the selectable marker genes were then removed by recombination.

In this yeast strain, the fifth construct was inserted and assembled by yeast transformation and homologue recombination. The fifth construct contained seven genes and was inserted at the YORWΔ22 locus. The DNA inserted contained: the *A. gossypii* TEF1 promoter expressing the *Schizosaccharomyces Pombe* HIS5 gene (selectable marker) followed by the TEF1 terminator from *A. gossypii*; *S. rebaudiana* KO-1 (SEQ ID NO: 23, GenBank ABA42921.1) expressed from the native yeast GPD1 promoter and followed by the native yeast CYC1 terminator; *S. rebaudiana* CPR-8 (SEQ ID NO: 5) expressed using the native yeast TPI1 promoter followed by the native yeast TDH1 terminator; *Arabidopsis thaliana* kaurene synthase (SEQ ID NO: 6, similar to GenBank AEE36246.1) expressed from the native yeast PDC1 promoter and followed by the native yeast FBA1 terminator; a codon optimized version of the rice gene Os03g0702000 (SEQ ID NO:18, encoding EUGT11) expressed using the native yeast TEF2 promoter and followed by the native yeast PGI1 terminator; DNA2.0 codon-optimized *S. rebaudiana* KAHe1 (SEQ ID NO: 8) expressed from the native yeast TEF1 promoter and followed by the native yeast ENO2 terminator; and *Zea mays* truncated CDPS (SEQ ID NO:133) expressed using the native yeast PGK1 promoter and followed by the native yeast ADH2 terminator.

The described yeast strain was made prototrophic by introduction of the two plasmids, EPSC2182 and EPSC2308. EPSC2182 was derived from a p415TEF CEN/

ARS shuttle plasmid with a LEU2 marker and contains another copy of *S. rebaudiana* KAHe1 expressed from the native yeast TEF1 promoter and succeeded by the native yeast CYC1 terminator. EPSC2308 was a p416TEF-based CEN/ARS shuttle plasmid with the URA3 marker wherein the EUGT11 gene was cloned and expressed from the native yeast TEF1 promoter and succeeded by the native yeast CYC1 terminator. This yeast strain was then designated EFSC 3044.

TABLE 11

List of Recombinant Genes in Strain EFSC 3044.

| Gene Designation | Yeast Location | Construct No. |
| --- | --- | --- |
| UGT85C2 | Genomic | 1 |
| *S. rebaudiana* CPR-8 | Genomic | 1 |
| *A thaliana* Kaurene synthase | Genomic | 1 |
| *Synechococcus* sp. GGPPS | Genomic | 1 |
| *S. rebaudiana* KAHe1 | Genomic | 1 |
| *S. rebaudiana* KO-1 | Genomic | 1 |
| *Zea mays* truncated CDPS | Genomic | 1 |
| *A. thaliana* ATR2 | Genomic | 2 |
| *S. rebaudiana* UGT74G1 | Genomic | 2 |
| *S. rebaudiana* UGT76G1 | Genomic | 2 |
| *Stevia* UGT91D2e-b altered | Genomic | 2 |
| *S. rebaudiana* KAHe1 | Genomic | 3 |
| *Zea mays* truncated CDPS | Genomic | 3 |
| *Synechococcus* sp. GGPPS | Genomic | 4 |
| *A. thaliana* Kaurene synthase | Genomic | 4 |
| *S. rebaudiana* KO-1 | Genomic | 5 |
| *S. rebaudiana* CPR-8 | Genomic | 5 |
| *A thaliana* Kaurene synthase | Genomic | 5 |
| Os03g0702000 (EUGT11) | Genomic | 5 |
| *S. rebaudiana* KAHe1 | Genomic | 5 |
| *Zea mays* truncated CDPS | Genomic | 5 |
| *S. rebaudiana* KAHe1 | Plasmid | 6 |
| EUGT11 | Plasmid | 7 |

Fed-batch fermentation was carried out aerobically in 2 L (working volume) fermenters which included a ~16 hour growth phase in the base medium (Synthetic Complete media) followed by ~100 hours of feeding with glucose utilized as the carbon and energy source combined with trace metals, vitamins, salts, and Yeast Nitrogen Base (YNB) and/or amino acid supplementation. The pH was kept near pH 5, and the temperature setpoint was 30° C. The feed rate was controlled to prevent oxygen depletion and to minimize ethanol formation (glucose-limited conditions). Whole culture samples (without cell removal) were taken and boiled in an equal volume of DMSO for total glycosides levels.

The following methodology was used to analyze steviol glycosides and steviol pathway intermediates, unless otherwise indicated. LC-MS analyses were performed using an UltiMate® 3000 UPLC system (Dionex, Sunnyvale, Calif.) fitted with an Acquity UPLC® BEH C18 column (100×2.1 mm, 1.7 µm particles; Waters, Milford, Mass.) connected to a TSQ Quantum Access (ThermoFisher Scientific) triple quadropole mass spectrometer with a heated electrospray ion (HESI) source. Elution was carried out using a mobile phase of eluent B (MeCN with 0.1% Formic acid) and eluent A (water with 0.1% Formic acid) by increasing the gradient from 29->48% B from min 0.0 to 4.0, increasing 48->100% B in min 4.0 to 4.2, holding 100% B from min 4.2 to 6.2, and re-equilibrating with 29% eluent B. The flow rate was 0.4 ml/min and the column temperature was kept at 55° C. Steviol glycosides were detected using SIM (Single Ion Monitoring) in positive mode with the following m/z-traces in Table 12.

TABLE 12

Summary of Analytical Compounds Detected by LC/MS.

| Description | Exact Mass | m/z trace | Compound (typical $t_R$ in min) |
| --- | --- | --- | --- |
| Steviol + 1 Glucose | [M + H]⁺ 481.2796 [M + Na]⁺ 503.2615 | 481.2 ± 0.5 503.1 ± 0.5 | 19-SMG (4.15), 13-SMG (4.38) |
| Steviol + 2 Glucose | [M + Na]⁺ 665.3149 | 665 ± 0.5 | Rubusoside (3.04) Steviol-1,2-bioside (3.48) Steviol-1,3-bioside (4.05) |
| Steviol + 3 Glucose | [M + Na]⁺ 827.3677 | 827.4 ± 0.5 | 1,2-Stevioside (2.28) 1,3-Stevioside (2.82) Rebaudioside B (3.9) |
| Steviol + 4 Glucose | [M + Na]⁺ 989.4200 | 989.4 ± 0.5 | Rebaudioside A (2.23) |
| Steviol + 5 Glucose | [M + Na]⁺ 1151.4728 | 1151.4 ± 0.5 | Rebaudioside D (1.19) |
| Steviol + 6 Glucose | [M + Na]⁺ 1313.5257 | 1313.5 ± 0.5 | Rebaudioside M (1.31) |

Figure 5:
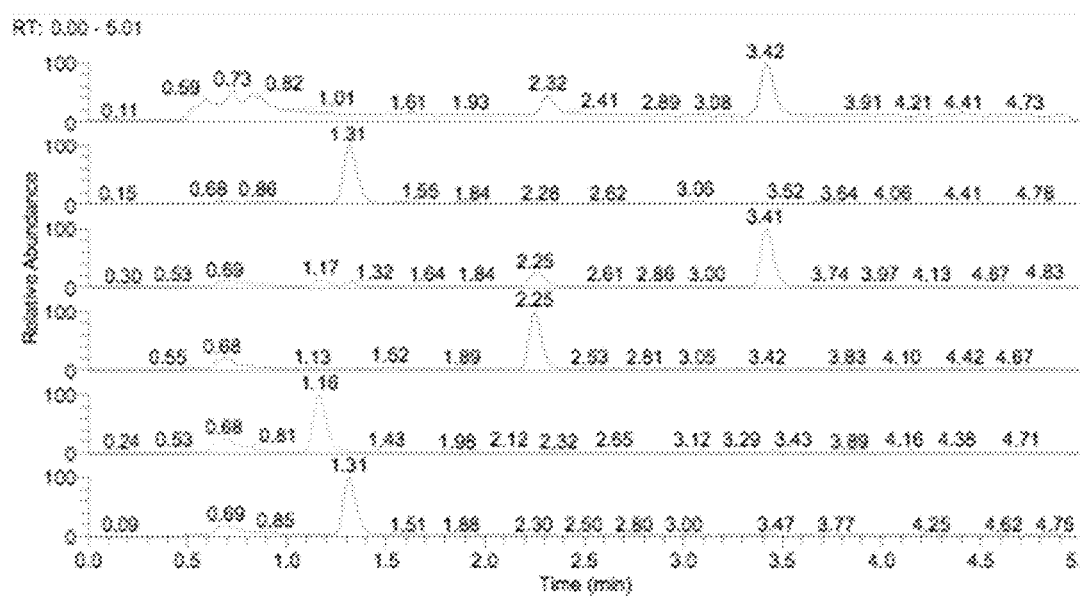
FIG. 5 is a representative chromatogram of Liquid Chromatography-Mass Spectrometry (LC-MS) analysis showing formation of a hexa-glycosylated steviol glycoside at 1.31 min retention time. The traces, from top to bottom, correspond to the m/z indicated in Table 12.

The level of steviol glycosides were quantified by comparing with calibration curves obtained with authentic standards from LGC Standards. For example, standard solutions of 0.5 to 100 µM Rebaudioside A (RebA) were typically utilized to construct a calibration curve. FIG. 5 contains representative mass spectra of fermentations that resulted in the formation of a hexaglycosylated steviol glycoside (retention time 1.31, mass traces corresponding to a hexa-glucose steviol glycoside and stevioside).

A modified LC-MS methodology (using a BEH RPshield C18 HPLC column (50×2.1 mm, 1.7 µm particles; Waters, Milford, Mass.) was used to analyze compounds described in Example 5 and in vitro experiment to determine relative rates for UGT76G1. The elution was carried out using a mobile phase of eluent B (MeCN with 0.1% formic acid) and eluent A (water with 0.1% formic acid) by increasing the gradient from 25->47% B from min 0.0 to 4.0, increasing 47->100% B in min 4.0 to 5.0, holding 100% B from min 5.0 to 6.5, and finally re-equilibrating with 25% B. The flow rate was 0.4 ml/min and the column temperature was kept at 35° C. A modified LC-MS methodology resulted in shorter retention time for the compounds shown in Table 12. Typical retention times using the modified LC-MS methodology ($t_R$ in min) were: 3.34 for 19-SMG; 3.54 for 13-SMG; 2.55 for Rubusoside; 2.95 for Steviol-1,2-bioside; 3.31 for Steviol-1,3-bioside; 2.04 for 1,2-Stevioside; 2.42 for 1,3-Stevioside; 2.91 for Rebaudioside B; 2.03 for Rebaudioside A; 1.1 for Rebaudioside D; and 1.32 for Rebaudioside M.

Example 2: In Vitro Characterization of Reactions that Produce a Hexa-Glycosylated Steviol Glycoside As described in Example 1, a hexa-glucosyl steviol glycoside was observed when EUGT11 was expressed at high levels in steviol-glycoside producing yeast strains. To characterize the reactions that were occurring to produce this molecule, further in vitro work was done with individual UGTs.

UGT76G1 (SEQ ID NO: 1) was cloned into the pET30a plasmid (EMD Millipore). The resulting vector was transformed into an appropriate DE3 *E. coli* strain and transformants were grown and induced according to manufacturer's protocols. The corresponding fusion protein (6× HIStagged) was purified by immobilized metal affinity chromatography using standard methods.

Approximately 0.08 μg of purified UGT76G1 per μL of reaction was incubated with 100 μM RebD, 300 μM UDP-glucose, and 10 U/mL Alkaline Phosphatase (Fermentas/Thermo Fisher, Waltham, Mass.). The reactions were performed at 30° C. in 20 mM Hepes-NaOH, pH 7.6, for 24 hours. Prior to LC-MS analysis, one volume of 100% DMSO was added to each reaction and vortexed, and samples were centrifuged at 16,000×g for 1 minute.

A new peak appeared during the reaction at a mass corresponding to steviol+6 glucose moieties, eluting at 1.31 min and corresponding to a trace of one of the hexaglucosyl steviol glycosides found upon the overexpression of EUGT11 in vivo. This result suggested that UGT76G1 can further glycosylate RebD, resulting in a hexaglycoside. It was hypothesized that UGT76G1, in addition to making a 1,3-glucose linkage with the primary glucose at C13 of the steviol backbone, has a secondary activity of adding a 1,3-bound glucose to the primary glucose at C19. It is likely that the only glycosylation site available in RebD available for UGT76G1 is the glucose at C19, which would result in the production of a hexaglycoside designated RebM. The hexaglycoside detected was isolated and determined to be Rebaudioside M, as shown in Examples 3 and 4.

Example 3: Isolation of the Hexa-Glycosylated Molecule

Figure 6:
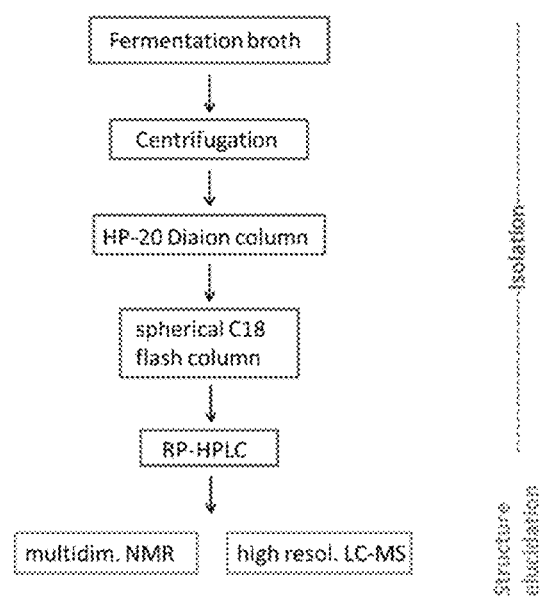
FIG. 6 is a schematic of the methods for isolating hexa-glycosylated steviol glycosides.

The hexa-glucosyl steviol glycoside product was isolated from a fermentation similar to that described in Example 1 for structural analysis following the scheme outlined in FIG. 6.

Figure 7:
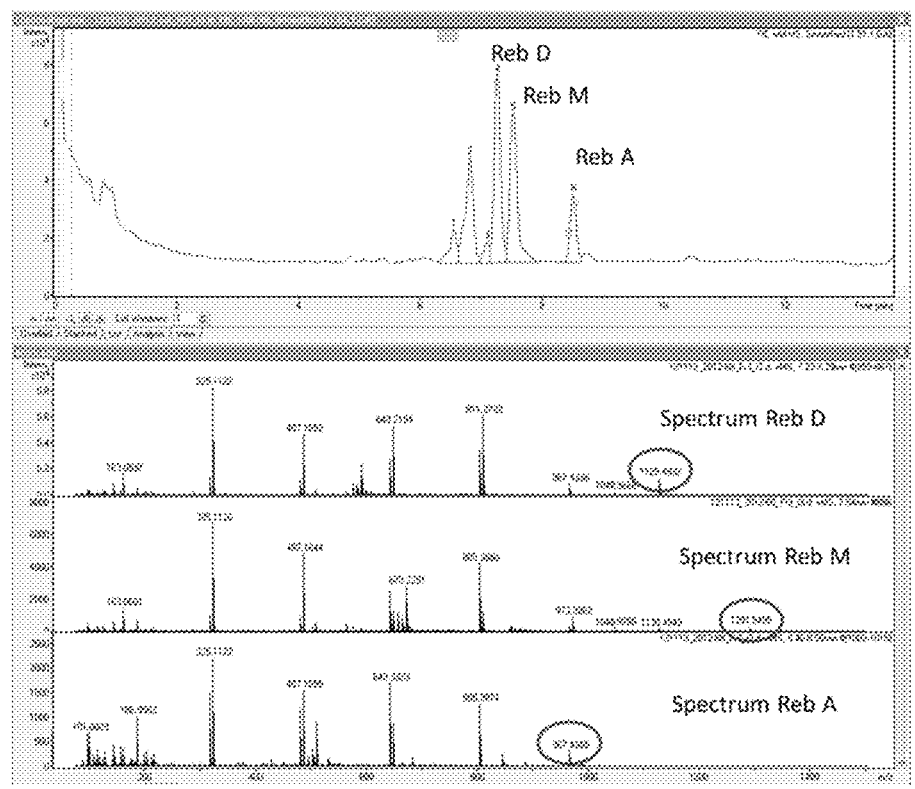
FIG. 7 is a representative chromatogram and mass spectra from a liquid chromatography-quadrupole time-of-flight (LC-QTOF) analysis of the semi-purified hexa-glycosylated steviol glycoside after flash chromatography.

After the fermentation, the culture broth was centrifuged for 30 min at 7000 rpm at 4° C. and the supernatant was purified as follows: A glass column was filled with 150 mL HP20 Diaion® resin (Supelco), and an aliquot of 300 mL supernatant was loaded on to the column and washed with 2×250 mL MilliQ water. The glycoside product was eluted by stepwise incremental increases in the methanol concentration in MilliQ water (in 250 mL portions—starting with 0%→10%→40%→60%→80%→100% MeOH). The levels of steviol glycosides in each fraction were analyzed by LC-MS. The most promising fractions (60-80% MeOH) were combined and reduced to total of 10 mL using a vacuum evaporator. A glass column filled with 600 mL spherical C18 bonded flash silica gel (45-70 um, 70 Å/Supelco) was equilibrated with 5% aqueous acetonitrile (Acetonitrile: HPLC grade—Water: MilliQ). The concentrated residue from the HP20 purification was loaded on the column and eluted by stepwise increases in the acetonitrile contribution. The starting eluent was 5% acetonitrile in water. The level of acetonitrile was raised by 5% per step (each 400 mL). After reaching 50% acetonitrile 10% steps were made. All fractions were analyzed by LC-MS, pooled according to their steviol glycoside composition, and dried under vacuum. Table 13 contains a summary of the glycosides found in each of the fractions. FIG. 7 contains a chromatogram and mass spectra from LC-QTOF analysis of the semi-purified hexa-glycosylated compound after flash chromatography.

TABLE 13

Summary of Fractionation of Steviol Glycosides.

| mg | Fraction | Description |
| --- | --- | --- |
| 321.1 | 2-11 | RebD and some 6X glycosylated steviol glycoside |
| 138.3 | 12-20 | RebD and some 6X glycosylated steviol glycoside |
| 357.4 | 21-27 | Bulk of 6X glycosylated steviol glycoside |
| 98.9 | 28-30 | RebA |
| 68.4 | 31-36 | Rubusoside, steviol-1,2-bioside |
| 14.8 | 34-45 | Mostly 13-SMG |
| 852.8 | Wash | Acetonitrile wash |

Example 4: NMR Confirmation of Structure

To produce a pure sample for NMR, approximately 50 mg of the hexa-glycosylated enriched residue obtained in Example 3 were further purified on a semi-preparative HPLC system. The system was equipped with an Aqua® C18 column (Phenomenex: Dimension 250×21.2 mm, 5 micron). Elution was carried out using a mobile phase of eluent B (MeCN with 0.1% trifluoroacetic acid) and eluent A (water with 0.1% triflouroacidic acid) by increasing the gradient from 1%→50% B from min 0.0 to 21, 50->100% min 21.0 to 27.0 and finally washing with 100% B and re-equilibration. The flow rate was 14 mL/min at room temperature. The fractions were collected by time and analyzed by LC-QTOF-MS for the presence of steviol glycosides. The system used was a UPLC (Waters) coupled to a MicrOTOFII Mass Spectrometer (Bruker). The column used was Acquity UPLC® BEH C18, 100×2.1 mm, 1.7 μm (Waters). Mobile phases were A: 0.1% Formic Acid in water and B: 0.1% Formic Acid in Acetonitrile. The gradient applied was from 1% B to 50% B in 12 minutes and then to 100% B in 3 minutes. The flow rate was 0.4 ml/min.

Fraction 93 was utilized for NMR analysis. All NMR experiments were performed in DMSO-d6 at 25 C using a Bruker Avance III 600 MHz NMR spectrometer equipped with a 1.7 mm cryogenic TCI probe.

The structures were solved by means of standard homo- and heteronuclear multipulse NMR experiments, namely $^1H,^1H$—COSY, $^1H,^{13}C$—HSQC and $^1H,^{13}C$—HMBC experiments. The NMR data obtained was as follows:

1H NMR (600 MHz, DMSO-d6) δ ppm 0.78 (br. s., 1H) 0.83 (s, 3H) 0.92 (d, J=7.39 Hz, 2H) 0.97-1.04 (m, 1H) 1.17 (s, 3H) 1.30-1.54 (m, 6H) 1.67 (d, J=10.40 Hz, 1H) 1.72-1.86 (m, 4H) 1.92 (d, J=6.49 Hz, 1H) 1.96-2.05 (m, 2H) 2.08 (d, J=10.82 Hz, 1H) 2.32 (d, J=12.71 Hz, 1H) 2.91 (t, J=8.82 Hz, 1H) 2.95-3.01 (m, 1H) 3.02-3.27 (m, 14H) 3.31-3.55 (m, 10H) 3.57-3.86 (m, 10H) 4.47 (d, J=7.86 Hz, 1H) 4.51 (d, J=8.00 Hz, 1H) 4.53 (d, J=7.62 Hz, 1H) 4.66 (d, J=7.81 Hz, 1H) 4.73 (br. s., 1H) 4.80 (d, J=7.86 Hz, 1H) 5.11 (br. s., 1H) 5.53 (d, J=8.19 Hz, 1H)

13C NMR (150.91 MHz, DMSO-d6) δ ppm 16.4, 19.4, 19.9, 21.8, 28.3, 36.7, 37.2, 39.3, 40.3, 41.6, 43.2, 43.7, 47.0, 47.2, 53.2, 57.0, 60.7, 61.2, 61.4, 61.8, 62.0, 62.1, 68.5, 68.9, 70.4 (3C), 71.2, 71.6, 74.1-74.3 (4C), 74.8, 75.8, 76.9-77.1 (6C), 77.6, 79.6, 85.8, 86.8, 87.1, 92.1, 96.2, 102.1, 102.8, 103.2, 103.3, 104.5, 153.1, 175.1

The confirmed structure of RebM (systematic name: 13-[β-D-glucopyranosyl-(1->3)-β-D-glucopyranosyl-(1->2)-□β-D-glucopyranosyl-1-oxy] kaur-16-en-18-oic acid, 18-M-D-glucopyranosyl-(1->3)-U3-D-glucopyranosyl-(1->2) [3-D-glucopyranosyl-1-ester]) is shown in FIG. 2.

Example 5: Isolation and Determination of Additional Fermentation Products of EFSC 3044

Figure 8C:
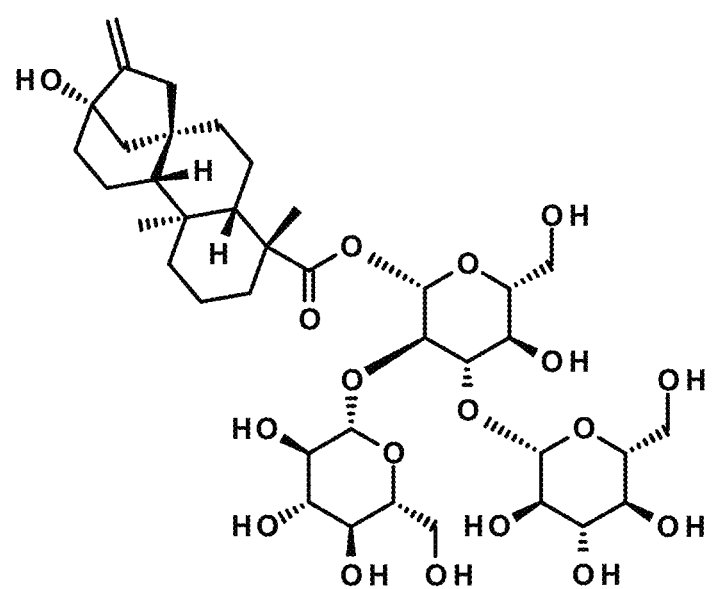
FIG. 8C is the structure of the NMR structure of the indicated tri-glycosylated steviol glycoside (13-hydroxy kaur-16-en-18-oic acid; [2-O-β-D-glucopyranosyl-3-O-☐β-D-glucopyranosyl-β-D-glucopyranosyl] ester, an isomer of RebB. The IUPAC name for tri-glycosylated steviol glycoside is (2S,3R,4S,5R,6R)-5-hydroxy-6-(hydroxymethyl)-3,4-bis({[(2S,3R,4S,5S,6R)-3,4,5-trihydroxy-6-(hydroxymethyl)oxan-2-yl]oxy})oxan-2-yl (1R,4S,5R,9S,10R,13S)-13-hydroxy-5,9-dimethyl-14-methylidenetetracyclo[11.2.1.0^{1,10}.0^{4,9}] hexadecane-5-carboxylate.

In addition to RebM, fermentation of EFSC 3044 resulted in formation of a di-glycosylated steviol glycoside (13- hydroxy kaur-16-en-18-oic acid, [2-O-β-D-glucopyranosyl-13-D-glucopyranosyl] ester) with a retention time of 2.31 (FIG. 8B) and a tri-glycosylated steviol glycoside (13-hydroxy kaur-16-en-18-oic acid; [2-O-β-D-glucopyranosyl-3-O-☐β-D-glucopyranosyl-β-D-glucopyranosyl] ester) with a retention time of 2.15 (FIG. 8C).

These compounds were isolated according to the following method. After the fermentation, the culture broth was centrifuged for 10 min at 5000 rpm at 4° C. and the supernatant was purified as follows: A glass column was filled with 300 mL HP20 Diaion® resin (Supelco), and an aliquot of 1700 mL supernatant was loaded on to the column and washed with 3.5 Liters of ddH2O. The compounds were eluted by using 2 L MeOH and fractions of 500 mL each collected. After LC-MS analysis, the fractions containing the majority of the target compounds were pooled and evaporated on a rotary evaporation system (Rotavap, Büchi, Switzerland) yielding 1.85 grams of dark grey material. The crude extract was re-dissolved in 3.5 mL of DMSO and injected in aliquots of 0.7 mL in a semi-preparative LC-MS for further purification. The column used was a XBridge C18, 19×250 mm, 5 um (Waters Corporation). Mobile phases were A: 0.1% TFA in water and B: 0.1% TFA in Acetonitrile. Elution was done by a linear gradient from 1% B to 60% B in 44 min. Fractions of 2.1 mL were continuously collected during the run. Fractions collected were analysed by LC-MS in order to evaluate the presence and purity of target analytes. Fractions containing compounds identified as 'Peak 8' and 'Peak 9' were neutralized by adding 0.8 mL of NH3 (aq.), pooled and dried by Genevac centrifugal evaporation system.

Structures of these compounds were determined by NMR with the method of Example 4.

The NMR data obtained for the di-glycosylated steviol glycoside are as follows:

1H NMR (600 MHz, DMSO-$d_6$) δ ppm 0.72-0.79 (m, 1H) 0.81 (s, 3H) 0.93 (d, J=8.07 Hz, 1H) 0.98-1.05 (m, 1H) 1.17 (s, 3H) 1.20 (d, J=11.37 Hz, 1H) 1.36 (d, J=4.03 Hz, 2H) 1.40-1.52 (m, 1H) 1.55-1.70 (m, 1H) 1.77 (d, J=9.54 Hz, 3H) 1.84-1.90 (m, 1H) 2.03 (d, J=8.07 Hz, 1H) 2.31-2.41 (m, 1H) 2.79-2.87 (m, 1H) 2.89-2.96 (m, 1H) 3.08 (s, 2H) 3.12-3.18 (m, 3H) 3.19-3.24 (m, 1H) 3.34 (d, J=4.77 Hz, 2H) 3.41-3.45 (m, 2H) 3.46-3.55 (m, 1H) 3.65 (d, J=11.37 Hz, 1H) 3.73 (dd, J=15.41, 8.44 Hz, 4H) 4.26-4.40 (m, 1H) 4.48 (d, J=7.70 Hz, 1H) 4.52-4.62 (m, 1H) 4.69 (br.s., 1H) 4.81 (d, J=7.70 Hz, 1H) 4.88 (br.s., 1H) 4.91-5.03 (m, 1H) 5.05-5.26 (m, 2H) 5.51 (d, J=7.70 Hz, 1H) 5.55 (br.s., 1H; the formula is $C_{32}H_{50}O_{13}$; formula weight is 642.7316).

The NMR data obtained for the tri-glycosylated steviol glycoside are as follows:

1H NMR (600 MHz, DMSO-$d_6$) δ ppm 0.73-0.79 (m, 1H) 0.81 (s, 3H) 0.89-0.97 (m, 2H) 0.99-1.05 (m, 1H) 1.17 (s, 3H) 1.19 (d, J=11.37 Hz, 1H) 1.24 (s, 2H) 1.31-1.40 (m, 4H) 1.40-1.51 (m, 3H) 1.55-1.63 (m, 1H) 1.67 (dd, J=14.12, 5.32 Hz, 1H) 1.71-1.82 (m, 5H) 1.88 (d, J=11.00 Hz, 1H) 1.98-2.08 (m, 2H) 2.23-2.30 (m, 1H) 2.94 (t, J=8.44 Hz, 1H) 3.01-3.11 (m, 3H) 3.12-3.17 (m, 1H) 3.19-3.28 (m, 3H) 3.44-3.52 (m, 5H) 3.54-3.60 (m, 1H) 3.61-3.71 (m, 3H) 4.36 (br. s., 1H) 4.49 (br. s., 1H) 4.55 (d, J=7.70 Hz, 1H) 4.69 (s, 1H) 4.73 (br. s., 1H) 4.88 (br. s., 1H) 4.91-5.05 (m, 2H) 5.17 (br.s., 1H) 5.31 (br.s., 1H) 5.44 (d, J=8.07 Hz, 1H) 5.55 (br. s., 1H; the formula is $C_{38}H_{60}O_{18}$; formula weight is 804.8722).

The di-glycosylated steviol glycoside ester was determined to be an analog of steviol-1,2-bioside (FIG. 8B), and the tri-glycosylated steviol glycoside was determined to be an isomer of RebB, both of which are glycosylated at the 19-O position (FIG. 8C) instead of the 13-O position of their respective isomers. This data suggests that these compounds form when the activity of UGT85C is low compared to the activity of EUGT11, UGT76G1, or UGT74G1.

Example 6: Engineering and Fermentation of EFSC 3261

The wild type *Saccharomyces* strain utilized in Example 1 was modified to contain the heterologous genes in Table 14 involved in steviol glycoside production. The genes were all integrated into the chromosome of the host strain using similar methods described in Example 1.

TABLE 14

List of Recombinant Genes and Promoters Used in Strain EFSC 3261.

| Heterologous pathway gene | Number of copies | Promoter(s) used |
|---|---|---|
| GGPPS7 (*Synechococcus* sp) synthetic gene | 2 | TEF2, GPD1 |
| CDPS (truncated, *Zea mays*) native gene | 3 | PGK1 (X2), TPI1 |
| KS5 (*A. thaliana*) native gene | 3 | TPI1, PDC1 (X2) |
| KO (*S. rebaudiana* KO1) synthetic gene | 2 | FBA1, GPD1 |
| ATR2 synthetic gene | 1 | PGK1 |
| KAH (*S. rebaudiana* KAHe1) synthetic gene | 3 | GPD1, TEF1 (X2) |
| *S. rebaudiana* CPR 8 native gene | 2 | TPI1 (X2) |
| 85C2 (*S. rebaudiana*) synthetic | 1 | GPD1 |
| 74G1 native (*S. rebaudiana*) | 1 | TPI1 |
| 76G1 synthetic (*S. rebaudiana*) | 1 | TEF1 |
| 91d2e-b 2X mutant from *S. rebaudiana* | 1 | GPD1 |
| EUGT11 synthetic (*Oryza sativa*) | 1 | TEF2 |

Fed-batch fermentation was carried out aerobically in 2 L (working volume) fermenters which included a ~16 hour growth phase in the base medium (minimal medium containing glucose, ammonium sulfate, trace metals, vitamins, salts, and buffer) followed by ~100 hours of feeding with a glucose-containing defined feed medium. Glucose was utilized as the carbon and energy source and combined with trace metals, vitamins, and salts. The pH was kept near pH 5 and the temperature setpoint was 30° C. The feed rate was controlled to prevent oxygen depletion and to minimize ethanol formation (glucose-limited conditions). Whole culture samples (without cell removal) were taken and boiled in an equal volume of DMSO for total glycosides levels.

Figure 9:
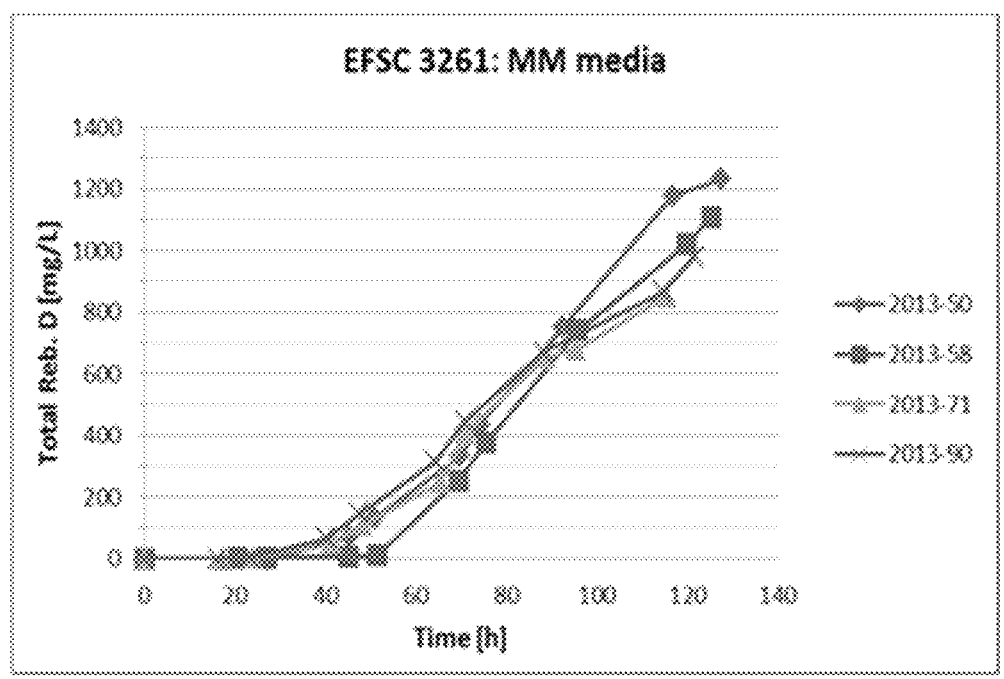
FIG. 9 shows RebD production by the EFSC 3261 yeast strain. Four fermentations of the EFSC 3261 yeast strain in minimal medium (MM) are shown.

FIG. 9 shows production of RebD by EFSC 3261 in four separate trials. Total production (intracellular and extracellular combined) averaged titer were between 800-1200 mg/L. For fermentation run 58, the final total titer at 123 hours was 1109 mg/L RebD, 695 mg/L RebM; the ratio of D:M on a mass basis was 1.6. 394 mg/L RebA were also produced.

Example 7: Strain Engineering and Fermentation of EFSC 3297 for Increased Production of RebD and RebM The same wild type *Saccharomyces* strain utilized in Example 1 was modified to contain the heterologous genes in Table 15 involved in steviol glycoside production. The genes were all integrated into the chromosome of the host strain using similar methods described in Example 1. Although the genes used are identical to those in Example 1, increased copy numbers of bottleneck enzymes in the steviol pathway allowed for increased production of RebD and RebM. Fermentation of strain 3297 was carried out in a manner similar to that described above for strain 3261.

TABLE 15

List of Recombinant Genes and Promoters Used in Strain EFSC 3297.

| Heterologous pathway gene | Number of copies | Promoter(s) used |
|---|---|---|
| GGPPS7 (*Synechococcus* sp) synthetic gene | 3 | TEF2 (X2), GPD1 |
| CDPS (truncated, *Zea mays*) native gene | 4 | PGK1 (X3), TPI1 |
| KS5 (*A. thaliana*) native gene | 4 | TPI1, PDC1 (X3) |
| KO (*S. rebaudiana* KO1) synthetic gene | 2 | FBA1, GPD1 |
| ATR2 synthetic gene | 1 | PGK1 |
| KAH (*S. rebaudiana* KAHe1) synthetic gene | 4 | GPD1 (X2), TEF1 (X2) |
| *S. rebaudiana* CPR 8 native gene | 3 | TPI1 (X3) |
| 85C2 (*S. rebaudiana*) synthetic | 1 | GPD1 |
| 74G1 native (*S. rebaudiana*) | 1 | TPI1 |
| 76G1 synthetic (*S. rebaudiana*) | 1 | TEF1 |
| 91d2e-b 2X mutant from *S. rebaudiana* | 1 | GPD1 |
| EUGT11 synthetic (*Oryza sativa*) | 2 | TEF2 (X2) |

Figure 10:
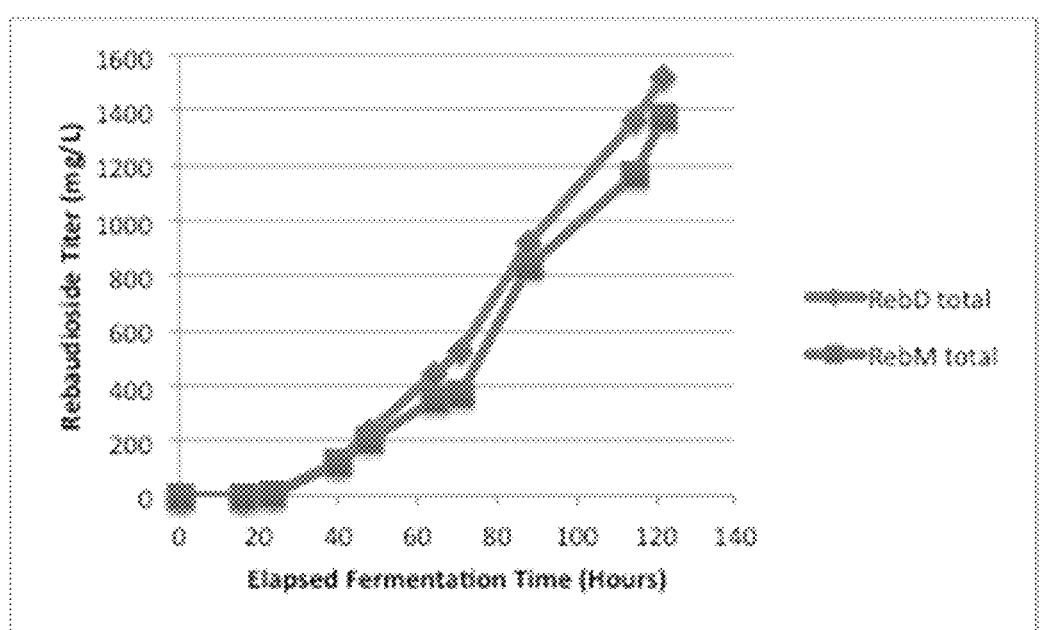
FIG. 10 shows RebD and RebM production by the EFSC 3297 yeast strain.

Production of RebD and RebM by EFSC 3297 is shown in FIG. 10. The ratio of D:M on a mass basis was 1.1. 1517 mg/L RebD was produced at the end of the fermentation (total, intracellular plus extracellular) and 1375 mg/L of RebM was produced.

Example 8: Strain Engineering and Fermentation of EFSC 3841 with Two Copies of the UGT76G1 Gene The wild type *Saccharomyces* strain utilized in Example 1 was modified to contain the heterologous genes in Table 16 involved in steviol glycoside production. The genes were all integrated into the chromosome of the host strain using similar methods described in Example 1. Fermentation conditions for 3841 were similar to those described above for strain 3261.

TABLE 16

List of Recombinant Genes and Promoters Used in Strain EFSC 3841.

| Heterologous pathway gene | Number of copies | Promoter(s) used |
|---|---|---|
| GGPPS7 (*Synechococcus* sp) synthetic gene | 3 | TEF2 (X3) |
| CDPS (truncated, *Zea mays*) native gene | 4 | PGK1 (X4) |
| KS5 (*A. thaliana*) native gene | 4 | PDC1 (X4) |
| KO (*S. rebaudiana* KO1) synthetic gene | 3 | FBA1, GPD1, TPI1 |
| ATR2 synthetic gene | 2 | PGK1 (X2) |
| KAH (*S. rebaudiana* KAHe1) synthetic gene | 4 | GPD1, TEF1 (X3) |
| *S. rebaudiana* CPR 8 native gene | 3 | TPI1 (X3) |

TABLE 16-continued

List of Recombinant Genes and Promoters Used in Strain EFSC 3841.

| Heterologous pathway gene | Number of copies | Promoter(s) used |
|---|---|---|
| 85C2 (*S. rebaudiana*) synthetic | 2 | GPD1 (X2) |
| 74G1 native (*S. rebaudiana*) | 2 | TPI1 (X2) |
| 76G1 synthetic (*S. rebaudiana*) | 2 | TEF1 (X2) |
| 91d2e-b 2X mutant from *S. rebaudiana* | 2 | GPD1 (X2) |
| EUGT11 synthetic (*Oryza sativa*) | 2 | TEF2, TEF1 |

Figure 11:
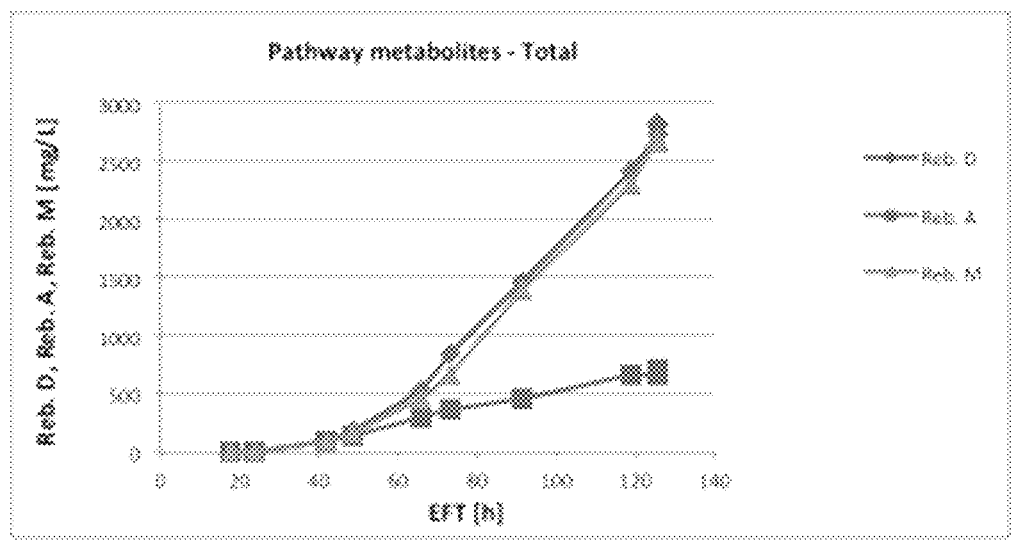
FIG. 11 shows RebD, RebM, and RebA production by the EFSC 3841 yeast strain.

Production of RebD, RebM, and RebA by EFSC 3841 is shown in FIG. 11. Here, the total amount of RebD produced was 2786 mg/L, and the total amount of RebM produced was 2673 mg/L for a ratio of 1.04 D:M (g per g). 703.7 mg/L RebA was also produced.

Example 9: Knockdown of One UGT76G1 Gene from EFSC 3841 and Decreased Production of RebD and RebM An auxotrophic (leu2, ura3) version of strain EFSC 3841 described above, designated EFSC 3643, was further modified to delete one of the wild type 76G1 UGT genes. The performance of 3 colonies containing one copy of UGT 76G1 was tested versus 4 colonies of the unmodified strain which contains 2 copies of UGT 76G1. PCR was used to verify that the new strain only harbored one copy of the 76G1. Briefly, the disruption of one copy of UGT76G1 was verified by two PCR reactions amplifying a region upstream of the insertion site with part of the integration cassette and a region downstream of the insertion site with part of the integration cassette used for disruption. PCR primers designed for the wildtype 76G1 confirmed that wildtype 76G1 was still intact and present in the strain. The colonies were grown in 96 deep-well plates for 96 hours at 30° C. and 400 RPM. The total amounts of RebD and RebM were determined by LC/MS analysis.

From FIG. 12, it can be seen that the copy number of 76G1 significantly changes the RebD/RebM ratio. The ratio of RebD to RebM was plotted for the 3 colonies containing only one 76G1 copy (bars on the left-hand side of the graph), versus 4 colonies of the parent strain that contained 2 copies of the 76G1 UGT (right-hand bars of the graph).

Example 10: Determination of Relative Rates of RebD and RebM Production p416GPD containing WT-76G1 was expressed in the protease deficient yeast strain DSY6 for 48 h in SC-ura media. 100 µL of cells were then reinoculated in 3 mL of SC-ura media for 16 h. The cells were lysed with 200 µL CelLytic™ Y according to manufacturer's description. 6 µL of the lysate were added to 24 µL of the reaction mixture consisting of 20 mM Tris-buffer (pH 8.0), 0.3 µMUDPG, and 0.1 µM Reb D or Reb E. The reactions were incubated at 30° C. and stopped at 0, 1, 2, and 18 h by transferring 25 µL of the 30 µL reaction mixture to 25 µL DMSO. Amounts of RebD, RebE, and RebM were analyzed by LC-MS and assessed by peak integration during data processing as "area under the curve."

Figure 13A:
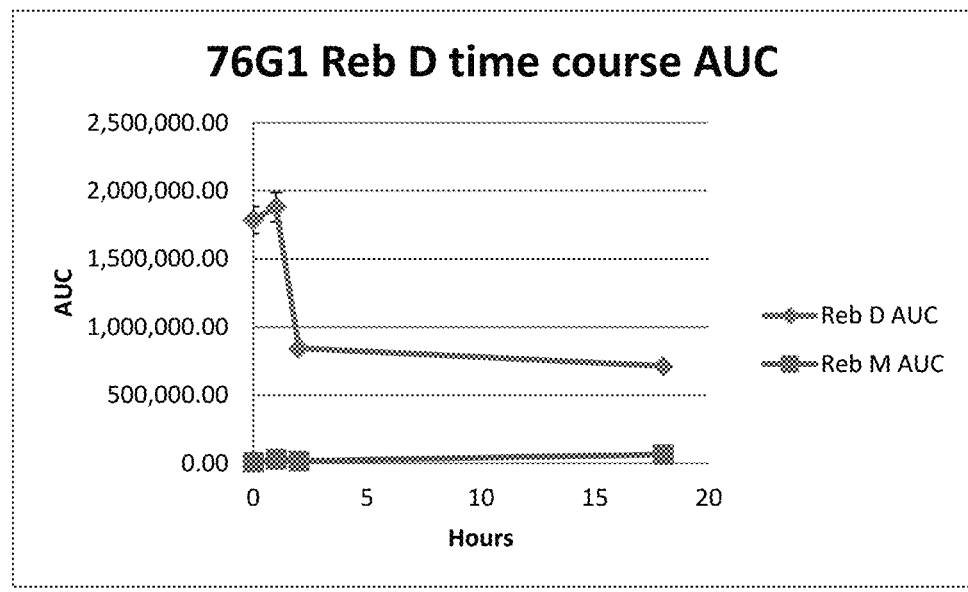
FIG. 13A shows the relative rates of consumption of RebD and production of RebM by UGT76G1.
Figure 13B:
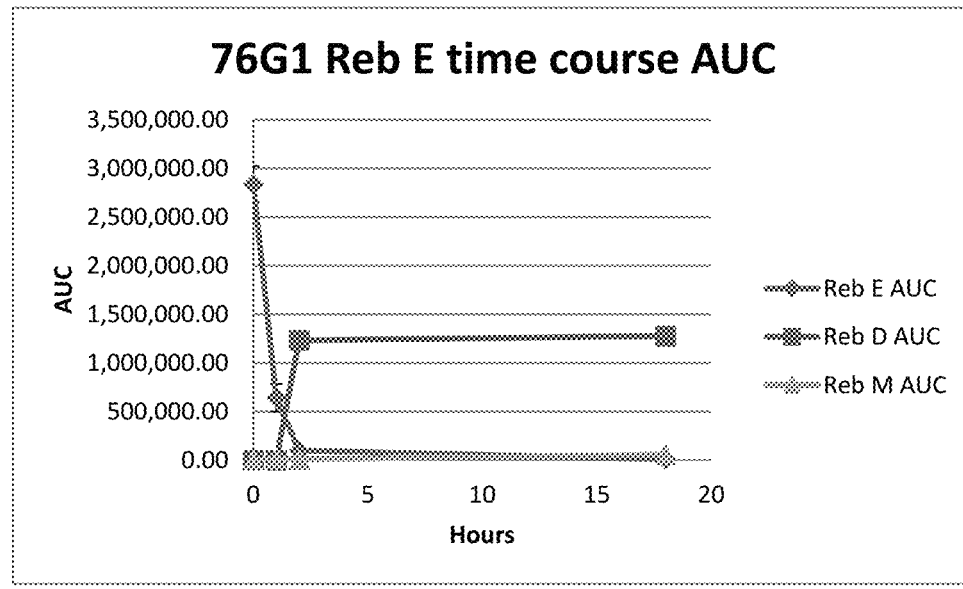
FIG. 13B shows the relative rates of consumption of RebE and production of RebD and RebM by UGT76G1.

FIG. 13 shows that a large portion of RebD is consumed without generating a corresponding amount of RebM. It is also shown that RebE is consumed within 2 h and converted to RebD. This finding confirms an alternative glycosylation route from steviol to RebM through RebE instead of RebA is possible, which is first observed at the 18 h time point.

Example 11: Prediction of Amino Acids Involved in RebM and RebD Binding in UGT76G1

As a means for identifying UGT76G1 variants with increased activity and regioselectivity towards RebM or RebD, homology modeling and docking studies were performed. Three homology models were generated using standard setting in the SybylX program with a combination of the following PDB-files 2PQ6 (% ID=31), 2C1X (% ID=28), 3HBF (% ID=28), 2VCE (% ID=35) as templates. The ligands present in PDB2VCE were used during the generation of main- and side-chains but removed prior to energy minimization. To yield the highest quality structures, models were energy minimized using an AMBER FF99 forcefield with either the standard settings or a gradient termination with a threshold of 0.1 kJ, a cutoff radius of 10 Å, and a maximum iteration of 5000 cycles. Statistics for the models are shown in Table 17, and variance between the models can be found in FIG. 14.

TABLE 17

Summary of UGT76G1 homology models.

| Statistic | Model 1 | Model 2 | Model 3 | Goal |
|---|---|---|---|---|
| Clashscore, all atoms | 1.1 ($99^{th}$ percentile) | 0.42 ($99^{th}$ percentile) | 3.38 ($97^{th}$ percentile) | |
| Poor rotamers | 16 (4.47%) | 6 (1.52%) | 8 (2.02%) | <1% |
| Ramachandran outliers | 5 (1.26%) | 12 (2.70%) | 6 (1.35%) | <0.05% |
| Ramachandran favored | 354 (88.94%) | 375 (84.27%) | 404 (90.79%) | >98% |
| MolProbity score | 1.89 ($81^{st}$ percentile) | 1.46 ($96^{th}$ percentile) | 1.89 ($81^{st}$ percentile) | |
| Cβ deviations > 0.25 Å | 3 (0.80%) | 1 (0.24%) | 5 (1.20%) | 0 |
| Bad backbone bonds | 0/1599 (0%) | 0/1780 (0%) | 0/1780 (0%) | 0% |
| Bad backbone angles | 0/1996 (0%) | 1/2224 (0.04%) | 0/2224 (0%) | <0.1% |

After model generation, substrates were docked into the active site of the enzyme using the Surflex Dock suite in SybylX to predict the amino acids forming the binding pocket. The UDPG portion of the UGT76G1 binding groove was located by aligning the 76G1 models with PDB2VCE and importing the ligand, UDPF2G, directly from the template. To dock the acceptor substrates, a protocol was generated using standard values covering the remaining part of the binding site. The dockings were performed using the GeomX settings on a ligand library containing steviol glycosides allowed with protein flexibility (model 1) or no flexibility (model 2). The docking results were analyzed using a combination of the scoring functions in SybylX using top 3 docking results in base mode and top 1 docking result with protein flexibility.

All UGT76G1 amino acids are shown in Table 18 below. The sites for the saturation library were determined by selecting all residues found to be within 5 Å of RebD and RebM in the docking analysis on two or more models (shown as bold "x"). Furthermore, all residues found to be within 5 Å of the RebM and RebD 19-O-glucose moiety, which were positioned in the binding site for the RebD→RebM reaction, were selected. Residues completely conserved between similar enzymes, which are shown in bold and with a "!," were omitted from the screen.

TABLE 18

Prediction of amino acids involved in RebM and RebD binding in UGT76G1.

| | | Enzyme UGT76G1 | | | | | | | | |
|---|---|---|---|---|---|---|---|---|---|---|
| | | Top3 (base) | Top3 (Base) | Top1 (PF) | Top1 (PF) | Top1 (Base) | Model | | | |
| | | Model no. | | | | | | | | |
| | | 2 | 1 | 1 | 1 | 1 | 1 + 2 minus cons. AAs: | Unique 5 Å: RebM 19Glc: | Unique RebD 19Glcs: | Total screened residues: |
| | | Substrate: | | | | | | | | |
| | | RebM | RebM | RebM | RebM 19Glcs | RebD 19Glcs | | | | |
| Residue | Å: | 5 | 5 | 5 | 5 | 5 | 5 | 5 | 5 | 5 |
| | No. of res in group: | 73 | 58 | 42 | 15 | 11 | 23 | 12 | 3 | 38 |
| VAL | 20 | | 20 | 20 | 20 | | X | | | x |
| PRO | 21! | | 21 | 21 | 21 | 21 | 21 | | | |
| PHE | 22 | 22 | 22 | 22 | 22 | 22 | X | | | x |
| GLN | 23 | | 23 | 23 | 23 | 23 | | x | | x |
| GLY | 24 | 24 | 24 | 24 | | 24 | X | | | x |
| HIS | 25! | | 25 | 25 | 25 | 25 | | | | |
| ILE | 26 | | | 26 | 26 | | 26 | | x | x |
| ASN | 27 | | | 27 | 27 | | | | | |
| THR | 48 | | | 48 | | | | | | |
| ASN | 49 | | | 49 | 49 | 49 | 49 | | x | x |
| PHE | 50 | | | 50 | 50 | 50 | 50 | | x | x |
| ASN | 51 | | | 51 | 51 | 51 | | | x | x |
| PRO | 53 | | | 53 | 53 | 53 | | | x | x |

TABLE 18-continued

Prediction of amino acids involved in RebM and RebD binding in UGT76G1.

| | | Enzyme UGT76G1 | | | | | Model | | | |
|---|---|---|---|---|---|---|---|---|---|---|
| | | Top3 (base) | Top3 (Base) | Top1 (PF) | Top1 (PF) | Top1 (Base) | | | | |
| | | Model no. | | | | | | | | |
| | | 2 | 1 | 1 | 1 | 1 | 1 + 2 minus cons. AAs: | Unique 5 Å: RebM 19Glc: | Unique RebD 19Glcs: | Total screened residues: |
| | | Substrate: | | | | | | | | |
| | | RebM | RebM | RebM | RebM 19Glcs | RebD 19Glcs | | | | |
| LYS | 54 | | 54 | 54 | 54 | 54 | | x | | x |
| THR | 55 | | 55 | 55 | 55 | 55 | | x | | x |
| SER | 56 | | 56 | 56 | 56 | 56 | | x | | x |
| PRO | 80 | 80 | | | | | | | | |
| THR | 81 | 81 | | | | | | | | |
| HIS | 82 | 82 | | | | | | | | |
| GLY | 83 | 83 | | | | | | | | |
| PRO | 84 | 84 | | | | | | | | |
| LEU | 85 | 85 | 85 | | | | X | | | x |
| MET | 88 | 88 | | | | | | | | |
| ARG | 89 | 89 | | | | | | | | |
| ILE | 92 | | 92 | | | | | | | |
| GLU | 95 | | 95 | 95 | | | | | | |
| HIS | 96 | | 96 | 96 | | | | | | |
| ASP | 99 | | 99 | 99 | | | | | | |
| ARG | 103 | | 103 | 103 | | | | | | |
| THR | 123 | 123 | | | | | | | | |
| ASP | 124! | 124 | 124 | | | | | | | |
| ALA | 125 | 125 | 125 | | | | | | | |
| LEU | 126 | 126 | 126 | 126 | | | X | | | x |
| TRP | 127 | 127 | 127 | 127 | | | X | | | x |
| TYR | 128 | 128 | 128 | 128 | | | X | | | x |
| VAL | 143 | 143 | 143 | | | | | | | |
| LEU | 144 | 144 | 144 | | | | | | | |
| MET | 145 | 145 | 145 | 145 | | | X | | | x |
| THR | 146 | 146 | 146 | 146 | 146 | | X | | | x |
| SER | 147 | 147 | 147 | 147 | 147 | | X | | | x |
| SER | 148 | 148 | 148 | | | | | | | |
| PHE | 150 | 150 | 150 | | | | | | | |
| ASN | 151 | 151 | 151 | 151 | 151 | | X | | | x |
| PHE | 152 | 152 | 152 | | | | | | | |
| ALA | 154 | 154 | 154 | | | | | | | |
| HIS | 155 | 155 | 155 | 155 | 155 | | X | | | x |
| VAL | 156 | 156 | 156 | | | | | | | |
| SER | 157 | 157 | 157 | | | | | | | |
| LEU | 158 | 158 | 158 | | | | | | | |
| PRO | 159 | 159 | 159 | | | | | | | |
| GLN | 160 | 160 | 160 | | | | | | | |
| PHE | 161 | 161 | 161 | | | | | | | |
| ASP | 162 | 162 | 162 | | | | | | | |
| GLU | 163 | 163 | 163 | | | | | | | |
| GLY | 165 | 165 | 165 | | | | | | | |
| TYR | 166 | 166 | 166 | | | | | | | |
| LEU | 167 | 167 | 167 | | | | | | | |
| ASP | 168 | 168 | 168 | | | | | | | |
| ASP | 189 | 189 | 189 | | | | | | | |
| ILE | 190 | 190 | 190 | | | | | | | |
| LYS | 191 | 191 | 191 | 191 | 191 | | X | | | x |
| SER | 192 | 192 | 192 | | | | | | | |
| ALA | 193 | 193 | 193 | | | | | | | |
| TYR | 194 | 194 | 194 | | | | | | | |
| SER | 195 | 195 | 195 | 195 | 195 | | X | | | x |
| ASN | 196 | 196 | 196 | | | | | | | |
| TRP | 197 | 197 | 197 | | | | | | | |
| GLN | 198 | 198 | 198 | 198 | 198 | | X | | | x |
| ILE | 199 | 199 | 199 | 199 | | | X | | | x |
| LEU | 200 | 200 | 200 | 200 | 200 | | X | | | x |
| LYS | 201 | 201 | 201 | | | | | | | |
| GLU | 202 | 202 | 202 | | | | | | | |
| ILE | 203 | 203 | 203 | 203 | 203 | | X | | | x |
| LEU | 204 | 204 | 204 | 204 | 204 | | X | | | x |
| GLY | 205 | 205 | 205 | | | | | | | |
| LYS | 206 | 206 | 206 | | | | | | | |
| MET | 207 | 207 | 207 | 207 | | | | | | |
| ILE | 208 | 208 | 208 | | | | | | | |

TABLE 18-continued

Prediction of amino acids involved in RebM and RebD binding in UGT76G1.

| | | Enzyme UGT76G1 | | | | | | | |
|---|---|---|---|---|---|---|---|---|---|
| | | Top3 (base) | Top3 (Base) | Top1 (PF) | Top1 (PF) | Top1 (Base) | Model | | |
| | | Model no. | | | | | | | |
| | | 2 | 1 | 1 | 1 | 1 | 1 + 2 minus cons. AAs: | Unique 5 Å | Unique |  Total screened residues: |
| | | Substrate: | | | | | | | | |
| | | RebM | RebM | RebM | RebD 19Glcs | RebD 19Glcs | | RebM 19Glc: | RebD 19Glcs: | |
| LYS | 209 | 209 | | | | | | | | |
| SER | 253 | | 253 | 253 | 253 | 253 | | x | | x |
| LEU | 257 | | 257 | 257 | 257 | | | x | | x |
| PHE | 281! | | | | | 281 | | | | |
| GLY | 282! | | 282 | 282 | | 282 | | | | |
| SER | 283 | | 283 | 283 | 283 | 283 | | x | | x |
| THR | 284 | 284 | 284 | 284 | | 284 | X | | | x |
| SER | 285 | | 285 | 285 | | 285 | | | x | x |
| GLU | 286 | | 286 | | | | | | | |
| VAL | 309 | | 309 | | | | | | | |
| ARG | 311! | | 311 | | | | | | | |
| PHE | 314 | | 314 | 314 | 314 | 314 | | x | | x |
| LYS | 337 | | 337 | | | 337 | | | x | x |
| TRP | 338! | | 338 | 338 | 338 | 338 | | | | |
| HIS | 356! | | | | | 356 | | | | |
| GLY | 358! | 358 | | | | | | | | |
| TRP | 359! | 359 | 359 | | | | | | | |
| ASN | 360! | | 360 | | | | | | | |
| PHE | 377 | | 377 | | | | | | | |
| GLY | 378 | 378 | 378 | | | | X | | | x |
| LEU | 379 | 379 | 379 | 379 | | | X | | | x |
| ASP | 380 | 380 | 380 | 380 | | | X | | | x |
| GLN | 381! | 381 | 381 | 381 | | | | | | |
| PRO | 382 | 382 | | | | | | | | |
| LEU | 383 | 383 | | | | | | | | |
| ASN | 384 | 384 | | | | | | | | |

Bold indicates complete conservation in amino acid.
Bold "!" indicates amino acid residues that are completely conserved between similar enzymes and were omitted from the screen.

Example 12: UGT76G1 Site Saturation Library Prescreen

Prior to performing the UGT76G1 site saturation library screening as described herein, culture growth and production of RebM and RebD were monitored in 96 and 4×24 deep-well plates. Using the standard lithium acetate protocol, the EFSC 3385 strain was transformed with p416GPD containing WT-76G1, and the transformants were plated on SC-URA plates. EFSC 3385 is a strain that is deficient in UGT76G1 and thus will make RebE until transformed with a plasmid containing an active UGT76G1. The strain contained a disruption in the UGT76G1 coding region, which was replaced with the spHIS5 marker, and also contained integrated copies of the UGT91D2e-2× mutant, UGT74G1, ATR2, UGT85C2, S. rebaudiana CPR8 (2 copies), A. thaliana KS5 (2 copies), Synechococcus GGPPS7, codon optimized S. rebaudiana KAHe1 (2 copies), S. rebaudiana KO (two copies), the truncated Zea mays CDPS5 (2 copies), and EUGT11.

For the 96 deep-well plate condition, 96 colonies were transferred to a plate containing 1 mL SC-URA, and the plate was incubated at 30° C. and 400 RPM for 96 h. For the 4×24 deep-well plate condition, 96 colonies were transferred to a plate containing 3 mL SC-URA. The plate was incubated at 30° C. and 320 RPM for 96 h, and 200 μL were then transferred from each well to a 96 deep-well plate.

50 μL of the cultures from each plate were transferred to 96 well polymerase chain reaction (PCR) plates and diluted 1:1 with 100% dimethyl sulfoxide (DMSO). The plates were heat sealed, incubated at 80° C. for 10 min, and subsequently cooled to 25° C. The plates were spun at 4000 RPM for 10 min, and 50 μL of the culture mixtures were transferred to a new plate for LC-MS analysis.

Figure 15A:
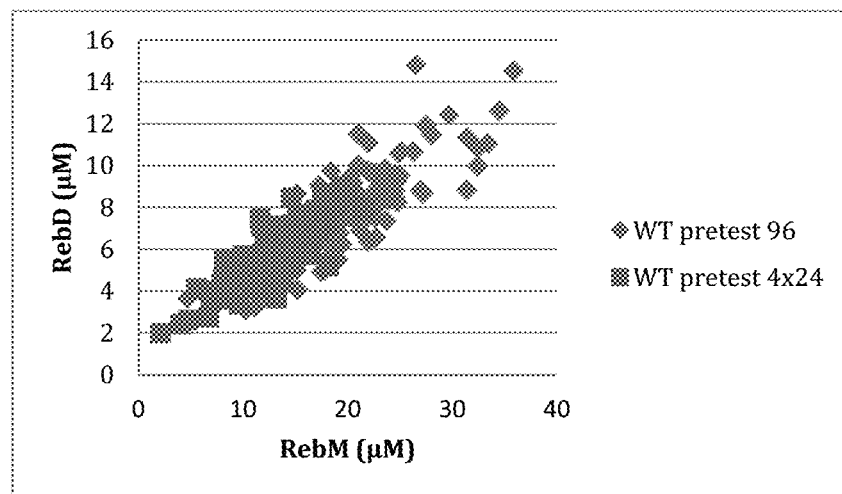
FIG. 15A is a scatter-plot of production of RebD and RebM in 96 and 4×24 deep-well plates.
Figure 15B:
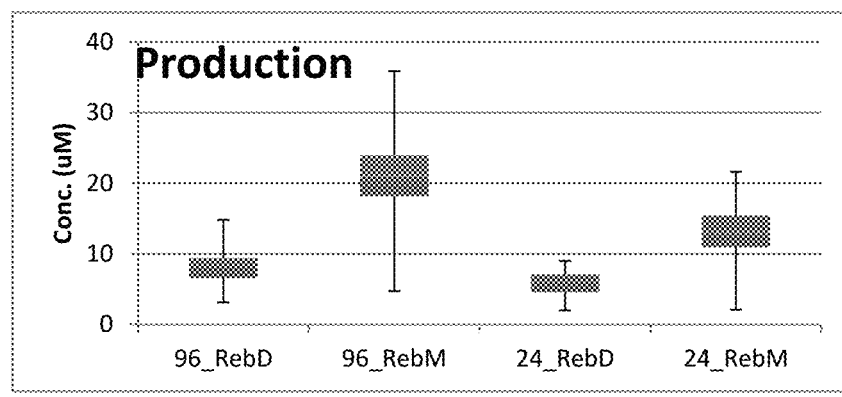
FIG. 15B is a box-plot of RebD and RebM production in 96 and 4×24 deep-well plates.
Figure 15C:
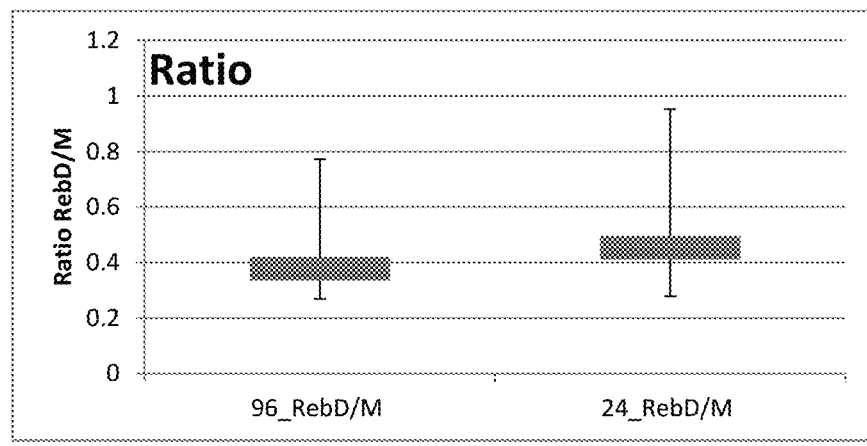
FIG. 15C is a box-plot of RebD/RebM production in 96 and 4×24 deep-well plates.

Results of the UGT76G1 site saturation library prescreen can be found in FIG. 15. Variance in RebD and RebM production can be explained by evaporation, particularly in the wells located at the edges of the plate, over the course of the 96 h incubation period. The higher concentrations of RebM and RebD produced by colonies grown in 96 deep-well plates suggest that these plates are better suited for LC-MS analysis, as compared to 4×24 deep-well plate, and were thus selected for use in the UGT76G1 site saturation library screen.

Example 13: UGT76G1 Site Saturation Library Screen

Through the company, Baseclear, UGT76G1 was subcloned from EPSC2060 (p423GPD) to EPSB492 (p416GPD) using the SpeI and XhoI restriction sites, and the site saturation libraries were created using degenerate NNS-primers. Using the standard lithium acetate protocol, the EFSC3385 strain was transformed with the library or with control plasmid containing WT-76G1, and the transformants were plated on SC-URA plates.

1 mL of SC-URA media was added to 96 deep-well plates, and colonies from each of the 38 site saturation library residues identified in Example 9 were picked and incubated in the 96 deep-well plates at 30° C. and 400 RPM for 96 h. 50 µL of each culture samples were then transferred to 96 well PCR plates containing 50 µL 100% DMSO. The plates were then heat sealed, incubated at 80° C. for 10 min, subsequently cooled to 12° C., and spun at 4000 RPM for 10 min. 70 µL of each supernatant were transferred to a new plate for LC-MS analysis.

Figure 16:
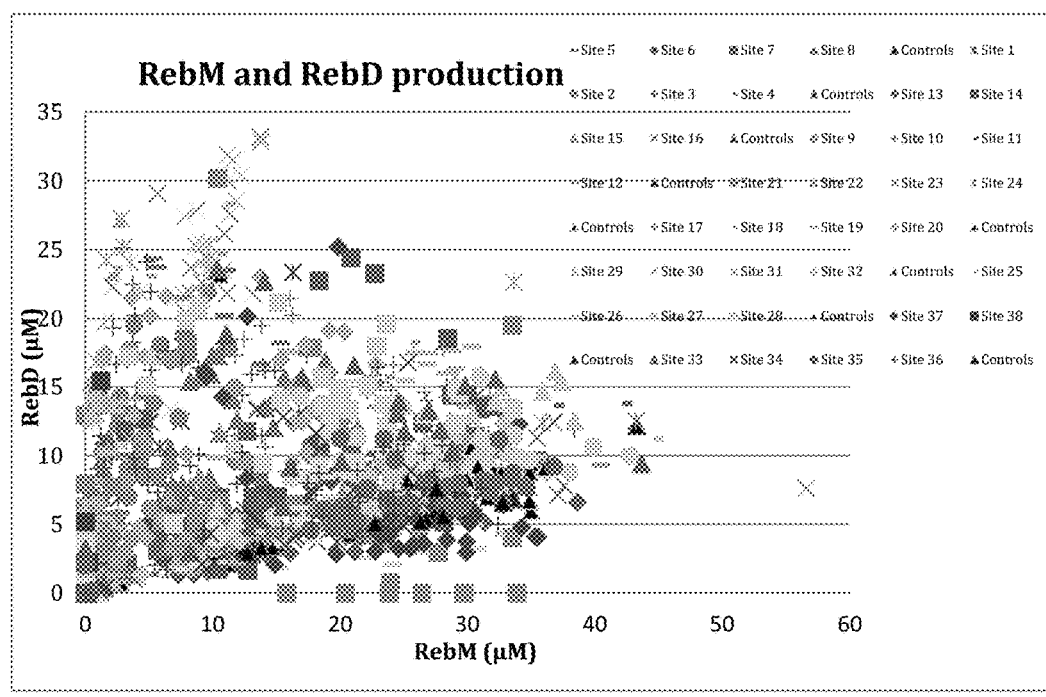
FIG. 16 shows all data points of the initial UGT76G1 site saturation screen with wild type production shown as black triangles.

FIG. 16 shows all data points of the UGT76G1 site saturation library screen, with wild type production depicted with black triangles. The variant numbering system can be found in Table 19.

TABLE 19

Numbering for UGT76G1 site saturation library variants.

| Number | Residue |
|---|---|
| 1 | VAL 20 |
| 2 | PHE 22 |
| 3 | GLN 23 |
| 4 | GLY 24 |
| 5 | ILE 26 |
| 6 | ASN 49 |
| 7 | PHE 50 |
| 8 | ASN 51 |
| 9 | PRO 53 |
| 10 | LYS 54 |
| 11 | THR 55 |
| 12 | SER 56 |
| 13 | LEU 85 |
| 14 | LEU 126 |
| 15 | TRP 127 |
| 16 | TYR 128 |
| 17 | MET 145 |
| 18 | THR 146 |
| 19 | SER 147 |
| 20 | ASN 151 |
| 21 | HIS 155 |
| 22 | LYS 191 |
| 23 | SER 195 |
| 24 | GLN 198 |
| 25 | ILE 199 |
| 26 | LEU 200 |
| 27 | GLU 202 |
| 28 | ILE 203 |
| 29 | SER 253 |
| 30 | LEU 257 |
| 31 | SER 283 |
| 32 | THR 284 |
| 33 | SER 285 |
| 34 | PHE 314 |
| 35 | LYS 337 |
| 36 | GLY 378 |
| 37 | LEU 379 |
| 38 | ASP 380 |

Figure 17:
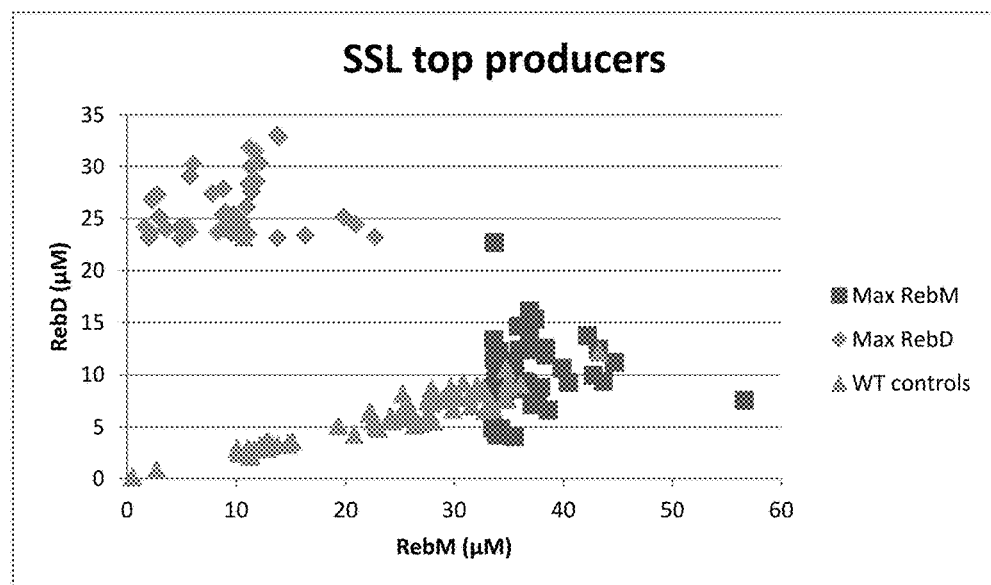
FIG. 17 shows the top RebD and RebM producing colonies selected for further study.
Figure 18:
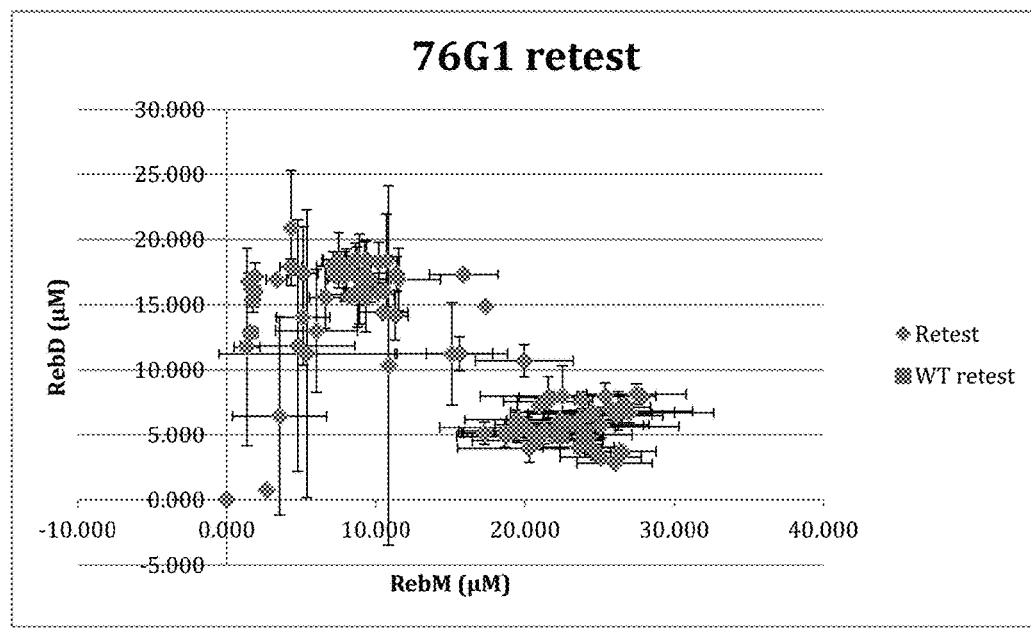
FIG. 18 shows a rescreen of UGT76G1 RebD and RebM top producers (as shown in FIG. 17) run in triplicate showing the same trends as the initial screen.

Table 20 and FIG. 17 show the UGT76G1 variant colonies with the highest selectivity towards production of either RebM or RebD, which were selected for further study. In FIG. 17, all data points with the "WT" prefix indicate RebM and RebD production of the wild type enzyme. It is shown that selected enzyme variants exhibited an inhibited RebD to RebM activity or an increased production of RebM, as compared to wild type controls.

TABLE 20

Top RebM- and RebD-producing colonies.

| Colony | RebM (µM) | RebD (µM) |
|---|---|---|
| A1 | 16.28 | 23.35 |
| A2 | 4.83 | 24.12 |
| A3 | 2.92 | 25.13 |
| A4 | 34.07 | 12.24 |
| A5 | 5.66 | 23.72 |
| A6 | 11.08 | 23.50 |
| A7 | 5.33 | 24.35 |
| A8 | 38.36 | 11.90 |
| A9 | 42.18 | 13.76 |
| A10 | 33.80 | 8.95 |
| A11 | 34.66 | 10.13 |
| A12 | 40.44 | 9.30 |
| B1 | 36.86 | 13.64 |
| B2 | 34.88 | 9.05 |
| B3 | 38.61 | 6.64 |
| B4 | 20.84 | 24.42 |
| B5 | 22.70 | 23.28 |
| B6 | 35.49 | 9.63 |
| B7 | 34.55 | 8.71 |
| B8 | 35.47 | 11.31 |
| B9 | 35.62 | 9.17 |
| B10 | 37.59 | 7.80 |
| B11 | 36.76 | 12.41 |
| B12 | 2.31 | 26.75 |
| C1 | 2.21 | 23.66 |
| C2 | 9.24 | 24.56 |
| C3 | 1.93 | 23.18 |
| C4 | 10.47 | 24.70 |
| C5 | 4.91 | 23.09 |
| C6 | 2.38 | 27.11 |
| C7 | 11.06 | 28.32 |
| C8 | 13.77 | 23.07 |
| C9 | 35.58 | 9.92 |
| C10 | 33.51 | 5.02 |
| C11 | 33.87 | 4.24 |
| C12 | 6.04 | 30.20 |
| D1 | 33.51 | 4.93 |
| D2 | 43.18 | 12.50 |
| D3 | 34.04 | 8.06 |
| D4 | 35.92 | 12.38 |
| D5 | 37.11 | 7.14 |
| D6 | 44.66 | 11.19 |
| D7 | 33.61 | 13.36 |
| D8 | 36.19 | 8.68 |
| D9 | 36.88 | 16.12 |
| D10 | 11.25 | 30.00 |
| D11 | 11.68 | 31.55 |
| E1 | 56.60 | 7.58 |
| E2 | 12.18 | 30.41 |
| E3 | 13.75 | 33.16 |
| E4 | 8.79 | 27.90 |
| E5 | 8.69 | 25.33 |
| E6 | 11.78 | 28.56 |
| E7 | 8.31 | 23.67 |
| E8 | 9.19 | 25.35 |
| E9 | 7.77 | 27.41 |
| E10 | 8.96 | 24.06 |
| E11 | 11.25 | 31.88 |
| E12 | 10.18 | 24.20 |
| F1 | 9.94 | 23.65 |
| F2 | 38.36 | 12.57 |
| F3 | 37.37 | 15.35 |
| F4 | 8.89 | 25.59 |
| F5 | 10.78 | 23.51 |
| F6 | 11.41 | 27.57 |
| F7 | 10.96 | 26.18 |
| F8 | 35.86 | 14.67 |
| F9 | 5.69 | 29.07 |
| F10 | 13.84 | 32.85 |
| F11 | 2.81 | 27.27 |
| F12 | 39.86 | 10.64 |
| G1 | 37.94 | 8.80 |
| G2 | 9.56 | 23.64 |
| G3 | 33.80 | 9.62 |
| G4 | 3.01 | 25.15 |
| G5 | 9.81 | 25.41 |

TABLE 20-continued

Top RebM- and RebD-producing colonies.

| Colony | RebM (μM) | RebD (μM) |
|---|---|---|
| G6 | 42.71 | 9.96 |
| G7 | 1.65 | 24.20 |
| G8 | 9.63 | 24.28 |
| G9 | 33.65 | 22.69 |
| G10 | 34.87 | 9.69 |
| G11 | 33.66 | 11.49 |
| G12 | 3.58 | 24.04 |
| H1 | 33.94 | 9.84 |
| H2 | 10.39 | 23.59 |
| H3 | 43.64 | 9.40 |
| H4 | 33.50 | 8.73 |
| H5 | 36.32 | 9.39 |
| H6 | 34.61 | 7.69 |
| H7 | 36.73 | 9.20 |
| H8 | 35.49 | 4.09 |
| H9 | 34.25 | 4.82 |
| H10 | 35.36 | 4.10 |
| H11 | 19.87 | 25.19 |

Example 14: UGT76G1 Site Saturation Library Rescreen and Variant Sequencing

Figure 19A:
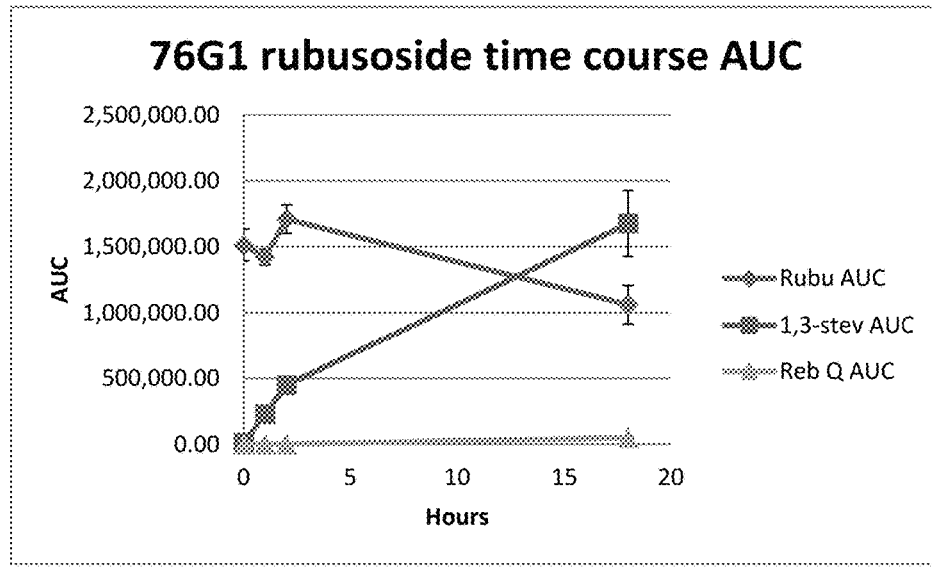
FIG. 19A shows the relative rates of consumption of Rubusoside and production of 1,3-stevioside (RebG) and Rebaudioside Q ("RebQ") by UGT76G1.
Figure 19B:
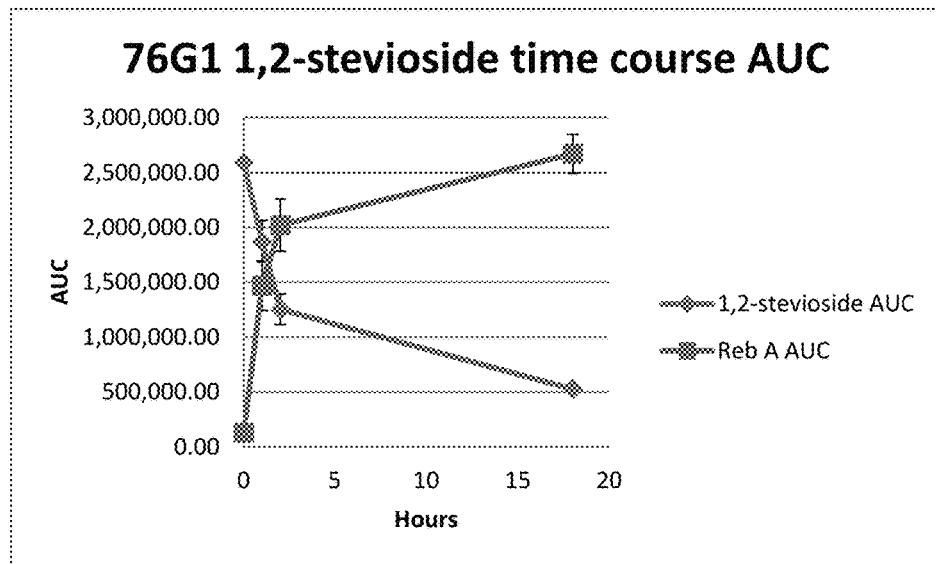
FIG. 19B shows the relative rates of consumption of 1,2-stevioside and production of RebA by UGT76G1.
Figure 19C:
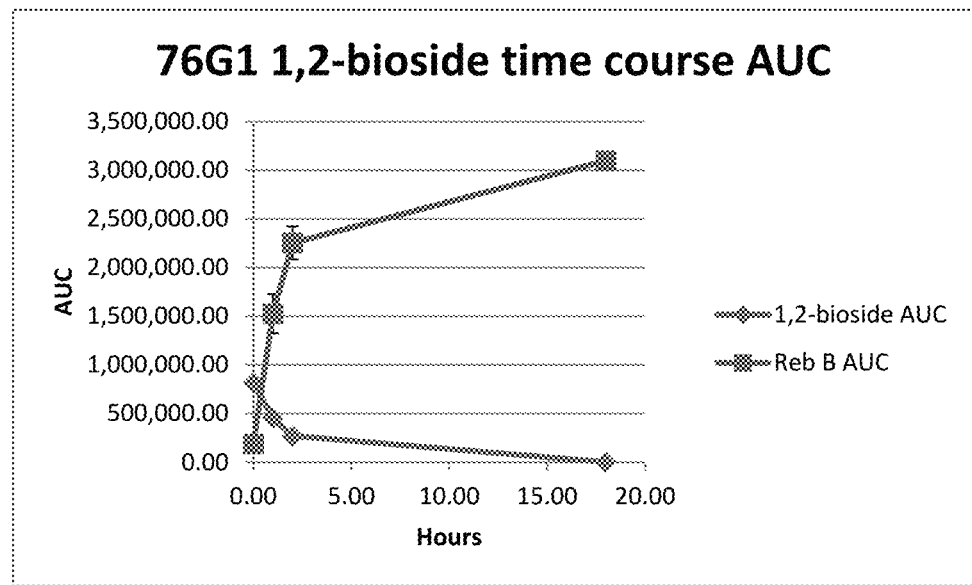
FIG. 19C shows the relative rates of consumption of 1,2-bioside and production of RebB by UGT76G1.

A rescreen of the 47 UGT76G1 variant colonies producing either the highest amounts of RebD or RebM was done in triplicate and showed the same trends as the initial screen (FIG. 19). The colonies to be sequenced were selected by compiling the results from the screen and rescreen. As the production levels of the screen and rescreen could not be directly compared, the colonies were ranked from highest producers to lowest producers of RebD and RebM, respectively, and the ranks from the screen and rescreen were averaged. From the averages, the top 16 RebD-, top 16 RebM-, and top 16 RebD/M-producing colonies (a total of 48 colonies) were identified. As some of the top RebD and top RebD/M producers were found to be the same colonies, duplicate colonies were counted only once, and additional colonies were chosen to reach the 48 total colonies to be sequenced. These colonies were then sequenced in duplicate with the GPDseq_fWd and CYC1seq-rev primers, shown below.

```
GPDseq_fwd primer seq:
CGG TAG GTA TTG ATT GTA ATT    (SEQ ID NO: 87)

CYC1seq_rev primer seq:
CTT TTC GGT TAG AGC GGA TGT    (SEQ ID NO: 88)
```

Tables 21-23 show the amounts and rankings of RebD, RebM, and RebD/RebM produced by the indicated variants, and Table 24 summarizes the mutations that selectively increase either RebD or RebM production. Amounts of RebM, RebD, RebA, Rubusoside, and RebB produced by wild type and UGT76G1 variant colonies are shown in Table 25.

TABLE 21

Identities of top RebD-producing UGT76G1 variants.

| | Screen | | Rescreen | | | | | | Average | | |
|---|---|---|---|---|---|---|---|---|---|---|---|
| | | | Sample 1 | | Sample 2 | | Sample 3 | | | | |
| Colony | RebD (μM) | Rank | RebD (μM) | Rank | RebD (μM) | Rank | RebD (μM) | Rank | RebD (μM) | RANK | Mutation |
| E2 | 25.33 | 21 | 17.00 | 21 | 18.99 | 7 | 19.35 | 3 | 20.17 | 13 | L257A |
| E5 | 33.16 | 1 | 17.51 | 15 | 15.34 | 29 | 18.49 | 8 | 21.13 | 13 | L257G |
| F9 | 29.07 | 8 | 21.05 | 3 | 17.23 | 15 | 13.89 | 28 | 20.31 | 14 | L257T |
| G5 | 25.15 | 23 | 21.53 | 2 | 19.07 | 4 | 14.50 | 25 | 20.06 | 14 | S283G |
| E3 | 28.56 | 9 | 16.42 | 22 | — | — | 18.28 | 10 | 21.09 | 14 | L257W |
| C7 | 27.11 | 15 | 18.64 | 8 | 14.64 | 32 | 18.97 | 4 | 19.84 | 15 | T146A |
| F6 | 25.59 | 18 | 18.17 | 11 | 15.55 | 25 | 18.87 | 5 | 19.55 | 15 | L257R, (S389F) |
| C5 | 28.32 | 10 | — | — | — | — | 16.03 | 20 | 22.18 | 15 | T146A |
| D11 | 30.00 | 7 | — | — | 15.58 | 24 | — | — | 22.79 | 16 | L257R |
| A5 | 23.72 | 35 | 18.52 | 10 | 16.76 | 19 | 18.66 | 6 | 19.42 | 18 | I26F |
| F1 | 24.06 | 33 | 19.91 | 4 | 16.90 | 17 | — | — | 20.29 | 18 | L257G |
| B12 | 24.56 | 26 | 18.11 | 12 | 17.29 | 14 | 15.98 | 21 | 18.99 | 18 | T146G |
| E4 | 30.41 | 5 | 16.30 | 23 | 17.46 | 11 | 12.88 | 34 | 19.26 | 18 | L257P |
| E10 | 23.65 | 38 | — | — | 19.31 | 3 | 17.12 | 15 | 20.03 | 19 | L257G |
| F4 | 12.57 | 55 | 19.36 | 5 | 17.43 | 13 | 18.55 | 7 | 16.98 | 20 | L257E |
| E9 | 24.20 | 31 | 17.49 | 16 | 16.93 | 16 | — | — | 19.54 | 21 | L257G |
| E7 | 23.67 | 36 | 19.24 | 6 | 15.51 | 26 | 16.74 | 17 | 18.79 | 21 | L257G |
| H2 | 23.59 | 40 | 15.85 | 26 | 17.95 | 8 | 17.63 | 12 | 18.75 | 22 | S285R |
| G7 | 24.20 | 30 | — | — | 16.34 | 21 | 17.22 | 14 | 19.26 | 22 | S283N |
| C12 | 30.20 | 6 | — | — | 14.50 | 33 | 14.36 | 27 | 19.68 | 22 | H155R |
| C1 | 26.75 | 16 | 15.32 | 27 | 16.30 | 22 | 14.43 | 26 | 18.20 | 23 | T146G |
| A6 | 23.50 | 42 | 14.96 | 29 | 19.59 | 2 | 16.25 | 19 | 18.57 | 23 | I26W |
| C4 | 24.70 | 25 | — | — | — | — | 15.94 | 22 | 20.32 | 24 | T146P |

TABLE 22

Identities of the top RebM-producing UGT76G1 variants.

| | Screen | | Rescreen | | | | | | | |
|---|---|---|---|---|---|---|---|---|---|---|
| | | | Sample 1 | | Sample 2 | | Sample 3 | | Average | |
| Colony | RebD (μM) | Rank | RebD (μM) | Rank | RebD (μM) | Rank | RebD (μM) | Rank | RebD (μM) | RANK | Mutation |
| G1 | 37.94 | 12 | — | — | 26.68 | 7 | 26.77 | 6 | 30.46 | 8 | T284G |
| H7 | 36.73 | 19 | — | — | 29.81 | 1 | 25.11 | 12 | 30.55 | 11 | K337P |
| B1 | 36.86 | 17 | — | — | — | — | 27.82 | 5 | 32.34 | 11 | T55K |
| D2 | 43.18 | 4 | 21.39 | 30 | 27.28 | 4 | — | — | 30.62 | 13 | Q198R |
| H3 | 43.64 | 3 | 23.32 | 21 | 24.67 | 14 | 22.03 | 23 | 28.42 | 15 | S285T |
| C11 | 33.87 | 39 | 28.92 | 3 | 26.07 | 8 | 24.21 | 14 | 28.27 | 16 | H155L |
| A10 | 33.80 | 41 | 25.52 | 10 | 23.48 | 15 | 29.50 | 1 | 28.08 | 17 | S56A |
| B11 | 36.76 | 18 | 25.28 | 12 | 20.88 | 28 | 24.69 | 13 | 26.90 | 18 | Y128S |
| H04 | 33.50 | 47 | 25.34 | 11 | 24.98 | 13 | 28.71 | 3 | 28.13 | 19 | K337E |
| B02 | 34.88 | 30 | 28.40 | 4 | — | — | 20.65 | 27 | 27.98 | 20 | T55E |
| D09 | 56.60 | 1 | 21.14 | 32 | 20.84 | 29 | — | — | 32.86 | 21 | S253G |
| D01 | 33.51 | 45 | 23.48 | 20 | 25.27 | 11 | 25.33 | 10 | 26.89 | 22 | H155L |
| H09 | 34.25 | 35 | — | — | 21.90 | 21 | 25.28 | 11 | 27.14 | 22 | L379V |
| G11 | 33.65 | 43 | 22.95 | 22 | 27.77 | 3 | — | — | 28.12 | 23 | T284R |
| B8 | 35.47 | 28 | 25.66 | 9 | 21.01 | 26 | 20.13 | 28 | 25.57 | 23 | Y128E |
| F2 | 11.41 | 58 | 31.01 | 1 | 21.06 | 25 | 26.62 | 7 | 22.53 | 23 | S253W |
| C10 | 33.51 | 46 | 22.04 | 28 | 25.54 | 10 | 25.42 | 8 | 26.63 | 23 | H155L |

TABLE 23

Identities of the top RebD/M-producing UGT76G1 variants.

| Colony | Average RebD (μM) | Average Rank RebD | Average RebM (μM) | Average Rank RebM | Rank RebD + Rank RebM (96-M) | Mutation |
|---|---|---|---|---|---|---|
| G7 | 19.26 | 22 | 1.51 | 84 | 34 | S283N |
| F9 | 20.31 | 14 | 5.27 | 71 | 38 | L257T |
| C1 | 18.20 | 23 | 1.90 | 79 | 40 | T146G |
| B12 | 18.99 | 18 | 3.74 | 74 | 41 | T146G |
| A5 | 19.42 | 18 | 6.76 | 68 | 46 | I26F |
| F6 | 19.55 | 15 | 8.23 | 63 | 48 | L257R + S389F |
| C6 | 17.74 | 29 | 2.59 | 77 | 48 | T146G |
| F1 | 20.29 | 18 | 7.98 | 65 | 49 | L257G |
| E2 | 20.17 | 13 | 8.64 | 60 | 49 | L257A |
| C7 | 19.84 | 16 | 7.52 | 61 | 50 | T146A |
| C3 | 16.30 | 37 | 1.74 | 83 | 50 | T146G |
| E11 | 17.80 | 25 | 6.48 | 69 | 52 | L257G |
| A2 | 15.34 | 32 | 4.48 | 76 | 52 | Q23H |
| E5 | 21.13 | 13 | 9.32 | 57 | 52 | L257G |
| E4 | 19.26 | 18 | 8.00 | 61 | 54 | L257P |
| G5 | 20.06 | 14 | 8.79 | 56 | 54 | S283G |
| D11 | 22.79 | 16 | 9.75 | 58 | 54 | L257R |
| C5 | 22.18 | 15 | 10.81 | 57 | 54 | T146A |
| E9 | 19.54 | 21 | 8.21 | 62 | 55 | L257G |
| E7 | 18.79 | 21 | 8.00 | 62 | 55 | L257G |
| C2 | 18.29 | 26 | 6.95 | 67 | 55 | T146A |
| A3 | 15.25 | 35 | 3.19 | 76 | 56 | Q23G |
| E12 | 17.28 | 25 | 7.26 | 65 | 56 | L257W |
| E10 | 20.03 | 19 | 10.10 | 57 | 57 | L257G |

TABLE 24

Summary of UGT76G1 variants for RebD production and RebM production.

| RebD | Q23G, Q23H, I26F, I26W, T146A, T146G, T146P, H155R, L257P, L257W, L257G, L257A, L257R, L257E, S283G and S283N |
|---|---|
| RebM | T55K, T55E, S56A, Y128S, Y128E, H155L, H155R, Q198R, S285R, S285T, S253W, S253G, T284R, T284G, S285G, K337E, K337P and L379V |

TABLE 25

Production of steviol glycosides by UGT76G1 variants.

| Mutation | RebM | RebD | RebA AVG (μM) | Rubu | RebB | Total RebA→RebM SUM |
|---|---|---|---|---|---|---|
| WT | 22.35 | 4.98 | 7.03 | 0.65 | 2.54 | 34.37 |
| WT | 24.01 | 5.14 | 5.68 | 0.77 | 2.43 | 34.83 |
| RebD-optimizing mutations | | | | | | |
| L257W | 9.35 | 18.46 | 4.70 | | 2.03 | 32.52 |
| L257A | 8.62 | 18.45 | 4.75 | | 1.97 | 31.82 |
| L257E | 8.72 | 18.44 | 3.70 | | 1.54 | 30.87 |
| L257G | 7.49 | 18.40 | 4.44 | 0.18 | 1.80 | 30.34 |
| S283G | 10.71 | 18.37 | 3.77 | | 1.58 | 32.85 |
| L257G | 10.18 | 18.22 | 4.47 | 0.20 | 1.87 | 32.86 |
| I26F | 7.13 | 17.98 | 3.81 | | 1.64 | 28.92 |
| Q23H | 4.30 | 17.88 | 3.04 | | 1.38 | 25.22 |
| L257R, S389F | 8.01 | 17.53 | 4.21 | | 1.92 | 29.75 |
| T146A | 9.24 | 17.41 | 4.16 | 0.18 | 1.72 | 30.82 |
| L257T | 5.13 | 17.39 | 2.73 | 0.25 | 1.29 | 25.24 |
| L257W | 11.40 | 17.35 | 4.28 | | 1.94 | 33.04 |
| L257G | 7.23 | 17.21 | 4.19 | 0.45 | 1.81 | 28.62 |
| L257G | 7.90 | 17.16 | 4.16 | | 1.73 | 29.22 |
| S285R | 8.66 | 17.14 | 3.44 | | 1.70 | 29.25 |
| T146G | 1.91 | 17.13 | 1.69 | | 0.74 | 20.73 |
| L257G | 7.84 | 17.12 | 3.93 | | 1.80 | 28.88 |
| I26W | 11.51 | 16.93 | 5.22 | | 1.93 | 33.67 |
| S283N | 1.45 | 16.78 | 1.48 | | 0.67 | 19.70 |
| T146A | 10.57 | 16.03 | 4.07 | | 1.86 | 30.68 |
| T146G | 1.82 | 15.95 | 1.75 | 0.22 | 0.72 | 19.52 |
| T146P | 10.12 | 15.94 | 4.05 | | 1.96 | 30.11 |
| T146A | 9.31 | 15.60 | 4.34 | | 1.91 | 29.25 |
| L257R | 8.26 | 15.58 | 3.60 | 0.17 | 1.88 | 27.44 |
| L257P | 6.61 | 15.55 | 3.62 | 0.15 | 1.59 | 25.78 |
| T146G | 1.76 | 15.35 | 1.81 | 0.24 | 0.68 | 18.92 |
| H155R | 10.49 | 14.43 | 4.46 | 0.25 | 1.78 | 29.38 |
| L257G | 5.12 | 14.03 | 3.63 | | 0.95 | 22.78 |
| T146G | 1.64 | 12.86 | 1.65 | 0.21 | 0.67 | 16.14 |
| Q23G | 3.33 | 11.96 | 1.71 | 0.16 | 0.80 | 17.00 |
| RebM-optimizing mutations | | | | | | |
| T55K | 27.82 | 7.96 | 6.28 | 0.40 | 2.31 | 42.06 |
| K337P | 27.46 | 8.14 | 5.83 | 0.41 | 2.18 | 41.43 |
| T284G | 26.72 | 7.29 | 7.27 | 0.34 | 2.72 | 41.28 |
| H155L | 26.40 | 3.70 | 6.79 | 0.30 | 2.50 | 36.89 |
| K337E | 26.34 | 7.14 | 6.35 | 0.39 | 2.66 | 39.83 |
| S253W | 26.23 | 6.83 | 5.82 | 0.37 | 2.26 | 38.89 |

TABLE 25-continued

Production of steviol glycosides by UGT76G1 variants.

| Mutation | RebM | RebD | RebA | Rubu | RebB | Total RebA-->RebM |
|---|---|---|---|---|---|---|
| | | AVG (µM) | | | | SUM |
| S56A | 26.17 | 6.50 | 6.94 | 0.66 | 2.46 | 39.61 |
| T284R | 25.36 | 7.99 | 6.24 | 0.24 | 2.56 | 39.58 |
| H155L | 24.69 | 3.65 | 7.38 | 0.39 | 2.66 | 35.72 |
| T55E | 24.52 | 6.73 | 5.84 | 0.46 | 2.09 | 37.09 |
| Q198R | 24.33 | 6.61 | 6.37 | 0.60 | 2.33 | 37.32 |
| H155L | 24.33 | 4.00 | 7.43 | 0.29 | 2.53 | 35.76 |
| Y128S | 23.62 | 6.20 | 6.48 | 0.43 | 2.29 | 36.29 |
| L379V | 23.59 | 4.01 | 7.09 | 0.28 | 2.72 | 34.69 |
| S285T | 23.34 | 5.90 | 5.73 | 0.44 | 2.30 | 34.97 |
| Y128E | 22.27 | 5.04 | 5.78 | 0.41 | 2.17 | 33.09 |
| S253G | 20.99 | 7.26 | 5.78 | 0.27 | 2.42 | 34.04 |

Example 15: Determination of Relative Rates of UGT76G1 Glycosylation Reactions

UGT76G1 was only known in the literature to catalyze the 1,3-glycosylation of 1,2-stevioside to convert it into RebA and converting 1,2-bioside to RebB. The inventors have newly discovered that the reactions shown in Table 26 are catalyzed by UGT76G1.

TABLE 26

Newly discovered UGT76G1 reactions.

| Substrate | Product |
|---|---|
| Rebaudioside D | Rebaudioside M |
| Rubusoside | "Rebaudioside Q" (1,3-O-glycoside linkages on both the 13- and 19-O-glucose position) |
| Steviol 1,2 bioside isomer (19-O) | Rebaudioside B isomer (19-O) |

Similar to Example 9, p416GPD containing WT-76G1 was expressed in the protease deficient yeast strain DSY6 for 48 h in SC-ura media. 100 µL of cells were then reinoculated in 3 mL of SC-ura media for 16 h. The cells were lysed with 200 µL CelLytic™ Y according to manufacturer's description. 6 µL of the lysate were added to 24 µL of the reaction mixture consisting of 20 mM Tris-buffer (pH 8.0), 0.3 pMUDPG, and either 0.1 µM rubusoside, 0.2 µM 1,2-bioside, 0.2 µM 1,2-stevioside, 0.2 µM RebA, or 0.1 µM RebE. The reactions were incubated at 30° C. and stopped at 0, 1, 2, and 18 h by transferring 25 µL of the 30 µL reaction mixture to 25 µL DMSO. Amounts of steviol glycosides were analyzed by LC-MS and assessed by peak integration during data processing as "area under the curve."

In FIG. 19, it is shown that an approximately 50% decrease in the "area under the curve" for rubusoside resulted in considerable production of 1,3-stevioside (RebG) over 18 h. RebQ, newly discovered by the inventors, was first detected at 18 h. Additionally, FIG. 19 shows that 1,2-stevioside was not completely consumed over the 18 h period for the production of RebA as 1,2-bioside was for the production of RebB.

Figure 20:
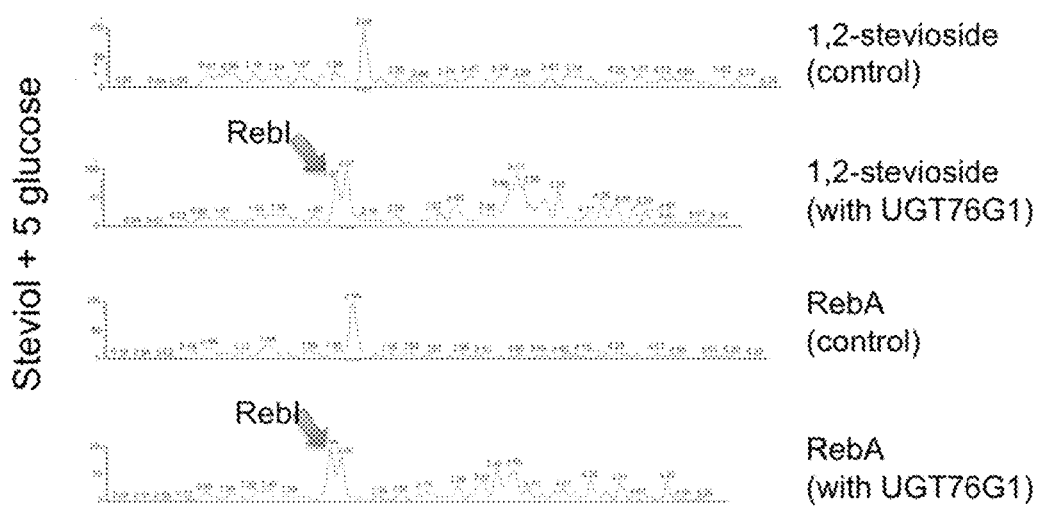
FIG. 20 shows chromatograms of 1,2-stevioside and RebA with or without UGT76G1 peaks indicating production of RebI.

Furthermore, using either 1,2-stevioside or RebA as a substrate, a peak eluting at 1.96 min on the steviol+5 glucose chromatogram appeared (FIG. 20). Because RebD elutes at 1.11 min and UGT76G1 only catalyzes 1,3-glycosylation reactions, the peak eluting at 1.96 min appeared to be RebI. However, it was not possible to integrate the RebI peak because it was situated in a substrate artifact peak (FIG. 20).

These results collectively indicated that UGT76G1 preferentially catalyzed glycosylation of steviol glycoside substrates that are 1,2-di-glycosylated on the 13-O-position, followed by steviol glycoside substrates that are mono-glycosylated at the 13-O-position. There appeared to be little preference arising from the glycosylation state of the 19-O-position. FIG. 1 summarizes steviol glycoside glycosylation reactions and the enzymes by which they are known to be catalyzed.

Example 16: Production of Steviol Glycosides by UGT76G1 Variants

Quantitative standards are not commercially available for each steviol glycoside, which prevented some concentration measurements. Therefore, production of additional steviol glycosides by the enzyme variants, as compared to the wild type enzyme, was assessed by peak integration during data processing. The "area under the curve" data for each variant was normalized to the wild type UGT76G1 and is shown in Table 27. These data were in agreement with previous examples but also showed that some of the variants did not produce 1,3-stevioside (RebG), rubusoside, "Reb Q," and/or a steviol-tetraglycoside eluting at 1.43 min, as the wild type controls did. Increases in RebM and RebD production can be explained by this observation.

TABLE 27

"Area under the curve" data as a measure of the production of steviol glycosides by UGT76G1 variants relative to wildtype UGT76G1 production.

| Variant | Reb M | Reb D | RebA | 1,2 Stev | 1,3 Stev | RebB | Rubu | 1,2-Bios | 1,3-Bios | 19-SMG | 13-SMG | Stev | 0.95 min Stv4Glc (suspect RebE) | 1.43 min Stv4Glc | 1,3 at 13 and 19Pos "Reb Q" |
|---|---|---|---|---|---|---|---|---|---|---|---|---|---|---|---|
| Q23H | 0.2 | 2.6 | 0.4 | 2.5 | — | 0.5 | — | — | — | — | 1.0 | — | 3.7 | 0.5 | — |
| Q23G | 0.2 | 2.5 | 0.3 | 2.0 | — | 0.3 | 0.3 | — | — | — | 0.6 | — | 2.8 | 0.4 | — |
| I26F | 0.3 | 3.8 | 0.6 | 2.2 | — | 0.7 | — | — | — | — | 1.1 | — | 3.0 | 0.5 | — |
| I26W | 0.5 | 3.6 | 0.9 | 1.8 | — | 0.8 | — | — | — | — | 0.8 | — | 2.5 | 0.4 | — |
| S56A | 1.2 | 1.4 | 1.2 | 1.2 | 0.7 | 1.0 | 1.0 | — | — | — | 1.2 | — | 1.4 | 0.3 | 0.7 |
| T55K | 1.3 | 1.7 | 1.0 | 1.0 | — | 1.0 | 0.6 | — | — | — | 1.0 | — | 1.1 | 0.9 | — |
| T55E | 1.2 | 1.4 | 1.0 | 1.3 | 0.8 | 0.9 | 0.7 | — | — | — | 0.9 | — | 1.7 | 0.3 | 0.9 |
| Y128E | 1.1 | 1.1 | 1.0 | 1.1 | — | 0.9 | 0.6 | — | — | — | 1.0 | — | 1.0 | 0.7 | 0.4 |
| Y128S | 1.1 | 1.3 | 1.1 | 1.2 | 0.6 | 1.0 | 0.7 | — | — | — | 1.0 | — | 1.3 | 1.0 | 0.6 |
| T146G | 0.1 | 3.6 | 0.3 | 3.7 | — | 0.3 | — | — | — | — | 1.0 | — | 7.6 | 0.9 | — |
| T146G | 0.1 | 3.3 | 0.3 | 4.0 | — | 0.3 | 0.4 | — | — | — | 1.4 | — | 7.3 | 1.0 | — |
| T146A | 0.4 | 3.3 | 0.7 | 2.1 | — | 0.8 | — | — | — | — | 0.9 | — | 3.2 | 0.5 | — |
| T146G | 0.1 | 2.7 | 0.3 | 3.8 | — | 0.3 | 0.3 | — | — | — | 1.2 | — | 6.2 | 0.9 | — |

TABLE 27-continued

"Area under the curve" data as a measure of the production of steviol
glycosides by UGT76G1 variants relative to wildtype UGT76G1 production.

| Variant | Reb M | Reb D | RebA | 1,2 Stev | 1,3 Stev | RebB | Rubu | 1,2-Bios | 1,3-Bios | 19-SMG | 13-SMG | Stev | 0.95 min Stv4Glc (suspect RebE) | 1.43 min Stv4Glc | 1,3 at 13 and 19Pos "Reb Q" |
|---|---|---|---|---|---|---|---|---|---|---|---|---|---|---|---|
| T146P | 0.5 | 3.4 | 0.7 | 2.2 | — | 0.8 | — | — | — | — | 0.9 | — | 3.0 | 0.5 | — |
| T146A | 0.5 | 3.4 | 0.7 | 2.2 | — | 0.8 | — | — | — | — | 0.8 | — | 3.3 | 0.5 | — |
| T146G | 0.1 | 3.4 | 0.3 | 3.7 | — | 0.3 | 0.3 | — | — | — | 1.2 | — | 6.6 | 0.9 | — |
| T146A | 0.4 | 3.7 | 0.7 | 2.2 | — | 0.7 | 0.3 | — | — | — | 1.1 | — | 3.8 | 0.5 | — |
| H155L | 1.2 | 0.8 | 1.2 | 1.0 | — | 1.1 | 0.4 | — | — | — | 1.0 | — | 0.6 | — | 0.4 |
| H155L | 1.3 | 0.8 | 1.1 | 0.8 | — | 1.1 | 0.5 | — | — | — | 1.0 | — | 0.5 | — | 0.3 |
| H155R | 0.5 | 3.1 | 0.7 | 2.2 | — | 0.8 | 0.4 | — | — | — | 0.9 | — | 2.8 | 0.6 | — |
| H155L | 1.2 | 0.8 | 1.2 | 1.0 | — | 1.1 | 0.6 | — | — | — | 1.1 | — | 0.8 | 0.5 | 0.5 |
| Q198R | 1.2 | 1.4 | 1.1 | 1.3 | 0.8 | 1.0 | 0.9 | — | — | — | 1.1 | — | 1.6 | — | 0.6 |
| S253G | 1.0 | 1.5 | 1.0 | 1.1 | — | 1.0 | 0.4 | — | — | — | 1.2 | — | 1.2 | 0.2 | — |
| L257R | 0.4 | 3.3 | 0.6 | 2.4 | — | 0.8 | 0.3 | — | — | — | 1.1 | — | 2.8 | 0.6 | — |
| L257A | 0.4 | 3.9 | 0.8 | 2.8 | — | 0.8 | — | — | — | — | 1.3 | — | 4.3 | 0.7 | — |
| L257W | 0.5 | 3.7 | 0.7 | 2.5 | — | 0.8 | — | — | — | — | 0.9 | — | 3.8 | 0.6 | — |
| L257P | 0.3 | 3.3 | 0.6 | 2.3 | — | 0.7 | 0.2 | — | — | — | 0.9 | — | 3.1 | 0.5 | — |
| L257G | 0.4 | 3.6 | 0.7 | 2.4 | — | 0.8 | — | — | — | — | 1.2 | — | 3.3 | 0.5 | — |
| L257G | 0.4 | 3.6 | 0.7 | 2.4 | — | 0.7 | — | — | — | — | 1.2 | — | 3.6 | 0.6 | — |
| L257G | 0.3 | 3.6 | 0.7 | 3.7 | — | 0.8 | 0.7 | — | — | — | 1.2 | — | 7.9 | 0.9 | — |
| L257G | 0.5 | 3.9 | 0.7 | 2.6 | — | 0.8 | 0.3 | — | — | — | 1.1 | — | 3.2 | 0.7 | — |
| L257G | 0.2 | 3.0 | 0.6 | 2.2 | — | 0.4 | — | — | — | — | 1.0 | — | 3.0 | 0.5 | — |
| L257W | 0.3 | 2.9 | 1.8 | 4.1 | — | 1.8 | 0.8 | — | — | — | 1.3 | — | 4.0 | 0.5 | — |
| L257G | 0.4 | 3.9 | 0.7 | 2.6 | — | 0.8 | 0.3 | — | — | — | 1.4 | — | 4.1 | 0.7 | — |
| S253W | 1.3 | 1.4 | 1.0 | 1.3 | — | 1.0 | 0.6 | — | — | — | 0.9 | — | 1.4 | 0.7 | 0.4 |
| L257E | 0.4 | 3.9 | 0.6 | 2.4 | — | 0.7 | — | — | — | — | 0.9 | — | 3.9 | 0.6 | — |
| L257R, S389F | 0.4 | 3.7 | 0.7 | 2.5 | — | 0.8 | — | — | — | — | 1.1 | — | 3.5 | 0.5 | — |
| L257T | 0.2 | 3.7 | 0.5 | 2.6 | — | 0.5 | 0.4 | — | — | — | 0.8 | — | 4.0 | 0.6 | — |
| T284G | 1.3 | 1.5 | 1.2 | 1.3 | — | 1.2 | 0.5 | — | — | — | 1.1 | — | 2.2 | 0.7 | — |
| S283G | 0.5 | 3.9 | 0.6 | 1.9 | — | 0.7 | — | — | — | — | 1.1 | — | 3.5 | 0.4 | — |
| S283N | 0.1 | 3.6 | 0.2 | 3.9 | — | 0.3 | — | — | — | — | 1.1 | — | 6.8 | 1.0 | — |
| T284R | 1.2 | 1.7 | 1.0 | 1.4 | — | 1.1 | 0.4 | — | — | — | 1.0 | — | 2.2 | 0.4 | — |
| S285R | 0.4 | 3.6 | 0.6 | 2.6 | — | 0.7 | — | — | — | — | 1.3 | — | 4.4 | 0.6 | — |
| S285T | 1.1 | 1.3 | 1.0 | 1.0 | — | 1.0 | 0.7 | — | — | — | 1.0 | — | 1.2 | 0.9 | 0.3 |
| K337E | 1.3 | 1.5 | 1.1 | 1.1 | — | 1.1 | 0.6 | — | — | — | 1.2 | — | 1.2 | 0.7 | — |
| K337P | 1.3 | 1.7 | 1.0 | 1.3 | — | 0.9 | 0.6 | — | — | — | 1.1 | — | 1.6 | 1.1 | 0.4 |
| L379V | 1.1 | 0.9 | 1.2 | 1.2 | — | 1.2 | 0.4 | — | — | — | 1.1 | — | 1.1 | 0.4 | — |

Table 28 summarizes trends in steviol glycoside production through RebD-optimizing and RebM-optimizing mutations, compared to the normalized production of wild type controls. The variants with increased RebD production appeared to primarily be the result of inhibiting the RebD→RebM reaction. Additional RebD production can stem from inhibition of the Rubu→RebG→RebQ steviol glycosylation branch as well as a reduction in RebB and of a tetraglucoside eluting at 1.43 min. The four-fold increase in 1,2-Stevioside and seven-fold increase in RebE were unexpected, but the RebE increase could be a seven-fold increase in a very small amount of sideproduct found in the wild type controls. Nevertheless, this finding indicated that the Stevioside→RebA reaction had also been partially inhibited by the RebD-optimizing mutations, which was seen as a reduction in RebA intermediate.

TABLE 28

Steviol glycoside production by the UGT76G1 wild type or RebD and RebM-optimizing mutations.

| | RebM | RebD | RebA | 1,2 Stev | 1,3 Stev | RebB | Rubu | 1,2 Bios | 1,3 Bios | 19-SMG | 13-SMG | Stev | 0.95 min Stv4Glc (RebE) | 1.43 min Stv4Glc (UNK) | 1,3 at 13 and 19 Pos ("RebQ") |
|---|---|---|---|---|---|---|---|---|---|---|---|---|---|---|---|
| RebD | 0.1-0.5x | 2.5-3.9x | 0.3-0.8x | 1.8-4.0x | 0.0x | 0.3-0.8x | 0.0-0.4x | — | — | — | 0.9-1.3x | — | 3.0-7.0x | 0.4-0.9x | 0.0x |
| RebM | 1.0-1.3x | 0.8-1.7x | 1.0-1.2x | 0.8-1.3x | 0.0-0.8x | 0.9-1.1x | 0.4-1.0x | — | — | — | 0.9-1.2x | — | 0.5-2.0x | 0.0-0.9x | 0.0-0.8x |
| WT | 23.2 μM | 5.1 μM | 6.4 μM | AUC | AUC | 2.5 μM | 0.7 μM | — | — | — | AUC | — | AUC | AUC | AUC |

The mutation resulting in the highest RebD levels, L257G, produced nearly four-fold the RebD of the wild type and was found in six colonies sequenced. Other L257 mutations demonstrated nearly the same productivity. Mutants I26W and S283G showed the highest RebD/stevioside ratio, indicating that these mutations lead to the greatest inhibition of the RebD→M reaction without mitigating the Stev→RebA reaction. These two mutations also completely abolished the Rubu→RebG→RebQ pathway and reduced the amount of the tetraglucoside eluting at 1.43 min while minimally affecting RebB production. The best RebD/RebM ratios were found with T146G and S283N mutants, which showed a 40-50-fold increase over the wild type. The S389Fmutation found with L257R demonstrated higher RebD production than L257R alone.

Generally, increases in RebM also resulted in increases in RebD, while decreasing or completely blocking the Rubu-→RebG→RebQ glycosylation pathway and the tetraglucoside eluting at 1.43 min. Yet, the remaining steviol glycosides studied appeared unaffected. The top RebM producers, T55K and K337P, each increased RebM by 1.3-fold and decreased rubusoside by 0.6-fold, compared to the wild type. Since rubusoside was only present at 0.7 µM in the wild type, this observed decrease was insufficient to explain the increase in RebM. The Rubu→RebG→RebQ pathway was almost removed, with no 1,3-stevioside (RebG) produced by these mutants. As well, the variant with the K337P mutation produced 0.6-fold the levels of RebQ with the wild type. The mutations H155L and L379V each produced more RebM to RebD, with the wild type UGT76G1 producing approximately 4.58 RebM per RebD, and H155L and L379 producing approximately 6.66 and 5.88 RebM per RebD, respectively. Through the data uncovered by this study, UGT76G1 enzymes can be screened to identify species having improved kinetics towards RebD and RebM and that minimize side products, thereby increasing the flux towards the desired steviol glycosides.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

REFERENCES

1. Critical Reviews in Food Science and Nutrition, 52:11, 988-998, DOI:10.1080/10408398.2010.519447.
2. J Nat Prod. 2013 Jun. 28; 76(6):1201-28. doi: 10.1021/np400203b. Epub 2013 May 28.
3. Plant Physiology and Biochemistry 63 (2013) 245e253.
4. Praveen Guleria and Sudesh Kumar Yadav, 2013. Insights into Steviol Glycoside Biosynthesis Pathway Enzymes Through Structural Homology Modelling. American Journal of Biochemistry and Molecular Biology, 3: 1-19.
5. The Plant Journal (2005) 41, 56-67 doi: 10.1111/j.1365-313X.2004.02275.
6. Madhav et al., "Functional and structural variation of uridine diphosphate glycosyltransferase (UGT) gene of Stevia rebaudianaeUGTSr involved in the synthesis of rebaudioside A" Plant Physiology and Biochemistry 63 (2013) 245e253.
7. Jewett M C, et al., Molecular Systems Biology, Vol. 4, article 220 (2008).
8. Masada S et al., FEBS Letters, Vol. 581, 2562-2566 (2007).

What is claimed is:

1. A method of producing a steviol glycoside composition in a cell culture, comprising growing a recombinant host cell, comprising:
    (a) a gene encoding a polypeptide capable of synthesizing geranylgeranyl pyrophosphate (GGPP) from farnesyl diphosphate (FPP) and isopentenyl diphosphate (IPP);
    (b) a gene encoding a polypeptide capable of synthesizing ent-copalyl diphosphate from GGPP;
    (c) a gene encoding a polypeptide capable of synthesizing ent-kaurene from ent-copalyl pyrophosphate;
    (d) a gene encoding a polypeptide capable of synthesizing ent-kaurenoic acid from ent-kaurene;
    (e) a gene encoding a polypeptide capable of synthesizing steviol from ent-kaurenoic acid;
    (f) a gene encoding a polypeptide capable of reducing cytochrome P450 complex;
    (g) a first gene encoding a first polypeptide capable of beta 1,2 glycosylation of the C2' of the 13-O-glucose, 19-O-glucose, or both 13-O-glucose and 19-O-glucose of a steviol glycoside;
        wherein the gene has a copy number of 2 or more; and
        wherein the first polypeptide comprises a polypeptide having 65% or greater sequence identity to the amino acid sequence set forth in SEQ ID NO:16; and
    a second gene encoding a second polypeptide capable of beta 1,2 glycosylation of the C2' of the 13-O-glucose, 19-O-glucose, or both 13-O-glucose and 19-O-glucose of a steviol glycoside;
        wherein the second polypeptide comprises a polypeptide having 90% or greater sequence identity to the amino acid sequence set forth in any one of SEQ ID NOs:15 or 86;
    (h) a gene encoding a polypeptide capable of beta 1,3 glycosylation of the C3' of the 13-O-glucose, 19-O-glucose, or both 13-O-glucose and 19-O-glucose of the steviol glycoside;
    (i) a gene encoding a polypeptide capable of glycosylating steviol or the steviol glycoside at its C-13 hydroxyl group; and
    (j) a gene encoding a polypeptide capable of glycosylating steviol or the steviol glycoside at its C-19 carboxyl group;
    under conditions in which the genes are expressed;
    wherein at least one of the genes is a recombinant gene;
    wherein the steviol glycoside comprises steviol-13-O-glucoside, steviol-19-O-glucoside, rubusoside, stevioside, 1,2-bioside, Rebaudioside A, Rebaudioside B, Rebaudioside D, or Rebaudioside E; and
    wherein the steviol glycoside composition produced by the host cell comprises Rebaudioside M that is produced by the host cell at a concentration of at least about 600 mg/L of the cell culture; and further comprising isolating Rebaudioside M that is produced by the host cell from the cell culture.

2. The method of claim 1, wherein one or more of the genes is constitutively expressed and/or expression of one or more of the genes is induced.

3. The method of claim 1, wherein:
    (a) the second polypeptide capable of beta 1,2 glycosylation of the C2' of the 13-O-glucose, 19-O-glucose, or both 13-O-glucose and 19-O-glucose of the steviol glycoside comprises a polypeptide having a substitution at residues 211 and 286 of SEQ ID NO:15;
    (b) the polypeptide capable of beta 1,3 glycosylation of the C3' of the 13-O-glucose, 19-O-glucose, or both 13-O-glucose and 19-O-glucose of the steviol glycoside comprises a polypeptide having 50% or greater sequence identity to the amino acid sequence set forth in SEQ ID NO:2;
    (c) the polypeptide capable of glycosylating steviol or a steviol glycoside at its C-13 hydroxyl group comprises a polypeptide having 55% or greater sequence identity to the amino acid sequence set forth in SEQ ID NO:26; and
    (d) the polypeptide capable of glycosylating steviol or a steviol glycoside at its C-19 carboxyl group comprises a polypeptide having 55% or greater sequence identity to the amino acid sequence set forth in SEQ ID NO:19;
    wherein at least one of the polypeptides is a recombinant polypeptide.

4. The method of claim 3, wherein the polypeptide capable of beta 1,3 glycosylation of the C3' of the 13-O-glucose, 19-O-glucose, or both 13-O-glucose and 19-O-glucose of the steviol glycoside comprises at least one amino acid substitution of SEQ ID NO:2 that is Q23G, Q23H, T55K, T55E, S56A, 126F, 126W, Y128S, Y128E, T146A, T146G, T146P, H155L, H155R, Q198R, S285R, S285T, S253W, S253G, L257P, L257W, L257T, L257G, L257A, L257R, L257E, S283N, T284R, T284G, S285G, K337E, K337P or L379V of SEQ ID NO:2.

5. The method of claim 1, wherein the cell culture further comprises glucose, uridine diphosphate (UDP)-glucose, UDP-rhamnose, UDP-xylose, N-acetyl-glucosamine, and/or yeast nitrogen base (YNB).

6. The method of claim 1, wherein the host cell comprises a plant cell, a mammalian cell, an insect cell, a fungal cell, an algal cell, or a bacterial cell.

7. The method of claim 6, wherein the fungal cell comprises a yeast cell.

8. The method of claim 7, wherein the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* species.

9. The method of claim 7, wherein the yeast cell is a *Saccharomycete*.

10. The method of claim 9, wherein the yeast cell is a cell from *Saccharomyces cerevisiae* species.

11. The method of claim 1, wherein:
    (a) the polypeptide capable of synthesizing geranylgeranyl pyrophosphate (GGPP) from farnesyl diphosphate (FPP) and isopentenyl diphosphate (IPP) comprises a polypeptide having at 70% or greater sequence identity to the amino acid sequence set forth in SEQ ID NO:24;
    (b) the polypeptide capable of synthesizing ent-copalyl diphosphate from GGPP comprises a polypeptide having 80% or greater sequence identity to the amino acid sequence set forth in SEQ ID NO:13;
    (c) the polypeptide capable of synthesizing ent-kaurene from ent-copalyl pyrophosphate comprises a polypeptide having 40% or greater sequence identity to the amino acid sequence set forth in SEQ ID NO:21;
    (d) the polypeptide capable of synthesizing ent-kaurenoic acid from ent-kaurene comprises a polypeptide having 70% or greater sequence identity to the amino acid sequence set forth in SEQ ID NO:25;
    (e) the polypeptide capable of synthesizing steviol from ent-kaurenoic acid comprises a polypeptide having 60% or greater sequence identity to the amino acid sequence set forth in SEQ ID NO:11; and/or (f) the polypeptide capable of reducing cytochrome P450 complex comprises a polypeptide having 65% or greater sequence identity to the amino acid sequence set forth in any one of SEQ ID NOs:4 or 9.

12. The method of claim 1, wherein the isolating step comprises:
(a) separating a liquid phase of the cell culture from a solid phase of the cell culture to obtain a supernatant comprising the produced Rebaudioside M; and
(b) contacting the supernatant with one or more adsorbent resins in order to obtain at least a portion of the produced Rebaudioside M, thereby isolating the produced Rebaudioside M.

13. The method of claim 1, wherein the isolating step comprises:
(a) separating a liquid phase of the cell culture from a solid phase of the cell culture to obtain a supernatant comprising the produced Rebaudioside M; and
(b) contacting the supernatant with one or more ion exchange or reversed-phase chromatography columns in order to obtain at least a portion of the produced Rebaudioside M, thereby isolating the produced Rebaudioside M.

14. The method of claim 1, wherein the isolating step comprises:
(a) separating a liquid phase of the cell culture from a solid phase of the cell culture to obtain a supernatant comprising the produced Rebaudioside M; and
(b) crystallizing or extracting the produced Rebaudioside M, thereby isolating the produced Rebaudioside M.

15. The method of claim 1, further comprising recovering the steviol glycoside composition comprising Rebaudioside M that is produced by the host cell, from the cell culture.

16. The method of claim 15, wherein the recovered steviol glycoside composition is enriched for Rebaudioside M relative to a steviol glycoside composition from a *Stevia* plant and has a reduced level of *Stevia* plant-derived components relative to a steviol glycoside composition obtained from a plant-derived *Stevia* extract.

17. The method of claim 1, wherein the cell culture comprises:
(a) the steviol glycoside composition produced by the host cell,
(b) glucose, uridine diphosphate (UDP)-glucose, UDP-rhamnose, UDP-xylose, and/or N-acetyl-glucosamine; and
(c) supplemental nutrients comprising trace metals, vitamins, salts, yeast nitrogen base (YNB) and/or amino acids.

18. The method of claim 1, wherein the cell culture comprises:
(a) the steviol glycoside composition produced by the host cell,
wherein the steviol glycoside composition further comprises Rebaudioside D that is produced by the host cell;
wherein Rebaudioside M and Rebaudioside D that are produced by the host cell are present at a ratio of between 1:0.1 to 0.1:1 in the cell culture;
(b) glucose, uridine diphosphate (UDP)-glucose, UDP-rhamnose, UDP-xylose; and/or N-acetyl-glucosamine; and
(c) supplemental nutrients comprising trace metals, vitamins, salts, yeast nitrogen base (YNB) and/or amino acid.

19. The method of claim 1, wherein the host cell is grown in a fermentor at a temperature for a period of time, wherein the temperature and period of time facilitate the production of the steviol glycoside composition.

20. The method of claim 1, wherein the host cell produces Rebaudioside M at a concentration of at least about 1000 mg/L of the cell culture.

21. The method of claim 1, wherein the host cell further produces Rebaudioside D at a concentration of at least about 1000 mg/L of the cell culture.

22. The method of claim 1, wherein the steviol glycoside composition produced by the host cell further comprises Rebaudioside D that is produced by the host cell.

23. The method of claim 1, wherein the steviol glycoside composition produced by the host cell further comprises Rebaudioside D that is produced by the host cell at a concentration of at least about 600 mg/L of the cell culture.

24. The method of claim 1, wherein the steviol glycoside composition produced by the host cell comprises Rebaudioside M and Rebaudioside D that are produced by the host cell at a ratio of at least 1:0.1 in the cell culture.

25. The method of claim 1, wherein the steviol glycoside composition produced by the host cell comprises Rebaudioside D and Rebaudioside M that are produced by the host cell at a ratio of at least 1:0.1 in the cell culture.

26. The method of claim 1, that further comprises recovering the steviol glycoside composition comprising Rebaudioside D that is produced by the host cell, alone or together with at least one other steviol glycoside from the cell culture.

27. The method of claim 26, wherein the recovered steviol glycoside composition is enriched for Rebaudioside D relative to a steviol glycoside composition from a *Stevia* plant and has a reduced level of *Stevia* plant-derived components relative to a plant-derived *Stevia* extract.

28. The method of claim 1, wherein the recombinant host cell is a *Yarrowia lipolytica* cell.

29. A method of producing a steviol glycoside composition, comprising whole-cell bioconversion of plant-derived or synthetic steviol and/or steviol glycosides in a cell culture of a recombinant host cell using:
(a) a first polypeptide capable of beta 1,2 glycosylation of the C2' of the 13-O-glucose, 19-O-glucose, or both 13-O-glucose and 19-O-glucose of a steviol glycoside;
wherein the first polypeptide comprises a polypeptide having 65% or greater sequence identity to the amino acid sequence set forth in SEQ ID NO:16; and
a second polypeptide capable of beta 1,2 glycosylation of the C2' of the 13-O-glucose, 19-O-glucose, or both 13-O-glucose and 19-O-glucose of a steviol glycoside;
wherein the second polypeptide comprises a polypeptide having 90% or greater sequence identity to the amino acid sequence set forth in any one of SEQ ID NOs:15 or 86, a polypeptide having a substitution at residues 211 and 286 of SEQ ID NO:15, or a combination thereof;
(b) a polypeptide capable of beta 1,3 glycosylation of the C3' of the 13-O-glucose, 19-O-glucose, or both 13-O-glucose and 19-O-glucose of the steviol glycoside, comprising a polypeptide having 50% or greater sequence identity to the amino acid sequence set forth in SEQ ID NO:2;
(c) a polypeptide capable of glycosylating steviol or a steviol glycoside at its C-13 hydroxyl group, comprising a polypeptide having 55% or greater sequence identity to the amino acid sequence set forth in SEQ ID NO:26; and/or
(d) a polypeptide capable of glycosylating steviol or a steviol glycoside at its C-19 carboxyl group, comprising a polypeptide having 55% or greater sequence identity to the amino acid sequence set forth in SEQ ID NO:19;

wherein at least one of the polypeptides is a recombinant polypeptide expressed in the recombinant host cell; and producing the steviol glycoside composition thereby;

wherein the steviol glycoside comprises steviol-13-O-glucoside, steviol-19-O-glucoside, rubusoside, stevioside, 1,2-bioside, Rebaudioside A, Rebaudioside B, Rebaudioside D, or Rebaudioside E; and wherein the steviol glycoside composition comprises Rebaudioside M that is produced at a concentration of at least about 600 mg/L of the cell culture; and further comprising isolating the produced Rebaudioside M from the cell culture.

30. An in vitro method of producing a steviol glycoside composition, comprising adding:

(a) a first polypeptide capable of beta 1,2 glycosylation of the C2' of the 13-O-glucose, 19-O-glucose, or both 13-O-glucose and 19-O-glucose of a steviol glycoside;
    wherein the first polypeptide comprises a polypeptide having 65% or greater sequence identity to the amino acid sequence set forth in SEQ ID NO:16; and
a second polypeptide capable of beta 1,2 glycosylation of the C2' of the 13-O-glucose, 19-O-glucose, or both 13-O-glucose and 19-O-glucose of a steviol glycoside;
    wherein the second polypeptide comprises a polypeptide having 90% or greater sequence identity to the amino acid sequence set forth in any one of SEQ ID NOs:15 or 86, a polypeptide having a substitution at residues 211 and 286 of SEQ ID NO:15, or a combination thereof; and one or more of:

(b) a polypeptide capable of beta 1,3 glycosylation of the C3' of the 13-O-glucose, 19-O-glucose, or both 13-O-glucose and 19-O-glucose of the steviol glycoside;

(c) a polypeptide capable of glycosylating steviol or the steviol glycoside at its C-13 hydroxyl group; or (d) a polypeptide capable of glycosylating steviol or the steviol glycoside at its C-19 carboxyl group;

and a plant-derived or synthetic steviol precursor, a steviol, a steviol glycoside precursor, and/or a steviol glycoside to a reaction mixture;

wherein at least one of the polypeptides is a recombinant polypeptide; and producing the steviol glycoside composition thereby; and wherein the steviol glycoside composition comprises Rebaudioside M that is produced at a concentration of at least about 600 mg/L of the reaction mixture; and further comprising isolating the produced Rebaudioside M from the reaction mixture.

* * * * *